(12) United States Patent
Aukerman et al.

(10) Patent No.: US 9,085,633 B2
(45) Date of Patent: Jul. 21, 2015

(54) PLANTS HAVING ALTERED AGRONOMIC CHARACTERISTICS UNDER NITROGEN LIMITING CONDITIONS AND RELATED CONSTRUCTS AND METHODS INVOLVING GENES ENCODING SNF2 DOMAIN-CONTAINING POLYPEPTIDES

(75) Inventors: Milo Aukerman, Newark, DE (US); Carl R. Simmons, Des Moines, IA (US); Stephen M. Allen, Wilmington, DE (US); Dale Loussaert, Clive, IA (US); Stanley Luck, Wilmington, DE (US); Hajime Sakai, Newark, DE (US); Scott V. Tingey, Wilmington, DE (US)

(73) Assignees: E I DU PONT DE NEMOURS AND COMPANY, Wilmington, DE (US); PIONEER HI-BRED INTERNATIONAL INC, Johnston, IA (US)

( * ) Notice: Subject to any disclaimer, the term of this patent is extended or adjusted under 35 U.S.C. 154(b) by 803 days.

(21) Appl. No.: 13/259,582

(22) PCT Filed: Mar. 26, 2010

(86) PCT No.: PCT/US2010/028773
§ 371 (c)(1),
(2), (4) Date: Sep. 23, 2011

(87) PCT Pub. No.: WO2010/111568
PCT Pub. Date: Sep. 30, 2010

(65) Prior Publication Data
US 2012/0023617 A1 Jan. 26, 2012

Related U.S. Application Data

(60) Provisional application No. 61/163,887, filed on Mar. 27, 2009.

(51) Int. Cl.
*A01H 5/00* (2006.01)
*C12N 9/90* (2006.01)
*C12N 15/82* (2006.01)
*A01H 1/00* (2006.01)
*C07H 21/04* (2006.01)
*C07K 14/415* (2006.01)
*C12N 15/00* (2006.01)
*C12N 15/63* (2006.01)

(52) U.S. Cl.
CPC ............... *C07K 14/415* (2013.01); *C12N 9/90* (2013.01); *C12N 15/8261* (2013.01); *Y10T 436/17* (2015.01)

(58) Field of Classification Search
None
See application file for complete search history.

(56) References Cited

U.S. PATENT DOCUMENTS

| 2005/0108791 A1* | 5/2005 | Edgerton | 800/284 |
| 2009/0100536 A1* | 4/2009 | Adams et al. | 800/260 |

FOREIGN PATENT DOCUMENTS

| EP | 1647181 A1 | 4/2006 |
| WO | 2005/047516 A2 | 5/2005 |
| WO | 2006/069017 A2 | 6/2006 |
| WO | 2007/076115 A2 | 7/2007 |
| WO | 2007/084385 A2 | 7/2007 |
| WO | 2008/051608 A2 | 5/2008 |

OTHER PUBLICATIONS

Allen G. Good et al., Engineering nitrogen use efficiency with alanine aminotransferase, Can. J. Bot., 2007, pp. 252-262, vol. 85 •.
Ravi Ramesh Pathak et al., Molecular physiology of plant nitrogen use efficiency and biotechnological options for its enhancement, Current Science, Jun. 10, 2008, pp. 1394-1403, vol. 94, No. 11.
Detlef Weigel et al., Activation Tagging in Arabidopsis, Plant Physiology, pp. 1003-1013, vol. 122, Apr. 2000.
A. Theologis et al., Sequence and analysis of chromosome 1 of the plant Arabidopsis thaliana, GI No. 186492169, Jan. 22, 2014.
A. Theologis et al., Sequence and analysis of chromosome 1 of the plant Arabidopsis thaliana, GI No. 186492170, Jan. 22, 2014.
A. Theologis et al., Sequence and analysis of chromosome 1 of the plant Arabidopsis thaliana, GI No. 186492171, Jan. 22, 2014.
A. Theologis et al., Sequence and analysis of chromosome 1 of the plant Arabidopsis thaliana, GI No. 186492172, Jan. 22, 2014.
A. Theologis et al., Sequence and analysis of chromosome 1 of the plant Arabidopsis thaliana, GI No. 186492174, Jan. 22, 2014.
A. Theologis et al., Sequence and analysis of chromosome 1 of the plant Arabidopsis thaliana, GI No. 186492175, Jan. 22, 2014..
T. Sasaki et al., The genome sequence and structure of rice chromosome 1, GI No. 53792213, Feb. 16, 2008.
Maize Genome, GI No. 545262546, Sep. 23, 2013.
GI No. 21800575, Jul. 10, 2002.
A. H. Paterson et al., The Sorghum bicolor genome and the diversification of grassses, GI No. 242058897, Jul. 13, 2009.
Q. Feng et al., Sequence and analysis of rice chromosome 4, GI No. 90399293, Mar. 23, 2006.
International Search Report PCT/US2010/028773 Sep. 17, 2010.

* cited by examiner

*Primary Examiner* — Phuong Bui

(57) ABSTRACT

Isolated polynucleotides and polypeptides and recombinant DNA constructs particularly useful for altering agronomic characteristics of plants under nitrogen limiting conditions, compositions (such as plants or seeds) comprising these recombinant DNA constructs, and methods utilizing these recombinant DNA constructs. The recombinant DNA construct comprises a polynucleotide operably linked to a promoter functional in a plant, wherein said polynucleotide encodes a SNF2 domain-containing polypeptide.

3 Claims, 55 Drawing Sheets

FIG. 12

| | | | | | | | |
|---|---|---|---|---|---|---|---|
| ○ 3 | ○ 4 | ○ 2 | ○ 1 | ○ 5 | ○ 3 | ○ C1 | ○ 4 |
| ○ 4 | ○ 2 | ○ 1 | ○ 5 | ○ 3 | ○ C1 | ○ 4 | ○ 2 |
| ○ 2 | ○ 1 | ○ 5 | ○ 3 | ○ C1 | ○ 4 | ○ 2 | ○ 5 |
| ○ 1 | ○ 5 | ○ 3 | ○ C1 | ○ 4 | ○ 2 | ○ 5 | ○ 4 |
| ○ 5 | ○ 3 | ○ C1 | ○ 1 | ○ 2 | ○ 5 | ○ 4 | ○ 3 |
| ○ 3 | ○ C1 | ○ 1 | ○ 2 | ○ 5 | ○ 4 | ○ 3 | ○ 1 |
| ○ C1 | ○ 1 | ○ 2 | ○ 5 | ○ 4 | ○ 3 | ○ 1 | ○ C1 |
| ○ 1 | ○ 2 | ○ 5 | ○ 4 | ○ 3 | ○ 1 | ○ C1 | ○ 2 |

Typical grid pattern for 5 lines (labeled 1 through 5), plus wild-type control C1, used in screens.

FIG. 14

Modified Hoagland's solutions -
16X concentrations for semi-hydroponics maize growth.

| Nutrient | 1 mM KNO₃ | 2 mM KNO₃ | 3 mM KNO₃ | 4 mM KNO₃ |
|---|---|---|---|---|
| KNO₃ | 16 mM | 32 mM | 48 mM | 64 mM |
| KCl | 48 mM | 32 mM | 16 mM | ---- |
| KH$_2$PO$_4$ | 11 mM | 11 mM | 11 mM | 11 mM |
| MgSO$_4$ | 16 mM | 16 mM | 16 mM | 16 mM |
| CaCl$_2$·2H$_2$O | 16 mM | 16 mM | 16 mM | 16 mM |
| Sprint 330 | 1.6 g/L | 1.6 g/L | 1.6 g/L | 1.6 g/L |
| H$_3$BO$_3$ | 24 μM | 24 μM | 24 μM | 24 μM |
| 5 mM MnCl$_2$·4H$_2$O | 8 μM | 8 μM | 8 μM | 8 μM |
| 5 mM ZnSO$_4$·7H$_2$O | 8 M | 8 μM | 8 μM | 8 μM |
| 0.5 mM CuSO$_4$·5H$_2$O | 800 nM | 800 nM | 800 nM | 800 nM |
| 0.5 mM H$_2$MoO$_4$·H$_2$O | 800 nM | 800 nM | 800 nM | 800 nM |

Dilute 16X with tap water and determine the pH of the final mixture.
Add 3-12 mL H$_2$SO$_4$ if the pH is above 6.5.
Optimum pH is 5.0 - 5.5

FIG. 15

The effect of different nitrate concentrations on the growth and development of Gaspe Flint derived maize lines (see Example 18).

| [nitrate] | root (g dwt) | shoot (g dwt) | total vegetative (g dwt) | ear & husk (g dwt) | tassel (g dwt) | tiller # | tiller (g dwt) |
|---|---|---|---|---|---|---|---|
| 1 week after emergence | | | | | | | |
| 1 mM | 0.070a | 0.105b | 0.175b | | | | |
| 2 mM | 0.073a | 0.137ab | 0.209ab | | | | |
| 3 mM | 0.056a | 0.120ab | 0.176ab | | | | |
| 4 mM | 0.074a | 0.157a | 0.231a | | | | |
| 2 weeks after emergence | | | | | | | |
| 1 mM | 0.331ab | 0.544c | 0.875c | | | | |
| 2 mM | 0.266b | 0.951b | 1.217b | | | | |
| 3 mM | 0.352a | 1.171a | 1.523a | | | | |
| 4 mM | 0.303ab | 1.209a | 1.512a | | | | |
| 3 weeks after emergence | | | | | | | |
| 1 mM | 0.757a | 1.283b | 2.040b | 0.379c | 0.239c | 0.8c | 0.080b |
| 2 mM | 0.785a | 2.033a | 2.819a | 0.718a | 0.363bc | 2.3 | 0.506a |
| 3 mM | 0.664a | 1.911a | 2.574a | 0.451bc | 0.403ab | 2.8ab | 0.441a |
| 4 mM | 0.845a | 2.129a | 2.974a | 0.650ab | 0.506a | 3.3a | 0.688a |
| 4 weeks after emergence | | | | | | | |
| 1 mM | 0.842b | 2.010b | 2.852b | 1.318b | 0.677b | * | * |
| 2 mM | 1.493a | 3.772a | 5.265a | 3.130a | 1.018a | * | * |
| 3 mM | 1.232ab | 3.563a | 4.795a | 3.060a | 0.875ab | * | * |
| 4 mM | 1.010b | 2.943a | 3.952a | 2.787a | 0.891ab | * | * |

* Tillers removed 3 weeks after emergence
Means with similar letters are not different by protected Least Significant Difference (LSD) (0.05)

```
          130             140             150             160
          |               |               |               |
     EQMIDHTEKSK--L-XNDLQSQSRTSNXDNEHFPRDASNH    Majority 115  EQMIDHTEASRYELESNDLQSQSRTSNLDNEHFPRDASNH    SEQ ID NO:19  (Zea mays)
 39  EGRINFEDED-------------------------W         SEQ ID NO:21  (Zea mays)
  8  ARMLPS----NMDIDLSSDGEQEIIDLSDSEDMNTL        SEQ ID NO:23  (Zea mays)
107  EQPVETCGVSQ---SEMTSCSISSFSDPDGNMMAFNP        SEQ ID NO:25  (Arabidopsis thaliana)
114  EQPVETCGVSQ---SEMTSCSISSFSDPDGNMMAFNP        SEQ ID NO:27  (Arabidopsis thaliana)
  3  -----------------------------------         SEQ ID NO:29  (Arabidopsis thaliana)
 99  GESFDHSEDTSYRELSNDFLENSRNGN-PEMHLPMDALNH     SEQ ID NO:30  (Oryza sativa)
 70  VGDVAVLQDGESALSAHALHVLMRSGIQTPSCSPRGPSIW     SEQ ID NO:31  (Oryza sativa)
 11  EEYFSPYSDTEDNLDFDDPNDGVNQVVLHNTAFGNNSSEL     SEQ ID NO:32  (Oryza sativa)
  1  -----------------------------------         SEQ ID NO:36  (Eragrostis nindensis)
115  EKMIDHTEPSPYGLYSNDLQNQSRTCNEFDNEHFARDALNH    SEQ ID NO:38  (Paspalum notatum)
107  EQPVETCGVSQ---SEMTSCSISSFSDSDHDGNMMAFNP      SEQ ID NO:40  (Arabidopsis lyrata)
 95  ETAVQSFADP---ENGGLGPSATCFSDYCGNVVSY-F        SEQ ID NO:42  (Arabidopsis lyrata)
116  EQMIDHTERASRYELESNDLQSQSRTSNLDNEHFPRDASNH    SEQ ID NO:44  (Zea mays)
116  EQMIDHTEASRYELESNDLQSQSRTSNLDNEHFPRDASNH     SEQ ID NO:46  (Zea mays)
 84  GESFDHSEDTSYRLLSNDFLENSRNGN-PEMHLPMDALNH     SEQ ID NO:48  (Oryza sativa)
112  EQMIDHTEASPYEFSNDLQNQSRTSNLDNEHFPRDASNH      SEQ ID NO:49  (Sorghum bicolor)
```

FIG. 16E

| Position | Sequence | SEQ ID | Organism |
|---|---|---|---|
| | Majority: AN--E--PPY-D--NG-------------------E--PPY-D--NG | | |
| | 170        180        190        200 | | |
| 155 | ANV--EATGPPY-DLSNG------------------- | SEQ ID NO:19 | (Zea mays) |
| 51 | ---------------------------------------- | SEQ ID NO:21 | (Zea mays) |
| 42 | FRSYRE---------------------DYDYD | SEQ ID NO:23 | (Zea mays) |
| 142 | VNCDVDTVSKQDDKIIDSK------------------- | SEQ ID NO:25 | (Arabidopsis thaliana) |
| 149 | VNCDVDTVSKQDDKIIDSK------------------- | SEQ ID NO:27 | (Arabidopsis thaliana) |
| 3 | AKTVDEEIVPPYEDYTNGLY------------------- | SEQ ID NO:29 | (Arabidopsis thaliana) |
| 138 | AKTVDEEIVPPYEDYTNGLY-------YDSGCDM- | SEQ ID NO:30 | (Oryza sativa) |
| 118 | TSALKDHP--------LPADATVITVCRVADAVRHQ | SEQ ID NO:31 | (Oryza sativa) |
| 51 | LVGLDD-------------DNWLNM | SEQ ID NO:32 | (Oryza sativa) |
| 1 | ----------------------QVENNME | SEQ ID NO:36 | (Eragrostis nindensis) |
| 155 | DK-FEEATGPPYEDLSNGSYLGQETMYSGEIQLOVENGTG | SEQ ID NO:38 | (Paspalum notatum) |
| 142 | ---DTVSKQDDKIIDSKF----------TS | SEQ ID NO:40 | (Arabidopsis lyrata) |
| 129 | VNCEDGNVSNLYDMRIDSKF---------TP | SEQ ID NO:42 | (Arabidopsis lyrata) |
| 156 | ANV--EATGPPY-DLSNG------------------- | SEQ ID NO:44 | (Zea mays) |
| 156 | ANV--EATGPPY-DLSNG------------------- | SEQ ID NO:46 | (Zea mays) |
| 123 | AKTVDEEIVPPYEDYTNGLY-------YDSGCDM- | SEQ ID NO:48 | (Oryza sativa) |
| 152 | AN-VEEVAGPPYEDLSMGLYLRQQTLYSGQTQFOVENNTE | SEQ ID NO:49 | (Sorghum bicolor) |

```
         SSCLTXQGEHLQDECGNYPHPDYISEDMNKEXSXHDLPHG  Majority
                |         |         |         |
               290       300       310       320

236  SSCLTMQEEHLQAECGGYPHPDYISVDMIDERSLHDLPHG     SEQ ID NO:19  (Zea mays)
56   ----------------------------------------     SEQ ID NO:21  (Zea mays)
82   R---VLAKK-EYDDW------------LSSKASSYS-PVDDI   SEQ ID NO:23  (Zea mays)
208  QDCYNTSGTSLSDDHTPNSVQNFAEEFPNKEAVNDVESG      SEQ ID NO:25  (Arabidopsis thaliana)
215  ODCYNTSGTSLSDDHTPNSVQNFAEEFPNKEAVNDVESG      SEQ ID NO:27  (Arabidopsis thaliana)
50   QDCYNTSGTSLSDDHTPNSVQNFAEEFPNKEAVNDVESG      SEQ ID NO:29  (Arabidopsis thaliana)
227  GSCLTVQGEYLQGEYPQPDYGSEDMANEIYLHDLP--        SEQ ID NO:30  (Oryza sativa)
205  R--MLAGNMNDNYIDLSSDSDIDRFDSDDSVGGLDQE        SEQ ID NO:31  (Oryza sativa)
97   B--TLPHTFMSSSYKSRP-LSLTGGNNYVESTHPT          SEQ ID NO:32  (Oryza sativa)
86   SSCLTVQGEHLQVDCGDYPHPDYSSVDMVAEQSLPDLPHD     SEQ ID NO:36  (Eragrostis nindensis)
260  SSCLTMQEEHLQTECGEYPHPDYISVDMYQRSVHDLPHD      SEQ ID NO:38  (Paspalum notatum)
209  KDCYNTSGTSLSDDHTPNFVHNEAFQFFPNKEEAVIDVESG    SEQ ID NO:40  (Arabidopsis lyrata)
197  PYGHMDAPLSEVSPNLVPGYAFQFFPNKEELINDLKSA       SEQ ID NO:42  (Arabidopsis lyrata)
237  SSCLTMQEEHLQAECGGYPHPDYISVDMIDERSLHDLPHG     SEQ ID NO:44  (Zea mays)
237  SSCLTMQEEHLQAECGGYPHPDYISVDMIDERSLHDLPHG     SEQ ID NO:46  (Zea mays)
212  GSCLTVQGEYLQGEYPQPDYGSEDMANEIVLHDLP--        SEQ ID NO:48  (Oryza sativa)
259  SSCLTMQ-E--ARCGGYPHPDCISSVDMVDERSLHDLPHG     SEQ ID NO:49  (Sorghum bicolor)
```

| | | | | | |
|---|---|---|---|---|---|
| | 370 | 380 | 390 | 400 | |
| Majority | -KF-DDTSLSDAYMD-VSSPDSNSCEQNQPEDIFKSESS | | | | |
| 313 | -QYCDDTSLSDFYMD-VSSPESISCEQNQPEDIFKSESS | | | | SEQ ID NO:19 (Zea mays) |
| 76 | -SLITNGRHAESSRYTFGSVDRI--HPHANFYMA-MR | | | | SEQ ID NO:21 (Zea mays) |
| 120 | -SF-TYGGFIP- | | | | SEQ ID NO:23 (Zea mays) |
| 288 | RKFFESNPSVSPACVKPYNSFDSHLADSDLDRPNNYSCSFQ | | | | SEQ ID NO:25 (Arabidopsis thaliana) |
| 295 | RKFFESNPSVSPACVKPYNSFDSHLADSDLDRPNNYSCSFQ | | | | SEQ ID NO:27 (Arabidopsis thaliana) |
| 130 | FKFFESNPSVSPACVKPYNSFDSHLADSDLDRPNNYSCSFQ | | | | SEQ ID NO:29 (Arabidopsis thaliana) |
| 295 | -DDTSLSDYYMDDVSSIESMSSEQNRSEDICFRSESS | | | | SEQ ID NO:30 (Oryza sativa) |
| 263 | -SF-TNGRHVDNARHALGSGDRA---YPHSSSYRG-SP | | | | SEQ ID NO:31 (Oryza sativa) |
| 149 | -PA-IASGYKPYVSYG- | | | | SEQ ID NO:32 (Oryza sativa) |
| 158 | -DDTSLSDLYID-VSSPESVSCEQNOTEDICFKSESS | | | | SEQ ID NO:36 (Eragrostis nindensis) |
| 340 | -SDIYMD-VSSPDSVSSFEQNQSEDICFKSESS | | | | SEQ ID NO:38 (Paspalum notatum) |
| 289 | RKFFESNPSVSPACVKPYNSFDSHLADDHDLDRPDNYSSSFQ | | | | SEQ ID NO:40 (Arabidopsis lyrata) |
| 277 | IKYEIIPSVSPACVNPYNSFDGHQVDKRLEQPSNCSSSEFQ | | | | SEQ ID NO:42 (Arabidopsis lyrata) |
| 313 | -QYCDDTSLSDFYMD-VSSPESISCEQNQPEDIFFKSESS | | | | SEQ ID NO:44 (Zea mays) |
| 313 | -DDTSLSDYIMDDVSSIESMSSEQNRSEDICFKSESS | | | | SEQ ID NO:46 (Zea mays) |
| 280 | -QYCDDTSLSDFYMD-VSSPESISCEQNQSEDICFKSESS | | | | SEQ ID NO:48 (Oryza sativa) |
| 327 | -DDTSLSDFYMD-VSSPESISCEQNQSEDICFKSESS | | | | SEQ ID NO:49 (Sorghum bicolor) |

FIG. 16K

```
                 TDSSFVPSSRNSTTEDADKYLGVPSKQLXDSXXIVPZSNQ        Majority
                          |         |         |         |
                         410       420       430       440

350   TDSSFVPSSRNSTTEDADKYLGVPSKQLLDSK-IVPFSNQ                SEQ ID NO:19  (Zea mays)
108   ------PGHSTSSRIDSVVEKHNSSTADANDNKKRVLPSSFS              SEQ ID NO:21  (Zea mays)
129   -----------------------------------QSCA                SEQ ID NO:23  (Zea mays)
328   DNKTVHVKVKPEAESEKVVYSSVPGEFSVRDDAYLSGETN                SEQ ID NO:25  (Arabidopsis thaliana)
335   DNKTVHVKVKPEAESEKVVYSSVPGEFSVRDDAYLSGETN                SEQ ID NO:27  (Arabidopsis thaliana)
170   DNKTVHVKVKPEAESEKVVYSSVPGEFSVRDDAYLSGETN                SEQ ID NO:29  (Arabidopsis thaliana)
331   TDSSPVPSSRNSTTEDADKYFGDAPKHLQNSMFPVSTQHQ                SEQ ID NO:30  (Oryza sativa)
295   NDSARAAPASNRTDIVVKKHNGFASDENDGKRILPSSFS                 SEQ ID NO:31  (Oryza sativa)
157   ---------------QGVSIDDDDYFEVLHQPFP                      SEQ ID NO:32  (Oryza sativa)
193   TDSSPVPSSRNSTTEDADKYLSHTSKQLPDSNKFLEISNQ                SEQ ID NO:36  (Eragrostis nindensis)
372   TDSSPVPSSRNSVPGDADKYIGHTPKQLPDS-NIVBFSNQ                SEQ ID NO:38  (Paspalum notatum)
329   DNKAVHVTVKPEVESEKVVYSSVPGEYSVRDDAYVSGETN                SEQ ID NO:40  (Arabidopsis lyrata)
317   ENEAVPVKVKPELDLENTVFSTVPGNSICSDVHTVGSTT                 SEQ ID NO:42  (Arabidopsis lyrata)
351   IDSSPVPSSRNSTTEDADKYLGQPSKQLLDSK-IVPFSNQ                SEQ ID NO:44  (Zea mays)
351   TDSSPVPSSRNSTTEDADKYLGQPSKQLLDSK-ITVPFSNQ               SEQ ID NO:46  (Zea mays)
316   TDSSPVPSSRNSTTEDADKYFGDAPKHLQNSMFPVSTQHQ                SEQ ID NO:48  (Oryza sativa)
362   TDSSPHPSSRNSTTEDADKYLGQTSKQLLDS-KIVPFSNQ                SEQ ID NO:49  (Sorghum bicolor)
```

```
          SRDGXYDSDLCXLEGNRXPAPXHRLEQSXFXHNFQQPVX  Majority
                 490       500       510       520

424  SRDGDMVSDLCVLEGNRNPAPAHLWPYQGKFHHNFQQPVY----  SEQ ID NO:19  (Zea mays)
180  GPNIANGNLQ-------------FPSSIMARGTSSTLNTHKY--  SEQ ID NO:21  (Zea mays)
155  QGCTASGNGM-------------LPSSBTV--------------  SEQ ID NO:23  (Zea mays)
406  SSNHFYDSDTCLQYVVEDPSPVTQNNEYKDFQIQGDREY-----  SEQ ID NO:25  (Arabidopsis thaliana)
413  SSNHFYDSDTCLQYVVEDPSPVTQNNEYKDFQIQQGDREY----  SEQ ID NO:27  (Arabidopsis thaliana)
248  SSNHFYDSDTCLQYVVEDPSPVTQNNEYKDFQIQQGDREY----  SEQ ID NO:29  (Arabidopsis thaliana)
408  LDSNRFYDSDLCHLEGSRSLASGNVLPQG-LQHNFQQSVC----  SEQ ID NO:30  (Oryza sativa)
371  GKNVANGIGE-------------LPSSSRFPSSSFGTDNKKVIT  SEQ ID NO:31  (Oryza sativa)
200  QTSSAYGIEM-------------PATSAR1--------------  SEQ ID NO:32  (Oryza sativa)
269  SMDGSASDLCFLEGNRSSAPDXRLPLQRPIHHNFQMSVY-----  SEQ ID NO:36  (Eragrostis hindensis)
447  SIDGNVASDLCVLEGNGNPVPDHRSSFQGKFHHNFQQPMY----  SEQ ID NO:38  (Paspalum notatum)
407  SANHFYDSDTCLQYVAEDPSSEYLDFQIQ-GGHEY---------  SEQ ID NO:40  (Arabidopsis lyrata)
395  SFYNCFVSDDCLQNVT-DFDPATSRTESLDYLVGDEDHEY----  SEQ ID NO:42  (Arabidopsis lyrata)
425  SRDGDMVSDLCVLEGNRNPAPAHLWPYQGKFHHNFQQPVY----  SEQ ID NO:44  (Zea mays)
425  SRDGDMVSDLCVLEGNRNPAPAHLWPYQGKFHHNFQQPVY----  SEQ ID NO:46  (Zea mays)
393  LDSNRDSDLCILEGSRSLASGNVLPQG-LQHNFQQSVC------  SEQ ID NO:48  (Oryza sativa)
436  NRDGDASDLCVLEGNRMPAPDHRLPYQGKFHHNFQQHNY-----  SEQ ID NO:49  (Sorghum bicolor)
```

FIG. 16N

| | | | | | | Majority | |
|---|---|---|---|---|---|---|---|
| | : GNXG - IPAFGGARYKPHD - | | | | | | |
| | 520 | 530 | 540 | 550 | 560 | | |
| 464 | : GNSI - IPAFGGTRYKPHDERTTLRLALQ - | | | | | | SEQ ID NO:19 (Zea mays) |
| 209 | : DDDDVIVYGGS - ISSHR | | | | | | SEQ ID NO:21 (Zea mays) |
| 170 | : - PIGP I - | | KPHR | | | | SEQ ID NO:23 (Zea mays) |
| 446 | : IQPRGIDSQFSNASFES | | | | VQSHSS | | SEQ ID NO:25 (Arabidopsis thaliana) |
| 453 | : IQPRGIDSQFSNASFES | | | | VQSHSS | | SEQ ID NO:27 (Arabidopsis thaliana) |
| 288 | : IQPRGIDSQFSNASFES | | | | VQSHSS | | SEQ ID NO:29 (Arabidopsis thaliana) |
| 447 | : A - MPN - LPRFGG - MYRPHEERMTLRLALQ - | | | | | | SEQ ID NO:30 (Oryza sativa) |
| 402 | : DSDNEDVYYGGS - ISSHR | | | | | | SEQ ID NO:31 (Oryza sativa) |
| 215 | : - ISTGGVSAYGGL - NSHR | | | | | | SEQ ID NO:32 (Oryza sativa) |
| 309 | : PNNHI - IPTFGGGMRYKPHDERMTLRLALQ - | | | | | | SEQ ID NO:36 (Eragrostis hindensis) |
| 487 | : GNHII - IPTYGGMRYKPHDERITLRLALQ - | | | | | | SEQ ID NO:38 (Paspalum notatum) |
| 446 | : VQPRGIDSNFSNASFES | | | | VQSHSS | | SEQ ID NO:40 (Arabidopsis lyrata) |
| 434 | : IGRTGF - NLSSLSSGT - | | | | VESLSS | | SEQ ID NO:42 (Arabidopsis lyrata) |
| 465 | : GNSII - IPAFGGTRYKPHDERTTLRLALQFWYYILSSLGM | | | | | | SEQ ID NO:44 (Zea mays) |
| 465 | : GNSII - IPAFGGTRYKPHDERTTLRLALQ - | | | | | | SEQ ID NO:46 (Zea mays) |
| 433 | : A - MPN - LPRFGG - RYRPHEERMTLRLALQ - | | | | | | SEQ ID NO:48 (Oryza sativa) |
| 476 | : SNSM - IPAFGGMRYKPHDERITLRLALQ - | | | | | | SEQ ID NO:49 (Sorghum bicolor) |

FIG. 16O

```
                                                 Majority 570              580              590              600

491  - - - - - - - - - - ECISDSDDDS.DVC - - - - - - - - - - - - - - - - - - - - - -   SEQ ID NO:19 (Zea mays)
225  - - - - - - - - - - ECISDSDDDS.DVC - - - - - - - - - - - - - - - - - - - - - -   SEQ ID NO:21 (Zea mays)
178  - - - - - - - - - - ECISDSDDDS.DVC - - - - - - - - - - - - - - - - - - - - - -   SEQ ID NO:23 (Zea mays)
469  - - - - - - - - - - - - - - - - - - - - - - - - - - - - - - - - - - - - - - -   SEQ ID NO:25 (Arabidopsis thaliana)
476  - - - - - - - - - - - - - - - - - - - - - - - - - - - - - - - - - - - - - - -   SEQ ID NO:27 (Arabidopsis thaliana)
311  - - - - - - - - - - - - - - - - - - - - - - - - - - - - - - - - - - - - - - -   SEQ ID NO:29 (Arabidopsis thaliana)
473  - - - - - - - - - - - - - - - - - - - - - - - - - - - - - - - - - - - - - - -   SEQ ID NO:30 (Oryza sativa)
419  - - - - - - - - - - - - - - - - - - - - - - - - - - - - - - - - - - - - - - -   SEQ ID NO:31 (Oryza sativa)
230  - - - - - - - - - - - - - - - - - - - - - - - - - - - - - - - - - - - - - - -   SEQ ID NO:32 (Oryza sativa)
337  - - - - - - - - - - - - - - - - - - - - - - - - - - - - - - - - - - - - - - -   SEQ ID NO:36 (Eragrostis nindensis)
514  - - - - - - - - - - - - - - - - - - - - - - - - - - - - - - - - - - - - - - -   SEQ ID NO:38 (Paspalum notatum)
469  - - - - - - - - - - ECISDSDDDS.DIC - - - - - - - - - - - - - - - - - - - - - -   SEQ ID NO:40 (Arabidopsis lyrata)
455  - - - - - - - - - - KRIPEGDDDSBIH - - - - - - - - - - - - - - - - - - - - - -   SEQ ID NO:42 (Arabidopsis lyrata)
503  ANLSPDSNESTFRADWMAKSFNYWHKGIFFWMKLSSGGLPV                                        SEQ ID NO:44 (Zea mays)
492  - - - - - - - - - - - - - - - - - - - - - - - - - - - - - - - - - - - - - - -   SEQ ID NO:46 (Zea mays)
458  - - - - - - - - - - - - - - - - - - - - - - - - - - - - - - - - - - - - - - -   SEQ ID NO:48 (Oryza sativa)
503  - - - - - - - - - - - - - - - - - - - - - - - - - - - - - - - - - - - - - - -   SEQ ID NO:49 (Sorghum bicolor)
```

| | | | | | | | |
|---|---|---|---|---|---|---|---|
| | | | | Majority | | | |
| | 650 | | 660 | | 670 | 680 | |
| 491 | N N S E V A K G F E T H S R I N P E N R V L D Y A E R A V Y Q E A L Q - - - - - - - - - | | | | | | SEQ ID NO:19 (Zea mays) |
| 236 | N Z K - - - - - - - - - - - - - Y D V E Q R L F S D E R A V Y E E A L K - - - - - - - - - | | | | | | SEQ ID NO:21 (Zea mays) |
| 188 | N D I K V - E - - - - - - - - - Y D V E Q R L F S D E R A V Y E E A L K - - - - - - - - - | | | | | | SEQ ID NO:23 (Zea mays) |
| 509 | - - - - T V S B N F N O S G G L K L Q S N - - K E N M I F Q A A L - - - - - - - - - - - - | | | | | | SEQ ID NO:25 (Arabidopsis thaliana) |
| 516 | - - - - T V S B N F N O S G G I K L Q S N - - K E N M I F Q A A L - - - - - - - - - - - - | | | | | | SEQ ID NO:27 (Arabidopsis thaliana) |
| 351 | - - - - T V S B N F N O S G G L M L Q S N - - K E N M I F Q A A L - - - - - - - - - - - - | | | | | | SEQ ID NO:29 (Arabidopsis thaliana) |
| 473 | N H S E F A N G I D M Q G R L N L E N R T I D S D E R A V Y Q E A L Q - - - - - - - - - - | | | | | | SEQ ID NO:30 (Oryza sativa) |
| 431 | N N F G V - N G L G T Q S H L N I E K R L F G R D E R V Y Y D E A L K - - - - - - - - - - | | | | | | SEQ ID NO:31 (Oryza sativa) |
| 242 | - - - - - - - - - - - - - - - - - - - - - - - - - - - - - - - - - - - - - - - - - - - - | | | | | | SEQ ID NO:32 (Oryza sativa) |
| 337 | - - - - T V G H N Y N O S G G I K L Q S M - - K E N M I F Q A A L - - - - - - - - - - - - | | | | | | SEQ ID NO:36 (Eragrostis bindensis) |
| 514 | - - - - T G S Q T L N N C G G L K F E E S M - - K G N M N F H A D L - - - - - - - - - - - | | | | | | SEQ ID NO:38 (Paspalum notatum) |
| 509 | H E Q K L P S L P E S K R L T P D Q K T L Q A Q L S V S Y B A P A Q T S T F D - - - - - - | | | | | | SEQ ID NO:40 (Arabidopsis lyrata) |
| 495 | - - - - - - - - - - - - - - - - - - - - - - - - - - - - - - - - - - - - - - - - - - - - | | | | | | SEQ ID NO:42 (Arabidopsis lyrata) |
| 503 | - - - - - - - - - - - - - - - - - - - - - - - - - - - - - - - - - - - - - - - - - - - - | | | | | | SEQ ID NO:44 (Zea mays) |
| 492 | - - - - - - - - - - - - - - - - - - - - - - - - - - - - - - - - - - - - - - - - - - - - | | | | | | SEQ ID NO:46 (Zea mays) |
| 450 | - - - - - - - - - - - - - - - - - - - - - - - - - - - - - - - - - - - - - - - - - - - - | | | | | | SEQ ID NO:48 (Oryza sativa) |
| 503 | - - - - - - - - - - - - - - - - - - - - - - - - - - - - - - - - - - - - - - - - - - - - | | | | | | SEQ ID NO:49 (Sorghum bicolor) |

FIG. 16R

```
            DISQPKSEANPPDGVLAVPLLRHQKIALSWMVQK                Majority
                  690       700        710        720
491   : --------DISQPKSEANPPDGVLAVPLLRHQKIALSWMVQK :   SEQ ID NO:19 (Zea mays)
271   : NISREKSEDDLPEGVLAVPLLRHQKMALAWMVSK--------- :   SEQ ID NO:21 (Zea mays)
215   : HITQETKEEDLPKGVMSVLLKHQ------------------- :   SEQ ID NO:23 (Zea mays)
536   : QDLTQPNSEAILPDGVLTVPLLRHQRIALSWMAQK-------- :   SEQ ID NO:25 (Arabidopsis thaliana)
543   : QDLTQPNSEAILPDGVLTVPLLRHQRIALSWMAQK-------- :   SEQ ID NO:27 (Arabidopsis thaliana)
378   : --------DISQPKSEANPPDGVLSVPLLRHQKIALSWMAQK :   SEQ ID NO:29 (Arabidopsis thaliana)
473   : NIHQDKREDDLPEGVMSVSLLKHQKMALAWMVSR-------- :   SEQ ID NO:30 (Oryza sativa)
466   : --------QISQEBTEENLPEGVMSVSLLKHQKIALSWMVQK :   SEQ ID NO:31 (Oryza sativa)
276   : --------DISQPKSEANPPDGVLAVPLLRHQKIALSWMVQK :   SEQ ID NO:32 (Oryza sativa)
337   : --------DISQPKTEANPPDGVLTVPLLRHQKIALSWMAQK :   SEQ ID NO:36 (Eragrostis bindensis)
514   : --------QDLSQPNSEAS PFEGVLAVSLLRHQKIALAWMSEK :   SEQ ID NO:38 (Paspalum notatum)
536   : --------QVLSQPRSEAS PFEGVLAVSLLRHQKIALAWMSEK :   SEQ ID NO:40 (Arabidopsis lyrata)
522   : HFGDWQDISQPNSEANPPDGVLAVPLLRHQKIALSWMVKK   :   SEQ ID NO:42 (Arabidopsis lyrata)
623   : --------DISQPNSEANPPDGVLAVPLLRHQKIALSWMVKK :   SEQ ID NO:44 (Zea mays)
492   : --------DISQPKSEANPPDGVLAVPLLRHQKIALSWMVQK :   SEQ ID NO:46 (Zea mays)
458   : --------DISQPKSEANPPDGVLAVPLLRHQKIALSWMVQK :   SEQ ID NO:48 (Oryza sativa)
509   : --------DISQPKSEANPPDGVLAVPLLRHQKIALSWMVQK :   SEQ ID NO:49 (Sorghum bicolor)
```

| | 810 | 820 | 830 | 840 | |
|---|---|---|---|---|---|
| | | | TCAKLXTSGTSKQENPS---- | | Majority |
| 491 | :--------- | :--------- | :--------- | :---- | |
| 375 | GACSL---- | STSAGTSA- | ELFVNQPNHVVNKMVET- | -KAER | SEQ ID NO:19 (Zea mays) |
| 300 | DGSARLHV- | -ASSLKLCDSKPNTATD- | --KAEP | | SEQ ID NO:21 (Zea mays) |
| 627 | :--------- | CAPLKPEATSKHEHSQLLS | | | SEQ ID NO:23 (Zea mays) |
| 634 | :--------- | CAPLKPSGRSKHFEHSQLLS | | | SEQ ID NO:25 (Arabidopsis thaliana) |
| 469 | :--------- | CAPLKPSGRSKHFEHSQLLS | | | SEQ ID NO:27 (Arabidopsis thaliana) |
| 572 | PALAHLADTCKPEATSSTIKTENPI- | | | | SEQ ID NO:29 (Arabidopsis thaliana) |
| 578 | GAGSS---- | SEAAGTGDVETCASIMNTAPDKTVER- | -NVER | | SEQ ID NO:30 (Oryza sativa) |
| 384 | QDSTLFFSSEAASDAADLKPWASLPGSAVDRMVNAVKVEP- | | | | SEQ ID NO:31 (Oryza sativa) |
| 437 | :--------- | PTL---- | TFIPEGANDTVKEENPV- | | SEQ ID NO:32 (Oryza sativa) |
| 614 | :--------- | PTQ---- | KCSSEVTSDTAKQENPF- | | SEQ ID NO:36 (Eragrostis nindensis) |
| 627 | :--------- | CAPLKTSGKSERFEHSQLLS | | | SEQ ID NO:38 (Paspalum notatum) |
| 602 | :--------- | GGSNQFDHSQVVF | | | SEQ ID NO:40 (Arabidopsis lyrata) |
| 726 | LMRTCSSQVTSNTVKQENPI- | | | | SEQ ID NO:42 (Arabidopsis lyrata) |
| 589 | LMRTCSSQVTSNTVKQENPI- | | | | SEQ ID NO:44 (Zea mays) |
| 557 | :--------- | TCSSKVTTNTYRQENPF- | | | SEQ ID NO:46 (Zea mays) |
| 603 | PALAHLADTCKPEATSSTIRTENPI- | | | | SEQ ID NO:48 (Oryza sativa) |
| | LMQ---- | TCSSKVTTNTYRQENPF- | | | SEQ ID NO:49 (Sorghum bicolor) |

```
     KNKVTSKANLSVLYYHGSNRTEDPNELKKYDVXXTYSIV  Majority
                 |         |         |         |
                890       900       910       920

491  - - - - - - - - - - - - - - - - - - - - - - - - - - - - - - - - - - - - - - - -                                    SEQ ID NO:19 (Zea mays)
449  T D K V S E S A K L S V L Y Y H G G A R T K D P K E L A K Y D V V V T T Y T I I V                                   SEQ ID NO:21 (Zea mays)
367  S V K V M E D N K L S V L V Y H G S S R T K D P N E L A T Y D V V V T T Y M T V                                     SEQ ID NO:23 (Zea mays)
604  H K K V T S E A N L S V L V Y H G S S R T K D P H E L A K Y D V V V T T F S I V                                     SEQ ID NO:25 (Arabidopsis thaliana)
691  H K K V T S E A N L S V L V Y H G S S R T K D P H E L A K Y D V V V T T F S I V                                     SEQ ID NO:27 (Arabidopsis thaliana)
526  H K K V T S E A N L S V L V Y H G S S R T K D P H E L A K Y D V V V T T F S I V                                     SEQ ID NO:29 (Arabidopsis thaliana)
624  R N K V T S K A N L T F L V Y H G S N R T K D P N E L A K Y D V L T F Y T I V                                       SEQ ID NO:30 (Oryza sativa)
651  T D K V G E S A K L S V L V Y H G G S R T K D P N E L A K Y D V V I T T Y T I V                                     SEQ ID NO:31 (Oryza sativa)
464  A A K V T E S S K L S V L V Y H G G S R T M D P T E L T K Y D V L T T Y S I V                                       SEQ ID NO:32 (Oryza sativa)
484  K N K V T N K A N L S F L I Y H G S N R T K D P N E L T K Y D V L T T Y S I V                                       SEQ ID NO:36 (Eragrostis nindensis)
661  K N K V T S K A N L S F L I Y H G S N R T K D P M E L T K Y D V V T T F S I V                                       SEQ ID NO:38 (Paspalum notatum)
684  H K K V T S E A N L S V L V Y H G S S R T K D P Y E L A K Y D V V I T T F S I V                                     SEQ ID NO:40 (Arabidopsis lyrata)
652  C K K V T L E A N L S V L V Y H G C N R T K D P M E L T K Y D V V I T T S L V                                       SEQ ID NO:42 (Arabidopsis lyrata)
773  K N K V T S K A N L S F L I Y H G S N R T K D P N E L T K Y D V V I T T Y S I V                                     SEQ ID NO:44 (Zea mays)
636  K N K V T S K A N L S F L I Y H G S N R T K D P N E L T K Y D V L T T Y S I V                                       SEQ ID NO:46 (Zea mays)
609  R N K V T S K A N L S F L V Y H G S N R T K D P N E L T K Y D V V L T T Y S I V                                     SEQ ID NO:48 (Oryza sativa)
650  K N K V T S K A N L S F L I Y H G S N R T K D P N E L T K Y D V L T T Y S I V                                       SEQ ID NO:49 (Sorghum bicolor)
```

```
     TQVARACWGLRAKRRWCLSGTPIQNAIDDLYSYFRFLKYD  Majority
                 1010          1020          1030          1040
```

| Pos | Sequence | SEQ ID | Organism |
|---|---|---|---|
| 491 | -------------------------------------- | | |
| 565 | TVVARACCGLRAKRRWCLSGTPIQNAIDDLFSYFRFLKYE | SEQ ID NO:19 | (Zea mays) |
| 478 | TQVARACCGLRAQRRWCLSGTPIQNKIDDLYSYFRCLKYD | SEQ ID NO:21 | (Zea mays) |
| 803 | TQVARACWGLRAKRRWCLSGTPIQNSIDDLYSYFRFLKYD | SEQ ID NO:23 | (Zea mays) |
| 810 | TQVARACWGLRAKRRWCLSGTPIQNSIDDLYSYFRFLKYD | SEQ ID NO:25 | (Arabidopsis thaliana) |
| 645 | TQVARACWGLRAKRRWCLSGTPIQNAVEDLYSYFRFLKYD | SEQ ID NO:27 | (Arabidopsis thaliana) |
| 742 | TQVARACWGLRAKRRWCLSGTPIQNAIDELYSYFRFLKYE | SEQ ID NO:29 | (Arabidopsis thaliana) |
| 767 | TQVARACWGLRAKRRWCLSGTPIQNTIDDLYSYFRFLKYE | SEQ ID NO:30 | (Oryza sativa) |
| 591 | TQVARACWGLRAKRRWCLSGTPIQNAIEDLYSYFRFLKYE | SEQ ID NO:31 | (Oryza sativa) |
| 602 | TQVARACWGLRAKRRWCLSGTPIQNAVEDLYSYFRFLKYD | SEQ ID NO:32 | (Oryza sativa) |
| 779 | TQVARACWGLRAKRRWCLSGTPIQNSIDDLYSYFRFLKYD | SEQ ID NO:36 | (Eragrostis nindensis) |
| 804 | TQASTACSGLHAKRRWCLSGTPIQNAVEDLYSYFRFLKYD | SEQ ID NO:38 | (Paspalum notatum) |
| 730 | -------------------------------------- | SEQ ID NO:40 | (Arabidopsis lyrata) |
| 691 | TQ------------------------------------- | SEQ ID NO:42 | (Arabidopsis lyrata) |
| 754 | TQVARACWGLRAKRRWCLSGTPIQNAVEDLYSYFRYLRYD | SEQ ID NO:44 | (Zea mays) |
| 727 | TQVARACWGLRAKRRWCLSGTPIQNAVEDLYSYFRFLRYD | SEQ ID NO:46 | (Oryza sativa) |
| 767 | TQVARACWGLRAKRRWCLSGTPIQNAVEDLYSYFRFLRYD | SEQ ID NO:48 | (Zea mays) |
| | TQVARACWGLRAKRRWCLSGTPIQNAVEDLYSYFRFLRYD | SEQ ID NO:49 | (Sorghum bicolor) |

FIG. 16AA

| | | | | | | Majority |
|---|---|---|---|---|---|---|
| PYSVYKKFCXMIKNPISRNPVNGYKKLQAVLKTVMLRRTK | | | | | | |
| 1050 | 1060 | 1070 | 1080 | | | |

| | | | | |
|---|---|---|---|---|
| 491 | PYS-VYKKFC-MIKNPISRNPVNGYKKLQAVLKTVMLRRTK | | | |
| 605 | PYCTYNSPCTMIKHPIARDAINGYKKLDQAVLKVVLLRRTK | SEQ ID NO:19 | (Zea mays) | |
| 518 | PYSKFSNFKYMIKHQITRDSVRGYKLQAILRIILLRRTK | SEQ ID NO:21 | (Zea mays) | |
| 643 | PYSSYVLFCSTIKNPITRNPITGYKLQILKTVMLRRTK | SEQ ID NO:23 | (Zea mays) | |
| 650 | PYSSYVLFCSTIKNPITRNPVKGYQLQAILKTVMLRRTK | SEQ ID NO:25 | (Arabidopsis thaliana) | |
| 685 | PYSSYVLFCSTIKNPITRNPVKGYQLQAILKTVMLRRTK | SEQ ID NO:27 | (Arabidopsis thaliana) | |
| 782 | PYAEYKKFCFMIKTPITRNPISRNPITGYKKLQVVLKTVMLRRTK | SEQ ID NO:29 | (Arabidopsis thaliana) | |
| 807 | PYSTYNSFCTMIKHPIARNAVHGYKKLOTYLRIVLLRRTK | SEQ ID NO:30 | (Oryza sativa) | |
| 621 | PYSVYGSFRSMIKYQISRDATRGYKKLQAVLKTVLLRRTK | SEQ ID NO:31 | (Oryza sativa) | |
| 642 | PYAYYKKFCSMIKLPISRNPTNGYKKLQVVLKTVMLRRTK | SEQ ID NO:32 | (Oryza sativa) | |
| 819 | PYSSYVLFCSTIKNPIITRNPISYKGYQKLQAILKTVKIMLRRTK | SEQ ID NO:36 | (Eragrostis nindensis) | |
| 844 | PYAYYKKFCSMIKNPISRNPVKGYKKLQAVLKPVMLRRTK | SEQ ID NO:38 | (Paspalum notatum) | |
| 770 | SYSCYQTFCETIKNPISTYPVKGYOTLQAILKIMLRRTK | SEQ ID NO:40 | (Arabidopsis lyrata) | |
| 893 | -FCTIIKIPIRNPISRNPENNGYKKLQVVLKTVMLRRTK | SEQ ID NO:42 | (Arabidopsis lyrata) | |
| 794 | PYAYYKKFCTMIKIPISRNPISRNPITGYKKLQVVLKTVMLRRTK | SEQ ID NO:44 | (Zea mays) | |
| 767 | PYAEYKKFCFMIKTPISRNPISRNPITGYKKLQVVLKTVMLRRTK | SEQ ID NO:46 | (Zea mays) | |
| 807 | PYAVYKQFCGMIKIPISRNPTNGYKKLQVVLKTVMLRRTK | SEQ ID NO:48 | (Oryza sativa) | |
| | | SEQ ID NO:49 | (Sorghum bicolor) | |

```
       EQFKEYAAAGTVKQNYVNILLMLLRLRQACDHPLLVRG-E  Majority
                1130      1140      1150      1160
491    -QQFKAFAAAGTVKQNYANILLVLLRLRQACDHPLLVKGNQE  SEQ ID NO:19 (Zea mays)
685    QKFKAYDAAGTIRENYANILLMLLRLRQACDHPLLLNGHEE  SEQ ID NO:21 (Zea mays)
598    TQFKEYAEAGTVKQNYVNILLMLLRLRQACDHPLLVNG-E   SEQ ID NO:23 (Zea mays)
923    TQFKEYAAAGTVKQNYVNILLMLLRLRQACDHPLLVNG-E   SEQ ID NO:25 (Arabidopsis thaliana)
930    EQFKEYAAAGTVKQNYVNILLMLLRLRQACDHPLLVNG-E   SEQ ID NO:27 (Arabidopsis thaliana)
765    QQFKEYAAAGTVKQNYVNILLMLLRLRQACDHPLLVRGHE   SEQ ID NO:29 (Arabidopsis thaliana)
862    EKFKEYASAGTIRENYANILLVLLRLRQACDHPLLVRGHE   SEQ ID NO:30 (Oryza sativa)
887    EQFKEYAAAGTVKQNYVNILLMLLRLRQACDHPLLLKGKE   SEQ ID NO:31 (Oryza sativa)
701    EQFKEYAAAGTVKQNYVNILLMLLRLRQACDHPRLVRGHQ   SEQ ID NO:32 (Oryza sativa)
722    TQFKEYAAAGTVKQNYVNILLMLLRLRQACDHPLLVRGYE   SEQ ID NO:36 (Eragrostis nindensis)
899    EQFKEYAAAGTVKQNYVNILLMLLRLRQACDHPLLVNG-E   SEQ ID NO:38 (Paspalum notatum)
924    TQFKEYAAAGTVKQNYVNILLMLLRLRQACDHPLLVS--    SEQ ID NO:40 (Arabidopsis lyrata)
850    DQFKEYAAAGTVKQNYVNILLMLLRLRQACDHPLLVRGYD   SEQ ID NO:42 (Arabidopsis lyrata)
966    EQFKEYAAAGTVKQNYVNILLMLLRLRQACDHPLLVRGHE   SEQ ID NO:44 (Zea mays)
874    EQFKEYAAAGTVKQNYVNILLMLLRLRQACDHPRLVRGHE   SEQ ID NO:46 (Zea mays)
847    EQFKEYAAAGTVKQNYVNILLMLLRLRQACDHPRLVRGHE   SEQ ID NO:48 (Oryza sativa)
887    EQFKEYAAAGTVKQNYVNILLMLLRLRQACDHPRLVRGYN   SEQ ID NO:49 (Sorghum bicolor)
```

FIG. 16AE

|  |  | 1210 | 1220 | 1230 | 1240 |  |  |
|---|---|---|---|---|---|---|---|
|  |  | DAPEDAVVTICGHVFCNQCI | Majority | | | | |
| 491 | | -------------------- | | | | | |
| 763 | | -------------------- | DTPEDAIVTICGHVFCYQCI | | SEQ ID NO:19 | (Zea mays) |
| 676 | | -------------------- | DAPEDAVVTICGHVFCTQCI | | SEQ ID NO:21 | (Zea mays) |
| 991 | | -------------------- | DAPEDAVASVCGHVFCKQCI | | SEQ ID NO:23 | (Zea mays) |
| 996 | | -------------------- | -VRFFCLVNYYTTICF | | SEQ ID NO:25 | (Arabidopsis thaliana) |
| 893 | | -------------------- | DAPEDAVVTICGHVFCNQCI | | SEQ ID NO:27 | (Arabidopsis thaliana) |
| 940 | | -------------------- | DAPEDAVVTMCGHVFCYQCI | | SEQ ID NO:29 | (Arabidopsis thaliana) |
| 964 | | -------------------- | DVPEDAVVVATCGHVFCYQCV | | SEQ ID NO:30 | (Oryza sativa) |
| 779 | | -------------------- | DPPEDAVVYVCGHVFCNQCI | | SEQ ID NO:31 | (Oryza sativa) |
| 800 | | -------------------- | DAPEDAVVTICGHVFCKQCI | | SEQ ID NO:32 | (Oryza sativa) |
| 977 | | -------------------- | DAPEDAVYYSVCGHVFCKQCI | | SEQ ID NO:36 | (Eragrostis hindensis) |
| 992 | | -------------------- | DAPEDAVVTICGHVFCNQCI | | SEQ ID NO:38 | (Paspalum notatum) |
| 924 | | -------------------- | GAPEDAVVTICGHVFCNQCI | | SEQ ID NO:40 | (Arabidopsis lyrata) |
| 1046 | GKGPVLTDLVVRGAGVGKLA | DAPEDPVVLCGHVFCNQCI | | SEQ ID NO:42 | (Arabidopsis lyrata) |
| 953 | | -------------------- | DAPEDAVVTLCGHVFCNQCI | | SEQ ID NO:44 | (Zea mays) |
| 925 | | -------------------- | DAPEDAVVTICGHVFCNQCI | | SEQ ID NO:46 | (Zea mays) |
| 965 | | -------------------- | DAPEDPVVTICGHAFCNQCI | | SEQ ID NO:48 | (Oryza sativa) |
|  | | -------------------- | | | SEQ ID NO:49 | (Sorghum bicolor) |

FIG. 16AF

```
         LEQLTGDDXVCPVSNCRVRLNTSSLFSRGTLE-CXLSXLX  Majority
                  1250          1260          1270         1280

491     ---------------------------------------------------  
 793     HERITTDENMCPAPNCSRTLGLELLFSSGALKICISGNKSS             SEQ ID NO:19  (Zea mays)
 696     HERLTSDGHYCPYALCGNKLSFRSVFTPAVLKLCTSPKPE             SEQ ID NO:21  (Zea mays)
1011     YERLTGDSNHCPFANCNVRLTISSLSKTRLDDAMPDMQ-              SEQ ID NO:23  (Zea mays)
1012     F----------------------------------------            SEQ ID NO:25  (Arabidopsis thaliana)
 853     YERLTGDSNHCPFANCNVRLTISSLSSKTRLDDAMPDMQ-             SEQ ID NO:27  (Arabidopsis thaliana)
 960     LEQLTGDDSVCPVSNCRVRLNST-SLFSRGTLE-CALSRST            SEQ ID NO:29  (Arabidopsis thaliana)
 984     YERITTDENNCPFANCNVRLNST-SLFSRGTLE-CALSRST            SEQ ID NO:30  (Oryza sativa)
 799     HXSLKSDBNVCPSPNCGNTLSTDSVESSGALRICMSGVSS             SEQ ID NO:31  (Oryza sativa)
 820     LEQLTGDDSNHCPVSNCRVRLNTTSLFSRGTLE-CSLRRLT            SEQ ID NO:32  (Oryza sativa)
 997     LEQLTGDDSICPVSNCPLANCNVRLTISSLSKTRSDDAMPDMQ-         SEQ ID NO:36  (Eragrostis nindensis)
1012     YERLTGDNNCPLANCNVRLTIISSSKTRSDDAMPDMQ-               SEQ ID NO:38  (Paspalum notatum)
 944     YECLTHDONNOCPLSLLCKVGVEISSLFSRETLENAMLGHNK           SEQ ID NO:40  (Arabidopsis lyrata)
1086     LEQLTGDDSVCPVSNCRVRLNTSSLFSBETTLERSRGTLE-CSLSKLA     SEQ ID NO:42  (Arabidopsis lyrata)
 972     LEQLTGDDSVCPVSNCRVRLNTSSLFSRGTLE-CSLSKLA             SEQ ID NO:44  (Zea mays)
 945     LEQLTGDDSVCPVSNCRVRLNSTSLFSRGTLE-CALSRST             SEQ ID NO:46  (Zea mays)
 985     LEQLTGDDSVCPVSNCRVRLNTTSLFSRGTLE-CSLSRLT             SEQ ID NO:48  (Oryza sativa)
                                                              SEQ ID NO:49  (Sorghum bicolor)
```

| | | | | Majority | |
|---|---|---|---|---|---|
| | 1330 | 1340 | 1350 | 1360 | |
| SLPK-–D––---DKXNSIKEXSEKF------------- | | | | | |
| 491 | ---------- | ---------- | ---------- | ---------- | |
| 855 | ---------- | -NSIIVMDPLITE | ---------- | ---------- | SEQ ID NO:19 (Zea mays) |
| 770 | ---------- | -NSIIKTPALTA- | ---------- | ---------- | SEQ ID NO:21 (Zea mays) |
| 1081 | SLPKAHD--- | -LTDSMQISENREYS | -GLSITPVK | ---------- | SEQ ID NO:23 (Zea mays) |
| 1013 | SLPKAHD--- | -LTDSMQISENREYS | ---------- | ---------- | SEQ ID NO:25 (Arabidopsis thaliana) |
| 923 | SLPKLI-DLTHMSDDKNKIVHPDKING | | | | SEQ ID NO:27 (Arabidopsis thaliana) |
| 1036 | SLPKLI-DLTHMSDDKNKIVHPDKING | -GLSITPVK | | | SEQ ID NO:29 (Arabidopsis thaliana) |
| 1057 | ---------- | -NSHIENTYALTD- | ---------- | ---------- | SEQ ID NO:30 (Oryza sativa) |
| 873 | ---------- | -NSIVNTPALTW- | ---------- | ---------- | SEQ ID NO:31 (Oryza sativa) |
| 897 | SLPKII-DPTQMSDSEKSIGETSEKFG | | | | SEQ ID NO:33 (Oryza sativa) |
| 1074 | SLPRII-DPTQWHIDSKNSIRLDSEKFG | | | | SEQ ID NO:36 (Eragrostis nindensis) |
| 1082 | SLPKFQD--- | -LTDFMQISQMSEYS | -SLPVTPVK | ---------- | SEQ ID NO:38 (Paspalum notatum) |
| 1022 | SLSRPQSPTTVMNDVDQSSENGEKNQLEKSFSLPATPAK | | | | SEQ ID NO:40 (Arabidopsis lyrata) |
| 1163 | SLPKNI-DPT----HDSKCSIGIESEKFD | | | | SEQ ID NO:42 (Arabidopsis lyrata) |
| 1049 | SLPKII-DPT----HDSKCSIGIESEKFD | | | | SEQ ID NO:44 (Zea mays) |
| 1021 | SLPKLI-DLTHMSDDKNKIVHPDKING | | | | SEQ ID NO:46 (Zea mays) |
| 1063 | SLPRII-DPTQMTDSKCSIGLESEKFD | | | | SEQ ID NO:48 (Oryza sativa) |
| | | | | | SEQ ID NO:49 (Sorghum bicolor) |

FIG. 16AI

|  | 1370 | 1380 | 1390 | 1400 |  |  |  |
|---|---|---|---|---|---|---|---|
|  | GXGMSEQXXTKVT-EKAIVFSQWTRMLDLLEVXLKSSHIQ | | | | Majority | | |
| 491 | ------- | --------- | ------- | ------- | | | |
| 666 | SYTMESSRSGLGP-VKAIVFSQWTGMLDLLELSLNIMCIQ | | | | SEQ ID NO:19 | (Zea mays) |
| 781 | GDTTESIPSMAPP-VKAIVFSQWTGMLDLLELSLNRNGIQ | | | | SEQ ID NO:21 | (Zea mays) |
| 1110 | NEGMSVDVPIKVAGEKAIVFSQWTKMLNLLEASLVSSHIQ | | | | SEQ ID NO:23 | (Zea mays) |
| 1013 | ------------- ---FS- ----------LMNVRGQ | | | | SEQ ID NO:25 | (Arabidopsis thaliana) |
| 952 | NEGMSVDVPIKVAGEKAIVFSQWTKMLDLLEASLVSSHIQ | | | | SEQ ID NO:27 | (Arabidopsis thaliana) |
| 1061 | NSTPESEYAGTKIT-EKAIVFSQWTRMLDLVEVHLKSSHLS | | | | SEQ ID NO:29 | (Arabidopsis thaliana) |
| 1068 | SDTVESNPSRVAP-VKAIVFSQWTGMLDLLELSLMSNLIQ | | | | SEQ ID NO:30 | (Oryza sativa) |
| 884 | SDTMESSPSEVAP-SKAIVFSQWTGLLDLLELSLDSSRIK | | | | SEQ ID NO:31 | (Oryza sativa) |
| 922 | GKSPSEHIDPTKMT-EKAIVFSQWTRMLDLLEVHLKASHVT | | | | SEQ ID NO:32 | (Eragrostis nindensis) |
| 1099 | GNGSSEQTETRKFT-EKAIVFSQWTRMLDLLEASLVSSHIQ | | | | SEQ ID NO:36 | (Paspalum notatum) |
| 1111 | NEGISVVVPVKVAGEKAIVFTQWTRMLDLLEAGLKSSGIQ | | | | SEQ ID NO:38 | (Arabidopsis lyrata) |
| 1062 | S--SVDGLVKVVGEKAIVFSQWTRMLDLLEVRLKASHVT | | | | SEQ ID NO:40 | (Arabidopsis lyrata) |
| 1166 | GKGISEQTDTKLT-EKAIVFSQWTRMLDLLEVHLKASHVT | | | | SEQ ID NO:42 | (Zea mays) |
| 1072 | NSTPSEYAGTKIT-EKAIVFSQWTRMLDLVEVHLKSSHLS | | | | SEQ ID NO:44 | (Zea mays) |
| 1046 | GKGISEQIDTKLT-EKAIVFSQWTRMLDLLEVHLKASHVT | | | | SEQ ID NO:46 | (Oryza sativa) |
| 1088 | GRGTSEQIDTKLT-EKAIVFSQWTRMLDLLEVHLKASHVT | | | | SEQ ID NO:49 | (Sorghum bicolor) |

FIG. 16AJ

```
         YRRLDGTMSVAARDKAVXDFNTVPEVTVMIMSLKAASLGL  Majority
                  |         |         |         |
                 1410      1420      1430      1440

491   : ------------------------------------- :  SEQ ID NO:19 (Zea mays)
  905   : YRRLDGTMSLNIREKNVKDFNTDPEVRVMIMSLKAGNLGL :  SEQ ID NO:21 (Zea mays)
  820   : FRRLDGAMSLDIREKEVNGFKTDPEVRVNLMSLKAASLGL :  SEQ ID NO:23 (Zea mays)
 1150   : YRRLDGTMSVAARDKAVQDFNTLPEVTVMIMSLKAASLGL :  SEQ ID NO:25 (Arabidopsis thaliana)
 1022   : F------------------------------------- :  SEQ ID NO:27 (Arabidopsis thaliana)
  992   : YRRLDGTMSVAARDKAVQDFNTLPEVTVMIMSLKAGNLGL :  SEQ ID NO:29 (Arabidopsis thaliana)
 1100   : YRRLDGTMSVAARDRAVKDFNTNPEVSVMIMSLKAASLGL :  SEQ ID NO:30 (Oryza sativa)
 1107   : YRRLDGTMSLNSRDKAVKDFNTDPEVRVMIMSLKAGNLGL :  SEQ ID NO:31 (Oryza sativa)
  923   : YRRLDGTMSVAARDKAVREFNTDPEVRVMLMSLKAASLGL :  SEQ ID NO:32 (Oryza sativa)
  961   : FRRLDGAMSLNLREAAVRFFNTDPEVSVMIMSLKAGNLGL :  SEQ ID NO:36 (Eragrostis nindensis)
 1138   : YRRLDGTMSVAARDKAVDKFNTVPEVSVMIMSLKAASLGL :  SEQ ID NO:39 (Paspalum notatum)
 1151   : YRRLDGTMSVAARDRAVQDFNTLPEVTVMIMSLKAASLGL :  SEQ ID NO:40 (Arabidopsis lyrata)
 1099   : YRRLDGKMTVPARDAAVRDFNTLPEVSVMIMSLKAASLGL :  SEQ ID NO:42 (Arabidopsis lyrata)
 1225   : YRRLDGTMSVAARDKAVNDFNMVPEVTVMIMSLKAASLGL :  SEQ ID NO:44 (Zea mays)
 1111   : YRRLDGTMSVAARDRAVKDFNTNPEVSVMIMSLKAASLGL :  SEQ ID NO:46 (Zea mays)
 1085   : YRRLDGTMSVAARDRAVKDFNTNPEVSVMIMSLKAASLGL :  SEQ ID NO:48 (Oryza sativa)
 1127   : YRRLDGTMSVAARDKAVKDFNTVPEVTVMIMSLKAASLGL :  SEQ ID NO:49 (Sorghum bicolor)
```

FIG. 16AK

| | 1450 | 1460 | 1470 | 1480 | | |
|---|---|---|---|---|---|---|
| Majority | NMVAACHVLMLDLWNPTTEDQAVDRARRIGQTRPVTVSR | | | | | |
| 491 | - - - - - - - - - - - - - - - - - - - - - - - - - - - - - - - - - - - - - - - | | | | | |
| 945 | NMVSACHVILLDLWWNPYAEDQAVDRARRIGQTRPVTVSR | | | | SEQ ID NO:19 | (Zea mays) |
| 860 | NMVAACHVIMLDPWWNPYAEDQAVDRARRIGQTRPVTVSR | | | | SEQ ID NO:21 | (Zea mays) |
| 1190 | NMVAACHVLMLDLWWNPTTEDQAVDRARRIGQTRPVTVSR | | | | SEQ ID NO:23 | (Zea mays) |
| 1022 | NMVAACHVLMLDLWWNPTTEDQAIDRAIDRARRIGQTRPVTVVR | | | | SEQ ID NO:25 | (Arabidopsis thaliana) |
| 1032 | NMVAACHVLMLDLWWNPTTEDQAIDRARRIGQTRPVTVSR | | | | SEQ ID NO:27 | (Arabidopsis thaliana) |
| 1140 | NMVAACHVLLDLWWNPTTEDQAVDRARRIGQTRPVTVVR | | | | SEQ ID NO:29 | (Oryza sativa) |
| 1147 | NMVAACHVIMLDPWWNPTTEDQAVDRARRIGQTRPVTVSR | | | | SEQ ID NO:30 | (Oryza sativa) |
| 963 | NMVAACHVIMIDPWWNPYAEDQAVDRARRIGQTRPVTVSR | | | | SEQ ID NO:31 | (Oryza sativa) |
| 1001 | NMVAACHVLMLDLWWNPTTEDQAVDRARRIGQTRPVTVSR | | | | SEQ ID NO:32 | (Eragrostis nindensis) |
| 1178 | NMVAACHVLMLDLWWNPTTEDQAVDRARRIGQTRPVLVSR | | | | SEQ ID NO:36 | (Paspalum notatum) |
| 1191 | NMVAACHVLMLDLWWNPTTEDQAIDRARRIGQTRPVTVVR | | | | SEQ ID NO:38 | (Arabidopsis lyrata) |
| 1139 | NMVAACHVLMLDLWWNPTTEDQAVDRARRIGQKRPVKVVR | | | | SEQ ID NO:40 | (Arabidopsis lyrata) |
| 1265 | NMVAACHVLMLDLWWNPTTEDQAVDRARRIGQKRPVTVSR | | | | SEQ ID NO:42 | (Zea mays) |
| 1151 | NMVAACHVLMLDLWWNPTTEDQAVDRARRIGQKRPVTVSR | | | | SEQ ID NO:44 | (Zea mays) |
| 1135 | NMVAACHVLLDLWWNPTTEDQAVDRARRIGQTRPVTVSR | | | | SEQ ID NO:46 | (Oryza sativa) |
| 1167 | NMVAACHVLMLDLWWNPTTEDQAVDRARRIGQTRPVTVSR | | | | SEQ ID NO:49 | (Sorghum bicolor) |

FIG. 16AL

| | 1490 | 1500 | 1510 | 1520 | |
|---|---|---|---|---|---|
| | LTIKDTVEDRILALQEKKREMVASAFGEDKSGSRQTRLTV | | | | Majority |
| 491 | ------------------------------------- | | | | |
| 985 | LTVKDTVEDRILALQEEKKRTMVNSAFGDDKAGGRHATRLTV | | | | SEQ ID NO:19 (Zea mays) |
| 900 | FTVKDTVEDRILALQEKKRTMVESAFGEDGSRGTATRKLTV | | | | SEQ ID NO:21 (Zea mays) |
| 1230 | FTVKDTVEDRILALQQKKREMVESAFGEDEKGSROSHLTV | | | | SEQ ID NO:23 (Zea mays) |
| 1022 | FTVKDTVEDRILALQEKKREMMVSAFGEDEKSGRSRQSHLTV | | | | SEQ ID NO:25 (Arabidopsis thaliana) |
| 1072 | FTVKDTVEDRILALQEKKREMVASAFGEDKSGAHQTRLTV | | | | SEQ ID NO:27 (Arabidopsis thaliana) |
| 1180 | LTIKDTVEDRILALQEKKRAMVSSAFGEDDKSGEKATRLTV | | | | SEQ ID NO:29 (Oryza sativa) |
| 1187 | LTIKDTVEDRILALQEKKRKMVSAFGEDKPGGSATRLTI | | | | SEQ ID NO:30 (Oryza sativa) |
| 1003 | LTIKDTVEDRILALQEKKREMVASAFGEDEKSGSRQTRLTV | | | | SEQ ID NO:31 (Oryza sativa) |
| 1041 | LTIKDTVEDRILALQEKKREMVASAFGEHEKGSRESHLSV | | | | SEQ ID NO:32 (Oryza sativa) |
| 1218 | LTIKDTVEDRILALQEKKREMMVASAFGEDEKSGSRQTRLTV | | | | SEQ ID NO:36 (Eragrostis nindensis) |
| 1231 | FTVKDTVEDRILALQQKKREMMVASAFGEHEKGRESHLSV | | | | SEQ ID NO:38 (Paspalum notatum) |
| 1179 | FTVKDTVEDRILALQEKKREMVASAFGEDKSGAHQTRLTV | | | | SEQ ID NO:40 (Arabidopsis lyrata) |
| 1305 | LTIKDTVEDRILALQEKKREMVASAFGEDKSGSRQTRLTV | | | | SEQ ID NO:42 (Arabidopsis lyrata) |
| 1191 | LTIKDTVEDRILALQEKKREMVASAFGEDKSGSRQTRLTV | | | | SEQ ID NO:44 (Zea mays) |
| 1165 | LTIKDTVEDRILALQEKKREMVASAFGEDKSGAHQTRLTV | | | | SEQ ID NO:46 (Zea mays) |
| 1207 | LTIKDTVEDRILALQEKKREMVASAFGEDKSGSRQTRLTV | | | | SEQ ID NO:48 (Oryza sativa) |
| | | | | | SEQ ID NO:49 (Sorghum bicolor) |

FIG. 16AM

|  | Majority |  |
|---|---|---|
| 491 | EDLNYLFMV- |  |
|  | 1530 |  |
| 1025 | ----VI |  | SEQ ID NO:19 (Zea mays)
| 940 | EDLRYLFRI |  | SEQ ID NO:21 (Zea mays)
| 1270 | EDLRYLFMV |  | SEQ ID NO:23 (Zea mays)
| 1022 | EDLSYLFMADS |  | SEQ ID NO:25 (Arabidopsis thaliana)
| 1112 | EDLSYLFMADS |  | SEQ ID NO:27 (Arabidopsis thaliana)
| 1220 | EDLNYLFMV |  | SEQ ID NO:29 (Arabidopsis thaliana)
| 1227 | EDLKYLFRI |  | SEQ ID NO:30 (Oryza sativa)
| 1043 | DDLQYLFGI |  | SEQ ID NO:31 (Oryza sativa)
| 1081 | DDLKYLFMV |  | SEQ ID NO:32 (Oryza sativa)
| 1258 | EDLNYLFMV |  | SEQ ID NO:36 (Eragrostis nindensis)
| 1271 | EDLSYLFMADS |  | SEQ ID NO:38 (Paspalum notatum)
| 1219 | EDLNYLFMA |  | SEQ ID NO:40 (Arabidopsis lyrata)
| 1345 | EDLNYLFMV |  | SEQ ID NO:42 (Arabidopsis lyrata)
| 1231 | EDLNYLFMV |  | SEQ ID NO:44 (Zea mays)
| 1205 | EDLNYLFMV |  | SEQ ID NO:46 (Zea mays)
| 1347 | EDLNYLFMV |  | SEQ ID NO:48 (Oryza sativa)
|  |  |  | SEQ ID NO:49 (Sorghum bicolor)

SEQUENCE LISTING

<160> NUMBER OF SEQ ID NOS: 49

<210> SEQ ID NO 1
<211> LENGTH: 18491
<212> TYPE: DNA
<213> ORGANISM: Artificial Sequence
<220> FEATURE:
<223> OTHER INFORMATION: pHSbarEND2s activation tagging vector

<400> SEQUENCE: 1

```
catgaatcaa acaaacatac acagcgactt attcacacga gctcaaatta caacggtata      60
tatcctgccg tcgacaacca tggtctagac aggatccccg ggtaccgagc tcgaatttgc     120
aggtcgactg cgtcatccct tacgtcagtg gagatatcac atcaatccac ttgctttgaa     180
gacgtggttg gaacgtcttc tttttccacg atgctcctcg tgggtggggg tccatctttg     240
ggaccactgt cggcagaggc atcttgaacg atagcctttc ctttatcgca atgatggcat     300
ttgtaggtgc caccttcctt ttctactgtc cttttgatga agtgacagat agctgggcaa     360
tggaatccga ggaggtttcc cgatattacc ctttgttgaa agtctcaat tgccctttgg      420
tcttctgaga ctgttgcgtc atcccttacg tcagtggaga tatcacatca atccacttgc     480
tttgaagacg tggttggaac gtcttctttt tccacgatgc tcctcgtggg tggggtcca      540
tctttgggac cactgtcggc agaggcatct tgaacgatag cctttccttt atcgcaatga     600
tggcatttgt aggtgccacc ttcctttcct actgtccttt tgatgaagtg acagatagct     660
gggcaatgga atccgaggag gtttcccgat attaccctt gttgaaaagt ctcagttaac      720
ccgcgatcct gcgtcatccc ttacgtcagt ggagatatca catcaatcca cttgctttga     780
agacgtggtt ggaacgtctt cttttccac gatgctcctc gtgggtgggg gtccatcttt      840
gggaccactg tcggcagagg catcttgaac gatagccttt cctttatcgc aatgatggca     900
tttgtaggtg ccaccttcct tttctactgt ccttttgatg aagtgacaga tagctgggca     960
atggaatccg aggaggtttc cgatattac cctttgttga aaagtctcaa ttgccctttg     1020
gtcttctgag actgttgcgt catcccttac gtcagtggag atatcacatc aatccacttg    1080
ctttgaagac gtggttggaa cgtcttcttt tccacgatg ctcctcgtgg gtggggtcc      1140
atctttggga ccactgtcgg cagaggcatc ttgaacgata gcctttcctt tatcgcaatg    1200
atggcatttg taggtgccac cttccttttc tactgtcctt tgatgaagt gacagatagc     1260
tgggcaatgg aatccgagga ggtttcccga tattaccctt tgttgaaaag tctcagttaa    1320
cccgcaattc actggccgtc gttttacaac gtcgtgactg gaaaaccct ggcgttaccc     1380
aacttaatcg ccttgcagca catccccctt tcgccagctg gcgtaatagc gaagaggccc    1440
gcaccgatcg cccttcccaa cagttgcgca gcctgaatgg cgaatggatc gatccgtcga    1500
tcgaccaaag cggccatcgt gcctcccac tcctgcagtt cggggcatg atgcgcgga      1560
tagccgctgc tggtttcctg gatgccgacg gatttgcact gccggtagaa ctccgcgagg    1620
tcgtccagcc tcaggcagca gctgaaccaa ctcgcgaggg gatcgagccc ctgctgagcc    1680
tcgacatgtt gtcgcaaaat tcgccctgga cccgcccaac gatttgtcgt cactgtcaag    1740
gtttgacctg cacttcattt ggggcccaca tacaccaaaa aaatgctgca taattctcgg    1800
ggcagcaagt cggttacccg gccgccgtgc tggacccggt tgaatggtgc ccgtaacttt    1860
cggtagagcg gacggccaat actcaacttc aaggaatctc acccatgcgc gccggcgggg    1920
aaccggagtt cccttcagtg aacgttatta gttcgccgct cggtgtgtcg tagatactag    1980
cccctggggc cttttgaaat ttgaataaga tttatgtaat cagtcttta ggtttgaccg     2040
```

```
gttctgccgc tttttttaaa attggatttg taataataaa acgcaattgt ttgttattgt    2100
ggcgctctat catagatgtc gctataaacc tattcagcac aatatattgt tttcatttta    2160
atattgtaca tataagtagt agggtacaat cagtaaattg aacggagaat attattcata    2220
aaaatacgat agtaacgggt gatatattca ttagaatgaa ccgaaaccgg cggtaaggat    2280
ctgagctaca catgctcagg ttttttacaa cgtgcacaac agaattgaaa gcaaatatca    2340
tgcgatcata ggcgtctcgc atatctcatt aaagcagggg gtgggcgaag aactccagca    2400
tgagatcccc gcgctggagg atcatccagc cggcgtcccg gaaaacgatt ccgaagccca    2460
acctttcata gaaggcggcg gtggaatcga aatctcgtga tggcaggttg ggcgtcgctt    2520
ggtcggtcat ttcgaacccc agagtcccgc tcagaagaac tcgtcaagaa ggcgatagaa    2580
ggcgatgcgc tgcgaatcgg gagcggcgat accgtaaagc acgaggaagc ggtcagccca    2640
ttcgccgcca agctcttcag caatatcacg ggtagccaac gctatgtcct gatagcggtc    2700
cgccacaccc agccggccac agtcgatgaa tccagaaaag cggccatttt ccaccatgat    2760
attcggcaag caggcatcgc catgggtcac gacgagatcc tcgccgtcgg catgccccc    2820 caattcactg gccgtcgttt tacaacgtcg tgactgggaa aaccctggcg ttacccaact    2880
taatcgcctt gcagcacatc cccctttcgc cagctggcgt aatagcgaag aggcccgcac    2940
cgatcgccct tcccaacagt tgcgcagcct gaatggcgaa tggcgcctga tgcggtattt    3000
tctccttacg catctgtgcg gtatttcaca ccgcatatgg tgcactctca gtacaatctg    3060
ctctgatgcc gcatagttaa gccagccccg acacccgcca cacccgctg acgcgccctg    3120 acgggcttgt ctgctcccgg catccgctta cagacaagct gtgaccgtct ccgggagctg    3180
catgtgtcag aggttttcac cgtcatcacc gaaacgcgcg agacgaaagg gcctcgtgat    3240
acgcctattt ttataggtta atgtcatgat aataatggtt tcttagacgt caggtggcac    3300
ttttcgggga atgtgcgcg gaaccccctat ttgtttattt ttctaaatac attcaaatat    3360
gtatccgctc atgagacaat aaccctgata aatgcttcaa taatattgaa aaaggaagag    3420
tatgagtatt caacatttcc gtgtcgccct tattcccttt tttgcggcat tttgccttcc    3480
tgtttttgct cacccagaaa cgctggtgaa agtaaaagat gctgaagatc agttgggtgc    3540
acgagtgggt tacatcgaac tggatctcaa cagcggtaag atccttgaga gttttcgccc    3600
cgaagaacgt tttccaatga tgagcacttt taaagttctg ctatgtggcg cggtattatc    3660
ccgtattgac gccgggcaag agcaactcgg tcgccgcata cactattctc agaatgactt    3720
ggttgagtac tcaccagtca cagaaaagca tcttacggat ggcatgacag taagagaatt    3780
atgcagtgct gccataacca tgagtgataa cactgcggcc aacttacttc tgacaacgat    3840
cggaggaccg aaggagctaa ccgcttttt gcacaacatg gggatcatg taactcgcct    3900 tgatcgttgg gaaccggagc tgaatgaagc cataccaaac gacgagcgtg acaccacgat    3960
gcctgtagca atggcaacaa cgttgcgcaa actattaact ggcgaactac ttactctagc    4020
ttcccggcaa caattaatag actggatgga ggcggataaa gttgcaggac cacttctgcg    4080
ctcggccctt ccggctggct ggtttattgc tgataaatct ggagccggtg agcgtgggtc    4140
tcgcggtatc attgcagcac tggggccaga tggtaagccc tcccgtatcg tagttatcta    4200
cacgacgggg agtcaggcaa ctatggatga acgaaataga cagatcgctg agataggtgc    4260
ctcactgatt aagcattggt aactgtcaga ccaagtttac tcatatatac tttagattga    4320
tttaaaactt cattttttaat ttaaaaggat ctaggtgaag atcctttttg ataatctcat    4380
```

```
gaccaaaatc ccttaacgtg agttttcgtt ccactgagcg tcagaccccg tagaaaagat    4440
caaaggatct tcttgagatc ctttttttct gcgcgtaatc tgctgcttgc aaacaaaaaa    4500
accaccgcta ccagcggtgg tttgtttgcc ggatcaagag ctaccaactc tttttccgaa    4560
ggtaactggc ttcagcagag cgcagatacc aaatactgtc cttctagtgt agccgtagtt    4620
aggccaccac ttcaagaact ctgtagcacc gcctacatac ctcgctctgc taatcctgtt    4680
accagtggct gctgccagtg gcgataagtc gtgtcttacc gggttggact caagacgata    4740
gttaccggat aaggcgcagc ggtcgggctg aacggggggt tcgtgcacac agcccagctt    4800
ggagcgaacg acctacaccg aactgagata cctacagcgt gagcattgag aaagcgccac    4860
gcttcccgaa gggagaaagg cggacaggta tccggtaagc ggcagggtcg aacaggaga    4920
gcgcacgagg gagcttccag ggggaaacgc ctggtatctt tatagtcctg tcgggtttcg    4980
ccacctctga cttgagcgtc gatttttgtg atgctcgtca gggggggcgga gcctatggaa    5040
aaacgccagc aacgcggcct ttttacggtt cctggccttt tgctggcctt ttgctcacat    5100
gttctttcct gcgttatccc ctgattctgt ggataaccgt attaccgcct ttgagtgagc    5160
tgataccgct cgccgcagcc gaacgaccga gcgcagcgag tcagtgagcg aggaagcgga    5220
agagcgccca atacgcaaac cgcctctccc cgcgcgttgg ccgattcatt aatgcagctg    5280
gcacgacagg tttcccgact ggaaagcggg cagtgagcgc aacgcaatta atgtgagtta    5340
gctcactcat taggcacccc aggctttaca ctttatgctt ccggctcgta tgttgtgtgg    5400
aattgtgagc ggataacaat ttcacacagg aaacagctat gaccatgatt acgccaagct    5460
ttctaggggg ggggtaccga tctgagatcg gtaacgaaaa cgaacgggta gggatgaaaa    5520
cggtcggtaa cggtcggtaa aatacctcta ccgttttcat tttcatattt aacttgcggg    5580
acggaaacga aaacgggata taccggtaac gaaaacgaac gggataaata cggtaatcga    5640
aaaccgatac gatccggtcg ggttaaagtc gaaatcggac gggaaccggt attttttgttc    5700
ggtaaaatca cacatgaaaa catatattca aaacttaaaa acaaatataa aaaattgtaa    5760
acacaagtct taatgatcac tagtggcgcg cctaggagat ctcgagtagg gataacaggg    5820
taatacatag ataaaatcca tataaatctg gagcacacat agtttaatgt agcacataag    5880
tgataagtct tgggctcttg gctaacataa gaagccatat aagtctacta gcacacatga    5940
cacaatataa agtttaaaac acatattcat aatcacttgc tcacatctgg atcacttagc    6000
atgctacagc tagtgcaata ttagacactt tccaatattt ctcaaacttt tcactcattg    6060
caacggccat tctcctaatg acaaattttt catgaacaca ccattggtca atcaaatcct    6120
ttatctcaca gaaacctttg taaaataaat ttgcagtgga atattgagta ccagatagga    6180
gttcagtgag atcaaaaaac ttcttcaaac acttaaaaag agttaatgcc atcttccact    6240
cctcggcttt aggacaaatt gcatcgtacc tacaataatt gacatttgat taattgagaa    6300
tttataatga tgacatgtac aacaattgag acaaacatac ctgcgaggat cacttgtttt    6360
aagccgtgtt agtgcaggct tataaatataa ggcatccctc aacatcaaat aggttgaatt    6420
ccatctagtt gagacatcat atgagatccc tttagattta ccaagtcac attcactagc    6480
acacttcatt agttcttccc actgcaaagg agaagatttt acagcaagaa caatcgcttt    6540
gattttctca attgttcctg caattacagc caagccatcc tttgcaacca gttcagtat    6600
gtgacaagca cacctcacat gaaagaaagc accatcacaa actagatttg aatcagtgtc    6660
ctgcaaatcc tcaattatat cgtgcacagc tacttcattt gcactagcat tatccaaaga    6720
caaggcaaac aattttttct caatgttcca cttaaccatg attgcagtga aggtttgtga    6780
```

```
taacctttgg ccagtgtggc gcccttcaac atgaaaaaag ccaacaattc ttttttggag    6840
acaccaatca tcatcaatcc aatggatggt gacacacatg tatgacttat tttgacaaga    6900
tgtccacata tccatagttg tactgaagcg agactgaaca tcttttagtt ttccatacaa    6960
cttttctttt tcttccaaat acaaatccat gatatatttt ctagcagtga cacgggactt    7020
tattggaaag tgagggcgca gagacttaac aaactcaaca aagtactcat gttctacaat    7080
attgaaagga tattcatgca tgattattgc caaatgaagc ttctttaggc taaccacttc    7140
atcgtactta taaggctcaa tgagatttat gtctttgcca tgatccttt cacttttag     7200 acacaactga cctttaacta aactatgtga tgttctcaag tgatttcgaa atccgcttgt    7260
tccatgatga ccctcagccc tatacttagc cttgcaatta ggaaagttgc aatgtcccca    7320
tacctgaacg tatttctttc catcgacctc cacttcaatt tccttcttgg tgaaatgctg    7380
ccatacatcc gatgtgcact tctttgccct cttctgtggt gcttcttctt cgggttcagg    7440
ttgtggctgt ggttgtggtt ctggttgtgg ttgtggttgt ggttgtggtt catgaacaat    7500
agccatatca tcttgactcg gatctgtagc tgtaccattt gcattactac tgcttacact    7560
ctgaataaaa tgcctctcgg cctcagctgt tgatgatgat ggtgatgtgc ggccacatcc    7620
atgcccacgc gcacgtgcac gtacattctg aatccgacta aagaggctt cagcttttct     7680 tttcaaccct gttataaaca gatttttcgt attattctac agtcaatatg atgcttccca    7740
atctacaacc aattagtaat gctaatgcta ttgctactgt ttttctaata tataccttga    7800
gcatatgcag agaatacgga atttgttttg cgagtagaag gcgctcttgt ggtagacatc    7860
aacttggcca atcttatggc tgagcctgag ggaggattat ttccaaccgg aggcgtcatc    7920
tgaggaatgg agtcgtagcc ggctagccga agtggagagc agagccctgg acagcaggtg    7980
ttcagcaatc agcttggtgc tgtactgctg tgacttgtga gcacctggac ggctggacag    8040
caatcagcag gtgttgcaga gcccctggac agcacacaaa tgacacaaca gcttggtgca    8100
atggtgctga cgtgctgtac tgctaagtgc tgtgagcctg tgagcagccg tggagacagg    8160
gagaccgcgg atggccggat gggcgagcgc cgagcagtgg aggtctggag gaccgctgac    8220
cgcagatggc ggatggcgga tgggcggacc gcggatgggc gagcagtgga gtggaggtct    8280
gggcggatgg gcggaccgcg gcgcggatgg gcgagtcgcg agcagtggag tggagggcgg    8340
accgtggatg gcggcgtctg cgtccggcgt gccgcgtcac ggccgtcacc gcgtgtggtg    8400
cctggtgcag cccagcggcc ggccggctgg gagacaggga gagtcggaga gagcaggcga    8460
gagcgagacg cgtcgccggc gtcggcgtgc ggctggcggc gtccggactc cggcgtgggc    8520
gcgtggcggc gtgtgaatgt gtgatgctgt tactcgtgtg gtgcctggcc gcctgggaga    8580
gaggcagagc agcgttcgct aggtatttct tacatgggct gggcctcagt ggttatggat    8640
gggagttgga gctggccata ttgcagtcat cccgaattag aaaatacggt aacgaaacgg    8700
gatcatcccg attaaaaacg ggatcccggt gaaacggtcg ggaaactagc tctaccgttt    8760
ccgtttccgt ttaccgtttt gtatatcccg tttccgttcc gttttcgttt tttacctcgg    8820
gttcgaaatc gatcgggata aaactaacaa atcggttat acgataacgg tcggtacggg     8880
attttcccat cctactttca tccctgagat tattgtcgtt tctttcgcag atcggtaccc    8940 ccccctaga gtcgacatcg atctagtaac atagatgaca ccgcgcgcga taatttatcc     9000
tagtttgcgc gctatatttt gttttctatc gcgtattaaa tgtataattg cgggactcta    9060
atcataaaaa cccatctcat aaataacgtc atgcattaca tgttaattat tacatgctta    9120
```

```
acgtaattca acagaaatta tatgataatc atcgcaagac cggcaacagg attcaatctt    9180
aagaaacttt attgccaaat gtttgaacga tctgcttcga cgcactcctt ctttaggtac    9240
ggactagatc tcggtgacgg gcaggaccgg acggggcggt accggcaggc tgaagtccag    9300
ctgccagaaa cccacgtcat gccagttccc gtgcttgaag ccggccgccc gcagcatgcc    9360 gcgggggggca tatccgagcg cctcgtgcat gcgcacgctc gggtcgttgg gcagcccgat    9420
gacagcgacc acgctcttga agccctgtgc ctccagggac ttcagcaggt gggtgtagag    9480
cgtggagccc agtcccgtcc gctggtggcg gggggagacg tacacggtcg actcggccgt    9540
ccagtcgtag gcgttgcgtg ccttccaggg gcccgcgtag gcgatgccgg cgacctcgcc    9600
gtccacctcg gcgacgagcc agggatagcg ctcccgcaga cggacgaggt cgtccgtcca    9660
ctcctgcggt tcctgcggct cggtacggaa gttgaccgtg cttgtctcga tgtagtggtt    9720
gacgatggtg cagaccgccg gcatgtccgc ctcggtggca cggcggatgt cggccgggcg    9780
tcgttctggg ctcatggatc tggattgaga gtgaatatga gactctaatt ggataccgag    9840
gggaatttat ggaacgtcag tggagcattt ttgacaagaa atatttgcta gctgatagtg    9900
accttaggcg acttttgaac gcgcaataat ggtttctgac gtatgtgctt agctcattaa    9960
actccagaaa cccgcggctg agtggctcct tcaatcgttg cggttctgtc agttccaaac    10020
gtaaaacggc ttgtcccgcg tcatcggcgg gggtcataac gtgactccct taattctccg    10080
ctcatgatcc ccgggtaccg agctcgaatt gcggctgagt ggctccttca atcgttgcgg    10140
ttctgtcagt ccaaacgta aaacggcttg tcccgcgtca tcggcggggg tcataacgtg    10200
actcccttaa ttctccgctc atgatcttga tcccctgcgc catcagatcc ttggcggcaa    10260
gaaagccatc cagtttactt tgcagggctt cccaacctta ccagagggcg ccccagctgg    10320
caattccggt tcgcttgctg tatcgatatg gtggatttat cacaaatggg acccgccgcc    10380
gacagaggtg tgatgttagg ccaggacttt gaaaatttgc gcaactatcg tatagtggcc    10440
gacaaattga cgccgagttg acagactgcc tagcatttga gtgaattatg tgaggtaatg    10500
ggctacactg aattggtagc tcaaactgtc agtatttatg tatatgagtg tatattttcg    10560
cataatctca gaccaatctg aagatgaaat gggtatctgg gaatggcgaa atcaaggcat    10620
cgatcgtgaa gtttctcatc taagcccccca tttggacgtg aatgtagaca cgtcgaaata    10680
aagatttccg aattagaata atttgtttat tgctttcgcc tataaatacg acggatcgta    10740
atttgtcgtt ttatcaaaat gtactttcat tttataataa cgctgcggac atctacattt    10800
ttgaattgaa aaaaaattgg taattactct ttcttttttct ccatattgac catcatactc    10860
attgctgatc catgtagatt tcccggacat gaagccattt acaattgaat atatcctgcc    10920
gccgctgccg ctttgcaccc ggtggagctt gcatgttggt ttctacgcag aactgagccg    10980
gttaggcaga taatttccat tgagaactga gccatgtgca ccttccccccc aacacggtga    11040 gcgacgggc aacggagtga tccacatggg acttttaaac atcatccgtc ggatggcgtt    11100
gcgagagaag cagtcgatcc gtgagatcag ccgacgcacc gggcaggcgc gcaacacgat    11160
cgcaaagtat ttgaacgcag gtacaatcga gccgacgttc accgtcaccc tggatgctgt    11220
aggcataggc ttggttatgc cggtactgcc gggcctcttg cggatatcg tccattccga    11280 cagcatcgcc agtcactatg gcgtgctgct agcgctatat gcgttgatgc aatttctatg    11340
cgcacccgtt ctcggagcac tgtccgaccg ctttggccgc cgcccagtcc tgctcgcttc    11400
gctacttgga gccactatcg actacgcgat catggcgacc acacccgtcc tgtggtccaa    11460
cccctccgct gctatagtgc agtcggcttc tgacgttcag tgcagccgtc ttctgaaaac    11520
```

```
gacatgtcgc acaagtccta agttacgcga caggctgccg ccctgccctt ttcctggcgt   11580
tttcttgtcg cgtgttttag tcgcataaag tagaatactt gcgactagaa ccggagacat   11640
tacgccatga acaagagcgc cgccgctggc ctgctgggct atgcccgcgt cagcaccgac   11700
gaccaggact tgaccaacca acgggccgaa ctgcacgcgg ccggctgcac caagctgttt   11760
tccgagaaga tcaccggcac caggcgcgac cgcccggagc tggccaggat gcttgaccac   11820
ctacgccctg cgacgttgt gacagtgacc aggctagacc gctggcccg cagcaccgc     11880 gacctactgg acattgccga gcgcatccag gaggccggcg cgggcctgcg tagcctggca   11940
gagccgtggg ccgacaccac cacgccgcc ggccgcatgg tgttgaccgt gttcgccggc    12000
attgccgagt tcgagcgttc cctaatcatc gaccgcaccc ggagcgggcg cgaggccgcc   12060
aaggcccgag gcgtgaagtt tggccccgc cctaccctca ccccggcaca gatcgcgcac    12120
gcccgcgagc tgatcgacca ggaaggccgc accgtgaaag aggcggctgc actgcttggc   12180
gtgcatcgct cgaccctgta ccgcgcactt gagcgcagcg aggaagtgac gcccaccgag   12240
gccaggcggc gcggtgcctt ccgtgaggac gcattgaccg aggccgacgc cctggcggcc   12300
gccgagaatg aacgccaaga ggaacaagca tgaaaccgca ccaggacggc caggacgaac   12360 cgttttcat taccgaagag atcgaggcgg agatgatcgc ggccgggtac gtgttcgagc    12420
cgcccgcgca cgtctcaacc gtgcggctgc atgaaatcct ggccggtttg tctgatgcca   12480
agctggcggc ctggccggcc agcttggccg ctgaagaaac cgagcgccgc cgtctaaaaa   12540
ggtgatgtgt atttgagtaa acagcttgc gtcatgcggt cgctgcgtat atgatgcgat    12600
gagtaaataa acaaatacgc aagggaacgc atgaagttat cgctgtactt aaccagaaag   12660
gcgggtcagg caagacgacc atcgcaaccc atctagcccg cgccctgcaa ctcgccgggg   12720
ccgatgttct gttagtcgat tccgatcccc agggcagtgc ccgcgattgg gcggccgtgc   12780
gggaagatca accgctaacc gttgtcggca tcgaccgccc gacgattgac cgcgacgtga   12840
aggccatcgg ccggcgcgac ttcgtagtga tcgacggagc gccccaggcg gcggacttgg   12900
ctgtgtccgc gatcaaggca gccgacttcg tgctgattcc ggtgcagcca agcccttacg   12960
acatatgggc caccgccgac ctggtggagc tggttaagca gcgcattgag gtcacggatg   13020
gaaggctaca agcggccttt gtcgtgtcgc gggcgatcaa aggcacgcgc atcggcggtg   13080
aggttgccga ggcgctggcc gggtacgagc tgcccattct tgagtcccgt atcacgcagc   13140
gcgtgagcta cccaggcact gccgccgccg gcacaaccgt tcttgaatca gaacccgagg   13200
gcgacgctgc ccgcgaggtc caggcgctgg ccgctgaaat taaatcaaaa ctcatttgag   13260
ttaatgaggt aaagagaaaa tgagcaaaag cacaaacacg ctaagtgccg gccgtccgag   13320
cgcacgcagc agcaaggctg caacgttggc cagcctggca gacacgccag ccatgaagcg   13380
ggtcaacttt cagttgccgg cggaggatca caccaagctg aagatgtacg cggtacgcca   13440
aggcaagacc attaccgagc tgctatctga atacatcgcg cagctaccag agtaaatgag   13500
caaatgaata aatgagtaga tgaattttag cggctaaagg aggcggcatg gaaaatcaag   13560
aacaaccagg caccgacgcc gtggaatgcc ccatgtgtgg aggaacgggc ggttggccag   13620
gcgtaagcgg ctgggttgtc tgccggccct gcaatggcac tggaaccccc aagcccgagg   13680
aatcggcgtg agcggtcgca aaccatccgg cccggtacaa atcggcgcgg cgctgggtga   13740
tgacctggtg gagaagttga aggccgcgca ggccgcccag cggcaacgca tcgaggcaga   13800
agcacgcccc ggtgaatcgt ggcaagcggc cgctgatcga atccgcaaag aatcccggca   13860
```

```
accgccggca gccggtgcgc cgtcgattag gaagccgccc aagggcgacg agcaaccaga   13920
ttttttcgtt ccgatgctct atgacgtggg cacccgcgat agtcgcagca tcatggacgt   13980
ggccgttttc cgtctgtcga agcgtgaccg acgagctggc gaggtgatcc gctacgagct   14040
tccagacggg cacgtagagg tttccgcagg gccggccggc atggccagtg tgtgggatta   14100
cgacctggta ctgatggcgg tttcccatct aaccgaatcc atgaaccgat accgggaagg   14160
gaagggagac aagcccggcc gcgtgttccg tccacacgtt gcggacgtac tcaagttctg   14220
ccggcgagcc gatggcggaa agcagaaaga cgacctggta gaaacctgca ttcggttaaa   14280
caccacgcac gttgccatgc agcgtacgaa gaaggccaag aacggccgcc tggtgacggt   14340
atccgagggt gaagccttga ttagccgcta caagatcgta aagagcgaaa ccgggcggcc   14400
ggagtacatc gagatcgagc tagctgattg gatgtaccgc gagatcacag aaggcaagaa   14460
cccggacgtg ctgacggttc accccgatta cttttttgatc gatcccggca tcggccgttt   14520
tctctaccgc ctggcacgcc gcgccgcagg caaggcagaa gccagatggt tgttcaagac   14580
gatctacgaa cgcagtggca gcgccggaga gttcaagaag ttctgttttca ccgtgcgcaa   14640 gctgatcggg tcaaatgacc tgccggagta cgatttgaag gaggaggcgg ggcaggctgg   14700
cccgatccta gtcatgcgct accgcaacct gatcgagggc gaagcatccg ccggttccta   14760
atgtacggag cagatgctag ggcaaattgc cctagcaggg gaaaaaggtc gaaaaggtct   14820 cttttcctgtg gatagcacgt acattgggaa cccaaagccg tacattggga accggaaccc   14880
gtacattggg aacccaaagc cgtacattgg gaaccggtca cacatgtaag tgactgatat   14940
aaaagagaaa aaaggcgatt tttccgccta aaactcttta aaacttatta aaactcttaa   15000
aacccgcctg gcctgtgcat aactgtctgg ccagcgcaca gccgaagagc tgcaaaaagc   15060
gcctaccctt cggtcgctgc gctccctacg ccccgccgct tcgcgtcggc ctatcgcggg   15120
cgctggccgc tcaaaaatgg ctggcctacg gccaggcaat ctaccagggc gcggacaagc   15180
cgcgccgtcg ccactcgacc gccggcgccc acatcaaggc accctgcctc gcgcgttttcg   15240 gtgatgacgg tgaaaacctc tgacacatgc agctcccgga gacggtcaca gcttgtctgt   15300
aagcggatgc cggagcaga caagcccgtc agggcgcgtc agcgggtgtt ggcgggtgtc   15360
ggggcgcagc catgacccag tcacgtagcg atagcggagt gtatactggc ttaactatgc   15420
ggcatcagag cagattgtac tgagagtgca ccatatgcgg tgtgaaatac cgcacagatg   15480
cgtaaggaga aaataccgca tcaggcgctc ttccgcttcc tcgctcactg actcgctgcg   15540
ctcggtcgtt cggctgcggc gagcggtatc agctcactca aaggcggtaa tacggttatc   15600
cacagaatca ggggataacg caggaaagaa catgtgagca aaaggccagc aaaaggccag   15660
gaaccgtaaa aaggccgcgt tgctggcgtt tttccatagg ctccgccccc ctgacgagca   15720
tcacaaaaat cgacgctcaa gtcagaggtg gcgaaacccg acaggactat aaagatacca   15780
ggcgtttccc cctggaagct ccctcgtgcg ctctcctgtt ccgaccctgc cgcttaccgg   15840
atacctgtcc gcctttctcc cttcgggaag cgtggcgctt tctcatagct cacgctgtag   15900
gtatctcagt tcggtgtagg tcgttcgctc caagctgggc tgtgtgcacg aaccccccgt   15960
tcagcccgac cgctgcgcct tatccggtaa ctatcgtctt gagtccaacc cggtaagaca   16020
cgacttatcg ccactggcag cagccactgg taacaggatt agcagagcga ggtatgtagg   16080
cggtgctaca gagttcttga agtggtggcc taactacggc tacactagaa ggacagtatt   16140
tggtatctgc gctctgctga agccagttac cttcggaaaa agagttggta gctcttgatc   16200
cggcaaacaa accaccgctg gtagcggtgg tttttttgtt tgcaagcagc agattacgcg   16260
```

```
cagaaaaaaa ggatctcaag aagatccttt gatcttttct acggggtctg acgctcagtg    16320
gaacgaaaac tcacgttaag ggattttggt catgagatta tcaaaaagga tcttcaccta    16380 gatccttta aattaaaaat gaagttttaa atcaatctaa agtatatatg agtaaacttg    16440
gtctgacagt taccaatgct taatcagtga ggcacctatc tcagcgatct gtctatttcg    16500
ttcatccata gttgcctgac tccccgtcgt gtagataact acgatacggg agggcttacc    16560
atctggcccc agtgctgcaa tgataccgcg agcccacgc tcaccggctc cagatttatc    16620
agcaataaac cagccagccg aagggccga gcgcagaagt ggtcctgcaa ctttatccgc    16680
ctccatccag tctattaatt gttgccggga agctagagta agtagttcgc cagttaatag    16740
tttgcgcaac gttgttgcca ttgctacagg catcgtggtg tcacgctcgt cgtttggtat    16800
ggcttcattc agctccggtt cccaacgatc aaggcgagtt acatgatccc ccatgttgtg    16860
caaaaaagcg gttagctcct tcggtcctcc gatcgttgtc agaagtaagt tggccgcagt    16920
gttatcactc atggttatgg cagcactgca taattctctt actgtcatgc catccgtaag    16980
atgcttttct gtgactggtg agtactcaac caagtcattc tgagaatagt gtatgcggcg    17040
accgagttgc tcttgcccgg cgtcaacacg ggataatacc gcgccacata gcagaacttt    17100
aaaagtgctc atcattggaa aagacctgca ggggggggg ggaaagccac gttgtgtctc    17160
aaaatctctg atgttacatt gcacaagata aaaatatatc atcatgaaca ataaaactgt    17220
ctgcttacat aaacagtaat acaaggggtg ttatgagcca tattcaacgg gaaacgtctt    17280
gctcgaggcc gcgattaaat tccaacatgg atgctgattt atatgggtat aaatgggctc    17340
gcgataatgt cgggcaatca ggtgcgacaa tctatcgatt gtatgggaag cccgatgcgc    17400
cagagttgtt tctgaaacat ggcaaaggta gcgttgccaa tgatgttaca gatgagatgg    17460
tcagactaaa ctggctgacg gaatttatgc ctcttccgac catcaagcat tttatccgta    17520
ctcctgatga tgcatggtta ctcaccactg cgatccccgg gaaaacagca ttccaggtat    17580
tagaagaata tcctgattca ggtgaaaata ttgttgatgc gctggcagtg ttcctgcgcc    17640
ggttgcattc gattcctgtt tgtaattgtc cttttaacag cgatcgcgta tttcgtctcg    17700
ctcaggcgca atcacgaatg aataacggtt tggttgatgc gagtgatttt gatgacgagc    17760
gtaatggctg gcctgttgaa caagtctgga agaaatgca taagcttttg ccattctcac    17820
cggattcagt cgtcactcat ggtgatttct cacttgataa ccttattttt gacgagggga    17880
aattaatagg ttgtattgat gttggacgag tcggaatcgc agaccgatac caggatcttg    17940
ccatcctatg gaactgcctc ggtgagtttt ctccttcatt acagaaacgg cttttttcaaa   18000 aatatggtat tgataatcct gatatgaata aattgcagtt tcatttgatg ctcgatgagt    18060
ttttctaatc agaattggtt aattggttgt aacactggca gagcattacg ctgacttgac    18120
gggacggcgg ctttgttgaa taaatcgaac ttttgctgag ttgaaggatc agatcacgca    18180
tcttcccgac aacgcagacc gttccgtggc aaagcaaaag ttcaaaatca ccaactggtc    18240
cacctacaac aaagctctca tcaaccgtgg ctccctcact ttctggctgg atgatggggc    18300
gattcaggcc tggtatgagt cagcaacacc ttcttcacga ggcagacctc agcgccccc    18360 ccccctgca ggtcaattcg gtcgatatgg ctattacgaa gaaggctcgt gcgcggagtc    18420
ccgtgaactt tcccacgcaa caagtgaacc gcaccgggtt tgccggaggc catttcgtta    18480
aaatgcgcag c                                                          18491
```

<210> SEQ ID NO 2

<211> LENGTH: 4291
<212> TYPE: DNA
<213> ORGANISM: Artificial Sequence
<220> FEATURE:
<223> OTHER INFORMATION: pDONRZeo construct

<400> SEQUENCE: 2

| | | | | | |
|---|---|---|---|---|---|
| ctttcctgcg | ttatccctg | attctgtgga | taaccgtatt | accgcctttg | agtgagctga | 60 |
| taccgctcgc | cgcagccgaa | cgaccgagcg | cagcgagtca | gtgagcgagg | aagcggaaga | 120 |
| gcgcccaata | cgcaaaccgc | ctctccccgc | gcgttggccg | attcattaat | gcagctggca | 180 |
| cgacaggttt | cccgactgga | aagcgggcag | tgagcgcaac | gcaattaata | cgcgtaccgc | 240 |
| tagccaggaa | gagtttgtag | aaacgcaaaa | aggccatccg | tcaggatggc | cttctgctta | 300 |
| gtttgatgcc | tggcagttta | tggcgggcgt | cctgcccgcc | accctccggg | ccgttgcttc | 360 |
| acaacgttca | aatccgctcc | cggcggattt | gtcctactca | ggagagcgtt | caccgacaaa | 420 |
| caacagataa | aacgaaaggc | ccagtcttcc | gactgagcct | ttcgttttat | ttgatgcctg | 480 |
| gcagttccct | actctcgcgt | taacgctagc | atggatgttt | tcccagtcac | gacgttgtaa | 540 |
| aacgacggcc | agtcttaagc | tcgggcccca | aataatgatt | ttattttgac | tgatagtgac | 600 |
| ctgttcgttg | caacacattg | atgagcaatg | ctttttata | atgccaactt | tgtacaaaaa | 660 |
| agctgaacga | gaaacgtaaa | atgatataaa | tatcaatata | ttaaattaga | ttttgcataa | 720 |
| aaaacagact | acataatact | gtaaaacaca | acatatccag | tcactatgaa | tcaactactt | 780 |
| agatggtatt | agtgacctgt | agtcgaccga | cagccttcca | aatgttcttc | gggtgatgct | 840 |
| gccaacttag | tcgaccgaca | gccttccaaa | tgttcttctc | aaacggaatc | gtcgtatcca | 900 |
| gcctactcgc | tattgtcctc | aatgccgtat | taaatcataa | aagaaataa | gaaaaagagg | 960 |
| tgcgagcctc | ttttttgtgt | gacaaaataa | aacatctac | ctattcatat | acgctagtgt | 1020 |
| catagtcctg | aaaatcatct | gcatcaagaa | caattttcaca | actcttatac | ttttctctta | 1080 |
| caagtcgttc | ggcttcatct | ggattttcag | cctctatact | tactaaacgt | gataaagttt | 1140 |
| ctgtaatttc | tactgtatcg | acctgcagac | tggctgtgta | taagggagcc | tgacatttat | 1200 |
| attcccagaa | acatcaggtt | aatggcgttt | ttgatgtcat | tttcgcggtg | gctgagatca | 1260 |
| gccacttctt | ccccgataac | ggagaccggc | acactggcca | tatcggtggt | catcatgcgc | 1320 |
| cagctttcat | ccccgatatg | caccaccggg | taaagttcac | gggagacttt | atctgacagc | 1380 |
| agacgtgcac | tggccagggg | gatcaccatc | cgtcgcccgg | gcgtgtcaat | aatatcactc | 1440 |
| tgtacatcca | caaacagacg | ataacggctc | tctcttttat | aggtgtaaac | cttaaactgc | 1500 |
| atttcaccag | ccctgttct | cgtcagcaaa | agagccgttc | atttcaataa | accgggcgac | 1560 |
| ctcagccatc | ccttcctgat | tttccgcttt | ccagcgttcg | gcacgcagac | gacgggcttc | 1620 |
| attctgcatg | gttgtgctta | ccagaccgga | gatattgaca | tcatatatgc | cttgagcaac | 1680 |
| tgatagctgt | cgctgtcaac | tgtcactgta | atacgctgct | tcatagcata | cctctttttg | 1740 |
| acatacttcg | ggtatacata | tcagtatata | ttccttatacc | gcaaaaatca | gcgcgcaaat | 1800 |
| acgcatactg | ttatctggct | tttagtaagc | cggatccacg | cggcgtttac | gccccgccct | 1860 |
| gccactcatc | gcagtactgt | tgtaattcat | taagcattct | gccgacatgg | aagccatcac | 1920 |
| agacggcatg | atgaacctga | atcgccagcg | gcatcagcac | cttgtcgcct | tgcgtataat | 1980 |
| atttgcccat | ggtgaaaacg | ggggcgaaga | agttgtccat | attggccacg | tttaaatcaa | 2040 |
| aactggtgaa | actcacccag | ggattggctg | agacgaaaaa | catattctca | ataaaccctt | 2100 |
| tagggaaata | ggccaggttt | tcaccgtaac | acgccacatc | ttgcgaatat | atgtgtagaa | 2160 |

```
actgccggaa atcgtcgtgg tattcactcc agagcgatga aaacgtttca gtttgctcat    2220
ggaaaacggt gtaacaaggg tgaacactat cccatatcac cagctcaccg tctttcattg    2280
ccatacggaa ttccggatga gcattcatca ggcgggcaag aatgtgaata aaggccggat    2340
aaaacttgtg cttattttc tttacggtct ttaaaaaggc cgtaatatcc agctgaacgg     2400
tctggttata ggtacattga gcaactgact gaaatgcctc aaaatgttct ttacgatgcc    2460
attgggatat atcaacggtg gtatatccag tgattttttt ctccatttta gcttccttag    2520
ctcctgaaaa tctcgataac tcaaaaaata cgcccggtag tgatcttatt tcattatggt    2580
gaaagttgga acctcttacg tgccgatcaa cgtctcattt tcgccaaaag ttggcccagg    2640
gcttcccggt atcaacaggg acaccaggat ttatttattc tgcgaagtga tcttccgtca    2700
caggtattta ttcggcgcaa agtgcgtcgg gtgatgctgc caacttagtc gactacaggt    2760
cactaatacc atctaagtag ttgattcata gtgactggat atgttgtgtt ttacagtatt    2820
atgtagtctg tttttatgc aaaatctaat ttaatatatt gatatttata tcattttacg     2880
tttctcgttc agctttcttg tacaaagttg gcattataag aaagcattgc ttatcaattt    2940
gttgcaacga acaggtcact atcagtcaaa ataaaatcat tatttgccat ccagctgata    3000
tcccctatag tgagtcgtat tacatggtca tagctgtttc ctggcagctc tggcccgtgt    3060
ctcaaaatct ctgatgttac attgcacaag ataaaataat atcatcatga tcagtcctgc    3120
tcctcggcca cgaagtgcac gcagttgccg gccgggtcgc gcagggcgaa ctcccgcccc    3180
cacggctgct cgccgatctc ggtcatggcc ggcccgagg cgtcccggaa gttcgtggac      3240
acgacctccg accactcggc gtacagctcg tccaggccgc gcacccacac ccaggccagg    3300
gtgttgtccg gcaccacctg gtcctggacc gcgctgatga acagggtcac gtcgtcccgg    3360
accacaccgg cgaagtcgtc ctccacgaag tcccgggaga acccgagccg gtcggtccag    3420
aactcgaccg ctccggcgac gtcgcgcgcg gtgagcaccg gaacggcact ggtcaacttg    3480
gccatggttt agttcctcac cttgtcgtat tatactatgc cgatatacta tgccgatgat    3540
taattgtcaa cacgtgctga tcatgaccaa aatcccttaa cgtgagttac gcgtcgttcc    3600
actgagcgtc agaccccgta gaaaagatca aaggatcttc ttgagatcct ttttttctgc    3660
gcgtaatctg ctgcttgcaa acaaaaaaac caccgctacc agcggtggtt tgtttgccgg    3720
atcaagagct accaactctt tttccgaagg taactggctt cagcagagcg cagataccaa    3780
atactgttct tctagtgtag ccgtagttag gccaccactt caagaactct gtagcaccgc    3840
ctacatacct cgctctgcta atcctgttac cagtggctgc tgccagtggc gataagtcgt    3900
gtcttaccgg gttggactca agacgatagt taccggataa ggcgcagcgg tcgggctgaa    3960
cggggggttc gtgcacacag cccagcttgg agcgaacgac ctacaccgaa ctgagatacc    4020
tacagcgtga gctatgagaa agcgccacgc ttcccgaagg gagaaaggcg gacaggtatc    4080
cggtaagcgg cagggtcgga acaggagagc gcacagggga gcttccaggg ggaaacgcct    4140
ggtatcttta tagtcctgtc gggtttcgcc acctctgact tgagcgtcga ttttttgtgat   4200
gctcgtcagg ggggcggagc ctatggaaaa acgccagcaa cgcggccttt ttacggttcc    4260
tggccttttg ctggcctttt gctcacatgt t                                    4291
```

<210> SEQ ID NO 3
<211> LENGTH: 4762
<212> TYPE: DNA
<213> ORGANISM: Artificial Sequence
<220> FEATURE:

<223> OTHER INFORMATION: pDONR221

<400> SEQUENCE: 3

| | | | | | |
|---|---|---|---|---|---|
| ctttcctgcg | ttatcccctg | attctgtgga | taaccgtatt | accgcctttg | agtgagctga | 60 |
| taccgctcgc | cgcagccgaa | cgaccgagcg | cagcgagtca | gtgagcgagg | aagcggaaga | 120 |
| gcgcccaata | cgcaaaccgc | ctctccccgc | gcgttggccg | attcattaat | gcagctggca | 180 |
| cgacaggttt | cccgactgga | aagcgggcag | tgagcgcaac | gcaattaata | cgcgtaccgc | 240 |
| tagccaggaa | gagtttgtag | aaacgcaaaa | aggccatccg | tcaggatggc | cttctgctta | 300 |
| gtttgatgcc | tggcagttta | tggcgggcgt | cctgcccgcc | accctccggg | ccgttgcttc | 360 |
| acaacgttca | atccgctcc | cggcggattt | gtcctactca | ggagagcgtt | caccgacaaa | 420 |
| caacagataa | aacgaaaggc | ccagtcttcc | gactgagcct | ttcgttttat | ttgatgcctg | 480 |
| gcagttccct | actctcgcgt | taacgctagc | atggatgttt | tcccagtcac | gacgttgtaa | 540 |
| aacgacggcc | agtcttaagc | tcgggcccca | aataatgatt | ttattttgac | tgatagtgac | 600 |
| ctgttcgttg | caacacattg | atgagcaatg | cttttttata | atgccaactt | tgtacaaaaa | 660 |
| agctgaacga | gaaacgtaaa | atgatataaa | tatcaatata | ttaaattaga | ttttgcataa | 720 |
| aaaacagact | acataatact | gtaaaacaca | acatatccag | tcactatgaa | tcaactactt | 780 |
| agatggtatt | agtgacctgt | agtcgaccga | cagccttcca | aatgttcttc | gggtgatgct | 840 |
| gccaacttag | tcgaccgaca | gccttccaaa | tgttcttctc | aaacggaatc | gtcgtatcca | 900 |
| gcctactcgc | tattgtcctc | aatgccgtat | aaatcataa | aagaaataa | gaaaagagg | 960 |
| tgcgagcctc | ttttttgtgt | gacaaaataa | aaacatctac | ctattcatat | acgctagtgt | 1020 |
| catagtcctg | aaaatcatct | gcatcaagaa | caatttcaca | actcttatac | tttctctta | 1080 |
| caagtcgttc | ggcttcatct | ggattttcag | cctctatact | tactaaacgt | gataaagttt | 1140 |
| ctgtaatttc | tactgtatcg | acctgcagac | tggctgtgta | taagggagcc | tgacatttat | 1200 |
| attccccaga | acatcaggtt | aatggcgttt | ttgatgtcat | tttcgcggtg | gctgagatca | 1260 |
| gccacttctt | ccccgataac | ggagaccggc | acactggcca | tatcggtggt | catcatgcgc | 1320 |
| cagctttcat | ccccgatatg | caccaccggg | taaagttcac | gggagacttt | atctgacagc | 1380 |
| agacgtgcac | tggccagggg | gatcaccatc | cgtcgcccgg | cgtgtcaat | aatatcactc | 1440 |
| tgtacatcca | caaacagacg | ataacggctc | tctcttttat | aggtgtaaac | cttaaactgc | 1500 |
| atttcaccag | cccctgttct | cgtcagcaaa | agagccgttc | atttcaataa | accgggcgac | 1560 |
| ctcagccatc | ccttcctgat | tttccgcttt | ccagcgttcg | gcacgcagac | gacgggcttc | 1620 |
| attctgcatg | gttgtgctta | ccagaccgga | gatattgaca | tcatatatgc | cttgagcaac | 1680 |
| tgatagctgt | cgctgtcaac | tgtcactgta | atacgctgct | tcatagcata | cctcttttg | 1740 |
| acatacttcg | ggtatacata | tcagtatata | ttcttatacc | gcaaaaatca | gcgcgcaaat | 1800 |
| acgcatactg | ttatctggct | tttagtaagc | cggatccacg | cggcgtttac | gccccgccct | 1860 |
| gccactcatc | gcagtactgt | tgtaattcat | taagcattct | gccgacatgg | aagccatcac | 1920 |
| agacggcatg | atgaacctga | atcgccagcg | gcatcagcac | cttgtcgcct | tgcgtataat | 1980 |
| atttgcccat | ggtgaaaacg | ggggcgaaga | agttgtccat | attggccacg | tttaaatcaa | 2040 |
| aactggtgaa | actcacccag | ggattggctg | agacgaaaaa | catattctca | ataaaccctt | 2100 |
| tagggaaata | ggccaggttt | tcaccgtaac | acgccacatc | ttgcgaatat | atgtgtagaa | 2160 |
| actgccggaa | atcgtcgtgg | tattcactcc | agagcgatga | aaacgtttca | gtttgctcat | 2220 |
| ggaaaacggt | gtaacaaggg | tgaacactat | cccatatcac | cagctcaccg | tctttcattg | 2280 |

```
ccatacggaa ttccggatga gcattcatca ggcgggcaag aatgtgaata aaggccggat   2340
aaaacttgtg cttattttc tttacggtct ttaaaaaggc cgtaatatcc agctgaacgg    2400 tctggtttata ggtacattga gcaactgact gaaatgcctc aaaatgttct ttacgatgcc  2460
attgggatat atcaacggtg gtatatccag tgatttttt ctccatttta gcttccttag    2520
ctcctgaaaa tctcgataac tcaaaaaata cgcccggtag tgatcttatt tcattatggt   2580
gaaagttgga acctcttacg tgccgatcaa cgtctcattt tcgccaaaag ttggcccagg   2640
gcttcccggt atcaacaggg acaccaggat ttatttattc tgcgaagtga tcttccgtca   2700
caggtattta ttcggcgcaa agtgcgtcgg gtgatgctgc caacttagtc gactacaggt   2760
cactaatacc atctaagtag ttgattcata gtgactggat atgttgtgtt ttacagtatt   2820
atgtagtctg ttttttatgc aaaatctaat ttaatatatt gatatttata tcattttacg   2880
tttctcgttc agctttcttg tacaaagttg gcattataag aaagcattgc ttatcaattt   2940
gttgcaacga acaggtcact atcagtcaaa ataaaatcat tatttgccat ccagctgata   3000 tccctatag tgagtcgtat tacatggtca tagctgtttc ctggcagctc tggcccgtgt    3060
ctcaaaatct ctgatgttac attgcacaag ataaataat atcatcatga acaataaaac    3120
tgtctgctta cataaacagt aatacaaggg gtgttatgag ccatattcaa cgggaaacgt   3180
cgaggccgcg attaaattcc aacatggatg ctgatttata tgggtataaa tgggctcgcg   3240
ataatgtcgg gcaatcaggt gcgacaatct atcgcttgta tgggaagccc gatgcgccag   3300
agttgtttct gaaacatggc aaaggtagcg ttgccaatga tgttacagat gagatggtca   3360
gactaaactg gctgacggaa tttatgcctc ttccgaccat caagcatttt atccgtactc   3420
ctgatgatgc atggttactc accactgcga tccccggaaa aacagcattc caggtattag   3480
aagaatatcc tgattcaggt gaaaatattg ttgatgcgct ggcagtgttc ctgcgccggt   3540
tgcattcgat tcctgtttgt aattgtcctt ttaacagcga tcgcgtattt cgtctcgctc   3600
aggcgcaatc acgaatgaat aacggtttgg ttgatgcgag tgattttgat gacgagcgta   3660
atggctggcc tgttgaacaa gtctggaaag aaatgcataa acttttgcca ttctcaccgg   3720
attcagtcgt cactcatggt gatttctcac ttgataacct tattttttgac gaggggaaat   3780 taataggttg tattgatgtt ggacgagtcg gaatcgcaga ccgataccag gatcttgcca   3840
tcctatggaa ctgcctcggt gagttttctc cttcattaca gaaacggctt tttcaaaaat   3900
atggtattga taatcctgat atgaataaat tgcagtttca tttgatgctc gatgagtttt   3960
tctaatcaga attggttaat tggttgtaac actggcagag cattacgctg acttgacggg   4020
acggcgcaag ctcatgacca aaatccctta acgtgagtta cgcgtcgttc cactgagcgt   4080 cagacccgt agaaaagatc aaaggatctt cttgagatcc tttttttctg cgcgtaatct    4140
gctgcttgca acaaaaaaa ccaccgctac cagcggtggt ttgtttgccg gatcaagagc    4200
taccaactct ttttccgaag gtaactggct tcagcagagc gcagatacca atactgttc    4260 ttctagtgta gccgtagtta ggccaccact tcaagaactc tgtagcaccg cctacatacc   4320
tcgctctgct aatcctgtta ccagtggctg ctgccagtgg cgataagtcg tgtcttaccg   4380
ggttggactc aagacgatag ttaccggata aggcgcagcg tcgggctga acggggggtt    4440 cgtgcacaca gcccagcttg gagcgaacga cctacaccga actgagatac ctacagcgtg   4500
agctatgaga aagcgccacg cttcccgaag ggagaaaggc ggacaggtat ccggtaagcg   4560
gcagggtcgg aacaggagag cgcacgaggg agcttccagg gggaaacgcc tggtatcttt   4620
```

```
atagtcctgt cgggtttcgc cacctctgac ttgagcgtcg attttttgtga tgctcgtcag    4680 gggggcggag cctatggaaa aacgccagca acgcggcctt tttacggttc ctggccttttt   4740 gctggccttt tgctcacatg tt                                              4762

<210> SEQ ID NO 4
<211> LENGTH: 16843
<212> TYPE: DNA
<213> ORGANISM: Artificial Sequence
<220> FEATURE:
<223> OTHER INFORMATION: pBC-yellow construct

<400> SEQUENCE: 4
ccgggctggt tgccctcgcc gctgggctgg cggccgtcta tggccctgca aacgcgccag     60
aaacgccgtc gaagccgtgt gcgagacacc gcggccgccg gcgttgtgga tacctcgcgg    120
aaaacttggc cctcactgac agatgagggg cggacgttga cacttgaggg gccgactcac    180
ccggcgcggc gttgacagat gaggggcagg ctcgatttcg gccggcgacg tggagctggc    240
cagcctcgca aatcggcgaa aacgcctgat tttacgcgag tttcccacag atgatgtgga    300
caagcctggg gataagtgcc ctgcggtatt gacacttgag gggcgcgact actgacagat    360
gaggggcgcg atccttgaca cttgaggggc agagtgctga cagatgaggg gcgcacctat    420
tgacatttga gggctgtcc acaggcagaa atccagcat ttgcaagggt ttccgcccgt    480
ttttcggcca ccgctaacct gtcttttaac ctgcttttaa accaatattt ataaaccttg    540
tttttaacca gggctgcgcc ctgtgcgcgt gaccgcgcac gccgaagggg ggtgccccc    600 cttctcgaac cctcccggcc cgctaacgcg ggcctcccat cccccaggg gctgcgcccc    660 tcggccgcga acggcctcac cccaaaaatg gcagcgctgg cagtccttgc cattgccggg    720
atcggggcag taacgggatg ggcgatcagc ccgagcgcga cgcccggaag cattgacgtg    780
ccgcaggtgc tggcatcgac attcagcgac caggtgccgg gcagtgaggg cggcggcctg    840 ggtggcggc tgcccttcac ttcggccgtc ggggcattca cggacttcat ggcggggccg    900
gcaattttta ccttgggcat tcttggcata gtggtcgcgg gtgccgtgct cgtgttcggg    960
ggtgcgataa acccagcgaa ccatttgagg tgataggtaa gattataccg aggtatgaaa   1020
acgagaattg gacctttaca gaattactct atgaagcgcc atatttaaaa agctaccaag   1080
acgaagagga tgaagaggat gaggaggcag attgccttga atatattgac aatactgata   1140
agataatata tcttttatat agaagatatc gccgtatgta aggatttcag ggggcaaggc   1200
ataggcagcg cgcttatcaa tatatctata gaatgggcaa agcataaaaa cttgcatgga   1260
ctaatgcttg aaacccagga caataacctt atagcttgta aattctatca taattgggta   1320
atgactccaa cttattgata gtgttttatg ttcagataat gcccgatgac tttgtcatgc   1380
agctccaccg attttgagaa cgacagcgac ttccgtccca gccgtgccag gtgctgcctc   1440
agattcaggt tatgccgctc aattcgctgc gtatatcgct tgctgattac gtgcagcttt   1500
cccttcaggc gggattcata cagcggccag ccatccgtca tccatatcac cacgtcaaag   1560
ggtgacagca ggctcataag acgccccagc gtcgccatag tgcgttcacc gaatacgtgc   1620
gcaacaaccg tcttccggag actgtcatac gcgtaaaaca gccagcgctg gcgcgattta   1680
gccccgacat agccccactg ttcgtccatt tccgcgcaga cgatgacgtc actgcccggc   1740
tgtatgcgcg aggttaccga ctgcggcctg agttttttaa gtgacgtaaa atcgtgttga   1800
ggccaacgcc cataatgcgg gctgttgccc ggcatccaac gccattcatg gccatatcaa   1860 tgatttctg gtgcgtaccg ggttgagaag cggtgtaagt gaactgcagt tgccatgttt   1920
```

```
tacggcagtg agagcagaga tagcgctgat gtccggcggt gcttttgccg ttacgcacca   1980
ccccgtcagt agctgaacag gagggacagc tgatagacac agaagccact ggagcacctc   2040
aaaaacacca tcatacacta aatcagtaag ttggcagcat cacccataat tgtggtttca   2100
aaatcggctc cgtcgatact atgttatacg ccaactttga aaacaacttt gaaaaagctg   2160
ttttctggta tttaaggttt tagaatgcaa ggaacagtga attggagttc gtcttgttat   2220
aattagcttc ttggggtatc tttaaatact gtagaaaaga ggaaggaaat aataaatggc   2280
taaaatgaga atatcaccgg aattgaaaaa actgatcgaa aaataccgct gcgtaaaaga   2340 tacgaagga atgtctcctg ctaaggtata taagctggtg ggagaaaatg aaaacctata   2400
tttaaaaatg acggacagcc ggtataaagg gaccacctat gatgtggaac gggaaaagga   2460
catgatgcta tggctggaag gaaagctgcc tgttccaaag gtcctgcact ttgaacggca   2520
tgatggctgg agcaatctgc tcatgagtga ggccgatggc gtcctttgct cggaagagta   2580
tgaagatgaa caaagccctg aaaagattat cgagctgtat gcggagtgca tcaggctctt   2640
tcactccatc gacatatcgg attgtcccta tacgaatagc ttagacagcc gcttagccga   2700
attggattac ttactgaata cgatctggc cgatgtggat tgcgaaaact gggaagaaga   2760
cactccattt aaagatccgc gcgagctgta tgatttttta aagacggaaa agcccgaaga   2820
ggaacttgtc ttttcccacg gcgacctggg agacagcaac atctttgtga agatggcaa   2880 agtaagtggc tttattgatc ttgggagaag cggcagggcg gacaagtggt atgacattgc   2940
cttctgcgtc cggtcgatca gggaggatat cggggaagaa cagtatgtcg agctattttt   3000
tgacttactg gggatcaagc ctgattggga gaaaataaaa tattatattt tactggatga   3060
attgttttag tacctagatg tggcgcaacg atgccggcga caagcaggag cgcaccgact   3120
tcttccgcat caagtgtttt ggctctcagg ccgaggccca cggcaagtat ttgggcaagg   3180
ggtcgctggt attcgtgcag ggcaagattc ggaataccaa gtacgagaag gacggccaga   3240
cggtctacgg gaccgacttc attgccgata aggtggatta tctggacacc aaggcaccag   3300
gcgggtcaaa tcaggaataa gggcacattg ccccggcgtg agtcggggca atcccgcaag   3360
gagggtgaat gaatcggacg tttgaccgga aggcatacag gcaagaactg atcgacgcgg   3420
ggttttccgc cgaggatgcc gaaaccatcc aagccgcac cgtcatgcgt gcgccccgcg   3480
aaaccttcca gtccgtcggc tcgatggtcc agcaagctac ggccaagatc gagcgcgaca   3540
gcgtgcaact ggctccccct gccctgcccg cgccatcggc cgccgtggag cgttcgcgtc   3600
gtctcgaaca ggaggcggca ggtttggcga agtcgatgac catcgacacg cgaggaacta   3660
tgacgaccaa gaagcgaaaa accgccggcg aggacctggc aaaacaggtc agcgaggcca   3720
agcaggccgc gttgctgaaa cacacgaagc agcagatcaa ggaaatgcag ctttccttgt   3780
tcgatattgc gccgtggccg gacacgatgc gagcgatgcc aaacgacacg gccgctctg   3840 ccctgttcac cacgcgcaac aagaaaatcc gcgcgaggc gctgcaaaac aaggtcattt   3900
tccacgtcaa caaggacgtg aagatcacct acaccggcgt cgagctgcgg ccgacgatg   3960 acgaactggt gtggcagcag gtgttggagt acgcgaagcg cacccctatc ggcgagccga   4020
tcaccttcac gttctacgag ctttgccagg acctgggctg gtcgatcaat ggccggtatt   4080
acacgaaggc cgaggaatgc ctgtcgcgcc tacaggcgac ggcgatgggc ttcacgtccg   4140
accgcgttgg gcacctggaa tcggtgtcgc tgctgcaccg cttccgcgtc ctggaccgtg   4200
gcaagaaaac gtcccgttgc caggtcctga tcgacgagga atcgtcgtg ctgtttgctg   4260
```

-continued

```
gcgaccacta cacgaaattc atatgggaga agtaccgcaa gctgtcgccg acggcccgac    4320
ggatgttcga ctatttcagc tcgcaccggg agccgtaccc gctcaagctg gaaaccttcc    4380
gcctcatgtg cggatcggat ccacccgcg  tgaagaagtg gcgcgagcag gtcggcgaag    4440
cctgcgaaga gttgcgaggc agcggcctgg tggaacacgc ctgggtcaat gatgacctgg    4500
tgcattgcaa acgctagggc cttgtggggt cagttccggc tggggttca  gcagccagcg    4560 ctttactggc atttcaggaa caagcgggca ctgctcgacg cacttgcttc gctcagtatc    4620
gctcgggacg cacggcgcgc tctacgaact gccgataaac agaggattaa aattgacaat    4680
tgtgattaag gctcagattc gacggcttgg agcggccgac gtgcaggatt ccgcgagat    4740 ccgattgtcg gccctgaaga aagctccaga gatgttcggg tccgtttacg agcacgagga    4800
gaaaaagccc atggaggcgt tcgctgaacg gttgcgagat gccgtggcat tcggcgccta    4860
catcgacggc gagatcattg gctgtcggt  cttcaaacag gaggacggcc ccaaggacgc    4920
tcacaaggcg catctgtccg gcgttttcgt ggagcccgaa cagcgaggcc gagggggtcgc   4980 cggtatgctg ctgcgggcgt tgccggcggg tttattgctc gtgatgatcg tccgacagat    5040
tccaacggga atctggtgga tgcgcatctt catcctcggc gcacttaata tttcgctatt    5100
ctggagcttg ttgtttattt cggtctaccg cctgccgggc ggggtcgcgg cgacggtagg    5160
cgctgtgcag ccgctgatgg tcgtgttcat ctctgccgct ctgctaggta gcccgatacg    5220
attgatggcg gtcctggggg ctatttgcgg aactgcgggc gtggcgctgt tggtgttgac    5280
accaaacgca gcgctagatc ctgtcggcgt cgcagcgggc ctggcggggg cggtttccat    5340
ggcgttcgga accgtgctga cccgcaagtg gcaacctccc gtgcctctgc tcacctttac    5400
cgcctggcaa ctggcggccg gaggacttct gctcgttcca gtagctttag tgtttgatcc    5460
gccaatcccg atgcctacag gaaccaatgt tctcggcctg gcgtggctcg gcctgatcgg    5520
agcgggttta acctacttcc tttggttccg ggggatctcg cgactcgaac ctacagttgt    5580
ttccttactg ggcttttctca gccccagatc tggggtcgat cagccgggga tgcatcaggc    5640
cgacagtcgg aacttcgggt ccccgacctg taccattcgg tgagcaatgg ataggggagt    5700
tgatatcgtc aacgttcact tctaaagaaa tagcgccact cagcttcctc agcggcttta    5760
tccagcgatt tcctattatg tcggcatagt tctcaagatc gacagcctgt cacggttaag    5820
cgagaaatga ataagaaggc tgataattcg gatctctgcg agggagatga tatttgatca    5880
caggcagcaa cgctctgtca tcgttacaat caacatgcta ccctccgcga gatcatccgt    5940
gtttcaaacc cggcagctta gttgccgttc ttccgaatag catcggtaac atgagcaaag    6000
tctgccgcct tacaacggct ctcccgctga cgccgtcccg gactgatggg ctgcctgtat    6060
cgagtggtga ttttgtgccg agctgccggt cggggagctg ttggctggct ggtggcagga    6120
tatattgtgg tgtaaacaaa ttgacgctta gacaacttaa taacacattg cggacgtttt    6180
taatgtactg gggtggtttt tcttttcacc agtgagacgg gcaacagctg attgcccttc    6240
accgcctggc cctgagagag ttgcagcaag cggtccacgc tggtttgccc cagcaggcga    6300
aaatcctgtt tgatggtggt tccgaaatcg gcaaaatccc ttataaatca aaagaatagc    6360
ccagataggg gttgagtgtt gttccagttt ggaacaagag tccactatta agaacgtgg    6420 actccaacgt caaagggcga aaaccgtct  atcagggcga tgcccacta  cctgtatggc    6480 cgcattcgca aaacacacct agactagatt tgttttgcta acccaattga tattaattat    6540
atatgattaa tatttatatg tatatggatt tggttaatga aatgcatctg gttcatcaaa    6600
gaattataaa gacacgtgac attcatttag gataagaaat atggatgatc tctttctctt    6660
```

```
ttattcagat aactagtaat tacacataac acacaacttt gatgcccaca ttatagtgat    6720
tagcatgtca ctatgtgtgc atcctttat  ttcatacatt aattaagttg gccaatccag    6780
aagatggaca agtctaggtt aaccatgtgg tacctacgcg ttcgaatatc catgggccgc    6840
ttcaggccag ggcgctgggg aaggcgatgg cgtgctcggt cagctgccac ttctggttct    6900
tggcgtcgct ccggtcctcc cgcagcagct tgtgctggat gaagtgccac tcgggcatct    6960
tgctgggcac gctcttggcc ttgtacacgg tgtcgaactg gcaccggtac cggccgccgt    7020
ccttcagcag caggtacatg ctcacgtcgc ccttcaggat gccctgctta ggcacgggca    7080
tgatcttctc gcagctggcc tcccagttgg tggtcatctt cttcatcacg gggccgtcgg    7140
cggggaagtt cacgccgttg aagatgctct tgtggtagat gcagttctcc ttcacgctca    7200
cggtgatgtc cacgttacag atgcacacgg cgccgtcctc gaacaggaag ctccggcccc    7260
aggtgtagcc ggcggggcag ctgttcttga agtagtccac gatgtcctgg gggtactcgg    7320
tgaagatccg gtcgccgtac ttgaagccgg cgctcaggat gtcctcgctg aagggcaggg    7380
ggccgccctc gatcacgcac aggttgatgg tctgcttgcc cttgaagggg tagccgatgc    7440
cctcgccggt gatcacgaac ttgtggccgt tcacgcagcc ctccatgtgg tacttcatgg    7500
tcatctcctc cttcaggccg tgcttgctgt gggccatggt ggcgaccggt gaattcgagc    7560
tcggtacccg gggatcctga gtaaaacaga ggagggtctc actaagttta tagagagact    7620
gagagagata aagggacacg tatgaagcgt ctgttttcgt ggtgtgacgt caaagtcatt    7680
ttgctctcta cgcgtgtctg tgtcggcttg atctttttt  ttgcttttg  gaactcatgt    7740 cggtagtata tcttttattt attttttctt ttttcccctt ttctttcaaa ctgatgtcgg    7800
tatgatattt attccatcct aaaatgtaac ttactattat tagtagtcgg tccatgtcta    7860
ttggcccatc atgtggtcat tttacgttta cgtcgtgtgg ctgtttatta taacaaacgg    7920 cacatcottc tcattcgaat tgtatttctc cttaatcgtt ctaataggta tgatctttta    7980
ttttatacgt aaaattaaaa ttgaatgatg tcaagaacga aaattaattt gtatttacaa    8040
aggagctaaa tattgtttat tcctctactg gtagaagata aagaagtag  atgaaataat    8100 gatcttacta gagaatattc ctcatttaca ctagtcaaat ggaaatcttg taaacttta    8160 caataattta tcctgaaaat atgaaaaaat agaagaaaat gtttacctcc tctctcctct    8220
taattcacct acgatcggtg cgggcctctt cgctattacg ccagctggcg aaaggggat    8280 gtgctgcaag gcgattaagt tgggtaacgc cagggttttc ccagtcacga cgttgtaaaa    8340
cgacggccag tgaattcgag ctcggtaccc ggggatcctc tagagtcgac ctgcaggcat    8400
gcaagcttgt tgaaacatcc ctgaagtgtc tcattttatt ttatttattc tttgctgata    8460
aaaaaataaa ataaagaag  ctaagcacac ggtcaaccat tgctctactg ctaaagggt    8520 tatgtgtagt gttttactgc ataaattatg cagcaaacaa gacaactcaa attaaaaat    8580 ttcctttgct tgtttttttg ttgtctctga cttgactttc ttgtggaagt tggttgtata    8640
aggattggga cacaccattg tccttcttaa tttaatttta tttctttgct gataaaaaaa    8700
aaaaatttca tatagtgtta aataataatt tgttaaataa ccaaaaagtc aaatatgttt    8760
actctcgttt aaataattga gagtcgtcca gcaaggctaa acgattgtat agatttatga    8820
caatatttac ttttttatag ataaatgtta tattataata aatttatata catatattat    8880
atgttattta ttatttatta ttatttaaa  tccttcaata ttatcaaa  ccaactcata    8940 atttttttt  tatctgtaag aagcaataaa attaaataga cccactttaa ggatgatcca    9000
```

```
accttttatac agagtaagag agttcaaata gtacccttc atatacatat caactaaaat    9060
attagaaata tcatggatca aaccttataa agacattaaa taagtggata agtataatat    9120
ataaatgggt agtatataat atataaatgg atacaaactt ctctctttat aattgttatg    9180
tctccttaac atcctaatat aatacataag tgggtaatat ataatatata aatggagaca    9240
aacttcttcc attataattg ttatgtcttc ttaacactta tgtctcgttc acaatgctaa    9300
agttagaatt gtttagaaag tcttatagta cacatttgtt tttgtactat ttgaagcatt    9360
ccataagccg tcacgattca gatgatttat aataataaga ggaaatttat catagaacaa    9420
taaggtgcat agatagagtg ttaatatatc ataacatcct ttgtttattc atagaagaag    9480
tgagatggag ctcagttatt atactgttac atggtcggat acaatattcc atgctctcca    9540
tgagctctta cacctacatg cattttagtt catacttcat gcacgtggcc atcacagcta    9600
gctgcagcta catatttaca ttttacaaca ccaggagaac tgccctgtta gtgcataaca    9660
atcagaagat ggccgtggct actcgagtta tcgaaccact ttgtacaaga aagctgaacg    9720
agaaacgtaa aatgatataa atatcaatat attaaattag attttgcata aaaaacagac    9780
tacataatac tgtaaaacac aacatatcca gtcactatgg tcgacctgca gactggctgt    9840
gtataaggga gcctgacatt tatattcccc agaaacatcag gttaatggcg ttttgatgt    9900
cattttcgcg gtggctgaga tcagccactt cttccccgat aacggagacc ggcacactgg    9960
ccatatcggt ggtcatcatg cgccagcttt catccccgat atgcaccacc gggtaaagtt   10020
cacgggagac tttatctgac agcagacgtg cactggccag ggggatcacc atccgtcgcc   10080
cgggcgtgtc aataatatca ctctgtacat ccacaaacag acgataacgg ctctctcttt   10140
tataggtgta aaccttaaac tgcatttcac cagtccctgt tctcgtcagc aaaagagccg   10200
ttcatttcaa taaccgggc gacctcagcc atcccttcct gattttccgc tttccagcgt   10260
tcggcacgca gacgacgggc ttcattctgc atggttgtgc ttaccagacc ggagatattg   10320
acatcatata tgccttgagc aactgatagc tgtcgctgtc aactgtcact gtaatacgct   10380
gcttcatagc acacctcttt ttgacatact tcgggtatac atatcagtat atattcttat   10440
accgcaaaaa tcagcgcgca aatacgcata ctgttatctg gcttttagta agccggatcc   10500
tctagattac gccccgccct gccactcatc gcagtactgt tgtaattcat taagcattct   10560
gccgacatgg aagccatcac agacggcatg atgaacctga atcgccagcg gcatcagcac   10620
cttgtcgcct tgcgtataat atttgcccat ggtgaaaacg ggggcgaaga agttgtccat   10680
attggccacg tttaaatcaa aactggtgaa actcacccag ggattggctg agacgaaaaa   10740
catattctca ataaaccctt tagggaaata ggccaggttt tcaccgtaac acgccacatc   10800
ttgcgaatat atgtgtagaa actgccggaa atcgtcgtgg tattcactcc agagcgatga   10860
aaacgtttca gtttgctcat ggaaaacggt gtaacaaggg tgaacactat cccatatcac   10920
cagctcaccg tctttcattg ccatacgaaa ttccggatga gcattcatca ggcgggcaag   10980
aatgtgaata aaggccggat aaaacttgtg cttatttttc tttacggtct ttaaaaaggc   11040
cgtaatatcc agctgaacgg tctggttata ggtacattga gcaactgact gaaatgcctc   11100
aaaatgttct ttacgatgcc attgggatat atcaacggtg gtatatccag tgatttttt    11160
ctccatttta gcttccttag ctcctgaaaa tctcgccgga tcctaactca aaatccacac   11220
attatacgag ccggaagcat aaagtgtaaa gcctggggtg cctaatgcgg ccgccatagt   11280
gactggatat gttgtgtttt acagtattat gtagtctgtt tttatgcaa aatctaattt    11340
aatatattga tatttatatc attttacgtt tctcgttcag ctttttttgta caaacttgtt   11400
```

```
tgataaccgg tactagtgtg cacgtcgagc gtgtcctctc caaatgaaat gaacttcctt    11460
atatagagga agggtcttgc gaaggatagt gggattgtgc gtcatccctt acgtcagtgg    11520
agatgtcaca tcaatccact tgctttgaag acgtggttgg aacgtcttct ttttccacga    11580
tgctcctcgt gggtgggggt ccatctttgg gaccactgtc ggcagaggca tcttgaatga    11640
tagcctttcc tttatcgcaa tgatggcatt tgtaggagcc accttccttt tctactgtcc    11700
tttcgatgaa gtgacagata gctgggcaat ggaatccgag gaggtttccc gaaattatcc    11760
tttgttgaaa agtctcaata gcccttggt cttctgagac tgtatctttg acattttgg    11820 agtagaccag agtgtcgtgc tccaccatgt tgacgaagat tttcttcttg tcattgagtc    11880
gtaaaagact ctgtatgaac tgttcgccag tcttcacggc gagttctgtt agatcctcga    11940
tttgaatctt agactccatg catggcctta gattcagtag gaactacctt tttagagact    12000
ccaatctcta ttacttgcct tggtttatga agcaagcctt gaatcgtcca tactggaata    12060
gtacttctga tcttgagaaa tatgtctttc tctgtgttct tgatgcaatt agtcctgaat    12120
cttttgactg catctttaac cttcttggga aggtatttga tctcctggag attgttactc    12180
gggtagatcg tcttgatgag acctgctgcg taggcctctc taaccatctg tgggtcagca    12240 ttcttttctga aattgaagag gctaaccttc tcattatcag tggtgaacat agtgtcgtca    12300
ccttcacctt cgaacttcct tcctagatcg taaagataga ggaaatcgtc cattgtaatc    12360
tccggggcaa aggagatctc ttttggggct ggatcactgc tgggcctttt ggttcctagc    12420
gtgagccagt gggcttttg ctttggtggg cttgttaggg ccttagcaaa gctcttgggc    12480
ttgagttgag cttctccttt ggggatgaag ttcaacctgt ctgtttgctg acttgttgtg    12540
tacgcgtcag ctgctgctct tgcctctgta atagtggcaa atttcttgtg tgcaactccg    12600
ggaacgccgt ttgttgccgc cttttgtacaa ccccagtcat cgtatatacc ggcatgtgga    12660
ccgttataca caacgtagta gttgatatga gggtgttgaa tacccgattc tgctctgaga    12720
ggagcaactg tgctgttaag ctcagatttt tgtgggattg gaattggatc tctctagagca    12780 aagcttggcg taatcatggt catagctgtt tcctgtgtga aattgttatc cgctcacaat    12840
tccacacaac atacgagccg gaagcataaa gtgtaaagcc tggggtgcct aatgagtgag    12900
ctaactcaca ttaattgcgt tgcgctcact gcccgctttc cagtcgggaa acctgtcgtg    12960
ccagctgcat taatgaatcg gccaacgcgc ggggagaggc ggtttgcgta ttgggccaaa    13020
gacaaagggg cgacattcaa ccgattgagg gagggaaggt aaatattgac ggaaattatt    13080
cattaaaggt gaattatcac cgtcaccgac ttgagccatt tgggaattag agccagcaaa    13140
atcaccagta gcaccattac cattagcaag gccggaaacg tcaccaatga aaccatcatc    13200
tagtaacata gatgacaccg cgcgcgataa tttatcctag tttgcgcgct atattttgtt    13260
ttctatcgcg tattaaatgt ataattgcgg gactctaatc ataaaaaccc atctcataaa    13320
taacgtcatg cattacatgt taattattac atgcttaacg taattcaaca gaaattatat    13380
gataatcatc gcaagaccgg caacaggatt caatcttaag aaactttatt gccaaatgtt    13440
tgaacgatct gcttcgacgc actccttctt taggtacgga ctagatctcg gtgacgggca    13500
ggaccggacg gggcggtacc ggcaggctga agtccagctg ccagaaaccc acgtcatgcc    13560
agttcccgtg cttgaagccg gccgcccgca gcatgccgcg ggggcatat ccgagcgcct    13620 cgtgcatgcg cacgctcggg tcgttgggca gcccgatgac agcgaccacg ctcttgaagc    13680
cctgtgcctc cagggacttc agcaggtggg tgtagagcgt ggagcccagt cccgtccgct    13740
```

```
ggtggcgggg ggagacgtac acggtcgact cggccgtcca gtcgtaggcg ttgcgtgcct   13800
tccaggggcc cgcgtaggcg atgccggcga cctcgccgtc cacctcggcg acgagccagg   13860
gatagcgctc ccgcagacgg acgaggtcgt ccgtccactc ctgcggttcc tgcggctcgg   13920
tacgaaagtt gaccgtgctt gtctcgatgt agtggttgac gatggtgcag accgccggca   13980
tgtccgcctc ggtggcacgg cggatgtcgg ccgggcgtcg ttctgggctc atggatctgg   14040
attgagagtg aatatgagac tctaattgga taccgagggg aatttatgga acgtcagtgg   14100
agcatttttg acaagaaata tttgctagct gatagtgacc ttaggcgact tttgaacgcg   14160
caataatggt ttctgacgta tgtgcttagc tcattaaact ccagaaaccc gcggctgagt   14220
ggctccttca acgttgcggt tctgtcagtt ccaaacgtaa aacggcttgt cccgcgtcat   14280 cggcggggt cataacgtga ctcccttaat tctccgctca tgatcagatt gtcgtttccc   14340
gccttcagtt taaactatca gtgtttgaca ggatatattg gcgggtaaac ctaagagaaa   14400
agagcgttta ttagaataat cggatatttta aaagggcgtg aaaaggttta tccgttcgtc   14460
catttgtatg tgcatgccaa ccacagggtt ccccagatct ggcgccggcc agcgagacga   14520
gcaagattgg ccgccgcccg aaacgatccg acagcgcgcc cagcacaggt gcgcaggcaa   14580
attgcaccaa cgcatacagc gccagcagaa tgccatagtg ggcggtgacg tcgttcgagt   14640
gaaccagatc gcgcaggagg cccggcagca ccggcataat caggccgatg ccgacacgcgt  14700 cgagcgcgac agtgctcaga attacgatca ggggtatgtt gggtttcacg tctggcctcc   14760
ggaccagcct ccgctggtcc gattgaacgc gcggattctt tatcactgat aagttggtgg   14820
acatattatg tttatcagtg ataaagtgtc aagcatgaca aagttgcagc cgaatacagt   14880
gatccgtgcc gccctggacc tgttgaacga ggtcggcgta gacggtctga cgacacgcaa   14940
actggcggaa cggttggggg ttcagcagcc ggcgctttac tggcacttca ggaacaagcg   15000
ggcgctgctc gacgcactgg ccgaagccat gctggcggag aatcatacgc attcggtgcc   15060
gagagccgac gacgactggc gctcatttct gatcgggaat gcccgcagct tcaggcaggc   15120
gctgctcgcc taccgcgatg gcgcgcgcat ccatgccggc acgcgaccgg gcgcaccgca   15180
gatggaaacg gccgacgcgc agcttcgctt cctctgcgag gcgggttttt cggccggga   15240 cgccgtcaat gcgctgatga caatcagcta cttcactgtt ggggccgtgc ttgaggagca   15300
ggccggcgac agcgatgccg gcgagcgcgg cggcaccgtt gaacaggctc cgctctcgcc   15360
gctgttgcgg gccgcgatag acgccttcga cgaagccggt ccggacgcag cgttcgagca   15420
gggactcgcg gtgattgtcg atggattggc gaaaaggagg ctcgttgtca ggaacgttga   15480
aggaccgaga aagggtgacg attgatcagg accgctgccg gagcgcaacc cactcactac   15540
agcagagcca tgtagacaac atcccctccc cctttccacc gcgtcagacg cccgtagcag   15600
cccgctacgg gcttttttcat gccctgccct agcgtccaag cctcacggcc gcgctcggcc   15660
tctctggcgg ccttctggcg ctcttccgct tcctcgctca ctgactcgct gcgctcggtc   15720
gttcggctgc ggcgagcggt atcagctcac tcaaaggcgg taatacggtt atccacagaa   15780
tcaggggata acgcaggaaa gaacatgtga gcaaaaggcc agcaaaaggc caggaaccgt   15840
aaaaaggccg cgttgctggc gttttttccat aggctccgcc cccctgacga gcatcacaaa   15900
aatcgacgct caagtcagag gtggcgaaac ccgacaggac tataaagata ccaggcgttt   15960 cccccctggaa gctccctcgt gcgctctcct gttccgaccc tgccgcttac cggatacctg   16020
tccgcctttc tcccttcggg aagcgtggcg ctttctccgct gcataaccct gcttcgggt   16080 cattatagcg attttttcgg tatatccatc ctttttcgca cgatatacag gatttttgcca  16140
```

```
aagggttcgt gtagactttc cttggtgtat ccaacggcgt cagccgggca ggataggtga    16200
agtaggccca cccgcgagcg ggtgttcctt cttcactgtc ccttattcgc acctggcggt    16260
gctcaacggg aatcctgctc tgcgaggctg gccggctacc gccggcgtaa cagatgaggg    16320
caagcggatg gctgatgaaa ccaagccaac caggaagggc agcccaccta tcaaggtgta    16380
ctgccttcca gacgaacgaa gagcgattga ggaaaaggcg gcggcggccg gcatgagcct    16440
gtcggcctac ctgctggccg tcggccaggg ctacaaaatc acgggcgtcg tggactatga    16500
gcacgtccgc gagctggccc gcatcaatgg cgacctgggc cgcctgggcg gcctgctgaa    16560
actctggctc accgacgacc cgcgcacggc gcggttcggt gatgccacga tcctcgccct    16620
gctggcgaag atcgaagaga agcaggacga gcttggcaag gtcatgatgg gcgtggtccg    16680
cccgagggca gagccatgac tttttttagcc gctaaaacgg ccggggggtg cgcgtgattg    16740
ccaagcacgt ccccatgcgc tccatcaaga gagcgactt cgcggagctg gtgaagtaca    16800
tcaccgacga gcaaggcaag accgagcgcc tttgcgacgc tca                      16843

<210> SEQ ID NO 5
<211> LENGTH: 9142
<212> TYPE: DNA
<213> ORGANISM: Artificial Sequence
<220> FEATURE:
<223> OTHER INFORMATION: PHP27840 construct

<400> SEQUENCE: 5
ctagttatct gaataaaaga gaaagagatc atccatattt cttatcctaa atgaatgtca      60 cgtgtctta taattctttg atgaaccaga tgcatttcat taaccaaatc catatacata     120
taaatattaa tcatatataa ttaatatcaa ttgggttagc aaaacaaatc tagtctaggt     180
gtgttttgcg aattcgatat caagcttgat gggtaccggc gcgcccgatc atccggatat     240
agttcctcct ttcagcaaaa aacccctcaa gacccgttta gaggcsccaa ggggttatgc     300
tagttattgc tcagcggtgg cagcagccaa ctcagcttcc tttcgggctt tgttagcagc     360
cggatcgatc caagctgtac ctcactattc ctttgccctc ggacgagtgc tggggcgtcg     420
gtttccacta tcggcgagta cttctacaca gccatcggtc cagacggccg cgcttctgcg     480
ggcgatttgt gtacgcccga cagtcccggc tccggatcgg acgattgcgt cgcatcgacc     540
ctgcgcccaa gctgcatcat cgaaattgcc gtcaaccaag ctctgataga gttggtcaag     600
accaatgcgg agcatatacg cccggagccg cggcgatcct gcaagctccg gatgcctccg     660
ctcgaagtag cgcgtctgct gctccataca agccaaccac ggcctccaga agaagatgtt     720
ggcgacctcg tattgggaat ccccgaacat cgcctcgctc cagtcaatga ccgctgttat     780
gcggccattg tccgtcagga cattgttgga gccgaaatcc gcgtgcacga ggtgccggac     840
ttcggggcag tcctcggccc aaagcatcag ctcatcgaga gcctgcgcga cggacgcact     900
gacggtgtcg tccatcacag tttgccagtg atacacatgg ggatcagcaa tcgcgcatat     960
gaaatcacgc catgtagtgt attgaccgat tccttgcggt ccgaatgggc cgaacccgct    1020
cgtctggcta agatcggccg cagcgatcgc atccatagcc tccgcgaccg gctgcagaac    1080
agcgggcagt tcggtttcag gcaggtcttg caacgtgaca ccctgtgcac ggcgggagat    1140
gcaataggtc aggctctcgc tgaattcccc aatgtcaagc acttccggaa tcgggagcgc    1200
ggccgatgca aagtgccgat aaacataacg atctttgtag aaaccatcgg cgcagctatt    1260
tacccgcagg acatatccac gccctcctac atcgaagctg aaagcacgag attcttcgcc    1320
```

```
ctccgagagc tgcatcaggt cggagacgct gtcgaacttt tcgatcagaa acttctcgac    1380
agacgtcgcg gtgagttcag gcttttccat gggtatatct ccttcttaaa gttaaacaaa    1440
attatttcta gagggaaacc gttgtggtct ccctatagtg agtcgtatta atttcgcggg    1500
atcgagatct gatcaacctg cattaatgaa tcggccaacg cgcggggaga ggcggtttgc    1560
gtattgggcg ctcttccgct tcctcgctca ctgactcgct gcgctcggtc gttcggctgc    1620
ggcgagcggt atcagctcac tcaaaggcgg taatacggtt atccacagaa tcaggggata    1680
acgcaggaaa gaacatgtga gcaaaaggcc agcaaaaggc caggaaccgt aaaaaggccg    1740
cgttgctggc gtttttccat aggctccgcc cccctgacga gcatcacaaa aatcgacgct    1800
caagtcagag gtggcgaaac ccgacaggac tataaagata ccaggcgttt ccccctggaa    1860
gctccctcgt gcgctctcct gttccgaccc tgccgcttac cggatacctg tccgcctttc    1920
tcccttcggg aagcgtggcg ctttctcaat gctcacgctg taggtatctc agttcggtgt    1980
aggtcgttcg ctccaagctg ggctgtgtgc acgaaccccc cgttcagccc gaccgctgcg    2040
ccttatccgg taactatcgt cttgagtcca acccggtaag acacgactta tcgccactgg    2100
cagcagccac tggtaacagg attagcagag cgaggtatgt aggcggtgct acagagttct    2160
tgaagtggtg gcctaactac ggctacacta aggacagt atttggtatc tgcgctctgc    2220
tgaagccagt taccttcgga aaaagagttg gtagctcttg atccggcaaa caaaccaccg    2280
ctggtagcgg tggttttttt gtttgcaagc agcagattac gcgcagaaaa aaaggatctc    2340
aagaagatcc tttgatcttt tctacggggt ctgacgctca gtggaacgaa aactcacgtt    2400
aagggatttt ggtcatgaca ttaacctata aaaataggcg tatcacgagg ccctttcgtc    2460
tcgcgcgttt cggtgatgac ggtgaaaacc tctgacacat gcagctcccg gagacggtca    2520
cagcttgtct gtaagcggat gccgggagca gacaagcccg tcagggcgcg tcagcgggtg    2580
ttggcgggtg tcggggctgg cttaactatg cggcatcaga gcagattgta ctgagagtgc    2640
accatatgga catattgtcg ttagaacgcg gctacaatta atacataacc ttatgtatca    2700
tacacatacg atttaggtga cactatagaa cggcgcgcca agctgggtct agaactagaa    2760
acgtgatgcc acttgttatt gaagtcgatt acagcatcta ttctgtttta ctatttataa    2820
ctttgccatt tctgactttt gaaaactatc tctggatttc ggtatcgctt tgtgaagatc    2880
gagcaaaaga gacgttttgt ggacgcaatg gtccaaatcc gttctacatg aacaaattgg    2940
tcacaatttc cactaaaagt aaataaatgg caagttaaaa aaggaatatg catttaactg    3000
attgcctagg tgagctccaa gagaagttga atctacacgt ctaccaaccg ctaaaaaaag    3060
aaaaacattg aatatgtaac ctgattccat tagcttttga cttcttcaac agattctcta    3120
cttagatttc taacagaaat attattacta gcacatcatt ttcagtctca ctacagcaaa    3180
aaatccaacg gcacaataca gacaacagga gatatcagac tacagagata gatagatgct    3240
actgcatgta gtaagttaaa taaaaggaaa ataaaatgtc ttgctaccaa aactactaca    3300
gactatgatg ctcaccacag gccaaatcct gcaactagga cagcattatc ttatatatat    3360
tgtacaaaac aagcatcaag gaacatttgg tctaggcaat cagtacctcg ttctaccatc    3420
accctcagtt atcacatcct tgaaggatcc attactggga atcatcggca acacatgctc    3480
ctgatggggc acaatgacat caagaaggta ggggccaggg gtgtccaaca ttctctgaat    3540
tgccgctcta agctcttcct tcttcgtcac tcgcgctgcc ggtatcccac aagcatcagc    3600
aaacttgagc atgtttggga atatctcgct ctcgctagcc ggatctccaa gataggtgtg    3660
agctctattg gacttgtaga acctatcctc caactgaacc accatacccg aatgctgatt    3720
```

```
gttcaacaac aatatcttaa ctgggagatt ctccactctt atagtggcca actcctgaac   3780
attcatgatg aaactaccat ccccatcaat gtcaaccaca acagcccag ggttagcaac    3840 agcagcacca atagccgcag gcaatccaaa acccatggct ccaagacccc ctgaggtcaa   3900
ccactgcctc ggtctcttgt acttgtaaaa ctgcgcagcc cacatttgat gctgcccaac   3960
cccagtacta acaatagcat ctccattagt caactcatca agaacctcga tagcatgctg   4020
cggagaaatc gcgtcctgga atgtcttgta acccaatgga aacttgtgtt tctgcacatt   4080
aatctcttct ctccaacctc caagatcaaa cttaccctcc actcctttct cctccaaaat   4140
catattaatt cccttcaagg ccaacttcaa atccgcgcaa accgacacgt gcgcctgctt   4200
gttcttccca atctcggcag aatcaatatc aatgtgaaca atcttagccc tactagcaaa   4260
agcctcaagc ttcccagtaa cacggtcatc aaaccttacc ccaaaggcaa gcaacaaatc   4320
actattgtca acagcatagt tagcataaac agtaccatgc atacccagca tctgaaggga   4380
atattcatca ccaataggaa aagttccaag acccattaaa gtgctagcaa cgggaatacc   4440
agtgagttca acaaagcgcc tcaattcagc actggaattc aaactgccac cgccgacgta   4500
gagaacgggt ttttgggcct ccatgatgag tctgacaatg tgttccaatt gggcctcggc   4560
ggggggcctg ggcagcctgg cgaggtaacc ggggaggtta acgggctcgt cccaattagg   4620
cacggcgagt tgctgctgaa cgtctttggg aatgtcgatg aggaccggac cggggcggcc   4680
ggaggtggcg acgaagaaag cctcggcgac gacgcggggg atgtcgtcga cgtcgaggat   4740
gaggtagttg tgcttcgtga tggatctgct cacctccacg atcggggttt cttggaaggc   4800
gtcggtgccg atcatccggc gggcgacctg gccggtgatg gcgacgactg ggacgctgtc   4860
cattaaagcg tcggcgaggc cgctcacgag gttggtggcg ccggggccgg aggtggcaat   4920
gcagacgccg gggaggccgg aggaacgcgc gtagccttcg gcggcgaaga gccgcccctg   4980
ctcgtggcgc gggagcacgt tgcggatggc ggcggagcgc gtgagcgcct ggtggatctc   5040
catcgacgca ccgccggggt acgcgaacac cgtcgtcacg ccctgcctct ccagcgcctc   5100
cacaaggatg tccgcgccct tgcgaggttc gccggaggcg aaccgtgaca cgaagggctc   5160
cgtggtcggc gcttccttgg tgaagggcgc cgccgtgggg ggtttggaga tggaacattt   5220
gattttgaga gcgtggttgg gtttggtgag ggtttgatga gagagaggga gggtggatct   5280
agtaatgcgt ttggggaagg tggggtgtga agaggaagaa gagaatcggg tggttctgga   5340
agcggtggcc gccattgtgt tgtgtggcat ggttatactt caaaaactgc acaacaagcc   5400
tagagttagt acctaaacag taaatttaca acagagagca aagacacatg caaaaatttc   5460
agccataaaa aaagttataa tagaatttaa agcaaaagtt tcatttttta acatatata    5520 caaacaaact ggatttgaag gaagggatta attcccctgc tcaaagtttg aattcctatt   5580
gtgacctata ctcgaataaa attgaagcct aaggaatgta tgagaaacaa gaaaacaaaa   5640
caaaactaca gacaaacaag tacaattaca aaattcgcta aaattctgta atcaccaaac   5700
cccatctcag tcagcacaag gcccaaggtt tattttgaaa taaaaaaaaa gtgatttat    5760 ttctcataag ctaaagaaa gaaaggcaat tatgaaatga tttcgactag atctgaaagt    5820
caaacgcgta ttccgcagat attaaagaaa gagtagagtt tcacatggat cctagatgga   5880
cccagttgag gaaaaagcaa ggcaaagcaa accagaagtg caagatccga aattgaacca   5940
cggaatctag gatttggtag agggagaaga aaagtacctt gagaggtaga agagaagaga   6000
agagcagaga gatatatgaa cgagtgtgtc ttggtctcaa ctctgaagcg atacgagttt   6060
```

```
agagggagc attgagttcc aatttatagg gaaaccgggt ggcagggtg agttaatgac      6120
ggaaaagccc ctaagtaacg agattggatt gtgggttaga ttcaaccgtt tgcatccgcg      6180
gcttagattg gggaagtcag agtgaatctc aaccgttgac tgagttgaaa attgaatgta      6240
gcaaccaatt gagccaaccc cagcctttgc cctttgattt tgatttgttt gttgcatact      6300
ttttatttgt cttctggttc tgactctctt tctctcgttt caatgccagg ttgcctactc      6360
ccacaccact cacaagaaga ttctactgtt agtattaaat attttttaat gtattaaatg      6420
atgaatgctt ttgtaaacag aacaagacta tgtctaataa gtgtcttgca acatttttta      6480
agaaattaaa aaaatatat ttattatcaa aatcaaatgt atgaaaaatc atgaataata      6540
taattttata catttttta aaaatctttt aatttctta attaatatct taaaaataat      6600
gattaatatt taacccaaaa taattagtat gattggtaag gaagatatcc atgttatgtt      6660
tggatgtgag tttgatctag agcaaagctt actagagtcg acctgcagcc cctccaccgc      6720
ggtggcggcc gctctagaga tccgtcaaca tggtggagca cgacactctc gtctactcca      6780
agaatatcaa agatacagtc tcagaagacc aaagggctat tgagctttt caacaaaggg      6840
taatatcggg aaacctcctc ggattccatt gcccagctat ctgtcacttc atcaaaagga      6900
cagtagaaaa ggaaggtggc acctacaaat gccatcattg cgataaagga aaggctatcg      6960
ttcaagatgc ctctgccgac agtggtccca aagatggacc cccacccacg aggagcatcg      7020
tggaaaaaga agacgttcca accacgtctt caaagcaagt ggattgatgt gatgatccta      7080
tgcgtatggt atgacgtgtg ttcaagatga tgacttcaaa cctacctatg acgtatggta      7140
tgacgtgtgt cgactgatga cttagatcca ctcgagcggc tataaatacg tacctacgca      7200
ccctgcgcta ccatccctag agctgcagct tatttttaca acaattacca acaacaacaa      7260
acaacaaaca acattacaat tactatttac aattacagtc gacccatcaa caagtttgta      7320
caaaaagct gaacgagaaa cgtaaaatga tataaatatc aatatattaa attagatttt      7380
gcataaaaaa cagactacat aatactgtaa aacacaacat atccagtcat attggcggcc      7440
gcattaggca ccccaggctt tacactttat gcttccggct cgtataatgt gtggattttg      7500
agttaggatc cgtcgagatt ttcaggagct aaggaagcta aaatggagaa aaaatcact      7560
ggatatacca ccgttgatat atcccaatgg catcgtaaag aacattttga ggcattcag      7620
tcagttgctc aatgtaccta taaccagacc gttcagctgg atattacggc ctttttaaag      7680
accgtaaaga aaataagca caagttttat ccggccttta ttcacattct tgcccgcctg      7740
atgaatgctc atccggaatt ccgtatggca atgaaagacg gtgagctggt gatatgggat      7800
agtgttcacc cttgttacac cgttttccat gagcaaactg aaacgttttc atcgctctgg      7860
agtgaatacc acgacgattt ccggcagttt ctacacatat attcgcaaga tgtggcgtgt      7920
tacggtgaaa acctggccta tttccctaaa gggtttattg agaatatgtt tttcgtctca      7980
gccaatccct gggtgagttt caccagtttt gatttaaacg tggccaatat ggacaacttc      8040
ttcgccccg ttttcaccat gggcaaatat tatacgcaag cgacaaggt gctgatgccg      8100
ctggcgattc aggttcatca tgccgtttgt gatggcttcc atgtcggcag aatgcttaat      8160
gaattacaac agtactgcga tgagtggcag ggcgggcgt aaagatctgg atccggctta      8220
ctaaaagcca gataacagta tgcgtatttg cgcgctgatt tttgcggtat aagaatatat      8280
actgatatgt atacccgaag tatgtcaaaa agaggtatgc tatgaagcag cgtattacag      8340
tgacagttga cagcgacagc tatcagttgc tcaaggcata tatgatgtca atatctccgg      8400
tctggtaagc acaaccatgc agaatgaagc ccgtcgtctg cgtgccgaac gctggaaagc      8460
```

| | |
|---|---|
| ggaaaatcag gaagggatgg ctgaggtcgc ccggtttatt gaaatgaacg gctcttttgc | 8520 |
| tgacgagaac aggggctggt gaaatgcagt ttaaggttta ccctataaa agagagagcc | 8580 |
| gttatcgtct gtttgtggat gtacagagtg atattattga cacgcccggg cgacggatgg | 8640 |
| tgatccccct ggccagtgca cgtctgctgt cagataaagt ctcccgtgaa ctttacccgg | 8700 |
| tggtgcatat cggggatgaa agctggcgca tgatgaccac cgatatggcc agtgtgccgg | 8760 |
| tctccgttat cggggaagaa gtggctgatc tcagccaccg cgaaaatgac atcaaaaacg | 8820 |
| ccattaacct gatgttctgg ggaatataaa tgtcaggctc ccttatacac agccagtctg | 8880 |
| caggtcgacc atagtgactg gatatgttgt gttttacagt attatgtagt ctgttttta | 8940 |
| tgcaaaatct aatttaatat attgatattt atatcatttt acgtttctcg ttcagctttc | 9000 |
| ttgtacaaag tggttgataa cctagacttg tccatcttct ggattggcca acttaattaa | 9060 |
| tgtatgaaat aaaaggatgc acacatagtg acatgctaat cactataatg tgggcatcaa | 9120 |
| agttgtgtgt tatgtgtaat ta | 9142 |

<210> SEQ ID NO 6
<211> LENGTH: 49911
<212> TYPE: DNA
<213> ORGANISM: Artificial Sequence
<220> FEATURE:
<223> OTHER INFORMATION: PHP23236 construct

<400> SEQUENCE: 6

| | |
|---|---|
| gtgcagcgtg acccggtcgt gcccctctct agagataatg agcattgcat gtctaagtta | 60 |
| taaaaaatta ccacatattt tttttgtcac acttgtttga agtgcagttt atctatcttt | 120 |
| atacatatat ttaaacttta ctctacgaat aatataatct atagtactac aataatatca | 180 |
| gtgttttaga gaatcatata aatgaacagt tagacatggt ctaaaggaca attgagtatt | 240 |
| ttgacaacag gactctacag ttttatcttt ttagtgtgca tgtgttctcc ttttttttg | 300 |
| caaatagctt cacctatata atacttcatc cattttatta gtacatccat ttagggttta | 360 |
| gggttaatgg ttttatagga ctaatttttt tagtacatct attttattct attttagcct | 420 |
| ctaaattaag aaaactaaaa ctctatttta gttttttat ttaataattt agatataaaa | 480 |
| tagaataaaa taaagtgact aaaaattaaa caaatacccct ttaagaaatt aaaaaaacta | 540 |
| aggaaacatt tttcttgttt cgagtagata atgccagcct gttaaacgcc gtcgacgagt | 600 |
| ctaacggaca ccaaccagcg aaccagcagc gtcgcgtcgg gccaagcgaa gcagacggca | 660 |
| cggcatctct gtcgctgcct ctggaccct ctcgagagtt ccgctccacc gttggacttg | 720 |
| ctccgctgtc ggcatccaga aattgcgtgg cggagcggca gacgtgagcc ggcacggcag | 780 |
| gcggcctcct cctcctctca cggcacggca gctacggggg attcctttcc caccgctcct | 840 |
| tcgctttccc ttcctcgccc gccgtaataa atagacaccc cctccacacc ctctttcccc | 900 |
| aacctcgtgt tgttcggagc gcacacacac acaaccagat ctcccccaaa tccacccgtc | 960 |
| ggcacctccg cttcaaggta cgccgctcgt cctcccccc cccccctctc taccttctct | 1020 |
| agatcggcgt tccggtccat ggttagggcc cggtagttct acttctgttc atgtttgtgt | 1080 |
| tagatccgtg tttgtgttag atccgtgctg ctagcgttcg tacacggatg cgacctgtac | 1140 |
| gtcagacacg ttctgattgc taacttgcca gtgtttctct ttggggaatc ctgggatggc | 1200 |
| tctagccgtt ccgcagacgg gatcgatttc atgattttt ttgtttcgtt gcataggggtt | 1260 |
| tggtttgccc ttttccttta tttcaatata tgccgtgcac ttgtttgtcg ggtcatcttt | 1320 |

-continued

```
tcatgcttttt ttttgtcttg gttgtgatga tgtggtctgg ttgggcggtc gttctagatc     1380
ggagtagaat tctgtttcaa actacctggt ggatttatta attttggatc tgtatgtgtg     1440
tgccatacat attcatagtt acgaattgaa gatgatggat ggaaatatcg atctaggata     1500
ggtatacatg ttgatgcggg ttttactgat gcatatacag agatgctttt tgttcgcttg     1560
gttgtgatga tgtggtgtgg ttgggcggtc gttcattcgt tctagatcgg agtagaatac     1620
tgtttcaaac tacctggtgt atttattaat tttggaactg tatgtgtgtg tcatacatct     1680
tcatagttac gagtttaaga tggatggaaa tatcgatcta ggataggtat acatgttgat     1740
gtgggtttta ctgatgcata tacatgatgg catatgcagc atctattcat atgctctaac     1800
cttgagtacc tatctattat aataaacaag tatgttttat aattattttg atcttgatat     1860
acttggatga tggcatatgc agcagctata tgtggatttt tttagccctg ccttcatacg     1920
ctatttattt gcttggtact gtttcttttg tcgatgctca ccctgttgtt tggtgttact     1980
tctgcaggtc gactctagag gatccacaag tttgtacaaa aaagctgaac gagaaacgta     2040
aaatgatata aatatcaata tattaaatta gattttgcat aaaaaacaga ctacataata     2100
ctgtaaaaca caacatatcc agtcactatg gcggccgcat taggcacccc aggctttaca     2160
ctttatgctt ccggctcgta taatgtgtgg attttgagtt aggatttaaa tacgcgttga     2220
tccggcttac taaaagccag ataacagtat gcgtatttgc gcgctgattt ttgcggtata     2280
agaatatata ctgatatgta tacccgaagt atgtcaaaaa gaggtatgct atgaagcagc     2340
gtattacagt gacagttgac agcgacagct atcagttgct caaggcatat atgatgtcaa     2400
tatctccggt ctggtaagca caaccatgca gaatgaagcc cgtcgtctgc gtgccgaacg     2460
ctggaaagcg gaaaatcagg aagggatggc tgaggtcgcc cggtttattg aaatgaacgg     2520
ctcttttgct gacgagaaca ggggctggtg aaatgcagtt taaggtttac acctataaaa     2580
gagagagccg ttatcgtctg tttgtggatg tacagagtga tatcattgac acgcccggtc     2640
gacggatggt gatcccccctg gccagtgcac gtctgctgtc agataaagtc tcccgtgaac     2700
tttacccggt ggtgcatatc ggggatgaaa gctggcgcat gatgaccacc gatatggcca     2760
gtgtgccggt ctccgttatc ggggaagaag tggctgatct cagccaccgc gaaaatgaca     2820
tcaaaaacgc cattaacctg atgttctggg aatataaat gtcaggctcc cttatacaca     2880
gccagtctgc aggtcgacca tagtgactgg atatgttgtg ttttacagta ttatgtagtc     2940
tgttttttat gcaaaatcta atttaatata ttgatattta tatcattta cgtttctcgt     3000 tcagctttct tgtacaaagt ggtgttaacc tagacttgtc catcttctgg attggccaac     3060
ttaattaatg tatgaaataa aaggatgcac acatagtgac atgctaatca ctataatgtg     3120
ggcatcaaag ttgtgtgtta tgtgtaatta ctagttatct gaataaaaga gaaagagatc     3180 atccatatt cttatcctaa atgaatgtca cgtgtcttta taattctttg atgaaccaga     3240
tgcatttcat taaccaaatc catatacata taaatattaa tcatatataa ttaatatcaa     3300
ttgggttagc aaaacaaatc tagtctaggt gtgttttgcg aattgcggcc gccaccgcgg     3360
tggagctcga attccggtcc gggtcacctt tgtccaccaa gatggaactg cggccgctca     3420
ttaattaagt caggcgcgcc tctagttgaa gacacgttca tgtcttcatc gtaagaagac     3480
actcagtagt cttcggccag aatggccatc tggattcagc aggcctagaa ggccatttaa     3540
atcctgagga tctggtcttc ctaaggaccc gggatatcgg accgattaaa ctttaattcg     3600
gtccgaagct tgcatgcctg cagtgcagcg tgacccggtc gtgcccctct ctagagataa     3660
tgagcattgc atgtctaagt tataaaaaat taccacatat ttttttttgtc acacttgttt     3720
```

```
gaagtgcagt ttatctatct ttatacatat atttaaactt tactctacga ataatataat    3780
ctatagtact acaataatat cagtgtttta gagaatcata taaatgaaca gttagacatg    3840
gtctaaagga caattgagta ttttgacaac aggactctac agttttatct ttttagtgtg    3900
catgtgttct ccttttttt tgcaaatagc ttcacctata taatacttca tccattttat    3960
tagtacatcc atttagggtt tagggttaat ggttttata gactaatttt tttagtacat     4020
ctattttatt ctattttagc ctctaaatta agaaaactaa aactctattt tagttttttt    4080
atttaataat ttagatataa aatagaataa aataaagtga ctaaaaatta aacaaatacc    4140
cttaagaaa ttaaaaaaac taaggaaaca tttttcttgt ttcgagtaga taatgccagc     4200
ctgttaaacg ccgtcgacga gtctaacgga caccaaccag cgaaccagca gcgtcgcgtc    4260
gggccaagcg aagcagacgg cacggcatct ctgtcgctgc ctctggaccc ctctcgagag    4320
ttccgctcca ccgttggact tgctccgctg tcggcatcca gaaattgcgt ggcggagcgg    4380
cagacgtgag ccggcacggc aggcggcctc ctcctcctct cacggcaccg gcagctacgg    4440
gggattcctt tcccaccgct ccttcgcttt cccttcctcg cccgccgtaa taaatagaca    4500
cccctccac accctctttc cccaacctcg tgttgttcgg agcgcacaca cacacaacca     4560
gatctccccc aaatccaccc gtcggcacct ccgcttcaag gtacgccgct cgtcctcccc    4620
ccccccctc tctaccttct ctagatcggc gttccggtcc atgcatggtt agggcccggt     4680
agttctactt ctgttcatgt ttgtgttaga tccgtgtttg tgttagatcc gtgctgctag    4740
cgttcgtaca cggatgcgac ctgtacgtca gacacgttct gattgctaac ttgccagtgt    4800
ttctctttgg ggaatcctgg gatggctcta gccgttccgc agacgggatc gatttcatga    4860
tttttttgt ttcgttgcat agggttggt ttgccctttt cctttatttc aatatatgcc      4920
gtgcacttgt ttgtcgggtc atcttttcat gctttttttt gtcttggttg tgatgatgtg    4980
gtctggttgg gcggtcgttc tagatcggag tagaattctg tttcaaacta cctggtggat    5040
ttattaattt tggatctgta tgtgtgtgcc atacatattc atagttacga attgaagatg    5100
atggatggaa atatcgatct aggataggta tacatgttga tgcgggtttt actgatgcat    5160
atacagagat gcttttttgtt cgcttggttg tgatgatgtg gtgtggttgg gcggtcgttc   5220
attcgttcta gatcggagta gaatactgtt tcaaactacc tggtgtattt attaattttg    5280
gaactgtatg tgtgtgtcat acatcttcat agttacgagt ttaagatgga tggaaatatc    5340
gatctaggat aggtatacat gttgatgtgg gttttactga tgcatataca tgatggcata    5400
tgcagcatct attcatatgc tctaaccttg agtacctatc tattataata aacaagtatg    5460
ttttataatt attttgatct tgatatactt ggatgatggc atatgcagca gctatatgtg    5520
gattttttta gccctgcctt catacgctat ttatttgctt ggtactgttt cttttgtcga    5580
tgctcaccct gttgtttggt gttacttctg caggtcgact ttaacttagc ctaggatcca    5640
cacgacacca tgtcccccga gcgccgcccc gtcgagatcc gccggccac cgccgccgac     5700
atggccgccg tgtgcgacat cgtgaaccac tacatcgaga cctccaccgt gaacttccgc    5760
accgagccgc agaccccgca ggagtggatc gacgacctgg agcgcctcca ggaccgctac    5820
ccgtggctcg tggccgaggt ggagggcgtg gtggccggca tcgcctacgc cggcccgtgg    5880
aaggcccgca acgcctacga ctggaccgtg gagtccaccg tgtacgtgtc ccaccgccac    5940
cagcgcctcg gcctcggctc cacccttctac acccacctcc tcaagagcat ggaggccag   6000
ggcttcaagt ccgtggtggc cgtgatcggc ctcccgaacg acccgtccgt gcgcctccac    6060
```

```
gaggccctcg gctacaccgc ccgcggcacc ctccgcgccg ccggctacaa gcacggcggc    6120
tggcacgacg tcggcttctg gcagcgcgac ttcgagctgc cggccccgcc gcgcccggtg    6180
cgcccggtga cgcagatctg agtcgaaacc tagacttgtc catcttctgg attggccaac    6240
ttaattaatg tatgaaataa aaggatgcac acatagtgac atgctaatca ctataatgtg    6300
ggcatcaaag ttgtgtgtta tgtgtaatta ctagttatct gaataaaaga gaaagagatc    6360
atccatattt cttatcctaa atgaatgtca cgtgtcttta taattctttg atgaaccaga    6420
tgcatttcat taaccaaatc catatacata taaatattaa tcatatataa ttaatatcaa    6480
ttgggttagc aaaacaaatc tagtctaggt gtgttttgcg aattgcggcc gccaccgcgg    6540
tggagctcga attcattccg attaatcgtg gcctcttgct cttcaggatg aagagctatg    6600
tttaaacgtg caagcgctac tagacaattc agtacattaa aaacgtccgc aatgtgttat    6660
taagttgtct aagcgtcaat ttggtttaca ccacaatata tcctgccacc agccagccaa    6720
cagctccccg accggcagct cggcacaaaa tcaccactcg atacaggcag cccatcagtc    6780
cgggacggcg tcagcgggag agccgttgta aggcggcaga cttttgctcat gttaccgatg    6840 ctattcggaa gaacggcaac taagctgccg ggtttgaaac acggatgatc tcgcggaggg    6900
tagcatgttg attgtaacga tgacagagcg ttgctgcctg tgatcaaata tcatctccct    6960
cgcagagatc cgaattatca gccttcttat tcatttctcg cttaaccgtg acaggctgtc    7020
gatcttgaga actatgccga cataatagga aatcgctgga taaagccgct gaggaagctg    7080
agtggcgcta tttctttaga agtgaacgtt gacgatcgtc gaccgtaccc cgatgaatta    7140
attcggacgt acgttctgaa cacagctgga tacttacttg ggcgattgtc atacatgaca    7200
tcaacaatgt acccgtttgt gtaaccgtct cttggaggtt cgtatgacac tagtggttcc    7260
cctcagcttg cgactagatg ttgaggccta acattttatt agagagcagg ctagttgctt    7320
agatacatga tcttcaggcc gttatctgtc agggcaagcg aaaattggcc atttatgacg    7380
accaatgccc cgcagaagct cccatctttg ccgccataga cgccgcgccc ccttttggg     7440 gtgtagaaca tccttttgcc agatgtggaa aagaagttcg ttgtcccatt gttggcaatg    7500
acgtagtagc cggcgaaagt gcgagaccca tttgcgctat atataagcct acgatttccg    7560
ttgcgactat tgtcgtaatt ggatgaacta ttatcgtagt tgctctcaga gttgtcgtaa    7620
tttgatggac tattgtcgta attgcttatg gagttgtcgt agttgcttgg agaaatgtcg    7680
tagttggatg gggagtagtc atagggaaga cgagcttcat ccactaaaac aattggcagg    7740
tcagcaagtg cctgccccga tgccatcgca agtacgaggc ttagaaccac cttcaacaga    7800
tcgcgcatag tcttccccag ctctctaacg cttgagttaa gccgcgccgc gaagcggcgt    7860
cggcttgaac gaattgttag acattatttg ccgactacct tggtgatctc gcctttcacg    7920
tagtgaacaa attcttccaa ctgatctgcg cgcgaggcca agcgatcttc ttgtccaaga    7980
taagcctgcc tagcttcaag tatgacgggc tgatactggg ccggcaggcg ctccattgcc    8040
cagtcggcag cgacatcctt cggcgcgatt ttgccggtta ctgcgctgta ccaaatgcgg    8100
gacaacgtaa gcactacatt tcgctcatcg ccagcccagt cgggcggcga gttccatagc    8160
gttaaggttt catttagcgc ctcaaataga tcctgttcag gaaccggatc aaagagttcc    8220
tccgccgctg gacctaccaa ggcaacgcta tgttctcttg cttttgtcag caagatagcc    8280
agatcaatgt cgatcgtggc tggctcgaag atacctgcaa gaatgtcatt gcgctgccat    8340
tctccaaatt gcagttcgcg cttagctgga taacgccacg gaatgatgtc gtcgtgcaca    8400
acaatggtga cttctacagc gcggagaatc tcgctctctc caggggaagc cgaagtttcc    8460
```

```
aaaaggtcgt tgatcaaagc tcgccgcgtt gtttcatcaa gccttacagt caccgtaacc    8520
agcaaatcaa tatcactgtg tggcttcagg ccgccatcca ctgcggagcc gtacaaatgt    8580
acggccagca acgtcggttc gagatggcgc tcgatgacgc caactacctc tgatagttga    8640
gtcgatactt cggcgatcac cgcttccctc atgatgttta actcctgaat taagccgcgc    8700
cgcgaagcgg tgtcggcttg aatgaattgt taggcgtcat cctgtgctcc cgagaaccag    8760
taccagtaca tcgctgtttc gttcgagact tgaggtctag ttttatacgt gaacaggtca    8820
atgccgccga gagtaaagcc acattttgcg tacaaattgc aggcaggtac attgttcgtt    8880
tgtgtctcta atcgtatgcc aaggagctgt ctgcttagtg cccactttt cgcaaattcg    8940 atgagactgt gcgcgactcc tttgcctcgg tgcgtgtgcg acacaacaat gtgttcgata    9000
gaggctagat cgttccatgt tgagttgagt tcaatcttcc cgacaagctc ttggtcgatg    9060
aatgcgccat agcaagcaga gtcttcatca gagtcatcat ccgagatgta atccttccgg    9120
taggggctca cacttctggt agatagttca aagccttggt cggataggtg cacatcgaac    9180
acttcacgaa caatgaaatg gttctcagca tccaatgttt ccgccacctg ctcagggatc    9240
accgaaatct tcatatgacg cctaacgcct ggcacagcgg atcgcaaacc tggcgcggct    9300
tttggcacaa aaggcgtgac aggtttgcga atccgttgct gccacttgtt aaccctttg    9360 ccagatttgg taactataat ttatgttaga ggcgaagtct tgggtaaaaa ctggcctaaa    9420
attgctgggg atttcaggaa agtaaacatc accttccggc tcgatgtcta ttgtagatat    9480
atgtagtgta tctacttgat cgggggatct gctgcctcgc gcgtttcggt gatgacggtg    9540
aaaacctctg acacatgcag ctcccggaga cggtcacagc ttgtctgtaa gcggatgccg    9600
ggagcagaca agcccgtcag ggcgcgtcag cgggtgttgg cgggtgtcgg ggcgcagcca    9660
tgacccagtc acgtagcgat agcggagtgt atactggctt aactatgcgg catcagagca    9720
gattgtactg agagtgcacc atatgcggtg tgaaataccg cacagatgcg taaggagaaa    9780
ataccgcatc aggcgctctt ccgcttcctc gctcactgac tcgctgcgct cggtcgttcg    9840
gctgcggcga gcggtatcag ctcactcaaa ggcggtaata cggttatcca cagaatcagg    9900
ggataacgca ggaaagaaca tgtgagcaaa aggccagcaa aaggccagga accgtaaaaa    9960
ggccgcgttg ctggcgtttt tccataggct ccgcccccct gacgagcatc acaaaaatcg    10020
acgctcaagt cagaggtggc gaaacccgac aggactataa agataccagg cgtttccccc    10080
tggaagctcc ctcgtgcgct ctcctgttcc gaccctgccg cttaccggat acctgtccgc    10140
ctttctccct tcgggaagcg tggcgctttc tcatagctca cgctgtaggt atctcagttc    10200
ggtgtaggtc gttcgctcca agctgggctg tgtgcacgaa ccccccgttc agcccgaccg    10260
ctgcgcctta tccggtaact atcgtcttga gtccaacccg gtaagacacg acttatcgcc    10320
actggcagca gccactggta acaggattag cagagcgagg tatgtaggcg gtgctacaga    10380
gttcttgaag tggtggccta actacggcta cactagaagg acagtatttg gtatctgcgc    10440
tctgctgaag ccagttacct tcggaaaaag agttggtagc tcttgatccg gcaaacaaac    10500
caccgctggt agcggtggtt ttttgtttg caagcagcag attacgcgca gaaaaaagg    10560 atctcaagaa gatcctttga tcttttctac ggggtctgac gctcagtgga acgaaaactc    10620
acgttaaggg attttggtca tgagattatc aaaaaggatc ttcacctaga tccttttaaa    10680
ttaaaaatga agttttaaat caatctaaag tatatatgag taaacttggt ctgacagtta    10740
ccaatgctta atcagtgagg cacctatctc agcgatctgt ctatttcgtt catccatagt    10800
```

```
tgcctgactc cccgtcgtgt agataactac gatacgggag ggcttaccat ctggccccag    10860
tgctgcaatg ataccgcgag acccacgctc accggctcca gatttatcag caataaacca    10920
gccagccgga agggccgagc gcagaagtgg tcctgcaact ttatccgcct ccatccagtc    10980
tattaattgt tgccgggaag ctagagtaag tagttcgcca gttaatagtt tgcgcaacgt    11040
tgttgccatt gctgcagggg ggggggggg ggggacttc cattgttcat ccacggaca      11100
aaaacagaga aaggaaacga cagaggccaa aaagcctcgc tttcagcacc tgtcgtttcc    11160
tttcttttca gagggtattt aaataaaaa cattaagtta tgacgaagaa gaacggaaac     11220
gccttaaacc ggaaaatttt cataaatagc gaaaacccgc gaggtcgccg cccgtaacc     11280
tacctgtcgg atcaccggaa aggacccgta aagtgataat gattatcatc tacatatcac    11340
aacgtgcgtg gaggccatca aaccacgtca ataatcaat tatgacgcag gtatcgtatt     11400
aattgatctg catcaactta acgtaaaaac aacttcagac aatacaaatc agcgacactg    11460
aatacgggc aacctcatgt ccccccccc ccccccctg caggcatcgt ggtgtcacgc       11520
tcgtcgtttg gtatggcttc attcagctcc ggttcccaac gatcaaggcg agttacatga    11580
tcccccatgt tgtgcaaaaa agcggttagc tccttcggtc ctccgatcgt tgtcagaagt    11640
aagttggccg cagtgttatc actcatggtt atggcagcac tgcataattc tcttactgtc    11700
atgccatccg taagatgctt ttctgtgact ggtgagtact caaccaagtc attctgagaa    11760
tagtgtatgc ggcgaccgag ttgctcttgc ccggcgtcaa cacgggataa taccgcgcca    11820
catagcagaa ctttaaaagt gctcatcatt ggaaaacgtt cttcggggcg aaaactctca    11880
aggatcttac cgctgttgag atccagttcg atgtaaccca ctcgtgcacc caactgatct    11940
tcagcatctt ttactttcac cagcgtttct gggtgagcaa aaacaggaag gcaaaatgcc    12000
gcaaaaaagg gaataagggc gacacggaaa tgttgaatac tcatactctt cctttttcaa    12060
tattattgaa gcatttatca gggttattgt ctcatgagcg gatacatatt tgaatgtatt    12120
tagaaaaata aacaaatagg ggttccgcgc acatttcccc gaaaagtgcc acctgacgtc    12180
taagaaacca ttattatcat gacattaacc tataaaaata ggcgtatcac gaggcccttt    12240
cgtcttcaag aattcggagc ttttgccatt ctcaccggat tcagtcgtca ctcatggtga    12300
tttctcactt gataaccttat ttttgacga ggggaaatta ataggttgta ttgatgttgg    12360
acgagtcgga atcgcagacc gataccagga tcttgccatc ctatggaact gcctcggtga    12420
gttttctcct tcattacaga acggcttttt tcaaaaatat ggtattgata atcctgatat    12480
gaataaattg cagtttcatt tgatgctcga tgagttttte taatcagaat tggttaattg    12540
gttgtaacac tggcagagca ttacgctgac ttgacgggac ggcggctttg ttgaataaat    12600
cgaacttttg ctgagttgaa ggatcagatc acgcatcttc ccgacaacgc agaccgttcc    12660
gtggcaaagc aaaagttcaa aatcaccaac tggtccacct acaacaaagc tctcatcaac    12720
cgtggctccc tcactttctg gctggatgat ggggcgattc aggcctggta tgagtcagca    12780
acaccttctt cacgaggcag acctcagcgc cagaaggccg ccagagaggc cgagcgcggc    12840
cgtgaggctt ggacgctagg gcagggcatg aaaaagcccg tagcgggctg ctacgggcgt    12900
ctgacgcgt ggaaagggg aggggatgtt gtctacatgg ctctgctgta gtgagtgggt     12960
tgcgctccgg cagcggtcct gatcaatcgt caccctttct cggtccttca acgttcctga    13020
caacgagcct ccttttcgcc aatccatcga caatcaccgc gagtccctgc tcgaacgctg    13080
cgtccggacc ggcttcgtcg aaggcgtcta tcgcggcccg caacagcggc gagagcgag     13140
cctgttcaac ggtgccgccg cgctcgccgg catcgctgtc gccggcctgc tcctcaagca    13200
```

```
cggccccaac agtgaagtag ctgattgtca tcagcgcatt gacggcgtcc ccggccgaaa   13260
aacccgcctc gcagaggaag cgaagctgcg cgtcggccgt ttccatctgc ggtgcgcccg   13320
gtcgcgtgcc ggcatggatg cgcgcgccat cgcggtaggc gagcagcgcc tgcctgaagc   13380
tgcgggcatt cccgatcaga aatgagcgcc agtcgtcgtc ggctctcggc accgaatgcg   13440
tatgattctc cgccagcatg gcttcggcca gtgcgtcgag cagcgcccgc ttgttcctga   13500
agtgccagta aagcgccggc tgctgaaccc ccaaccgttc cgccagtttg cgtgtcgtca   13560
gaccgtctac gccgacctcg ttcaacaggt ccagggcggc acggatcact gtattcggct   13620
gcaactttgt catgcttgac actttatcac tgataaacat aatatgtcca ccaacttatc   13680
agtgataaag aatccgcgcg ttcaatcgga ccagcggagg ctggtccgga ggccagacgt   13740
gaaacccaac atacccctga tcgtaattct gagcactgtc gcgctcgacg ctgtcggcat   13800
cggcctgatt atgccggtgc tgccgggcct cctgcgcgat ctggttcact cgaacgacgt   13860
caccgcccac tatggcattc tgctggcgct gtatgcgttg gtgcaatttg cctgcgcacc   13920
tgtgctgggc gcgctgtcgg atcgtttcgg gcggcggcca atcttgctcg tctcgctggc   13980
cggcgccact gtcgactacg ccatcatggc gacagcgcct ttccttt ggg ttctctatat   14040 cgggcggatc gtggccggca tcaccggggc gactggggcg gtagccggcg cttatattgc   14100
cgatatcact gatggcgatg agcgcgcgcg gcacttcggc ttcatgagcg cctgtttcgg   14160
gttcgggatg gtcgcgggac ctgtgctcgg tgggctgatg ggcggtttct ccccccacgc   14220
tccgttcttc gccgcggcag ccttgaacgg cctcaatttc ctgacgggct gtttcctttt   14280
gccggagtcg cacaaaggcg aacgccggcc gttacgccgg gaggctctca acccgctcgc   14340
ttcgttccgg tgggcccggg gcatgaccgt cgtcgccgcc ctgatggcgg tcttcttcat   14400
catgcaactt gtcggacagg tgccggccgc gctttgggtc attttcggcg aggatcgctt   14460
tcactgggac gcgaccacga tcggcatttc gcttgccgca tttggcattc tgcattcact   14520
cgcccaggca atgatcaccg gccctgtagc cgcccggctc ggcgaaaggc gggcactcat   14580
gctcggaatg attgccgacg gcacaggcta catcctgctt gccttcgcga cacggggatg   14640
gatggcgttc ccgatcatgg tcctgcttgc ttcgggtggc atcggaatgc cggcgctgca   14700
agcaatgttg tccaggcagg tggatgagga acgtcagggg cagctgcaag gctcactggc   14760
ggcgctcacc agcctgacct cgatcgtcgg acccctcctc ttcacggcga tctatgcggc   14820
ttctataaca acgtggaacg ggtgggcatg gattgcaggc gctgccctct acttgctctg   14880
cctgccggcg ctgcgtcgcg ggcttttggag cggcgcaggg caacgagccg atcgctgatc   14940
gtggaaacga taggcctatg ccatgcgggt caaggcgact tccggcaagc tatacgcgcc   15000
ctaggagtgc ggttgaaacg ttggcccagc cagatactcc cgatcacgag caggacgccg   15060
atgatttgaa gcgcactcag cgtctgatcc aagaacaacc atcctagcaa cacggcggtc   15120
cccgggctga gaaagcccag taaggaaaca actgtaggtt cgagtcgcga gatccccgg   15180 aaccaaagga agtaggttaa acccgctccg atcaggccga gccacgccag gccgagaaca   15240
ttggttcctg taggcatcgg gattggcgga tcaaacacta aagctactgg aacgagcaga   15300
agtcctccgg ccgccagttg ccaggcggta aggtgagca gaggcacggg aggttgccac   15360
ttgcgggtca gcacggttcc gaacgccatg gaaaccgccc ccgcaggcc cgctgcgacg   15420 ccgacaggat ctagcgctgc gtttggtgtc aacaccaaca gcgccacgcc cgcagttccg   15480
caaatagccc ccaggaccgc catcaatcgt atcgggctac ctagcagagc ggcagagatg   15540
```

```
aacacgacca tcagcggctg cacagcgcct accgtcgccg cgaccccgcc cggcaggcgg   15600
tagaccgaaa taaacaacaa gctccagaat agcgaaatat taagtgcgcc gaggatgaag   15660
atgcgcatcc accagattcc cgttggaatc tgtcggacga tcatcacgag caataaaccc   15720
gccggcaacg cccgcagcag cataccggcg acccctcggc ctcgctgttc gggctccacg   15780
aaaacgccgg acagatgcgc cttgtgagcg tccttgggcc cgtcctcctg tttgaagacc   15840
gacagcccaa tgatctcgcc gtcgatgtag gcgccgaatg ccacggcatc tcgcaaccgt   15900
tcagcgaacg cctccatggg cttttttctcc tcgtgctcgt aaacggaccc gaacatctct   15960
ggagctttct tcagggccga caatcggatc tcgcggaaat cctgcacgtc ggccgctcca   16020
agccgtcgaa tctgagcctt aatcacaatt gtcaatttta atcctctgtt tatcggcagt   16080
tcgtagagcg cgccgtgcgt cccgagcgat actgagcgaa gcaagtgcgt cgagcagtgc   16140
ccgcttgttc ctgaaatgcc agtaaagcgc tggctgctga acccccagcc ggaactgacc   16200
ccacaaggcc ctagcgtttg caatgcacca ggtcatcatt gacccaggcg tgttccacca   16260
ggccgctgcc tcgcaactct tcgcaggctt cgccgacctg ctcgcgccac ttcttcacgc   16320
gggtggaatc cgatccgcac atgaggcgga aggtttccag cttgagcggg tacggctccc   16380
ggtgcgagct gaaatagtcg aacatccgtc gggccgtcgg cgacagcttg cggtacttct   16440
cccatatgaa tttcgtgtag tggtcgccag caaacagcac gacgatttcc tcgtcgatca   16500
ggacctggca acgggacgtt ttcttgccac ggtccaggac gcggaagcgg tgcagcagcg   16560
acaccgattc caggtgccca acgcggtcgg acgtgaagcc catcgccgtc gcctgtaggc   16620
gcgacaggca ttcctcggcc ttcgtgtaat accggccatt gatcgaccag cccaggtcct   16680
ggcaaagctc gtagaacgtg aaggtgatcg gctcgccgat aggggtgcgc ttcgcgtact   16740
ccaacacctg ctgccacacc agttcgtcat cgtcggcccg cagctcgacg ccggtgtagg   16800
tgatcttcac gtccttgttg acgtggaaaa tgaccttgtt ttgcagcgcc tcgcgcggga   16860
ttttcttgtt gcgcgtggtg aacagggcag agcgggccgt gtcgtttggc atcgctcgca   16920
tcgtgtccgg ccacggcgca atatcgaaca aggaaagctg catttccttg atctgctgct   16980
tcgtgtgttt cagcaacgcg gcctgcttgg cctcgctgac ctgttttgcc aggtcctcgc   17040
cggcggtttt tcgcttcttg gtcgtcatag ttcctcgcgt gtcgatggtc atcgacttcg   17100
ccaaacctgc cgcctcctgt tcgagacgac gcgaacgctc cacggcggcc gatgcgcgg    17160 gcagggcagg gggagccagt tgcacgctgt cgcgctcgat cttggccgta gcttgctgga   17220
ccatcgagcc gacggactgg aaggtttcgc ggggcgcacg catgacggtg cggcttgcga   17280
tggtttcggc atcctcggcg gaaaacccg cgtcgatcag ttcttgcctg tatgccttcc    17340
ggtcaaacgt ccgattcatt caccctcctt gcgggattgc cccgactcac gccggggcaa   17400 tgtgcccta ttcctgattt gacccgcctg gtgccttggt gtccagataa tccaccttat     17460
cggcaatgaa gtcggtcccg tagaccgtct ggccgtcctt tcgtacttg gtattccgaa     17520 tcttgccctg cacgaatacc agcgaccct tgcccaaata cttgccgtgg gctcggcct     17580 gagagccaaa acacttgatg cggaagaagt cggtgcgctc ctgcttgtcg ccggcatcgt   17640
tgcgccactc ttcattaacc gctatatcga aaattgcttg cggcttgtta gaattgccat   17700
gacgtacctc ggtgtcacgg gtaagattac cgataaactg gaactgatta tggctcatat   17760
cgaaagtctc cttgagaaag gagactctag tttagctaaa cattggttcc gctgtcaaga   17820
actttagcgg ctaaaatttt gcgggccgcg accaaaggtg cgaggggcgg cttccgctgt   17880
gtacaaccag atatttttca ccaacatcct tcgtctgctc gatgagcggg gcatgacgaa   17940
```

```
acatgagctg tcggagaggg caggggtttc aatttcgttt ttatcagact taaccaacgg   18000
taaggccaac ccctcgttga aggtgatgga ggccattgcc gacgccctgg aaactcccct   18060
acctcttctc ctggagtcca ccgaccttga ccgcgaggca ctcgcggaga ttgcgggtca   18120
tcctttcaag agcagcgtgc cgcccggata cgaacgcatc agtgtggttt tgccgtcaca   18180
taaggcgttt atcgtaaaga aatggggcga cgacacccga aaaagctgc gtggaaggct    18240
ctgacgccaa gggttagggc ttgcacttcc ttctttagcc gctaaaacgg cccttctct    18300
gcgggccgtc ggctcgcgca tcatatcgac atcctcaacg aagccgtgc cgcgaatggc    18360
atcgggcggg tgcgctttga cagttgtttt ctatcagaac ccctacgtcg tgcggttcga   18420
ttagctgttt gtcttgcagg ctaaacactt tcggtatatc gtttgcctgt gcgataatgt   18480
tgctaatgat ttgttgcgta ggggttactg aaaagtgagc gggaaagaag agtttcagac   18540
catcaaggag cgggccaagc gcaagctgga acgcgacatg ggtgcggacc tgttggccgc   18600
gctcaacgac ccgaaaaccg ttgaagtcat gctcaacgcg gacggcaagg tgtggcacga   18660
acgccttggc gagccgatgc ggtacatctg cgacatgcgg cccagccagt cgcaggcgat   18720
tatagaaacg gtgccggat tccacggcaa agaggtcacg cggcattcgc ccatcctgga    18780
aggcgagttc cccttggatg gcagccgctt tgccggccaa ttgccgccgg tcgtggccgc   18840
gccaaccttt gcgatccgca agcgcgcggt cgccatcttc acgctggaac agtacgtcga   18900
ggcgggcatc atgacccgcg agcaatacga ggtcattaaa agcgccgtcg cggcgcatcg   18960
aaacatcctc gtcattggcg gtactggctc gggcaagacc acgctcgtca acgcgatcat   19020
caatgaaatg gtcgccttca acccgtctga gcgcgtcgtc atcatcgagg acaccggcga   19080
aatccagtgc gccgcagaga acgccgtcca ataccacacc agcatcgacg tctcgatgac   19140
gctgctgctc aagacaacgc tgcgtatgcg ccccgaccgc atcctggtcg gtgaggtacg   19200
tggcccgaa gccctttgatc tgttgatggc ctggaacacc gggcatgaag gaggtgccgc    19260
caccctgcac gcaaacaacc ccaaagcggg cctgagccgg ctcgccatgc ttatcagcat   19320
gcacccggat tcaccgaaac ccattgagcg gctgattggc gaggcggttc atgtggtcgt   19380
ccatatcgcc aggacccta gcggccgtcg agtgcaagaa attctcgaag ttcttggtta    19440
cgagaacggc cagtacatca ccaaaaccct gtaaggagta tttccaatga caacggctgt   19500
tccgttccgt ctgaccatga atcgcggcat tttgttctac cttgccgtgt tcttcgttct   19560
cgctctcgcg ttatccgcgc atccggcgat ggcctcggaa ggcaccggcg gcagcttgcc   19620
atatgagagc tggctgacga acctgcgcaa ctccgtaacc ggcccggtgg ccttcgcgct   19680
gtccatcatc ggcatcgtcg tcgccggcgg cgtgctgatc ttcggcggcg aactcaacgc   19740
cttcttccga accctgatct tcctggttct ggtgatggcc ctgctggtcg gcgcgcagaa   19800
cgtgatgagc accttcttcg gtcgtggtgc cgaaatcgcg ccctcggca acggggcgct    19860
gcaccaggtg caagtcgcgg cggcggatgc cgtgcgtgcg gtagcggctg gacggctcgc   19920
ctaatcatgg ctctgcgcac gatccccatc cgtcgcgcag gcaaccgaga aaacctgttc   19980
atgggtggtg atcgtgaact ggtgatgttc tcgggcctga tggcgtttgc gctgattttc   20040
agcgcccaag agctgcgggc caccgtggtc ggtctgatcc tgtggttcgg ggcgctctat   20100
gcgttccgaa tcatggcgaa ggccgatccg aagatgcggt tcgtgtacct gcgtcaccgc   20160
cggtacaagc cgtattaccc ggcccgctcg acccgttcc gcgagaacac caatagccaa    20220
gggaagcaat accgatgatc caagcaattg cgattgcaat cgcgggcctc ggcgcgcttc   20280
```

```
tgttgttcat cctctttgcc cgcatccgcg cggtcgatgc cgaactgaaa ctgaaaaagc    20340
atcgttccaa ggacgccggc ctggccgatc tgctcaacta cgccgctgtc gtcgatgacg    20400
gcgtaatcgt gggcaagaac ggcagcttta tggctgcctg gctgtacaag ggcgatgaca    20460
acgcaagcag caccgaccag cagcgcgaag tagtgtccgc ccgcatcaac caggccctcg    20520
cgggcctggg aagtgggtgg atgatccatg tggacgccgt gcggcgtcct gctccgaact    20580
acgcggagcg gggcctgtcg gcgttccctg accgtctgac ggcagcgatt gaagaagagc    20640
gctcggtctt gccttgctcg tcggtgatgt acttcaccag ctccgcgaag tcgctcttct    20700
tgatggagcg catggggacg tgcttggcaa tcacgcgcac cccccggccg ttttagcggc    20760
taaaaaagtc atggctctgc cctcgggcgg accacgccca tcatgacctt gccaagctcg    20820
tcctgcttct cttcgatctt cgccagcagg gcgaggatcg tggcatcacc gaaccgcgcc    20880
gtgcgcgggt cgtcggtgag ccagagtttc agcaggccgc ccaggcggcc caggtcgcca    20940
ttgatgcggg ccagctcgcg gacgtgctca tagtccacga cgcccgtgat tttgtagccc    21000
tggccgacgg ccagcaggta ggccgacagg ctcatgccgg ccgccgccgc cttttcctca    21060
atcgctcttc gttcgtctgg aaggcagtac accttgatag gtgggctgcc cttcctggtt    21120
ggcttggttt catcagccat ccgcttgccc tcatctgtta cgccggcggt agccggccag    21180
cctcgcagag caggattccc gttgagcacc gccaggtgcg aataagggac agtgaagaag    21240
gaacacccgc tcgcgggtgg gcctacttca cctatcctgc ccggctgacg ccgttggata    21300
caccaaggaa agtctacacg aacccttggg caaaatcctg tatatcgtgc gaaaaaggat    21360
ggatataccg aaaaaatcgc tataatgacc ccgaagcagg gttatgcagc ggaaaagcgc    21420
tgcttccctg ctgttttgtg gaatatctac cgactggaaa caggcaaatg caggaaatta    21480
ctgaactgag gggacaggcg agagacgatg ccaaagagct acaccgacga gctggccgag    21540
tgggttgaat cccgcgcggc caagaagcgc cggcgtgatg aggctgcggt tgcgttcctg    21600
gcggtgaggc cggatgtcga ggcggcgtta gcgtccggct atgcgctcgt caccatttgg    21660
gagcacatgc gggaaacggg gaaggtcaag ttctcctacg agacgttccg ctcgcacgcc    21720
aggcggcaca tcaaggccaa gcccgccgat gtgcccgcac cgcaggccaa ggctgcggaa    21780
cccgcgccgg cacccaagac gccggagcca cggcggccga agcaggggg caaggctgaa    21840
aagccggccc ccgctgcggc cccgaccggc ttcaccttca acccaacacc ggacaaaaag    21900
gatctactgt aatggcgaaa attcacatgg ttttgcaggg caagggcggg gtcggcaagt    21960
cggccatcgc cgcgatcatt gcgcagtaca agatggacaa ggggcagaca cccttgtgca    22020
tcgacaccga cccggtgaac gcgacgttcg agggctacaa ggccctgaac gtccgccggc    22080
tgaacatcat ggccggcgac gaaattaact cgcgcaactt cgacaccctg tcgagctga    22140
ttgcgccgac caaggatgac gtggtgatcg acaacggtgc cagctcgttc gtgcctctgt    22200
cgcattacct catcagcaac caggtgccgg ctctgctgca agaaatgggg catgagctgg    22260
tcatccatac cgtcgtcacc ggcggccagg ctctcctgga cacggtgagc ggcttcgccc    22320
agctcgccag ccagttcccg gccgaagcgc ttttcgtggt ctggctgaac ccgtattggg    22380
ggcctatcga gcatgagggc aagagctttg agcagatgaa ggcgtacacg gccaacaagg    22440
cccgcgtgtc gtccatcatc cagattccgg ccctcaagga agaaacctac ggccgcgatt    22500
tcagcgacat gctgcaagag cggctgacgt tcgaccaggc gctggccgat gaatcgctca    22560
cgatcatgac gcgcaacgc ctcaagatcg tgcggcgcgg cctgtttgaa cagctcgacg    22620
cggcggccgt gctatgagcg accagattga agagctgatc cgggagattg cggccaagca    22680
```

```
cggcatcgcc gtcggccgcg acgacccggt gctgatcctg cataccatca acgcccggct   22740
catggccgac agtgcggcca agcaagagga aatccttgcc gcgttcaagg aagagctgga   22800
agggatcgcc catcgttggg gcgaggacgc caaggccaaa gcggagcgga tgctgaacgc   22860
ggccctggcg gccagcaagg acgcaatggc gaaggtaatg aaggacagcg ccgcgcaggc   22920
ggccgaagcg atccgcaggg aaatcgacga cggccttggc cgccagctcg cggccaaggt   22980
cgcggacgcg cggcgcgtgg cgatgatgaa catgatcgcc ggcggcatgg tgttgttcgc   23040
ggccgccctg gtggtgtggg cctcgttatg aatcgcagag gcgcagatga aaagcccgg    23100 cgttgccggg ctttgttttt gcgttagctg ggcttgtttg acaggcccaa gctctgactg   23160
cgcccgcgct cgcgctcctg ggcctgtttc ttctcctgct cctgcttgcg catcagggcc   23220
tggtgccgtc gggctgcttc acgcatcgaa tcccagtcgc cggccagctc gggatgctcc   23280
gcgcgcatct tgcgcgtcgc cagttcctcg atcttgggcg cgtgaatgcc catgccttcc   23340
ttgatttcgc gcaccatgtc cagccgcgtg tgcagggtct gcaagcgggc ttgctgttgg   23400
gcctgctgct gctgccaggc ggcctttgta cgcggcaggg acagcaagcc ggggcattg    23460 gactgtagct gctgcaaacg cgcctgctga cggtctacga gctgttctag gcggcctcg    23520 atgcgctcca cctggtcatg cttttgcctgc acgtagagcg caagggtctg ctggtaggtc   23580
tgctcgatgg gcgcggattc taagagggcc tgctgttccg tctcggcctc ctgggccgcc   23640
tgtagcaaat cctcgccgct gttgccgctg gactgcttta ctgccgggga ctgctgttgc   23700
cctgctcgcg ccgtcgtcgc agttcggctt gcccccactc gattgactgc ttcatttcga   23760
gccgcagcga tgcgatctcg gattgcgtca acggacgggg cagcgcggag gtgtccggct   23820
tctccttggg tgagtcggtc gatgccatag ccaaaggttt ccttccaaaa tgcgtccatt   23880
gctggaccgt gtttctcatt gatgcccgca agcatcttcg gcttgaccgc caggtcaagc   23940
gcgccttcat gggcggtcat gacgacgcc gccatgacct tgccgccgtt gttctcgatg    24000
tagccgcgta atgaggcaat ggtgccgccc atcgtcagcg tgtcatcgac aacgatgtac   24060
ttctggccgg ggatcacctc cccctcgaaa gtcgggttga acgccaggcg atgatctgaa   24120
ccggctccgg ttcgggcgac cttctcccgc tgcacaatgt ccgtttcgac ctcaaggcca   24180
aggcggtcgg ccagaacgac cgccatcatg gccggaatct tgttgttccc cgccgcctcg   24240
acggcgagga ctgaacgat gcggggcttg tcgtcgccga tcagcgtctt gagctgggca    24300
acagtgtcgt ccgaaatcag gcgctcgacc aaattaagcg ccgcttccgc gtcgccctgc   24360
ttcgcagcct ggtattcagg ctcgttggtc aaagaaccaa ggtcgccgtt gcgaaccacc   24420
ttcgggaagt ctccccacgg tgcgcgctcg gctctgctgt agctgctcaa gacgcctccc   24480
tttttagccg ctaaaactct aacgagtgcg cccgcgactc aacttgacgc tttcggcact   24540
tacctgtgcc ttgccacttg cgtcataggt gatgcttttc gcactccgga tttcaggtac   24600
tttatcgaaa tctgaccggg cgtgcattac aaagttcttc cccacctgtt ggtaaatgct   24660
gccgctatct gcgtggacga tgctgccgtc gtggcgctgc gacttatcgg ccttttgggc   24720
catatagatg ttgtaaatgc caggtttcag ggccccggct ttatctacct tctggttcgt   24780
ccatgcgcct tggttctcgg tctggacaat tctttgccca ttcatgacca ggaggcggtg   24840
tttcattggg tgactcctga cggttgcctc tggtgttaaa cgtgtcctgg tcgcttgccg   24900
gctaaaaaaa agccgacctc ggcagttcga ggccggcttt ccctagagcc gggcgcgtca   24960
aggttgttcc atctattttta gtgaactgcg ttcgatttat cagttacttt cctcccgctt   25020
```

```
tgtgtttcct cccactcgtt tccgcgtcta gccgacccct caacatagcg gcctcttctt    25080
gggctgcctt tgcctcttgc cgcgcttcgt cacgctcggc ttgcaccgtc gtaaagcgct    25140
cggcctgcct ggccgcctct tgcgccgcca acttcctttg ctcctggtgg gcctcggcgt    25200
cggcctgcgc cttcgctttc accgctgcca actccgtgcg caaactctcc gcttcgcgcc    25260
tggtggcgtc gcgctcgccg cgaagcgcct gcatttcctg gttggccgcg tccagggtct    25320
tgcggctctc ttctttgaat gcgcgggcgt cctggtgagc gtagtccagc tcggcgcgca    25380
gctcctgcgc tcgacgctcc acctcgtcgg cccgctgcgt cgccagcgcg gcccgctgct    25440
cggctcctgc cagggcggtg cgtgcttcgg ccagggcttg ccgctggcgt gcggccagct    25500
cggccgcctc ggcggcctgc tgctctagca atgtaacgcg cgcctgggct tcttccagct    25560
cgcgggcctg cgcctcgaag gcgtcggcca gctccccgcg cacggcttcc aactcgttgc    25620
gctcacgatc ccagccggct tgcgctgcct gcaacgattc attggcaagg gcctgggcgg    25680
cttgccagag ggcggccacg gcctggttgc cggcctgctg caccgcgtcc ggcacctgga    25740
ctgccagcgg ggcggcctgc gccgtgcgct ggcgtcgcca ttcgcgcatg ccggcgctgg    25800
cgtcgttcat gttgacgcgg gcggccttac gcactgcatc cacggtcggg aagttctccc    25860
ggtcgccttg ctcgaacagc tcgtccgcag ccgcaaaaat gcggtcgcgc gtctctttgt    25920
tcagttccat gttggctccg gtaattggta agaataataa tactcttacc taccttatca    25980
gcgcaagagt ttagctgaac agttctcgac ttaacggcag gttttttagc ggctgaaggg    26040
caggcaaaaa aagccccgca cggtcggcgg gggcaagggg tcagcgggaa ggggattagc    26100
gggcgtcggg cttcttcatg cgtcggggcc gcgcttcttg ggatggagca cgacgaagcg    26160
cgcacgcgca tcgtcctcgg ccctatcggc ccgcgtcgcg gtcaggaact tgtcgcgcgc    26220
taggtcctcc ctggtgggca ccaggggcat gaactcggcc tgctcgatgt aggtccactc    26280
catgaccgca tcgcagtcga ggccgcgttc cttcaccgtc tcttgcaggt cgcggtacgc    26340
ccgctcgttg agcggctggt aacgggccaa ttggtcgtaa atggctgtcg gccatgagcg    26400
gcctttcctg ttgagccagc agccgacgac gaagccggca atgcaggccc ctggcacaac    26460
caggccgacg ccggggggcag gggatggcag cagctcgcca accaggaacc ccgccgcgat    26520
gatgccgatg ccggtcaacc agcccttgaa actatccggc cccgaaacac ccctgcgcat    26580
tgcctggatg ctgcgccgga tagcttgcaa catcaggagc cgtttctttt gttcgtcagt    26640
catggtccgc cctcaccagt tgttcgtatc ggtgtcggac gaactgaaat cgcaagagct    26700
gccggtatcg gtccagccgc tgtccgtgtc gctgctgccg aagcacgcg aggggtccgc    26760 gaacgccgca gacggcgtat ccggccgcag cgcatcgccc agcatggccc cggtcagcga    26820
gccgccggcc aggtagccca gcatggtgct gttggtcgcc ccggccacca gggccgacgt    26880
gacgaaatcg ccgtcattcc ctctggattg ttcgctgctc ggcggggcag tgcgccgcgc    26940
cggcggcgtc gtggatggct cgggttggct ggcctgcgac ggccggcgaa aggtgcgcag    27000
cagctcgtta tcgaccggct gcggcgtcgg ggccgccgcc ttgcgctgcg gtcggtgttc    27060
cttcttcggc tcgcgcagct tgaacagcat gatcgcggaa accagcagca acgccgcgcc    27120
tacgcctccc gcgatgtaga acagcatcgg attcattctt cggtcctcct tgtagcggaa    27180
ccgttgtctg tgcggcgcgg gtggcccgcg ccgctgtctt tggggatcag ccctcgatga    27240
gcgcgaccag tttcacgtcg gcaaggttcg cctcgaactc ctggccgtcg tcctcgtact    27300
tcaaccaggc atagccttcc gccggcggcc gacggttgag gataaggcgg gcagggcgct    27360
cgtcgtgctc gacctggacg atggcctttt tcagcttgtc cgggtccggc tccttcgcgc    27420
```

```
ccttttcctt ggcgtcctta ccgtcctggt cgccgtcctc gccgtcctgg ccgtcgccgg    27480
cctccgcgtc acgctcggca tcagtctggc cgttgaaggc atcgacggtg ttgggatcgc    27540
ggcccttctc gtccaggaac tcgcgcagca gcttgaccgt gccgcgcgtg atttcctggg    27600
tgtcgtcgtc aagccacgcc tcgacttcct ccgggcgctt cttgaaggcc gtcaccagct    27660
cgttcaccac ggtcacgtcg cgcacgcggc cggtgttgaa cgcatcggcg atcttctccg    27720
gcaggtccag cagcgtgacg tgctgggtga tgaacgccgg cgacttgccg atttccttgg    27780
cgatatcgcc tttcttcttg cccttcgcca gctcgcggcc aatgaagtcg gcaatttcgc    27840
gcggggtcag ctcgttgcgt tgcaggttct cgataacctg gtcggcttcg ttgtagtcgt    27900
tgtcgatgaa cgccgggatg gacttcttgc cggcccactt cgagccacgg tagcggcggg    27960
cgccgtgatt gatgatatag cggcccggct gctcctggtt ctcgcgcacc gaaatgggtg    28020
acttcacccc gcgctctttg atcgtggcac cgatttccgc gatgctctcc ggggaaaagc    28080
cggggttgtc ggccgtccgc ggctgatgcg gatcttcgtc gatcaggtcc aggtccagct    28140
cgatagggcc ggaaccgccc tgagacgccg caggagcgtc caggaggctc gacaggtcgc    28200
cgatgctatc caaccccagg ccggacggct gcgccgcgcc tgcggcttcc tgagcggccg    28260
cagcggtgtt tttcttggtg gtcttggctt gagccgcagt cattgggaaa tctccatctt    28320
cgtgaacacg taatcagcca gggcgcgaac ctctttcgat gccttgcgcg cggccgtttt    28380
cttgatcttc cagaccggca caccggatgc gagggcatcg gcgatgctgc tgcgcaggcc    28440
aacggtggcc ggaatcatca tcttggggta cgcggccagc agctcggctt ggtggcgcgc    28500
gtggcgcgga ttccgcgcat cgaccttgct gggcaccatg ccaaggaatt gcagcttggc    28560
gttcttctgg cgcacgttcg caatggtcgt gaccatcttc ttgatgccct ggatgctgta    28620
cgcctcaagc tcgatggggg acagcacata gtcgccgcg aagagggcgg ccgccaggcc    28680
gacgccaagg gtcggggccg tgtcgatcag gcacacgtcg aagccttggt tcgccagggc    28740
cttgatgttc gccccgaaca gctcgcgggc gtcgtccagc gacagccgtt cggcgttcgc    28800
cagtaccggg ttggactcga tgagggcgag gcgcgcggcc tggccgtcgc cggctgcggg    28860
tgcggtttcg gtccagccgc cggcaggac agcgccgaac agcttgcttg catgcaggcc    28920
ggtagcaaag tccttgagcg tgtaggacgc attgccctgg gggtccaggt cgatcacggc    28980
aacccgcaag ccgcgctcga aaagtcgaa ggcaagatgc acaagggtcg aagtcttgcc    29040
gacgccgcct ttctggttgg ccgtgaccaa agttttcatc gtttggtttc ctgttttttc    29100
ttggcgtccg cttcccactt ccggacgatg tacgcctgat gttccggcag aaccgccgtt    29160
acccgcgcgt accccctcggg caagttcttg tcctcgaacg cggcccacac gcgatgcacc    29220
gcttgcgaca ctgcgcccct ggtcagtccc agcgacgttg cgaacgtcgc ctgtggcttc    29280
ccatcgacta agacgccccg cgctatctcg atggtctgct gccccacttc cagcccctgg    29340
atcgcctcct ggaactggct ttcggtaagc cgtttcttca tggataacac ccataatttg    29400
ctccgcgcct tggttgaaca tagcggtgac agccgccagc acatgagaga gtttagcta    29460 aacatttctc gcacgtcaac acctttagcc gctaaaactc gtccttggcg taacaaaaca    29520
aaagcccgga aacgggcttt tcgtctcttg ccgcttatgg ctctgcaccc ggctccatca    29580
ccaacaggtc gcgcacgcgc ttcactcggt tgcggatcga cactgccagc caacaaagc    29640 cggttgccgc cgccgccagg atcgcgccga tgatgccggc cacaccggcc atcgcccacc    29700
aggtcgccgc cttccggttc cattcctgct ggtactgctt cgcaatgctg gacctcggct    29760
```

```
caccataggc tgaccgctcg atggcgtatg ccgcttctcc ccttggcgta aaacccagcg    29820
ccgcaggcgg cattgccatg ctgcccgccg cttccccgac cacgacgcgc gcaccaggct    29880
tgcggtccag accttcggcc acggcgagct gcgcaaggac ataatcagcc gccgacttgg    29940
ctccacgcgc ctcgatcagc tcttgcactc gcgcgaaatc cttggcctcc acggccgcca    30000
tgaatcgcgc acgcggcgaa ggctccgcag ggccggcgtc gtgatcgccg ccgagaatgc    30060
ccttcaccaa gttcgacgac acgaaaatca tgctgacggc tatcaccatc atgcagacgg    30120
atcgcacgaa cccgctgaat tgaacacgag cacggcaccc gcgaccacta tgccaagaat    30180
gcccaaggta aaaattgccg gccccgccat gaagtccgtg aatgcccga cggccgaagt     30240 gaagggcagg ccgccaccca ggccgccgcc ctcactgccc ggcacctggt cgctgaatgt    30300
cgatgccagc acctgcggca cgtcaatgct tccgggcgtc gcgctcgggc tgatcgccca    30360
tcccgttact gccccgatcc cggcaatggc aaggactgcc agcgctgcca ttttgggt      30420 gaggccgttc gcggccgagg ggcgcagccc ctgggggat gggaggcccg cgttagcggg     30480
ccgggagggt tcgagaaggg ggggcacccc ccttcggcgt gcgcggtcac gcgcacaggg    30540
cgcagccctg gttaaaaaca aggtttataa atattggttt aaaagcaggt taaaagacag    30600
gttagcggtg gccgaaaaac gggcggaaac ccttgcaaat gctggatttt ctgcctgtgg    30660
acagcccctc aaatgtcaat aggtgcgccc ctcatctgtc agcactctgc ccctcaagtg    30720
tcaaggatcg cgccctcat ctgtcagtag tcgcgcccct caagtgtcaa taccgcaggg     30780
cacttatccc caggcttgtc cacatcatct gtgggaaact cgcgtaaaat caggcgtttt    30840
cgccgatttg cgaggctggc cagctccacg tcgccggccg aaatcgagcc tgcccctcat    30900
ctgtcaacgc cgcgccgggt gagtcggccc ctcaagtgtc aacgtccgcc cctcatctgt    30960
cagtgagggc caagttttcc gcgaggtatc cacaacgccg gcggccgcgg tgtctcgcac    31020
acggcttcga cggcgtttct ggcgcgtttg cagggccata gacggccgcc agcccagcgg    31080
cgagggcaac cagcccggtg agcgtcggaa aggcgctgga agccccgtag cgacgcggag    31140
aggggcgaga caagccaagg gcgcaggctc gatgcgcagc acgacatagc cggttctcgc    31200
aaggacgaga atttccctgc ggtgcccctc aagtgtcaat gaaagtttcc aacgcgagcc    31260
attcgcgaga gccttgagtc cacgctagat gagagctttg ttgtaggtgg accagttggt    31320
gattttgaac ttttgctttg ccacggaacg gtctgcgttg tcgggaagat gcgtgatctg    31380
atccttcaac tcagcaaaag ttcgatttat tcaacaaagc cacgttgtgt ctcaaaatct    31440
ctgatgttac attgcacaag ataaaaatat atcatcatga acaataaaac tgtctgctta    31500
cataaacagt aatacaaggg gtgttatgag ccatattcaa cgggaaacgt cttgctcgac    31560
tctagagctc gttcctcgag aacggtacc tgcggggaag cttacaataa tgtgtgttgt     31620
taagtcttgt tgcctgtcat cgtctgactg actttcgtca taaatcccgg cctccgtaac    31680
ccagctttgg gcaagctcac ggatttgatc cggcggaacg ggaatatcga gatgccgggc    31740
tgaacgctgc agttccagct ttccctttcg ggacaggtac tccagctgat tgattatctg    31800
ctgaagggtc ttggttccac ctcctggcac aatgcgaatg attacttgag cgcgatcggg    31860
catccaattt tctcccgtca ggtgcgtggt caagtgctac aaggcacctt tcagtaacga    31920
gcgaccgtcg atccgtcgcc gggatacgga caaaatggag cgcagtagtc catcgagggc    31980
ggcgaaagcc tcgccaaaag caatacgttc atctcgcaca gcctccagat ccgatcgagg    32040
gtcttcggcg taggcagata gaagcatgga tacattgctt gagagtattc cgatggactg    32100
aagtatggct tccatctttt ctcgtgtgtc tgcatctatt tcgagaaagc ccccgatgcg    32160
```

```
gcgcaccgca acgcgaattg ccatactatc cgaaagtccc agcaggcgcg cttgatagga   32220
aaaggtttca tactcggccg atcgcagacg ggcactcacg accttgaacc cttcaacttt   32280
cagggatcga tgctggttga tggtagtctc actcgacgtg gctctggtgt gttttgacat   32340
agcttcctcc aaagaaagcg gaaggtctgg atactccagc acgaaatgtg cccgggtaga   32400
cggatggaag tctagccctg ctcaatatga aatcaacagt acatttacag tcaatactga   32460
atatacttgc tacatttgca attgtcttat aacgaatgtg aaataaaaat agtgtaacaa   32520
cgcttttact catcgataat cacaaaaaca tttatacgaa caaaaataca aatgcactcc   32580
ggtttcacag dataggcggg atcagaatat gcaacttttg acgttttgtt ctttcaaagg   32640
gggtgctggc aaaaccaccg cactcatggg cctttgcgct gctttggcaa atgacggtaa   32700
acgagtggcc ctctttgatg ccgacgaaaa ccggcctctg acgcgatgga gagaaaacgc   32760
cttacaaagc agtactggga tcctcgctgt gaagtctatt ccgccgacga aatgcccctt   32820
cttgaagcag cctatgaaaa tgccgagctc gaaggatttg attatgcgtt ggccgatacg   32880
cgtggcggct cgagcgagct caacaacaca atcatcgcta gctcaaacct gcttctgatc   32940
cccaccatgc taacgccgct cgacatcgat gaggcactat ctacctaccg ctacgtcatc   33000
gagctgctgt tgagtgaaaa tttggcaatt cctacagctg ttttgcgcca acgcgtcccg   33060
gtcggccgat tgacaacatc gcaacgcagg atgtcagaga cgctagagag ccttccagtt   33120
gtaccgtctc ccatgcatga aagagatgca tttgccgcga tgaaagaacg cggcatgttg   33180
catcttacat tactaaacac gggaactgat ccgacgatgc gcctcataga gaggaatctt   33240
cggattgcga tggaggaagt cgtggtcatt tcgaaactga tcagcaaaat cttggaggct   33300
tgaagatggc aattcgcaag cccgcattgt cggtcggcga agcacggcgg cttgctggtg   33360
ctcgacccga gatccaccat cccaacccga cacttgttcc ccagaagctg gacctccagc   33420
acttgcctga aaaagccgac gagaaagacc agcaacgtga gcctctcgtc gccgatcaca   33480
tttacagtcc cgatcgacaa cttaagctaa ctgtggatgc ccttagtcca cctccgtccc   33540
cgaaaaagct ccaggttttt ctttcagcgc gaccgcccgc gcctcaagtg tcgaaaacat   33600
atgacaacct cgttcggcaa tacagtccct cgaagtcgct acaaatgatt ttaaggcgcg   33660
cgttggacga tttcgaaagc atgctggcag atggatcatt tcgcgtggcc ccgaaaagtt   33720
atccgatccc ttcaactaca gaaaaatccg ttctcgttca gacctcacgc atgttcccgg   33780
ttgcgttgct cgaggtcgct cgaagtcatt ttgatccgtt ggggttggag accgctcgag   33840 cttcggcca caagctggct accgccgcgc tcgcgtcatt cttgctgga gagagccat    33900 cgagcaattg gtgaagaggg acctatcgga acccctcacc aaatattgag tgtaggtttg   33960
aggccgctgg ccgcgtcctc agtcacccttt tgagccagat aattaagagc caaatgcaat   34020
tggctcaggc tgccatcgtc cccccgtgcg aaacctgcac gtccgcgtca aagaaataac   34080
cggcacctct tgctgttttt atcagttgag ggcttgacgg atccgcctca gtttgcggc   34140 gcagccgcaa aatgagaaca tctatactcc tgtcgtaaac ctcctcgtcg cgtactcgac   34200
tggcaatgag aagttgctcg cgcgatagaa cgtcgcgggg tttctctaaa aacgcgagga   34260
gaagattgaa ctcacctgcc gtaagtttca cctcaccgcc agcttcggac atcaagcgac   34320
gttgcctgag attaagtgtc cagtcagtaa aacaaaaaga ccgtcggtct tggagcgga   34380 caacgttggg gcgcacgcgc aaggcaaccc gaatgcgtgc aagaaactct ctcgtactaa   34440
acggcttagc gataaaatca cttgctccta gctcgagtgc aacaacttta tccgtctcct   34500
```

```
caaggcggtc gccactgata attatgattg aatatcaga ctttgccgcc agatttcgaa    34560
cgatctcaag cccatcttca cgacctaaat ttagatcaac aaccacgaca tcgaccgtcg    34620
cggaagagag tactctagtg aactgggtgc tgtcggctac cgcggtcact ttgaaggcgt    34680
ggatcgtaag gtattcgata ataagatgcc gcatagcgac atcgtcatcg ataagaagaa    34740
cgtgtttcaa cggctcacct ttcaatctaa aatctgaacc cttgttcaca gcgcttgaga    34800
aattttcacg tgaaggatgt acaatcatct ccagctaaat gggcagttcg tcagaattgc    34860
ggctgaccgc ggatgacgaa aatgcgaacc aagtatttca atttatgac aaaagttctc    34920
aatcgttgtt acaagtgaaa cgcttcgagg ttacagctac tattgattaa ggagatcgcc    34980
tatggtctcg ccccggcgtc gtgcgtccgc cgcgagccag atctcgccta cttcataaac    35040
gtcctcatag gcacggaatg gaatgatgac atcgatcgcc gtagagagca tgtcaatcag    35100
tgtgcgatct tccaagctag caccttgggc gctacttttg acaagggaaa acagtttctt    35160
gaatccttgg attggattcg cgccgtgtat tgttgaaatc gatcccggat gtcccgagac    35220
gacttcactc agataagccc atgctgcatc gtcgcgcatc tcgccaagca atatccggtc    35280
cggccgcata cgcagacttg cttggagcaa gtgctcggcg ctcacagcac ccagcccagc    35340
accgttcttg gagtagagta gtctaacatg attatcgtgt ggaatgacga gttcgagcgt    35400
atcttctatg gtgattagcc tttcctgggg ggggatggcg ctgatcaagg tcttgctcat    35460
tgttgtcttg ccgcttccgg tagggccaca tagcaacatc gtcagtcggc tgacgacgca    35520
tgcgtgcaga aacgcttcca aatcccgtt gtcaaaatgc tgaaggatag cttcatcatc    35580
ctgattttgg cgtttccttc gtgtctgcca ctggttccac ctcgaagcat cataacggga    35640
ggagacttct ttaagaccag aaacacgcga gcttggccgt cgaatggtca agctgacggt    35700
gcccgaggga acgtcggcg gcagacagat ttgtagtcgt tcaccaccag gaagttcagt    35760
ggcgcagagg gggttacgtg gtccgacatc ctgctttctc agcgcgcccg ctaaaatagc    35820
gatatcttca agatcatcat aagagacggg caaaggcatc ttggtaaaaa tgccggcttg    35880
gcgcacaaat gcctctccag gtcgattgat cgcaatttct tcagtcttcg ggtcatcgag    35940
ccattccaaa atcggcttca gaagaaagcg tagttgcgga tccacttcca tttacaatgt    36000
atcctatctc taagcggaaa tttgaattca ttaagagcgg cggttcctcc cccgcgtggc    36060
gccgccagtc aggcggagct ggtaaacacc aaagaaatcg aggtcccgtg ctacgaaaat    36120
ggaaacggtg tcaccctgat tcttcttcag ggttggcggt atgttgatgg ttgccttaag    36180
ggctgtctca gttgtctgct caccgttatt ttgaaagctg ttgaagctca tcccgccacc    36240
cgagctgccg gcgtaggtgc tagctgcctg gaaggcgcct tgaacaacac tcaagagcat    36300
agctccgcta aaacgctgcc agaagtggct gtcgaccgag cccggcaatc ctgagcgacc    36360
gagttcgtcc gcgcttggcg atgttaacga gatcatcgca tggtcaggtg tctcggcgcg    36420
atcccacaac acaaaaacgc gcccatctcc ctgttgcaag ccacgctgta tttcgccaac    36480
aacggtggtg ccacgatcaa gaagcacgat attgttcgtt gttccacgaa tatcctgagg    36540
caagacacac tttacatagc ctgccaaatt tgtgtcgatt gcggtttgca agatgcacgg    36600
aattattgtc ccttgcgtta ccataaaatc ggggtgcggc aagagcgtgg cgctgctggg    36660
ctgcagctcg gtgggtttca tacgtatcga caaatcgttc tcgccggaca cttcgccatt    36720
cggcaaggag ttgtcgtcac gcttgccttc ttgtcttcgg cccgtgtcgc cctgaatggc    36780
gcgtttgctc accccttgat cgccgctgct atatgcaaaa atcggtgttt cttccggccg    36840
tggctcatgc cgctccggtt cgcccctcgg cggtagagga gcagcaggct gaacagcctc    36900
```

```
ttgaaccgct ggaggatccg gcggcacctc aatcggagct ggatgaaatg gcttggtgtt    36960
tgttgcgatc aaagttgacg gcgatgcgtt ctcattcacc ttcttttggc gcccacctag    37020
ccaaatgagg cttaatgata acgcgagaac gacacctccg acgatcaatt tctgagaccc    37080
cgaaagacgc cggcgatgtt tgtcggagac cagggatcca gatgcatcaa cctcatgtgc    37140
cgcttgctga ctatcgttat tcatcccttc gcccccttca ggacgcgttt cacatcgggc    37200
ctcaccgtgc ccgtttgcgg cctttggcca acgggatcgt aagcggtgtt ccagatacat    37260
agtactgtgt ggccatccct cagacgccaa cctcgggaaa ccgaagaaat ctcgacatcg    37320 ctcccttaa ctgaatagtt ggcaacagct tccttgccat caggattgat ggtgtagatg     37380
gagggtatgc gtacattgcc cggaaagtgg aataccgtcg taaatccatt gtcgaagact    37440
tcgagtggca acagcgaacg atcgccttgg gcgacgtagt gccaattact gtccgccgca    37500
ccaagggctg tgacaggctg atccaataaa ttctcagctt tccgttgata ttgtgcttcc    37560
gcgtgtagtc tgtccacaac agccttctgt tgtgcctccc ttcgccgagc cgccgcatcg    37620 tcggcgggt aggcgaattg gacgctgtaa tagagatcgg gctgctcttt atcgaggtgg     37680
gacagagtct tggaacttat actgaaaaca taacggcgca tcccggagtc gcttgcggtt    37740
agcacgatta ctggctgagg cgtgaggacc tggcttgcct tgaaaaatag ataatttccc    37800
cgcggtaggg ctgctagatc tttgctattt gaaacggcaa ccgctgtcac cgtttcgttc    37860
gtggcgaatg ttacgaccaa agtagctcca accgccgtcg agaggcgcac cacttgatcg    37920
ggattgtaag ccaaataacg catgcgcgga tctagcttgc ccgccattgg agtgtcttca    37980
gcctccgcac cagtcgcagc ggcaaataaa catgctaaaa tgaaaagtgc ttttctgatc    38040
atggttcgct gtggcctacg tttgaaacgg tatcttccga tgtctgatag gaggtgacaa    38100
ccagacctgc cgggttggtt agtctcaatc tgccgggcaa gctggtcacc ttttcgtagc    38160
gaactgtcgc ggtccacgta ctcaccacag gcattttgcc gtcaacgacg agggtccttt    38220
tatagcgaat tgctgcgtg cttggagtta catcatttga agcgatgtgc tcgacctcca     38280
ccctgccgcg tttgccaaga atgacttgag gcgaactggg attgggatag ttgaagaatt    38340
gctggtaatc ctggcgcact gttggggcac tgaagttcga taccaggtcg taggcgtact    38400
gagcggtgtc ggcatcataa ctctcgcgca ggcgaacgta ctcccacaat gaggcgttaa    38460
cgacggcctc ctcttgagtt gcaggcaatc gcgagacaga cacctcgctg tcaacggtgc    38520
cgtccggccg tatccataga tatacgggca caagcctgct caacggcacc attgtggcta    38580
tagcgaacgc ttgagcaaca tttcccaaaa tcgcgatagc tgcgacagct gcaatgagtt    38640
tggagagacg tcgcgccgat ttcgctcgcg cggtttgaaa ggcttctact tccttatagt    38700
gctcggcaag gctttcgcgc gccactagca tggcatattc aggccccgtc atagcgtcca    38760
cccgaattgc cgagctgaag atctgacgga gtaggctgcc atcgcccac attcagcggg     38820 aagatcgggc ctttgcagct cgctaatgtg tcgtttgtct ggcagccgct caaagcgaca    38880
actaggcaca gcaggcaata cttcatagaa ttctccattg aggcgaattt tgcgcgacc     38940 tagcctcgct caacctgagc gaagcgacgg tacaagctgc tggcagattg ggttgcgccg    39000
ctccagtaac tgcctccaat gttgccgcg atcgccggca aagcgacaat gagcgcatcc     39060
cctgtcagaa aaaacatatc gagttcgtaa agaccaatga tcttggccgc ggtcgtaccg    39120
gcgaaggtga ttcaccaag cataagggtg agcgcagtcg cttcggttag gatgacgatc     39180
gttgccacga ggtttaagag gagaagcaag agaccgtagg tgataagttg cccgatccac    39240
```

```
ttagctgcga tgtcccgcgt gcgatcaaaa atatatccga cgaggatcag aggcccgatc    39300
gcgagaagca ctttcgtgag aattccaacg gcgtcgtaaa ctccgaaggc agaccagagc    39360
gtgccgtaaa ggacccactg tgccccttgg aaagcaagga tgtcctggtc gttcatcgga    39420
ccgatttcgg atgcgatttt ctgaaaaacg gcctgggtca cggcgaacat tgtatccaac    39480
tgtgccggaa cagtctgcag aggcaagccg gttacactaa actgctgaac aaagtttggg    39540
accgtctttt cgaagatgga aaccacatag tcttggtagt tagcctgccc aacaattaga    39600
gcaacaacga tggtgaccgt gatcacccga gtgataccgc tacgggtatc gacttcgccg    39660
cgtatgacta aaatacccctg aacaataatc aaagagtga cacaggcgat caatggcgca    39720
ctcaccgcct cctggatagt ctcaagcatc gagtccaagc ctgtcgtgaa ggctacatcg    39780
aagatcgtat gaatgccgt aaacggcgcc ggaatcgtga aattcatcga ttggacctga    39840
acttgactgg tttgtcgcat aatgttggat aaaatgagct cgcattcggc gaggatgcgg    39900
gcggatgaac aaatcgccca gccttagggg agggcaccaa agatgacagc ggtcttttga    39960
tgctccttgc gttgagcggc cgcctcttcc gcctcgtgaa ggccggcctg cgcggtagtc    40020
atcgttaata ggcttgtcgc ctgtacattt tgaatcattg cgtcatggat ctgcttgaga    40080
agcaaaccat tggtcacggt tgcctgcatg atattgcgag atcgggaaag ctgagcagac    40140
gtatcagcat tcgccgtcaa gcgtttgtcc atcgtttcca gattgtcagc cgcaatgcca    40200
gcgctgtttg cggaaccggt gatctgcgat cgcaacaggt ccgcttcagc atcactaccc    40260
acgactgcac gatctgtatc gctggtgatc gcacgtgccg tggtcgacat tggcattcgc    40320
ggcgaaaaca tttcattgtc taggtccttc gtcgaaggat actgattttt ctggttgagc    40380
gaagtcagta gtccagtaac gccgtaggcc gacgtcaaca tcgtaaccat cgctatagtc    40440
tgagtgagat tctccgcagt cgcgagcgca gtcgcgagcg tctcagcctc cgttgccggg    40500
tcgctaacaa caaactgcgc ccgcgcgggc tgaatatata gaaagctgca ggtcaaaact    40560
gttgcaataa gttgcgtcgt cttcatcgtt tcctaccttta tcaatcttct gcctcgtggt    40620
gacgggccat gaattcgctg agccagccag atgagttgcc ttcttgtgcc tcgcgtagtc    40680
gagttgcaaa gcgcaccgtg ttggcacgcc ccgaaagcac ggcgacatat tcacgcatat    40740
cccgcagatc aaattcgcag atgacgcttc cactttctcg tttaagaaga aacttacggc    40800
tgccgaccgt catgtcttca cggatcgcct gaaattcctt ttcggtacat ttcagtccat    40860
cgacataagc cgatcgatct gcggttggtg atggatagaa aatcttcgtc atacattgcg    40920
caaccaagct ggctcctagc ggcgattcca gaacatgctc tggttgctgc gttgccagta    40980
ttagcatccc gttgttttt cgaacggtca ggaggaattt gtcgacgaca gtcgaaaatt    41040
tagggtttaa caaataggcg cgaaactcat cgcagctcat cacaaaacgg cggccgtcga    41100
tcatggctcc aatccgatgc aggagatatg ctgcagcggg agcgcatact tcctcgtatt    41160
cgagaagatg cgtcatgtcg aagccggtaa tcgacggatc taactttact tcgtcaactt    41220
cgccgtcaaa tgcccagcca agcgcatggc cccggcacca gcgttggagc gcgctcctg    41280 cgccttcggc gggcccatgc aacaaaaatt cacgtaaccc cgcgattgaa cgcatttgtg    41340
gatcaaacga gagctgacga tggataccac ggaccgacg gcggttctct tccgagagaa    41400
tcccaccccg accatcactc tcgatgagag ccacgatcca ttcgcgcaga aaatcgtgtg    41460
aggctgctgt gtttttctagg ccacgcaacg gcgccaaccc gctgggtgtg cctctgtgaa    41520
gtgccaaata tgttcctcct gtggcgcgaa ccagcaattc gccaccccgg tccttgtcaa    41580
agaacacgac cgtacctgca cggtcgacca tgctctgttc gagcatggct agaacaaaca    41640
```

```
tcatgagcgt cgtcttaccc ctcccgatag gcccgaatat tgccgtcatg ccaacatcgt   41700
gctcatgcgg gatatagtcg aaaggcgttc cgccattggt acgaaatcgg gcaatcgcgt   41760
tgccccagtg gcctgagctg gcgccctctg gaaagttttc gaaagagaca aaccctgcga   41820
aattgcgtga agtgattgcg ccagggcgtg tgcgccactt aaaattcccc ggcaattggg   41880
accaataggc cgcttccata ccaatacctt cttggacaac cacggcacct gcatccgcca   41940
ttcgtgtccg agcccgcgcg cccctgtccc caagactatt gagatcgtct gcatagacgc   42000
aaaggctcaa atgatgtgag cccataacga attcgttgct cgcaagtgcg tcctcagcct   42060
cggataattt gccgatttga gtcacggctt tatcgccgga actcagcatc tggctcgatt   42120
tgaggctaag tttcgcgtgc gcttgcgggc gagtcaggaa cgaaaaactc tgcgtgagaa   42180
caagtggaaa atcgagggat agcagcgcgt tgagcatgcc cggccgtgtt tttgcagggt   42240
attcgcgaaa cgaatagatg gatccaacgt aactgtcttt tggcgttctg atctcgagtc   42300
ctcgcttgcc gcaaatgact ctgtcggtat aaatcgaagc gccgagtgag ccgctgacga   42360
ccggaaccgg tgtgaaccga ccagtcatga tcaaccgtag cgcttcgcca atttcggtga   42420
agagcacacc ctgcttctcg cggatgccaa gacgatgcag gccatacgct ttaagagagc   42480
cagcgacaac atgccaaaga tcttccatgt tcctgatctg gcccgtgaga tcgttttccc   42540 ttttccgct tagcttggtg aacctcctct ttaccttccc taaagccgcc tgtgggtaga   42600
caatcaacgt aaggaagtgt tcattgcgga ggagttggcc ggagagcacg cgctgttcaa   42660
aagcttcgtt caggctagcg gcgaaaacac tacggaagtg tcgcggcgcc gatgatggca   42720
cgtcggcatg acgtacgagg tgagcatata ttgacacatg atcatcagcg atattgcgca   42780
acagcgtgtt gaacgcacga caacgcgcat tgcgcatttc agtttcctca agctcgaatg   42840
caacgccatc aattctcgca atggtcatga tcgatccgtc ttcaagaagg acgatatggt   42900
cgctgaggtg gccaatataa gggagataga tctcaccgga tctttcggtc gttccactcg   42960
cgccgagcat cacaccattc ctctccctcg tgggggaacc ctaattggat ttgggctaac   43020
agtagcgccc ccccaaactg cactatcaat gcttcttccc gcggtccgca aaaatagcag   43080
gacgacgctc gccgcattgt agtctcgctc cacgatgagc cgggctgcaa accataacgg   43140
cacgagaacg acttcgtaga gcgggttctg aacgataacg atgacaaagc cggcgaacat   43200
catgaataac cctgccaatg tcagtggcac cccaagaaac aatgcgggcc gtgtggctgc   43260
gaggtaaagg gtcgattctt ccaaacgatc agccatcaac taccgccagt gagcgtttgg   43320
ccgaggaagc tcgccccaaa catgataaca atgccgccga cgacgccggc aaccagccca   43380
agcgaagccc gcccgaacat ccaggagatc ccgatagcga caatgccgag aacagcgagt   43440
gactggccga acgaccaag gataaacgtg catatattgt taaccattgt ggcggggtca   43500
gtgccgccac ccgcagattg cgctgcggcg ggtccggatg aggaaatgct ccatgcaatt   43560
gcaccgcaca agcttggggc gcagctcgat atcacgcgca tcatcgcatt cgagagcgag   43620
aggcgattta gatgtaaacg gtatctctca aagcatcgca tcaatgcgca cctccttagt   43680
ataagtcgaa taagacttga ttgtcgtctg cggatttgcc gttgtcctgg tgtggcggtg   43740
gcggagcgat taaccgcca gcgccatcct cctgcgagcg gcgctgatat gacccccaaa   43800
catcccacgt ctcttcggat tttagcgcct cgtgatcgtc ttttggaggc tcgattaacg   43860
cgggcaccag cgattgagca gctgtttcaa cttttcgcac gtagccgttt gcaaaaccgc   43920
cgatgaaatt accggtgttg taagcggaga tcgcccgacg aagcgcaaat tgcttctcgt   43980
```

```
caatcgtttc gccgcctgca taacgacttt tcagcatgtt tgcagcggca gataatgatg    44040
tgcacgcctg gagcgcaccg tcaggtgtca gaccgagcat agaaaaattt cgagagttta    44100
tttgcatgag gccaacatcc agcgaatgcc gtgcatcgag acggtgcctg acgacttggg    44160
ttgcttggct gtgatcttgc cagtgaagcg tttcgccggt cgtgttgtca tgaatcgcta    44220
aaggatcaaa gcgactctcc accttagcta tcgccgcaag cgtagatgtc gcaactgatg    44280
gggcacactt gcgagcaaca tggtcaaact cagcagatga gagtggcgtg gcaaggctcg    44340
acgaacagaa ggagaccatc aaggcaagag aaagcgaccc cgatctctta agcatacctt    44400
atctccttag ctcgcaacta acaccgcctc tcccgttgga agaagtgcgt tgttttatgt    44460
tgaagattat cgggagggtc ggttactcga aaattttcaa ttgcttcttt atgatttcaa    44520
ttgaagcgag aaacctcgcc cggcgtcttg gaacgcaaca tggaccgaga accgcgcatc    44580
catgactaag caaccggatc gacctattca ggccgcagtt ggtcaggtca ggctcagaac    44640
gaaaatgctc ggcgaggtta cgctgtctgt aaacccattc gatgaacggg aagcttcctt    44700
ccgattgctc ttggcaggaa tattggccca tgcctgcttg cgctttgcaa atgctcttat    44760
cgcgttggta tcatatgcct tgtccgccag cagaaacgca ctctaagcga ttatttgtaa    44820
aaatgttcg gtcatgcggc ggtcatgggc ttgacccgct gtcagcgcaa gacggatcgg    44880
tcaaccgtcg gcatcgacaa cagcgtgaat cttggtggtc aaaccgccac gggaacgtcc    44940
catacagcca tcgtcttgat cccgctgttt cccgtcgccg catgttggtg gacgcgggaca   45000
caggaactgt caatcatgac gacattctat cgaaagcctt ggaaatcaca ctcagaatat    45060
gatcccagac gtctgcctca cgccatcgta caaagcgatt gtagcaggtt gtacaggaac    45120
cgtatcgatc aggaacgtct gcccagggcg ggcccgtccg gaagcgccac aagatgacat    45180
tgatcacccg cgtcaacgcg cggcacgcga cgcggcttat ttgggaacaa aggactgaac    45240
aacagtccat tcgaaatcgg tgacatcaaa gcggggacgg ttatcagtg gcctccaagt     45300
caagcctcaa tgaatcaaaa tcagaccgat ttgcaaacct gatttatgag tgtgcggcct    45360
aaatgatgaa atcgtccttc tagatcgcct ccgtggtgta gcaacacctc gcagtatcgc    45420
cgtgctgacc ttggccaggg aattgactgg caagggtgct ttcacatgac cgctctttg     45480
gccgcgatag atgatttcgt tgctgctttg ggcacgtaga aggagagaag tcatatcgga    45540
gaaattcctc ctggcgcgag agcctgctct atcgcgacgg catcccactg tcgggaacag    45600
accggatcat tcacgaggcg aaagtcgtca acacatgcgt tataggcatc ttcccttgaa    45660
ggatgatctt gttgctgcca atctggaggt gcggcagccg caggcagatg cgatctcagc    45720
gcaacttgcg gcaaaacatc tcactcacct gaaaaccact agcgagtctc gcgatcagac    45780
gaaggccttt tacttaacga cacaatatcc gatgtctgca tcacaggcgt cgctatccca    45840
gtcaatacta aagcggtgca ggaactaaag attactgatg acttaggcgt gccacgaggc    45900
ctgagacgac gcgcgtagac agttttttga aatcattatc aaagtgatgg cctccgctga    45960
agcctatcac ctctgcgccg gtctgtcgga gagatgggca agcattatta cggtcttcgc    46020
gcccgtacat gcattggacg attgcagggt caatggatct gagatcatcc agaggattgc    46080
cgcccttacc ttccgtttcg agttggagcc agccctaaa tgagacgaca tagtcgactt     46140
gatgtgacaa tgccaagaga gagatttgct taacccgatt tttttgctca agcgtaagcc    46200
tattgaagct tgccggcatg acgtccgcgc cgaaagaata tcctacaagt aaaacattct    46260
gcacaccgaa atgcttggtg tagacatcga ttatgtgacc aagatcctta gcagtttcgc    46320
ttggggaccg ctccgaccag aaataccgaa gtgaactgac gccaatgaca ggaatccctt    46380
```

```
ccgtctgcag ataggtacca tcgatagatc tgctgcctcg cgcgtttcgg tgatgacggt   46440
gaaaacctct gacacatgca gctcccggag acggtcacag cttgtctgta agcggatgcc   46500
gggagcagac aagcccgtca gggcgcgtca gcgggtgttg gcgggtgtcg gggcgcagcc   46560
atgacccagt cacgtagcga tagcggagtg tatactggct taactatgcg gcatcagagc   46620
agattgtact gagagtgcac catatgcggt gtgaaatacc gcacagatgc gtaaggagaa   46680
aataccgcat caggcgctct tccgcttcct cgctcactga ctcgctgcgc tcggtcgttc   46740
ggctgcggcg agcggtatca gctcactcaa aggcggtaat acggttatcc acagaatcag   46800
gggataacgc aggaaagaac atgtgagcaa aaggccagca aaaggccagg aaccgtaaaa   46860
aggccgcgtt gctggcgttt ttccataggc tccgcccccc tgacgagcat cacaaaaatc   46920
gacgctcaag tcagaggtgg cgaaacccga caggactata agataccagg cgtttccccc   46980
ctggaagctc cctcgtgcgc tctcctgttc cgaccctgcc gcttaccgga tacctgtccg   47040
cctttctccc ttcgggaagc gtggcgcttt ctcatagctc acgctgtagg tatctcagtt   47100
cggtgtaggt cgttcgctcc aagctgggct gtgtgcacga accccccgtt cagcccgacc   47160
gctgcgcctt atccggtaac tatcgtcttg agtccaaccc ggtaagacac gacttatcgc   47220
cactggcagc agccactggt aacaggatta gcagagcgag gtatgtaggc ggtgctacag   47280
agttcttgaa gtggtggcct aactacggct acactagaag gacagtattt ggtatctgcg   47340
ctctgctgaa gccagttacc ttcggaaaaa gagttggtag ctcttgatcc ggcaaacaaa   47400
ccaccgctgg tagcggtggt ttttttgttt gcaagcagca gattacgcgc agaaaaaaag   47460
gatctcaaga agatcctttg atcttttcta cggggtctga cgctcagtgg aacgaaaact   47520
cacgttaagg gattttggtc atgagattat caaaaaggat cttcacctag atccttttaa   47580
attaaaaatg aagttttaaa tcaatctaaa gtatatatga gtaaacttgg tctgacagtt   47640
accaatgctt aatcagtgag gcacctatct cagcgatctg tctatttcgt tcatccatag   47700
ttgcctgact ccccgtcgtg tagataacta cgatacggga gggcttacca tctggcccca   47760
gtgctgcaat gataccgcga gacccacgct caccggctcc agatttatca gcaataaacc   47820
agccagccgg aagggccgag cgcagaagtg gtcctgcaac tttatccgcc tccatccagt   47880
ctattaattg ttgccgggaa gctagagtaa gtagttcgcc agttaatagt ttgcgcaacg   47940
ttgttgccat tgctgcaggg gggggggggg gggggactt ccattgttca ttccacggac   48000
aaaaacagag aaaggaaacg acagaggcca aaaagcctcg ctttcagcac ctgtcgtttc   48060
cttttctttc agagggtatt ttaaataaaa acattaagtt atgacgaaga agaacggaaa   48120
cgccttaaac cggaaaattt tcataaatag cgaaacccg cgaggtcgcc gccccgtagt   48180
cggatcaccg gaaaggaccc gtaaagtgat aatgattatc atctacatat cacaacgtgc   48240
gtggaggcca tcaaaccacg tcaataatc aattatgacg caggtatcgt attaattgat   48300
ctgcatcaac ttaacgtaaa aacaacttca gacaatacaa atcagcgaca ctgaatacgg   48360
ggcaacctca tgtccccccc ccccccccc ctgcaggcat cgtggtgtca cgctcgtcgt   48420
ttggtatggc ttcattcagc tccggttccc aacgatcaag gcgagttaca tgatccccca   48480
tgttgtgcaa aaaagcggtt agctccttcg gtcctccgat cgttgtcaga agtaagttgg   48540
ccgcagtgtt atcactcatg gttatggcag cactgcataa ttctcttact gtcatgccat   48600
ccgtaagatg cttttctgtg actggtgagt actcaaccaa gtcattctga gaatagtgta   48660
tgcggcgacc gagttgctct tgcccggcgt caacacggga taataccgcg ccacatagca   48720
```

-continued

| | |
|---|---|
| gaactttaaa agtgctcatc attggaaaac gttcttcggg gcgaaaactc tcaaggatct | 48780 |
| taccgctgtt gagatccagt tcgatgtaac ccactcgtgc acccaactga tcttcagcat | 48840 |
| cttttacttt caccagcgtt tctgggtgag caaaaacagg aaggcaaaat gccgcaaaaa | 48900 |
| agggaataag ggcgacacgg aaatgttgaa tactcatact cttccttttt caatattatt | 48960 |
| gaagcattta tcagggttat tgtctcatga gcggatacat atttgaatgt atttagaaaa | 49020 |
| ataaacaaat aggggttccg cgcacatttc cccgaaaagt gccacctgac gtctaagaaa | 49080 |
| ccattattat catgacatta acctataaaa ataggcgtat cacgaggccc tttcgtcttc | 49140 |
| aagaattggt cgacgatctt gctgcgttcg gatattttcg tggagttccc gccacagacc | 49200 |
| cggattgaag gcgagatcca gcaactcgcg ccagatcatc ctgtgacgga actttggcgc | 49260 |
| gtgatgactg gccaggacgt cggccgaaag agcgacaagc agatcacgct tttcgacagc | 49320 |
| gtcggatttg cgatcgagga tttttcggcg ctgcgctacg tccgcgaccg cgttgaggga | 49380 |
| tcaagccaca gcagcccact cgaccttcta gccgacccag acgagccaag ggatcttttt | 49440 |
| ggaatgctgc tccgtcgtca ggcttttcga cgtttgggtg gttgaacaga agtcattatc | 49500 |
| gtacggaatg ccaagcactc ccgaggggaa ccctgtggtt ggcatgcaca tacaaatgga | 49560 |
| cgaacgataa accttttca cgcccttta aatatccgtt attctaataa acgctctttt | 49620 |
| ctcttaggtt tacccgccaa tatatcctgt caaacactga tagtttaaac tgaaggcggg | 49680 |
| aaacgacaat ctgatcatga gcggagaatt aagggagtca cgttatgacc cccgccgatg | 49740 |
| acgcgggaca agccgtttta cgtttggaac tgacagaacc gcaacgttga aggagccact | 49800 |
| cagcaagctg gtacgattgt aatacgactc actatagggc gaattgagcg ctgtttaaac | 49860 |
| gctcttcaac tggaagagcg gttacccgga ccgaagcttg catgcctgca g | 49911 |

<210> SEQ ID NO 7
<211> LENGTH: 36909
<212> TYPE: DNA
<213> ORGANISM: Artificial Sequence
<220> FEATURE:
<223> OTHER INFORMATION: PHP10523 construct

<400> SEQUENCE: 7

| | |
|---|---|
| tctagagctc gttcctcgag gcctcgaggc ctcgaggaac ggtacctgcg gggaagctta | 60 |
| caataatgtg tgttgttaag tcttgttgcc tgtcatcgtc tgactgactt tcgtcataaa | 120 |
| tcccggcctc cgtaacccag cttgggcaa gctcacggat ttgatccggc ggaacgggaa | 180 |
| tatcgagatg ccgggctgaa cgctgcagtt ccagctttcc ctttcgggac aggtactcca | 240 |
| gctgattgat tatctgctga agggtcttgg ttccacctcc tggcacaatg cgaatgatta | 300 |
| cttgagcgcg atcgggcatc caattttctc ccgtcaggtg cgtggtcaag tgctacaagg | 360 |
| cacctttcag taacgagcga ccgtcgatcc gtcgccggga tacggacaaa atggagcgca | 420 |
| gtagtccatc gagggcggcg aaagcctcgc caaaagcaat acgttcatct cgcacagcct | 480 |
| ccagatccga tcgagggtct tcggcgtagg cagatagaag catggataca ttgcttgaga | 540 |
| gtattccgat ggactgaagt atggcttcca tctttctcg tgtgtctgca tctatttcga | 600 |
| gaaagccccc gatgcggcgc accgcaacgc gaattgccat actatccgaa agtcccagca | 660 |
| ggcgcgcttg ataggaaaag gttcatact cggccgatcg cagacgggca ctcacgacct | 720 |
| tgaacccttc aactttcagg gatcgatgct ggttgatggt agtctcactc gacgtggctc | 780 |
| tggtgtgttt tgacatagct tcctccaaag aaagcggaag gtctggatac tccagcacga | 840 |
| aatgtgcccg ggtagacgga tggaagtcta gccctgctca atatgaaatc aacagtacat | 900 |

-continued

| | |
|---|---|
| ttacagtcaa tactgaatat acttgctaca tttgcaattg tcttataacg aatgtgaaat | 960 |
| aaaaatagtg taacaacgct tttactcatc gataatcaca aaaacattta tacgaacaaa | 1020 |
| aatacaaatg cactccggtt tcacaggata ggcgggatca gaatatgcaa cttttgacgt | 1080 |
| tttgttcttt caaaggggt gctggcaaaa ccaccgcact catgggcctt tgcgctgctt | 1140 |
| tggcaaatga cggtaaacga gtggccctct tgatgccga cgaaaaccgg cctctgacgc | 1200 |
| gatggagaga aaacgcctta caaagcagta ctgggatcct cgctgtgaag tctattccgc | 1260 |
| cgacgaaatg ccccttcttg aagcagccta tgaaaatgcc gagctcgaag gatttgatta | 1320 |
| tgcgttggcc gatacgcgtg gcggctcgag cgagctcaac aacacaatca tcgctagctc | 1380 |
| aaacctgctt ctgatcccca ccatgctaac gccgctcgac atcgatgagg cactatctac | 1440 |
| ctaccgctac gtcatcgagc tgctgttgag tgaaaatttg gcaattccta cagctgtttt | 1500 |
| gcgccaacgc gtcccggtcg gccgattgac aacatcgcaa cgcaggatgt cagagacgct | 1560 |
| agagagcctt ccagttgtac cgtctcccat gcatgaaaga gatgcatttg ccgcgatgaa | 1620 |
| agaacgcggc atgttgcatc ttacattact aaacacggga actgatccga cgatgcgcct | 1680 |
| catagagagg aatcttcgga ttgcgatgga ggaagtcgtg gtcatttcga aactgatcag | 1740 |
| caaaatcttg gaggcttgaa gatggcaatt cgcaagcccg cattgtcggt cggcgaagca | 1800 |
| cggcggcttg ctggtgctcg acccgagatc caccatccca acccgacact tgttccccag | 1860 |
| aagctggacc tccagcactt gcctgaaaaa gccgacgaga aagaccagca acgtgagcct | 1920 |
| ctcgtcgccg atcacattta cagtcccgat cgacaactta agctaactgt ggatgccctt | 1980 |
| agtccacctc cgtccccgaa aaagctccag gttttctttt cagcgcgacc gccgcgcct | 2040 |
| caagtgtcga aaacatatga caacctcgtt cggcaataca gtccctcgaa gtcgctacaa | 2100 |
| atgattttaa ggcgcgcgtt ggacgatttc gaaagcatgc tggcagatgg atcatttcgc | 2160 |
| gtggccccga aaagttatcc gatcccttca actacagaaa aatccgttct cgttcagacc | 2220 |
| tcacgcatgt tcccggttgc gttgctcgag gtcgctcgaa gtcatttga tccgttgggg | 2280 |
| ttggagaccg ctcgagcttt cggccacaag ctggctaccg ccgcgctcgc gtcattcttt | 2340 |
| gctggagaga agccatcgag caattggtga agagggacct atcggaaccc ctcaccaaat | 2400 |
| attgagtgta ggtttgaggc cgctggccgc gtcctcagtc accttttgag ccagataatt | 2460 |
| aagagccaaa tgcaattggc tcaggctgcc atcgtccccc cgtgcgaaac ctgcacgtcc | 2520 |
| gcgtcaaaga aataaccggc acctcttgct gtttttatca gttgagggct tgacggatcc | 2580 |
| gcctcaagtt tgcggcgcag ccgcaaaatg agaacatcta tactcctgtc gtaaacctcc | 2640 |
| tcgtcgcgta ctcgactggc aatgagaagt tgctcgcgcg atagaacgtc gcggggtttc | 2700 |
| tctaaaaacg cgaggagaag attgaactca cctgccgtaa gtttcacctc accgccagct | 2760 |
| tcggacatca agcgacgttg cctgagatta agtgtccagt cagtaaaaca aaaagaccgt | 2820 |
| cggtctttgg agcggacaac gttggggcgc acgcgcaagg caacccgaat gcgtgcaaga | 2880 |
| aactctctcg tactaaacgg cttagcgata aaatcacttg ctcctagctc gagtgcaaca | 2940 |
| actttatccg tctcctcaag gcggtcgcca ctgataatta tgattggaat atcagacttt | 3000 |
| gccgccagat ttcgaacgat ctcaagccca tcttcacgac ctaaatttag atcaacaacc | 3060 |
| acgacatcga ccgtcgcgga agagagtact ctagtgaact gggtgctgtc ggctaccgcg | 3120 |
| gtcactttga aggcgtggat cgtaaggtat tcgataataa gatgccgcat agcgacatcg | 3180 |
| tcatcgataa gaagaacgtg tttcaacggc tcaccttca atctaaaatc tgaacccttg | 3240 |

```
ttcacagcgc ttgagaaatt ttcacgtgaa ggatgtacaa tcatctccag ctaaatgggc    3300
agttcgtcag aattgcggct gaccgcggat gacgaaaatg cgaaccaagt atttcaattt    3360
tatgacaaaa gttctcaatc gttgttacaa gtgaaacgct tcgaggttac agctactatt    3420
gattaaggag atcgcctatg gtctcgcccc ggcgtcgtgc gtccgccgcg agccagatct    3480
cgcctacttc ataaacgtcc tcataggcac ggaatggaat gatgacatcg atcgccgtag    3540
agagcatgtc aatcagtgtg cgatcttcca agctagcacc ttgggcgcta cttttgacaa    3600
gggaaaacag tttcttgaat ccttggattg gattcgcgcc gtgtattgtt gaaatcgatc    3660
ccggatgtcc cgagacgact tcactcagat aagcccatgc tgcatcgtcg cgcatctcgc    3720
caagcaatat ccggtccggc cgcatacgca gacttgcttg gagcaagtgc tcggcgctca    3780
cagcacccag cccagcaccg ttcttggagt agagtagtct aacatgatta tcgtgtggaa    3840
tgacgagttc gagcgtatct tctatggtga ttagcctttc ctgggggggg atggcgctga    3900
tcaaggtctt gctcattgtt gtcttgccgc ttccggtagg gccacatagc aacatcgtca    3960
gtcggctgac gacgcatgcg tgcagaaacg cttccaaatc cccgttgtca aaatgctgaa    4020
ggatagcttc atcatcctga ttttggcgtt tccttcgtgt ctgccactgg ttccacctcg    4080
aagcatcata acgggaggag acttcttaa gaccagaaac acgcgagctt ggccgtcgaa    4140
tggtcaagct gacggtgccc gagggaacgg tcggcggcag acagatttgt agtcgttcac    4200
caccaggaag ttcagtggcg cagagggggt tacgtggtcc gacatcctgc tttctcagcg    4260
cgcccgctaa aatagcgata tcttcaagat catcataaga gacgggcaaa ggcatcttgg    4320
taaaaatgcc ggcttggcgc acaaatgcct ctccaggtcg attgatcgca atttcttcag    4380
tcttcgggtc atcgagccat tccaaaatcg gcttcagaag aaagcgtagt gcggatcca    4440 cttccatta caatgtatcc tatctctaag cggaaatttg aattcattaa gagcggcggt    4500 tcctccccg cgtggcgccg ccagtcaggc ggagctggta acaccaaag aaatcgaggt    4560 cccgtgctac gaaaatggaa acggtgtcac cctgattctt cttcagggtt ggcggtatgt    4620
tgatggttgc cttaagggct gtctcagttg tctgctcacc gttattttga aagctgttga    4680
agctcatccc gccacccgag ctgccggcgt aggtgctagc tgcctggaag cgccttgaa    4740 caacactcaa gagcatagct ccgctaaaac gctgccagaa gtggctgtcg accgagcccg    4800
gcaatcctga gcgaccgagt tcgtccgcgc ttggcgatgt taacgagatc atcgcatggt    4860
caggtgtctc ggcgcgatcc cacaacacaa aaacgcgccc atctccctgt tgcaagccac    4920
gctgtatttc gccaacaacg gtggtgccac gatcaagaag cacgatattg ttcgttgttc    4980
cacgaatatc ctgaggcaag acacacttta catagcctgc caaatttgtg tcgattgcgg    5040
tttgcaagat gcacggaatt attgtcccctt gcgttaccat aaaatcgggg tgcggcaaga    5100
gcgtggcgct gctgggctgc agctcggtgg gtttcatacg tatcgacaaa tcgttctcgc    5160
cggacacttc gccattcggc aaggagttgt cgtcacgctt gccttcttgt cttcggcccg    5220
tgtcgccctg aatggcgcgt ttgctgaccc cttgatcgcc gctgctatat gcaaaaatcg    5280
gtgtttcttc cggccgtggc tcatgccgct ccggttcgcc cctcggcggt agaggagcag    5340
caggctgaac agcctcttga accgctggag gatccggcgg cacctcaatc ggagctggat    5400
gaaatggctt ggtgtttgtt gcgatcaaag ttgacggcga tgcgttctca ttcacccttct    5460 tttggcgccc acctagccaa atgaggctta atgataacgc gagaacgaca cctccgacga    5520
tcaatttctg agaccccgaa agacgccggc gatgtttgtc ggagaccagg gatccagatg    5580
catcaacctc atgtgccgct tgctgactat cgttattcat cccttcgccc ccttcaggac    5640
```

```
gcgtttcaca tcgggcctca ccgtgcccgt ttgcggcctt tggccaacgg gatcgtaagc    5700
ggtgttccag atacatagta ctgtgtggcc atccctcaga cgccaacctc gggaaaccga    5760
agaaatctcg acatcgctcc ctttaactga atagttggca acagcttcct tgccatcagg    5820
attgatggtg tagatggagg gtatgcgtac attgcccgga aagtggaata ccgtcgtaaa    5880
tccattgtcg aagacttcga gtggcaacag cgaacgatcg ccttgggcga cgtagtgcca    5940
attactgtcc gccgcaccaa gggctgtgac aggctgatcc aataaattct cagctttccg    6000
ttgatattgt gcttccgcgt gtagtctgtc cacaacagcc ttctgttgtg cctcccttcg    6060
ccgagccgcc gcatcgtcgg cggggtaggc gaattggacg ctgtaataga gatcgggctg    6120
ctctttatcg aggtgggaca gagtcttgga acttatactg aaaacataac ggcgcatccc    6180
ggagtcgctt gcgttagca cgattactgg ctgaggcgtg aggacctggc ttgccttgaa     6240
aaatagataa tttccccgcg gtagggctgc tagatctttg ctatttgaaa cggcaaccgc    6300
tgtcaccgtt tcgttcgtgg cgaatgttac gaccaaagta gctccaaccg ccgtcgagag    6360
gcgcaccact tgatcgggat tgtaagccaa ataacgcatg cgcggatcta gcttgcccgc    6420
cattggagtg tcttcagcct ccgcaccagt cgcagcggca aataaacatg ctaaaatgaa    6480
aagtgctttt ctgatcatgg ttcgctgtgg cctacgtttg aaacggtatc ttccgatgtc    6540
tgataggagg tgacaaccag acctgccggg ttggttagtc tcaatctgcc gggcaagctg    6600
gtcacctttt cgtagcgaac tgtcgcggtc cacgtactca ccacaggcat tttgccgtca    6660
acgacgaggg tccttttata gcgaatttgc tgcgtgcttg gagttacatc atttgaagcg    6720
atgtgctcga cctccaccct gccgcgtttg ccaagaatga cttgaggcga actgggattg    6780
ggatagttga agaattgctg gtaatcctgg cgcactgttg gggcactgaa gttcgatacc    6840
aggtcgtagg cgtactgagc ggtgtcggca tcataactct cgcgcaggcg aacgtactcc    6900
cacaatgagg cgttaacgac ggcctcctct tgagttgcag gcaatcgcga gacagacacc    6960
tcgctgtcaa cggtgccgtc cggccgtatc catagatata cgggcacaag cctgctcaac    7020
ggcaccattg tggctatagc gaacgcttga gcaacatttc ccaaaatcgc gatagctgcg    7080
acagctgcaa tgagtttgga gagacgtcgc gccgatttcg ctcgcgcggt ttgaaaggct    7140
tctacttcct tatagtgctc ggcaaggctt tcgcgcgcca ctagcatggc atattcaggc    7200
cccgtcatag cgtccacccg aattgccgag ctgaagatct gacggagtag gctgccatcg    7260
ccccacattc agcgggaaga tcgggccttt gcagctcgct aatgtgtcgt ttgtctggca    7320
gccgctcaaa gcgacaacta ggcacagcag gcaatacttc atagaattct ccattggagc    7380 gaattttgc gcgacctagc ctcgctcaac ctgagcgaag cgacggtaca agctgctggc     7440
agattgggtt gcgccgctcc agtaactgcc tccaatgttg ccggcgatcg ccggcaaagc    7500
gacaatgagc gcatcccctg tcagaaaaaa catatcgagt tcgtaaagac caatgatctt    7560
ggccgcggtc gtaccggcga aggtgattac accaagcata agggtgagcg cagtcgcttc    7620
ggttaggatg acgatcgttg ccacgaggtt aagaggaga agcaagagac cgtaggtgat     7680
aagttgcccg atccacttag ctgcgatgtc ccgcgtgcga tcaaaatat atccgacgag     7740 gatcagaggc ccgatcgcga gaagcacttt cgtgagaatt ccaacggcgt cgtaaactcc    7800
gaaggcagac cagagcgtgc cgtaaaggac ccactgtgcc ccttggaaag caaggatgtc    7860
ctggtcgttc atcggaccga tttcggatgc gatttctga aaaacggcct gggtcacggc     7920
gaacattgta tccaactgtg ccggaacagt ctgcagaggc aagccggtta cactaaactg    7980
```

```
ctgaacaaag tttgggaccg tcttttcgaa gatggaaacc acatagtctt ggtagttagc    8040
ctgcccaaca attagagcaa caacgatggt gaccgtgatc acccgagtga taccgctacg    8100
ggtatcgact tcgccgcgta tgactaaaat accctgaaca ataatccaaa gagtgacaca    8160
ggcgatcaat ggcgcactca ccgcctcctg gatagtctca agcatcgagt ccaagcctgt    8220
cgtgaaggct acatcgaaga tcgtatgaat ggccgtaaac ggcgccggaa tcgtgaaatt    8280
catcgattgg acctgaactt gactggtttg tcgcataatg ttggataaaa tgagctcgca    8340
ttcggcgagg atgcgggcgg atgaacaaat cgcccagcct taggggaggg caccaaagat    8400
gacagcggtc ttttgatgct ccttgcgttg agcggccgcc tcttccgcct cgtgaaggcc    8460
ggcctgcgcg gtagtcatcg ttaataggct tgtcgcctgt acattttgaa tcattgcgtc    8520
atggatctgc ttgagaagca aaccattggt cacggttgcc tgcatgatat tgcgagatcg    8580
ggaaagctga gcagacgtat cagcattcgc cgtcaagcgt ttgtccatcg tttccagatt    8640
gtcagccgca atgccagcgc tgtttgcgga accggtgatc tgcgatcgca acaggtccgc    8700
ttcagcatca ctacccacga ctgcacgatc tgtatcgctg gtgatcgcac gtgccgtggt    8760
cgacattggc attcgcggcg aaaacatttc attgtctagg tccttcgtcg aaggatactg    8820
attttctgg ttgagcgaag tcagtagtcc agtaacgccg taggccgacg tcaacatcgt    8880
aaccatcgct atagtctgag tgagattctc cgcagtcgcg agcgcagtcg cgagcgtctc    8940
agcctccgtt gccgggtcgc taacaacaaa ctgcgcccgc gcgggctgaa tatatagaaa    9000
gctgcaggtc aaaactgttg caataagttg cgtcgtcttc atcgtttcct accttatcaa    9060
tcttctgcct cgtggtgacg ggccatgaat tcgctgagcc agccagatga gttgccttct    9120
tgtgcctcgc gtagtcgagt tgcaaagcgc accgtgttgg cacgccccga aagcacggcg    9180
acatattcac gcatatcccg cagatcaaat tcgcagatga cgcttccact ttctcgttta    9240
agaagaaact tacggctgcc gaccgtcatg tcttcacgga tcgcctgaaa ttccttttcg    9300
gtacatttca gtccatcgac ataagccgat cgatctgcgg ttggtgatgg atagaaaatc    9360
ttcgtcatac attgcgcaac caagctggct cctagcggcg attccagaac atgctctggt    9420
tgctgcgttg ccagtattag catcccgttg ttttttcgaa cggtcaggag gaatttgtcg    9480
acgacagtcg aaaatttagg gtttaacaaa taggcgcgaa actcatcgca gctcatcaca    9540
aaacggcggc cgtcgatcat ggctccaatc cgatgcagga gatatgctgc agcgggagcg    9600
catacttcct cgtattcgag aagatgcgtc atgtcgaagc cggtaatcga cggatctaac    9660
tttacttcgt caacttcgcc gtcaaatgcc cagccaagcg catggccccg gcaccagcgt    9720
tggagccgcg ctcctgcgcc ttcggcgggc ccatgcaaca aaaattcacg taaccccgcg    9780
attgaacgca tttgtggatc aaacgagagc tgacgatgga taccacggac cagacggcgg    9840
ttctcttccg gagaaatccc accccgacca tcactctcga tgagagccac gatccattcg    9900
cgcagaaaat cgtgtgaggc tgctgtgttt tctaggccac gcaacggcgc caacccgctg    9960
ggtgtgcctc tgtgaagtgc caaatatgtt cctcctgtgg cgcgaaccag caattcgcca   10020
ccccggtcct tgtcaaagaa cacgaccgta cctgcacggt cgaccatgct ctgttcgagc   10080
atggctagaa caaacatcat gagcgtcgtc ttaccctcc cgataggccc gaatattgcc   10140
gtcatgccaa catcgtgctc atgcgggata tagtcgaaag gcgttccgcc attggtacga   10200
aatcgggcaa tcgcgttgcc ccagtggcct gagctggcgc cctctggaaa gttttcgaaa   10260
gagacaaacc ctgcgaaatt gcgtgaagtg attgcgccag ggcgtgtgcg ccacttaaaa   10320
ttccccggca attgggacca ataggccgct tccataccaa taccttcttg gacaaccacg   10380
```

```
gcacctgcat ccgccattcg tgtccgagcc cgcgcgcccc tgtccccaag actattgaga    10440
tcgtctgcat agacgcaaag gctcaaatga tgtgagccca taacgaattc gttgctcgca    10500
agtgcgtcct cagcctcgga taatttgccg atttgagtca cggctttatc gccggaactc    10560
agcatctggc tcgatttgag gctaagtttc gcgtgcgctt gcgggcgagt caggaacgaa    10620
aaactctgcg tgagaacaag tggaaatcg agggatagca gcgcgttgag catgcccggc     10680 cgtgttttg cagggtattc gcgaaacgaa tagatggatc caacgtaact gtcttttggc     10740
gttctgatct cgagtcctcg cttgccgcaa atgactctgt cggtataaat cgaagcgccg    10800
agtgagccgc tgacgaccgg aaccggtgtg aaccgaccag tcatgatcaa ccgtagcgct    10860
tcgccaattt cggtgaagag cacaccctgc ttctcgcgga tgccaagacg atgcaggcca    10920
tacgctttaa gagagccagc gacaacatgc caaagatctt ccatgttcct gatctggccc    10980
gtgagatcgt tttcccttt tccgcttagc ttggtgaacc tcctctttac cttccctaaa     11040
gccgcctgtg ggtagacaat caacgtaagg aagtgttcat tgcggaggag ttggccggag    11100
agcacgcgct gttcaaaagc ttcgttcagg ctagcggcga aaacactacg gaagtgtcgc    11160
ggcgccgatg atggcacgtc ggcatgacgt acgaggtgag catatattga cacatgatca    11220
tcagcgatat tgcgcaacag cgtgttgaac gcacgacaac gcgcattgcg catttcagtt    11280
tcctcaagct cgaatgcaac gccatcaatt ctcgcaatgg tcatgatcga tccgtcttca    11340
agaaggacga tatggtcgct gaggtggcca atataaggga gatagatctc accggatctt    11400
tcggtcgttc cactcgcgcc gagcatcaca ccattcctct ccctcgtggg ggaaccctaa    11460
ttggatttgg gctaacagta gcgccccccc aaactgcact atcaatgctt cttcccgcgg    11520
tccgcaaaaa tagcaggacg acgctcgccg cattgtagtc tcgctccacg atgagccggg    11580
ctgcaaacca taacggcacg agaacgactt cgtagagcgg gttctgaacg ataacgatga    11640
caaagccggc gaacatcatg aataaccctg ccaatgtcag tggcaccccca agaaacaatg    11700 cgggccgtgt ggctgcgagg taaagggtcg attcttccaa acgatcagcc atcaactacc    11760
gccagtgagc gtttggccga ggaagctcgc cccaaacatg ataacaatgc cgccgacgac    11820
gccggcaacc agcccaagcg aagcccgccc gaacatccag gagatcccga tagcgacaat    11880
gccgagaaca gcgagtgact ggccgaacgg accaaggata aacgtgcata tattgttaac    11940
cattgtggcg gggtcagtgc cgccacccgc agattgcgct gcggcgggtc cggatgagga    12000
aatgctccat gcaattgcac cgcacaagct tggggcgcag ctcgatatca cgcgcatcat    12060
cgcattcgag agcgagaggc gatttagatg taaacggtat ctctcaaagc atcgcatcaa    12120
tgcgcacctc cttagtataa gtcgaataag acttgattgt cgtctgcgga tttgccgttg    12180
tcctggtgtg gcggtggcgg agcgattaaa ccgccagcgc catcctcctg cgagcggcgc    12240
tgatatgacc cccaaacatc ccacgtctct tcggattta gcgcctcgtg atcgtctttt     12300
ggaggctcga ttaacgcggg caccagcgat tgagcagctg tttcaacttt tcgcactag     12360 ccgtttgcaa aaccgccgat gaaattaccg gtgttgtaag cggagatcgc ccgacgaagc    12420
gcaaattgct tctcgtcaat cgtttcgccg cctgcataac gacttttcag catgtttgca    12480
gcggcagata atgatgtgca cgcctggagc gcaccgtcag gtgtcagacc gagcatagaa    12540
aaatttcgag agtttatttg catgaggcca acatccagcg aatgccgtgc atcgagacgg    12600
tgcctgacga cttgggttgc ttggctgtga tcttgccagt gaagcgtttc gccggtcgtg    12660
ttgtcatgaa tcgctaaagg atcaaagcga ctctccacct tagctatcgc cgcaagcgta    12720
```

| | |
|---|---|
| gatgtcgcaa ctgatggggc acacttgcga gcaacatggt caaactcagc agatgagagt | 12780 |
| ggcgtggcaa ggctcgacga acagaaggag accatcaagg caagagaaag cgaccccgat | 12840 |
| ctcttaagca taccttatct ccttagctcg caactaacac cgcctctccc gttggaagaa | 12900 |
| gtgcgttgtt ttatgttgaa gattatcggg agggtcggtt actcgaaaat tttcaattgc | 12960 |
| ttctttatga tttcaattga agcgagaaac ctcgcccggc gtcttggaac gcaacatgga | 13020 |
| ccgagaaccg cgcatccatg actaagcaac cggatcgacc tattcaggcc gcagttggtc | 13080 |
| aggtcaggct cagaacgaaa atgctcggcg aggttacgct gtctgtaaac ccattcgatg | 13140 |
| aacgggaagc ttccttccga ttgctcttgg caggaatatt ggcccatgcc tgcttgcgct | 13200 |
| ttgcaaatgc tcttatcgcg ttggtatcat atgccttgtc cgccagcaga aacgcactct | 13260 |
| aagcgattat ttgtaaaaat gtttcggtca tgcggcggtc atgggcttga cccgctgtca | 13320 |
| gcgcaagacg gatcggtcaa ccgtcggcat cgacaacagc gtgaatcttg gtggtcaaac | 13380 |
| cgccacggga acgtcccata cagccatcgt cttgatcccg ctgtttcccg tcgccgcatg | 13440 |
| ttggtggacg cggacacagg aactgtcaat catgacgaca ttctatcgaa agccttggaa | 13500 |
| atcacactca gaatatgatc ccagacgtct gcctcacgcc atcgtacaaa gcgattgtag | 13560 |
| caggttgtac aggaaccgta tcgatcagga acgtctgccc agggcgggcc cgtccggaag | 13620 |
| cgccacaaga tgacattgat cacccgcgtc aacgcgcggc acgcgacgcg gcttatttgg | 13680 |
| gaacaaagga ctgaacaaca gtccattcga aatcggtgac atcaaagcgg ggacgggtta | 13740 |
| tcagtggcct ccaagtcaag cctcaatgaa tcaaaatcag accgatttgc aaacctgatt | 13800 |
| tatgagtgtg cggcctaaat gatgaaatcg tccttctaga tcgcctccgt ggtgtagcaa | 13860 |
| cacctcgcag tatcgccgtg ctgaccttgg ccagggaatt gactggcaag ggtgctttca | 13920 |
| catgaccgct cttttggccg cgatagatga tttcgttgct gctttgggca cgtagaagga | 13980 |
| gagaagtcat atcggagaaa ttcctcctgg cgcgagagcc tgctctatcg cgacggcatc | 14040 |
| ccactgtcgg gaacagaccg gatcattcac gaggcgaaag tcgtcaacac atgcgttata | 14100 |
| ggcatcttcc cttgaaggat gatcttgttg ctgccaatct ggaggtgcgg cagccgcagg | 14160 |
| cagatgcgat ctcagcgcaa cttgcggcaa aacatctcac tcacctgaaa accactagcg | 14220 |
| agtctcgcga tcagacgaag gccttttact taacgacaca atatccgatg tctgcatcac | 14280 |
| aggcgtcgct atcccagtca atactaaagc ggtgcaggaa ctaaagatta ctgatgactt | 14340 |
| aggcgtgcca cgaggcctga cgacgcgcgc gtagacagtt ttttgaaatc attatcaaag | 14400 |
| tgatggcctc cgctgaagcc tatcacctct gcgccggtct gtcggagaga tgggcaagca | 14460 |
| ttattacggt cttcgcgccc gtacatgcat tggacgattg cagggtcaat ggatctgaga | 14520 |
| tcatccagag gattgccgcc cttaccttcc gtttcgagtt ggagccagcc cctaaatgag | 14580 |
| acgacatagt cgacttgatg tgacaatgcc aagagagaga tttgcttaac ccgatttttt | 14640 |
| tgctcaagcg taagcctatt gaagcttgcc ggcatgacgt ccgcgccgaa agaatatcct | 14700 |
| acaagtaaaa cattctgcac accgaaatgc ttggtgtaga catcgattat gtgaccaaga | 14760 |
| tccttagcag tttcgcttgg ggaccgctcc gaccagaaat accgaagtga actgacgcca | 14820 |
| atgacaggaa tcccttccgt ctgcagatag gtaccatcga tagatctgct gcctcgcgcg | 14880 |
| tttcggtgat gacggtgaaa acctctgaca catgcagctc ccggagacgg tcacagcttg | 14940 |
| tctgtaagcg gatgccggga gcagacaagc ccgtcagggc gcgtcagcgg gtgttggcgg | 15000 |
| gtgtcggggc gcagccatga cccagtcacg tagcgatagc ggagtgtata ctggcttaac | 15060 |
| tatgcggcat cagagcagat tgtactgaga gtgcaccata tgcggtgtga ataccgcac | 15120 |

```
agatgcgtaa ggagaaaata ccgcatcagg cgctcttccg cttcctcgct cactgactcg   15180
ctgcgctcgg tcgttcggct gcggcgagcg gtatcagctc actcaaaggc ggtaatacgg   15240
ttatccacag aatcagggga taacgcagga agaacatgt  gagcaaaagg ccagcaaaag   15300
gccaggaacc gtaaaaaggc gcgcgttgctg gcgttttttcc ataggctccg cccccctgac   15360
gagcatcaca aaaatcgacg ctcaagtcag aggtggcgaa acccgacagg actataaaga   15420
taccaggcgt ttccccctgg aagctccctc gtgcgctctc ctgttccgac cctgccgctt   15480
accggatacc tgtccgcctt tctcccttcg ggaagcgtgg cgctttctca tagctcacgc   15540
tgtaggtatc tcagttcggt gtaggtcgtt cgctccaagc tgggctgtgt gcacgaaccc   15600
cccgttcagc ccgaccgctg cgccttatcc ggtaactatc gtcttgagtc caacccggta   15660
agacacgact tatcgccact ggcagcagcc actggtaaca ggattagcag agcgaggtat   15720
gtaggcggtg ctacagagtt cttgaagtgg tggcctaact acggctacac tagaaggaca   15780
gtatttggta tctgcgctct gctgaagcca gttaccttcg gaaaaagagt tggtagctct   15840
tgatccggca acaaaccac  cgctggtagc ggtggttttt ttgtttgcaa gcagcagatt   15900
acgcgcagaa aaaaggatc  tcaagaagat cctttgatct tttctacggg gtctgacgct   15960
cagtggaacg aaaactcacg ttaagggatt ttggtcatga gattatcaaa aaggatcttc   16020
acctagatcc ttttaaatta aaaatgaagt tttaaatcaa tctaaagtat atatgagtaa   16080
acttggtctg acagttacca atgcttaatc agtgaggcac ctatctcagc gatctgtcta   16140
tttcgttcat ccatagttgc ctgactcccc gtcgtgtaga taactacgat acgggagggc   16200
ttaccatctg gccccagtgc tgcaatgata ccgcgagacc cacgctcacc ggctccagat   16260
ttatcagcaa taaaccagcc agccggaagg gccgagcgca gaagtggtcc tgcaacttta   16320
tccgcctcca tccagtctat taattgttgc cgggaagcta gagtaagtag ttcgccagtt   16380
aatagtttgc gcaacgttgt tgccattgct gcaggggggg ggggggggg  gttccattgt   16440 tcattccacg gacaaaaaca gagaaaggaa acgacagagg ccaaaaagct cgctttcagc   16500
acctgtcgtt tcctttcttt tcagagggta ttttaaataa aaacattaag ttatgacgaa   16560
gaagaacgga aacgccttaa accggaaaat tttcataaat agcgaaaacc cgcgaggtcg   16620
ccgccccgta acctgtcgga tcaccggaaa ggacccgtaa agtgataatg attatcatct   16680
acatatcaca acgtgcgtgg aggccatcaa accacgtcaa ataatcaatt atgacgcagg   16740
tatcgtatta attgatctgc atcaacttaa cgtaaaaaca acttcagaca atacaaatca   16800
gcgacactga atacggggca acctcatgtc cccccccccc ccccccctgc aggcatcgtg   16860
gtgtcacgct cgtcgtttgg tatggcttca ttcagctccg gttcccaacg atcaaggcga   16920
gttacatgat cccccatgtt gtgcaaaaaa gcggttagct ccttcggtcc tccgatcgtt   16980
gtcagaagta agttggccgc agtgttatca ctcatggtta tggcagcact gcataattct   17040
cttactgtca tgccatccgt aagatgcttt tctgtgactg gtgagtactc aaccaagtca   17100
ttctgagaat agtgtatgcg gcgaccgagt tgctcttgcc cggcgtcaac acgggataat   17160
accgcgccac atagcagaac tttaaaagtg ctcatcattg gaaaacgttc ttcggggcga   17220
aaactctcaa ggatcttacc gctgttgaga tccagttcga tgtaacccac tcgtgcaccc   17280
aactgatctt cagcatcttt tactttcacc agcgtttctg ggtgagcaaa aacaggaagg   17340
caaaatgccg caaaaaaggg aataagggcg acacggaaat gttgaatact catactcttc   17400 cttttttcaat attattgaag catttatcag ggttattgtc tcatgagcgg atacatattt   17460
```

```
gaatgtattt agaaaaataa acaaataggg gttccgcgca catttccccg aaaagtgcca    17520
cctgacgtct aagaaaccat tattatcatg acattaacct ataaaaatag gcgtatcacg    17580
aggccctttc gtcttcaaga attcggagct tttgccattc tcaccggatt cagtcgtcac    17640
tcatggtgat ttctcacttg ataaccttat ttttgacgag gggaaattaa taggttgtat    17700
tgatgttgga cgagtcggaa tcgcagaccg ataccaggat cttgccatcc tatggaactg    17760
cctcggtgag ttttctcctt cattacagaa acggctttt caaaaatatg gtattgataa    17820
tcctgatatg aataaattgc agtttcattt gatgctcgat gagttttct aatcagaatt    17880 ggttaattgg ttgtaacact ggcagagcat tacgctgact tgacgggacg gcggcttgt    17940 tgaataaatc gaacttttgc tgagttgaag gatcagatca cgcatcttcc cgacaacgca    18000
gaccgttccg tggcaaagca aaagttcaaa atcaccaact ggtccaccta caacaaagct    18060
ctcatcaacc gtggctccct cactttctgg ctggatgatg gggcgattca ggcctggtat    18120
gagtcagcaa caccttcttc acgaggcaga cctcagcgcc agaaggccgc cagagaggcc    18180
gagcgcggcc gtgaggcttg gacgctaggg cagggcatga aaaagcccgt agcgggctgc    18240
tacgggcgtc tgacgcggtg gaaaggggga ggggatgttg tctacatggc tctgctgtag    18300
tgagtgggtt gcgctccggc agcggtcctg atcaatcgtc acccttctc ggtccttcaa    18360 cgttcctgac aacgagcctc cttttcgcca atccatcgac aatcaccgcg agtccctgct    18420
cgaacgctgc gtccggaccg gcttcgtcga aggcgtctat cgcggcccgc aacagcggcg    18480
agagcggagc ctgttcaacg gtgccgccgc gctcgccggc atcgctgtcg ccggcctgct    18540
cctcaagcac ggccccaaca gtgaagtagc tgattgtcat cagcgcattg acggcgtccc    18600
cggccgaaaa accgcctcg cagaggaagc gaagctgcgc gtcggccgtt ccatctgcg    18660 gtgcgcccgg tcgcgtgccg gcatggatgc gcgcgccatc gcggtaggcg agcagcgcct    18720
gcctgaagct gcgggcattc ccgatcagaa atgagcgcca gtcgtcgtcg gctctcggca    18780
ccgaatgcgt atgattctcc gccagcatgg cttcggccag tgcgtcgagc agcgcccgct    18840
tgttcctgaa gtgccagtaa agcgccggct gctgaacccc caaccgttcc gccagtttgc    18900
gtgtcgtcag accgtctacg ccgacctcgt tcaacaggtc cagggcggca cggatcactg    18960
tattcggctg caactttgtc atgcttgaca ctttatcact gataaacata atatgtccac    19020
caacttatca gtgataaaga atccgcgcgt tcaatcggac cagcggaggc tggtccggag    19080
gccagacgtg aaacccaaca taccctgat cgtaattctg agcactgtcg cgctcgacgc    19140
tgtcggcatc ggcctgatta tgccggtgct gccgggcctc ctgcgcgatc tggttcactc    19200
gaacgacgtc accgcccact atggcattct gctggcgctg tatgcgttgg tgcaatttgc    19260
ctgcgcacct gtgctgggcg cgctgtcgga tcgtttcggg cggcggccaa tcttgctcgt    19320
ctcgctggcc ggcgccactg tcgactacgc catcatggcg acagcgcctt tcctttgggt    19380
tctctatatc gggcggatcg tggccggcat caccggggcg actggggcgg tagccggcgc    19440
ttatattgcc gatatcactg atggcgatga gcgcgcgcgg cacttcggct tcatgagcgc    19500
ctgtttcggg ttcgggatgg tcgcgggacc tgtgctcggt gggctgatgg gcggtttctc    19560
cccccacgct ccgttcttcg ccgcggcagc cttgaacggc ctcaatttcc tgacgggctg    19620
tttccttttg ccggagtcgc acaaaggcga acgccggccg ttacgccggg aggctctcaa    19680
cccgctcgct tcgttccggt gggccggggg catgaccgtc gtcgccgccc tgatggcggt    19740
cttcttcatc atgcaacttg tcggacaggt gccggccgcg ctttgggtca tttttcggcga    19800 ggatcgcttt cactgggacg cgaccacgat cggcatttcg cttgccgcat ttggcattct    19860
```

-continued

```
gcattcactc gcccaggcaa tgatcaccgg ccctgtagcc gcccggctcg gcgaaaggcg    19920
ggcactcatg ctcggaatga ttgccgacgg cacaggctac atcctgcttg ccttcgcgac    19980
acggggatgg atggcgttcc cgatcatggt cctgcttgct tcgggtggca tcggaatgcc    20040
ggcgctgcaa gcaatgttgt ccaggcaggt ggatgaggaa cgtcaggggc agctgcaagg    20100
ctcactggcg gcgctcacca gcctgacctc gatcgtcgga ccctcctct tcacggcgat     20160
ctatgcggct tctataacaa cgtggaacgg gtgggcatgg attgcaggcg ctgccctcta    20220
cttgctctgc ctgccggcgc tgcgtcgcgg gctttggagc ggcgcagggc aacgagccga    20280
tcgctgatcg tggaaacgat aggcctatgc catgcgggtc aaggcgactt ccggcaagct    20340
atacgcgccc taggagtgcg gttggaacgt tggcccagcc agatactccc gatcacgagc    20400
aggacgccga tgatttgaag cgcactcagc gtctgatcca agaacaacca tcctagcaac    20460
acggcggtcc ccgggctgag aaagcccagt aaggaaacaa ctgtaggttc gagtcgcgag    20520
atcccccgga accaaaggaa gtaggttaaa cccgctccga tcaggccgag ccacgccagg    20580
ccgagaacat tggttcctgt aggcatcggg attggcggat caaacactaa agctactgga    20640
acgagcagaa gtcctccggc cgccagttgc caggcggtaa aggtgagcag aggcacggga    20700
ggttgccact tgcgggtcag cacggttccg aacgccatgg aaaccgcccc cgccaggccc    20760
gctgcgacgc cgacaggatc tagcgctgcg tttggtgtca acaccaacag cgccacgccc    20820
gcagttccgc aaatagcccc caggaccgcc atcaatcgta tcgggctacc tagcagagcg    20880
gcagagatga acacgaccat cagcggctgc acagcgccta ccgtcgccgc gaccccgccc    20940
ggcaggcggt agaccgaaat aaacaacaag ctccagaata gcgaaatatt aagtgcgccg    21000
aggatgaaga tgcgcatcca ccagattccc gttggaatct gtcggacgat catcacgagc    21060
aataaacccg ccggcaacgc ccgcagcagc ataccggcga ccctcggcc tcgctgttcg      21120
ggctccacga aaacgccgga cagatgcgcc ttgtgagcgt ccttgggcc gtcctcctgt       21180
ttgaagaccg acagcccaat gatctcgccg tcgatgtagg cgccgaatgc cacggcatct    21240
cgcaaccgtt cagcgaacgc ctccatgggc ttttctcct cgtgctcgta aacggacccg       21300
aacatctctg gagctttctt cagggccgac aatcggatct cgcggaaatc ctgcacgtcg    21360
gccgctccaa gccgtcgaat ctgagcctta atcacaattg tcaattttaa tcctctgttt    21420
atcggcagtt cgtagagcgc gccgtgcgtc ccgagcgata ctgagcgaag caagtgcgtc    21480
gagcagtgcc cgcttgttcc tgaaatgcca gtaaagcgct ggctgctgaa ccccagccg      21540
gaactgaccc cacaaggccc tagcgtttgc aatgcaccag gtcatcattg acccaggcgt    21600
gttccaccag gccgctgcct cgcaactctt cgcaggcttc gccgacctgc tcgcgccact    21660
tcttcacgcg ggtggaatcc gatccgcaca tgaggcggaa ggtttccagc ttgagcgggt    21720
acggctcccg gtgcgagctg aaatagtcga acatccgtcg ggccgtcggc gacagcttgc    21780
ggtacttctc ccatatgaat ttcgtgtagt ggtcgccagc aaacagcacg acgatttcct    21840
cgtcgatcag gacctggcaa cgggacgttt tcttgccacg gtccaggacg cggaagcggt    21900
gcagcagcga caccgattcc aggtgcccaa cgcggtcgga cgtgaagccc atcgccgtcg    21960
cctgtaggcg cgacaggcat tcctcggcct tcgtgtaata ccggccattg atcgaccagc    22020
ccaggtcctg gcaaagctcg tagaacgtga aggtgatcgg ctcgccgata ggggtgcgct    22080
tcgcgtactc caaacctgc tgccacacca gttcgtcatc gtcggcccgc agctcgacgc      22140
cggtgtaggt gatcttcacg tccttgttga cgtggaaaat gaccttgttt tgcagcgcct    22200
```

```
cgcgcgggat tttcttgttg cgcgtggtga acagggcaga gcgggccgtg tcgtttggca   22260
tcgctcgcat cgtgtccggc cacggcgcaa tatcgaacaa ggaaagctgc atttccttga   22320
tctgctgctt cgtgtgtttc agcaacgcgg cctgcttggc ctcgctgacc tgttttgcca   22380
ggtcctcgcc ggcggttttt cgcttcttgg tcgtcatagt tcctcgcgtg tcgatggtca   22440
tcgacttcgc caaacctgcc gcctcctgtt cgagacgacg cgaacgctcc acggcggccg   22500
atggcgcggg cagggcaggg ggagccagtt gcacgctgtc gcgctcgatc ttggccgtag   22560
cttgctggac catcgagccg acggactgga aggtttcgcg gggcgcacgc atgacggtgc   22620
ggcttgcgat ggtttcggca tcctcggcgg aaaaccccgc gtcgatcagt tcttgcctgt   22680
atgccttccg gtcaaacgtc cgattcattc accctccttg cgggattgcc ccgactcacg   22740
ccggggcaat gtgcccttat tcctgatttg acccgcctgg tgccttggtg tccagataat   22800
ccaccttatc ggcaatgaag tcggtcccgt agaccgtctg gccgtccttc tcgtacttgg   22860
tattccgaat cttgccctgc acgaatacca gcgaccccett gcccaaatac ttgccgtggg   22920
cctcggcctg agagccaaaa cacttgatgc ggaagaagtc ggtgcgctcc tgcttgtcgc   22980
cggcatcgtt gcgccactct tcattaaccg ctatatcgaa aattgcttgc ggcttgttag   23040
aattgccatg acgtacctcg gtgtcacggg taagattacc gataaactgg aactgattat   23100
ggctcatatc gaaagtctcc ttgagaaagg agactctagt ttagctaaac attggttccg   23160
ctgtcaagaa cttagcggc taaaattttg cgggccgcga ccaaaggtgc gaggggcggc   23220
ttccgctgtg tacaaccaga tattttcac caacatcctt cgtctgctcg atgagcgggg   23280
catgacgaaa catgagctgt cggagagggc aggggtttca atttcgtttt tatcagactt   23340
aaccaacggt aaggccaacc cctcgttgaa ggtgatggag gccattgccg acgccctgga   23400
aactccccta cctcttctcc tggagtccac cgaccttgac cgcgaggcac tcgcggagat   23460
tgcgggtcat cctttcaaga gcagcgtgcc gcccggatac gaacgcatca gtgtggtttt   23520
gccgtcacat aaggcgttta tcgtaaagaa atggggcgac gacacccgaa aaaagctgcg   23580
tggaaggctc tgacgccaag ggttagggct tgcacttcct tctttagccg ctaaaacggc   23640
cccttctctg cgggccgtcg gctcgcgcat catatcgaca tcctcaacgg aagccgtgcc   23700
gcgaatggca tcgggcgggt gcgctttgac agttgttttc tatcagaacc cctacgtcgt   23760
gcggttcgat tagctgtttg tcttgcaggc taaacacttt cggtatatcg tttgcctgtg   23820
cgataatgtt gctaatgatt tgttgcgtag gggttactga aaagtgagcg ggaaagaaga   23880
gtttcagacc atcaaggagc gggccaagcg caagctggaa cgcgacatgg gtgcggacct   23940
gttggccgcg ctcaacgacc cgaaaaccgt tgaagtcatg ctcaacgcgg acggcaaggt   24000
gtggcacgaa cgccttggcg agccgatgcg gtacatctgc gacatgcggc ccagccagtc   24060
gcaggcgatt atagaaacgg tggccggatt ccacggcaaa gaggtcacgc ggcattcgcc   24120
catcctggaa ggcgagttcc ccttggatgg cagccgcttt gccggccaat tgccgccggt   24180
cgtggccgcg ccaacctttg cgatccgcaa gcgcgcggtc gccatcttca cgctggaaca   24240
gtacgtcgag gcgggcatca tgacccgcga gcaatacgag gtcattaaaa gcgccgtcgc   24300
ggcgcatcga aacatcctcg tcattggcgg tactggctcg gcaagacca cgtcgtcaa   24360 cgcgatcatc aatgaaatgg tcgccttcaa cccgtctgag cgcgtcgtca tcatcgagga   24420
caccggcgaa atccagtgcg ccgcagagaa cgccgtccaa taccacacca gcatcgacgt   24480
ctcgatgacg ctgctgctca agacaacgct gcgtatgcgc cccgaccgca tcctggtcgg   24540
tgaggtacgt ggccccgaag cccttgatct gttgatggcc tggaacaccg gcatgaagg   24600
```

```
aggtgccgcc accctgcacg caaacaaccc caaagcgggc ctgagccggc tcgccatgct   24660
tatcagcatg cacccggatt caccgaaacc cattgagccg ctgattggcg aggcggttca   24720
tgtggtcgtc catatcgcca ggaccnctag cggccgtcga gtgcaagaaa ttctcgaagt   24780
tcttggttac gagaacggcc agtacatcac caaaaccctg taaggagtat ttccaatgac   24840
aacggctgtt ccgttccgtc tgaccatgaa tcgcggcatt ttgttctacc ttgccgtgtt   24900
cttcgttctc gctctcgcgt tatccgcgca tccggcgatg gcctcggaag caccggcgg    24960
cagcttgcca tatgagagct ggctgacgaa cctgcgcaac tccgtaaccg gcccggtggc   25020
cttcgcgctg tccatcatcg gcatcgtcgt cgccggcggc gtgctgatct tcggcggcga   25080
actcaacgcc ttcttccgaa ccctgatctt cctggttctg gtgatggcgc tgctggtcgg   25140
cgcgcagaac gtgatgagca ccttcttcgg tcgtggtgcc gaaatcgcgg ccctcggcaa   25200
cggggcgctg caccaggtgc aagtcgcggc ggcggatgcc gtgcgtgcgg tagcggctgg   25260
acggctcgcc taatcatggc tctgcgcacg atccccatcc gtcgcgcagg caaccgagaa   25320
aacctgttca tgggtggtga tcgtgaactg gtgatgttct cgggcctgat ggcgtttgcg   25380
ctgattttca gcgcccaaga gctgcgggcc accgtggtcg gtctgatcct gtggttcggg   25440
gcgctctatg cgttccgaat catggcgaag gccgatccga agatgcggtt cgtgtacctg   25500
cgtcaccgcc ggtacaagcc gtattacccg gcccgctcga ccccgttccg cgagaacacc   25560
aatagccaag ggaagcaata ccgatgatcc aagcaattgc gattgcaatc gcgggcctcg   25620
gcgcgcttct gttgttcatc ctctttgccc gcatccgcgc ggtcgatgcc gaactgaaac   25680
tgaaaaagca tcgttccaag gacgccggcc tggccgatct gctcaactac gccgctgtcg   25740
tcgatgacgg cgtaatcgtg ggcaagaacg gcagctttat ggctgcctgg ctgtacaagg   25800
gcgatgacaa cgcaagcagc accgaccagc agcgcgaagt agtgtccgcc cgcatcaacc   25860
aggccctcgc gggcctggga agtgggtgga tgatccatgt ggacgccgtg cggcgtcctg   25920
ctccgaacta cgcggagcgg ggcctgtcgg cgttccctga ccgtctgacg gcagcgattg   25980
aagaagagcg ctcggtcttg ccttgctcgt cggtgatgta cttcaccagc tccgcgaagt   26040
cgctcttctt gatggagcgc atggggacgt gcttggcaat cacgcgcacc ccccggccgt   26100
tttagcggct aaaaaagtca tggctctgcc ctcgggcgga ccacgcccat catgaccttg   26160
ccaagctcgt cctgcttctc ttcgatcttc gccagcaggg cgaggatcgt ggcatcaccg   26220
aaccgcgccg tgcgcgggtc gtcggtgagc cagagtttca gcaggccgcc caggcggccc   26280
aggtcgccat tgatgcgggc cagctcgcgg acgtgctcat agtccacgac gcccgtgatt   26340
ttgtagccct ggccgacggc cagcaggtag gccgacaggc tcatgccggc cgccgccgcc   26400
ttttcctcaa tcgctcttcg ttcgtctgga aggcagtaca ccttgatagg tgggctgccc   26460
ttcctggttg gcttggtttc atcagccatc cgcttgccct catctgttac gccggcggta   26520
gccggccagc ctcgcagagc aggattcccg ttgagcaccg ccaggtgcga ataagggaca   26580
gtgaagaagg aacacccgct cgcgggtggg cctacttcac ctatcctgcc cggctgacgc   26640
cgttggatac accaaggaaa gtctacacga acccctttggc aaaatcctgt atatcgtgcg   26700
aaaaaggatg gatataccga aaaaatcgct ataatgaccc cgaagcaggg ttatgcagcg   26760
gaaaagcgct gcttccctgc tgttttgtgg aatatctacc gactggaaac aggcaaatgc   26820
aggaaattac tgaactgagg ggacaggcga gagacgatgc caaagagcta caccgacgag   26880
ctggccgagt gggttgaatc ccgcgcggcc aagaagcgcc ggcgtgatga ggctgcggtt   26940
```

```
gcgttcctgg cggtgagggc ggatgtcgag gcggcgttag cgtccggcta tgcgctcgtc    27000
accatttggg agcacatgcg ggaaacgggg aaggtcaagt tctcctacga gacgttccgc    27060
tcgcacgcca ggcggcacat caaggccaag cccgccgatg tgcccgcacc gcaggccaag    27120
gctgcggaac ccgcgccggc acccaagacg ccggagccac ggcggccgaa gcagggggc    27180 aaggctgaaa agccggcccc cgctgcggcc ccgaccggct tcaccttcaa cccaacaccg    27240
gacaaaaagg atctactgta atggcgaaaa ttcacatggt tttgcagggc aagggcgggg    27300
tcggcaagtc ggccatcgcc gcgatcattg cgcagtacaa gatggacaag gggcagacac    27360
ccttgtgcat cgacaccgac ccggtgaacg cgacgttcga gggctacaag gccctgaacg    27420
tccgccggct gaacatcatg gccggcgacg aaattaactc gcgcaacttc gacaccctgg    27480
tcgagctgat tgcgccgacc aaggatgacg tggtgatcga caacggtgcc agctcgttcg    27540
tgcctctgtc gcattacctc atcagcaacc aggtgccggc tctgctgcaa gaaatggggc    27600
atgagctggt catccatacc gtcgtcaccg gcggccaggc tctcctggac acggtgagcg    27660
gcttcgccca gctcgccagc cagttcccgg ccgaagcgct tttcgtggtc tggctgaacc    27720
cgtattgggg gcctatcgag catgagggca agagctttga gcagatgaag gcgtacacgg    27780
ccaacaaggc ccgcgtgtcg tccatcatcc agattccggc cctcaaggaa gaaacctacg    27840
gccgcgattt cagcgacatg ctgcaagagc ggctgacgtt cgaccaggcg ctggccgatg    27900
aatcgctcac gatcatgacg cggcaacgcc tcaagatcgt gcggcgcggc ctgtttgaac    27960
agctcgacgc ggcggccgtg ctatgagcga ccagattgaa gagctgatcc gggagattgc    28020
ggccaagcac ggcatcgccg tcggccgcga cgacccggtg ctgatcctgc ataccatcaa    28080
cgcccggctc atggccgaca gtgcggccaa gcaagaggaa atccttgccg cgttcaagga    28140
agagctggaa gggatcgccc atcgttgggg cgaggacgcc aaggccaaag cggagcggat    28200
gctgaacgcg gccctggcgg ccagcaagga cgcaatggcg aaggtaatga aggacagcgc    28260
cgcgcaggcg gccgaagcga tccgcaggga aatcgacgac ggccttggcc gccagctcgc    28320
ggccaaggtc gcggacgcgc ggcgcgtggc gatgatgaac atgatcgccg gcggcatggt    28380
gttgttcgcg gccgccctgg tggtgtgggc ctcgttatga atcgcagagg gcagatgaa    28440 aaagcccggc gttgccgggc tttgtttttg cgttagctgg gcttgtttga caggcccaag    28500
ctctgactgc gcccgcgctc gcgctcctgg gcctgtttct tctcctgctc ctgcttgcgc    28560
atcagggcct ggtgccgtcg ggctgcttca cgcatcgaat cccagtcgcc ggccagctcg    28620
ggatgctccg cgcgcatctt gcgcgtcgcc agttcctcga tcttgggcgc gtgaatgccc    28680
atgccttcct tgatttcgcg caccatgtcc agccgcgtgt gcagggtctg caagcgggct    28740
tgctgttggg cctgctgctg ctgccaggcg gcctttgtac gcggcaggga cagcaagccg    28800
ggggcattgg actgtagctg ctgcaaacgc gcctgctgac ggtctacgag ctgttctagg    28860
cggtcctcga tgcgctccac ctggtcatgc tttgcctgca cgtagagcgc aagggtctgc    28920
tggtaggtct gctcgatggg cgcggattct aagagggcct gctgttccgt ctcggcctcc    28980
tgggccgcct gtagcaaatc ctcgccgctg ttgccgctgg actgctttac tgccggggac    29040
tgctgttgcc ctgctcgcgc cgtcgtcgca gttcggcttg ccccactcg attgactgct    29100 tcatttcgag ccgcagcgat gcgatctcgg attgcgtcaa cggacggggc agcgcggagg    29160
tgtccggctt ctccttgggt gagtcggtcg atgccatagc caaggtttc cttccaaaat    29220 gcgtccattg ctggaccgtg tttctcattg atgcccgcaa gcatcttcgg cttgaccgcc    29280
aggtcaagcg cgccttcatg ggcggtcatg acggacgccg ccatgacctt gccgccgttg    29340
```

```
ttctcgatgt agccgcgtaa tgaggcaatg gtgccgccca tcgtcagcgt gtcatcgaca  29400
acgatgtact tctggccggg gatcacctcc ccctcgaaag tcgggttgaa cgccaggcga  29460
tgatctgaac cggctccggt tcgggcgacc ttctcccgct gcacaatgtc cgtttcgacc  29520
tcaaggccaa ggcggtcggc cagaacgacc gccatcatgg ccggaatctt gttgttcccc  29580
gccgcctcga cggcgaggac tggaacgatg cggggcttgt cgtcgccgat cagcgtcttg  29640
agctgggcaa cagtgtcgtc cgaaatcagg cgctcgacca aattaagcgc cgcttccgcg  29700
tcgccctgct tcgcagcctg gtattcaggc tcgttggtca aagaaccaag gtcgccgttg  29760
cgaaccacct tcgggaagtc tccccacggt gcgcgctcgg ctctgctgta gctgctcaag  29820
acgcctccct ttttagccgc taaaactcta acgagtgcgc ccgcgactca acttgacgct  29880
tcggcactt acctgtgcct tgccacttgc gtcataggtg atgcttttcg cactcccgat  29940
ttcaggtact ttatcgaaat ctgaccgggc gtgcattaca aagttcttcc ccacctgttg  30000
gtaaatgctg ccgctatctg cgtggacgat gctgccgtcg tggcgctgcg acttatcggc  30060
cttttgggcc atatagatgt tgtaaatgcc aggtttcagg gccccggctt tatctacctt  30120
ctggttcgtc catgcgcctt ggttctcggt ctggacaatt ctttgcccat tcatgaccag  30180
gaggcggtgt ttcattgggt gactcctgac ggttgcctct ggtgttaaac gtgtcctggt  30240
cgcttgccgg ctaaaaaaa gccgacctcg gcagttcgag gccggctttc cctagagccg  30300
ggcgcgtcaa ggttgttcca tctattttag tgaactgcgt tcgatttatc agttactttc  30360
ctcccgcttt gtgtttcctc ccactcgttt ccgcgtctag ccgacccctc aacatagcgg  30420
cctcttcttg ggctgccttt gcctcttgcc gcgcttcgtc acgctcggct tgcaccgtcg  30480
taaagcgctc ggcctgcctg gccgcctctt gcgccgccaa cttcctttgc tcctggtggg  30540
cctcggcgtc ggcctgcgcc ttcgctttca ccgctgccaa ctccgtgcgc aaactctccg  30600
cttcgcgcct ggtggcgtcg cgctcgccgc gaagcgcctg catttcctgg ttggccgcgt  30660
ccagggtctt gcggctctct tctttgaatg cgcgggcgtc ctggtgagcg tagtccagct  30720
cggcgcgcag ctcctgcgct cgacgctcca cctcgtcggc ccgctgcgtc gccagcgcgg  30780
cccgctgctc ggctcctgcc agggcggtgc gtgcttcggc cagggcttgc cgctggcgtg  30840
cggccagctc ggccgcctcg gcggcctgct gctctagcaa tgtaacgcgc gcctgggctt  30900
cttccagctc gcgggcctgc gcctcgaagg cgtcggccag ctccccgcgc acggcttcca  30960
actcgttgcg ctcacgatcc cagccggctt gcgctgcctg caacgattca ttggcaaggg  31020
cctgggcggc ttgccagagg gcggccacgg cctggttgcc ggcctgctgc accgcgtccg  31080
gcacctggac tgccagcggg gcggcctgcg ccgtgcgctg gcgtcgccat tcgcgcatgc  31140
cggcgctggc gtcgttcatg ttgacgcggg cggccttacg cactgcatcc acggtcggga  31200
agttctcccg gtcgccttgc tcgaacagct cgtccgcagc cgcaaaaatg cggtcgcgcg  31260
tctctttgtt cagttccatg ttggctccgg taattggtaa gaataataat actcttacct  31320
accttatcag cgcaagagtt tagctgaaca gttctcgact taacggcagg tttttagcg  31380
gctgaagggc aggcaaaaaa agccccgcac ggtcggcggg ggcaaagggt cagcgggaag  31440
gggattagcg ggcgtcgggc ttcttcatgc gtcgggccg cgcttcttgg gatggagcac  31500
gacgaagcgc gcacgcgcat cgtcctcggc cctatcggcc cgcgtcgcgg tcaggaactt  31560
gtcgcgcgct aggtcctccc tggtgggcac caggggcatg aactcggcct gctcgatgta  31620
ggtccactcc atgaccgcat cgcagtcgag gccgcgttcc ttcaccgtct cttgcaggtc  31680
```

```
gcggtacgcc cgctcgttga gcggctggta acgggccaat tggtcgtaaa tggctgtcgg   31740
ccatgagcgg cctttcctgt tgagccagca gccgacgacg aagccggcaa tgcaggcccc   31800
tggcacaacc aggccgacgc cgggggcagg ggatggcagc agctcgccaa ccaggaaccc   31860
cgccgcgatg atgccgatgc cggtcaacca gcccttgaaa ctatccggcc ccgaaacacc   31920
cctgcgcatt gcctggatgc tgcgccggat agcttgcaac atcaggagcc gtttcttttg   31980
ttcgtcagtc atggtccgcc ctcaccagtt gttcgtatcg gtgtcggacg aactgaaatc   32040
gcaagagctg ccggtatcgg tccagccgct gtccgtgtcg ctgctgccga agcacggcga   32100
ggggtccgcg aacgccgcag acggcgtatc cggccgcagc gcatcgccca gcatggcccc   32160
ggtcagcgag ccgccggcca ggtagcccag catggtgctg ttggtcgccc cggccaccag   32220
ggccgacgtg acgaaatcgc cgtcattccc tctggattgt tcgctgctcg gcggggcagt   32280
gcgccgcgcc ggcggcgtcg tggatggctc gggttggctg gcctgcgacg gccggcgaaa   32340
ggtgcgcagc agctcgttat cgaccggctg cggcgtcggg gccgccgcct tgcgctgcgg   32400
tcggtgttcc ttcttcggct cgcgcagctt gaacagcatg atcgcggaaa ccagcagcaa   32460
cgccgcgcct acgcctcccg cgatgtagaa cagcatcgga ttcattcttc ggtcctcctt   32520
gtagcggaac cgttgtctgt gcggcgcggg tggcccgcgc cgctgtcttt ggggatcagc   32580
cctcgatgag cgcgaccagt ttcacgtcgg caaggttcgc ctcgaactcc tggccgtcgt   32640
cctcgtactt caaccaggca tagccttccg ccggcggccg acggttgagg ataaggcggg   32700
cagggcgctc gtcgtgctcg acctggacga tggccttttt cagcttgtcc gggtccggct   32760
ccttcgcgcc cttttccttg gcgtccttac cgtcctggtc gccgtcctcg ccgtcctggc   32820
cgtcgccggc ctccgcgtca cgctcggcat cagtctggcc gttgaaggca tcgacggtgt   32880
tgggatcgcg gcccttctcg tccaggaact cgcgcagcag cttgaccgtg ccgcgcgtga   32940
tttcctgggt gtcgtcgtca agccacgcct cgacttcctc cgggcgcttc ttgaaggccg   33000
tcaccagctc gttcaccacg gtcacgtcgc gcacgcggcc ggtgttgaac gcatcggcga   33060
tcttctccgg caggtccagc agcgtgacgt gctgggtgat gaacgccggc gacttgccga   33120
tttccttggc gatatcgcct tcttcttgc ccttcgccag ctcgcggcca atgaagtcgg   33180
caatttcgcg cggggtcagc tcgttgcgtt gcaggttctc gataacctgg tcggcttcgt   33240
tgtagtcgtt gtcgatgaac gccgggatgg acttcttgcc ggcccacttc gagccacggt   33300
agcggcgggc gccgtgattg atgatatagc ggcccggctg ctcctggttc tcgcgcaccg   33360
aaatgggtga cttcaccccg cgctctttga tcgtggcacc gatttccgcg atgctctccg   33420
gggaaaagcc ggggttgtcg gccgtccgcg gctgatgcgg atcttcgtcg atcaggtcca   33480
ggtccagctc gatagggccg gaaccgcccc gagacgccgc aggagcgtcc aggaggctcg   33540
acaggtcgcc gatgctatcc aaccccaggc cggacggctg cgccgcgcct gcggcttcct   33600
gagcggccgc agcggtgttt ttcttggtgg tcttggcttg agccgcagtc attgggaaat   33660
ctccatcttc gtgaacacgt aatcagccag ggcgcgaacc tctttcgatg ccttgcgcgc   33720
ggccgttttc ttgatcttcc agaccggcac accggatgcg agggcatcgg cgatgctgct   33780
gcgcaggcca acgtggccg gaatcatcat cttggggtac gcggccagca gctcggcttg   33840
gtggcgcgcg tggcgcggat ccgcgcatc gaccttgctg gcaccatgc caaggaattg   33900 cagcttggcg ttcttctggc gcacgttcgc aatggtcgtg accatcttct tgatgccctg   33960
gatgctgtac gcctcaagct cgatggggga cagcacatag tcggccgcga agagggcggc   34020
cgccaggccg acgccaaggg tcggggccgt gtcgatcagg cacacgtcga agccttggtt   34080
```

```
cgccagggcc ttgatgttcg ccccgaacag ctcgcgggcg tcgtccagcg acagccgttc    34140
ggcgttcgcc agtaccgggt tggactcgat gagggcgagg cgcgcggcct ggccgtcgcc    34200
ggctgcgggt gcggtttcgg tccagccgcc ggcagggaca gcgccgaaca gcttgcttgc    34260
atgcaggccg gtagcaaagt ccttgagcgt gtaggacgac ttgccctggg ggtccaggtc    34320
gatcacggca acccgcaagc cgcgctcgaa aaagtcgaag gcaagatgca cagggtcga    34380 agtcttgccg acgccgcctt tctggttggc cgtgaccaaa gttttcatcg tttggtttcc    34440
tgttttttct tggcgtccgc ttcccacttc cggacgatgt acgcctgatg ttccggcaga    34500
accgccgtta cccgcgcgta cccctcgggc aagttcttgt cctcgaacgc ggcccacacg    34560
cgatgcaccg cttgcgacac tgcgcccctg gtcagtccca gcgacgttgc gaacgtcgcc    34620
tgtggcttcc catcgactaa gacgcccgc gctatctcga tggtctgctg ccccacttcc    34680
agcccctgga tcgcctcctg gaactggctt tcggtaagcc gtttcttcat ggataacacc    34740
cataatttgc tccgcgcctt ggttgaacat agcggtgaca gccgccagca catgagagaa    34800
gtttagctaa acatttctcg cacgtcaaca cctttagccg ctaaaactcg tccttggcgt    34860
aacaaaacaa aagcccggaa accgggcttt cgtctcttgc cgcttatggc tctgcacccg    34920
gctccatcac caacaggtcg cgcacgcgct tcactcggtt gcggatcgac actgccagcc    34980
caacaaagcc ggttgccgcc gccgccagga tcgcgccgat gatgccggcc acaccggcca    35040
tcgcccacca ggtcgccgcc ttccggttcc attcctgctg gtactgcttc gcaatgctgg    35100
acctcggctc accataggct gaccgctcga tggcgtatgc cgcttctccc cttggcgtaa    35160
aacccagcgc cgcaggcggc attgccatgc tgcccgccgc tttcccgacc acgacgcgcg    35220
caccaggctt gcggtccaga ccttcggcca cggcagctg cgcaaggaca taatcagccg    35280
ccgacttggc tccacgcgcc tcgatcagct cttgcactcg cgcgaaatcc ttggcctcca    35340
cggccgccat gaatcgcgca cgcggcgaag gctccgcagg gccggcgtcg tgatcgccgc    35400
cgagaatgcc cttcaccaag ttcgacgaca cgaaaatcat gctgacggct atcaccatca    35460
tgcagacgga tcgcacgaac ccgctgaatt gaacacgagc acggcacccg cgaccactat    35520
gccaagaatg cccaaggtaa aaattgccgg ccccgccatg aagtccgtga atgccccgac    35580
ggccgaagtg aagggcaggc cgccacccag gccgccgccc tcactgcccg gcacctggtc    35640
gctgaatgtc gatgccagca cctgcggcac gtcaatgctt ccgggcgtcg cgctcgggct    35700
gatcgcccat cccgttactg ccccgatccc ggcaatggca aggactgcca gcgctgccat    35760
ttttggggtg aggccgttcg cggccgaggg gcgcagcccc tggggggatg ggaggccgc    35820 gttagcgggc cggagggtt cgagaagggg gggcaccccc cttcggcgtg cgcggtcacg    35880
cgcacagggc gcagccctgg ttaaaaacaa ggtttataaa tattggttta aaagcaggtt    35940
aaaagacagg ttagcggtgg ccgaaaaacg ggcggaaacc cttgcaaatg ctggattttc    36000
tgcctgtgga cagcccctca aatgtcaata ggtgcgcccc tcatctgtca gcactctgcc    36060
cctcaagtgt caaggatcgc gccctcatc tgtcagtagt cgcgcccctc aagtgtcaat    36120
accgcagggc acttatcccc aggcttgtcc acatcatctg tgggaaactc gcgtaaaatc    36180
aggcgttttc gccgatttgc gaggctggcc agctccacgt cgccgccga aatcgagcct    36240 gcccctcatc tgtcaacgcc gcgccgggtg agtcggcccc tcaagtgtca acgtccgccc    36300
ctcatctgtc agtgagggcc aagttttccg cgaggtatcc acaacgccgg cggccgcggt    36360
gtctcgcaca cggcttcgac ggcgtttctg gcgcgtttgc agggccatag acggccgcca    36420
```

-continued

| | |
|---|---|
| gcccagcggc gagggcaacc agcccggtga gcgtcggaaa ggcgctggaa gccccgtagc | 36480 |
| gacgcggaga ggggcgagac aagccaaggg cgcaggctcg atgcgcagca cgacatagcc | 36540 |
| ggttctcgca aggacgagaa tttccctgcg gtgcccctca agtgtcaatg aaagtttcca | 36600 |
| acgcgagcca ttcgcgagag ccttgagtcc acgctagatg agagctttgt tgtaggtgga | 36660 |
| ccagttggtg attttgaact tttgctttgc cacggaacgg tctgcgttgt cgggaagatg | 36720 |
| cgtgatctga tccttcaact cagcaaaagt tcgatttatt caacaaagcc acgttgtgtc | 36780 |
| tcaaaatctc tgatgttaca ttgcacaaga taaaaatata tcatcatgaa caataaaact | 36840 |
| gtctgcttac ataaacagta atacaagggg tgttatgagc catattcaac gggaaacgtc | 36900 |
| ttgctcgac | 36909 |

<210> SEQ ID NO 8
<211> LENGTH: 13019
<212> TYPE: DNA
<213> ORGANISM: Artificial Sequence
<220> FEATURE:
<223> OTHER INFORMATION: PHP23235 construct

<400> SEQUENCE: 8

| | |
|---|---|
| gttacccgga ccgaagctta gcccgggcat gcctgcagtg cagcgtgacc cggtcgtgcc | 60 |
| cctctctaga gataatgagc attgcatgtc taagttataa aaaattacca catattttt | 120 |
| ttgtcacact tgtttgaagt gcagtttatc tatctttata catatattta aactttactc | 180 |
| tacgaataat ataatctata gtactacaat aatatcagtg ttttagagaa tcatataaat | 240 |
| gaacagttag acatggtcta aaggacaatt gagtattttg acaacaggac tctacagttt | 300 |
| tatcttttta gtgtgcatgt gttctccttt ttttttgcaa atagcttcac ctatataata | 360 |
| cttcatccat tttattagta catccattta gggtttaggg ttaatggttt ttatagacta | 420 |
| atttttttag tacatctatt ttattctatt ttagcctcta aattaagaaa actaaaactc | 480 |
| tattttagtt tttttattta ataatttaga tataaaatag aataaaataa agtgactaaa | 540 |
| aattaaacaa ataccctttt agaaattaaa aaaactaagg aaacattttt cttgtttcga | 600 |
| gtagataatg ccagcctgtt aaacgccgtc gacgagtcta acggacacca accagcgaac | 660 |
| cagcagcgtc gcgtcgggcc aagcgaagca gacggcacgg catctctgtc gctgcctctg | 720 |
| gacccctctc gagagttccg ctccaccgtt ggacttgctc cgctgtcggc atccagaaat | 780 |
| tgcgtggcgg agcggcagac gtgagccggc acggcaggcg gcctcctcct cctctcacgg | 840 |
| cacggcagct acgggggatt cctttcccac cgctccttcg cttcccttc ctcgcccgcc | 900 |
| gtaataaata gacacccct ccacaccctc tttccccaac ctcgtgttgt tcggagcgca | 960 |
| cacacacaca accagatctc ccccaaatcc accgtcggc acctccgctt caaggtacgc | 1020 |
| cgctcgtcct cccccccccc ccctctctac cttctctaga tcggcgttcc ggtccatggt | 1080 |
| tagggcccgg tagttctact tctgttcatg tttgtgttag atccgtgttt gtgttagatc | 1140 |
| cgtgctgcta gcgttcgtac acggatgcga cctgtacgtc agacacgttc tgattgctaa | 1200 |
| cttgccagtg tttctctttg gggaatcctg ggatggctct agccgttccg cagacgggat | 1260 |
| cgatttcatg atttttttg tttcgttgca tagggtttgg tttgcccttt tcctttattt | 1320 |
| caatatatgc cgtgcacttg tttgtcgggt catcttttca tgcttttttt tgtcttggtt | 1380 |
| gtgatgatgt ggtctggttg ggcggtcgtt ctagatcgga gtagaattct gtttcaaact | 1440 |
| acctggtgga tttattaatt ttggatctgt atgtgtgtgc catacatatt catagttacg | 1500 |
| aattgaagat gatggatgga aatatcgatc taggataggt atacatgttg atgcgggttt | 1560 |

```
tactgatgca tatacagaga tgctttttgt tcgcttggtt gtgatgatgt ggtgtggttg    1620
ggcggtcgtt cattcgttct agatcggagt agaatactgt ttcaaactac ctggtgtatt    1680
tattaatttt ggaactgtat gtgtgtgtca tacatcttca tagttacgag tttaagatgg    1740
atggaaatat cgatctagga taggtataca tgttgatgtg ggttttactg atgcatatac    1800
atgatggcat atgcagcatc tattcatatg ctctaacctt gagtacctat ctattataat    1860
aaacaagtat gttttataat tattttgatc ttgatatact tggatgatgg catatgcagc    1920
agctatatgt ggatttttt agccctgcct tcatacgcta tttatttgct tggtactgtt    1980
tcttttgtcg atgctcaccc tgttgtttgg tgttacttct gcaggtcgac tctagaggat    2040
ccacaagttt gtacaaaaaa gctgaacgag aaacgtaaaa tgatataaat atcaatatat    2100
taaattagat tttgcataaa aaacagacta cataatactg taaaacacaa catatccagt    2160
cactatggcg gccgcattag gcaccccagg ctttacactt tatgcttccg gctcgtataa    2220
tgtgtggatt ttgagttagg atttaaatac gcgttgatcc ggcttactaa agccagata    2280 acagtatgcg tatttgcgcg ctgattttg cggtataaga atatatactg atatgtatac    2340
ccgaagtatg tcaaaaagag gtatgctatg aagcagcgta ttacagtgac agttgacagc    2400
gacagctatc agttgctcaa ggcatatatg atgtcaatat ctccggtctg gtaagcacaa    2460
ccatgcagaa tgaagcccgt cgtctgcgtg ccgaacgctg gaaagcggaa atcaggaag    2520 ggatggctga ggtcgcccgg tttattgaaa tgaacggctc ttttgctgac gagaacaggg    2580
gctggtgaaa tgcagtttaa ggtttacacc tataaaagag agagccgtta tcgtctgttt    2640
gtggatgtac agagtgatat cattgacacg cccggtcgac ggatggtgat cccctggcc    2700 agtgcacgtc tgctgtcaga taaagtctcc cgtgaacttt accggtggt gcatatcggg    2760 gatgaaagct ggcgcatgat gaccaccgat atggccagtg tgccggtctc cgttatcggg    2820
gaagaagtgg ctgatctcag ccaccgcgaa aatgacatca aaaacgccat taacctgatg    2880
ttctggggaa tataaatgtc aggctccctt atacacagcc agtctgcagg tcgaccatag    2940
tgactggata tgttgtgttt tacagtatta tgtagtctgt tttttatgca aaatctaatt    3000
taatatattg atatttatat cattttacgt ttctcgttca gctttcttgt acaaagtggt    3060
gttaacctag acttgtccat cttctggatt ggccaactta attaatgtat gaaataaaag    3120
gatgcacaca tagtgacatg ctaatcacta taatgtgggc atcaaagttg tgtgttatgt    3180
gtaattacta gttatctgaa taaaagagaa agagatcatc catatttctt atcctaaatg    3240
aatgtcacgt gtctttataa ttctttgatg aaccagatgc atttcattaa ccaaatccat    3300
atacatataa atattaatca tatataatta atatcaattg ggttagcaaa acaaatctag    3360
tctaggtgtg ttttgcgaat tgcggccgcc accgcgtgg agctcgaatt ccggtccggg    3420
tcacctttgt ccaccaagat ggaactgcgg ccgctcatta attaagtcag gcgcgcctct    3480
agttgaagac acgttcatgt cttcatcgta agaagacact cagtagtctt cggccagaat    3540
ggccatctgg attcagcagg cctagaaggc catttaaatc ctgaggatct ggtcttccta    3600
aggacccggg atatcggacc gattaaactt taattcggtc cgaagcttgc atgcctgcag    3660
tgcagcgtga cccggtcgtg cccctctcta gagataatga gcattgcatg tctaagttat    3720
aaaaaattac cacatatttt ttttgtcaca cttgtttgaa gtgcagttta tctatcttta    3780
tacatatatt taaactttac tctacgaata atataatcta tagtactaca ataatatcag    3840
tgttttagag aatcatataa atgaacagtt agacatggtc taaaggacaa ttgagtattt    3900
```

```
tgacaacagg actctacagt tttatctttt tagtgtgcat gtgttctcct ttttttttgc    3960
aaatagcttc acctatataa tacttcatcc attttattag tacatccatt tagggtttag    4020
ggttaatggt ttttatagac taattttttt agtacatcta ttttattcta ttttagcctc    4080
taaattaaga aaactaaaac tctattttag ttttttttatt taataattta gatataaaat    4140
agaataaaat aaagtgacta aaattaaac aaatacccctt taagaaatta aaaaaactaa    4200
ggaaacattt ttcttgtttc gagtagataa tgccagcctg ttaaacgccg tcgacgagtc    4260
taacggacac caaccagcga accagcagcg tcgcgtcggg ccaagcgaag cagacggcac    4320
ggcatctctg tcgctgcctc tggacccctc tcgagagttc cgctccaccg ttggacttgc    4380
tccgctgtcg gcatccagaa attgcgtggc ggagcggcag acgtgagccg gcacggcagg    4440
cggcctcctc ctcctctcac ggcaccggca gctacggggg attccttttcc caccgctcct    4500 tcgctttccc ttcctcgccc gccgtaataa atagacaccc cctccacacc ctctttcccc    4560
aacctcgtgt tgttcggagc gcacacacac acaaccagat ctcccccaaa tccacccgtc    4620
ggcacctccg cttcaaggta cgccgctcgt cctccccccc cccctctct accttctcta    4680 gatcggcgtt ccggtccatg catggttagg gcccggtagt tctacttctg ttcatgtttg    4740
tgttagatcc gtgtttgtgt tagatccgtg ctgctagcgt tcgtacacgg atgcgacctg    4800
tacgtcagac acgttctgat tgctaacttg ccagtgtttc tctttgggga atcctgggat    4860
ggctctagcc gttccgcaga cgggatcgat ttcatgattt ttttttgtttc gttgcatagg    4920 gtttggtttg cccttttcct ttatttcaat atatgccgtg cacttgtttg tcgggtcatc    4980
ttttcatgct tttttttgtc ttggttgtga tgatgtggtc tggttgggcg gtcgttctag    5040
atcggagtag aattctgttt caaactacct ggtggattta ttaattttgg atctgtatgt    5100
gtgtgccata catattcata gttacgaatt gaagatgatg gatggaaata tcgatctagg    5160
ataggtatac atgttgatgc gggttttact gatgcatata cagagatgct ttttgttcgc    5220
ttggttgtga tgatgtggtg tggttgggcg gtcgttcatt cgttctagat cggagtagaa    5280
tactgtttca aactacctgg tgtatttatt aattttggaa ctgtatgtgt gtgtcataca    5340
tcttcatagt tacgagttta agatggatgg aaatatcgat ctaggatagg tatacatgtt    5400
gatgtgggtt ttactgatgc atatacatga tggcatatgc agcatctatt catatgctct    5460
aaccttgagt acctatctat tataataaac aagtatgttt tataattatt ttgatcttga    5520
tatacttgga tgatggcata tgcagcagct atatgtggat ttttttagcc ctgccttcat    5580
acgctattta tttgcttggt actgtttctt ttgtcgatgc tcaccctgtt gtttggtgtt    5640
acttctgcag gtcgacttta acttagccta ggatccacac gacaccatgt cccccgagcg    5700 ccgcccgtc gagatccgcc cggccaccgc cgccgacatg gccgccgtgt gcgacatcgt    5760
gaaccactac atcgagacct ccaccgtgaa cttccgcacc gagccgcaga ccccgcagga    5820
gtggatcgac gacctggagc gcctccagga ccgctacccg tggctcgtgg ccgaggtgga    5880
gggcgtggtg gccggcatcg cctacgccgg cccgtggaag gccgcaacg cctacgactg    5940 gaccgtggag tccaccgtgt acgtgtccca ccgccaccag cgcctcggcc tcggctccac    6000
cctctacacc cacctcctca agagcatgga ggccagggc ttcaagtccg tggtggccgt    6060
gatcggcctc ccgaacgacc cgtccgtgcg cctccacgag gccctcggct acaccgcccg    6120
cggcaccctc cgcgccgccg gctacaagca cggcggctgg cacgacgtcg gcttctggca    6180
gcgcgacttc gagctgccgg ccccgccgcg ccggtgcgc ccggtgacgc agatctgagt    6240
cgaaacctag acttgtccat cttctggatt ggccaactta attaatgtat gaaataaaag    6300
```

```
gatgcacaca tagtgacatg ctaatcacta taatgtgggc atcaaagttg tgtgttatgt    6360
gtaattacta gttatctgaa taaaagagaa agagatcatc catatttctt atcctaaatg    6420
aatgtcacgt gtctttataa ttctttgatg aaccagatgc atttcattaa ccaaatccat    6480
atacatataa atattaatca tatataatta atatcaattg ggttagcaaa acaaatctag    6540
tctaggtgtg ttttgcgaat tgcggccgcc accgcggtgg agctcgaatt cattccgatt    6600
aatcgtggcc tcttgctctt caggatgaag agctatgttt aaacgtgcaa gcgctactag    6660
acaattcagt acattaaaaa cgtccgcaat gtgttattaa gttgtctaag cgtcaatttg    6720
tttacaccac aatatatcct gccaccagcc agccaacagc tccccgaccg gcagctcggc    6780
acaaaatcac cactcgatac aggcagccca tcagtccggg acggcgtcag cgggagagcc    6840
gttgtaaggc ggcagacttt gctcatgtta ccgatgctat tcggaagaac ggcaactaag    6900
ctgccgggtt tgaaacacgg atgatctcgc ggagggtagc atgttgattg taacgatgac    6960
agagcgttgc tgcctgtgat caaatatcat ctccctcgca gagatccgaa ttatcagcct    7020
tcttattcat ttctcgctta accgtgacag gctgtcgatc ttgagaacta tgccgacata    7080
ataggaaatc gctggataaa gccgctgagg aagctgagtg gcgctatttc tttagaagtg    7140
aacgttgacg atcgtcgacc gtaccccgat gaattaattc ggacgtacgt tctgaacaca    7200
gctggatact tacttgggcg attgtcatac atgacatcaa caatgtaccc gtttgtgtaa    7260
ccgtctcttg gaggttcgta tgacactagt ggttcccctc agcttgcgac tagatgttga    7320
ggcctaacat tttattagag agcaggctag ttgcttagat acatgatctt caggccgtta    7380
tctgtcaggg caagcgaaaa ttggccattt atgacgacca atgccccgca gaagctccca    7440
tctttgccgc catagacgcc gcgcccccct tttggggtgt agaacatcct tttgccagat    7500
gtggaaaaga agttcgttgt cccattgttg gcaatgacgt agtagccggc gaaagtgcga    7560
gacccatttg cgctatatat aagcctacga tttccgttgc gactattgtc gtaattggat    7620
gaactattat cgtagttgct ctcagagttg tcgtaatttg atggactatt gtcgtaattg    7680
cttatggagt tgtcgtagtt gcttggagaa atgtcgtagt tggatgggga gtagtcatag    7740
ggaagacgag cttcatccac taaaacaatt ggcaggtcag caagtgcctg ccccgatgcc    7800
atcgcaagta cgaggcttag aaccaccttc aacagatcgc gcatagtctt ccccagctct    7860
ctaacgcttg agttaagccg cgccgcgaag cggcgtcggc ttgaacgaat tgttagacat    7920
tatttgccga ctaccttggt gatctcgcct ttcacgtagt gaacaaattc ttccaactga    7980
tctgcgcgcg aggccaagcg atcttcttgt ccaagataag cctgcctagc ttcaagtatg    8040
acgggctgat actgggccgg caggcgctcc attgcccagt cggcagcgac atccttcggc    8100
gcgattttgc cggttactgc gctgtaccaa atgcgggaca acgtaagcac tacatttcgc    8160
tcatcgccag cccagtcggg cggcgagttc catagcgtta aggtttcatt tagcgcctca    8220
aatagatcct gttcaggaac cggatcaaag agttcctccg ccgctggacc taccaaggca    8280
acgctatgtt ctcttgcttt tgtcagcaag atagccagat caatgtcgat cgtggctggc    8340
tcgaagatac ctgcaagaat gtcattgcgc tgccattctc caaattgcag ttcgcgctta    8400
gctggataac gccacggaat gatgtcgtcg tgcacaacaa tggtgacttc tacagcgcgg    8460
agaatctcgc tctctccagg ggaagccgaa gtttccaaaa ggtcgttgat caaagctcgc    8520
cgcgttgttt catcaagcct tacagtcacc gtaaccagca aatcaatatc actgtgtggc    8580
ttcaggccgc catccactgc ggagccgtac aaatgtacgg ccagcaacgt cggttcgaga    8640
```

```
tggcgctcga tgacgccaac tacctctgat agttgagtcg atacttcggc gatcaccgct    8700
tccctcatga tgtttaactc ctgaattaag ccgcgccgcg aagcggtgtc ggcttgaatg    8760
aattgttagg cgtcatcctg tgctcccgag aaccagtacc agtacatcgc tgtttcgttc    8820
gagacttgag gtctagtttt atacgtgaac aggtcaatgc cgccgagagt aaagccacat    8880
tttgcgtaca aattgcaggc aggtacattg ttcgtttgtg tctctaatcg tatgccaagg    8940
agctgtctgc ttagtgccca cttttcgca aattcgatga gactgtgcgc gactcctttg    9000
cctcggtgcg tgtgcgacac aacaatgtgt tcgatagagg ctagatcgtt ccatgttgag    9060
ttgagttcaa tcttcccgac aagctcttgg tcgatgaatg cgccatagca agcagagtct    9120
tcatcagagt catcatccga gatgtaatcc ttccggtagg ggctcacact tctggtagat    9180
agttcaaagc cttggtcgga taggtgcaca tcgaacactt cacgaacaat gaaatggttc    9240
tcagcatcca atgtttccgc cacctgctca gggatcaccg aaatcttcat atgacgccta    9300
acgcctggca cagcggatcg caaacctggc gcggcttttg gcacaaaagg cgtgacaggt    9360
ttgcgaatcc gttgctgcca cttgttaacc cttttgccag atttggtaac tataatttat    9420
gttagaggcg aagtcttggg taaaaactgg cctaaaattg ctggggattt caggaaagta    9480
aacatcacct tccggctcga tgtctattgt agatatatgt agtgtatcta cttgatcggg    9540
ggatctgctg cctcgcgcgt ttcggtgatg acggtgaaaa cctctgacac atgcagctcc    9600
cggagacggt cacagcttgt ctgtaagcgg atgccgggag cagacaagcc cgtcagggcg    9660
cgtcagcggg tgttggcggg tgtcgggggcg cagccatgac ccagtcacgt agcgatagcg    9720
gagtgtatac tggcttaact atgcggcatc agagcagatt gtactgagag tgcaccatat    9780
gcggtgtgaa ataccgcaca gatgcgtaag gagaaaatac cgcatcaggc gctcttccgc    9840
ttcctcgctc actgactcgc tgcgctcggt cgttcggctg cggcgagcgg tatcagctca    9900
ctcaaaggcg gtaatacggt tatccacaga atcagggggat aacgcaggaa agaacatgtg    9960
agcaaaaggc cagcaaaagg ccaggaaccg taaaaaggcc gcgttgctgg cgttttcca    10020 taggctccgc ccccctgacg agcatcacaa aaatcgacgc tcaagtcaga ggtggcgaaa    10080
cccgacagga ctataaagat accaggcgtt tcccctgga agctccctcg tgcgctctcc    10140
tgttccgacc ctgccgctta ccggatacct gtccgccttt ctcccttcgg gaagcgtggc    10200
gctttctcat agctcacgct gtaggtatct cagttcggtg taggtcgttc gctccaagct    10260
gggctgtgtg cacgaacccc ccgttcagcc cgaccgctgc gccttatccg gtaactatcg    10320
tcttgagtcc aacccggtaa gacacgactt atcgccactg gcagcagcca ctggtaacag    10380
gattagcaga gcgaggtatg taggcggtgc tacagagttc ttgaagtggt ggcctaacta    10440
cggctacact agaaggacag tatttggtat ctgcgctctg ctgaagccag ttaccttcgg    10500
aaaaagagtt ggtagctctt gatccggcaa acaaaccacc gctggtagcg tggtttttt    10560 tgtttgcaag cagcagatta cgcgcagaaa aaaaggatct caagaagatc ctttgatctt    10620
ttctacgggg tctgacgctc agtggaacga aaactcacgt taagggattt tggtcatgag    10680
attatcaaaa aggatcttca cctagatcct tttaaattaa aaatgaagtt ttaaatcaat    10740
ctaaagtata tatgagtaaa cttggtctga cagttaccaa tgcttaatca gtgaggcacc    10800
tatctcagcg atctgtctat ttcgttcatc catagttgcc tgactccccg tcgtgtagat    10860
aactacgata cgggagggct taccatctgg ccccagtgct gcaatgatac cgcgagaccc    10920
acgctcaccg gctccagatt tatcagcaat aaaccagcca gccggaaggg ccgagcgcag    10980
aagtggtcct gcaactttat ccgcctccat ccagtctatt aattgttgcc gggaagctag    11040
```

```
agtaagtagt tcgccagtta atagtttgcg caacgttgtt gccattgctg caggggggggg    11100 ggggggggggg gacttccatt gttcattcca cggacaaaaa cagagaaagg aaacgacaga    11160
ggccaaaaag cctcgctttc agcacctgtc gtttcctttc ttttcagagg gtattttaaa    11220
taaaaacatt aagttatgac gaagaagaac ggaaacgcct taaaccggaa aattttcata    11280
aatagcgaaa acccgcgagg tcgccgcccc gtaacctgtc ggatcaccgg aaaggacccg    11340
taaagtgata atgattatca tctacatatc acaacgtgcg tggaggccat caaaccacgt    11400
caaataatca attatgacgc aggtatcgta ttaattgatc tgcatcaact taacgtaaaa    11460
acaacttcag acaatacaaa tcagcgacac tgaatacggg gcaacctcat gtccccccc    11520 cccccccccc tgcaggcatc gtggtgtcac gctcgtcgtt tggtatggct tcattcagct    11580
ccggttccca acgatcaagg cgagttacat gatcccccat gttgtgcaaa aaagcggtta    11640
gctccttcgg tcctccgatc gttgtcagaa gtaagttggc cgcagtgtta tcactcatgg    11700
ttatggcagc actgcataat tctcttactg tcatgccatc cgtaagatgc ttttctgtga    11760
ctggtgagta ctcaaccaag tcattctgag aatagtgtat gcggcgaccg agttgctctt    11820
gcccggcgtc aacacgggat aataccgcgc cacatagcag aactttaaaa gtgctcatca    11880
ttggaaaacg ttcttcgggg cgaaaactct caaggatctt accgctgttg agatccagtt    11940
cgatgtaacc cactcgtgca cccaactgat cttcagcatc ttttactttc accagcgttt    12000
ctgggtgagc aaaaacagga aggcaaaatg ccgcaaaaaa gggaataagg gcgacacgga    12060
aatgttgaat actcatactc ttccttttc aatattattg aagcatttat cagggttatt    12120
gtctcatgag cggatacata tttgaatgta tttagaaaaa taaacaaata ggggttccgc    12180
gcacatttcc ccgaaaagtg ccacctgacg tctaagaaac cattattatc atgacattaa    12240
cctataaaaa taggcgtatc acgaggccct ttcgtcttca agaattggtc gacgatcttg    12300
ctgcgttcgg atattttcgt ggagttcccg ccacagaccc ggattgaagg cgagatccag    12360
caactcgcgc cagatcatcc tgtgacggaa ctttggcgcg tgatgactgg ccaggacgtc    12420
ggccgaaaga gcgacaagca gatcacgctt ttcgacagcg tcggatttgc gatcgaggat    12480
ttttcggcgc tgcgctacgt ccgcgaccgc gttgagggat caagcacag cagcccactc    12540 gaccttctag ccgacccaga cgagccaagg gatcttttg gaatgctgct ccgtcgtcag    12600
gctttccgac gtttgggtgg ttgaacagaa gtcattatcg tacggaatgc caagcactcc    12660 cgagggaac cctgtggttg gcatgcacat acaaatggac gaacggataa accttttcac    12720
gcccttttaa atatccgtta ttctaataaa cgctctttc tcttaggttt acccgccaat    12780
atatcctgtc aaacactgat agtttaaact gaaggcggga aacgacaatc tgatcatgag    12840
cggagaatta agggagtcac gttatgaccc ccgccgatga cgcgggacaa gccgttttac    12900
gtttggaact gacagaaccg caacgttgaa ggagccactc agcaagctgg tacgattgta    12960
atacgactca ctatagggcg aattgagcgc tgtttaaacg ctcttcaact ggaagagcg    13019
```

<210> SEQ ID NO 9
<211> LENGTH: 2991
<212> TYPE: DNA
<213> ORGANISM: Artificial Sequence
<220> FEATURE:
<223> OTHER INFORMATION: PHP20234 construct

<400> SEQUENCE: 9

```
ctttcctgcg ttatcccctg attctgtgga taaccgtatt accgcctttg agtgagctga    60
```

```
taccgctcgc cgcagccgaa cgaccgagcg cagcgagtca gtgagcgagg aagcggaaga    120
gcgcccaata cgcaaaccgc ctctccccgc gcgttggccg attcattaat gcagctggca    180
cgacaggttt cccgactgga aagcgggcag tgagcgcaac gcaattaata cgcgtaccgc    240
tagccaggaa gagtttgtag aaacgcaaaa aggccatccg tcaggatggc cttctgctta    300
gtttgatgcc tggcagttta tggcgggcgt cctgcccgcc accctccggg ccgttgcttc    360
acaacgttca atccgctcc cggcggattt gtcctactca ggagagcgtt caccgacaaa    420
caacagataa aacgaaaggc ccagtcttcc gactgagcct ttcgttttat ttgatgcctg    480
gcagttccct actctcgcgt taacgctagc atggatgttt cccagtcac gacgttgtaa     540 aacgacggcc agtcttaagc tcgggccctg cagctctaga gctcgaattc tacaggtcac    600
taataccatc taagtagttg gttcatagtg actgcatatg ttgtgtttta cagtattatg    660
tagtctgttt tttatgcaaa atctaattta atatattgat atttatatca ttttacgttt    720
ctcgttcaac tttcttgtac aaagtggccg ttaacggatc cagacttgtc catcttctgg    780
attggccaac ttaattaatg tatgaaataa aaggatgcac acatagtgac atgctaatca    840
ctataatgtg ggcatcaaag ttgtgtgtta tgtgtaatta ctagttatct gaataaaaga    900
gaaagagatc atccatattt cttatcctaa atgaatgtca cgtgtcttta taattctttg    960
atgaaccaga tgcatttcat taaccaaatc catatacata taaatattaa tcatatataa   1020
ttaatatcaa ttgggttagc aaaacaaatc tagtctaggt gtgttttgcg aattgcggca   1080
agcttgcggc cgccccgggc aactttatta tacaaagttg gcattataaa aaagcattgc   1140
ttatcaattt gttgcaacga acaggtcact atcagtcaaa ataaaatcat tatttggagc   1200
tccatggtag cgttaacgcg gccgcgatat ccctatagt gagtcgtatt acatggtcat    1260
agctgtttcc tggcagctct ggcccgtgtc tcaaaatctc tgatgttaca ttgcacaaga    1320
taaaaatata tcatcatgaa caataaaact gtctgcttac ataaacagta atacaagggg   1380
tgttatgagc catattcaac gggaaacgtc gaggccgcga ttaaattcca acatggatgc   1440
tgatttatat gggtataaat gggctcgcga taatgtcggg caatcaggtg cgacaatcta   1500
tcgcttgtat gggaagcccg atgcgccaga gttgtttctg aaacatggca aaggtagcgt   1560
tgccaatgat gttacagatg agatggtcag actaaactgg ctgacggaat ttatgcctct   1620
tccgaccatc aagcatttta tccgtactcc tgatgatgca tggttactca ccactgcgat   1680
ccccggaaaa acagcattcc aggtattaga agaatatcct gattcaggtg aaaatattgt   1740
tgatgcgctg gcagtgttcc tgcgccggtt gcattcgatt cctgtttgta attgtccttt   1800
taacagcgat cgcgtatttc gtctcgctca ggcgcaatca cgaatgaata cggtttggt    1860 tgatgcgagt gattttgatg acgagcgtaa tggctggcct gttgaacaag tctggaaaga   1920
aatgcataaa cttttgccat tctcaccgga ttcagtcgtc actcatggtg atttctcact   1980
tgataacctt attttgacg aggggaaatt aataggttgt attgatgttg acgagtcgg    2040 aatcgcagac cgataccagg atcttgccat cctatggaac tgcctcggtg agttttctcc   2100
ttcattacag aaacggcttt ttcaaaaata tggtattgat aatcctgata tgaataaatt   2160
gcagtttcat ttgatgctcg atgagttttt ctaatcagaa ttggttaatt ggttgtaaca   2220
ctggcagagc attacgctga cttgacggga cggcgcaagc tcatgaccaa aatcccttaa   2280
cgtgagttac gcgtcgttcc actgagcgtc agaccccgta gaaagatca aaggatcttc    2340 ttgagatcct ttttttctgc gcgtaatctg ctgcttgcaa acaaaaaaac caccgctacc   2400
agcggtggtt tgtttgccgg atcaagagct accaactctt tttccgaagg taactggctt   2460
```

| | |
|---|---:|
| cagcagagcg cagataccaa atactgtcct tctagtgtag ccgtagttag gccaccactt | 2520 |
| caagaactct gtagcaccgc ctacatacct cgctctgcta atcctgttac cagtggctgc | 2580 |
| tgccagtggc gataagtcgt gtcttaccgg gttggactca agacgatagt taccggataa | 2640 |
| ggcgcagcgg tcgggctgaa cggggggttc gtgcacacag cccagcttgg agcgaacgac | 2700 |
| ctacaccgaa ctgagatacc tacagcgtga gcattgagaa agcgccacgc ttcccgaagg | 2760 |
| gagaaaggcg gacaggtatc cggtaagcgg cagggtcgga acaggagagc gcacgaggga | 2820 |
| gcttccaggg ggaaacgcct ggtatcttta tagtcctgtc gggtttcgcc acctctgact | 2880 |
| tgagcgtcga ttttttgtgat gctcgtcagg ggggcggagc ctatggaaaa acgccagcaa | 2940 |
| cgcggccttt ttacggttcc tggccttttg ctggcctttt gctcacatgt t | 2991 |

<210> SEQ ID NO 10
<211> LENGTH: 13278
<212> TYPE: DNA
<213> ORGANISM: Artificial Sequence
<220> FEATURE:
<223> OTHER INFORMATION: PHP22655 construct (destination vector)

<400> SEQUENCE: 10

| | |
|---|---:|
| aagctggtac gattgtaata cgactcacta tagggcgaat tgagcgctgt ttaaacgctc | 60 |
| ttcaactgga agagcggtta ccagagctgg tcacctttgt ccaccaagat ggaactgcgg | 120 |
| ccgctcatta attaagtcag gcgcgcctct agttgaagac acgttcatgt cttcatcgta | 180 |
| agaagacact cagtagtctt cggccagaat ggcccggacc gaagctggcc gctctagaac | 240 |
| tagtggatct cgatgtgtag tctacgagaa gggttaaccg tctcttcgtg agaataaccg | 300 |
| tggcctaaaa ataagccgat gaggataaat aaaatgtggt ggtacagtac ttcaagaggt | 360 |
| ttactcatca agaggatgct tttccgatga gctctagtag tacatcggac ctcacatacc | 420 |
| tccattgtgg tgaaatattt tgtgctcatt tagtgatggg taaattttgt ttatgtcact | 480 |
| ctaggttttg acatttcagt tttgccactc ttaggttttg acaaataatt tccattccgc | 540 |
| ggcaaaagca aaacaatttt atttactttt taccactctt agctttcaca atgtatcaca | 600 |
| aatgccactc tagaaattct gtttatgcca cagaatgtga aaaaaacac tcacttattt | 660 |
| gaagccaagg tgttcatggc atggaaatgt gacataaagt aacgttcgtg tataagaaaa | 720 |
| aattgtactc ctcgtaacaa gagacggaaa catcatgaga caatcgcgtt tggaaggctt | 780 |
| tgcatcacct ttggatgatg cgcatgaatg gagtcgtctg cttgctagcc ttcgcctacc | 840 |
| gcccactgag tccgggcggc aactaccatc ggcgaacgac ccagctgacc tctaccgacc | 900 |
| ggacttgaat gcgctaccct cgtcagcgac gatggccgcg tacgctggcg acgtgccccc | 960 |
| gcatgcatgg cggcacatgg cgagctcaga ccgtgcgtgg ctggctacaa atacgtaccc | 1020 |
| cgtgagtgcc ctagctagaa acttacacct gcaactgcga gagcgagcgt gtgagtgtag | 1080 |
| ccgagtagat cccccggtcg ccaccatggc ctcctccgag aacgtcatca ccgagttcat | 1140 |
| gcgcttcaag gtgcgcatgg agggcaccgt gaacggccac gagttcgaga tcgagggcga | 1200 |
| gggcgagggc cgcccctacg agggccacaa caccgtgaag ctgaaggtga ccaagggcgg | 1260 |
| cccccctgccc ttcgcctggg acatcctgtc ccccagttc cagtacggct ccaaggtgta | 1320 |
| cgtgaagcac cccgccgaca tccccgacta caagaagctg tccttccccg agggcttcaa | 1380 |
| gtgggagcgc gtgatgaact tcgaggacgg cggcgtggcg accgtgaccc aggactcctc | 1440 |
| cctgcaggac ggctgcttca tctacaaggt gaagttcatc ggcgtgaact tcccctccga | 1500 |

```
cggccccgtg atgcagaaga agaccatggg ctgggaggcc tccaccgagc gcctgtaccc  1560
ccgcgacggc gtgctgaagg gcgagaccca caaggccctg aagctgaagg acggcggcca  1620
ctacctggtg gagttcaagt ccatctacat ggccaagaag cccgtgcagc tgcccggcta  1680
ctactacgtg gacgccaagc tggacatcac ctcccacaac gaggactaca ccatcgtgga  1740
gcagtacgag cgcaccgagg gccgccacca cctgttcctg tagcggccca tggatattcg  1800
aacgcgtagg taccacatgg ttaacctaga cttgtccatc ttctggattg gccaacttaa  1860
ttaatgtatg aaataaaagg atgcacacat agtgacatgc taatcactat aatgtgggca  1920
tcaaagttgt gtgttatgtg taattactag ttatctgaat aaaagagaaa gagatcatcc  1980
atatttctta tcctaaatga atgtcacgtg tctttataat tctttgatga accagatgca  2040
tttcattaac caaatccata tacatataaa tattaatcat atataattaa tatcaattgg  2100
gttagcaaaa caaatctagt ctaggtgtgt tttgcgaatg cggccgccac cgcggtggag  2160
ctcgaattcc ggtccgggcc tagaaggcca tttaaatcct gaggatctgg tcttcctaag  2220
gacccgggat atcgctatca actttgtata gaaaagttga cgagaaacg taaaatgata  2280 taaatatcaa tatattaaat tagattttgc ataaaaaaca gactacataa tactgtaaaa  2340
cacaacatat ccagtcacta tggtcgacct gcagactggc tgtgtataag ggagcctgac  2400
atttatattc cccagaacat caggttaatg gcgttttga tgtcattttc gcggtggctg  2460
agatcagcca cttcttcccc gataacggag accggcacac tggccatatc ggtggtcatc  2520
atgcgccagc tttcatcccc gatatgcacc accgggtaaa gttcacgggg gactttatct  2580
gacagcagac gtgcactggc cagggggatc accatccgtc gcccgggcgt gtcaataata  2640
tcactctgta catccacaaa cagacgataa cggctctctc ttttataggt gtaaaccta  2700 aactgcattt caccagcccc tgttctcgtc ggcaaaagag ccgttcattt caataaaccg  2760
ggcgacctca gccatccctt cctgattttc cgctttccag cgttcggcac gcagacgacg  2820
ggcttcattc tgcatggttg tgcttaccga accggagata ttgacatcat atatgccttg  2880
agcaactgat agctgtcgct gtcaactgtc actgtaatac gctgcttcat agcatacctc  2940
tttttgacat acttcgggta tacatatcag tatatattct tataccgcaa aaatcagcgc  3000
gcaaatacgc atactgttat ctggctttta gtaagccgga tcctctagat tacgccccgc  3060
ctgccactca tcgcagtact gttgtaattc attaagcatt ctgccgacat ggaagccatc  3120
acaaacggca tgatgaacct gaatcgccag cggcatcagc accttgtcgc cttgcgtata  3180
atatttgccc atggtgaaaa cggggggcgaa gaagttgtcc atattggcca cgtttaaatc  3240
aaaactggtg aaactcaccc agggattggc tgagacgaaa aacatattct caataaaccc  3300
tttagggaaa taggccaggt tttcaccgta acacgccaca tcttgcgaat atatgtgtag  3360
aaactgccgg aaatcgtcgt ggtattcact ccagagcgat gaaaacgttt cagtttgctc  3420
atggaaaacg gtgtaacaag ggtgaacact atcccatatc accagctcac cgtctttcat  3480
tgccatacgg aattccggat gagcattcat caggcgggca agaatgtgaa taaaggccgg  3540
ataaaacttg tgcttatttt tctttacggt ctttaaaaag gccgtaatat ccagctgaac  3600
ggtctggtta taggtacatt gagcaactga ctgaaatgcc tcaaaatgtt ctttacgatg  3660
ccattgggat atatcaacgg tggtatatcc agtgattttt ttctccattt tagcttcctt  3720
agctcctgaa atctcgacga tcctaact caaaatccac acattatacg agccggaagc  3780
ataaagtgta aagcctgggg tgcctaatg cggccgccat agtgactgga tatgttgtgt  3840
tttacagtat tatgtagtct gttttttatg caaaatctaa tttaatatat tgatatttat  3900
```

| | |
|---|---|
| atcattttac gtttctcgtt caactttatt atacaaagtt gatagatatc ggaccgatta | 3960 |
| aactttaatt cggtccgaag cttgcatgcc tgcagtgcag cgtgacccgg tcgtgcccct | 4020 |
| ctctagagat aatgagcatt gcatgtctaa gttataaaaa attaccacat attttttttg | 4080 |
| tcacacttgt ttgaagtgca gtttatctat ctttatacat atatttaaac tttactctac | 4140 |
| gaataatata atctatagta ctacaataat atcagtgttt tagagaatca tataaatgaa | 4200 |
| cagttagaca tggtctaaag gacaattgag tattttgaca acaggactct acagttttat | 4260 |
| cttttagtg tgcatgtgtt ctccttttt tttgcaaata gcttcaccta tataatactt | 4320 |
| catccatttt attagtacat ccatttaggg tttagggtta atggttttta tagactaatt | 4380 |
| tttttagtac atctattta ttctatttta gcctctaaat taagaaaact aaaactctat | 4440 |
| tttagttttt ttatttaata atttagatat aaaatagaat aaaataaagt gactaaaaat | 4500 |
| taaacaaata ccctttaaga aattaaaaaa actaaggaaa catttttctt gtttcgagta | 4560 |
| gataatgcca gcctgttaaa cgccgtcgac gagtctaacg dacaccaacc agcgaaccag | 4620 |
| cagcgtcgcg tcgggccaag cgaagcagac ggcacggcat ctctgtcgct gcctctggac | 4680 |
| ccctctcgag agttccgctc caccgttgga cttgctccgc tgtcggcatc cagaaattgc | 4740 |
| gtggcggagc ggcagacgtg agccggcacg gcaggcggcc tcctcctcct ctcacggcac | 4800 |
| cggcagctac gggggattcc tttcccaccg ctccttcgct ttcccttcct cgcccgccgt | 4860 |
| aataaataga cacccctcc acacctctt tccccaacct cgtgttgttc ggagcgcaca | 4920 |
| cacacacaac cagatctccc ccaaatccac ccgtcggcac ctccgcttca aggtacgccg | 4980 |
| ctcgtcctcc ccccccccc tctctacctt ctctagatcg gcgttccggt ccatgcatgg | 5040 |
| ttagggcccg gtagttctac ttctgttcat gtttgtgtta gatccgtgtt tgtgttagat | 5100 |
| ccgtgctgct agcgttcgta cacggatgcg acctgtacgt cagacacgtt ctgattgcta | 5160 |
| acttgccagt gtttctcttt ggggaatcct gggatggctc tagccgttcc gcagacggga | 5220 |
| tcgatttcat gatttttttt gtttcgttgc atagggtttg gtttgccctt ttccttttat | 5280 |
| tcaatatatg ccgtgcactt gttttgtcggg tcatcttttc atgcttttt ttgtcttggt | 5340 |
| tgtgatgatg tggtctggtt gggcggtcgt tctagatcgg agtagaattc tgtttcaaac | 5400 |
| tacctggtgg atttattaat tttggatctg tatgtgtgtg ccatacatat tcatagttac | 5460 |
| gaattgaaga tgatggatgg aaatatcgat ctaggatagg tatacatgtt gatgcgggtt | 5520 |
| ttactgatgc atatacagag atgcttttg ttcgcttggt tgtgatgatg tggtgtggtt | 5580 |
| gggcggtcgt tcattcgttc tagatcggag tagaatactg tttcaaacta cctggtgtat | 5640 |
| ttattaattt tggaactgta tgtgtgtgtc atacatcttc atagttacga gtttaagatg | 5700 |
| gatgaaata tcgatctagg ataggtatac atgttgatgt gggttttact gatgcatata | 5760 |
| catgatggca tatgcagcat ctattcatat gctctaacct tgagtaccta tctattataa | 5820 |
| taaacaagta tgttttataa ttattttgat cttgatatac ttggatgatg gcatatgcag | 5880 |
| cagctatatg tggattttt tagccctgcc ttcatacgct atttatttgc ttggtactgt | 5940 |
| ttcttttgtc gatgctcacc ctgttgtttg gtgttacttc tgcaggtcga ctttaactta | 6000 |
| gcctaggatc cacacgacac catgtccccc gagcgccgcc ccgtcgagat ccgcccggcc | 6060 |
| accgccgccg acatggccgc cgtgtgcgac atcgtgaacc actacatcga gacctccacc | 6120 |
| gtgaacttcc gcaccgagcc gcagacccog caggagtgga tcgacgacct ggagcgcctc | 6180 |
| caggaccgct acccgtggct cgtggccgag gtggagggcg tggtggccgg catcgcctac | 6240 |

```
gccggcccgt ggaaggcccg caacgcctac gactggaccg tggagtccac cgtgtacgtg    6300
tcccaccgcc accagcgcct cggcctcggc tccaccctct acacccacct cctcaagagc    6360
atggaggccc agggcttcaa gtccgtggtg gccgtgatcg gcctcccgaa cgacccgtcc    6420
gtgcgcctcc acgaggccct cggctacacc gcccgcggca ccctccgcgc cgccggctac    6480
aagcacggcg gctggcacga cgtcggcttc tggcagcgcg acttcgagct gccggccccg    6540
ccgcgcccgg tgcgcccggt gacgcagatc tgagtcgaaa cctagacttg tccatcttct    6600
ggattggcca acttaattaa tgtatgaaat aaaaggatgc acacatagtg acatgctaat    6660
cactataatg tgggcatcaa agttgtgtgt tatgtgtaat tactagttat ctgaataaaa    6720
gagaaagaga tcatccatat ttcttatcct aaatgaatgt cacgtgtctt tataattctt    6780
tgatgaacca gatgcatttc attaaccaaa tccatataca tataaatatt aatcatatat    6840
aattaatatc aattgggtta gcaaaacaaa tctagtctag gtgtgttttg cgaattgcgg    6900
ccgccaccgc ggtggagctc gaattcattc cgattaatcg tggcctcttg ctcttcagga    6960
tgaagagcta tgtttaaacg tgcaagcgct actagacaat tcagtacatt aaaaacgtcc    7020
gcaatgtgtt attaagttgt ctaagcgtca atttgtttac accacaatat atcctgccac    7080
cagccagcca acagctcccc gaccggcagc tcggcacaaa atcaccactc gatacaggca    7140
gcccatcagt ccgggacggc gtcagcggga gagccgttgt aaggcggcag actttgctca    7200
tgttaccgat gctattcgga agaacggcaa ctaagctgcc gggtttgaaa cacgatgat     7260 ctcgcggagg gtagcatgtt gattgtaacg atgacagagc gttgctgcct gtgatcaaat    7320
atcatctccc tcgcagagat ccgaattatc agccttctta ttcatttctc gcttaaccgt    7380
gacaggctgt cgatcttgag aactatgccg acataatagg aaatcgctgg ataaagccgc    7440
tgaggaagct gagtggcgct atttctttag aagtgaacgt tgacgatcgt cgaccgtacc    7500
ccgatgaatt aattcggacg tacgttctga acacagctgg atacttactt gggcgattgt    7560
catacatgac atcaacaatg tacccgtttg tgtaaccgtc tcttggaggt tcgtatgaca    7620
ctagtggttc ccctcagctt gcgactagat gttgaggcct aacattttat tagagagcag    7680
gctagttgct tagatacatg atcttcaggc cgttatctgt cagggcaagc gaaaattggc    7740
catttatgac gaccaatgcc ccgcagaagc tcccatcttt gccgccatag acgccgcgcc    7800 cccttttgg ggtgtagaac atcctttgc cagatgtgga aaagaagttc gttgtcccat      7860
tgttggcaat gacgtagtag ccggcgaaag tgcgagaccc atttgcgcta tatataagcc    7920
tacgatttcc gttgcgacta ttgtcgtaat tggatgaact attatcgtag ttgctctcag    7980
agttgtcgta atttgatgga ctattgtcgt aattgcttat ggagttgtcg tagttgcttg    8040
gagaaatgtc gtagttggat ggggagtagt cataggaag acgagcttca tccactaaaa     8100
caattggcag gtcagcaagt gcctgccccg atgccatcgc aagtacgagg cttagaacca    8160
ccttcaacag atcgcgcata gtcttcccca gctctctaac gcttgagtta agccgcgccg    8220
cgaagcggcg tcggcttgaa cgaattgtta gacattattt gccgactacc ttggtgatct    8280
cgcctttcac gtagtgaaca aattcttcca actgatctgc gcgcgaggcc aagcgatctt    8340
cttgtccaag ataagcctgc ctagcttcaa gtatgacggg ctgatactgg gccggcaggc    8400
gctccattgc ccagtcggca gcgacatcct tcggcgcgat tttgccggtt actgcgctgt    8460
accaaatgcg ggacaacgta agcactacat ttcgctcatc gccagccag tcgggcggcg     8520 agttccatag cgttaaggtt tcatttagcg cctcaaatag atcctgttca ggaaccggat    8580
caaagagttc ctccgccgct ggacctacca aggcaacgct atgttctctt gcttttgtca    8640
```

-continued

```
gcaagatagc cagatcaatg tcgatcgtgg ctggctcgaa gatacctgca agaatgtcat    8700
tgcgctgcca ttctccaaat tgcagttcgc gcttagctgg ataacgccac ggaatgatgt    8760
cgtcgtgcac aacaatggtg acttctacag cgcggagaat ctcgctctct ccaggggaag    8820
ccgaagtttc caaaaggtcg ttgatcaaag ctcgccgcgt tgtttcatca agccttacag    8880
tcaccgtaac cagcaaatca atatcactgt gtggcttcag gccgccatcc actgcggagc    8940
cgtacaaatg tacggccagc aacgtcggtt cgagatggcg ctcgatgacg ccaactacct    9000
ctgatagttg agtcgatact tcggcgatca ccgcttccct catgatgttt aactcctgaa    9060
ttaagccgcg ccgcgaagcg gtgtcggctt gaatgaattg ttaggcgtca tcctgtgctc    9120
ccgagaacca gtaccagtac atcgctgttt cgttcgagac ttgaggtcta gttttatacg    9180
tgaacaggtc aatgccgccg agagtaaagc cacattttgc gtacaaattg caggcaggta    9240
cattgttcgt ttgtgtctct aatcgtatgc caaggagctg tctgcttagt gcccacttttc   9300
tcgcaaattc gatgagactg tgcgcgactc ctttgcctcg gtgcgtgtgc gacacaacaa    9360
tgtgttcgat agaggctaga tcgttccatg ttgagttgag ttcaatcttc ccgacaagct    9420
cttggtcgat gaatgcgcca tagcaagcag agtcttcatc agagtcatca tccgagatgt    9480
aatccttccg gtagggctc acacttctgg tagatagttc aaagccttgg tcggataggt     9540
gcacatcgaa cacttcacga acaatgaaat ggttctcagc atccaatgtt ccgccacct    9600
gctcagggat caccgaaatc ttcatatgac gcctaacgcc tggcacagcg gatcgcaaac    9660
ctggcgcggc ttttggcaca aaaggcgtga caggtttgcg aatccgttgc tgccacttgt    9720
taaccttttt gccagatttg gtaactataa tttatgttag aggcgaagtc ttgggtaaaa    9780
actggcctaa aattgctggg gatttcagga aagtaaacat caccttccgg ctcgatgtct    9840
attgtagata tatgtagtgt atctacttga tcggggatc tgctgcctcg cgcgtttcgg     9900
tgatgacggt gaaaacctct gacacatgca gctcccggag acggtcacag cttgtctgta    9960
agcggatgcc gggagcagac aagcccgtca gggcgcgtca gcgggtgttg gcgggtgtcg   10020
gggcgcagcc atgacccagt cacgtagcga tagcggagtg tatactggct taactatgcg   10080
gcatcagagc agattgtact gagagtgcac catatgcggt gtgaaatacc gcacagatgc   10140
gtaaggagaa ataccgcat caggcgctct tccgcttcct cgctcactga ctcgctgcgc    10200
tcggtcgttc ggctgcggcg agcggtatca gctcactcaa aggcggtaat acggttatcc   10260
acagaatcag gggataacgc aggaaagaac atgtgagcaa aaggccagca aaaggccagg   10320
aaccgtaaaa aggccgcgtt gctggcgttt ttccataggc tccgcccccc tgacgagcat   10380
cacaaaaatc gacgctcaag tcagaggtgg cgaaacccga caggactata aagataccag   10440
gcgtttcccc ctggaagctc cctcgtgcgc tctcctgttc cgaccctgcc gcttaccgga   10500
tacctgtccg cctttctccc ttcgggaagc gtggcgcttt ctcatagctc acgctgtagg   10560
tatctcagtt cggtgtaggt cgttcgctcc aagctgggct gtgtgcacga accccccgtt   10620
cagcccgacc gctgcgcctt atccggtaac tatcgtcttg agtccaaccc ggtaagacac   10680
gacttatcgc cactggcagc agccactggt aacaggatta gcagagcgag gtatgtaggc   10740
ggtgctacag agttcttgaa gtggtggcct aactacggct acactagaag gacagtattt   10800
ggtatctgcg ctctgctgaa gccagttacc ttcggaaaaa gagttggtag ctcttgatcc   10860
ggcaaacaaa ccaccgctgg tagcggtggt ttttttgttt gcaagcagca gattacgcgc   10920
agaaaaaaag gatctcaaga agatcctttg atcttttcta cggggtctga cgctcagtgg   10980
```

```
aacgaaaact cacgttaagg gattttggtc atgagattat caaaaggat cttcacctag    11040
atccttttaa attaaaaatg aagttttaaa tcaatctaaa gtatatatga gtaaacttgg   11100
tctgacagtt accaatgctt aatcagtgag gcacctatct cagcgatctg tctatttcgt   11160
tcatccatag ttgcctgact ccccgtcgtg tagataacta cgatacggga gggcttacca   11220
tctggcccca gtgctgcaat gataccgcga gacccacgct caccggctcc agatttatca   11280
gcaataaacc agccagccgg aagggccgag cgcagaagtg gtcctgcaac tttatccgcc   11340
tccatccagt ctattaattg ttgccgggaa gctagagtaa gtagttcgcc agttaatagt   11400
ttgcgcaacg ttgttgccat tgctgcaggg ggggggggg gggggacttc cattgttca    11460
ttccacggac aaaacagag aaaggaaacg acagaggcca aaaagcctcg ctttcagcac    11520
ctgtcgtttc ctttcttttc agagggtatt ttaaataaaa acattaagtt atgacgaaga   11580
agaacggaaa cgccttaaac cggaaaattt tcataaatag cgaaacccg cgaggtcgcc    11640
gccccgtaac ctgtcggatc accggaaagg accgtaaag tgataatgat tatcatctac    11700
atatcacaac gtgcgtggag gccatcaaac cacgtcaaat aatcaattat gacgcaggta   11760
tcgtattaat tgatctgcat caacttaacg taaaaacaac ttcagacaat acaaatcagc   11820
gacactgaat acgggcaac ctcatgtccc ccccccccc ccccctgcag gcatcgtggt    11880
gtcacgctcg tcgtttggta tggcttcatt cagctccggt tcccaacgat caaggcgagt   11940
tacatgatcc cccatgttgt gcaaaaagc ggttagctcc ttcggtcctc cgatcgttgt    12000
cagaagtaag ttggccgcag tgttatcact catggttatg gcagcactgc ataattctct   12060
tactgtcatg ccatccgtaa gatgcttttc tgtgactggt gagtactcaa ccaagtcatt   12120
ctgagaatag tgtatgcggc gaccgagttg ctcttgcccg gcgtcaacac gggataatac   12180
cgcgccacat agcagaactt taaaagtgct catcattgga aaacgttctt cggggcgaaa   12240
actctcaagg atcttaccgc tgttgagatc cagttcgatg taacccactc gtgcacccaa   12300
ctgatcttca gcatctttta ctttcaccag cgtttctggg tgagcaaaaa caggaaggca   12360
aaatgccgca aaaaagggaa taagggcgac acggaaatgt tgaatactca tactcttcct   12420
tttttcaatat tattgaagca tttatcaggg ttattgtctc atgagcggat acatatttga   12480
atgtatttag aaaaataaac aaatagggt tccgcgcaca tttccccgaa aagtgccacc    12540
tgacgtctaa gaaaccatta ttatcatgac attaacctat aaaaataggc gtatcacgag   12600
gcccttcgt cttcaagaat tggtcgacga tcttgctgcg ttcggatatt ttcgtggagt    12660
tcccgccaca gacccggatt gaaggcgaga tccagcaact cgcgccagat catcctgtga   12720
cggaactttg gcgcgtgatg actggccagg acgtcggccg aaagagcgac aagcagatca   12780
cgcttttcga cagcgtcgga tttgcgatcg aggattttc ggcgctgcgc tacgtccgcg    12840
accgcgttga gggatcaagc cacagcagcc cactcgacct tctagccgac ccagacgagc   12900
caagggatct ttttggaatg ctgctccgtc gtcaggcttt ccgacgtttg ggtggttgaa   12960
cagaagtcat tatcgtacgg aatgccaagc actcccgagg ggaaccctgt ggttggcatg   13020
cacatacaaa tggacgaacg gataaacctt ttcacgccct tttaaatatc cgttattcta   13080
ataaacgctc ttttctctta ggtttacccg ccaatatatc ctgtcaaaca ctgatagttt   13140
aaactgaagg cgggaaacga caatctgatc atgagcggag aattaaggga gtcacgttat   13200
gacccccgcc gatgacgcgg gacaagccgt tttacgtttg gaactgacag aaccgcaacg   13260
ttgaaggagc cactcagc                                                 13278
```

-continued

```
<210> SEQ ID NO 11
<211> LENGTH: 50
<212> TYPE: DNA
<213> ORGANISM: Artificial Sequence
<220> FEATURE:
<223> OTHER INFORMATION: poly-linker

<400> SEQUENCE: 11
gatcactagt ggcgcgccta ggagatctcg agtagggata acagggtaat          50

<210> SEQ ID NO 12
<211> LENGTH: 25
<212> TYPE: DNA
<213> ORGANISM: Artificial Sequence
<220> FEATURE:
<223> OTHER INFORMATION: attB1 seqeunce

<400> SEQUENCE: 12
acaagtttgt acaaaaaagc aggct                                     25

<210> SEQ ID NO 13
<211> LENGTH: 25
<212> TYPE: DNA
<213> ORGANISM: Artificial Sequence
<220> FEATURE:
<223> OTHER INFORMATION: attB2 sequence

<400> SEQUENCE: 13
accactttgt acaagaaagc tgggt                                     25

<210> SEQ ID NO 14
<211> LENGTH: 4778
<212> TYPE: DNA
<213> ORGANISM: Artificial Sequence
<220> FEATURE:
<223> OTHER INFORMATION: PHP23112 construct

<400> SEQUENCE: 14
gaaaggccca gtcttccgac tgagcctttc gttttatttg atgcctggca gttccctact    60
ctcgcgttaa cgctagcatg gatgttttcc cagtcacgac gttgtaaaac gacggccagt   120
cttaagctcg ggcccgcgtt aacgctacca tggagctcca ataatgatt ttattttgac    180 tgatagtgac ctgttcgttg caacaaattg ataagcaatg cttttttata atgccaactt   240
tgtatagaaa agttgggccg aattcgagct cggtacggcc agaatggccc ggaccgggtt   300
accgaattcg agctcggtac cctgggatca gcttgcatgc ctgcagtgca gcgtgacccg   360
gtcgtgcccc tctctagaga taatgagcat tgcatgtcta agttataaaa aattaccaca   420 tattttttt gtcacacttg tttgaagtgc agtttatcta tctttataca tatatttaaa   480
ctttactcta cgaataatat aatctatagt actacaataa tatcagtgtt ttagagaatc   540
atataaatga acagttagac atggtctaaa ggacaattga gtattttgac aacaggactc   600
tacagtttta tcttttagt gtgcatgtgt tctccttttt ttttgcaaat agcttcacct   660
atataatact tcatccattt tattagtaca tccatttagg gtttagggtt aatggttttt   720
atagactaat ttttttagta catctatttt attctatttt agcctctaaa ttaagaaaac   780
taaaactcta tttagttttt tttatttaat aatttagata taaatagaa taaaataaag   840 tgactaaaaa ttaaacaaat acccttaag aaattaaaaa aactaaggaa acattttct    900 tgtttcgagt agataatgcc agcctgttaa acgccgtcga cgagtctaac ggacaccaac   960
cagcgaacca gcagcgtcgc gtcgggccaa gcgaagcaga cggcacggca tctctgtcgc  1020
```

```
tgcctctgga cccctctcga gagttccgct ccaccgttgg acttgctccg ctgtcggcat   1080
ccagaaattg cgtggcggag cggcagacgt gagccggcac ggcaggcggc ctcctcctcc   1140
tctcacggca ccggcagcta cggggattc ctttcccacc gctccttcgc tttcccttcc    1200
tcgcccgccg taataaatag cacccccctc cacaccctct ttccccaacc tcgtgttgtt   1260
cggagcgcac acacacacaa ccagatctcc cccaaatcca cccgtcggca cctccgcttc   1320
aaggtacgcc gctcgtcctc ccccccccc ctctctacct tctctagatc ggcgttccgg    1380
tccatgcatg gttagggccc ggtagttcta cttctgttca tgtttgtgtt agatccgtgt   1440
ttgtgttaga tccgtgctgc tagcgttcgt acacggatgc gacctgtacg tcagacacgt   1500
tctgattgct aacttgccag tgtttctctt tggggaatcc tgggatggct ctagccgttc   1560
cgcagacggg atcgatttca tgatttttt tgtttcgttg catagggttt ggtttgccct    1620
tttcctttat ttcaatatat gccgtgcact tgtttgtcgg gtcatctttt catgcttttt   1680
tttgtcttgg ttgtgatgat gtggtctggt tgggcggtcg ttctagatcg gagtagaatt   1740
ctgtttcaaa ctacctggtg gatttattaa ttttggatct gtatgtgtgt gcatacata    1800 ttcatagtta cgaattgaag atgatggatg gaaatatcga tctaggatag gtatacatgt   1860
tgatgcgggt tttactgatg catatacaga gatgcttttt gttcgcttgg ttgtgatgat   1920
gtggtgtggt tgggcggtcg ttcattcgtt ctagatcgga gtagaatact gtttcaaact   1980
acctggtgta tttattaatt ttggaactgt atgtgtgtgt catacatctt catagttacg   2040
agtttaagat ggatggaaat atcgatctag gataggtata catgttgatg tgggttttac   2100
tgatgcatat acatgatggc atatgcagca tctattcata tgctctaacc ttgagtacct   2160
atctattata ataaacaagt atgttttata attattttga tcttgatata cttggatgat   2220
ggcatatgca gcagctatat gtggattttt ttagccctgc cttcatacgc tatttatttg   2280
cttggtactg tttcttttgt cgatgctcac cctgttgttt ggtgttactt ctgcaggtcg   2340
actctagagg atcagcttgg tcacccggtc cgggcctaga aggccagctt caagtttgta   2400
caaaaaagtt gaacgagaaa cgtaaaatga tataaatatc aatatattaa attagatttt   2460
gcataaaaaa cagactacat aatactgtaa aacacaacat atgcagtcac tatgaatcaa   2520
ctacttagat ggtattagtg acctgtagaa ttcgagctct agagctgcag ggcggccgcg   2580
atatccccta tagtgagtcg tattacatgg tcatagctgt ttcctggcag ctctggcccg   2640
tgtctcaaaa tctctgatgt tacattgcac aagataaaaa tatatcatca tgaacaataa   2700
aactgtctgc ttacataaac agtaatacaa ggggtgttat gagccatatt caacgggaaa   2760
cgtcgaggcc gcgattaaat tccaacatgg atgctgattt atatgggtat aaatgggctc   2820
gcgataatgt cgggcaatca ggtgcgacaa tctatcgctt gtatgggaag cccgatgcgc   2880
cagagttgtt tctgaaacat ggcaaaggta gcgttgccaa tgatgttaca gatgagatgg   2940
tcagactaaa ctggctgacg gaatttatgc ctcttccgac catcaagcat tttatccgta   3000
ctcctgatga tgcatggtta ctcaccactg cgatccccgg aaaaacagca ttccaggtat   3060
tagaagaata tcctgattca ggtgaaaata ttgttgatgc gctggcagtg ttcctgcgcc   3120
ggttgcattc gattcctgtt tgtaattgtc cttttaacag cgatcgcgta tttcgtctcg   3180
ctcaggcgca atcacgaatg aataacggtt tggttgatgc gagtgatttt gatgacgagc   3240
gtaatggctg gcctgttgaa caagtctgga aagaaatgca taaacttttg ccattctcac   3300
cggattcagt cgtcactcat ggtgatttct cacttgataa ccttattttt gacgagggga   3360
aattaatagg ttgtattgat gttggacgag tcggaatcgc agaccgatac caggatcttg   3420
```

```
ccatcctatg gaactgcctc ggtgagtttt ctccttcatt acagaaacgg cttttttcaaa    3480
aatatggtat tgataatcct gatatgaata aattgcagtt tcatttgatg ctcgatgagt    3540
ttttctaatc agaattggtt aattggttgt aacactggca gagcattacg ctgacttgac    3600
gggacggcgc aagctcatga ccaaaatccc ttaacgtgag ttacgcgtcg ttccactgag    3660
cgtcagaccc cgtagaaaag atcaaaggat cttcttgaga tcctttttttt ctgcgcgtaa    3720
tctgctgctt gcaaacaaaa aaaccaccgc taccagcggt ggtttgtttg ccggatcaag    3780
agctaccaac tcttttttccg aaggtaactg gcttcagcag agcgcagata ccaaatactg    3840
tccttctagt gtagccgtag ttaggccacc acttcaagaa ctctgtagca ccgcctacat    3900
acctcgctct gctaatcctg ttaccagtgg ctgctgccag tggcgataag tcgtgtctta    3960
ccgggttgga ctcaagacga tagttaccgg ataaggcgca gcggtcgggc tgaacggggg    4020
gttcgtgcac acagcccagc ttggagcgaa cgacctacac cgaactgaga tacctacagc    4080
gtgagcattg agaaagcgcc acgcttcccg aagggagaaa ggcggacagg tatccggtaa    4140
gcggcagggt cggaacagga gagcgcacga gggagcttcc agggggaaac gcctggtatc    4200
tttatagtcc tgtcgggttt cgccacctct gacttgagcg tcgatttttg tgatgctcgt    4260
caggggggcg gagcctatgg aaaaacgcca gcaacgcggc cttttttacgg ttcctggcct    4320
tttgctggcc ttttgctcac atgttctttc ctgcgttatc ccctgattct gtggataacc    4380
gtattaccgc ctttgagtga gctgataccg ctcgccgcag ccgaacgacc gagcgcagcg    4440
agtcagtgag cgaggaagcg gaagagcgcc caatacgcaa accgcctctc cccgcgcgtt    4500
ggccgattca ttaatgcagc tggcacgaca ggtttcccga ctggaaagcg ggcagtgagc    4560
gcaacgcaat taatacgcgt accgctagcc aggaagagtt tgtagaaacg caaaaaggcc    4620
atccgtcagg atggccttct gcttagtttg atgcctggca gtttatggcg ggcgtcctgc    4680
ccgccaccct ccgggccgtt gcttcacaac gttcaaatcc gctcccggcg gatttgtcct    4740
actcaggaga gcgttcaccg acaaacaaca gataaaac                            4778

<210> SEQ ID NO 15
<211> LENGTH: 50905
<212> TYPE: DNA
<213> ORGANISM: Artificial
<220> FEATURE:
<223> OTHER INFORMATION: PHP29634 vector sequence

<400> SEQUENCE: 15
gggggggggg ggggggggtt ccattgttca ttccacggac aaaaacagag aaaggaaacg      60
acagaggcca aaaagctcgc tttcagcacc tgtcgtttcc tttcttttca gagggtattt     120
taaataaaaa cattaagtta tgacgaagaa gaacggaaac gccttaaacc ggaaaatttt     180
cataaatagc gaaaacccgc gaggtcgccg ccccgtaacc tgtcggatca ccggaaagga     240
cccgtaaagt gataatgatt atcatctaca tatcacaacg tgcgtggagg ccatcaaacc     300
acgtcaaata atcaattatg acgcaggtat cgtattaatt gatctgcatc aacttaacgt     360
aaaaacaact tcagacaata caaatcagcg acactgaata cggggcaacc tcatgtcccc     420
cccccccccc cccctgcagg catcgtggtg tcacgctcgt cgtttggtat ggcttcattc     480
agctccggtt cccaacgatc aaggcgagtt acatgatccc ccatgttgtg caaaaaagcg     540
gttagctcct tcggtcctcc gatcgttgtc agaagtaagt tggccgcagt gttatcactc     600
atggttatgg cagcactgca taattctctt actgtcatgc catccgtaag atgcttttct     660
```

```
gtgactggtg agtactcaac caagtcattc tgagaatagt gtatgcggcg accgagttgc     720
tcttgcccgg cgtcaacacg ggataatacc gcgccacata gcagaacttt aaaagtgctc     780
atcattggaa aacgttcttc ggggcgaaaa ctctcaagga tcttaccgct gttgagatcc     840
agttcgatgt aacccactcg tgcacccaac tgatcttcag catcttttac tttcaccagc     900
gtttctgggt gagcaaaaac aggaaggcaa aatgccgcaa aaagggaat aagggcgaca      960 cggaaatgtt gaatactcat actcttcctt tttcaatatt attgaagcat ttatcagggt    1020
tattgtctca tgagcggata catatttgaa tgtatttaga aaaataaaca aatagggtt     1080 ccgcgcacat ttccccgaaa agtgccacct gacgtctaag aaaccattat tatcatgaca   1140
ttaacctata aaaataggcg tatcacgagg ccctttcgtc ttcaagaatt cggagctttt   1200
gccattctca ccggattcag tcgtcactca tggtgatttc tcacttgata accttatttt   1260
tgacgagggg aaattaatag gttgtattga tgttggacga gtcggaatcg cagaccgata   1320
ccaggatctt gccatcctat ggaactgcct cggtgagttt tctccttcat tacagaaacg   1380 gcttttcaa aaatatggta ttgataatcc tgatatgaat aaattgcagt ttcatttgat    1440
gctcgatgag ttttttctaat cagaattggt taattggttg taacactggc agagcattac  1500
gctgacttga cgggacggcg ctttgttga ataaatcgaa cttttgctga gttgaaggat    1560
cagatcacgc atcttcccga caacgcagac cgttccgtgg caaagcaaaa gttcaaaatc   1620
accaactggt ccacctacaa caaagctctc atcaaccgtg ctccctcac tttctggctg    1680 gatgatgggg cgattcaggc ctggtatgag tcagcaacac cttcttcacg aggcagacct   1740
cagcgccaga aggccgccag agaggccgag cgcggccgtg aggcttggac gctagggcag   1800
ggcatgaaaa agcccgtagc gggctgctac gggcgtctga cgcggtggaa aggggagggg   1860
gatgttgtct acatggctct gctgtagtga gtgggttgcg ctccggcagc ggtcctgatc   1920
aatcgtcacc ctttctcggt ccttcaacgt tcctgacaac gagcctcctt ttcgccaatc   1980
catcgacaat caccgcgagt ccctgctcga acgctgcgtc cggaccggct tcgtcgaagg   2040
cgtctatcgc ggcccgcaac agcggcgaga gcggagcctg ttcaacggtg ccgccgcgct   2100
cgccggcatc gctgtcgccg gcctgctcct caagcacggc cccaacagtg aagtagctga   2160
ttgtcatcag cgcattgacg gcgtccccgg ccgaaaaacc cgcctcgcag aggaagcgaa   2220
gctgcgcgtc ggccgtttcc atctgcggtg cgcccggtcg cgtgccggca tggatgcgcg   2280
cgccatcgcg gtaggcgagc agcgcctgcc tgaagctgcg ggcattcccg atcagaaatg   2340
agcgccagtc gtcgtcggct ctcggcaccg aatgcgtatg attctccgcc agcatggctt   2400
cggccagtgc gtcgagcagc gcccgcttgt tcctgaagtg ccagtaaagc gccggctgct   2460
gaacccccaa ccgttccgcc agtttgcgtg tcgtcagacc gtctacgccg acctcgttca   2520
acaggtccag ggcggcacgg atcactgtat tcggctgcaa cttttgtcatg cttgacactt   2580 tatcactgat aaacataata tgtccaccaa cttatcagtg ataaagaatc cgcgcgttca   2640
atcggaccag cggaggctgg tccggaggcc agacgtgaaa cccaacatac ccctgatcgt   2700
aattctgagc actgtcgcgc tcgacgctgt cggcatcggc ctgattatgc cggtgctgcc   2760
gggcctcctg cgcgatctgg ttcactcgaa cgacgtcacc gcccactatg gcattctgct   2820
ggcgctgtat gcgttggtgc aatttgcctg cgcacctgtg ctgggcgcgc tgtcggatcg   2880 tttcggggcgg cggccaatct tgctcgtctc gctggccggc gccactgtcg actacgccat   2940
catgcgcaca gcgcctttcc tttgggttct ctatatcggg cggatcgtgg ccggcatcac   3000
cggggcgact ggggcggtag ccggcgctta tattgccgat atcactgatg gcgatgagcg   3060
```

```
cgcgcggcac ttcggcttca tgagcgcctg tttcgggttc gggatggtcg cgggacctgt    3120
gctcggtggg ctgatgggcg gtttctcccc ccacgctccg ttcttcgccg cggcagcctg    3180
gaacggcctc aatttcctga cgggctgttt ccttttgccg gagtcgcaca aaggcgaacg    3240
ccggccgtta cgccgggagg ctctcaaccc gctcgcttcg ttccgtgggg cccggggcat    3300
gaccgtcgtc gccgccctga tggcggtctt cttcatcatg caacttgtcg acaggtgcc    3360 ggccgcgctt tgggtcattt tcggcgagga tcgctttcac tgggacgcga ccacgatcgg    3420
catttcgctt gccgcatttg gcattctgca ttcactcgcc caggcaatga tcaccggccc    3480
tgtagccgcc cggctcggcg aaaggcgggc actcatgctc ggaatgattg ccgacggcac    3540
aggctacatc ctgcttgcct tcgcgacacg gggatggatg gcgttcccga tcatggtcct    3600
gcttgcttcg ggtggcatcg gaatgccggc gctgcaagca atgttgtcca ggcaggtgga    3660
tgaggaacgt caggggcagc tgcaaggctc actggcggcg ctcaccagcc tgacctcgat    3720
cgtcggaccc ctcctcttca cggcgatcta tgcggcttct ataacaacgt ggaacgggtg    3780
ggcatggatt gcaggcgctg ccctctactt gctctgcctg ccggcgctgc gtcgcgggct    3840
ttggagcggc gcagggcaac gagccgatcg ctgatcgtgg aaacgatagg cctatgccat    3900
gcgggtcaag gcgacttccg gcaagctata cgcgccctag gagtgcggtt ggaacgttgg    3960
cccagccaga tactcccgat cacgagcagg acgccgatga tttgaagcgc actcagcgtc    4020
tgatccaaga caaccatcc tagcaacacg gcggtccccg ggctgagaaa gcccagtaag    4080
gaaacaactg taggttcgag tcgcgagatc ccccggaacc aaaggaagta ggttaaaccc    4140
gctccgatca ggccgagcca cgccaggccg agaacattgg ttcctgtagg catcgggatt    4200
ggcggatcaa acactaaagc tactggaacg agcagaagtc ctccggccgc cagttgccag    4260
gcggtaaagg tgagcagagg cacgggaggt tgccacttgc gggtcagcac ggttccgaac    4320
gccatggaaa ccgcccccgc caggcccgct gcgacgccga caggatctag cgctgcgttt    4380
ggtgtcaaca ccaacagcgc cacgcccgca gttccgcaaa tagcccccag gaccgccatc    4440
aatcgtatcg ggctacctag cagagcggca gagatgaaca cgaccatcag cggctgcaca    4500
gcgcctaccg tcgccgcgac cccgcccggc aggcggtaga ccgaaataaa caacaagctc    4560
cagaatagcg aaatattaag tgcgccgagg atgaagatgc gcatccacca gattcccgtt    4620
ggaatctgtc ggacgatcat cacgagcaat aaacccgccg gcaacgcccg cagcagcata    4680
ccggcgaccc ctcggcctcg ctgttcgggc tccacgaaaa cgccggacag atgcgccttg    4740
tgagcgtcct tggggccgtc ctcctgtttg aagaccgaca gcccaatgat ctcgccgtcg    4800
atgtaggcgc cgaatgccac ggcatctcgc aaccgttcag cgaacgcctc catgggcttt    4860
ttctcctcgt gctcgtaaac ggacccgaac atctctggag ctttcttcag ggccgacaat    4920
cggatctcgc ggaaatcctg cacgtcggcc gctccaagcc gtcgaatctg agccttaatc    4980
acaattgtca atttaatcc tctgtttatc ggcagttcgt agagcgcgcc gtgcgtcccg    5040
agcgatactg agcgaagcaa gtgcgtcgag cagtgcccgc ttgttcctga aatgccagta    5100
aagcgctggc tgctgaaccc ccagccggaa ctgaccccac aaggccctag cgtttgcaat    5160
gcaccaggtc atcattgacc caggcgtgtt ccaccaggcc gctgcctcgc aactcttcgc    5220
aggcttcgcc gacctgctcg cgccacttct tcacgcgggt ggaatccgat ccgcacatga    5280
ggcgaaaggt ttcagcttg agcgggtacg gctcccggtg cgagctgaaa tagtcgaaca    5340
tccgtcgggc cgtcggcgac agcttgcggt acttctccca tatgaatttc gtgtagtggt    5400
```

```
cgccagcaaa cagcacgacg atttcctcgt cgatcaggac ctggcaacgg gacgttttct    5460
tgccacggtc caggacgcgg aagcggtgca gcagcgacac cgattccagg tgcccaacgc    5520
ggtcggacgt gaagcccatc gccgtcgcct gtaggcgcga caggcattcc tcggccttcg    5580
tgtaataccg gccattgatc gaccagccca ggtcctggca aagctcgtag aacgtgaagg    5640
tgatcggctc gccgataggg gtgcgcttcg cgtactccaa cacctgctgc cacaccagtt    5700
cgtcatcgtc ggcccgcagc tcgacgccgg tgtaggtgat cttcacgtcc ttgttgacgt    5760
ggaaaatgac cttgttttgc agcgcctcgc gcgggatttt cttgttgcgc gtggtgaaca    5820
gggcagagcg ggccgtgtcg tttggcatcg ctcgcatcgt gtccggccac ggcgcaatat    5880
cgaacaagga aagctgcatt tccttgatct gctgcttcgt gtgtttcagc aacgcggcct    5940
gcttggcctc gctgacctgt tttgccaggt cctcgccggc ggttttcgc ttcttggtcg    6000
tcatagttcc tcgcgtgtcg atggtcatcg acttcgccaa acctgccgcc tcctgttcga    6060
gacgacgcga acgctccacg gcggccgatg gcgcgggcag ggcaggggga gccagttgca    6120
cgctgtcgcg ctcgatcttg gccgtagctt gctggaccat cgagccgacg gactggaagg    6180
tttcgcgggg cgcacgcatg acggtgcggc ttgcgatggt ttcggcatcc tcggcggaaa    6240
accccgcgtc gatcagttct tgcctgtatg ccttccggtc aaacgtccga ttcattcacc    6300
ctccttgcgg gattgccccg actcacgccg gggcaatgtg cccttattcc tgatttgacc    6360
cgcctggtgc cttggtgtcc agataatcca ccttatcggc aatgaagtcg gtcccgtaga    6420
ccgtctggcc gtccttctcg tacttggtat tccgaatctt gccctgcacg aataccagcg    6480
accccttgcc caaatacttg ccgtgggcct cggcctgaga gccaaaacac ttgatgcgga    6540
agaagtcggt gcgctcctgc ttgtcgccgg catcgttgcg ccactcttca ttaaccgcta    6600
tatcgaaaat tgcttgcggc ttgttagaat tgccatgacg tacctcggtg tcacgggtaa    6660
gattaccgat aaactggaac tgattatggc tcatatcgaa agtctccttg agaaaggaga    6720
ctctagttta gctaaacatt ggttccgctg tcaagaactt tagcggctaa aattttgcgg    6780
gccgcgacca aaggtgcgag gggcggcttc cgctgtgtac aaccagatat ttttcaccaa    6840
catccttcgt ctgctcgatg agcggggcat gacgaaacat gagctgtcgg agagggcagg    6900
ggtttcaatt tcgtttttat cagacttaac caacggtaag gccaacccct cgttgaaggt    6960
gatggaggcc attgccgacg ccctggaaac tcccctacct cttctcctgg agtccaccga    7020
ccttgaccgc gaggcactcg cggagattgc gggtcatcct ttcaagagca gcgtgccgcc    7080
cggatacgaa cgcatcagtg tggttttgcc gtcacataag gcgtttatcg taaagaaatg    7140
gggcgacgac acccgaaaaa agctgcgtgg aaggctctga cgccaagggt tagggcttgc    7200
acttccttct ttagccgcta aaacggcccc ttctctgcgg gccgtcggct cgcgcatcat    7260
atcgacatcc tcaacggaag ccgtgccgcg aatggcatcg ggcgggtgcg ctttgacagt    7320
tgttttctat cagaacccct acgtcgtgcg gttcgattag ctgtttgtct tgcaggctaa    7380
acactttcgg tatatcgttt gcctgtgcga taatgttgct aatgatttgt tgcgtagggg    7440
ttactgaaaa gtgagcggga aagaagagtt tcagaccatc aaggagcggg ccaagcgcaa    7500
gctggaacgc gacatgggtg cggacctgtt ggccgcgctc aacgacccga aaaccgttga    7560
agtcatgctc aacgcggacg gcaaggtgtg gcacgaacgc cttggcgagc cgatgcggta    7620
catctgcgac atgcggccca gccagtcgca ggcgattata gaaacggtgg ccggattcca    7680
cggcaaagag gtcacgcggc attcgcccat cctggaaggc gagttcccct ggatggcag    7740
ccgcttttgcc ggccaattgc cgccggtcgt ggccgcgcca acctttgcga tccgcaagcg    7800
```

```
cgcggtcgcc atcttcacgc tggaacagta cgtcgaggcg ggcatcatga cccgcgagca    7860
atacgaggtc attaaaagcg ccgtcgcggc gcatcgaaac atcctcgtca ttggcggtac    7920
tggctcgggc aagaccacgc tcgtcaacgc gatcatcaat gaaatggtcg ccttcaaccc    7980
gtctgagcgc gtcgtcatca tcgaggacac cggcgaaatc cagtgcgccg cagagaacgc    8040
cgtccaatac cacaccagca tcgacgtctc gatgacgctg ctgctcaaga caacgctgcg    8100
tatgcgcccc gaccgcatcc tggtcggtga ggtacgtggc cccgaagccc ttgatctgtt    8160
gatggcctgg aacaccgggc atgaaggagg tgccgccacc ctgcacgcaa caacccccaa    8220
agcgggcctg agccggctcg ccatgcttat cagcatgcac ccggattcac cgaaacccat    8280
tgagccgctg attggcgagg cggttcatgt ggtcgtccat atcgccagga cccctagcgg    8340
ccgtcgagtg caagaaattc tcgaagttct tggttacgag aacggccagt acatcaccaa    8400
aaccctgtaa ggagtatttc caatgacaac ggctgttccg ttccgtctga ccatgaatcg    8460
cggcattttg ttctaccttg ccgtgttctt cgttctcgct ctcgcgttat ccgcgcatcc    8520
ggcgatggcc tcggaaggca ccggcggcag cttgccatat gagagctggc tgacgaacct    8580
gcgcaactcc gtaaccggcc cggtggcctt cgcgctgtcc atcatcggca tcgtcgtcgc    8640
cggcggcgtg ctgatcttcg gcggcgaact caacgccttc ttccgaaccc tgatcttcct    8700
ggttctggtg atgcgcctgc tggtcggcgc gcagaacgtg atgagcacct tcttcggtcg    8760
tggtgccgaa atcgcggccc tcggcaacgg ggcgctgcac caggtgcaag tcgcggcggc    8820
ggatgccgtg cgtgcggtag cggctggacg gctcgcctaa tcatggctct gcgcacgatc    8880
cccatccgtc gcgcaggcaa ccgagaaaac ctgttcatgg gtggtgatcg tgaactggtg    8940
atgttctcgg gcctgatggc gtttgcgctg attttcagcg cccaagagct gcgggccacc    9000
gtggtcggtc tgatcctgtg gttcggggcg ctctatgcgt tccgaatcat ggcgaaggcc    9060
gatccgaaga tgcggttcgt gtacctgcgt caccgccggt acaagccgta ttacccggcc    9120
cgctcgaccc cgttccgcga gaacaccaat agccaaggga agcaataccg atgatccaag    9180
caattgcgat tgcaatcgcg ggcctcggcc cgcttctgtt gttcatcctc tttgcccgca    9240
tccgcgcggt cgatgccgaa ctgaaactga aaaagcatcg ttccaaggac gccggcctgg    9300
ccgatctgct caactacgcc gctgtcgtcg atgacggcgt aatcgtgggc aagaacggca    9360
gctttatggc tgcctggctg tacaagggcg atgcaacgc aagcagcacc gaccagcagc    9420
gcgaagtagt gtccgcccgc atcaaccagg ccctcgcggg cctgggaagt gggtggatga    9480
tccatgtgga cgccgtgcgg cgtcctgctc cgaactacgc ggagcggggc ctgtcggcgt    9540
tccctgaccg tctgacggca gcgattgaag aagagcgctc ggtcttgcct gctcgtcgg    9600 tgatgtactt caccagctcc gcgaagtcgc tcttcttgat ggagcgcatg ggacgtgct    9660 tggcaatcac gcgcaccccc cggccgtttt agcggctaaa aaagtcatgg ctctgccctc    9720
gggcggacca cgcccatcat gaccttgcca agctcgtcct gcttctcttc gatcttcgcc    9780
agcagggcga ggatcgtggc atcaccgaac cgcgccgtgc gcgggtcgtc ggtgagccag    9840
agtttcagca ggccgcccag gcggcccagg tcgccattga tgcgggccag ctcgcggacg    9900
tgctcatagt ccacgacgcc cgtgattttg tagccctggc cgacggccag caggtaggcc    9960
gacaggctca tgccggccgc cgccgccttt tcctcaatcg ctcttcgttc gtctggaagg   10020
cagtacacct tgataggtgg gctgcccttc ctggttggct tggtttcatc agccatccgc   10080
ttgccctcat ctgttacgcc ggcggtagcc ggccagcctc gcagagcagg attcccgttg   10140
```

```
agcaccgcca ggtgcgaata agggacagtg aagaaggaac acccgctcgc gggtgggcct    10200
acttcaccta tcctgcccgg ctgacgccgt tggatacacc aaggaaagtc tacacgaacc    10260
ctttggcaaa atcctgtata tcgtgcgaaa aaggatggat ataccgaaaa aatcgctata    10320
atgaccccga agcagggtta tgcagcgaaa agcgctgct tccctgctgt tttgtggaat    10380
atctaccgac tggaaacagg caaatgcagg aaattactga actgagggga caggcgagag    10440
acgatgccaa agagctacac cgacgagctg gccgagtggg ttgaatcccg cgcggccaag    10500
aagcgccggc gtgatgaggc tgcggttgcg ttcctggcgg tgagggcgga tgtcgaggcg    10560
gcgttagcgt ccggctatgc gctcgtcacc atttgggagc acatgcggga aacggggaag    10620
gtcaagttct cctacgagac gttccgctcg cacgccaggc ggcacatcaa ggccaagccc    10680
gccgatgtgc ccgcaccgca ggccaaggct gcggaacccg cgccggcacc caagacgccg    10740
gagccacggc ggccgaagca gggggcaag gctgaaaagc cggcccccgc tgcggccccg    10800
accggcttca ccttcaaccc aacaccggaa aaaaggatc tactgtaatg gcgaaaattc    10860
acatggtttt gcagggcaag ggcggggtcg gcaagtcggc catcgccgcg atcattgcgc    10920
agtacaagat ggacaagggg cagacaccct tgtgcatcga caccgacccg gtgaacgcga    10980
cgttcgaggg ctacaaggcc ctgaacgtcc gccggctgaa catcatggcc ggcgacgaaa    11040
ttaactcgcg caacttcgac accctggtcg agctgattgc gccgaccaag gatgacgtgg    11100
tgatcgacaa cggtgccagc tcgttcgtgc ctctgtcgca ttacctcatc agcaaccagg    11160
tgccggctct gctgcaagaa atggggcatg agctggtcat ccataccgtc gtcaccggcg    11220
gccaggctct cctggacacg tgagcggct tcgcccagct cgccagccag ttcccggccg    11280
aagcgctttt cgtggtctgg ctgaacccgt attgggggcc tatcgagcat gagggcaaga    11340
gctttgagca gatgaaggcg tacacggcca acaaggcccg cgtgtcgtcc atcatccaga    11400
ttccggccct caaggaagaa acctacggcc gcgatttcag cgacatgctg caagagcggc    11460
tgacgttcga ccaggcgctg gccgatgaat cgctcacgat catgacgcgg caacgcctca    11520
agatcgtgcg gcgcggcctg tttgaacagc tcgacgcggc ggccgtgcta tgagcgacca    11580
gattgaagag ctgatccggg agattgcggc caagcacggc atcgccgtcg gccgcgacga    11640
cccggtgctg atcctgcata ccatcaacgc ccggctcatg gccgacagtg cggccaagca    11700
agaggaaatc cttgccgcgt tcaaggaaga gctggaaggg atcgcccatc gttggggcga    11760
ggacgccaag gccaaagcgg agcggatgct gaacgcggcc ctggcggcca gcaaggacgc    11820
aatggcgaag gtaatgaagg acagcgccgc gcaggcggcc gaagcgatcc gcagggaaat    11880
cgacgacggc cttggccgcc agctcgcggc caaggtcgcg gacgcgcggc gcgtggcgat    11940
gatgaacatg atcgccggcg gcatggtgtt gttcgcggcc gccctggtgg tgtgggcctc    12000
gttatgaatc gcagaggcgc agatgaaaaa gcccggcgtt gccgggcttt gtttttgcgt    12060
tagctgggct tgtttgacag gcccaagctc tgactgcgcc cgcgctcgcg ctcctgggcc    12120
tgtttcttct cctgctcctg cttgcgcatc agggcctggt gccgtcggc tgcttcacgc    12180 atcgaatccc agtcgccggc cagctcggga tgctccgcgc gcatcttgcg cgtcgccagt    12240
tcctcgatct tgggcgcgtg aatgcccatg ccttccttga tttcgcgcac catgtccagc    12300
cgcgtgtgca gggtctgcaa gcgggcttgc tgtttgggcct gctgctgctg ccaggcggcc    12360
tttgtacgcg gcaggacag caagccgggg gcattggact gtagctgctg caaacgcgcc    12420
tgctgacggt ctacgagctg ttctaggcgg tcctcgatgc gctccacctg gtcatgcttt    12480
gcctgcacgt agagcgcaag ggtctgctgg taggtctgct cgatgggcgc ggattctaag    12540
```

```
agggcctgct gttccgtctc ggcctcctgg ccgcctgta gcaaatcctc gccgctgttg    12600
ccgctggact gctttactgc cggggactgc tgttgccctg ctcgcgccgt cgtcgcagtt    12660
cggcttgccc ccactcgatt gactgcttca tttcgagccg cagcgatgcg atctcggatt    12720
gcgtcaacgg acggggcagc gcggaggtgt ccggcttctc cttgggtgag tcggtcgatg    12780
ccatagccaa aggtttcctt ccaaaatgcg tccattgctg gaccgtgttt ctcattgatg    12840
cccgcaagca tcttcggctt gaccgccagg tcaagcgcgc cttcatgggc ggtcatgacg    12900
gacgccgcca tgaccttgcc gccgttgttc tcgatgtagc cgcgtaatga ggcaatggtg    12960
ccgcccatcg tcagcgtgtc atcgacaacg atgtacttct ggccggggat cacctccccc    13020
tcgaaagtcg ggttgaacgc caggcgatga tctgaaccgg ctccggttcg ggcgaccttc    13080
tcccgctgca caatgtccgt ttcgacctca aggccaaggc ggtcggccag aacgaccgcc    13140
atcatggccg gaatcttgtt gttccccgcc gcctcgacgg cgaggactgg aacgatgcgg    13200
ggcttgtcgt cgccgatcag cgtcttgagc tgggcaacag tgtcgtccga atcaggcgc    13260 tcgaccaaat taagcgccgc ttccgcgtcg ccctgcttcg cagcctggta ttcaggctcg    13320
ttggtcaaag aaccaaggtc gccgttgcga accaccttcg ggaagtctcc ccacggtgcg    13380
cgctcggctc tgctgtagct gctcaagacg cctcccttt tagccgctaa aactctaacg    13440
agtgcgcccg cgactcaact tgacgctttc ggcacttacc tgtgccttgc cacttgcgtc    13500
ataggtgatg cttttcgcac tcccgatttc aggtacttta tcgaaatctg accgggcgtg    13560
cattacaaag ttcttcccca cctgttggta aatgctgccg ctatctgcgt ggacgatgct    13620
gccgtcgtgg cgctgcgact tatcggcctt ttgggccata tagatgttgt aaatgccagg    13680
tttcagggcc ccggctttat ctaccttctg gttcgtccat gcgccttggt tctcggtctg    13740
gacaattctt tgcccattca tgaccaggag gcggtgtttc attgggtgac tcctgacggt    13800
tgcctctggt gttaaacgtg tcctggtcgc ttgccggcta aaaaaaagcc gacctcggca    13860
gttcgaggcc ggctttccct agagccgggc gcgtcaaggt tgttccatct attttagtga    13920
actgcgttcg atttatcagt tactttcctc ccgctttgtg tttcctccca ctcgtttccg    13980
cgtctagccg accccctcaac atagcggcct cttcttgggc tgccttttgcc tcttgccgcg    14040 cttcgtcacg ctcggcttgc accgtcgtaa agcgctcggc ctgcctggcc gcctcttgcg    14100
ccgccaactt cctttgctcc tggtgggcct cggcgtcggc ctgcgccttc gctttcaccg    14160
ctgccaactc cgtgcgcaaa ctctccgctt cgcgcctggt ggcgtcgcgc tcgccgcgaa    14220
gcgcctgcat ttcctggttg gccgcgtcca gggtcttgcg gctctcttct ttgaatgcgc    14280
gggcgtcctg gtgagcgtag tccagctcgg cgcgcagctc ctgcgctcga cgctccacct    14340
cgtcggcccg ctgcgtcgcc agcgcggcc gctgctcggc tcctgccagg gcggtgcgtg    14400
cttcggccag ggcttgccgc tggcgtgcgg ccagctcggc cgcctcggcg gcctgctgct    14460
ctagcaatgt aacgcgcgcc tgggcttctt ccagctcgcg ggcctgcgcc tcgaaggcgt    14520
cggccagctc cccgcgcacg gcttccaact cgttgcgctc acgatcccag ccggcttgcg    14580
ctgcctgcaa cgattcattg gcaagggcct gggcggcttg ccagagggcg gccacggcct    14640
ggttgccggc ctgctgcacc gcgtccggca cctggactgc cagcggggcg gcctgcgccg    14700
tgcgctggcg tcgccattcg cgcatgccgg cgctggcgtc gttcatgttg acgcgggcgg    14760
ccttacgcac tgcatccacg gtcgggaagt tctcccggtc gccttgctcg aacagctcgt    14820
ccgcagccgc aaaaatgcgg tcgcgcgtct ctttgttcag ttccatgttg gctccggtaa    14880
```

```
ttggtaagaa taataatact cttacctacc ttatcagcgc aagagtttag ctgaacagtt   14940
ctcgacttaa cggcaggttt tttagcggct gaagggcagg caaaaaaagc cccgcacggt   15000
cggcggggc aaagggtcag cgggaagggg attagcgggc gtcgggcttc ttcatgcgtc   15060
ggggccgcgc ttcttgggat ggagcacgac gaagcgcgca cgcgcatcgt cctcggccct   15120
atcggcccgc gtcgcggtca ggaacttgtc gcgcgctagg tcctccctgg tgggcaccag   15180
gggcatgaac tcggcctgct cgatgtaggt ccactccatg accgcatcgc agtcgaggcc   15240
gcgttccttc accgtctctt gcaggtcgcg gtacgcccgc tcgttgagcg gctggtaacg   15300
ggccaattgg tcgtaaatgg ctgtcggcca tgagcggcct ttcctgttga gccagcagcc   15360
gacgacgaag ccggcaatgc aggcccctgg cacaaccagg ccgacgccgg gggcagggga   15420
tggcagcagc tcgccaacca ggaaccccgc cgcgatgatg ccgatgccgg tcaaccagcc   15480
cttgaaacta tccggccccg aaacacccct gcgcattgcc tggatgctgc gccggatagc   15540
ttgcaacatc aggagccgtt tcttttgttc gtcagtcatg gtccgccctc accagttgtt   15600
cgtatcggtg tcggacgaac tgaaatcgca agagctgccg gtatcggtcc agccgctgtc   15660
cgtgtcgctg ctgccgaagc acggcgaggg gtccgcgaac gccgcagacg gcgtatccgg   15720
ccgcagcgca tcgcccagca tggccccggt cagcgagccg ccggccaggt agcccagcat   15780
ggtgctgttg gtcgccccgg ccaccagggc cgacgtgacg aaatcgccgt cattccctct   15840
ggattgttcg ctgctcggcg gggcagtgcg ccgcgccggc ggcgtcgtgg atggctcggg   15900
ttggctggcc tgcgacggcc ggcgaaaggt gcgcagcagc tcgttatcga ccggctgcgg   15960
cgtcggggcc gccgccttgc gctgcggtcg gtgttccttc ttcggctcgc gcagcttgaa   16020
cagcatgatc gcggaaacca gcagcaacgc cgcgcctacg cctcccgcga tgtagaacag   16080
catcggattc attcttcggt cctccttgta gcggaaccgt tgtctgtgcg gcgcgggtgg   16140
cccgcgccgc tgtctttggg gatcagccct cgatgagcgc gaccagtttc acgtcggcaa   16200
ggttcgcctc gaactcctgg ccgtcgtcct cgtacttcaa ccaggcatag ccttccgccg   16260
gcggccgacg gttgaggata aggcgggcag ggcgctcgtc gtgctcgacc tggacgatgg   16320
cctttttcag cttgtccggg tccggctcct tcgcgccctt ttccttggcg tccttaccgt   16380
cctggtcgcc gtcctcgccg tcctggccgt cgccggcctc cgcgtcacgc tcggcatcag   16440
tctggccgtt gaaggcatcg acggtgttgg gatcgcggcc cttctcgtcc aggaactcgc   16500
gcagcagctt gaccgtgccg cgcgtgattt cctgggtgtc gtcgtcaagc cacgcctcga   16560
cttcctccgg gcgcttcttg aaggccgtca ccagctcgtt caccacggtc acgtcgcgca   16620
cgcggccggt gttgaacgca tcggcgatct tctccggcag gtccagcagc gtgacgtgct   16680
gggtgatgaa cgccggcgac ttgccgattt ccttggcgat atcgcctttc ttcttgccct   16740
tcgccagctc gcggccaatg aagtcggcaa tttcgcgcgg ggtcagctcg ttgcgttgca   16800
ggttctcgat aacctggtcg gcttcgttgt agtcgttgtc gatgaacgcc gggatggact   16860
tcttgccggc ccacttcgag ccacggtagc ggcgggcgcc gtgattgatg atatagcggc   16920
ccggctgctc ctggttctcg cgcaccgaaa tgggtgactt caccccgcgc tctttgatcg   16980
tggcaccgat ttccgcgatg ctctccgggg aaaagccggg gttgtcggcc gtccgcggct   17040
gatgcggatc ttcgtcgatc aggtccaggt ccagctcgat agggccggaa ccgccctgag   17100
acgccgcagg agcgtccagg aggctcgaca ggtcgccgat gctatccaac cccaggccgg   17160
acggctcgcg cgcgcctgcg gcttcctgag cggccgcagc ggtgttttc ttggtggtct   17220
tggcttgagc cgcagtcatt gggaaatctc catcttcgtg aacacgtaat cagccagggc   17280
```

```
gcgaacctct ttcgatgcct tgcgcgcggc cgttttcttg atcttccaga ccggcacacc   17340
ggatgcgagg gcatcggcga tgctgctgcg caggccaacg gtggccggaa tcatcatctt   17400
ggggtacgcg gccagcagct cggcttggtg gcgcgcgtgg cgcggattcc gcgcatcgac   17460
cttgctgggc accatgccaa ggaattgcag cttggcgttc ttctggcgca cgttcgcaat   17520
ggtcgtgacc atcttcttga tgccctggat gctgtacgcc tcaagctcga tggggacag    17580
cacatagtcg gccgcgaaga gggcggccgc caggccgacg ccaagggtcg ggccgtgtc    17640
gatcaggcac acgtcgaagc cttggttcgc cagggccttg atgttcgccc cgaacagctc   17700
gcgggcgtcg tccagcgaca gccgttcggc gttcgccagt accgggttgg actcgatgag   17760
ggcgaggcgc gcggcctggc cgtcgccggc tgcgggtgcg gtttcggtcc agccgccggc   17820
agggacagcg ccgaacagct tgcttgcatg caggccggta gcaaagtcct tgagcgtgta   17880
ggacgcattg ccctgggggt ccaggtcgat cacggcaacc cgcaagccgc gctcgaaaaa   17940
gtcgaaggca agatgcacaa gggtcgaagt cttgccgacg ccgcctttct ggttggccgt   18000
gaccaaagtt ttcatcgttt ggtttcctgt tttttcttgg cgtccgcttc ccacttccgg   18060
acgatgtacg cctgatgttc cggcagaacc gccgttaccc gcgcgtaccc ctcgggcaag   18120
ttcttgtcct cgaacgcggc ccacacgcga tgcaccgctt gcgacactgc gccctggtc    18180
agtcccagcg acgttgcgaa cgtcgcctgt ggcttcccat cgactaagac gccccgcgct   18240
atctcgatgg tctgctgccc cacttccagc ccctggatcg cctcctggaa ctggctttcg   18300
gtaagccgtt tcttcatgga taacacccat aatttgctcc gcgccttggt tgaacatagc   18360
ggtgacagcc gccagcacat gagagaagtt tagctaaaca tttctcgcac gtcaacacct   18420
ttagccgcta aaactcgtcc ttggcgtaac aaaacaaaag cccggaaacc gggctttcgt   18480
ctcttgccgc ttatggctct gcacccggct ccatcaccaa caggtcgcgc acgcgcttca   18540
ctcggttgcg gatcgacact gccagcccaa caaagccggt tgccgccgcc gccaggatcg   18600
cgccgatgat gccggccaca ccggccatcg cccaccaggt cgccgccttc cggttccatt   18660
cctgctggta ctgcttcgca atgctggacc tcggctcacc ataggctgac cgctcgatgg   18720
cgtatgccgc ttctccccctt ggcgtaaaac ccagcgccgc aggcggcatt gccatgctgc   18780
ccgccgcttt cccgaccacg acgcgcgcac caggcttgcg gtccagacct tcggccacgg   18840
cgagctcgcg aaggacataa tcagccgccg acttggctcc acgcgcctcg atcagctctt   18900
gcactcgcgc gaaatccttg gcctccacgg ccgccatgaa tcgcgcacgc ggcgaaggct   18960
ccgcagggcc ggcgtcgtga tcgccgccga gaatgcccct taccaagttc gacgacacga   19020
aaatcatgct gacggctatc accatcatgc agacggatcg cacgaacccg ctgaattgaa   19080
cacgagcacg gcaccgcgca ccactatgcc aagaatgccc aaggtaaaaa ttgccggccc   19140
cgccatgaag tccgtgaatg ccccgacggc cgaagtgaag ggcaggccgc cacccaggcc   19200
gccgccctca ctgccggca cctggtcgct gaatgtcgat gccagcacct gcggcacgtc    19260
aatgcttccg ggcgtcgcgc tcgggctgat cgccatcccc gttactgccc cgatcccggc   19320
aatggcaagg actgccagcg ctgccatttt tggggtgagg ccgttcgcgg ccgaggggcg   19380
cagcccctgg ggggatggga ggcccgcgtt agcgggccgg gagggttcga agggggggg    19440
cacccccctt cggcgtgcgc ggtcacgcgc acagggcgca gccctggtta aaaacaaggt   19500
ttataaaatat tggtttaaaa gcaggttaaa agacaggtta gcggtggccg aaaaacgggc   19560
ggaaacccctt gcaaatgctg gattttctgc ctgtggacag cccctcaaat gtcaataggt   19620
```

-continued

```
gcgcccctca tctgtcagca ctctgcccct caagtgtcaa ggatcgcgcc cctcatctgt  19680
cagtagtcgc gcccctcaag tgtcaatacc gcagggcact tatccccagg cttgtccaca  19740
tcatctgtgg gaaactcgcg taaaatcagg cgttttcgcc gatttgcgag gctggccagc  19800
tccacgtcgc cggccgaaat cgagcctgcc cctcatctgt caacgccgcg ccgggtgagt  19860
cggcccctca agtgtcaacg tccgcccctc atctgtcagt gagggccaag ttttccgcga  19920
ggtatccaca acgccggcgg ccgcggtgtc tcgcacacgg cttcgacggc gtttctggcg  19980
cgtttgcagg gccatagacg gccgccagcc cagcggcgag ggcaaccagc ccggtgagcg  20040
tcggaaaggc gctggaagcc ccgtagcgac gcggagaggg gcgagacaag ccaagggcgc  20100
aggctcgatg cgcagcacga catagccggt tctcgcaagg acgagaattt ccctgcggtg  20160
cccctcaagt gtcaatgaaa gtttccaacg cgagccattc gcgagagcct tgagtccacg  20220
ctagatgaga gctttgttgt aggtggacca gttggtgatt ttgaactttt gctttgccac  20280
ggaacggtct gcgttgtcgg aagatgcgt gatctgatcc ttcaactcag caaaagttcg  20340
atttattcaa caaagccacg ttgtgtctca aaatctctga tgttacattg cacaagataa  20400
aaatatatca tcatgaacaa taaaactgtc tgcttacata aacagtaata caaggggtgt  20460
tatgagccat attcaacggg aaacgtcttg ctcgactcta gagctcgttc ctcgaggcct  20520
cgaggcctcg aggaacggta cctgcgggga agcttacaat aatgtgtgtt gttaagtctt  20580
gttgcctgtc atcgtctgac tgactttcgt cataaatccc ggcctccgta acccagcttt  20640
gggcaagctc acggatttga tccggcggaa cgggaatatc gagatgccgg ctgaacgct  20700
gcagttccag ctttcccttt cgggacaggt actccagctg attgattatc tgctgaaggg  20760
tcttggttcc acctcctggc acaatgcgaa tgattacttg agcgcgatcg ggcatccaat  20820
tttctcccgt caggtgcgtg gtcaagtgct acaaggcacc tttcagtaac gagcgaccgt  20880
cgatccgtcg ccgggatacg gacaaaatgg agcgcagtag tccatcgagg gcggcgaaag  20940
cctcgccaaa agcaatacgt tcatctcgca cagcctccag atccgatcga gggtcttcgg  21000
cgtaggcaga tagaagcatg gatacattgc ttgagagtat tccgatggac tgaagtatgg  21060
cttccatctt ttctcgtgtg tctgcatcta tttcgagaaa gccccgatg cggcgcaccg  21120
caacgcgaat tgccatacta tccgaaagtc ccagcaggcg cgcttgatag gaaaaggttt  21180
catactcggc cgatcgcaga cgggcactca cgaccttgaa cccttcaact ttcagggatc  21240
gatgctggtt gatggtagtc tcactcgacg tggctctggt gtgttttgac atagcttcct  21300
ccaaagaaag cggaaggtct ggatactcca gcacgaaatg tgcccgggta gacggatgga  21360
agtctagccc tgctcaatat gaaatcaaca gtacatttac agtcaatact gaatatactt  21420
gctacatttg caattgtctt ataacgaatg tgaaataaaa atagtgtaac aacgctttta  21480
ctcatcgata atcacaaaaa catttatacg aacaaaaata caaatgcact ccggtttcac  21540
aggataggcg ggatcagaat atgcaacttt tgacgttttg ttctttcaaa ggggtgctg  21600
gcaaaaccac cgcactcatg ggcctttgcg ctgctttggc aaatgacggt aaacgagtgg  21660
ccctctttga tgccgacgaa accggcctc tgacgcgatg gagagaaaac gccttacaaa  21720
gcagtactgg gatcctcgct gtgaagtcta ttccgccgac gaaatgcccc ttcttgaagc  21780
agcctatgaa aatgccgagc tcgaaggatt tgattatgcg ttggccgata cgcgtggcgg  21840
ctcgagcgag ctcaacaaca caatcatcgc tagctcaaac ctgcttctga tccccaccat  21900
gctaacgccg ctcgacatcg atgaggcact atctacctac cgctacgtca tcgagctgct  21960
gttgagtgaa aatttggcaa ttcctacagc tgttttgcgc caacgcgtcc cggtcggccg  22020
```

```
attgacaaca tcgcaacgca ggatgtcaga gacgctagag agccttccag ttgtaccgtc  22080
tcccatgcat gaaagagatg catttgccgc gatgaaagaa cgcggcatgt tgcatcttac  22140
attactaaac acgggaactg atccgacgat gcgcctcata gagaggaatc ttcggattgc  22200
gatggaggaa gtcgtggtca tttcgaaact gatcagcaaa atcttggagg cttgaagatg  22260
gcaattcgca agcccgcatt gtcggtcggc gaagcacggc ggcttgctgg tgctcgaccc  22320
gagatccacc atcccaaccc gacacttgtt ccccagaagc tggacctcca gcacttgcct  22380
gaaaaagccg acgagaaaga ccagcaacgt gagcctctcg tcgccgatca catttacagt  22440
cccgatcgac aacttaagct aactgtggat gcccttagtc cacctccgtc cccgaaaaag  22500
ctccaggttt ttctttcagc gcgaccgccc gcgcctcaag tgtcgaaaac atatgacaac  22560
ctcgttcggc aatacagtcc ctcgaagtcg ctacaaatga ttttaaggcg cgcgttggac  22620
gatttcgaaa gcatgctggc agatggatca tttcgcgtgg ccccgaaaag ttatccgatc  22680
ccttcaacta cagaaaaatc cgttctcgtt cagacctcac gcatgttccc ggttgcgttg  22740
ctcgaggtcg ctcgaagtca ttttgatccg ttggggttgg agaccgctcg agctttcggc  22800
cacaagctgg ctaccgccgc gctcgcgtca ttctttgctg gagagaagcc atcgagcaat  22860
tggtgaagag ggacctatcg gaaccccctca ccaaatattg agtgtaggtt tgaggccgct  22920
ggccgcgtcc tcagtcacct tttgagccag ataattaaga gccaaatgca attggctcag  22980
gctgccatcg tcccccgtg cgaaacctgc acgtccgcgt caaagaaata accggcacct  23040
cttgctgttt ttatcagttg agggcttgac ggatccgcct caagtttgcg gcgcagccgc  23100
aaaatgagaa catctatact cctgtcgtaa acctcctcgt cgcgtactcg actggcaatg  23160
agaagttgct cgcgcgatag aacgtcgcgg ggtttctcta aaaacgcgag gagaagattg  23220
aactcacctg ccgtaagttt cacctcaccg ccagcttcgg acatcaagcg acgttgcctg  23280
agattaagtg tccagtcagt aaaacaaaaa gaccgtcggt cttggagcg gacaacgttg  23340
gggcgcacgc gcaaggcaac ccgaatgcgt gcaagaaact ctctcgtact aaacggctta  23400
gcgataaaat cacttgctcc tagctcgagt gcaacaactt tatccgtctc ctcaaggcgg  23460
tcgccactga taattatgat tggaatatca gactttgccg ccagatttcg aacgatctca  23520
agcccatctt cacgacctaa atttagatca acaaccacga catcgaccgt cgcggaagag  23580
agtactctag tgaactgggt gctgtcggct accgcggtca ctttgaaggc gtggatcgta  23640
aggtattcga taataagatg ccgcatagcg acatcgtcat cgataagaag aacgtgtttc  23700
aacggctcac ctttcaatct aaaatctgaa cccttgttca cagcgcttga gaaattttca  23760
cgtgaaggat gtacaatcat ctccagctaa atgggcagtt cgtcagaatt gcggctgacc  23820
gcggatgacg aaaatgcgaa ccaagtattt caattttatg acaaaagttc tcaatcgttg  23880
ttacaagtga aacgcttcga ggttacagct actattgatt aaggagatcg cctatggtct  23940
cgccccggcg tcgtgcgtcc gccgcgagcc agatctcgcc tacttcataa acgtcctcat  24000
aggcacggaa tggaatgatg acatcgatcg ccgtagagag catgtcaatc agtgtgcgat  24060
cttccaagct agcaccttgg gcgctacttt tgacaaggga aaacagtttc ttgaatcctt  24120
ggattggatt cgcgccgtgt attgttgaaa tcgatcccgg atgtcccgag acgacttcac  24180
tcagataagc ccatgctgca tcgtcgcgca tctcgccaag caatatccgg tccggccgca  24240
tacgcagact tgcttggagc aagtgctcgg cgctcacagc acccagccca gcaccgttct  24300
tggagtagag tagtctaaca tgattatcgt gtggaatgac gagttcgagc gtatcttcta  24360
```

```
tggtgattag cctttcctgg gggggatgg cgctgatcaa ggtcttgctc attgttgtct   24420
tgccgcttcc ggtagggcca catagcaaca tcgtcagtcg gctgacgacg catgcgtgca   24480
gaaacgcttc caaatccccg ttgtcaaaat gctgaaggat agcttcatca tcctgatttt   24540
ggcgtttcct tcgtgtctgc cactggttcc acctcgaagc atcataacgg gaggagactt   24600
ctttaagacc agaaacacgc gagcttggcc gtcgaatggt caagctgacg gtgcccgagg   24660
gaacggtcgg cggcagacag atttgtagtc gttcaccacc aggaagttca gtggcgcaga   24720
gggggttacg tggtccgaca tcctgctttc tcagcgcgcc cgctaaaata gcgatatctt   24780
caagatcatc ataagagacg ggcaaaggca tcttggtaaa aatgccggct tggcgcacaa   24840
atgcctctcc aggtcgattg atcgcaattt cttcagtctt cgggtcatcg agccattcca   24900
aaatcggctt cagaagaaag cgtagttgcg gatccacttc catttacaat gtatcctatc   24960
tctaagcgga aatttgaatt cattaagagc ggcggttcct cccccgcgtg cgcgccgccag  25020
tcaggcggag ctggtaaaca ccaaagaaat cgaggtcccg tgctacgaaa atggaaacgg   25080
tgtcaccctg attcttcttc agggttggcg gtatgttgat ggttgcctta agggctgtct   25140
cagttgtctg ctcaccgtta ttttgaaagc tgttgaagct catcccgcca cccgagctgc   25200
cggcgtaggt gctagctgcc tggaaggcgc cttgaacaac actcaagagc atagctccgc   25260
taaaacgctg ccagaagtgg ctgtcgaccg agcccggcaa tcctgagcga ccgagttcgt   25320
ccgcgcttgg cgatgttaac gagatcatcg catggtcagg tgtctcggcg cgatcccaca   25380
acacaaaaac gcgcccatct ccctgttgca agccacgctg tatttcgcca acaacggtgg   25440
tgccacgatc aagaagcacg atattgttcg ttgttccacg aatatcctga ggcaagacac   25500
actttacata gcctgccaaa tttgtgtcga ttgcggtttg caagatgcac ggaattattg   25560
tcccttgcgt taccataaaa tcggggtgcg gcaagagcgt ggcgctgctg ggctgcagct   25620
cggtgggttt catacgtatc gacaaatcgt tctcgccgga cacttcgcca ttcggcaagg   25680
agttgtcgtc acgcttgcct tcttgtcttc ggcccgtgtc gccctgaatg gcgcgtttgc   25740
tgaccccttg atcgccgctg ctatatgcaa aaatcggtgt ttcttccggc cgtggctcat   25800
gccgctccgg ttcgcccctc ggcggtagag gagcagcagg ctgaacagcc tcttgaaccg   25860
ctggaggatc cggcggcacc tcaatcggag ctggatgaaa tggcttggtg tttgttgcga   25920
tcaaagttga cggcgatgcg ttctcattca ccttcttttg gcgcccacct agccaaatga   25980
ggcttaatga taacgcgaga acgacacctc cgacgatcaa tttctgagac cccgaaagac   26040
gccggcgatg tttgtcggag accagggatc cagatgcatc aacctcatgt gccgcttgct   26100
gactatcgtt attcatccct tcgcccccctt caggacgcgt ttcacatcgg gcctcaccgt   26160
gcccgtttgc ggccttttggc caacgggatc gtaagcggtg ttccagatac atagtactgt   26220
gtggccatcc ctcagacgcc aacctcggga aaccgaagaa atctcgacat cgctcccttt   26280
aactgaatag ttggcaacag cttccttgcc atcaggattg atggtgtaga tggagggtat   26340
gcgtacattg cccggaaagt ggaataccgt cgtaaatcca ttgtcgaaga cttcgagtgg   26400
caacagcgaa cgatcgcctt gggcgacgta gtgccaatta ctgtccgccg caccaagggc   26460
tgtgacaggc tgatccaata aattctcagc tttccgttga tattgtgctt ccgcgtgtag   26520
tctgtccaca acagccttct gttgtgcctc ccttcgccga gccgccgcat cgtcggcggg   26580
gtaggcgaat tggacgctgt aatagagatc gggctgctct ttatcgaggt gggacagagt   26640
cttgaacttt atactgaaaa cataacgcgg catcccggag tcgcttgcgg ttagcacgat   26700
tactggctga ggcgtgagga cctggcttgc cttgaaaaat agataatttc cccgcggtag   26760
```

```
ggctgctaga tctttgctat ttgaaacggc aaccgctgtc accgtttcgt tcgtggcgaa    26820
tgttacgacc aaagtagctc caaccgccgt cgagaggcgc accacttgat cgggattgta    26880
agccaaataa cgcatgcgcg gatctagctt gcccgccatt ggagtgtctt cagcctccgc    26940
accagtcgca gcggcaaata aacatgctaa aatgaaaagt gcttttctga tcatggttcg    27000
ctgtggccta cgtttgaaac ggtatcttcc gatgtctgat aggaggtgac aaccagacct    27060
gccgggttgg ttagtctcaa tctgccgggc aagctggtca cctttcgta gcgaactgtc    27120 gcggtccacg tactcaccac aggcattttg ccgtcaacga cgagggtcct tttatagcga    27180
atttgctgcg tgcttggagt tacatcattt gaagcgatgt gctcgacctc caccctgccg    27240
cgtttgccaa gaatgacttg aggcgaactg ggattgggat agttgaagaa ttgctggtaa    27300
tcctggcgca ctgttgggc actgaagttc gataccaggt cgtaggcgta ctgagcggtg    27360
tcggcatcat aactctcgcg caggcgaacg tactcccaca atgaggcgtt aacgacggcc    27420
tcctcttgag ttgcaggcaa tcgcgagaca gacacctcgc tgtcaacggt gccgtccggc    27480
cgtatccata gatatacggg cacaagcctg ctcaacggca ccattgtggc tatagcgaac    27540
gcttgagcaa catttcccaa aatcgcgata gctgcgacag ctgcaatgag tttggagaga    27600
cgtcgcgccg atttcgctcg cgcggtttga aaggcttcta cttccttata gtgctcggca    27660
aggctttcgc gcgccactag catggcatat tcaggcccg tcatagcgtc cacccgaatt    27720
gccgagctga agatctgacg gagtaggctg ccatcgcccc acattcagcg ggaagatcgg    27780
gcctttgcag ctcgctaatg tgtcgtttgt ctggcagccg ctcaaagcga caactaggca    27840
cagcaggcaa tacttcatag aattctccat tgaggcgaat ttttgcgcga cctagcctcg    27900
ctcaacctga gcgaagcgac ggtacaagct gctggcagat tgggttgcgc cgctccagta    27960
actgcctcca atgttgccgg cgatcgccgg caaagcgaca atgagcgcat cccctgtcag    28020
aaaaaacata tcgagttcgt aaagaccaat gatcttggcc gcggtcgtac cggcgaaggt    28080
gattacacca agcataaggg tgagcgcagt cgcttcggtt aggatgacga tcgttgccac    28140
gaggtttaag aggagaagca agagaccgta ggtgataagt tgcccgatcc acttagctgc    28200
gatgtcccgc gtgcgatcaa aaatatatcc gacgaggatc agaggcccga tcgcgagaag    28260
cactttcgtg agaattccaa cggcgtcgta aactccgaag gcagaccaga gcgtgccgta    28320
aaggacccac tgtgccccctt ggaaagcaag gatgtcctgg tcgttcatcg gaccgatttc    28380
ggatgcgatt ttctgaaaaa cggcctgggt cacggcgaac attgtatcca actgtgccgg    28440
aacagtctgc agaggcaagc cggttacact aaactgctga acaaagtttg ggaccgtctt    28500
ttcgaagatg gaaaccacat agtcttggta gttagcctgc ccaacaatta gagcaacaac    28560
gatggtgacc gtgatcaccc gagtgatacc gctacgggta tcgacttcgc cgcgtatgac    28620
taaaataccc tgaacaataa tccaaagagt gacacaggcg atcaatggcg cactcaccgc    28680
ctcctggata gtctcaagca tcgagtccaa gcctgtcgtg aaggctacat cgaagatcgt    28740
atgaatggcc gtaaacggcg ccggaatcgt gaaattcatc gattggacct gaacttgact    28800
ggtttgtcgc ataatgttgg ataaaatgag ctcgcattcg gcgaggatgc gggcggatga    28860
acaaatcgcc cagccttagg ggagggcacc aaagatgaca gcgtctttt gatgctcctt    28920 gcgttgagcg gccgcctctt ccgcctcgtg aaggccggcc tgcgcggtag tcatcgttaa    28980
taggcttgtc gcctgtacat tttgaatcat tgcgtcatgg atctgcttga gaagcaaacc    29040
attggtcacg gttgcctgca tgatattgcg agatcgggaa agctgagcag acgtatcagc    29100
```

```
attcgccgtc aagcgtttgt ccatcgtttc cagattgtca gccgcaatgc cagcgctgtt   29160
tgcggaaccg gtgatctgcg atcgcaacag gtccgcttca gcatcactac ccacgactgc   29220
acgatctgta tcgctggtga tcgcacgtgc cgtggtcgac attggcattc gcggcgaaaa   29280
catttcattg tctaggtcct tcgtcgaagg atactgattt ttctggttga gcgaagtcag   29340
tagtccagta acgccgtagg ccgacgtcaa catcgtaacc atcgctatag tctgagtgag   29400
attctccgca gtcgcgagcg cagtcgcgag cgtctcagcc tccgttgccg ggtcgctaac   29460
aacaaactgc gcccgcgcgg gctgaatata tagaaagctg caggtcaaaa ctgttgcaat   29520
aagttgcgtc gtcttcatcg tttcctacct tatcaatctt ctgcctcgtg gtgacgggcc   29580
atgaattcgc tgagccagcc agatgagttg ccttcttgtg cctcgcgtag tcgagttgca   29640
aagcgcaccg tgttggcacg ccccgaaagc acggcgacat attcacgcat atcccgcaga   29700
tcaaattcgc agatgacgct tccactttct cgtttaagaa gaaacttacg gctgccgacc   29760
gtcatgtctt cacgatcgc ctgaaattcc ttttcggtac atttcagtcc atcgacataa   29820
gccgatcgat ctgcggttgg tgatggatag aaaatcttcg tcatacattg cgcaaccaag   29880
ctggctccta gcggcgattc cagaacatgc tctggttgct gcgttgccag tattagcatc   29940
ccgttgtttt ttcgaacggt caggaggaat ttgtcgacga cagtcgaaaa tttagggttt   30000
aacaaatagg cgcgaaactc atcgcagctc atcacaaaac ggcggccgtc gatcatggct   30060
ccaatccgat gcaggagata tgctgcagcg ggagcgcata cttcctcgta ttcgagaaga   30120
tgcgtcatgt cgaagccggt aatcgacgga tctaacttta cttcgtcaac ttcgccgtca   30180
aatgcccagc caagcgcatg gccccggcac cagcgttgga gccgcgctcc tgcgccttcg   30240
gcgggcccat gcaacaaaaa ttcacgtaac cccgcgattg aacgcatttg tggatcaaac   30300
gagagctgac gatggatacc acggaccaga cggcggttct cttccggaga atcccaccc   30360
cgaccatcac tctcgatgag agccacgatc cattcgcgca gaaaatcgtg tgaggctgct   30420
gtgttttcta ggccacgcaa cggcgccaac ccgctgggtg tgcctctgtg aagtgccaaa   30480
tatgttcctc ctgtggcgcg aaccagcaat tcgccacccc ggtccttgtc aaagaacacg   30540
accgtacctg cacggtcgac catgctctgt tcgagcatgg ctagaacaaa catcatgagc   30600
gtcgtcttac ccctcccgat aggcccgaat attgccgtca tgccaacatc gtgctcatgc   30660
gggatatagt cgaaaggcgt tccgccattg gtacgaaatc gggcaatcgc gttgccccag   30720
tggcctgagc tggcgccctc tggaaagttt tcgaaagaga caaaccctgc gaaattgcgt   30780
gaagtgattg cgccagggcg tgtgcgccac ttaaaattcc ccggcaattg ggaccaatag   30840
gccgcttcca taccaatacc ttcttggaca accacggcac ctgcatccgc cattcgtgtc   30900
cgagcccgcg cgccccctgtc cccaagacta ttgagatcgt ctgcatagac gcaaaggctc   30960
aaatgatgtg agcccataac gaattcgttg ctcgcaagtc cgtcctcagc ctcggataat   31020
ttgccgattt gagtcacggc tttatcgccg gaactcagca tctggctcga tttgaggcta   31080
agtttcgcgt gcgcttgcgg gcgagtcagg aacgaaaaac tctgcgtgag aacaagtgga   31140
aaatcgaggg atagcagcgc gttgagcatg cccggccgtg tttttgcagg gtattcgcga   31200
aacgaataga tggatccaac gtaactgtct tttggcgttc tgatctcgag tcctcgcttg   31260
ccgcaaatga ctctgtcggt ataaatcgaa gcgccgagtg agccgctgac gaccggaacc   31320
ggtgtgaacc gaccagtcat gatcaaccgt agcgcttcgc caatttcggt gaagagcaca   31380
ccctgcttct cgcggatgcc aagacgatgc aggccatacg ctttaagaga gccagcgaca   31440
acatgccaaa gatcttccat gttcctgatc tggcccgtga gatcgttttc ccttttttccg   31500
```

```
cttagcttgg tgaacctcct ctttaccttc cctaaagccg cctgtgggta gacaatcaac    31560
gtaaggaagt gttcattgcg gaggagttgg ccggagagca cgcgctgttc aaaagcttcg    31620
ttcaggctag cggcgaaaac actacggaag tgtcgcggcg ccgatgatgg cacgtcggca    31680
tgacgtacga ggtgagcata tattgacaca tgatcatcag cgatattgcg caacagcgtg    31740
ttgaacgcac gacaacgcgc attgcgcatt tcagtttcct caagctcgaa tgcaacgcca    31800
tcaattctcg caatggtcat gatcgatccg tcttcaagaa ggacgatatg gtcgctgagg    31860
tggccaatat aagggagata gatctcaccg gatctttcgg tcgttccact cgcgccgagc    31920
atcacaccat tcctctccct cgtggggaa ccctaattgg atttgggcta acagtagcgc    31980 cccccaaac tgcactatca atgcttcttc ccgcggtccg caaaaatagc aggacgacgc    32040
tcgccgcatt gtagtctcgc tccacgatga gccgggctgc aaaccataac ggcacgagaa    32100
cgacttcgta gagcgggttc tgaacgataa cgatgacaaa gccggcgaac atcatgaata    32160
accctgccaa tgtcagtggc accccaagaa acaatgcggg ccgtgtggct gcgaggtaaa    32220
gggtcgattc ttccaaacga tcagccatca actaccgcca gtgagcgttt ggccgaggaa    32280
gctcgcccca aacatgataa caatgccgcc gacgacgccg gcaaccagcc caagcgaagc    32340
ccgcccgaac atccaggaga tcccgatagc gacaatgccg agaacagcga gtgactggcc    32400
gaacggacca aggataaacg tgcatatatt gttaaccatt gtggcggggt cagtgccgcc    32460
acccgcagat tgcgctgcgg cgggtccgga tgaggaaatg ctccatgcaa ttgcaccgca    32520
caagcttggg gcgcagctcg atatcacgcg catcatcgca ttcgagagcg agaggcgatt    32580
tagatgtaaa cggtatctct caaagcatcg catcaatgcg cacctcctta gtataagtcg    32640
aataagactt gattgtcgtc tgcggatttg ccgttgtcct ggtgtggcgg tggcggagcg    32700
attaaaccgc cagcgccatc ctcctgcgag cggcgctgat atgaccccca acatcccac    32760 gtctcttcgg attttagcgc ctcgtgatcg tcttttggag gctcgattaa cgcgggcacc    32820
agcgattgag cagctgtttc aacttttcgc acgtagccgt ttgcaaaacc gccgatgaaa    32880
ttaccggtgt tgtaagcgga gatcgcccga cgaagcgcaa attgcttctc gtcaatcgtt    32940
tcgccgcctg cataacgact tttcagcatg tttgcagcgg cagataatga tgtgcacgcc    33000
tggagcgcac cgtcaggtgt cagaccgagc atagaaaaat ttcgagagtt tatttgcatg    33060
aggccaacat ccagcgaatg ccgtgcatcg agacggtgcc tgacgacttg ggttgcttgg    33120
ctgtgatctt gccagtgaag cgtttcgccg gtcgtgttgt catgaatcgc taaaggatca    33180
aagcgactct ccaccttagc tatcgccgca agcgtagatg tcgcaactga tggggcacac    33240
ttgcgagcaa catggtcaaa ctcagcagat gagagtggcg tggcaaggct cgacgaacag    33300
aaggagacca tcaaggcaag agaaagcgac cccgatctct taagcatacc ttatctcctt    33360
agctcgcaac taacaccgcc tctcccgttg gaagaagtgc gttgttttat gttgaagatt    33420
atcgggaggg tcggttactc gaaaattttc aattgcttct ttatgatttc aattgaagcg    33480
agaaacctcg cccggcgtct tggaacgcaa catggaccga gaaccgcgca tccatgacta    33540
agcaaccgga tcgacctatt caggccgcag ttggtcaggt caggctcaga acgaaaatgc    33600
tcggcgaggt tacgctgtct gtaaacccat tcgatgaacg ggaagcttcc ttccgattgc    33660
tcttggcagg aatattggcc catgcctgct tgcgctttgc aaatgctctt atcgcgttgg    33720
tatcatatgc cttgtccgcc agcagaaacg cactctaagc gattatttgt aaaaatgttt    33780
cggtcatgcg gcggtcatgg gcttgacccg ctgtcagcgc aagacggatc ggtcaaccgt    33840
```

```
cggcatcgac aacagcgtga atcttggtgg tcaaaccgcc acgggaacgt cccatacagc    33900
catcgtcttg atcccgctgt ttcccgtcgc cgcatgttgg tggacgcgga cacaggaact    33960
gtcaatcatg acgacattct atcgaaagcc ttggaaatca cactcagaat atgatcccag    34020
acgtctgcct cacgccatcg tacaaagcga ttgtagcagg ttgtacagga accgtatcga    34080
tcaggaacgt ctgcccaggg cgggcccgtc cggaagcgcc acaagatgac attgatcacc    34140
cgcgtcaacg cgcggcacgc gacgcggctt atttgggaac aaaggactga acaacagtcc    34200
attcgaaatc ggtgacatca aagcggggac gggttatcag tggcctccaa gtcaagcctc    34260
aatgaatcaa aatcagaccg atttgcaaac ctgatttatg agtgtgcggc ctaaatgatg    34320
aaatcgtcct tctagatcgc ctccgtggtg tagcaacacc tcgcagtatc gccgtgctga    34380
ccttggccag ggaattgact ggcaagggtg cttttcacatg accgctcttt tggccgcgat    34440
agatgatttc gttgctgctt tgggcacgta gaaggagaga agtcatatcg gagaaattcc    34500
tcctggcgcg agagcctgct ctatcgcgac ggcatcccac tgtcgggaac agaccggatc    34560
attcacgagg cgaaagtcgt caacacatgc gttataggca tcttcccttg aaggatgatc    34620
ttgttgctgc caatctggag gtgcggcagc cgcaggcaga tgcgatctca gcgcaacttg    34680
cggcaaaaca tctcactcac ctgaaaacca ctagcgagtc tcgcgatcag acgaaggcct    34740
tttacttaac gacacaatat ccgatgtctg catcacaggc gtcgctatcc cagtcaatac    34800
taaagcggtg caggaactaa agattactga tgacttaggc gtgccacgag gcctgagacg    34860
acgcgcgtag acagtttttt gaaatcatta tcaaagtgat ggcctccgct gaagcctatc    34920
acctctgcgc cggtctgtcg gagagatggg caagcattat tacggtcttc gcgcccgtac    34980
atgcattgga cgattgcagg gtcaatggat ctgagatcat ccagaggatt gccgccctta    35040
ccttccgttt cgagttggag ccagccccta aatgagacga catagtcgac ttgatgtgac    35100
aatgccaaga gagagatttg cttaacccga ttttttgct caagcgtaag cctattgaag    35160
cttgccggca tgacgtccgc gccgaaagaa tatcctacaa gtaaaacatt ctgcacaccg    35220
aaatgcttgg tgtagacatc gattatgtga ccaagatcct tagcagtttc gcttggggac    35280
cgctccgacc agaaataccg aagtgaactg acgccaatga caggaatccc ttccgtctgc    35340
agataggtac catcgataga tctgctgcct cgcgcgtttc ggtgatgacg gtgaaaacct    35400
ctgacacatg cagctcccgg agacggtcac agcttgtctg taagcggatg ccgggagcag    35460
acaagcccgt cagggcgcgt cagcgggtgt tggcgggtgt cggggcgcag ccatgaccca    35520
gtcacgtagc gatagcggag tgtatactgg cttaactatg cggcatcaga gcagattgta    35580
ctgagagtgc accatatgcg gtgtgaaata ccgcacagat gcgtaaggag aaaataccgc    35640
atcaggcgct cttccgcttc ctcgctcact gactcgctgc gctcggtcgt tcggctgcgg    35700
cgagcggtat cagctcactc aaaggcggta atacggttat ccacagaatc aggggataac    35760
gcaggaaaga acatgtgagc aaaaggccag caaaaggcca ggaaccgtaa aaaggccgcg    35820
ttgctggcgt ttttccatag gctccgcccc cctgacgagc atcacaaaaa tcgacgctca    35880
agtcagaggt ggcgaaaccc gacaggacta taaagatacc aggcgtttcc ccctggaagc    35940
tccctcgtgc gctctcctgt tccgaccctg ccgcttaccg gatacctgtc cgcctttctc    36000
ccttcgggaa gcgtggcgct ttctcatagc tcacgctgta ggtatctcag ttcggtgtag    36060
gtcgttcgct ccaagctggg ctgtgtgcac gaaccccccg ttcagcccga ccgctgcgcc    36120
ttatccggta actatcgtct tgagtccaac ccggtaagac acgacttatc gccactggca    36180
gcagccactg gtaacaggat tagcagagcg aggtatgtag gcggtgctac agagttcttg    36240
```

```
aagtggtggc ctaactacgg ctacactaga aggacagtat ttggtatctg cgctctgctg   36300
aagccagtta ccttcggaaa aagagttggt agctcttgat ccggcaaaca aaccaccgct   36360
ggtagcggtg gtttttttgt ttgcaagcag cagattacgc gcagaaaaaa aggatctcaa   36420
gaagatcctt tgatcttttc tacggggtct gacgctcagt ggaacgaaaa ctcacgttaa   36480
gggattttgg tcatgagatt atcaaaaagg atcttcacct agatcctttt aaattaaaaa   36540
tgaagtttta aatcaatcta agtatatat gagtaaactt ggtctgacag ttaccaatgc   36600
ttaatcagtg aggcacctat ctcagcgatc tgtctatttc gttcatccat agttgcctga   36660
ctccccgtcg tgtagataac tacgatacgg gagggcttac catctggccc cagtgctgca   36720
atgataccgc gagacccacg ctcaccggct ccagatttat cagcaataaa ccagccagcc   36780
ggaagggccg agcgcagaag tggtcctgca actttatccg cctccatcca gtctattaat   36840
tgttgccggg aagctagagt aagtagttcg ccagttaata gtttgcgcaa cgttgttgcc   36900
attgctgcag ggggggggg gggggggac ttccattgtt cattccacgg acaaaaacag   36960
agaaaggaaa cgacagaggc caaaaagcct cgctttcagc acctgtcgtt tcctttcttt   37020
tcagagggta ttttaaataa aaacattaag ttatgacgaa gaagaacgga aacgccttaa   37080
accggaaaat tttcataaat agcgaaaacc cgcgaggtcg ccgccccgta acctgtcgga   37140
tcaccggaaa ggacccgtaa agtgataatg attatcatct acatatcaca acgtgcgtgg   37200
aggccatcaa accacgtcaa ataatcaatt atgacgcagg tatcgtatta attgatctgc   37260
atcaacttaa cgtaaaaaca acttcagaca atacaaatca gcgacactga atacggggca   37320
acctcatgtc ccccccccc cccccctgc aggcatcgtg gtgtcacgct cgtcgtttgg   37380
tatggcttca ttcagctccg gttcccaacg atcaaggcga gttacatgat cccccatgtt   37440
gtgcaaaaaa gcggttagct ccttcggtcc tccgatcgtt gtcagaagta agttggccgc   37500
agtgttatca ctcatggtta tggcagcact gcataattct cttactgtca tgccatccgt   37560
aagatgcttt tctgtgactg gtgagtactc aaccaagtca ttctgagaat agtgtatgcg   37620
gcgaccgagt tgctcttgcc cggcgtcaac acgggataat accgcgccac atagcagaac   37680
tttaaaagtg ctcatcattg gaaaacgttc ttcggggcga aaactctcaa ggatcttacc   37740
gctgttgaga tccagttcga tgtaacccac tcgtgcaccc aactgatctt cagcatcttt   37800
tactttcacc agcgtttctg ggtgagcaaa aacaggaagg caaaatgccg caaaaaaggg   37860
aataagggcg acacggaaat gttgaatact catactcttc cttttcaat attattgaag   37920 catttatcag ggttattgtc tcatgagcgg atacatattt gaatgtattt agaaaaataa   37980
acaaataggg gttccgcgca catttccccg aaaagtgcca cctgacgtct aagaaaccat   38040
tattatcatg acattaacct ataaaaatag gcgtatcacg aggccctttc gtcttcaaga   38100
attggtcgac gatcttgctg cgttcggata ttttcgtgga gttcccgcca cagacccgga   38160
ttgaaggcga gatccagcaa ctcgcgccag atcatcctgt gacggaactt tggcgcgtga   38220
tgactggcca ggacgtcggc cgaaagagcg acaagcagat cacgcttttc gacagcgtcg   38280
gatttgcgat cgaggatttt tcggcgctgc gctacgtccg cgaccgcgtt gagggatcaa   38340
gccacagcag cccactcgac cttctagccg acccagacga gccaagggat cttttggaa   38400 tgctgctccg tcgtcaggct ttccgacgtt tgggtggttg aacagaagtc attatcgtac   38460
ggaatgccaa gcactcccga ggggaaccct gtggttggca tgcacataca aatggacgaa   38520
cggataaacc ttttcacgcc cttttaaata tccgttattc taataaacgc tcttttctct   38580
```

```
taggtttacc cgccaatata tcctgtcaaa cactgatagt ttaaactgaa ggcgggaaac    38640
gacaatctga tcatgagcgg agaattaagg gagtcacgtt atgaccccg ccgatgacgc     38700 gggacaagcc gttttacgtt tggaactgac agaaccgcaa cgttgaagga gccactcagc    38760
aagctggtac gattgtaata cgactcacta tagggcgaat tgagcgctgt ttaaacgctc    38820
ttcaactgga agagcggtta cccggaccga agcttgaagt tcctattccg aagttcctat    38880
tctctagaaa gtataggaac ttcagatctc gatgctcacc ctgttgtttg gtgttacttc    38940
tgcaggtcga ctctagagga tccaccatga gcccagaacg acgcccggcc gacatccgcc    39000
gtgccaccga ggcggacatg ccggcggtct gcaccatcgt caaccactac atcgagacaa    39060
gcacggtcaa cttccgtacc gagccgcagg aaccgcagga ctggacggac gacctcgtcc    39120
gtctgcggga gcgctatccc tggctcgtcg ccgaggtgga cggcgaggtc gccggcatcg    39180
cctacgcggg ccccctggaag gcacgcaacg cctacgactg gacggccgag tcgaccgtgt    39240
acgtctcccc ccgccaccag cggacgggac tgggctccac gctctacacc cacctgctga    39300
agtccctgga ggcacagggc ttcaagagcg tggtcgctgt catcgggctg cccaacgacc    39360
cgagcgtgcg catgcacgag gcgctcggat atgcccccg cggcatgctg cgggcggccg    39420
gcttcaagca cgggaactgg catgacgtgg gtttctggca gctggacttc agcctgccgg    39480
taccgccccg tccggtcctg cccgtcaccg agatctgatc cgtcgaccaa cctagacttg    39540
tccatcttct ggattggcca acttaattaa tgtatgaaat aaaaggatgc acacatagtg    39600
acatgctaat cactataatg tgggcatcaa agttgtgtgt tatgtgtaat tactagttat    39660
ctgaataaaa gagaaagaga tcatccatat ttcttatcct aaatgaatgt cacgtgtctt    39720
tataattctt tgatgaacca gatgcatttc attaaccaaa tccatataca tataaatatt    39780
aatcatatat aattaatatc aattgggtta gcaaaacaaa tctagtctag gtgtgttttg    39840
cgaattgcgg ccgcgatctg gggaattccc atggacaccg gtgtgcagcg tgacccggtc    39900
gtgcccctct ctagagataa tgagcattgc atgtctaagt tataaaaaat taccacatat    39960 ttttttttgtc acacttgttt gaagtgcagt ttatctatct ttatacatat atttaaactt    40020
tactctacga ataatataat ctatagtact acaataatat cagtgttta gagaatcata    40080 taaatgaaca gttagacatg gtctaaagga caattgagta ttttgacaac aggactctac    40140
agttttatct ttttagtgtg catgtgttct ccttttttt tgcaaatagc ttcacctata    40200
taatacttca tccattttat tagtacatcc atttagggtt tagggttaat ggtttttata    40260
gactaatttt tttagtacat ctattttatt ctattttagc ctctaaatta agaaaactaa    40320
aactctattt tagtttttttt atttaataat ttagatataa aatagaataa aataaagtga    40380
ctaaaaatta aacaaatacc ctttaagaaa ttaaaaaaac taaggaaaca tttttcttgt    40440
ttcgagtaga taatgccagc ctgttaaacg ccgtcgacga gtctaacgga caccaaccag    40500
cgaaccagca gcgtcgcgtc gggccaagcg aagcagacgg cacggcatct ctgtcgctgc    40560
ctctggaccc ctctcgagag ttccgctcca ccgttggact tgctccgctg tcggcatcca    40620
gaaattgcgt ggcggagcgg cagacgtgag ccggcacggc aggcggcctc ctcctcctct    40680
cacggcaccg gcagctacgg gggattcctt tccaccgct ccttcgcttt ccttcctcg     40740 cccgccgtaa taaatagaca cccctccac accctctttc cccaacctcg tgttgttcgg    40800
agcgcacaca cacacaacca gatcccccc aaatccaccc gtcggcacct ccgcttcaag    40860
gtacgccgct cgtcctcccc cccccccctc tctaccttct ctagatcggc gttccggtcc    40920
atgcatggtt agggcccggt agttctactt ctgttcatgt ttgtgttaga tccgtgtttg    40980
```

```
tgttagatcc gtgctgctag cgttcgtaca cggatgcgac ctgtacgtca gacacgttct   41040
gattgctaac ttgccagtgt ttctctttgg ggaatcctgg gatggctcta gccgttccgc   41100
agacgggatc gatttcatga ttttttttgt ttcgttgcat agggtttggt ttgcccttt    41160 cctttatttc aatatatgcc gtgcacttgt ttgtcgggtc atctttcat gcttttttt     41220 gtcttggttg tgatgatgtg gtctggttgg gcggtcgttc tagatcggag tagaattctg   41280
tttcaaacta cctggtggat ttattaattt tggatctgta tgtgtgtgcc atacatattc   41340
atagttacga attgaagatg atggatggaa atatcgatct aggataggta tacatgttga   41400
tgcgggtttt actgatgcat atacagagat gcttttttgtt cgcttggttg tgatgatgtg  41460
gtgtggttgg gcggtcgttc attcgttcta gatcggagta gaatactgtt tcaaactacc   41520
tggtgtattt attaattttg gaactgtatg tgtgtgtcat acatcttcat agttacgagt   41580
ttaagatgga tggaaatatc gatctaggat aggtatacat gttgatgtgg gttttactga   41640
tgcatataca tgatggcata tgcagcatct attcatatgc tctaaccttg agtacctatc   41700
tattataata aacaagtatg ttttataatt attttgatct tgatatactt ggatgatggc   41760
atatgcagca gctatatgtg gatttttta gccctgcctt catacgctat ttatttgctt    41820
ggtactgttt cttttgtcga tgctcaccct gttgtttggt gttacttctg caggtaccgg   41880
tctctacgta cagtccggac tggcgccttg gcgcgccgat catccacaag tttgtacaaa   41940
aaagctgaac gagaaacgta aaatgatata aatatcaata tattaaatta gattttgcat   42000
aaaaaacaga ctacataata ctgtaaaaca caacatatcc agtcactatg gcggccgcat   42060
taggcacccc aggctttaca ctttatgctt ccggctcgta taatgtgtgg attttgagtt   42120
aggatttaaa tacgcgttga tccggcttac taaaagccag ataacagtat gcgtatttgc   42180
gcgctgattt ttgcggtata agaatatata ctgatatgta tacccgaagt atgtcaaaaa   42240
gaggtatgct atgaagcagc gtattacagt gacagttgac agcgacagct atcagttgct   42300
caaggcatat atgatgtcaa tatctccggt ctggtaagca caaccatgca gaatgaagcc   42360
cgtcgtctgc gtgccgaacg ctggaaagcg gaaaatcagg aagggatggc tgaggtcgcc   42420
cggtttattg aaatgaacgg ctcttttgct gacgagaaca gggctggtg aaatgcagtt    42480 taaggtttac acctataaaa gagagagccg ttatcgtctg tttgtggatg tacagagtga   42540
tatcattgac acgcccggtc gacggatggt gatcccctg gccagtgcac gtctgctgtc    42600
agataaagtc tcccgtgaac tttacccggt ggtgcatatc ggggatgaaa gctggcgcat   42660
gatgaccacc gatatggcca gtgtgccggt ctccgttatc ggggaagaag tggctgatct   42720
cagccaccgc gaaaatgaca tcaaaaacgc cattaacctg atgttctggg aatataaat    42780 gtcaggctcc cttatacaca gccagtctgc aggtcgacca tagtgactgg atatgttgtg   42840
ttttacagta ttatgtagtc tgttttttat gcaaaatcta atttaatata ttgatattta   42900 tatcattta cgtttctcgt tcagctttct tgtacaaagt ggtgttaacc tagacttgtc    42960
catcttctgg attggccaac ttaattaatg tatgaaataa aaggatgcac acatagtgac   43020
atgctaatca ctataatgtg gcatcaaag ttgtgtgtta tgtgtaatta ctagttatct    43080
gaataaaaga gaaagagatc atccatattt cttatcctaa atgaatgtca cgtgtcttta   43140
taattctttg atgaaccaga tgcatttcat taaccaaatc catatacata taaatattaa   43200
tcatatataa ttaatatcaa ttgggttagc aaaacaaatc tagtctaggt gtgttttgcg   43260
aattgcggcc gccaccgcgg tggagctcga attccggtcc gggtcacctt tgtccaccaa   43320
```

```
gatggaactg cggccgctca ttaattaagt caggcgcgcc tctagttgaa gacacgttca  43380
tgtcttcatc gtaagaagac actcagtagt cttcggccag aatggccatc tggattcagc  43440
aggcctagaa ggccatttaa atcctgagga tctggtcttc ctaaggaccc gggatatcgg  43500
accgattaaa cttttaattcg gtccgaagct tgaagttcct attccgaagt tcctattctc  43560
cagaaagtat aggaacttcg catgcctgca gtgcagcgtg acccggtcgt gcccctctct  43620
agagataatg agcattgcat gtctaagtta taaaaaatta ccacatattt ttttttgtcac  43680
acttgtttga agtgcagttt atctatcttt atacatatat ttaaacttta ctctacgaat  43740
aatataatct atagtactac aataatatca gtgttttaga gaatcatata aatgaacagt  43800
tagacatggt ctaaaggaca attgagtatt ttgacaacag gactctacag ttttatcttt  43860
ttagtgtgca tgtgttctcc ttttttttttg caaatagctt cacctatata atacttcatc  43920
cattttatta gtacatccat ttagggttta gggttaatgg ttttttataga ctaattttttt  43980
tagtacatct attttattct attttagcct ctaaattaag aaaactaaaa ctctatttta  44040
gttttttttat ttaataattt agatataaaa tagaataaaa taaagtgact aaaaattaaa  44100
caaatacccct ttaagaaatt aaaaaaacta aggaaacatt tttcttgttt cgagtagata  44160
atgccagcct gttaaacgcc gtcgacgagt ctaacgaca ccaaccagcg aaccagcagc  44220
gtcgcgtcgg gccaagcgaa gcagacggca cggcatctct gtcgctgcct ctggacccct  44280
ctcgagagtt ccgctccacc gttggacttg ctccgctgtc ggcatccaga aattgcgtgg  44340
cggagcggca gacgtgagcc ggcacggcag gcggcctcct cctcctctca cggcaccggc  44400
agctacgggg gattccttttc ccaccgctcc ttcgctttcc cttcctcgcc cgccgtaata  44460
aatagacacc ccctccacac cctctttccc caacctcgtg ttgttcggag cgcacacaca  44520
cacaaccaga tctcccccaa atccacccgt cggcacctcc gcttcaaggt acgccgctcg  44580
tcctccccccc cccccctctc taccttctct agatcggcgt tccggtccat gcatggttag  44640
ggcccggtag ttctacttct gttcatgttt gtgttagatc cgtgtttgtg ttagatccgt  44700
gctgctagcg ttcgtacacg gatgcgacct gtacgtcaga cacgttctga ttgctaactt  44760
gccagtgttt ctctttgggg aatcctggga tggctctagc cgttccgcag acgggatcga  44820
tttcatgatt ttttttgttt cgttgcatag ggtttggttt gcccttttcc tttatttcaa  44880
tatatgccgt gcacttgttt gtcgggtcat cttttcatgc ttttttttgt cttggttgtg  44940
atgatgtggt ctggttgggc ggtcgttcta gatcggagta gaattctgtt tcaaactacc  45000
tggtggattt attaattttg gatctgtatg tgtgtgccat acatattcat agttacgaat  45060
tgaagatgat ggatggaaat atcgatctag gataggtata catgttgatg cgggttttac  45120
tgatgcatat acagagatgc ttttttgttcg cttggttgtg atgatgtggt gtggttgggc  45180
ggtcgttcat tcgttctaga tcggagtaga atactgtttc aaactacctg gtgtatttat  45240
taattttgga actgtatgtg tgtgtcatac atcttcatag ttacgagttt aagatggatg  45300
gaaatatcga tctaggatag gtatacatgt tgatgtgggt tttactgatg catatacatg  45360
atggcatatg cagcatctat tcatatgctc taaccttgag tacctatcta ttataataaa  45420
caagtatgtt ttataattat tttgatcttg atatacttgg atgatggcat atgcagcagc  45480
tatatgtgga ttttttttagc cctgccttca tacgctattt atttgcttgg tactgtttct  45540
tttgtcgatg ctcaccctgt tgtttggtgt tacttctgca ggtcgacttt aacttagcct  45600
aggatccaca cgacaccatg atagaggtga aaccgattaa cgcagaggat acctatgaac  45660
taaggcatag aatactcaga ccaaaccagc cgatagaagc gtgtatgttt gaaagcgatt  45720
```

-continued

```
tacttcgtgg tgcatttcac ttaggcggct attacggggg caaactgatt tccatagctt   45780
cattccacca ggccgagcac tcagaactcc aaggccagaa acagtaccag ctccgaggta   45840
tggctacctt ggaaggttat cgtgagcaga aggcgggatc gagtctaatt aaacacgctg   45900
aagaaattct tcgtaagagg ggggcggact tgctttggtg taatgcgcgg acatccgcct   45960
caggctacta caaaaagtta ggcttcagcg agcagggaga ggtattcgac acgccgccag   46020
taggacctca catcctgatg tataaaagga tcacataact agctagtcag ttaacctaga   46080
cttgtccatc ttctggattg gccaacttaa ttaatgtatg aaataaaagg atgcacacat   46140
agtgacatgc taatcactat aatgtgggca tcaaagttgt gtgttatgtg taattactag   46200
ttatctgaat aaaagagaaa gagatcatcc atatttctta tcctaaatga atgtcacgtg   46260
tctttataat tctttgatga accagatgca tttcattaac caaatccata tacatataaa   46320
tattaatcat atataattaa tatcaattgg gttagcaaaa caaatctagt ctaggtgtgt   46380
tttgcgaatt cagagctcga attcattccg attaatcgtg gcctcttgct cttcaggatg   46440
aagagctatg tttaaacgtg caagcgctac tagacaattc agtacattaa aaacgtccgc   46500
aatgtgttat taagttgtct aagcgtcaat ttgtttacac cacaatatat cctgccacca   46560
gccagccaac agctccccga ccggcagctc ggcacaaaat caccactcga tacaggcagc   46620
ccatcagtcc gggacggcgt cagcgggaga gccgttgtaa ggcggcagac tttgctcatg   46680
ttaccgatgc tattcggaag aacggcaact aagctgccgg gtttgaaaca cggatgatct   46740
cgcggagggt agcatgttga ttgtaacgat gacagagcgt tgctgcctgt gatcaaaatat   46800 catctccctc gcagagatcc gaattatcag ccttcttatt catttctcgc ttaaccgtga   46860
caggctgtcg atcttgagaa ctatgccgac ataataggaa atcgctggat aaagccgctg   46920
aggaagctga gtggcgctat ttcttttagaa gtgaacgttg acgatcgtcg accgtacccc   46980
gatgaattaa ttcggacgta cgttctgaac acagctggat acttacttgg gcgattgtca   47040
tacatgacat caacaatgta cccgtttgtg taaccgtctc ttggaggttc gtatgacact   47100
agtggttccc ctcagcttgc gactagatgt tgaggcctaa cattttatta gagagcaggc   47160
tagttgctta gatacatgat cttcaggccg ttatctgtca gggcaagcga aaattggcca   47220
tttatgacga ccaatgcccc gcagaagctc ccatctttgc cgccatagac gccgcgcccc   47280
ccttttgggg tgtagaacat ccttttgcca gatgtgaaaa agaagttcgt tgtcccattg   47340
ttggcaatga cgtagtagcc ggcgaaagtg cgagacccat ttgcgctata tataagccta   47400
cgatttccgt tgcgactatt gtcgtaattg gatgaactat tatcgtagtt gctctcagag   47460
ttgtcgtaat ttgatggact attgtcgtaa ttgcttatgg agttgtcgta gttgcttgga   47520
gaaatgtcgt agttggatgg ggagtagtca tagggaagac gagcttcatc cactaaaaca   47580
attggcaggt cagcaagtgc ctgccccgat gccatcgcaa gtacgaggct tagaaccacc   47640
ttcaacagat cgcgcatagt cttccccagc tctctaacgc ttgagttaag ccgcgccgcg   47700
aagcggcgtc ggcttgaacg aattgttaga cattatttgc cgactacctt ggtgatctcg   47760
cctttcacgt agtgaacaaa ttcttccaac tgatctgcgc gcgaggccaa gcgatcttct   47820
tgtccaagat aagcctgcct agcttcaagt atgacgggct gatactgggc cggcaggcgc   47880
tccattgccc agtcggcagc gacatccttc ggcgcgattt tgccggttac tgcgctgtac   47940
caaatgcggg acaacgtaag cactacattt cgctcatcgc cagcccagtc gggcggcgag   48000
ttccatagcg ttaaggtttc atttagcgcc tcaaatagat cctgttcagg aaccggatca   48060
```

```
aagagttcct ccgccgctgg acctaccaag gcaacgctat gttctcttgc ttttgtcagc   48120
aagatagcca gatcaatgtc gatcgtggct ggctcgaaga tacctgcaag aatgtcattg   48180
cgctgccatt ctccaaattg cagttcgcgc ttagctggat aacgccacgg aatgatgtcg   48240
tcgtgcacaa caatggtgac ttctacagcg cggagaatct cgctctctcc aggggaagcc   48300
gaagtttcca aaaggtcgtt gatcaaagct cgccgcgttg tttcatcaag ccttacagtc   48360
accgtaacca gcaaatcaat atcactgtgt ggcttcaggc cgccatccac tgcggagccg   48420
tacaaatgta cggccagcaa cgtcggttcg agatggcgct cgatgacgcc aactacctct   48480
gatagttgag tcgatacttc ggcgatcacc gcttccctca tgatgtttaa ctcctgaatt   48540
aagccgcgcc gcgaagcggt gtcggcttga atgaattgtt aggcgtcatc ctgtgctccc   48600
gagaaccagt accagtacat cgctgtttcg ttcgagactt gaggtctagt tttatacgtg   48660
aacaggtcaa tgccgccgag agtaaagcca cattttgcgt acaaattgca ggcaggtaca   48720
ttgttcgttt gtgtctctaa tcgtatgcca aggagctgtc tgcttagtgc ccactttttc   48780
gcaaattcga tgagactgtg cgcgactcct ttgcctcggt gcgtgtgcga cacaacaatg   48840
tgttcgatag aggctagatc gttccatgtt gagttgagtt caatcttccc gacaagctct   48900
tggtcgatga atgcgccata gcaagcagag tcttcatcag agtcatcatc cgagatgtaa   48960
tccttccggt aggggctcac acttctggta gatagttcaa agccttggtc ggataggtgc   49020
acatcgaaca cttcacgaac aatgaaatgg ttctcagcat ccaatgtttc cgccacctgc   49080
tcagggatca ccgaaatctt catatgacgc ctaacgcctg gcacagcgga tcgcaaacct   49140
ggcgcggctt ttggcacaaa aggcgtgaca ggtttgcgaa tccgttgctg ccacttgtta   49200 accctttgc cagatttggt aactataatt tatgttagag gcgaagtctt gggtaaaaac   49260
tggcctaaaa ttgctgggga tttcaggaaa gtaaacatca ccttccggct cgatgtctat   49320
tgtagatata tgtagtgtat ctacttgatc ggggatctg ctgcctcgcg cgtttcggtg   49380
atgacggtga aaacctctga cacatgcagc tcccggagac ggtcacagct tgtctgtaag   49440
cggatgccgg gagcagacaa gcccgtcagg gcgcgtcagc gggtgttggc gggtgtcggg   49500
gcgcagccat gacccagtca cgtagcgata gcggagtgta tactggctta actatgcggc   49560
atcagagcag attgtactga gagtgcacca tatgcggtgt gaaataccgc acagatgcgt   49620
aaggagaaaa taccgcatca ggcgctcttc cgcttcctcg ctcactgact cgctgcgctc   49680
ggtcgttcgg ctgcggcgag cggtatcagc tcactcaaag gcggtaatac ggttatccac   49740
agaatcaggg gataacgcag gaaagaacat gtgagcaaaa ggccagcaaa aggccaggaa   49800
ccgtaaaaag gccgcgttgc tggcgttttt ccataggctc cgcccccctg acgagcatca   49860
caaaaatcga cgctcaagtc agaggtggcg aaacccgaca ggactataaa gataccaggc   49920
gtttccccct ggaagctccc tcgtgcgctc tcctgttccg accctgccgc ttaccggata   49980
cctgtccgcc tttctccctt cgggaagcgt ggcgctttct catagctcac gctgtaggta   50040
tctcagttcg gtgtaggtcg ttcgctccaa gctgggctgt gtgcacgaac cccccgttca   50100
gcccgaccgc tgcgccttat ccggtaacta tcgtcttgag tccaacccgg taagacacga   50160
cttatcgcca ctggcagcag ccactggtaa caggattagc agagcgaggt atgtaggcgg   50220
tgctacagag ttcttgaagt ggtggcctaa ctacggctac actagaagga cagtatttgg   50280
tatctgcgct ctgctgaagc cagttacctt cggaaaaaga gttggtagct cttgatccgg   50340
caaacaaacc accgctggta gcggtggttt ttttgtttgc aagcagcaga ttacgcgcag   50400
aaaaaaagga tctcaagaag atcctttgat cttttctacg gggtctgacg ctcagtggaa   50460
```

```
cgaaaactca cgttaaggga ttttggtcat gagattatca aaaggatct tcacctagat      50520 ccttttaaat taaaaatgaa gttttaaatc aatctaaagt atatatgagt aaacttggtc      50580
tgacagttac caatgcttaa tcagtgaggc acctatctca gcgatctgtc tatttcgttc      50640
atccatagtt gcctgactcc ccgtcgtgta gataactacg atacgggagg gcttaccatc      50700
tggccccagt gctgcaatga taccgcgaga cccacgctca ccggctccag atttatcagc      50760
aataaaccag ccagccggaa gggccgagcg cagaagtggg cctgcaactt tatccgcctc      50820
catccagtct attaattgtt gccgggaagc tagagtaagt agttcgccag ttaatagttt      50880
gcgcaacgtt gttgccattg ctgca                                            50905

<210> SEQ ID NO 16
<211> LENGTH: 54
<212> TYPE: DNA
<213> ORGANISM: Artificial Sequence
<220> FEATURE:
<223> OTHER INFORMATION: forward primer VC062

<400> SEQUENCE: 16
ttaaacaagt ttgtacaaaa aagcaggctg caattaaccc tcactaaagg gaac             54

<210> SEQ ID NO 17
<211> LENGTH: 53
<212> TYPE: DNA
<213> ORGANISM: Artificial Sequence
<220> FEATURE:
<223> OTHER INFORMATION: reverse primer VC063

<400> SEQUENCE: 17
ttaaaccact ttgtacaaga aagctgggtg cgtaatacga ctcactatag ggc              53

<210> SEQ ID NO 18
<211> LENGTH: 1830
<212> TYPE: DNA
<213> ORGANISM: Zea mays

<400> SEQUENCE: 18
gtttcgctct tccggagaag gcaaggcgtt tgcggtttgc ccgccgccgt gaatcgtatg        60
tgatcgaatc gcgcggcggg tgatggcgga ggaaccggtg gtcggttatg atggcttcga       120
ggccgccggt gatgctggcg ccggtggcgc ggaggacaac ctgtcgatgt ccctcggcga       180
cttcatggcg ttcctcgaaa ctgagcccac gtcacccgag gaaggctgga aggaggagca       240
gcagatgcag cctgcggtca atcaaggttg tttagagatg cctgccaaca ctgattgttc       300
tgaagattta ttccaaagcc atgaagaaat gcttgagaac gcagaatttt ggtcaaagtc       360
aaactactcc cctgtggagc atctggagtg ccatatggaa gttaacatgg agctgaacga       420
aggagaacaa atgattgatc acacagaagc tagccgatat gaattgttta gcaacgatct       480
gcagagccaa tcaagaactt ccaacttgga caatgaacat tttccaaggg atgcatcaaa       540
ccacgctaat gttgaagcaa ctggacctcc atatgatctc tcaaatggtg gtatatccac       600
agagcactca gattggagtg aaattaaatg ggggagtaca gatgagatgc ttggtaatac       660
tggtcaggat gatgaccatt tcactccgat gggcatgttt tgtcttacca ataacacaga       720
tattcttgat ctttcttgca ttgagtccaa catgggtgag agaacggaaa gcattcgcaa       780
tggcaacagt agttgcctta ctatgcagga agaacattta caggcagaat gtggaggata       840
tcctcatcca gattatatat ctgttgatat gattgatgaa agatcactgc atgatttgcc       900
```

```
acatgggtta tcacaaaaca atgagcagta tgagatggag cagctcccac agaatatatg   960
tgaaagtggt tctatgcaga tggcctctcc ggaccaatat tgttcctctc cggaccaata  1020
ttgtgatgat acatctttat cagattttta catggatgta tcctcccag agtcaatatc  1080 ctgtgagcag aaccagcctg aagatatttt tttcaagagc gagtctagca ctgactcttc  1140
tccagtaccc tctagcagaa attccaccac agaggatgct gataaatact taggtcaacc  1200
atcaaaacag ttgctggact ccaaaatcgt tcctttcagc aaccaacaca cgtttaagaa  1260
catggaatat caaaaacctc tggtattgga taaacaatat gcatatagaa gcaacaactc  1320
ttctattcac aattcaacaa aaggttgctt cagtagagat ggggacatgg tttctgattt  1380
atgtgtgcta gagggtaata ggaatcctgc tcctgctcac ctatggcctt atcagggaa   1440 gttccatcat aattttcagc aacctgtgta tggtaattcc atcattcctg catttggtgg  1500
tacgagatac aaaccacacg atgaaagaac cactctgcgc cttgcattgc aggtcatata  1560
gttctctagg ctgttgcttg cttattttc catgcttaat atattttcgc gcagctctcc   1620
tgcgctttcg agaattttt tttccatgct tattactttg tttaggatcc tcgtactata    1680
tttccttagt cctgtgcccc tgtttctgag tggtgatata taatgaataa ccattagcaa  1740
aacattatgt gaagaatgaa atgctaaacc ttggttgaat aaaaaaaaaa aaaaaaaaa   1800 aaaaaaaaa aaaaaaaaa aaaaaaagg                                     1830
```

```
<210> SEQ ID NO 19
<211> LENGTH: 492
<212> TYPE: PRT
<213> ORGANISM: Zea mays

<400> SEQUENCE: 19

Met Ala Glu Glu Pro Val Val Gly Tyr Asp Gly Phe Glu Ala Ala Gly
1               5                   10                  15

Asp Ala Gly Ala Gly Gly Ala Glu Asp Asn Leu Ser Met Ser Leu Gly
            20                  25                  30

Asp Phe Met Ala Phe Leu Glu Thr Glu Pro Thr Ser Pro Glu Glu Gly
        35                  40                  45

Trp Lys Glu Glu Gln Met Gln Pro Ala Val Asn Gln Gly Cys Leu
    50                  55                  60

Glu Met Pro Ala Asn Thr Asp Cys Ser Glu Asp Leu Phe Gln Ser His
65                  70                  75                  80

Glu Glu Met Leu Glu Asn Ala Glu Phe Trp Ser Lys Ser Asn Tyr Ser
                85                  90                  95

Pro Val Glu His Leu Glu Cys His Met Glu Val Asn Met Glu Leu Asn
            100                 105                 110

Glu Gly Glu Gln Met Ile Asp His Thr Glu Ala Ser Arg Tyr Glu Leu
        115                 120                 125

Phe Ser Asn Asp Leu Gln Ser Gln Ser Arg Thr Ser Asn Leu Asp Asn
    130                 135                 140

Glu His Phe Pro Arg Asp Ala Ser Asn His Ala Asn Val Glu Ala Thr
145                 150                 155                 160

Gly Pro Pro Tyr Asp Leu Ser Asn Gly Gly Ile Ser Thr Glu His Ser
                165                 170                 175

Asp Trp Ser Glu Ile Lys Trp Gly Ser Thr Asp Glu Met Leu Gly Asn
            180                 185                 190

Thr Gly Gln Asp Asp Asp His Phe Thr Pro Met Gly Met Phe Cys Leu
        195                 200                 205
```

Thr Asn Asn Thr Asp Ile Leu Asp Leu Ser Cys Ile Glu Ser Asn Met
210                 215                 220

Gly Glu Arg Thr Glu Ser Ile Arg Asn Gly Asn Ser Ser Cys Leu Thr
225                 230                 235                 240

Met Gln Glu Glu His Leu Gln Ala Glu Cys Gly Gly Tyr Pro His Pro
245                 250                 255

Asp Tyr Ile Ser Val Asp Met Ile Asp Glu Arg Ser Leu His Asp Leu
260                 265                 270

Pro His Gly Leu Ser Gln Asn Asn Glu Gln Tyr Glu Met Glu Gln Leu
275                 280                 285

Pro Gln Asn Ile Cys Glu Ser Gly Ser Met Gln Met Ala Ser Pro Asp
290                 295                 300

Gln Tyr Cys Ser Ser Pro Asp Gln Tyr Cys Asp Asp Thr Ser Leu Ser
305                 310                 315                 320

Asp Phe Tyr Met Asp Val Ser Ser Pro Glu Ser Ile Ser Cys Glu Gln
325                 330                 335

Asn Gln Pro Glu Asp Ile Phe Phe Lys Ser Glu Ser Ser Thr Asp Ser
340                 345                 350

Ser Pro Val Pro Ser Ser Arg Asn Ser Thr Thr Glu Asp Ala Asp Lys
355                 360                 365

Tyr Leu Gly Gln Pro Ser Lys Gln Leu Leu Asp Ser Lys Ile Val Pro
370                 375                 380

Phe Ser Asn Gln His Thr Phe Lys Asn Met Glu Tyr Gln Lys Pro Leu
385                 390                 395                 400

Val Leu Asp Lys Gln Tyr Ala Tyr Arg Ser Asn Ser Ser Ile His
405                 410                 415

Asn Ser Thr Lys Gly Cys Phe Ser Arg Asp Gly Asp Met Val Ser Asp
420                 425                 430

Leu Cys Val Leu Glu Gly Asn Arg Asn Pro Ala Pro Ala His Leu Trp
435                 440                 445

Pro Tyr Gln Gly Lys Phe His His Asn Phe Gln Gln Pro Val Tyr Gly
450                 455                 460

Asn Ser Ile Ile Pro Ala Phe Gly Gly Thr Arg Tyr Lys Pro His Asp
465                 470                 475                 480

Glu Arg Thr Thr Leu Arg Leu Ala Leu Gln Val Ile
485                 490

<210> SEQ ID NO 20
<211> LENGTH: 3850
<212> TYPE: DNA
<213> ORGANISM: Zea mays

<400> SEQUENCE: 20

```
cagttgcaag gactgaatat cccccgaccg caacggcgcc ggtctccctc gctccatcct      60
tctaggcagg ccctcgctct cccgtggatc ctccgccgcg ccgccgcccc tttatctgag     120
ccatccagcg gagcggagat ccatccgttg gggcgtggat tcagtccctt cccttctcgg     180
tggttactcc cacagtgagg gtaactcgaa taactgtgag tgctactgtg agatgggtgg     240
tgtgctctct cttttagctt ggtgatcatc tgaaaaaagg aagtgctgtt tatttctgta     300
agatagaaag caaaccattg gttcatgaat ggtttagtca tgctaagaaa acaaagttc      360 taagaacaca tatacagtgc acgtgcttgc tggcaatatg aatgaaaact ctgccattat     420
tatttcggat agtgatgatg actcaattgg ctcaatattc gatgatgacg accagccagc     480
gtctgcaatc gcaaggcttg atcaaaatgc tgaaggacga ataatcaatt ttgaggatga     540
```

```
agattggcaa aggagcgctc ctgctccacc atcgactaag cctactgaga acaacaatgg    600
tcaatacagg attcttccag catcccttac gaatggtaga catgctgaga gtagtcgtta    660
tacatttggt tcagtggaca ggattcatcc ccatgcaaat ccttatatgg ctatgcgacc    720
gggccattct acttccagta gaattgatag cgtagtggaa aagcacaaca gttctacagc    780
agatgcaaat gacaataaca agagggtcct tccatcatcc ttttcaaatg caacacatc     840 aaaatctatg catccaattg ttgctagcga aacacgcaag ctcccactgc ctttatccac    900
caaaaagtca ccaaatattg gtgaaaacag aatgggaca aatattgcca atggaaattt     960
gcagccttca tcttcaataa tggcaagagg aacttctagt acacttaata cccataaagt   1020
ggatgatgat gatgatgtca ttgtatatgg aggttctagc tcacataggg tactgccttc   1080
aacgtttgag gcaaccaatt ctaataacag tgaagttgct aagggctttg agacacacag   1140
tcgccttaat cctgaaaata gggtcttaga ttacgctgag agagcagtat atcaagaagc   1200
cctgcagaat attagtcgcg aaaaaagtga agatgatctg cctgagggtg tgctagcagt   1260
acctctgctt agacatcaga aaatggcatt ggcttggatg gtttcaaagg agaatagctc   1320
acattgtgct ggtggaattc ttgccgatga tcagggcctt gggaagacag tgtctactat   1380
tgcccttata caaaaacaga ggatggaaca gtcgaaattt atgtttgttg attcagatcg   1440
tttgaaatct gaagcactaa accttgatga agatgatgag ggagaacaaa ctgttagcaa   1500
tgaacctaaa aaggaccaag cgcttgttc attgtcaaca tctgctggta ctagtgctga    1560 acttttgtt aatcaaccga ataatgttgt gaataaaatg gttgaaacca agcagaacg     1620 caagaaaaaa gctaaagttt ccacatcatc tgcatccacc tcacgttcca tgacaaggcc   1680
agctgcaggt actctagtag tgtgccctgc tagtgttctt aagcagtggt ctaacgaatt   1740
aactgacaag gttagcgaaa gtgctaaatt atctgtttta gtctaccatg gtggtgcaag   1800
gaccaaagat ccacgtgagc tggcaaaata cgatgtagtt gttactacat atacaattgt   1860
ggccaatgaa gtacctaaac agatggctga tgatgacgca gatcaaaaga acagtgaaga   1920
accctctgct agcaataaaa gaaagccatc ggcgaatatg caaaacaagg ctaagaaaaa   1980
gaagaagaaa cttaaggact caaactttga ccttgacagt ggtccaattg caagagtgcg   2040
atggtttagg gttgtgcttg atgaagctca gacaataaaa aacttccgaa ctgtagtggc   2100
cagagcctgt tgtgggctaa gagcaaagcg agatggtgc ttatcaggaa cacctataca    2160
aaatgcaatt gatgatctgt ttagctattt ccgtttcttg aaatatgatc cgtattgcac   2220
gtataactcg ttttgcacaa tgattaagca cccaattgct agagatgcaa ttaatggata   2280
caagaaactt caggctgtgc tgaaggtagt tctcctgcgt cgtacgaaag aaactgtgat   2340
caatggcaaa ccaataataa atttacctcc taagacaatt aatctgaata agtagattt    2400 cacacaagag gagcggtcgt tttatttgat gctggaagaa cgctctcggc aacaattcaa   2460
ggcatttgct gcggctggga cactcaaaca aaactatgcc aacatccttt taatgttgct   2520
gcgacttcgg caagcctgtg atcatcctat tcttgtaaag ggcaatcagt cagaatatgg   2580
aggtgatggt tctatagaaa tggcaaagaa acttcctaag gaagtggtga tagatttgct   2640
tgcaaaactg gaagtggggt caacactttg tggcttatgc aatgatacac ctgaggatgc   2700
tattgtgaca atttgtggtc atgttttctg ctatcaatgt atacatgaac gaataacgac   2760
tgatgagaat atgtgccctg cccctaattg cagtagaaca ttaggtcttg aattgttatt   2820
ttcgtcagga gcttaaaaga tttgcatctc tggcaaatcg agttctgcag tagctagttc   2880
```

-continued

```
atcatcagat aacgagtcat cttcaatcag tcaaagcagc tttgtctcat ccaagataca   2940
agcagccatt gatatactga attcaatcat tgtcatggat cctcttactg aaagttatac   3000
aatggaatca agcagaagtg gactaggccc tgtgaaagcc attgtctttt cccaatggac   3060
tggcatgctg gatttgctgg agctttcact gaatatcaac tgtatacagt acaggagact   3120
agatggaaca atgtctctca atttaagaga aaaaaatgtg aaggatttta acactgaccc   3180
agaggttaga gttatgatta tgtcactgaa agctggtaat cttggtctca acatggtttc   3240
tgcttgccat gtaattctcc ttgatctctg gtggaaccct tatgctgagg accaggcagt   3300
tgatagggca cacaggattg ggcagactag gcctgttact gtatctcgct tgaccgttaa   3360
agacactgtg gaagatcgta ttttagctct gcaggaggaa aagagaacca tggtgaactc   3420
tgctttcggt gatgacaaag ccggcggcca tgcgacccgg ctcaccgtgg aagacctgcg   3480
gtacctattt aggatatgat tgcgagggaa ctctctcaat gcctcggtca acttgtcagg   3540
tcatgatgcg ttgtaccttg taatcgtagt ccggcaaaag ggcggtgtac cattgcgagg   3600
gtaggctcat tggtccatgt ccgccacgcc ttgctgcagc tccagttttg tggtgctcag   3660
atttctagat gggtaatcta gggctagata gcatgtgtaa ttataacccc caaccccccc   3720
ctccccgggg catggaggag agttccgcag tgccaatgct ttatgattta gtgtatgtat   3780
atacatgatc accatgtcta acttgcaatg agttgtttta gctaaaaaaa aaaaaaaaaa   3840
aaaaaaaag                                                            3850
```

<210> SEQ ID NO 21
<211> LENGTH: 1033
<212> TYPE: PRT
<213> ORGANISM: Zea mays

<400> SEQUENCE: 21

```
Met Asn Glu Asn Ser Ala Ile Ile Ile Ser Asp Ser Asp Asp Asp Ser
1               5                   10                  15

Ile Gly Ser Ile Phe Asp Asp Asp Gln Pro Ala Ser Ala Ile Ala
20                  25                  30

Arg Leu Asp Gln Asn Ala Glu Gly Arg Ile Ile Asn Phe Glu Asp Glu
35                  40                  45

Asp Trp Gln Arg Ser Ala Pro Ala Pro Pro Ser Thr Lys Pro Thr Glu
50                  55                  60

Asn Asn Asn Gly Gln Tyr Arg Ile Leu Pro Ala Ser Leu Thr Asn Gly
65                  70                  75                  80

Arg His Ala Glu Ser Ser Arg Tyr Thr Phe Gly Ser Val Asp Arg Ile
85                  90                  95

His Pro His Ala Asn Pro Tyr Met Ala Met Arg Pro Gly His Ser Thr
100                 105                 110

Ser Ser Arg Ile Asp Ser Val Val Glu Lys His Asn Ser Ser Thr Ala
115                 120                 125

Asp Ala Asn Asp Asn Asn Lys Arg Val Leu Pro Ser Ser Phe Ser Asn
130                 135                 140

Gly Asn Thr Ser Lys Ser Met His Pro Ile Val Ala Ser Glu Thr Arg
145                 150                 155                 160

Lys Leu Pro Leu Pro Leu Ser Thr Lys Lys Ser Pro Asn Ile Gly Glu
165                 170                 175

Asn Arg Met Gly Thr Asn Ile Ala Asn Gly Asn Leu Gln Pro Ser Ser
180                 185                 190

Ser Ile Met Ala Arg Gly Thr Ser Ser Thr Leu Asn Thr His Lys Val
```

-continued

```
            195                 200                 205
Asp Asp Asp Asp Val Ile Val Tyr Gly Gly Ser Ser His Arg
210                 215                 220
Val Leu Pro Ser Thr Phe Glu Ala Thr Asn Ser Asn Ser Glu Val
225                 230                 235                 240
Ala Lys Gly Phe Glu Thr His Ser Arg Leu Asn Pro Glu Asn Arg Val
245                 250                 255
Leu Asp Tyr Ala Glu Arg Ala Val Tyr Gln Glu Ala Leu Gln Asn Ile
260                 265                 270
Ser Arg Glu Lys Ser Glu Asp Asp Leu Pro Glu Gly Val Leu Ala Val
275                 280                 285
Pro Leu Leu Arg His Gln Lys Met Ala Leu Ala Trp Met Val Ser Lys
290                 295                 300
Glu Asn Ser Ser His Cys Ala Gly Gly Ile Leu Ala Asp Asp Gln Gly
305                 310                 315                 320
Leu Gly Lys Thr Val Ser Thr Ile Ala Leu Ile Gln Lys Gln Arg Met
325                 330                 335
Glu Gln Ser Lys Phe Met Phe Val Asp Ser Asp Arg Leu Lys Ser Glu
340                 345                 350
Ala Leu Asn Leu Asp Glu Asp Glu Gly Glu Gln Thr Val Ser Asn
355                 360                 365
Glu Pro Lys Lys Asp Gln Gly Ala Cys Ser Leu Ser Thr Ser Ala Gly
370                 375                 380
Thr Ser Ala Glu Leu Phe Val Asn Gln Pro Asn Asn Val Val Asn Lys
385                 390                 395                 400
Met Val Glu Thr Lys Ala Glu Arg Lys Lys Ala Lys Val Ser Thr
405                 410                 415
Ser Ser Ala Ser Thr Ser Arg Ser Met Thr Arg Pro Ala Ala Gly Thr
420                 425                 430
Leu Val Val Cys Pro Ala Ser Val Leu Lys Gln Trp Ser Asn Glu Leu
435                 440                 445
Thr Asp Lys Val Ser Glu Ser Ala Lys Leu Ser Val Leu Val Tyr His
450                 455                 460
Gly Gly Ala Arg Thr Lys Asp Pro Arg Glu Leu Ala Lys Tyr Asp Val
465                 470                 475                 480
Val Val Thr Thr Tyr Thr Ile Val Ala Asn Glu Val Pro Lys Gln Met
485                 490                 495
Ala Asp Asp Asp Ala Asp Gln Lys Asn Ser Glu Glu Pro Ser Ala Ser
500                 505                 510
Asn Lys Arg Lys Pro Ser Ala Asn Met Gln Asn Lys Ala Lys Lys Lys
515                 520                 525
Lys Lys Lys Leu Lys Asp Ser Asn Phe Asp Leu Asp Ser Gly Pro Ile
530                 535                 540
Ala Arg Val Arg Trp Phe Arg Val Val Leu Asp Glu Ala Gln Thr Ile
545                 550                 555                 560
Lys Asn Phe Arg Thr Val Val Ala Arg Ala Cys Cys Gly Leu Arg Ala
565                 570                 575
Lys Arg Arg Trp Cys Leu Ser Gly Thr Pro Ile Gln Asn Ala Ile Asp
580                 585                 590
Asp Leu Phe Ser Tyr Phe Arg Phe Leu Lys Tyr Asp Pro Tyr Cys Thr
595                 600                 605
Tyr Asn Ser Phe Cys Thr Met Ile Lys His Pro Ile Ala Arg Asp Ala
610                 615                 620
```

```
Ile Asn Gly Tyr Lys Lys Leu Gln Ala Val Leu Lys Val Val Leu Leu
625                 630                 635                 640

Arg Arg Thr Lys Glu Thr Val Ile Asn Gly Lys Pro Ile Ile Asn Leu
645                 650                 655

Pro Pro Lys Thr Ile Asn Leu Asn Lys Val Asp Phe Thr Gln Glu Glu
660                 665                 670

Arg Ser Phe Tyr Leu Met Leu Glu Glu Arg Ser Arg Gln Gln Phe Lys
675                 680                 685

Ala Phe Ala Ala Ala Gly Thr Leu Lys Gln Asn Tyr Ala Asn Ile Leu
690                 695                 700

Leu Met Leu Leu Arg Leu Arg Gln Ala Cys Asp His Pro Ile Leu Val
705                 710                 715                 720

Lys Gly Asn Gln Ser Glu Tyr Gly Gly Asp Gly Ser Ile Glu Met Ala
725                 730                 735

Lys Lys Leu Pro Lys Glu Val Val Ile Asp Leu Leu Ala Lys Leu Glu
740                 745                 750

Val Gly Ser Thr Leu Cys Gly Leu Cys Asn Asp Thr Pro Glu Asp Ala
755                 760                 765

Ile Val Thr Ile Cys Gly His Val Phe Cys Tyr Gln Cys Ile His Glu
770                 775                 780

Arg Ile Thr Thr Asp Glu Asn Met Cys Pro Ala Pro Asn Cys Ser Arg
785                 790                 795                 800

Thr Leu Gly Leu Glu Leu Leu Phe Ser Ser Gly Ala Leu Lys Ile Cys
805                 810                 815

Ile Ser Gly Lys Ser Ser Ser Ala Val Ala Ser Ser Ser Ser Asp Asn
820                 825                 830

Glu Ser Ser Ser Ile Ser Gln Ser Ser Phe Val Ser Ser Lys Ile Gln
835                 840                 845

Ala Ala Ile Asp Ile Leu Asn Ser Ile Ile Val Met Asp Pro Leu Thr
850                 855                 860

Glu Ser Tyr Thr Met Glu Ser Ser Arg Ser Gly Leu Gly Pro Val Lys
865                 870                 875                 880

Ala Ile Val Phe Ser Gln Trp Thr Gly Met Leu Asp Leu Leu Glu Leu
885                 890                 895

Ser Leu Asn Ile Asn Cys Ile Gln Tyr Arg Arg Leu Asp Gly Thr Met
900                 905                 910

Ser Leu Asn Leu Arg Glu Lys Asn Val Lys Asp Phe Asn Thr Asp Pro
915                 920                 925

Glu Val Arg Val Met Ile Met Ser Leu Lys Ala Gly Asn Leu Gly Leu
930                 935                 940

Asn Met Val Ser Ala Cys His Val Ile Leu Leu Asp Leu Trp Trp Asn
945                 950                 955                 960

Pro Tyr Ala Glu Asp Gln Ala Val Asp Arg Ala His Arg Ile Gly Gln
965                 970                 975

Thr Arg Pro Val Thr Val Ser Arg Leu Thr Val Lys Asp Thr Val Glu
980                 985                 990

Asp Arg Ile Leu Ala Leu Gln Glu Glu Lys Arg Thr Met Val Asn Ser
995                 1000                1005

Ala Phe Gly Asp Asp Lys Ala Gly Gly His Ala Thr Arg Leu Thr
1010                1015                1020

Val Glu Asp Leu Arg Tyr Leu Phe Arg Ile
1025                1030
```

<210> SEQ ID NO 22
<211> LENGTH: 2847
<212> TYPE: DNA
<213> ORGANISM: Zea mays

<400> SEQUENCE: 22

| | | | | | |
|---|---|---|---|---|---|
| atgtccgaca | aggcagatcc | agcacacatg | cttccaagca | atatggacat | tattgactta | 60 |
| agttcagatg | gcgagcaaga | gatcattgac | ctgtcttctg | acagtgaaga | caacaacact | 120 |
| cttttcgct | cttacagaga | agattacgtg | gactatgatg | atcctggtag | tccttttcac | 180 |
| ctgccttttt | tccctcacaa | cacagcacca | gactggaata | tcatggaaga | attagatgat | 240 |
| tggcgtgtgc | tcgcaaagaa | agaatacgat | gactggctta | gttcaaaggc | ttcatcctct | 300 |
| tatagccctg | ttgatgatat | attaaccact | gagatgaaca | gtaagcagct | gccacaatct | 360 |
| ttcacctacg | gaggcttcat | tcctcaatca | tgtgcacccg | gccattcaag | tttaggtgac | 420 |
| aacaggacca | aggaagagcc | ctctatgaca | tttagtggtt | ttcaaggatg | cactgccagt | 480 |
| ggaaacggaa | tgccttcatc | tacagtgcca | ataggtccac | gtccacatcg | gatcttccct | 540 |
| ccgccaatgc | catcttctgt | taatgatata | aaagttgaat | atgacgtaga | acaaaggctt | 600 |
| ttcagttctg | atgagagagc | tgtatatgaa | gaagccctga | agcatatcac | tcaggaaacg | 660 |
| aaggaggaag | atctgcccaa | aggtgttatg | tcagttttac | tgcttaagca | tcagggtctt | 720 |
| gggaagacaa | tttcaacgat | tgcccttata | cagaaggaga | tggttaagca | gtctaggttc | 780 |
| atgactgctg | gttcatacag | tacaaagttt | gtcccaaaca | gtgattatga | caatgacagt | 840 |
| gatgttgtga | ttgacatgga | caagaaagaa | ccgaaagatg | aacccttgaa | tgagctagat | 900 |
| ggttctgcac | gattgcatgt | cgccagcagt | cttaagctct | gtgatagtaa | gccaaacact | 960 |
| gctactgata | aagctgaacc | taagaagaag | gccagagtga | ggtactctgc | atcaaacttg | 1020 |
| aggtcgaaga | ctaggccagc | tgcaggaaca | ttggtcgtct | gccctgctag | tgttcttagg | 1080 |
| cagtgggcta | atgagctctc | tgtgaaggtt | atggaagaca | ataaattgtc | agtcttggtt | 1140 |
| tatcatggaa | gttcaaggac | tagagatcct | aatgagttgg | caacatatga | tgttgttgtc | 1200 |
| accacgtata | tgactgtggc | aaacgaagta | cctaaagaaa | attctaatga | tgagcgaaag | 1260 |
| aaatgtgaaa | tggacggaat | atgtccagaa | atttccatcg | gcagcaaaag | gaaaaagcag | 1320 |
| agcaagccaa | agaagaaaaa | caaacctagc | aattcagaag | gtggcccact | tgccagggta | 1380 |
| cgatggttca | gagttgtgct | tgatgaagct | caaacaataa | aaaattaccg | gactcaagtg | 1440 |
| tctagagctt | gttgtggact | gagggcacaa | aggagatggt | gcttatcagg | aacacctata | 1500 |
| caaaacaaaa | ttgatgatct | gtatagctac | ttctgtttct | tgaagtatga | accttactca | 1560 |
| aaatttagta | atttcaaata | tatgatcaag | caccaaatta | ctagagattc | agttcgtggc | 1620 |
| tataagaaac | ttcaagctat | cttgaggata | attctactgc | ggcgcacaaa | agaaacactt | 1680 |
| atagatgggg | aaccaatctt | aaagctgcca | ccaaagacaa | ttcagctgaa | taaaatagat | 1740 |
| ttcacccaaa | aagagcgagc | tttctatttg | acacttgaag | aaggctctcg | gcagaagttc | 1800 |
| aaggcatacg | atgcagctgg | gacgataagg | gaaaattacg | caaacattct | tgtgttattg | 1860 |
| ttgcggctta | ggcaggcttg | tgaccaccct | cttcttttga | acggacatga | atcagatcta | 1920 |
| gttgacagca | gttccataga | aagggcaaag | caacttccta | aggaaacagt | gacaaatttg | 1980 |
| attgaaaagc | tggaaagagg | cccggcaatt | tgttccatat | gcaatgatcc | acctgaggat | 2040 |
| gctgttgtca | cgacatgcgg | tcatgtcttc | tgctaccagt | gtgtgcatga | gaggttaaca | 2100 |
| agcgacggac | atgtttgccc | ctatgcactc | tgtggaaaca | agctaagttt | tcgatctgtt | 2160 |

-continued

```
tttacaccag cagtattaaa actctgtact tcgccaaagc cggagtttgg tgaagaaact    2220
agctgttcca cagcagccga caaaccatcc tcgatctgtg aaagcagtta catctcctcg    2280
aagatccggt cagcagtgga atacttaat tcaatcatca agacaccggc ccttacagcg     2340
ggggacacta ctgaatcgat tcccagcatg cacccctg tcaaggcaat agtcttctcc      2400
cagtggactg gcatgctgga cctgctagag cttcactga acagaaatgg catacagttt     2460
aggaggctgg atggtgcaat gtccctcgac ttgagagaaa aggaagtgaa cgggtttaaa    2520
actgatcctg aggtgagagt aatgcttatg tcactgaagg ctggcaatct gggtctaaac    2580
atggtagctg cttgccatgt gatcatgctt gatccgtggt ggaatcctta cgctgaggac    2640
caggcggttg acagagcaca caggatcggt cagacacgtc ctgttactgt ttcacggttc    2700
acagttaaag acactgtgga agaccgcatt ttggctctgc aggagaagaa gagagagatg    2760
gtggaatccg cgttcggcga ggacggttcc agaggcactg ctaccaagct gacggtggaa    2820
gatctcagat acctcttcat ggtgtga                                       2847
```

<210> SEQ ID NO 23
<211> LENGTH: 948
<212> TYPE: PRT
<213> ORGANISM: Zea mays

<400> SEQUENCE: 23

```
Met Ser Asp Lys Ala Asp Pro Ala His Met Leu Pro Ser Asn Met Asp
1               5                   10                  15

Ile Ile Asp Leu Ser Ser Asp Gly Glu Gln Glu Ile Ile Asp Leu Ser
            20                  25                  30

Ser Asp Ser Glu Asp Asn Asn Thr Leu Phe Arg Ser Tyr Arg Glu Asp
        35                  40                  45

Tyr Val Asp Tyr Asp Asp Pro Gly Ser Pro Phe His Leu Pro Phe Phe
    50                  55                  60

Pro His Asn Thr Ala Pro Asp Trp Asn Ile Met Glu Glu Leu Asp Asp
65                  70                  75                  80

Trp Arg Val Leu Ala Lys Lys Glu Tyr Asp Asp Trp Leu Ser Ser Lys
                85                  90                  95

Ala Ser Ser Ser Tyr Ser Pro Val Asp Asp Ile Leu Thr Thr Glu Met
            100                 105                 110

Asn Ser Lys Gln Leu Pro Gln Ser Phe Thr Tyr Gly Gly Phe Ile Pro
        115                 120                 125

Gln Ser Cys Ala Pro Gly His Ser Ser Leu Gly Asp Asn Arg Thr Lys
    130                 135                 140

Glu Glu Pro Ser Met Thr Phe Ser Gly Phe Gln Gly Cys Thr Ala Ser
145                 150                 155                 160

Gly Asn Gly Met Pro Ser Ser Thr Val Pro Ile Gly Pro Arg Pro His
                165                 170                 175

Arg Ile Phe Pro Pro Met Pro Ser Ser Val Asn Asp Ile Lys Val
            180                 185                 190

Glu Tyr Asp Val Glu Gln Arg Leu Phe Ser Ser Asp Glu Arg Ala Val
        195                 200                 205

Tyr Glu Glu Ala Leu Lys His Ile Thr Gln Thr Lys Glu Glu Asp
    210                 215                 220

Leu Pro Lys Gly Val Met Ser Val Leu Leu Lys His Gln Gly Leu
225                 230                 235                 240

Gly Lys Thr Ile Ser Thr Ile Ala Leu Ile Gln Lys Glu Met Val Lys
```

```
            245                 250                 255
Gln Ser Arg Phe Met Thr Ala Gly Ser Tyr Ser Thr Lys Phe Val Pro
260                 265                 270

Asn Ser Asp Tyr Asp Asn Asp Ser Asp Val Val Ile Asp Met Asp Lys
275                 280                 285

Lys Glu Pro Lys Asp Glu Pro Leu Asn Glu Leu Asp Gly Ser Ala Arg
290                 295                 300

Leu His Val Ala Ser Ser Leu Lys Leu Cys Asp Ser Lys Pro Asn Thr
305                 310                 315                 320

Ala Thr Asp Lys Ala Glu Pro Lys Lys Ala Arg Val Arg Tyr Ser
325                 330                 335

Ala Ser Asn Leu Arg Ser Lys Thr Arg Pro Ala Ala Gly Thr Leu Val
340                 345                 350

Val Cys Pro Ala Ser Val Leu Arg Gln Trp Ala Asn Glu Leu Ser Val
355                 360                 365

Lys Val Met Glu Asp Asn Lys Leu Ser Val Leu Val Tyr His Gly Ser
370                 375                 380

Ser Arg Thr Arg Asp Pro Asn Glu Leu Ala Thr Tyr Asp Val Val Val
385                 390                 395                 400

Thr Thr Tyr Met Thr Val Ala Asn Glu Val Pro Lys Glu Asn Ser Asn
405                 410                 415

Asp Glu Arg Lys Lys Cys Glu Met Asp Gly Ile Cys Pro Glu Ile Ser
420                 425                 430

Ile Gly Ser Lys Arg Lys Lys Gln Ser Lys Pro Lys Lys Asn Lys
435                 440                 445

Pro Ser Asn Ser Glu Gly Gly Pro Leu Ala Arg Val Arg Trp Phe Arg
450                 455                 460

Val Val Leu Asp Glu Ala Gln Thr Ile Lys Asn Tyr Arg Thr Gln Val
465                 470                 475                 480

Ser Arg Ala Cys Cys Gly Leu Arg Ala Gln Arg Arg Trp Cys Leu Ser
485                 490                 495

Gly Thr Pro Ile Gln Asn Lys Ile Asp Asp Leu Tyr Ser Tyr Phe Cys
500                 505                 510

Phe Leu Lys Tyr Glu Pro Tyr Ser Lys Phe Ser Asn Phe Lys Tyr Met
515                 520                 525

Ile Lys His Gln Ile Thr Arg Asp Ser Val Arg Gly Tyr Lys Lys Leu
530                 535                 540

Gln Ala Ile Leu Arg Ile Ile Leu Leu Arg Arg Thr Lys Glu Thr Leu
545                 550                 555                 560

Ile Asp Gly Glu Pro Ile Leu Lys Leu Pro Pro Lys Thr Ile Gln Leu
565                 570                 575

Asn Lys Ile Asp Phe Thr Gln Lys Glu Ala Phe Tyr Leu Thr Leu
580                 585                 590

Glu Gly Ser Arg Gln Lys Phe Lys Ala Tyr Asp Ala Ala Gly Thr
595                 600                 605

Ile Arg Glu Asn Tyr Ala Asn Ile Leu Val Leu Leu Arg Leu Arg
610                 615                 620

Gln Ala Cys Asp His Pro Leu Leu Asn Gly His Glu Ser Asp Leu
625                 630                 635                 640

Val Asp Ser Ser Ile Glu Arg Ala Lys Gln Leu Pro Lys Glu Thr
645                 650                 655

Val Thr Asn Leu Ile Glu Lys Leu Glu Arg Gly Pro Ala Ile Cys Ser
660                 665                 670
```

```
Ile Cys Asn Asp Pro Pro Glu Asp Ala Val Val Thr Thr Cys Gly His
675                 680                 685
Val Phe Cys Tyr Gln Cys Val His Glu Arg Leu Thr Ser Asp Gly His
690                 695                 700
Val Cys Pro Tyr Ala Leu Cys Gly Asn Lys Leu Ser Phe Arg Ser Val
705                 710                 715                 720
Phe Thr Pro Ala Val Leu Lys Leu Cys Thr Ser Pro Lys Pro Glu Phe
725                 730                 735
Gly Glu Glu Thr Ser Cys Ser Thr Ala Ala Asp Lys Pro Ser Ser Ile
740                 745                 750
Cys Glu Ser Ser Tyr Ile Ser Ser Lys Ile Arg Ser Ala Val Glu Ile
755                 760                 765
Leu Asn Ser Ile Ile Lys Thr Pro Ala Leu Thr Ala Gly Asp Thr Thr
770                 775                 780
Glu Ser Ile Pro Ser Met Ala Pro Pro Val Lys Ala Ile Val Phe Ser
785                 790                 795                 800
Gln Trp Thr Gly Met Leu Asp Leu Leu Glu Leu Ser Leu Asn Arg Asn
805                 810                 815
Gly Ile Gln Phe Arg Arg Leu Asp Gly Ala Met Ser Leu Asp Leu Arg
820                 825                 830
Glu Lys Glu Val Asn Gly Phe Lys Thr Asp Pro Glu Val Arg Val Met
835                 840                 845
Leu Met Ser Leu Lys Ala Gly Asn Leu Gly Leu Asn Met Val Ala Ala
850                 855                 860
Cys His Val Ile Met Leu Asp Pro Trp Trp Asn Pro Tyr Ala Glu Asp
865                 870                 875                 880
Gln Ala Val Asp Arg Ala His Arg Ile Gly Gln Thr Arg Pro Val Thr
885                 890                 895
Val Ser Arg Phe Thr Val Lys Asp Thr Val Glu Asp Arg Ile Leu Ala
900                 905                 910
Leu Gln Glu Lys Lys Arg Glu Met Val Glu Ser Ala Phe Gly Glu Asp
915                 920                 925
Gly Ser Arg Gly Thr Ala Thr Lys Leu Thr Val Glu Asp Leu Arg Tyr
930                 935                 940
Leu Phe Met Val
945
```

<210> SEQ ID NO 24
<211> LENGTH: 4404
<212> TYPE: DNA
<213> ORGANISM: Arabidopsis thaliana

<400> SEQUENCE: 24

```
ctctatccca actgctctct acctttcctc gaaaattcct tcaaaaccca attctcaagc      60
cttcttcttc gtcgtacctg aaaattctac aatctctgga tctacgcgtc tacttctgaa    120
tttcgatttg ggtttccgg gagctgaaat tccgtgactt ttgggttttc tgatttaggg    180
tttgttcctc ttctcgttct ttctcgggtt agtttttttt tttttttttt gtgattttg     240 atgggtgagg aaggttcaat gtttggtctg ggaggtgaat tccggttga tgattgtgat     300 ggtggtttg agtttgaaga tgatgacgag actattgaca tcgaaacgct ttatcggatt     360
ctagatgaga agcctgattc tgctgagggt agccaagaaa acttatcacc agttggttca    420
tctgctgacg agctcaagga ttcacagttg ctaaatggtt catttgatga acatgtgaaa    480
```

```
atggaagccg ggctgagtcc ttcacctgct catacttgct ctgcaagtct taaagattgg      540
ttttcgttaa gtcagggtga gcagcctgtg gaaacatgtg gagtatctca atctgagatg      600
actagttgta gtatatcgtc tagtttctct gatcctgatg gcaatatgat ggccttcaat      660
cctgtgaatt gtgacgttga cactgtttcc aagcaggatg ataagataat cgattccaaa      720
tctatgttga ctccatattt tgacaacgtg actggatacg gagtggggtt gggagccaat      780
cataattcgt ctgccatgtc tgttttttttt aataattcca attccctcag tgacagtgcg      840
gataactatg tctcttctgc acaagattgc tacaatacaa gtggtacatc cttgtcagac      900 catacccca attctgttca gaatttcgcg tttgagttct ttcctaataa agaagaagct      960
gtaaatgatg ttgagagtgg agtaagtgag tctcagtcgg atggtgccag ccggatgatt     1020
tttgatagac atggaagagt ggataatgga tctttagaaa ggaaacctcc tattgatttt     1080
tctagtgcaa gagggatcag tttcaagttt gaaagtaatc cttcagtttc tcctgcctgt     1140
gtcaaaccct acaacagttt tgacagtcat ttagctgata gtgaccttga ccggcctaat     1200
aattattcat gcagttttca ggataataaa actgttcatg tgaaggttaa accagaggct     1260
gaatcagaga aagttgtcta cagttcagtt ccaggggaat ttagtgtcag ggatgatgct     1320
tatctttctg gagaaaccaa tcgttggtgg tctggtgcat caagctctgc agtctcctat     1380
caaacagata ttgaaaaagg atactcatat atggcaccgc aaacagctct acctagccaa     1440
gacagtggca gataagctc caatcatttt tacgattcag atacatgttt gcaatatgtt     1500
gtagaagatc ccagcccagt gacacaaaac aatgagtata agactttca aattcaacaa     1560 ggagaccgga atatattca accgaggggc attgattctc aattctcaaa tgccagcttt     1620
gaatcagttc aaagccattc ttcagaatgt atatccgata gtgatgatga ttctgacgtc     1680
tgcataatag aacctatgg tcaatctgca atcccacatc gacctctagc tatgaaaatg     1740
ccggtagttt cttcagaata ttctacagtt agtcataatt ttaatcaatc tggaggcctg     1800
aagcttcagt caaataaaga aaatatgatc tttcaagctg cattgcagga tctcactcag     1860
cctaattctg aagcaattct gcctgatggt gtcttgacag tcccgcttct gagacatcag     1920
cgaatcgcat tgtcatggat ggcccagaag gagacaagtg gcttccctg ttcgggtgga     1980 attcttgctg atgatcaggg tcttgggaag acagtttcca ctatagctct tatactgaag     2040
gaaaggtcta aacctgccca agcatgtgaa gaaagtacga agaaagaaat ttttgaccta     2100
gaaagcgaga ctgagaatg tgcgccttta aaacccagtg gaagaagcaa gcattttgaa     2160
cactctcaat tgcttttccaa tgaaaacaaa gttggtggag acagtgtggg taaagtgacg     2220
ggaaggccag ctgctggaac gcttgttgta tgtcccacta gtgttatgcg gcagtgggct     2280
gatgaattac ataagaaggt gactagtgaa gcaaatctct ctgttctggt taccatggg      2340 tctagcagaa caaaggatcc tcatgagttg gctaaatatg atgttgttgt taccacattt     2400
tctattgtaa gtatgaagt gccaaagcag cctcttgttg atgatgagga tgaagagaag     2460
gatggtgtac atgatggtgg aactgcagct actggctttt gctcaaacaa gaaaggaaa     2520 tatcctcccg attctaaaaa gaagggttca agaagaaga agttgagtt tctgtctggc     2580 cctcttgcga aagtttcatg gtttagagtt gttctagatg aggcacagag cattaaaaat     2640
tacaaaaccc aagttgcaag agcatgctgg ggccttcgtg ctaaacggag gtggtgttg     2700 tctggcactc caatccagaa ttcaatcgat gaccttaca gctactttcg attcctcaaa     2760
tatgatcctt actcttccta cgtattgttc tgtagcacga ttaagaaccc tataactagg     2820
aacccagtga aaggatatca gaagctgcag gctatcctta aacagtgat gcttcgccga     2880
```

-continued

```
actaaaggtt cacttcttga tgggaaaccc ataatctctt tacctccgaa gtccattgag    2940
ttgagaaaag tggatttcac tgtggaggaa cgtgatttct actccaaact agaggctgaa    3000
tctcgtactc aattcaggga atatgcagaa gctggaacag tgaagcaaaa ttatgtaaat    3060
atcttgttga tgctcttgcg ccttcgccaa gcttgtgatc accctcttct cgtgaatggt    3120
gaatacagtt ttacctggga atcttctgtt ggattagcta agaagcagat tcagtcagac    3180
gcttcattgg caatttgtgg tatctgcaat gatgcacctg aagatgctgt tgcttcagtt    3240
tgcggtcatg ttttctgtaa acagtgcatt tatgaacgcc ttactggtga tagtaatcac    3300
tgtcccttg caaactgcaa tgtcagactc accatctcat cgttatcttc caaaacgaga    3360
ttggacgatg ctatgcctga catgcaggag cgtgctactt cgaatagcct tagcccttgt    3420
tctgatgaag atcttccata tggttcatct aaaatcaagg ctgctctaga gatcttacaa    3480
tcactgccca agcacatga tttgacagat tcaaatcaga tctctgaaaa cagagaatac     3540
tccggtcttt ctataactcc tgtgaagaat gagggtatga cgttgatgt tccgattaag     3600
gtagctggag aaaaagccat tgttttttcc caatggacaa agatgctaaa cctacttgaa    3660
gcttctcttg taagttcaca tattcagtat agaaggctcg atggaacaat gtcagttgct    3720
gctagggata aagcagtgca ggatttcaac actctccctg aggttactgt aatgataatg    3780
tctctcaagg ctgctagtct cggactgaac atggtggcag cttgtcatgt tctgatgctg    3840
gacttatggt ggaacccaac aaccgaggat caagcaatcg atagagcaca tcgtatagga    3900
cagacacgac cagtaacagt agttcgcttc acagtaaaag atacagtcga agatcggata    3960
ttagcccttc agcaaaagaa gagaatgatg gtagcctctg catttggaga agatgaaaag    4020
ggaagccgac agtctcacct cacagtagag gacttgagct atctgtttat ggctgattca    4080
tgagaacgag cttcgtgctc ttttgacca atgcgggcgg gtacatatga tagggttttt     4140
gtgcagtttt aggaggaaga aactcttcgt ttaactgact acaggtttgt gcaaaaaaaa    4200
aaaagattag aaaagacgat tattgggttt ggggtataaa aatagaaagc tgatccgatt    4260
tgattattgg ttacatttag actttaggta ttgacagtta aatggaagat gacaatacat    4320
aggagtgtat ttgcttttga atttctcatt gtaagatcac aatgcgattg gtccagcgag    4380
ttataatagc ttactttcaa gatc                                           4404
```

<210> SEQ ID NO 25
<211> LENGTH: 1280
<212> TYPE: PRT
<213> ORGANISM: Arabidopsis thaliana

<400> SEQUENCE: 25

```
Met Gly Glu Glu Gly Ser Met Phe Gly Leu Gly Gly Glu Phe Pro Val
1               5                   10                  15

Asp Asp Cys Asp Gly Gly Phe Glu Phe Glu Asp Asp Glu Thr Ile
20              25                  30

Asp Ile Glu Thr Leu Tyr Arg Ile Leu Asp Glu Lys Pro Asp Ser Ala
35              40                  45

Glu Gly Ser Gln Glu Asn Leu Ser Pro Val Gly Ser Ser Ala Asp Glu
50              55                  60

Leu Lys Asp Ser Gln Leu Leu Asn Gly Ser Phe Asp Glu His Val Lys
65              70                  75                  80

Met Glu Ala Gly Leu Ser Pro Ser Pro Ala His Thr Cys Ser Ala Ser
85              90                  95
```

```
Leu Lys Asp Trp Phe Ser Leu Ser Gln Gly Glu Gln Pro Val Glu Thr
100                 105                 110

Cys Gly Val Ser Gln Ser Glu Met Thr Ser Cys Ser Ile Ser Ser Ser
115                 120                 125

Phe Ser Asp Pro Asp Gly Asn Met Met Ala Phe Asn Pro Val Asn Cys
130                 135                 140

Asp Val Asp Thr Val Ser Lys Gln Asp Lys Ile Ile Asp Ser Lys
145                 150                 155                 160

Ser Met Leu Thr Pro Tyr Phe Asp Asn Val Thr Gly Tyr Gly Val Gly
165                 170                 175

Leu Gly Ala Asn His Asn Ser Ser Ala Met Ser Val Phe Phe Asn Asn
180                 185                 190

Ser Asn Ser Leu Ser Asp Ser Ala Asp Asn Tyr Val Ser Ser Ala Gln
195                 200                 205

Asp Cys Tyr Asn Thr Ser Gly Thr Ser Leu Ser Asp His Thr Pro Asn
210                 215                 220

Ser Val Gln Asn Phe Ala Phe Glu Phe Phe Pro Asn Lys Glu Glu Ala
225                 230                 235                 240

Val Asn Asp Val Glu Ser Gly Val Ser Glu Ser Gln Ser Asp Gly Ala
245                 250                 255

Ser Arg Met Ile Phe Asp Arg His Gly Arg Val Asp Asn Gly Ser Leu
260                 265                 270

Glu Arg Lys Pro Pro Ile Asp Phe Ser Ser Arg Gly Ile Ser Phe
275                 280                 285

Lys Phe Glu Ser Asn Pro Ser Val Ser Pro Ala Cys Val Lys Pro Tyr
290                 295                 300

Asn Ser Phe Asp Ser His Leu Ala Asp Ser Asp Leu Asp Arg Pro Asn
305                 310                 315                 320

Asn Tyr Ser Cys Ser Phe Gln Asp Asn Lys Thr Val His Val Lys Val
325                 330                 335

Lys Pro Glu Ala Glu Ser Glu Lys Val Val Tyr Ser Ser Val Pro Gly
340                 345                 350

Glu Phe Ser Val Arg Asp Asp Ala Tyr Leu Ser Gly Glu Thr Asn Arg
355                 360                 365

Trp Trp Ser Gly Ala Ser Ser Ala Val Ser Tyr Gln Thr Asp Ile
370                 375                 380

Glu Lys Gly Tyr Ser Tyr Met Ala Pro Gln Thr Ala Leu Pro Ser Gln
385                 390                 395                 400

Asp Ser Gly Lys Ile Ser Ser Asn His Phe Tyr Asp Ser Asp Thr Cys
405                 410                 415

Leu Gln Tyr Val Val Glu Asp Pro Ser Pro Val Thr Gln Asn Asn Glu
420                 425                 430

Tyr Lys Asp Phe Gln Ile Gln Gln Gly Asp Arg Glu Tyr Ile Gln Pro
435                 440                 445

Arg Gly Ile Asp Ser Gln Phe Ser Asn Ala Ser Phe Glu Ser Val Gln
450                 455                 460

Ser His Ser Ser Glu Cys Ile Ser Asp Ser Asp Asp Ser Asp Val
465                 470                 475                 480

Cys Ile Ile Glu Pro Tyr Gly Gln Ser Ala Ile Pro His Arg Pro Leu
485                 490                 495

Ala Met Lys Met Pro Val Val Ser Ser Glu Tyr Ser Thr Val Ser His
500                 505                 510

Asn Phe Asn Gln Ser Gly Gly Leu Lys Leu Gln Ser Asn Lys Glu Asn
```

```
                515                 520                 525
Met Ile Phe Gln Ala Ala Leu Gln Asp Leu Thr Gln Pro Asn Ser Glu
530                 535                 540

Ala Ile Leu Pro Asp Gly Val Leu Thr Val Pro Leu Leu Arg His Gln
545                 550                 555                 560

Arg Ile Ala Leu Ser Trp Met Ala Gln Lys Glu Thr Ser Gly Phe Pro
565                 570                 575

Cys Ser Gly Gly Ile Leu Ala Asp Asp Gln Gly Leu Gly Lys Thr Val
580                 585                 590

Ser Thr Ile Ala Leu Ile Leu Lys Glu Arg Ser Lys Pro Ala Gln Ala
595                 600                 605

Cys Glu Glu Ser Thr Lys Lys Glu Ile Phe Asp Leu Glu Ser Glu Thr
610                 615                 620

Gly Glu Cys Ala Pro Leu Lys Pro Ser Gly Arg Ser Lys His Phe Glu
625                 630                 635                 640

His Ser Gln Leu Leu Ser Asn Glu Asn Lys Val Gly Gly Asp Ser Val
645                 650                 655

Gly Lys Val Thr Gly Arg Pro Ala Ala Gly Thr Leu Val Val Cys Pro
660                 665                 670

Thr Ser Val Met Arg Gln Trp Ala Asp Glu Leu His Lys Lys Val Thr
675                 680                 685

Ser Glu Ala Asn Leu Ser Val Leu Val Tyr His Gly Ser Ser Arg Thr
690                 695                 700

Lys Asp Pro His Glu Leu Ala Lys Tyr Asp Val Val Thr Thr Phe
705                 710                 715                 720

Ser Ile Val Ser Met Glu Val Pro Lys Gln Pro Leu Val Asp Asp Glu
725                 730                 735

Asp Glu Glu Lys Asp Gly Val His Asp Gly Gly Thr Ala Ala Thr Gly
740                 745                 750

Phe Cys Ser Asn Lys Lys Arg Lys Tyr Pro Pro Asp Ser Lys Lys Lys
755                 760                 765

Gly Ser Lys Lys Lys Lys Val Glu Phe Leu Ser Gly Pro Leu Ala Lys
770                 775                 780

Val Ser Trp Phe Arg Val Val Leu Asp Glu Ala Gln Ser Ile Lys Asn
785                 790                 795                 800

Tyr Lys Thr Gln Val Ala Arg Ala Cys Trp Gly Leu Arg Ala Lys Arg
805                 810                 815

Arg Trp Cys Leu Ser Gly Thr Pro Ile Gln Asn Ser Ile Asp Asp Leu
820                 825                 830

Tyr Ser Tyr Phe Arg Phe Leu Lys Tyr Asp Pro Tyr Ser Ser Tyr Val
835                 840                 845

Leu Phe Cys Ser Thr Ile Lys Asn Pro Ile Thr Arg Asn Pro Val Lys
850                 855                 860

Gly Tyr Gln Lys Leu Gln Ala Ile Leu Lys Thr Val Met Leu Arg Arg
865                 870                 875                 880

Thr Lys Gly Ser Leu Leu Asp Gly Lys Pro Ile Ile Ser Leu Pro Pro
885                 890                 895

Lys Ser Ile Glu Leu Arg Lys Val Asp Phe Thr Val Glu Glu Arg Asp
900                 905                 910

Phe Tyr Ser Lys Leu Glu Ala Glu Ser Arg Thr Gln Phe Arg Glu Tyr
915                 920                 925

Ala Glu Ala Gly Thr Val Lys Gln Asn Tyr Val Asn Ile Leu Leu Met
930                 935                 940
```

Leu Leu Arg Leu Arg Gln Ala Cys Asp His Pro Leu Leu Val Asn Gly
945                 950                 955                 960

Glu Tyr Ser Phe Thr Trp Glu Ser Ser Val Gly Leu Ala Lys Lys Gln
965                 970                 975

Ile Gln Ser Asp Ala Ser Leu Ala Ile Cys Gly Ile Cys Asn Asp Ala
980                 985                 990

Pro Glu Asp Ala Val Ala Ser Val Cys Gly His Val Phe Cys Lys Gln
995                 1000                1005

Cys Ile Tyr Glu Arg Leu Thr Gly Asp Ser Asn His Cys Pro Phe
1010                1015                1020

Ala Asn Cys Asn Val Arg Leu Thr Ile Ser Leu Ser Ser Lys
1025                1030                1035

Thr Arg Leu Asp Asp Ala Met Pro Asp Met Gln Glu Arg Ala Thr
1040                1045                1050

Ser Asn Ser Leu Ser Pro Cys Ser Asp Glu Asp Leu Pro Tyr Gly
1055                1060                1065

Ser Ser Lys Ile Lys Ala Ala Leu Glu Ile Leu Gln Ser Leu Pro
1070                1075                1080

Lys Ala His Asp Leu Thr Asp Ser Asn Gln Ile Ser Glu Asn Arg
1085                1090                1095

Glu Tyr Ser Gly Leu Ser Ile Thr Pro Val Lys Asn Glu Gly Met
1100                1105                1110

Ser Val Asp Val Pro Ile Lys Val Ala Gly Glu Lys Ala Ile Val
1115                1120                1125

Phe Ser Gln Trp Thr Lys Met Leu Asn Leu Leu Glu Ala Ser Leu
1130                1135                1140

Val Ser Ser His Ile Gln Tyr Arg Arg Leu Asp Gly Thr Met Ser
1145                1150                1155

Val Ala Ala Arg Asp Lys Ala Val Gln Asp Phe Asn Thr Leu Pro
1160                1165                1170

Glu Val Thr Val Met Ile Met Ser Leu Lys Ala Ala Ser Leu Gly
1175                1180                1185

Leu Asn Met Val Ala Ala Cys His Val Leu Met Leu Asp Leu Trp
1190                1195                1200

Trp Asn Pro Thr Thr Glu Asp Gln Ala Ile Asp Arg Ala His Arg
1205                1210                1215

Ile Gly Gln Thr Arg Pro Val Thr Val Val Arg Phe Thr Val Lys
1220                1225                1230

Asp Thr Val Glu Asp Arg Ile Leu Ala Leu Gln Gln Lys Lys Arg
1235                1240                1245

Met Met Val Ala Ser Ala Phe Gly Glu Asp Glu Lys Gly Ser Arg
1250                1255                1260

Gln Ser His Leu Thr Val Glu Asp Leu Ser Tyr Leu Phe Met Ala
1265                1270                1275

Asp Ser
1280

<210> SEQ ID NO 26
<211> LENGTH: 3147
<212> TYPE: DNA
<213> ORGANISM: Arabidopsis thaliana

<400> SEQUENCE: 26
atgggtgagg aaggttcaat gtttggtctg ggaggtgaat ttccggttga tgattgtgat      60

```
ggtggttttg agtttgaaga tgatgacgag actattgaca tcgaaacgct ttatcggatt    120
ctagatgaga agcctgattc tgctgaggta gtttttctcg cttttgtggg tagccaagaa    180
aacttatcac cagttggttc atctgctgac gagctcaagg attcacagtt gctaaatggt    240
tcatttgatg aacatgtgaa aatggaagcc gggctgagtc cttcacctgc tcatacttgc    300
tctgcaagtc ttaaagattg gttttcgtta agtcagggtg agcagcctgt ggaaacatgt    360
ggagtatctc aatctgagat gactagttgt agtatatcgt ctagtttctc tgatcctgat    420
ggcaatatga tggccttcaa tcctgtgaat tgtgacgttg acactgtttc caagcaggat    480
gataagataa tcgattccaa atctatgttg actccatatt ttgacaacgt gactggatac    540
ggagtggggt tgggagccaa tcataattcg tctgccatgt ctgttttttt taataattcc    600
aattccctca gtgacagtgc ggataactat gtctcttctg cacaagattg ctacaataca    660
agtggtacat ccttgtcaga ccatacccccc aattctgttc agaatttcgc gtttgagttc    720
tttcctaata aagaagaagc tgtaaatgat gttgagagtg gagtaagtga gtctcagtcg    780
gatggtgcca gccggatgat ttttgataga catggaagag tggataatgg atctttagaa    840
aggaaacctc ctattgattt ttctagtgca gagggatca gtttcaagtt tgaaagtaat    900
ccttcagttt ctcctgcctg tgtcaaaccc tacaacagtt ttgacagtca tttagctgat    960
agtgaccttg accggcctaa taattattca tgcagttttc aggataataa aactgttcat    1020
gtgaaggtta accagaggc tgaatcagag aaagttgtct acagttcagt tccagggaa    1080 tttagtgtca gggatgatgc ttatcttcct ggagaaacca atcgttggtg gtctggtgca    1140
tcaagctctg cagtctccta tcaaacagat attgaaaaag gatactcata tatggcaccg    1200
caaacagctc tacctagcca agacagtggc aagataagct ccaatcattt ttacgattca    1260
gatacatgtt tgcaatatgt tgtagaagat cccagcccag tgacacaaaa caatgagtat    1320
aaagactttc aaattcaaca aggagaccgg gaatatattc aaccgagggg cattgattct    1380
caattctcaa atgccagctt tgaatcagtt caaagccatt cttcagaatg tatatccgat    1440
agtgatgatg attctgacgt ctgcataata gaaccttatg gtcaatctgc aatcccacat    1500
cgacctctag ctatgaaaat gccggtagtt tcttcagaat attctacagt tagtcataat    1560
tttaatcaat ctggaggcct gaagcttcag tcaaataaag aaaatatgat ctttcaagct    1620
gcattgcagg atctcactca gcctaattct gaagcaattc tgcctgatgg tgtcttgaca    1680
gtcccgcttc tgagacatca gcgaatcgca ttgtcatgga tggcccagaa ggagacaagt    1740 ggcttccccct gttcgggtgg aattcttgct gatgatcagg gtcttgggaa gacagtttcc    1800
actatagctc ttatactgaa ggaaaggtct aaacctgccc aagcatgtga agaaagtacg    1860
aagaaagaaa tttttgacct agaaagcgag actggagaat gtgcgccttt aaaacccagt    1920
ggaagaagca agcattttga acactctcaa ttgctttcca atgaaaacaa agttggtgga    1980
gacagtgtgg gtaaagtgac gggaaggcca gctgctggaa cgcttgttgt atgtcccact    2040
agtgttatgc ggcagtgggc tgatgaatta cataagaagg tgactagtga agcaaatctc    2100
tctgttctgg tataccatgg gtctagcaga acaaaggatc ctcatgagtt ggctaaaatat    2160 gatgttgttg ttaccacatt ttctattgta agtatggaag tgccaaagca gcctcttgtt    2220
gatgatgagg atgaagagaa ggatggtgta catgatggtg gaactgcagc tactggcttt    2280
tgctcaaaca agaaaaggaa atatcctccc gattctaaaa agaagggttc aaagaagaag    2340
aaagttgagt ttctgtctgg ccctcttgcg aaagtttcat ggtttagagt tgttctagat    2400
```

-continued

```
gaggcacaga gcattaaaaa ttacaaaacc caagttgcaa gagcatgctg gggccttcgt    2460
gctaaacgga ggtggtgttt gtctggcact ccaatccaga attcaatcga tgacctttac    2520
agctactttc gattcctcaa atatgatcct tactcttcct acgtattgtt ctgtagcacg    2580
attaagaacc ctataactag gaacccagtg aaaggatatc agaagctgca ggctatcctt    2640
aaaacagtga tgcttcgccg aactaaaggt tcacttcttg atgggaaacc cataatctct    2700
ttacctccga agtccattga gttgagaaaa gtggatttca ctgtggagga acgtgatttc    2760
tactccaaac tagaggctga atctcgtact caattcaggg aatatgcaga agctggaaca    2820
gtgaagcaaa attatgtaaa tatcttgttg atgctcttgc gccttcgcca agcttgtgat    2880
caccctcttc tcgtgaatgg tgaatacagt tttacctggg aatcttctgt tggattagct    2940
aagaagcaga ttcagtcaga cgcttcattg gcaatttgtg gtatctgcaa tgtaagattc    3000
ttttgtctcg taaattatta tacaacatgt ttttttttt ccctgatgaa cgtgagaggg    3060
cagttctaaa acattaaaaa agtcaagaca tggaattgaa agcatcagtg gatattaaca    3120
atcatattaa gcaatggttt ttactct                                         3147
```

<210> SEQ ID NO 27
<211> LENGTH: 1022
<212> TYPE: PRT
<213> ORGANISM: Arabidopsis thaliana

<400> SEQUENCE: 27

```
Met Gly Glu Glu Gly Ser Met Phe Gly Leu Gly Gly Glu Phe Pro Val
1               5                  10                  15

Asp Asp Cys Asp Gly Gly Phe Glu Phe Glu Asp Asp Asp Glu Thr Ile
            20                  25                  30

Asp Ile Glu Thr Leu Tyr Arg Ile Leu Asp Glu Lys Pro Asp Ser Ala
        35                  40                  45

Glu Val Val Phe Ser Ala Phe Val Gly Ser Gln Glu Asn Leu Ser Pro
    50                  55                  60

Val Gly Ser Ser Ala Asp Glu Leu Lys Asp Ser Gln Leu Leu Asn Gly
65                  70                  75                  80

Ser Phe Asp Glu His Val Lys Met Glu Ala Gly Leu Ser Pro Ser Pro
                85                  90                  95

Ala His Thr Cys Ser Ala Ser Leu Lys Asp Trp Phe Ser Leu Ser Gln
            100                 105                 110

Gly Glu Gln Pro Val Glu Thr Cys Gly Val Ser Gln Ser Glu Met Thr
        115                 120                 125

Ser Cys Ser Ile Ser Ser Ser Phe Ser Asp Pro Asp Gly Asn Met Met
    130                 135                 140

Ala Phe Asn Pro Val Asn Cys Asp Val Asp Thr Val Ser Lys Gln Asp
145                 150                 155                 160

Asp Lys Ile Ile Asp Ser Lys Ser Met Leu Thr Pro Tyr Phe Asp Asn
                165                 170                 175

Val Thr Gly Tyr Gly Val Gly Leu Gly Ala Asn His Asn Ser Ser Ala
            180                 185                 190

Met Ser Val Phe Phe Asn Asn Ser Asn Ser Leu Ser Asp Ser Ala Asp
        195                 200                 205

Asn Tyr Val Ser Ser Ala Gln Asp Cys Tyr Asn Thr Ser Gly Thr Ser
    210                 215                 220

Leu Ser Asp His Thr Pro Asn Ser Val Gln Asn Phe Ala Phe Glu Phe
225                 230                 235                 240
```

```
Phe Pro Asn Lys Glu Glu Ala Val Asn Asp Val Ser Gly Val Ser
245                 250                 255

Glu Ser Gln Ser Asp Gly Ala Ser Arg Met Ile Phe Asp Arg His Gly
260                 265                 270

Arg Val Asp Asn Gly Ser Leu Glu Arg Lys Pro Pro Ile Asp Phe Ser
275                 280                 285

Ser Ala Arg Gly Ile Ser Phe Lys Phe Glu Ser Asn Pro Ser Val Ser
290                 295                 300

Pro Ala Cys Val Lys Pro Tyr Asn Ser Phe Ser His Leu Ala Asp
305                 310                 315                 320

Ser Asp Leu Asp Arg Pro Asn Asn Tyr Ser Cys Ser Phe Gln Asp Asn
325                 330                 335

Lys Thr Val His Val Lys Val Lys Pro Glu Ala Glu Ser Glu Lys Val
340                 345                 350

Val Tyr Ser Ser Val Pro Gly Glu Phe Ser Val Arg Asp Asp Ala Tyr
355                 360                 365

Leu Ser Gly Glu Thr Asn Arg Trp Trp Ser Gly Ala Ser Ser Ser Ala
370                 375                 380

Val Ser Tyr Gln Thr Asp Ile Glu Lys Gly Tyr Ser Tyr Met Ala Pro
385                 390                 395                 400

Gln Thr Ala Leu Pro Ser Gln Asp Ser Gly Lys Ile Ser Ser Asn His
405                 410                 415

Phe Tyr Asp Ser Asp Thr Cys Leu Gln Tyr Val Glu Asp Pro Ser
420                 425                 430

Pro Val Thr Gln Asn Asn Glu Tyr Lys Asp Phe Gln Ile Gln Gln Gly
435                 440                 445

Asp Arg Glu Tyr Ile Gln Pro Arg Gly Ile Asp Ser Gln Phe Ser Asn
450                 455                 460

Ala Ser Phe Glu Ser Val Gln Ser His Ser Ser Glu Cys Ile Ser Asp
465                 470                 475                 480

Ser Asp Asp Asp Ser Asp Val Cys Ile Ile Glu Pro Tyr Gly Gln Ser
485                 490                 495

Ala Ile Pro His Arg Pro Leu Ala Met Lys Met Pro Val Val Ser Ser
500                 505                 510

Glu Tyr Ser Thr Val Ser His Asn Phe Asn Gln Ser Gly Gly Leu Lys
515                 520                 525

Leu Gln Ser Asn Lys Glu Asn Met Ile Phe Gln Ala Ala Leu Gln Asp
530                 535                 540

Leu Thr Gln Pro Asn Ser Glu Ala Ile Leu Pro Asp Gly Val Leu Thr
545                 550                 555                 560

Val Pro Leu Leu Arg His Gln Arg Ile Ala Leu Ser Trp Met Ala Gln
565                 570                 575

Lys Glu Thr Ser Gly Phe Pro Cys Ser Gly Gly Ile Leu Ala Asp Asp
580                 585                 590

Gln Gly Leu Gly Lys Thr Val Ser Thr Ile Ala Leu Ile Leu Lys Glu
595                 600                 605

Arg Ser Lys Pro Ala Gln Ala Cys Glu Glu Ser Thr Lys Lys Glu Ile
610                 615                 620

Phe Asp Leu Glu Ser Glu Thr Gly Glu Cys Ala Pro Leu Lys Pro Ser
625                 630                 635                 640

Gly Arg Ser Lys His Phe Glu His Ser Gln Leu Leu Ser Asn Glu Asn
645                 650                 655

Lys Val Gly Gly Asp Ser Val Gly Lys Val Thr Gly Arg Pro Ala Ala
```

```
                     660                665                670
Gly Thr Leu Val Val Cys Pro Thr Ser Val Met Arg Gln Trp Ala Asp
675                 680                685

Glu Leu His Lys Lys Val Thr Ser Glu Ala Asn Leu Ser Val Leu Val
690                 695                700

Tyr His Gly Ser Ser Arg Thr Lys Asp Pro His Glu Leu Ala Lys Tyr
705                 710                715                720

Asp Val Val Thr Thr Phe Ser Ile Val Ser Met Glu Val Pro Lys
725                 730                735

Gln Pro Leu Val Asp Asp Glu Asp Glu Lys Asp Gly Val His Asp
740                 745                750

Gly Gly Thr Ala Ala Thr Gly Phe Cys Ser Asn Lys Lys Arg Lys Tyr
755                 760                765

Pro Pro Asp Ser Lys Lys Lys Gly Ser Lys Lys Lys Val Glu Phe
770                 775                780

Leu Ser Gly Pro Leu Ala Lys Val Ser Trp Phe Arg Val Val Leu Asp
785                 790                795                800

Glu Ala Gln Ser Ile Lys Asn Tyr Lys Thr Gln Val Ala Arg Ala Cys
805                 810                815

Trp Gly Leu Arg Ala Lys Arg Arg Trp Cys Leu Ser Gly Thr Pro Ile
820                 825                830

Gln Asn Ser Ile Asp Asp Leu Tyr Ser Tyr Phe Arg Phe Leu Lys Tyr
835                 840                845

Asp Pro Tyr Ser Ser Tyr Val Leu Phe Cys Ser Thr Ile Lys Asn Pro
850                 855                860

Ile Thr Arg Asn Pro Val Lys Gly Tyr Gln Lys Leu Gln Ala Ile Leu
865                 870                875                880

Lys Thr Val Met Leu Arg Arg Thr Lys Gly Ser Leu Leu Asp Gly Lys
885                 890                895

Pro Ile Ile Ser Leu Pro Pro Lys Ser Ile Glu Leu Arg Lys Val Asp
900                 905                910

Phe Thr Val Glu Glu Arg Asp Phe Tyr Ser Lys Leu Glu Ala Glu Ser
915                 920                925

Arg Thr Gln Phe Arg Glu Tyr Ala Glu Ala Gly Thr Val Lys Gln Asn
930                 935                940

Tyr Val Asn Ile Leu Leu Met Leu Leu Arg Leu Arg Gln Ala Cys Asp
945                 950                955                960

His Pro Leu Leu Val Asn Gly Glu Tyr Ser Phe Thr Trp Glu Ser Ser
965                 970                975

Val Gly Leu Ala Lys Lys Gln Ile Gln Ser Asp Ala Ser Leu Ala Ile
980                 985                990

Cys Gly Ile Cys Asn Val Arg Phe  Cys Leu Val Asn  Tyr Tyr Thr
995                 1000                1005

Thr Cys Phe Phe Phe Ser Leu  Met Asn Val Arg Gly  Gln Phe
1010                1015                1020

<210> SEQ ID NO 28
<211> LENGTH: 4431
<212> TYPE: DNA
<213> ORGANISM: Arabidopsis thaliana

<400> SEQUENCE: 28
ctctatccca actgctctct acctttcctc gaaaattcct tcaaaaccca attctcaagc      60
cttcttcttc gtcgtacctg aaaattctac aatctctgga tctacgcgtc tacttctgaa     120
```

```
tttcgatttg ggtttcccgg gagctgaaat tccgtgactt ttgggttttc tgatttaggg      180
tttgttcctc ttctcgttct ttctcgggtt agttttttt ttttttttt gtgattttg        240
atgggtgagg aaggttcaat gtttggtctg ggaggtgaat ttccggttga tgattgtgat     300
ggtggttttg agtttgaaga tgatgacgag actattgaca tcgaaacgct ttatcggatt     360
ctagatgaga agcctgattc tgctgagggt agccaagaaa acttatcacc agttggttca     420
tctgctgacg agctcaagga ttcacagttg ctaaatggtt catttgatga acatgtgaaa     480
atggaagccg ggctgagtcc ttcacctgct catacttgct ctgcaagtct taaagattgg     540
ttttcgttaa gtcagggtga gcagcctgtg aaacatgtg gagtatctca atctgagatg      600
actagttgta gtatatcgtc tagtttctct gatcctgatg caatatgat ggccttcaat      660
cctgtgaatt gtgacgttga cactgtttcc aagcaggatg ataagataat cgattccaaa    720
tgtatgcacc ttatctacta aatgtcagct atgttgactc catattttga caacgtgact     780
ggatacggag tggggttggg agccaatcat aattcgtctg ccatgtctgt ttttttaat    840
aattccaatt ccctcagtga cagtgcggat aactatgtct cttctgcaca agattgctac     900
aatacaagtg gtacatcctt gtcagaccat accccaatt ctgttcagaa tttcgcgtt      960
gagttctttc ctaataaaga agaagctgta atgatgttg agagtggagt aagtgagtct      1020
cagtcggatg gtgccagccg gatgattttt gatagacatg gaagagtgga taatggatct    1080
ttagaaagga aacctcctat tgatttttct agtgcaagag ggatcagtt caagtttgaa     1140
agtaatcctt cagtttctcc tgcctgtgtc aaaccctaca acagttttga cagtcattta    1200
gctgatagtg accttgaccg gcctaataat tattcatgca gttttcagga taataaaact    1260
gttcatgtga aggttaaacc agaggctgaa tcagagaaag ttgtctacag ttcagttcca    1320
ggggaattta gtgtcaggga tgatgcttat ctttctggag aaaccaatcg ttggtggtct    1380
ggtgcatcaa gctctgcagt ctcctatcaa acagatattg aaaaaggata ctcatatatg   1440
gcaccgcaaa cagctctacc tagccaagac agtggcaaga taagctccaa tcattttta    1500
gattcagata catgtttgca atatgttgta gaagatccca gcccagtgac acaaaacaat    1560
gagtataaag actttcaaat tcaacaagga gaccgggaat atattcaacc gagggcatt    1620
gattctcaat tctcaaatgc cagctttgaa tcagttcaaa gccattcttc agaatgtata    1680
tccgatagtg atgatgattc tgacgtctgc ataatagaac cttatggtca atctgcaatc    1740
ccacatcgac ctctagctat gaaaatgccg gtagtttctt cagaatattc tacagttagt    1800
cataatttta atcaatctgg aggcctgaag cttcagtcaa ataaagaaaa tatgatctttt  1860
caagctgcat tgcaggatct cactcagcct aattctgaag caattctgcc tgatggtgtc    1920
ttgacagtcc cgcttctgag acatcagcga atcgcattgt catggatggc cagaaggag    1980
acaagtggct tcccctgttc gggtggaatt cttgctgatg atcagggtct tgggaagaca    2040
gtttccacta tagctcttat actgaaggaa aggtctaaac ctgcccaagc atgtgaagaa    2100
agtacgaaga aagaaatttt tgacctagaa agcgagactg gagaatgtgc gcctttaaaa    2160
cccagtggaa gaagcaagca ttttgaacac tctcaattgc tttccaatga aaacaaagtt    2220
ggtggagaca gtgtgggtaa agtgacggga aggccagctg ctggaacgct tgttgtatgt    2280
cccactagtg ttatgcggca gtgggctgat gaattacata agaaggtgac tagtgaagca    2340
aatctctctg ttctggtata ccatgggtct agcagaacaa aggatcctca tgagttggct    2400
aaatatgatg ttgttgttac cacatttttct attgtaagta tggaagtgcc aaagcagcct    2460
```

```
cttgttgatg atgaggatga agagaaggat ggtgtacatg atggtggaac tgcagctact    2520
ggcttttgct caaacaagaa aaggaaatat cctcccgatt ctaaaaagaa gggttcaaag    2580
aagaagaaag ttgagtttct gtctggccct cttgcgaaag tttcatggtt tagagttgtt    2640
ctagatgagg cacagagcat taaaaattac aaaacccaag ttgcaagagc atgctggggc    2700
cttcgtgcta acggaggtg gtgtttgtct ggcactccaa tccagaattc aatcgatgac    2760
ctttacagct actttcgatt cctcaaatat gatccttact cttcctacgt attgttctgt    2820
agcacgatta agaaccctat aactaggaac ccagtgaaag gatatcagaa gctgcaggct    2880
atccttaaaa cagtgatgct tcgccgaact aaaggttcac ttcttgatgg gaaacccata    2940
atctctttac ctccgaagtc cattgagttg agaaaagtgg atttcactgt ggaggaacgt    3000
gatttctact ccaaactaga ggctgaatct cgtactcaat tcagggaata tgcagaagct    3060
ggaacagtga agcaaaatta tgtaaatatc ttgttgatgc tcttgcgcct tcgccaagct    3120
tgtgatcacc ctcttctcgt gaatggtgaa tacagttttta cctgggaatc ttctgttgga    3180
ttagctaaga agcagattca gtcagacgct tcattggcaa tttgtggtat ctgcaatgat    3240
gcacctgaag atgctgttgc ttcagtttgc ggtcatgttt tctgtaaaca gtgcatttat    3300
gaacgcctta ctggtgatag taatcactgt ccctttgcaa actgcaatgt cagactcacc    3360
atctcatcgt tatcttccaa aacgagattg acgatgcta tgcctgacat gcaggagcgt    3420
gctacttcga atagccttag cccttgttct gatgaagatc ttccatatgg ttcatctaaa    3480
atcaaggctg ctctagagat cttacaatca ctgcccaaag cacatgattt gacagattca    3540
aatcagatct ctgaaaacag agaatactcc ggtctttcta taactcctgt gaagaatgag    3600
ggtatgagcg ttgatgttcc gattaaggta gctggagaaa aagccattgt tttttcccaa    3660
tggacaaaga tgctaaacct acttgaagct tctcttgtaa gttcacatat tcagtataga    3720
aggctcgatg gaacaatgtc agttgctgct agggataaag cagtgcagga tttcaacact    3780
ctccctgagg ttactgtaat gataatgtct ctcaaggctg ctagtctcgg actgaacatg    3840
gtggcagctt gtcatgttct gatgctggac ttatggtgga acccaacaac cgaggatcaa    3900
gcaatcgata gagcacatcg tataggacag acacgaccag taacagtagt tcgcttcaca    3960
gtaaaagata cagtcgaaga tcggatatta gcccttcagc aaaagaagag aatgatggta    4020
gcctctgcat ttggagaaga tgaaaaggga agccgacagt ctcacctcac agtagaggac    4080
ttgagctatc tgtttatggc tgattcatga gaacgagctt cgtgctcttt ttgaccaatg    4140
cgggcgggta catatgatag ggttttttgtg cagttttagg aggaagaaac tcttcgttta    4200
actgactaca ggtttgtgca aaaaaaaaaa agattagaaa agacgattat tgggtttggg    4260
gtataaaaat agaaagctga tccgatttga ttattggtta catttagact ttaggtattg    4320
acagttaaat ggaagatgac aatacatagg agtgtatttg cttttgaatt tctcattgta    4380
agatcacaat gcgattggtc cagcgagtta taatagctta ctttcaagat c              4431
```

<210> SEQ ID NO 29
<211> LENGTH: 1122
<212> TYPE: PRT
<213> ORGANISM: Arabidopsis thaliana

<400> SEQUENCE: 29

```
Met Ser Ala Met Leu Thr Pro Tyr Phe Asp Asn Val Thr Gly Tyr Gly
1               5                   10                  15

Val Gly Leu Gly Ala Asn His Asn Ser Ser Ala Met Ser Val Phe Phe
            20                  25                  30
```

```
Asn Asn Ser Asn Ser Leu Ser Asp Ser Ala Asp Asn Tyr Val Ser Ser
 35                  40                  45

Ala Gln Asp Cys Tyr Asn Thr Ser Gly Thr Ser Leu Ser Asp His Thr
 50                  55                  60

Pro Asn Ser Val Gln Asn Phe Ala Phe Glu Phe Phe Pro Asn Lys Glu
 65                  70                  75                  80

Glu Ala Val Asn Asp Val Glu Ser Gly Val Ser Glu Ser Gln Ser Asp
 85                  90                  95

Gly Ala Ser Arg Met Ile Phe Asp Arg His Gly Arg Val Asp Asn Gly
100                 105                 110

Ser Leu Glu Arg Lys Pro Pro Ile Asp Phe Ser Ala Arg Gly Ile
115                 120                 125

Ser Phe Lys Phe Glu Ser Asn Pro Ser Val Ser Pro Ala Cys Val Lys
130                 135                 140

Pro Tyr Asn Ser Phe Asp Ser His Leu Ala Asp Ser Asp Leu Asp Arg
145                 150                 155                 160

Pro Asn Asn Tyr Ser Cys Ser Phe Gln Asp Asn Lys Thr Val His Val
165                 170                 175

Lys Val Lys Pro Glu Ala Glu Ser Glu Lys Val Val Tyr Ser Ser Val
180                 185                 190

Pro Gly Glu Phe Ser Val Arg Asp Asp Ala Tyr Leu Ser Gly Glu Thr
195                 200                 205

Asn Arg Trp Trp Ser Gly Ala Ser Ser Ala Val Ser Tyr Gln Thr
210                 215                 220

Asp Ile Glu Lys Gly Tyr Ser Tyr Met Ala Pro Gln Thr Ala Leu Pro
225                 230                 235                 240

Ser Gln Asp Ser Gly Lys Ile Ser Ser Asn His Phe Tyr Asp Ser Asp
245                 250                 255

Thr Cys Leu Gln Tyr Val Val Glu Asp Pro Ser Pro Val Thr Gln Asn
260                 265                 270

Asn Glu Tyr Lys Asp Phe Gln Ile Gln Gln Gly Asp Arg Glu Tyr Ile
275                 280                 285

Gln Pro Arg Gly Ile Asp Ser Gln Phe Ser Asn Ala Ser Phe Glu Ser
290                 295                 300

Val Gln Ser His Ser Ser Glu Cys Ile Ser Asp Ser Asp Asp Ser
305                 310                 315                 320

Asp Val Cys Ile Ile Glu Pro Tyr Gly Gln Ser Ala Ile Pro His Arg
325                 330                 335

Pro Leu Ala Met Lys Met Pro Val Val Ser Ser Glu Tyr Ser Thr Val
340                 345                 350

Ser His Asn Phe Asn Gln Ser Gly Gly Leu Lys Leu Gln Ser Asn Lys
355                 360                 365

Glu Asn Met Ile Phe Gln Ala Ala Leu Gln Asp Leu Thr Gln Pro Asn
370                 375                 380

Ser Glu Ala Ile Leu Pro Asp Gly Val Leu Thr Val Pro Leu Leu Arg
385                 390                 395                 400

His Gln Arg Ile Ala Leu Ser Trp Met Ala Gln Lys Glu Thr Ser Gly
405                 410                 415

Phe Pro Cys Ser Gly Gly Ile Leu Ala Asp Asp Gln Gly Leu Gly Lys
420                 425                 430

Thr Val Ser Thr Ile Ala Leu Ile Leu Lys Glu Arg Ser Lys Pro Ala
435                 440                 445
```

```
Gln Ala Cys Glu Glu Ser Thr Lys Lys Glu Ile Phe Asp Leu Glu Ser
450                 455                 460

Glu Thr Gly Glu Cys Ala Pro Leu Lys Pro Ser Gly Arg Ser Lys His
465                 470                 475                 480

Phe Glu His Ser Gln Leu Leu Ser Asn Glu Asn Lys Val Gly Gly Asp
485                 490                 495

Ser Val Gly Lys Val Thr Gly Arg Pro Ala Ala Gly Thr Leu Val Val
500                 505                 510

Cys Pro Thr Ser Val Met Arg Gln Trp Ala Asp Glu Leu His Lys Lys
515                 520                 525

Val Thr Ser Glu Ala Asn Leu Ser Val Leu Val Tyr His Gly Ser Ser
530                 535                 540

Arg Thr Lys Asp Pro His Glu Leu Ala Lys Tyr Asp Val Val Val Thr
545                 550                 555                 560

Thr Phe Ser Ile Val Ser Met Glu Val Pro Lys Gln Pro Leu Val Asp
565                 570                 575

Asp Glu Asp Glu Glu Lys Asp Gly Val His Asp Gly Gly Thr Ala Ala
580                 585                 590

Thr Gly Phe Cys Ser Asn Lys Lys Arg Lys Tyr Pro Pro Asp Ser Lys
595                 600                 605

Lys Lys Gly Ser Lys Lys Lys Val Glu Phe Leu Ser Gly Pro Leu
610                 615                 620

Ala Lys Val Ser Trp Phe Arg Val Val Leu Asp Glu Ala Gln Ser Ile
625                 630                 635                 640

Lys Asn Tyr Lys Thr Gln Val Ala Arg Ala Cys Trp Gly Leu Arg Ala
645                 650                 655

Lys Arg Arg Trp Cys Leu Ser Gly Thr Pro Ile Gln Asn Ser Ile Asp
660                 665                 670

Asp Leu Tyr Ser Tyr Phe Arg Phe Leu Lys Tyr Asp Pro Tyr Ser Ser
675                 680                 685

Tyr Val Leu Phe Cys Ser Thr Ile Lys Asn Pro Ile Thr Arg Asn Pro
690                 695                 700

Val Lys Gly Tyr Gln Lys Leu Gln Ala Ile Leu Lys Thr Val Met Leu
705                 710                 715                 720

Arg Arg Thr Lys Gly Ser Leu Leu Asp Gly Lys Pro Ile Ile Ser Leu
725                 730                 735

Pro Pro Lys Ser Ile Glu Leu Arg Lys Val Asp Phe Thr Val Glu Glu
740                 745                 750

Arg Asp Phe Tyr Ser Lys Leu Glu Ala Glu Ser Arg Thr Gln Phe Arg
755                 760                 765

Glu Tyr Ala Glu Ala Gly Thr Val Lys Gln Asn Tyr Val Asn Ile Leu
770                 775                 780

Leu Met Leu Leu Arg Leu Arg Gln Ala Cys Asp His Pro Leu Leu Val
785                 790                 795                 800

Asn Gly Glu Tyr Ser Phe Thr Trp Glu Ser Ser Val Gly Leu Ala Lys
805                 810                 815

Lys Gln Ile Gln Ser Asp Ala Ser Leu Ala Ile Cys Gly Ile Cys Asn
820                 825                 830

Asp Ala Pro Glu Asp Ala Val Ala Ser Val Cys Gly His Val Phe Cys
835                 840                 845

Lys Gln Cys Ile Tyr Glu Arg Leu Thr Gly Asp Ser Asn His Cys Pro
850                 855                 860

Phe Ala Asn Cys Asn Val Arg Leu Thr Ile Ser Ser Leu Ser Ser Lys
```

```
                865                 870                 875                 880
Thr Arg Leu Asp Asp Ala Met Pro Asp Met Gln Glu Arg Ala Thr Ser
885                 890                 895

Asn Ser Leu Ser Pro Cys Ser Asp Glu Asp Leu Pro Tyr Gly Ser Ser
900                 905                 910

Lys Ile Lys Ala Ala Leu Glu Ile Leu Gln Ser Leu Pro Lys Ala His
915                 920                 925

Asp Leu Thr Asp Ser Asn Gln Ile Ser Glu Asn Arg Glu Tyr Ser Gly
930                 935                 940

Leu Ser Ile Thr Pro Val Lys Asn Glu Gly Met Ser Val Asp Val Pro
945                 950                 955                 960

Ile Lys Val Ala Gly Glu Lys Ala Ile Val Phe Ser Gln Trp Thr Lys
965                 970                 975

Met Leu Asn Leu Leu Glu Ala Ser Leu Val Ser Ser His Ile Gln Tyr
980                 985                 990

Arg Arg Leu Asp Gly Thr Met Ser  Val Ala Ala Arg Asp  Lys Ala Val
995                 1000                1005

Gln Asp  Phe Asn Thr Leu Pro  Glu Val Thr Val Met  Ile Met Ser
1010                1015                1020

Leu Lys  Ala Ala Ser Leu Gly  Leu Asn Met Val Ala  Ala Cys His
1025                1030                1035

Val Leu  Met Leu Asp Leu Trp  Trp Asn Pro Thr Thr  Glu Asp Gln
1040                1045                1050

Ala Ile  Asp Arg Ala His Arg  Ile Gly Gln Thr Arg  Pro Val Thr
1055                1060                1065

Val Val  Arg Phe Thr Val Lys  Asp Thr Val Glu Asp  Arg Ile Leu
1070                1075                1080

Ala Leu  Gln Gln Lys Lys Arg  Met Met Val Ala Ser  Ala Phe Gly
1085                1090                1095

Glu Asp  Glu Lys Gly Ser Arg  Gln Ser His Leu Thr  Val Glu Asp
1100                1105                1110

Leu Ser  Tyr Leu Phe Met Ala  Asp Ser
1115                1120

<210> SEQ ID NO 30
<211> LENGTH: 1228
<212> TYPE: PRT
<213> ORGANISM: Oryza sativa

<400> SEQUENCE: 30

Met Glu Glu Ala Ala Ala Ala Ala Asp Phe Asp Gly Gly Phe Gly
1               5                   10                  15

Gly Ala Gly Glu Asp Asn Leu Ser Met Pro Leu Gly Asp Phe Met Ala
20                  25                  30

Phe Leu Asp Asn Glu Asp Trp Lys Glu Gln His Glu Gly Asn Gln
35                  40                  45

Gly Leu Glu Met Pro Val Asp Ser Thr Ser Glu Asn Ala Phe Gln
50                  55                  60

Asn His Glu Glu Ile Phe Glu Asn Lys Glu Asn Trp Ser Asn Tyr Ser
65                  70                  75                  80

His Thr Asp Pro Ser His Ser Gln Met Asp Val Met Val Glu Leu Asn
85                  90                  95

Asn Gly Gly Glu Ser Phe Asp His Ser Glu Asp Thr Ser Tyr Arg Leu
100                 105                 110
```

```
Leu Ser Asn Asp Phe Leu Glu Asn Ser Arg Asn Gly Asn Pro Glu Met
115                 120                 125

His Leu Pro Met Asp Ala Leu Asn His Ala Lys Thr Val Asp Glu Glu
130                 135                 140

Ile Val Pro Pro Tyr Glu Asp Tyr Thr Asn Gly Leu Tyr Tyr Asp Ser
145                 150                 155                 160

Gly Cys Asp Met Phe Ala Glu Gln Ser Gly Leu Ser Glu Val Lys Cys
165                 170                 175

Glu Gly Thr Gly Pro Met Leu Gly Asn Ser Gln Glu Gly Asn His
180                 185                 190

Phe Thr Ser Val Pro Met Phe Asp His Ser Ala Val Ile Pro Asp Ile
195                 200                 205

Pro Tyr Thr Glu Leu Asn Ile Gly Asp Val Pro Gly Ser Met Gln Asn
210                 215                 220

Gly Asn Gly Ser Cys Leu Thr Val Gln Gly Glu Tyr Leu Gln Gly Glu
225                 230                 235                 240

Tyr Gln Glu Tyr Pro Gln Pro Asp Tyr Gly Ser Phe Asp Met Ala Asn
245                 250                 255

Glu Ile Val Leu His Asp Leu Pro Gln Asn Asn Gln Ser Tyr Glu Leu
260                 265                 270

Glu Gln Leu Pro Gln Asn Ile Cys Glu Ser Ser Ser Met Gln Val Gly
275                 280                 285

Ser Pro Asp Gln Tyr Cys Asp Asp Thr Ser Leu Ser Asp Tyr Tyr Met
290                 295                 300

Asp Asp Val Ser Ser Ile Glu Ser Met Ser Ser Glu Gln Asn Arg Ser
305                 310                 315                 320

Glu Asp Ile Cys Phe Arg Ser Glu Ser Ser Thr Asp Ser Ser Pro Val
325                 330                 335

Pro Ser Ser Arg Asn Ser Thr Thr Glu Asp Ala Asp Lys Tyr Phe Gly
340                 345                 350

Asp Ala Pro Lys His Leu Gln Asn Ser Met Phe Pro Val Ser Thr Gln
355                 360                 365

His Gln His Ser Phe Met Asn Ser Ser Asp Pro Met His Pro Thr Phe
370                 375                 380

His Lys Lys Tyr Asp Ile Pro Arg Asn Gly Ser Ser Ile Leu Gly
385                 390                 395                 400

Asn Ser Ser Arg Asn Cys Phe Ser Leu Asp Ser Asn Arg Asp Ser Asp
405                 410                 415

Leu Cys Ile Leu Glu Gly Ser Arg Ser Leu Ala Ser Gly His Val Leu
420                 425                 430

Pro Pro Gln Gly Leu Gln His Asn Phe Gln Gln Ser Val Cys Ala Asn
435                 440                 445

Pro Asn Leu Pro Arg Phe Gly Gly Arg Tyr Arg Pro His Glu Glu Arg
450                 455                 460

Met Thr Leu Arg Leu Ala Leu Gln Asp Ile Ser Gln Pro Lys Ser Glu
465                 470                 475                 480

Ala Asn Pro Pro Asp Gly Val Leu Ala Val Pro Leu Leu Arg His Gln
485                 490                 495

Lys Ile Ala Leu Ser Trp Met Val Gln Lys Glu Arg Asn Gly Ser Ser
500                 505                 510

Cys Ser Gly Gly Ile Leu Ala Asp Asp Gln Gly Leu Gly Lys Thr Val
515                 520                 525

Ser Thr Ile Ser Leu Ile Leu Thr Glu Arg Ser Pro Val Pro Ser Ser
```

```
                    530              535              540
Ala Val Lys Gln Glu Pro Cys Glu Ala Val Thr Leu Asp Asp Asp
545                      550              555              560

Glu Asp Asp Ala Glu Pro His Leu Lys Lys Pro Ala Leu Ala His
565                      570              575

Leu Ala Asp Thr Cys Lys Pro Glu Ala Thr Ser Ser Thr Ile Lys Thr
580                      585              590

Glu Asn Pro Ile Ala Asn Val Lys Ala Arg Pro Ala Ala Gly Thr Leu
595                      600              605

Val Val Cys Pro Thr Ser Val Leu Arg Gln Trp Ala Asp Glu Leu Arg
610                      615              620

Asn Lys Val Thr Ser Lys Ala Asn Leu Thr Phe Leu Val Tyr His Gly
625                      630              635              640

Ser Asn Arg Thr Lys Asp Pro Asn Asp Leu Thr Lys Tyr Asp Val Val
645                      650              655

Leu Thr Thr Tyr Ser Ile Val Ser Met Glu Val Pro Lys Gln Ser Ser
660                      665              670

Pro Asp Ser Asp Asp Glu Glu Lys Gly Lys Pro Asp Arg Tyr Gly Ala
675                      680              685

Pro Val Gly Ser Ser Gly Ser Lys Lys Arg Lys Thr Ser Ser Ser Lys
690                      695              700

Lys Asn Lys Ser Gly Ser Thr Pro Glu Ser Lys Leu Pro Glu Lys Pro
705                      710              715              720

Leu Ala Lys Val Ala Trp Phe Arg Val Ile Leu Asp Glu Ala Gln Ser
725                      730              735

Ile Lys Asn Tyr Arg Thr Gln Val Ala Arg Ala Cys Trp Gly Leu Arg
740                      745              750

Ala Lys Arg Arg Trp Cys Leu Ser Gly Thr Pro Ile Gln Asn Ala Val
755                      760              765

Glu Asp Leu Tyr Ser Tyr Phe Arg Phe Leu Arg Tyr Asp Pro Tyr Ala
770                      775              780

Glu Tyr Lys Lys Phe Cys Phe Met Ile Lys Thr Pro Ile Ser Arg Asn
785                      790              795              800

Pro Ile Thr Gly Tyr Lys Lys Leu Gln Val Val Leu Lys Thr Val Met
805                      810              815

Leu Arg Arg Thr Lys Ala Thr Met Leu Asp Gly Lys Pro Ile Ile Ser
820                      825              830

Leu Pro Pro Lys Thr Val Ser Leu Lys Thr Val Asp Phe Thr Ser Glu
835                      840              845

Glu Arg Ala Phe Tyr Asn Thr Leu Glu Ala Glu Ser Arg Glu Gln Phe
850                      855              860

Lys Glu Tyr Ala Ala Ala Gly Thr Val Lys Gln Asn Tyr Val Asn Ile
865                      870              875              880

Leu Leu Met Leu Leu Arg Leu Arg Gln Ala Cys Asp His Pro His Leu
885                      890              895

Val Arg Gly His Glu Ser Thr Ser Ser Trp Met Ser Ser Leu Glu Met
900                      905              910

Ala Lys Lys Leu Pro Val Glu Arg Gln Gln Ser Leu Leu Val Cys Leu
915                      920              925

Gln Ser Cys Ser Ala Ile Cys Ala Leu Cys Asn Asp Ala Pro Glu Asp
930                      935              940

Ala Val Val Thr Ile Cys Gly His Val Phe Cys Asn Gln Cys Ile Leu
945                      950              955              960
```

-continued

```
Glu Gln Leu Thr Gly Asp Asp Ser Val Cys Pro Val Ser Asn Cys Arg
965                 970                 975

Val Arg Leu Asn Ser Thr Ser Leu Phe Ser Arg Gly Thr Leu Glu Cys
980                 985                 990

Ala Leu Ser Arg Ser Thr Cys Glu Phe Leu Ser Asp Asp Ser Cys Glu
995                 1000                1005

Asp Met Val Gln Gly Lys Gln Pro Arg Phe Asp Ser Ser Tyr Ala
1010                1015                1020

Ser Ser Lys Val Arg Ala Ala Leu Asp Ile Leu Leu Ser Leu Pro
1025                1030                1035

Lys Leu Asp Leu Thr His Met Ser Asp Asp Lys Asn Lys Ile Val
1040                1045                1050

His Pro Asp Lys Ile Asn Gly Asn Ser Thr Pro Ser Glu Tyr Ala
1055                1060                1065

Gly Thr Lys Ile Thr Glu Lys Ala Ile Val Phe Ser Gln Trp Thr
1070                1075                1080

Arg Met Leu Asp Leu Val Glu Val His Leu Lys Ser Ser His Leu
1085                1090                1095

Ser Tyr Arg Arg Leu Asp Gly Thr Met Ser Val Ala Ala Arg Asp
1100                1105                1110

Arg Ala Val Lys Asp Phe Asn Thr Asn Pro Glu Val Ser Val Met
1115                1120                1125

Ile Met Ser Leu Lys Ala Ala Ser Leu Gly Leu Asn Met Val Ala
1130                1135                1140

Ala Cys His Val Leu Leu Leu Asp Leu Trp Trp Asn Pro Thr Thr
1145                1150                1155

Glu Asp Gln Ala Val Asp Arg Ala His Arg Ile Gly Gln Thr Arg
1160                1165                1170

Pro Val Thr Val Ser Arg Leu Thr Ile Lys Asp Thr Val Glu Asp
1175                1180                1185

Arg Ile Leu Ala Leu Gln Glu Lys Lys Arg Glu Met Val Ala Ser
1190                1195                1200

Ala Phe Gly Glu Asp Lys Ser Gly Ala His Gln Thr Arg Leu Thr
1205                1210                1215

Val Glu Asp Leu Asn Tyr Leu Phe Met Val
1220                1225

<210> SEQ ID NO 31
<211> LENGTH: 1235
<212> TYPE: PRT
<213> ORGANISM: Oryza sativa

<400> SEQUENCE: 31

Met Ser Arg Ile Glu Ser Leu Met Asn Arg Cys Thr Trp Arg Gln Gly
1               5                   10                  15

Gly Arg Val Glu Leu Ala Ile His Pro Thr Gly Ser Leu Leu Glu
20                  25                  30

Met Arg Asn Leu Pro Leu Gly Val Gly Gly Asp Gly Pro Leu His
35                  40                  45

Gln Glu Asp Asn Ser Glu Ser Asp Arg Ala Gly Arg Trp Cys Leu Arg
50                  55                  60

His Val Asp Ala Gln Arg Gln Arg Leu Thr Gly Gln Leu Val Gly Asp
65                  70                  75                  80

Val Ala Val Leu Gln Asp Gly Glu Ser Ala Leu Ser Ala His Ala Leu
```

```
            85                  90                  95
His Val Leu Met Arg Ser Gly Ile Gln Thr Pro Ser Cys Ser Pro Arg
100                 105                 110

Gly Pro Ser Ile Trp Thr Ser Ala Leu Lys Asp His Pro Leu Pro Ala
115                 120                 125

Asp Ala Thr Val Ile Thr Val Cys Arg Val Ala Asp Ala Val Arg His
130                 135                 140

Gln Ala Arg Ser Thr Ala Ser His Arg Arg Thr Gly Leu Ala Val Val
145                 150                 155                 160

Ala Gly Ser Gly Glu Asp Gly Arg Ala Pro Val Arg Arg Gly Gly
165                 170                 175

Leu Gly Glu Glu Gly Val Trp Trp Lys Met Glu Arg Val Cys Thr Ala
180                 185                 190

Lys His Asn Trp Ser Ser Asp Tyr Thr Asp Ala Val Arg Met Leu Ala
195                 200                 205

Gly Asn Met Asn Asn Asp Asn Tyr Ile Asp Leu Ser Ser Asp Ser Asp
210                 215                 220

Ile Asp Phe Asp Phe Asp Ser Asp Asp Ser Val Gly Gly Leu Asp Gln
225                 230                 235                 240

Glu Leu Ala Ser Ser Ser Ser Arg Pro Thr Glu Asn Ile Asn Gly Gln
245                 250                 255

Tyr Arg Thr Leu Pro Pro Ser Phe Thr Asn Gly Arg His Val Asp Asn
260                 265                 270

Ala Arg His Ala Leu Gly Ser Gly Asp Arg Ala Tyr Pro His Ser Ser
275                 280                 285

Ser Tyr Arg Gly Ser Pro Asn Asp Ser Ala Arg Ala Ala Pro Ala Ser
290                 295                 300

Asn Arg Thr Asp Ile Val Val Lys Lys His Asn Gly Phe Ala Ser Asp
305                 310                 315                 320

Glu Asn Asp Asn Gly Lys Arg Ile Leu Pro Ser Ser Phe Ser Asn Gly
325                 330                 335

Arg Thr Thr Asn Ala Met His Pro Val Val Ala Ser Glu Thr Arg Lys
340                 345                 350

Phe Pro Pro Ser Phe Thr Asn Gly Asn Ser Gln Arg Leu Ala Glu Asn
355                 360                 365

Arg Met Gly Lys Asn Val Ala Asn Gly Ile Gly Glu Pro Ser Ser Ser
370                 375                 380

Arg Phe Pro Ser Arg Ser Ser Phe Gly Thr Asp Asn Lys Lys Val Ile
385                 390                 395                 400

Thr Asp Ser Asp Asn Glu Asp Val Tyr Val Tyr Gly Ser Ser Ser Ser
405                 410                 415

His Arg Val Leu Pro Pro Ser Phe Gly Arg Asn Ser Ser Ala Asn His
420                 425                 430

Ser Glu Phe Ala Asn Gly Ile Asp Met Gln Gly Arg Leu Asn Leu Glu
435                 440                 445

Asn Arg Ile Ile Asp Ser Asp Glu Arg Ala Val Tyr Gln Glu Ala Leu
450                 455                 460

Gln Asn Ile Ile Gln Asp Lys Arg Glu Asp Leu Pro Glu Gly Val
465                 470                 475                 480

Leu Ser Val Pro Leu Leu Arg His Gln Lys Met Ala Leu Ala Trp Met
485                 490                 495

Val Ser Lys Glu Asn Ser Ser His Cys Ala Gly Gly Ile Leu Ala Asp
500                 505                 510
```

```
Asp Gln Gly Leu Gly Lys Thr Val Ser Thr Ile Ala Leu Ile Gln Lys
515                 520                 525

Gln Arg Ile Gln Gln Ser Lys Phe Met Ser Val Asp Ser Asp Arg Leu
530                 535                 540

Lys Ala Glu Ala Leu Asn Leu Asp Asp Asp Glu Ala Ala Pro Val
545                 550                 555                 560

Ala Asp Asn Lys Gly Glu Gln Thr Lys Asn Asp Glu Pro Arg Lys Asp
565                 570                 575

Leu Gly Ala Gly Ser Ser Thr Ala Ala Gly Thr Gly Asp Val Glu
580                 585                 590

Thr Cys Ala Ser Leu Met Asn Thr Ala Pro Asp Lys Thr Val Glu Arg
595                 600                 605

Asn Val Glu Arg Lys Lys Ser Lys Ala Ser Thr Ser Ser Thr Met
610                 615                 620

Gln Ser Met Thr Arg Pro Ala Ala Gly Thr Leu Val Val Cys Pro Ala
625                 630                 635                 640

Ser Val Leu Lys Gln Trp Ala Asn Glu Leu Thr Asp Lys Val Gly Glu
645                 650                 655

Ser Ala Lys Leu Ser Val Leu Val Tyr His Gly Gly Ser Arg Thr Lys
660                 665                 670

Asp Pro Asn Glu Leu Ala Lys Tyr Asp Val Val Ile Thr Thr Tyr Thr
675                 680                 685

Ile Val Ala Asn Glu Val Pro Lys Gln Asn Ala Asp Asp Thr Asp
690                 695                 700

Gln Lys Asn Gly Glu Glu Ser Ser Ala Gly Asn Lys Arg Lys Gln Pro
705                 710                 715                 720

Pro Lys Ala Gln Ser Lys Ser Lys Lys Lys Lys Lys Leu Lys Asp
725                 730                 735

Ser Asp Ile Tyr Leu Ala Ser Gly Pro Val Ala Arg Val Arg Trp Phe
740                 745                 750

Arg Val Val Leu Asp Glu Ala Gln Thr Ile Lys Asn Phe Arg Thr Gln
755                 760                 765

Val Ala Lys Ala Cys Cys Gly Leu Arg Ala Lys Arg Arg Trp Cys Leu
770                 775                 780

Ser Gly Thr Pro Ile Gln Asn Ala Ile Asp Glu Leu Tyr Ser Tyr Phe
785                 790                 795                 800

Arg Phe Leu Lys Tyr Asp Pro Tyr Ser Thr Tyr Asn Ser Phe Cys Thr
805                 810                 815

Met Ile Lys His Pro Ile Ala Arg Asn Ala Val His Gly Tyr Lys Lys
820                 825                 830

Leu Gln Thr Val Leu Arg Ile Val Leu Leu Arg Arg Thr Lys Glu Thr
835                 840                 845

Leu Ile Asp Gly Glu Pro Ile Ile Lys Leu Pro Pro Lys Thr Ile Asn
850                 855                 860

Leu Asp Lys Val Asp Phe Thr Lys Glu Glu Arg Ala Phe Tyr Leu Thr
865                 870                 875                 880

Leu Glu Glu Arg Ser Arg Gln Gln Phe Lys Ala Tyr Ala Ala Ala Gly
885                 890                 895

Thr Leu Lys Gln Asn Tyr Ala Asn Ile Leu Leu Met Leu Leu Arg Leu
900                 905                 910

Arg Gln Ala Cys Asp His Pro Leu Leu Val Lys Gly His Gln Ser Glu
915                 920                 925
```

```
Tyr Lys Gly Asp Gly Ser Ile Glu Met Ala Lys Gln Leu Pro Lys Glu
930                 935                 940
Met Ile Ile Asn Leu Leu Ala Lys Leu Glu Val Gly Glu Phe Cys Ser
945                 950                 955                 960
Val Cys Ser Asp Val Pro Glu Asp Ala Val Thr Met Cys Gly His
965                 970                 975
Val Phe Cys Tyr Gln Cys Ile Tyr Glu Arg Ile Thr Thr Asp Glu Asn
980                 985                 990
Met Cys Pro Ser Pro Asn Cys Gly Asn Thr Leu Ser Thr Asp Ser Val
995                 1000                1005
Phe Ser Ser Gly Ala Leu Arg Ile Cys Met Ser Gly Val Ser Ser
1010                1015                1020
Ser His Ala Ser Gly Ser Ser Ser Leu Asp Asp Glu Ser Ser Ser
1025                1030                1035
Ile Ser Gln Thr Ser Tyr Ile Ser Ser Lys Ile Gln Ala Ala Ile
1040                1045                1050
Asp Ile Leu Asn Ser Ile Ile Asn Thr Tyr Ala Leu Thr Asp Ser
1055                1060                1065
Asp Thr Val Glu Ser Asn Pro Ser Arg Val Ala Pro Val Lys Ala
1070                1075                1080
Ile Val Phe Ser Gln Trp Thr Gly Met Leu Asp Leu Leu Glu Leu
1085                1090                1095
Ser Leu Asn Ser Asn Leu Ile Gln Tyr Arg Arg Leu Asp Gly Thr
1100                1105                1110
Met Ser Leu Asn Ser Arg Asp Lys Ala Val Lys Asp Phe Asn Thr
1115                1120                1125
Asp Pro Glu Val Arg Val Met Ile Met Ser Leu Lys Ala Gly Asn
1130                1135                1140
Leu Gly Leu Asn Met Val Ala Ala Cys His Val Ile Leu Leu Asp
1145                1150                1155
Leu Trp Trp Asn Pro Tyr Ala Glu Asp Gln Ala Ile Asp Arg Ala
1160                1165                1170
His Arg Ile Gly Gln Thr Arg Pro Val Thr Val Ser Arg Leu Thr
1175                1180                1185
Ile Lys Asp Thr Val Glu Asp Arg Ile Leu Ala Leu Gln Glu Glu
1190                1195                1200
Lys Arg Ala Met Val Ser Ser Ala Phe Gly Glu Asp Lys Ser Gly
1205                1210                1215
Gly His Ala Thr Arg Leu Thr Val Asp Asp Leu Lys Tyr Leu Phe
1220                1225                1230
Arg Ile
1235

<210> SEQ ID NO 32
<211> LENGTH: 1051
<212> TYPE: PRT
<213> ORGANISM: Oryza sativa

<400> SEQUENCE: 32

Met Asp Ile Ile Asp Leu Cys Ser Asp Ser Glu Glu Tyr Phe Ser Pro
1               5                   10                  15
Tyr Ser Asp Thr Glu Asp Asn Leu Asp Phe Asp Asp Pro Asn Asp Gly
            20                  25                  30
Val Asn Gln Val Val Leu His Asn Thr Ala Phe Gly Asn Asn Ser Ser
        35                  40                  45
```

```
Glu Leu Leu Val Gly Leu Asp Asp Asp Asn Trp Leu Asn Asn Thr His
 50              55                  60

Ala Leu Ser Ser His Arg Pro Ala Glu Asn Arg Ser Asp Ile Ile Glu
 65              70                  75                   80

Ser Ser Ser Gly Val Asn Thr Asp Cys Gln Asn Ser Ala Trp Gln Tyr
 85              90                  95

Arg Thr Leu Pro His Thr Phe Met Ser Ser Tyr Lys Ser Arg Pro
100             105                 110

Leu Ser Leu Thr Gly Gly Asn Asn Val Glu Ser Thr His Pro Thr Val
115             120                 125

Lys Pro Asn Thr Val His Tyr Asn Gly Ile Gly Phe Pro Ser Pro Ala
130             135                 140

Ile Ala Ser Gly Tyr Lys Pro Tyr Val Ser Tyr Gly Gln Gly Val Ser
145             150                 155                 160

Ile Asp Asp Asp Asp Asp Val Tyr Glu Val Leu His Gln Pro Phe
165             170                 175

Pro Phe Ser His Ser Ser Leu Gly Asp Lys Lys Ile Glu Glu Glu Ser
180             185                 190

Thr Trp Lys Tyr Asn Gly Phe Gln Thr Ser Ser Ala Tyr Gly Ile Glu
195             200                 205

Met Pro Thr Ser Ala Arg Ser Thr Gly Gly Val Ser Ala Tyr Gly Gly
210             215                 220

Leu Asn Ser His Arg Ile Phe Pro Pro Ser Val Pro Tyr Asn Asn Ser
225             230                 235                 240

Val Asn Asn Phe Gly Val Asn Gly Leu Gly Thr Gln Ser His Leu Asn
245             250                 255

Ile Glu Lys Arg Leu Phe Gly Arg Asp Glu Arg Val Val Tyr Asp Glu
260             265                 270

Ala Leu Lys Gln Ile Ser Gln Glu Thr Thr Glu Glu Asn Leu Pro Glu
275             280                 285

Gly Val Met Ser Val Ser Leu Leu Lys His Gln Arg Ile Ala Leu Ala
290             295                 300

Trp Met Val Ser Arg Glu Asn Ser Ser His Cys Ser Gly Gly Ile Leu
305             310                 315                 320

Ala Asp Asp Gln Gly Leu Gly Lys Thr Ile Ser Thr Ile Ala Leu Ile
325             330                 335

Gln Lys Glu Arg Val Glu Gln Ser Lys Phe Met Ser Ala Asp Val Gly
340             345                 350

Ser Met Lys Ser Val Ala Asn Leu Asp Glu Asp Glu Val Val Ile
355             360                 365

Val Met Asp Lys Lys Gln Leu Lys Gly Glu Ser Val Asn Met Leu Gln
370             375                 380

Asp Ser Thr Leu Phe Pro Ser Ser Glu Ala Ala Ser Asp Ala Ala Asp
385             390                 395                 400

Leu Lys Pro Trp Ala Ser Leu Pro Gly Ser Ala Val Asp Arg Met Val
405             410                 415

Asn Ala Val Lys Val Glu Pro Lys Lys Lys Ala Arg Val Arg Pro Ser
420             425                 430

Ser Ser Ser Thr Leu Arg Ser Ala Asn Arg Ser Thr Ala Gly Thr Leu
435             440                 445

Val Val Cys Pro Ala Ser Val Leu Arg Gln Trp Ala Ser Glu Leu Ala
450             455                 460
```

-continued

```
Ala Lys Val Thr Glu Ser Ser Lys Leu Ser Val Leu Val Tyr His Gly
465                 470                 475                 480

Gly Ser Arg Thr Lys Asp Pro Thr Glu Leu Thr Lys Tyr Asp Val Val
        485                 490                 495

Val Thr Thr Tyr Thr Ile Val Ala Asn Glu Val Pro Lys Gln Asn Ser
500                 505                 510

Asp Glu Asp Met Glu Glu Lys Asn Ser Glu Thr Tyr Gly Leu Cys Pro
515                 520                 525

Ala Phe Ser Ile Gly Asn Lys Arg Lys Lys Asp Ser Glu Pro Lys Lys
530                 535                 540

Lys Lys Lys Pro Lys Asn Ser Asp Ala Asp Leu Asp Gly Gly Pro Leu
545                 550                 555                 560

Ala Arg Val Arg Trp Phe Arg Val Val Leu Asp Glu Ala Gln Thr Ile
565                 570                 575

Lys Asn His Asn Thr Gln Val Ala Arg Ala Cys Cys Gly Leu Arg Ala
580                 585                 590

Lys Arg Arg Trp Cys Leu Ser Gly Thr Pro Ile Gln Asn Thr Ile Asp
595                 600                 605

Asp Leu Tyr Ser Tyr Phe Arg Phe Leu Lys Tyr Glu Pro Tyr Ser Val
610                 615                 620

Tyr Gly Ser Phe Arg Ser Met Ile Lys Tyr Gln Ile Ser Arg Asp Ala
625                 630                 635                 640

Thr Arg Gly Tyr Lys Lys Leu Gln Ala Val Leu Lys Ile Val Leu Leu
645                 650                 655

Arg Arg Thr Lys Glu Thr Leu Ile Asp Gly Glu Pro Ile Ile Lys Leu
660                 665                 670

Pro Pro Lys Thr Ile Gln Leu Ser Lys Ile Asp Phe Ser Lys Glu Glu
675                 680                 685

Arg Thr Phe Tyr Met Met Leu Glu Glu Gly Ser Arg Glu Lys Phe Lys
690                 695                 700

Glu Tyr Ala Ser Ala Gly Thr Ile Arg Glu Asn Tyr Ala Asn Ile Leu
705                 710                 715                 720

Val Leu Leu Leu Arg Leu Arg Gln Ala Cys Asp His Pro Leu Leu Leu
725                 730                 735

Lys Gly Lys Glu Lys Asp Leu Ile Asp Thr Gly Ser Val Glu Val Ala
740                 745                 750

Lys Lys Leu Pro Lys Glu Thr Val Ile Asn Leu Leu Gly Gln Leu Glu
755                 760                 765

Gly Asp Tyr Ala Ile Cys Ser Arg Cys Ser Asp Pro Pro Glu Asp Val
770                 775                 780

Val Val Ala Thr Cys Gly His Val Phe Cys Tyr Gln Cys Val His Lys
785                 790                 795                 800

Ser Leu Lys Ser Asp Glu Asn Val Cys Pro Ser Pro Ser Cys Gly Lys
805                 810                 815

Lys Leu Ser Ala Gln Ser Val Phe Ser Pro Gly Val Leu Arg Phe Cys
820                 825                 830

Ile Ala Asp Lys Leu Glu Ser Gly Ala Thr Thr Ser Ser Ser Val Glu
835                 840                 845

Ala Asp Gly Ser Pro Ser Ile Cys Glu Ser Tyr Ile Ser Ser Lys
850                 855                 860

Ile Arg Ala Thr Thr Asp Ile Leu Asn Ser Ile Val Asn Thr Pro Ala
865                 870                 875                 880

Leu Thr Trp Ser Asp Thr Met Glu Ser Ser Pro Ser Glu Val Ala Pro
```

```
885                 890                 895
Ser Lys Ala Ile Val Phe Ser Gln Trp Thr Gly Leu Leu Asp Leu Leu
900                 905                 910

Glu Leu Ser Leu Asp Ser Ser Arg Ile Lys Phe Arg Arg Leu Asp Gly
915                 920                 925

Ala Met Ser Leu Asn Leu Arg Glu Ala Ala Val Arg Glu Phe Asn Thr
930                 935                 940

Asp Pro Glu Val Arg Val Met Leu Met Ser Leu Lys Ala Gly Asn Leu
945                 950                 955                 960

Gly Leu Asn Met Val Ala Ala Cys His Val Ile Met Ile Asp Pro Trp
965                 970                 975

Trp Asn Pro Tyr Ala Glu Asp Gln Ala Val Asp Arg Ala His Arg Ile
980                 985                 990

Gly Gln Thr Arg Pro Val Thr Val  Ser Arg Leu Thr Ile  Lys Asp Thr
995                 1000                 1005

Val Glu  Asp Arg Ile Leu Ala  Leu Gln Glu Lys Lys  Arg Lys Met
1010                 1015                 1020

Val Gln Ser Ala Phe Gly Glu  Asp Lys Pro Gly Gly  Ser Ala Thr
1025                 1030                 1035

Arg Leu  Thr Ile Asp Asp Leu  Gln Tyr Leu Phe Gly  Ile
1040                 1045                 1050

<210> SEQ ID NO 33
<211> LENGTH: 55
<212> TYPE: DNA
<213> ORGANISM: Artificial
<220> FEATURE:
<223> OTHER INFORMATION: At1g61140-5' attB forward primer

<400> SEQUENCE: 33
ttaaacaagt ttgtacaaaa aagcaggctc aacaatgggt gaggaaggtt caatg       55

<210> SEQ ID NO 34
<211> LENGTH: 50
<212> TYPE: DNA
<213> ORGANISM: Artificial
<220> FEATURE:
<223> OTHER INFORMATION: At1g61140-3' attB reverse primer

<400> SEQUENCE: 34
ttaaaccact ttgtacaaga aagctgggtt catgaatcag ccataaacag              50

<210> SEQ ID NO 35
<211> LENGTH: 3365
<212> TYPE: DNA
<213> ORGANISM: Eragrostis nindensis

<400> SEQUENCE: 35
tcaagtagag aacaacatgg aaggcatgga gacacaaatg aatacttatt tttcaggcga    60
tatatcggca gagcaatcag gtttgagtga tattaaatgg gagagtacag attcaatgct   120
tggtaatgct ggtcaggatg gtaaccattt cacctcgaca ggcgtatttt cccttgctca   180
gaatgcagct atgcctgacg cttcatgcac tgagttgaac atgggtgagg catctgaaag   240
cattcgcaat ggcaacagca gttgcctaac tgtgcaggaa gaacatttgc aggtggactg   300
tggggattat ccacatccag attattcttc tgttgatatg gttgctgaac aatcactgcc   360
tgatttgcca catgattttt cacaaaacaa tgagcaaatt gagatggaac agtttccaga   420
gaatatatgt gaaagcggtt cgatgcagat gggctctcca gatcaatatt gtgatgatac   480
```

```
atctttatca gatctctaca tagatgtatc ctcaccagag tcggtatcct gtgagcagaa    540
ccagactgaa gatatttgtt tcaagagcga gtctagcact gactcttctc cagtaccctc    600
tagtagaaac tccaccacag aggatgctga taaatactta ggtcacacat caaaacagtt    660
gccggactcc aacaagtttc tccctatcag caaccaactg ccgtttaaga acacaggata    720
ccagaaacct atagcattac ataaacagta tgattataga attggaaact cttctaccca    780
gggtagttca tcaagaggtt gcttcagtat ggatggcagc ggggcttctg atttatgctt    840
tcttgagggt aatcggagtt ctgctcctga ttaccgactg ccactgcaga gacctatcca    900
tcataatttt cagaattctg tatatcctaa taatcccatc attcctacat ttggtggaat    960
gagatacaaa ccacatgatg aaagaatgac actacgtctt gccttacagg atatttcaca   1020
gccaaagtct gaggctaatc cacctgatgg ggttttggcg gttcctttat tgagacatca   1080
gaaaattgcg ttgtcatgga tggtgcagaa ggaaacaagt agttcacact gttctggtgg   1140
aattcttgct gatgatcagg gcctgggcaa gactgtatca gctatatcac tgattttgac   1200
agaacgaccg ccagtgggac agtcatctac tgtaaagcaa gaaccatgtg aagctgtaac   1260
tctagatgac gatgatgatg aggattctac ggaacctcaa ttgaaaaaac caaccctcac   1320
attcattcct gaagggcaa atgacacagt taagaaagaa atcctgtag taccggttaa    1380
gacaaggcca gctgctggga cttgggttgt ttgccctaca agtgttttgc ggcagtgggc   1440
aggagaactg aagaataaag ttacaaataa agcgaagttg tccttttga tatatcatgg    1500
tagcaatcgt acgaaggatc ctaatgagct caccaagtat gatgttgtgc taactacata   1560
ttctattgta agcatggaag taccaaaaca atccaatcct gatagtgacg atgaagagaa   1620
agggaagcct gacagatatg tgctccagt ggcatcttca ggcagcaaaa agaggaaggc    1680
gtcctcttct aagaaaacaa aaaatggaaa cgcagcagag agtaacttgc ctgaaagacc   1740
tcttgcaaaa gttgcttggt ttagggttat tcttgatgag gcacaaagta ttaaaaacta   1800
ccgaactcag gttgccaggg cttgctgggg tttgcgagcc aaaagaagat ggtgtttgtc   1860
tgggacacct atacagaatg ctattgagga tctctatagt tattttcgtt ttctcagata   1920
cgacccttat gctgtataca agcagttttg ctcgatgata aaattgccaa ttagtaggaa   1980
cccgactaat ggttacaaaa aacttcaagt tgttttgaag acagttatgc tacgccggac   2040
taaagcaaca atgcttgagg ggaaaccaat catttcctta ccgccgaaga ctgtttctct   2100
caaaacagtg gactttacta atgaggagcg tgcttttttat aatgcattag aagctgaatc   2160
tcgagagcag ttcaaggaat atgcagctgc tggtactgtg aagcaaaatt atgtcaacat   2220
cctgctgatg ctttacggc tcagacaggc ttgcgatcac cctcacctag ttagaggcca    2280
tcagtctact tctagctgga tgtcttcatt ggagatggca agaaacttc caattgaaag    2340
gcagcaagag ttgcttattt gcttacagtc ttgttccgcg atatgtgttc tctgcaatga   2400
tgccccagaa gatgctgttg tcacactatg tggtcatgtt ttttgcaacc agtgcatact   2460
ggagcaactc actggcgatg acagcatgtg cccagtgtca aattgcagag ttcgactaaa   2520
tacgacctca ctattctcca gaggcactct tgaatgctct ctgagaagat taacatgtga   2580
tttcaagtct aacgattcgt cttttggaggt agtgcatgct gaaaagcggc ctggaattga   2640
ttcgtcatat gcatcttcca aagtgagagc tgcacttgat attattctct cattgcccaa   2700
aatagccccc acccaaatga gtgacagcga aaaatcaatt gggcctacct ctgaaaaatt   2760
tggtggaaag agcccttcag aacatattga taccaaaatg acagagaagg ccattgtttt   2820
```

-continued

```
ctcccaatgg actagaatgc tggatttgct ggaggttcat ttgaaagctt ctcatgtgac    2880
ctatcgaagg cttgatggaa caatgtctgt tgctgctcgg gataaagccg tgaatgactt    2940
caatacagtt ccagaggttt ctgttatgat catgtcactt aaggctgcaa gtcttggttt    3000
gaatatggtt gctgcctgcc acgtacttat gcttgatcta tggtggaatc aaccacaga    3060 agatcaagct gtggatagag cacaccgtat tggccaaaca agacctgtca cagtatcacg    3120
gttaactata aaagacaccg ttgaagatcg tattcttgct ctccaggaaa aaagcgggga   3180
gatggttgct tctgcatttg gggaagaccg gtctggttca cgccagacac ggttgactgt    3240
ggaggacctg aactacctgt ttatggttta gattgctcct gatggttaac agttttgctc    3300
attgggtggg tgtaggcagt ggtagataaa atatatctca acaaataac aaatagcatt     3360 tcttt                                                                3365
```

<210> SEQ ID NO 36
<211> LENGTH: 1089
<212> TYPE: PRT
<213> ORGANISM: Eragrostis nindensis

<400> SEQUENCE: 36

```
Gln Val Glu Asn Asn Met Glu Gly Met Glu Thr Gln Met Asn Thr Tyr
1               5                   10                  15

Phe Ser Gly Asp Ile Ser Ala Glu Gln Ser Gly Leu Ser Asp Ile Lys
            20                  25                  30

Trp Glu Ser Thr Asp Ser Met Leu Gly Asn Ala Gly Gln Asp Gly Asn
        35                  40                  45

His Phe Thr Ser Thr Gly Val Phe Ser Leu Ala Gln Asn Ala Ala Met
    50                  55                  60

Pro Asp Ala Ser Cys Thr Glu Leu Asn Met Gly Glu Ala Ser Glu Ser
65                  70                  75                  80

Ile Arg Asn Gly Asn Ser Ser Cys Leu Thr Val Gln Glu Glu His Leu
                85                  90                  95

Gln Val Asp Cys Gly Asp Tyr Pro His Pro Asp Tyr Ser Ser Val Asp
            100                 105                 110

Met Val Ala Glu Gln Ser Leu Pro Asp Leu Pro His Asp Phe Ser Gln
        115                 120                 125

Asn Asn Glu Gln Tyr Glu Met Glu Gln Phe Pro Glu Asn Ile Cys Glu
    130                 135                 140

Ser Gly Ser Met Gln Met Gly Ser Pro Asp Gln Tyr Cys Asp Asp Thr
145                 150                 155                 160

Ser Leu Ser Asp Leu Tyr Ile Asp Val Ser Pro Glu Ser Val Ser
                165                 170                 175

Cys Glu Gln Asn Gln Thr Glu Asp Ile Cys Phe Lys Ser Glu Ser Ser
            180                 185                 190

Thr Asp Ser Ser Pro Val Pro Ser Ser Arg Asn Ser Thr Thr Glu Asp
        195                 200                 205

Ala Asp Lys Tyr Leu Gly His Thr Ser Lys Gln Leu Pro Asp Ser Asn
    210                 215                 220

Lys Phe Leu Pro Ile Ser Asn Gln Leu Pro Phe Lys Asn Thr Gly Tyr
225                 230                 235                 240

Gln Lys Pro Ile Ala Leu His Lys Gln Tyr Asp Tyr Arg Ile Gly Asn
                245                 250                 255

Ser Ser Thr Gln Gly Ser Ser Ser Arg Gly Cys Phe Ser Met Asp Gly
            260                 265                 270
```

```
Ser Gly Ala Ser Asp Leu Cys Phe Leu Glu Gly Asn Arg Ser Ser Ala
275                 280                 285

Pro Asp Tyr Arg Leu Pro Leu Gln Arg Pro Ile His His Asn Phe Gln
290                 295                 300

Asn Ser Val Tyr Pro Asn Asn Pro Ile Ile Pro Thr Phe Gly Gly Met
305                 310                 315                 320

Arg Tyr Lys Pro His Asp Glu Arg Met Thr Leu Arg Leu Ala Leu Gln
325                 330                 335

Asp Ile Ser Gln Pro Lys Ser Glu Ala Asn Pro Pro Asp Gly Val Leu
340                 345                 350

Ala Val Pro Leu Leu Arg His Gln Lys Ile Ala Leu Ser Trp Met Val
355                 360                 365

Gln Lys Glu Thr Ser Ser His Cys Ser Gly Gly Ile Leu Ala Asp
370                 375                 380

Asp Gln Gly Leu Gly Lys Thr Val Ser Ala Ile Ser Leu Ile Leu Thr
385                 390                 395                 400

Glu Arg Pro Pro Val Gly Gln Ser Ser Thr Val Lys Gln Glu Pro Cys
405                 410                 415

Glu Ala Val Thr Leu Asp Asp Asp Asp Glu Asp Ser Thr Glu Pro
420                 425                 430

Gln Leu Lys Lys Pro Thr Leu Thr Phe Ile Pro Glu Gly Ala Asn Asp
435                 440                 445

Thr Val Lys Lys Glu Asn Pro Val Val Pro Val Lys Thr Arg Pro Ala
450                 455                 460

Ala Gly Thr Leu Val Val Cys Pro Thr Ser Val Leu Arg Gln Trp Ala
465                 470                 475                 480

Gly Glu Leu Lys Asn Lys Val Thr Asn Lys Ala Lys Leu Ser Phe Leu
485                 490                 495

Ile Tyr His Gly Ser Asn Arg Thr Lys Asp Pro Asn Glu Leu Thr Lys
500                 505                 510

Tyr Asp Val Val Leu Thr Thr Tyr Ser Ile Val Ser Met Glu Val Pro
515                 520                 525

Lys Gln Ser Asn Pro Asp Ser Asp Asp Glu Glu Lys Gly Lys Pro Asp
530                 535                 540

Arg Tyr Gly Ala Pro Val Ala Ser Ser Gly Ser Lys Lys Arg Lys Ala
545                 550                 555                 560

Ser Ser Ser Lys Lys Thr Lys Asn Gly Asn Ala Ala Glu Ser Asn Leu
565                 570                 575

Pro Glu Arg Pro Leu Ala Lys Val Ala Trp Phe Arg Val Ile Leu Asp
580                 585                 590

Glu Ala Gln Ser Ile Lys Asn Tyr Arg Thr Gln Val Ala Arg Ala Cys
595                 600                 605

Trp Gly Leu Arg Ala Lys Arg Arg Trp Cys Leu Ser Gly Thr Pro Ile
610                 615                 620

Gln Asn Ala Ile Glu Asp Leu Tyr Ser Tyr Phe Arg Phe Leu Arg Tyr
625                 630                 635                 640

Asp Pro Tyr Ala Val Tyr Lys Gln Phe Cys Ser Met Ile Lys Leu Pro
645                 650                 655

Ile Ser Arg Asn Pro Thr Asn Gly Tyr Lys Lys Leu Gln Val Val Leu
660                 665                 670

Lys Thr Val Met Leu Arg Arg Thr Lys Ala Thr Met Leu Glu Gly Lys
675                 680                 685

Pro Ile Ile Ser Leu Pro Pro Lys Thr Val Ser Leu Lys Thr Val Asp
```

```
                690            695              700
    Phe Thr Asn Glu Glu Arg Ala Phe Tyr Asn Ala Leu Glu Ala Glu Ser
    705                710              715                  720

Arg Glu Gln Phe Lys Glu Tyr Ala Ala Ala Gly Thr Val Lys Gln Asn
    725                730              735

Tyr Val Asn Ile Leu Leu Met Leu Leu Arg Leu Arg Gln Ala Cys Asp
    740                745              750

His Pro His Leu Val Arg Gly His Gln Ser Thr Ser Ser Trp Met Ser
    755                760              765

Ser Leu Glu Met Ala Lys Lys Leu Pro Ile Glu Arg Gln Gln Glu Leu
    770                775              780

Leu Ile Cys Leu Gln Ser Cys Ser Ala Ile Cys Val Leu Cys Asn Asp
    785                790              795                  800

Ala Pro Glu Asp Ala Val Val Thr Leu Cys Gly His Val Phe Cys Asn
    805                810              815

Gln Cys Ile Leu Glu Gln Leu Thr Gly Asp Asp Ser Met Cys Pro Val
    820                825              830

Ser Asn Cys Arg Val Arg Leu Asn Thr Thr Ser Leu Phe Ser Arg Gly
    835                840              845

Thr Leu Glu Cys Ser Leu Arg Arg Leu Thr Cys Asp Phe Lys Ser Asn
    850                855              860

Asp Ser Ser Leu Glu Val Val His Ala Glu Lys Arg Pro Gly Ile Asp
    865                870              875                  880

Ser Ser Tyr Ala Ser Ser Lys Val Arg Ala Ala Leu Asp Ile Ile Leu
    885                890              895

Ser Leu Pro Lys Ile Asp Pro Thr Gln Met Ser Asp Ser Glu Lys Ser
    900                905              910

Ile Gly Pro Thr Ser Glu Lys Phe Gly Gly Lys Ser Pro Ser Glu His
    915                920              925

Ile Asp Thr Lys Met Thr Glu Lys Ala Ile Val Phe Ser Gln Trp Thr
    930                935              940

Arg Met Leu Asp Leu Leu Glu Val His Leu Lys Ala Ser His Val Thr
    945                950              955                  960

Tyr Arg Arg Leu Asp Gly Thr Met Ser Val Ala Ala Arg Asp Lys Ala
    965                970              975

Val Asn Asp Phe Asn Thr Val Pro Glu Val Ser Val Met Ile Met Ser
    980                985              990

Leu Lys Ala Ala Ser Leu Gly Leu  Asn Met Val Ala Ala  Cys His Val
    995                1000                 1005

Leu Met  Leu Asp Leu Trp Trp  Asn Pro Thr Thr Glu  Asp Gln Ala
    1010               1015                 1020

Val Asp  Arg Ala His Arg Ile  Gly Gln Thr Arg Pro  Val Thr Val
    1025               1030                 1035

Ser Arg  Leu Thr Ile Lys Asp  Thr Val Glu Asp Arg  Ile Leu Ala
    1040               1045                 1050

Leu Gln  Glu Lys Lys Arg Glu  Met Val Ala Ser Ala  Phe Gly Glu
    1055               1060                 1065

Asp Arg  Ser Gly Ser Arg Gln  Thr Arg Leu Thr Val  Glu Asp Leu
    1070               1075                 1080

Asn Tyr  Leu Phe Met Val
    1085

<210> SEQ ID NO 37
```

```
<211> LENGTH: 4314
<212> TYPE: DNA
<213> ORGANISM: Paspalum notatum

<400> SEQUENCE: 37
cacttgggtt tcgttcgttc gacgcggacg caatctcccc cacgcccccg ccagccagac    60
cacagccgcc cgcccgattg aagaggggg ttcgcttgtc cggagaagcc aaggccaagg   120
cgtccgcccg cctgccaccg cgaatcgtat ggtcgaatcg cgccgcgggt gatgcggag    180 gaaccggtgg tcggttacga tggcttcgat gccgccgccg gcgctggcgt cggtggcgcg   240
gaggacaacc tgtctatgcc cctcggcgac ttcatggcct tcctcgagac tgaacccacg   300
tcgcccgagg agggcgggga ggaggaggag gaggggcagc agcagcctgg ggtcaatcat   360
gattgtttga ggatgcctgc aaacgtcaat ggttctgaag atttattcca aagccatgaa   420
gaaatgcttg acaatgcgga attttggtca aactactcgc atgcggaccc ttcggaaagc   480
caaatgaaag ttaacatgga gctcaatgat ggagaaaaaa tgatcgatca cacagagcct   540
agcccttatg ggttgtatag caatgatctg cagaatcaat caagaacctg taactttgac   600
aatgagcatt ttgcaaggga tgcattgaac catgataagt ttgaagaagc aactggccct   660
ccatacgaag atctctcaaa tggttcatac cttggacaag aaactatgta ctctggtgaa   720
atacaactcc aagtggagaa tggcacagga ggcatgggga cgcaaatgaa tacttatttc   780
tcaggtggta tgtccacaga gcagtcagct ttgagtgcag atgagatgct tgttaatggt   840
aacactggtc agggtagtga tcattttgct tcaatgggag tgtttcctct tacccataac   900
acttatgtcc ctgatgtttc ttgtaccgag ttcaacgtgg gtgagacaac tgaaagcatg   960
cgcaatggca acagcagttg ccttactatg caggaagaac atctgcagac agaatgtgga  1020
gaatatcctc atccagatta tatttctgtt gatatggttg gtcaaaggtc agtgcatgat  1080
ctgccgcatg attttttcaga aaacagcgag caatatgaga tggagcattt cccagagaat  1140
acttgtgaaa gtggttcgat gcagatgggc tctccggatg aatattgcga tgattcagat  1200
atttacatgg atgtgtcctc tccagattca tcatcctttg agcaaaacca gtctgaagat  1260
atttgtttca agagtgagtc tagcactgac tcatctccag taccctctag cagaaactct  1320
gtcccggagg atgctgataa atacttaggt cacacaccaa aacagttgcc ggactccaac  1380
attgttcctt tcagcaacca cacccattt aagaatatgt tatatcaaaa acctccagta  1440
ttgcataaac aatatgcata tagaagtgag aactctttta ttcagggcaa ctcatcaaga  1500
ggttgtttca gtatagacgg caatgtggca tctgatttat gtgtgcttga gggtaatggg  1560
aatcctgttc ctgatcaccg atcgtctttc cagggaaagt tccatcataa ttttcagcaa  1620
cctatgtatg gtaatcacat tattcctaca tatggtggga tgagatacaa gcccacatgat  1680 gaaaggatca ctctgcggct tgcattgcag gacatttcac agccgaaaac tgaggccaat  1740
ccgcctgatg gggtttttagc agttcccttta ctgaggcatc agaaaattgc cttgtcatgg  1800
atggtgcaaa aggagacaag tagttcacat tgctctggtg ggattctcgc agatgatcag  1860
ggcctgggta aaactgtatc agccatatca ctgattctga cagaacgctc gccggtgcca  1920
cagtcatcta ctattaagaa agagccatgt gaagctgtaa atctagatga cgatgatgag  1980
gatgattgcg ctgaacccca tttgaaaaag ccgacgcaga aatgtagctc tgaagtgaca  2040
agtgacacag caaagcaaga aaatcctttt gtacctgtta agacaaggcc agctgctggt  2100
actttggttg tttgccaac aagtgttttg cgacagtggg caggagaact gaagaacaaa  2160
gttacaagta aagctaattt gtctttctta atatatcatg gtagcaaccg cacaaaggat  2220
```

```
cctaatgaac tcaccaagta tgatgttgtg cttactacat attccatagt aagcatggaa    2280
gtaccaaaac aatcaaatcc tgatagtgat gacgaagaga aggggaagcc tgacagatat    2340
ggtgctcccg tgtcctcttc aggcagcaaa aagagaaagg catcctcttc taagaaatca    2400
aaaaacaaaa gtgttgcaga taatagcttg cctgaaaaac ctcttgctaa agtcgcttgg    2460
tttagggtta ttcttgatga ggcacagagt attaaaaatt atcgaactca agttgccagg    2520
gcttgctggg gtttgcgagc caaaagaaga tggtgtttgt ctgggacacc tatacagaat    2580
gctgtggagg atctatatag ttatttaga tttctcagat acgatcctta cgctgtatac     2640
aagcaatttt gcactatgat aaagattcca atcagcagga acccaactaa tggctacaag    2700
aagcttcaag ttgttttgaa gacggtaatg ctacgccgga ctaaagcaac tatgcttgat    2760
gggaaaccaa tcatatcctt accgccgaag actgtttcac ttaagacggt ggacttcact    2820
agcgaggaac gtgcttttta taacacttta gaagttgaat cacgagaaca gttcaaggaa    2880
tatgcagctg ctggtactgt aaagcaaaat tatgtcaaca tattattgat gcttttacgg    2940
ctaagacagg catgtgatca ccctcatcta gttagaggct atgagtctac ttctagctgg    3000
atgtcttcgt tggagatggc aaagaaactc cccatggaaa ggcagcaaga attacttgtt    3060
tgcttgcaat cttgttccgc gatatgtgct ctctgcaatg acgcaccaga agatgctgtt    3120
gtcactatat gtggtcatgt ttttttgcaac cagtgcatac tggagcaact cactggtgat    3180
gacagcatat gcccagtgtc aaattgcaga gtccgactaa atacaacttc actattctcg    3240
agaggcaccc ttgaatgctc tctgagtaga ttaacctgtg atttcaagtc tgatgatacc    3300
tgtatggaaa tgttacatgt tgaaaagcgt cctgggatag attcttccta tgcatcttca    3360
aaagtaagag cagcactaga tattctcctc tcattgccca gaatagatcc cacacaaatg    3420
attgatagca aaaattcaat tcggcttgac tctgagaagt ttggcggaaa tggttcttca    3480
gaacagactg aaaccaaatt tacagagaag gcaattgttt tctctcaatg gactagaatg    3540
ctagacctgc ttgaagttca tttgaaagct tctcatgtga catatcgaag gcttgatgga    3600
acaatgtctg ttgctgcacg ggataaagct gtgaatgatt tcaatacagt tccagaggtt    3660
actgttatga tcatgtcact caaagctgca agtcttggtt tgaacatggt tgctgcctgc    3720
cacgttctta tgctagatct ttggtggaac ccgaccacag aagatcaagc tgtggataga    3780
gcacatcgta ttggccaaac acggcctgtc ctggtatcaa gattaactat aaaagacact    3840
gttgaagatc gtattctggc tctccaggag aagaagcggg agatggttgc atctgcgttt    3900
ggggaagaca gatctggttc ccggcagact cgattgaccg tggaagacct gaattatctg    3960
tttatggttt agcatcgctc ctgggagtga acagttttgc tcattggatg gtgtagacag    4020
tagaagatga aatctctaaa aacaaataac aaatactagg gatttttagt gcttttgtag    4080
tttgtacagt tgcagagatt ttgtagtttg aaggtggca ttgtggtggt taggttcatc      4140
caattctttt ggcacttgaa gcagtatgtt attgaaccag gtgaattctt cagagagctg    4200
aagtagtgcc tgttgactaa atatcatgaa gagaacaatg acagttatta gctaacatga    4260
tatttgtaca tatttgttct tgcgtatctg acatgtggtc ttcaccgcct ccca          4314
```

<210> SEQ ID NO 38
<211> LENGTH: 1266
<212> TYPE: PRT
<213> ORGANISM: Paspalum notatum

<400> SEQUENCE: 38

-continued

```
Met Ala Glu Glu Pro Val Val Gly Tyr Asp Gly Phe Asp Ala Ala Ala
1               5                   10                  15

Gly Ala Gly Val Gly Gly Ala Glu Asp Asn Leu Ser Met Pro Leu Gly
    20              25                  30

Asp Phe Met Ala Phe Leu Glu Thr Glu Pro Thr Ser Pro Glu Glu Gly
35                  40                  45

Gly Glu Glu Glu Glu Gly Gln Gln Gln Pro Gly Val Asn His Asp
50                  55                  60

Cys Leu Arg Met Pro Ala Asn Val Asn Gly Glu Asp Leu Phe Gln
65                  70                  75                  80

Ser His Glu Glu Met Leu Asp Asn Ala Glu Phe Trp Ser Asn Tyr Ser
85                  90                  95

His Ala Asp Pro Ser Glu Ser Gln Met Glu Val Asn Met Glu Leu Asn
100                 105                 110

Asp Gly Glu Lys Met Ile Asp His Thr Glu Pro Ser Pro Tyr Gly Leu
115                 120                 125

Tyr Ser Asn Asp Leu Gln Asn Gln Ser Arg Thr Cys Asn Phe Asp Asn
130                 135                 140

Glu His Phe Ala Arg Asp Ala Leu Asn His Asp Lys Phe Glu Ala
145                 150                 155                 160

Thr Gly Pro Pro Tyr Glu Asp Leu Ser Asn Gly Ser Tyr Leu Gly Gln
165                 170                 175

Glu Thr Met Tyr Ser Gly Glu Ile Gln Leu Gln Val Glu Asn Gly Thr
180                 185                 190

Gly Gly Met Gly Thr Gln Met Asn Thr Tyr Phe Ser Gly Gly Met Ser
195                 200                 205

Thr Glu Gln Ser Ala Leu Ser Ala Asp Glu Met Leu Val Asn Gly Asn
210                 215                 220

Thr Gly Gln Gly Ser Asp His Phe Ala Ser Met Gly Val Phe Pro Leu
225                 230                 235                 240

Thr His Asn Thr Tyr Val Pro Asp Val Ser Cys Thr Glu Phe Asn Val
245                 250                 255

Gly Glu Thr Thr Glu Ser Met Arg Asn Gly Asn Ser Ser Cys Leu Thr
260                 265                 270

Met Gln Glu Glu His Leu Gln Thr Glu Cys Gly Glu Tyr Pro His Pro
275                 280                 285

Asp Tyr Ile Ser Val Asp Met Val Gly Gln Arg Ser Val His Asp Leu
290                 295                 300

Pro His Asp Phe Ser Glu Asn Ser Glu Gln Tyr Glu Met Glu His Phe
305                 310                 315                 320

Pro Glu Asn Thr Cys Glu Ser Gly Ser Met Gln Met Gly Ser Pro Asp
325                 330                 335

Glu Tyr Cys Asp Asp Ser Asp Ile Tyr Met Asp Val Ser Ser Pro Asp
340                 345                 350

Ser Ser Ser Phe Glu Gln Asn Gln Ser Glu Asp Ile Cys Phe Lys Ser
355                 360                 365

Glu Ser Ser Thr Asp Ser Ser Pro Val Pro Ser Ser Arg Asn Ser Val
370                 375                 380

Pro Glu Asp Ala Asp Lys Tyr Leu Gly His Thr Pro Lys Gln Leu Pro
385                 390                 395                 400

Asp Ser Asn Ile Val Pro Phe Ser Asn Gln His Pro Phe Lys Asn Met
405                 410                 415

Leu Tyr Gln Lys Pro Pro Val Leu His Lys Gln Tyr Ala Tyr Arg Ser
```

-continued

```
                420                 425                 430
Glu Asn Ser Phe Ile Gln Gly Asn Ser Arg Gly Cys Phe Ser Ile
435                 440                 445

Asp Gly Asn Val Ala Ser Asp Leu Cys Val Leu Glu Gly Asn Gly Asn
450                 455                 460

Pro Val Pro Asp His Arg Ser Ser Phe Gln Gly Lys Phe His His Asn
465                 470                 475                 480

Phe Gln Gln Pro Met Tyr Gly Asn His Ile Ile Pro Thr Tyr Gly Gly
485                 490                 495

Met Arg Tyr Lys Pro His Asp Glu Arg Ile Thr Leu Arg Leu Ala Leu
500                 505                 510

Gln Asp Ile Ser Gln Pro Lys Thr Glu Ala Asn Pro Pro Asp Gly Val
515                 520                 525

Leu Ala Val Pro Leu Leu Arg His Gln Lys Ile Ala Leu Ser Trp Met
530                 535                 540

Val Gln Lys Glu Thr Ser Ser Ser His Cys Ser Gly Gly Ile Leu Ala
545                 550                 555                 560

Asp Asp Gln Gly Leu Gly Lys Thr Val Ser Ala Ile Ser Leu Ile Leu
565                 570                 575

Thr Glu Arg Ser Pro Val Pro Gln Ser Ser Thr Ile Lys Lys Glu Pro
580                 585                 590

Cys Glu Ala Val Asn Leu Asp Asp Asp Glu Asp Asp Cys Ala Glu
595                 600                 605

Pro His Leu Lys Lys Pro Thr Gln Lys Cys Ser Ser Glu Val Thr Ser
610                 615                 620

Asp Thr Ala Lys Gln Glu Asn Pro Phe Val Pro Val Lys Thr Arg Pro
625                 630                 635                 640

Ala Ala Gly Thr Leu Val Val Cys Pro Thr Ser Val Leu Arg Gln Trp
645                 650                 655

Ala Gly Glu Leu Lys Asn Lys Val Thr Ser Lys Ala Asn Leu Ser Phe
660                 665                 670

Leu Ile Tyr His Gly Ser Asn Arg Thr Lys Asp Pro Asn Glu Leu Thr
675                 680                 685

Lys Tyr Asp Val Val Leu Thr Thr Tyr Ser Ile Val Ser Met Glu Val
690                 695                 700

Pro Lys Gln Ser Asn Pro Asp Ser Asp Asp Glu Glu Lys Gly Lys Pro
705                 710                 715                 720

Asp Arg Tyr Gly Ala Pro Val Ser Ser Ser Gly Ser Lys Lys Arg Lys
725                 730                 735

Ala Ser Ser Ser Lys Lys Ser Lys Asn Lys Ser Val Ala Asp Asn Ser
740                 745                 750

Leu Pro Glu Lys Pro Leu Ala Lys Val Ala Trp Phe Arg Val Ile Leu
755                 760                 765

Asp Glu Ala Gln Ser Ile Lys Asn Tyr Arg Thr Gln Val Ala Arg Ala
770                 775                 780

Cys Trp Gly Leu Arg Ala Lys Arg Arg Trp Cys Leu Ser Gly Thr Pro
785                 790                 795                 800

Ile Gln Asn Ala Val Glu Asp Leu Tyr Ser Tyr Phe Arg Phe Leu Arg
805                 810                 815

Tyr Asp Pro Tyr Ala Val Tyr Lys Gln Phe Cys Thr Met Ile Lys Ile
820                 825                 830

Pro Ile Ser Arg Asn Pro Thr Asn Gly Tyr Lys Lys Leu Gln Val Val
835                 840                 845
```

-continued

```
Leu Lys Thr Val Met Leu Arg Arg Thr Lys Ala Thr Met Leu Asp Gly
850                 855                 860

Lys Pro Ile Ile Ser Leu Pro Pro Lys Thr Val Ser Leu Lys Thr Val
865                 870                 875                 880

Asp Phe Thr Ser Glu Glu Arg Ala Phe Tyr Asn Thr Leu Glu Val Glu
885                 890                 895

Ser Arg Glu Gln Phe Lys Glu Tyr Ala Ala Gly Thr Val Lys Gln
900                 905                 910

Asn Tyr Val Asn Ile Leu Leu Met Leu Leu Arg Leu Arg Gln Ala Cys
915                 920                 925

Asp His Pro His Leu Val Arg Gly Tyr Glu Ser Thr Ser Ser Trp Met
930                 935                 940

Ser Ser Leu Glu Met Ala Lys Lys Leu Pro Met Glu Arg Gln Gln Glu
945                 950                 955                 960

Leu Leu Val Cys Leu Gln Ser Cys Ser Ala Ile Cys Ala Leu Cys Asn
965                 970                 975

Asp Ala Pro Glu Asp Ala Val Val Thr Ile Cys Gly His Val Phe Cys
980                 985                 990

Asn Gln Cys Ile Leu Glu Gln Leu Thr Gly Asp Asp Ser Ile Cys Pro
995                 1000                1005

Val Ser Asn Cys Arg Val Arg  Leu Asn Thr Thr Ser  Leu Phe Ser
1010                1015                 1020

Arg Gly Thr Leu Glu Cys Ser  Leu Ser Arg Leu Thr  Cys Asp Phe
1025                1030                 1035

Lys Ser Asp Asp Thr Cys Met  Glu Met Leu His Val  Glu Lys Arg
1040                1045                 1050

Pro Gly Ile Asp Ser Ser Tyr  Ala Ser Ser Lys Val  Arg Ala Ala
1055                1060                 1065

Leu Asp Ile Leu Leu Ser Leu  Pro Arg Ile Asp Pro  Thr Gln Met
1070                1075                 1080

Ile Asp Ser Lys Asn Ser Ile  Arg Leu Asp Ser Glu  Lys Phe Gly
1085                1090                 1095

Gly Asn Gly Ser Ser Glu Gln  Thr Glu Thr Lys Phe  Thr Glu Lys
1100                1105                 1110

Ala Ile Val Phe Ser Gln Trp  Thr Arg Met Leu Asp  Leu Leu Glu
1115                1120                 1125

Val His Leu Lys Ala Ser His  Val Thr Tyr Arg Arg  Leu Asp Gly
1130                1135                 1140

Thr Met Ser Val Ala Ala Arg  Asp Lys Ala Val Asn  Asp Phe Asn
1145                1150                 1155

Thr Val Pro Glu Val Thr Val  Met Ile Met Ser Leu  Lys Ala Ala
1160                1165                 1170

Ser Leu Gly Leu Asn Met Val  Ala Ala Cys His Val  Leu Met Leu
1175                1180                 1185

Asp Leu Trp Trp Asn Pro Thr  Thr Glu Asp Gln Ala  Val Asp Arg
1190                1195                 1200

Ala His Arg Ile Gly Gln Thr  Arg Pro Val Leu Val  Ser Arg Leu
1205                1210                 1215

Thr Ile Lys Asp Thr Val Glu  Asp Arg Ile Leu Ala  Leu Gln Glu
1220                1225                 1230

Lys Lys Arg Glu Met Val Ala  Ser Ala Phe Gly Glu  Asp Arg Ser
1235                1240                 1245
```

Gly Ser Arg Gln Thr Arg Leu Thr Val Glu Asp Leu Asn Tyr Leu
1250                1255                1260

Phe Met Val
1265

<210> SEQ ID NO 39
<211> LENGTH: 4353
<212> TYPE: DNA
<213> ORGANISM: Arabidopsis lyrata

<400> SEQUENCE: 39

| | | | | | |
|---|---|---|---|---|---|
| cccaactgct | ctctaccttt | cctggaaaat | tccttcaaaa | cccaattcac | aagccttctt | 60 |
| cttcatacct | gaaaattctc | aaatctctgg | atctactctt | caacttctga | atttcgattg | 120 |
| ggttttccgg | taggtaaatt | ccgtgacttt | tgggttttcc | gatttagggt | ttgtttaatc | 180 |
| tcttctcgtc | ctttctcggg | ttagtgatgg | gtgaggaagg | ttcagtgttt | ggtatgggag | 240 |
| atgaatttca | cgttgatgat | tgtgatggtg | gttttgagtt | tgaagatgat | gacgagacta | 300 |
| ttgacatcga | aacgctttat | cggattctag | atgagaagcc | tgattctgct | gagggaagcc | 360 |
| aagaaaattt | atcaccagtt | ggttcatctg | ctgacgagct | caaggattca | cacttgcaaa | 420 |
| atggttcatt | tgatgaacat | gtgaaaatgg | aagccgggct | gagtccttca | cctgctcata | 480 |
| cttgctctgc | aagtcttaaa | gattggtttt | cgttaagtca | gggtgagcag | cctgtggaaa | 540 |
| catgtggagt | atctcaatct | gagatgacta | gttgtagtat | atcgtctagt | ttctctgatc | 600 |
| atgatggcaa | tatgatggcc | ttcaatcctg | acactgtttc | caagcaggat | gacaagataa | 660 |
| ttgattccaa | atttacatcg | cacagcccca | caatggcgac | tccatatttt | gatgatgtgc | 720 |
| ctggatacgg | agtggggttg | ggagccaatc | ataattcctc | tgtcatgtct | ggttttttaa | 780 |
| ataattccaa | ttctctcagt | gacagtgcgg | ataactatgt | ctcttctgca | aaagattgct | 840 |
| acaatacaag | tggaacatcc | ttgtcagacc | atacccccaa | ttttgtccac | aatttcgcgt | 900 |
| ttcagttctt | tcctaataaa | gaagaagctg | taattgatgt | tgagagtgga | gtaagtgagt | 960 |
| cccagtcgga | tggtgccagc | cggatgattt | ttgatagaca | tggcagagtg | gatcatggat | 1020 |
| ctttagaaag | taaacctcct | attgattttt | ctagtgcaag | agggatcagt | ttcaagtttg | 1080 |
| aaagtaatcc | ttcagtttct | cctgcctgtg | tcaaaccgta | caacagtttt | gacagtcatt | 1140 |
| tagctgataa | tgaccttgac | cggccggata | ttattcaag | cagttttcag | gataataaag | 1200 |
| ctgttcatgt | gacggttaaa | ccagaggttg | agtcagagaa | agtggtctac | agttcagttc | 1260 |
| caggggaata | tagtgtcagg | gacgatgctt | atgtttctgg | agaaaccaat | ccttggtggt | 1320 |
| ctggtgcatc | aagctctgca | gcctcctatc | aaacagatat | tgagaaagga | tactcgtata | 1380 |
| tggcaccgca | aacagctcta | cctagccaag | acagtggcga | tagaagcgcc | aatcattttt | 1440 |
| atgattcaga | tacatgtttg | caatatgttg | cagaagatcc | cagcccagtg | acacaaagca | 1500 |
| gtgagtattt | agactttcaa | attcaaggag | gccatgaata | tgttcaaccg | aggggcattg | 1560 |
| attctaattt | ctcaaatgcc | agctttgaat | cagttcaaag | tcattcttca | gaatgtatat | 1620 |
| ccgatagtga | tgatgattct | gacatctgca | taatagaacc | taatggccaa | tctgcaatcc | 1680 |
| cacatcgacc | actagctatg | aaaaagccgc | tagtttcttc | agaatattct | acagttggtc | 1740 |
| ataattacaa | tcaatctgga | ggcctgaagc | ttcagtcaaa | taagaaaat | atgatctttc | 1800 |
| aagctgcatt | gcaggatctc | tctcagccta | attctgaagc | aagtccgcct | gatggtgtct | 1860 |
| tgacagtccc | gcttctgaga | catcagcgaa | ttgcattgtc | atggatggcc | cagaaggaga | 1920 |
| caagtggctt | ccctgttct | ggaggaattc | ttgctgatga | tcagggtctt | gggaagacag | 1980 |

```
tttccactat agctcttata ctgaaggaaa ggtctaaacc tgcccaaaca tgtgaagaaa    2040
gtatgaaaaa agaaatttttt gacctagaaa gtgagagtgg agaatgtgca cctttaaaga    2100
ccagtggaaa aagtgagcat tttgaacact ctcaattgct ttccaatgaa aacaaagttg    2160
gtcgagatag tgtgggtaaa gtgaggggaa ggccagctgc tggaacactc gttgtctgtc    2220
ccactagtgt tatgcggcag tgggctgatg aattacataa gaaggtgact agtgaagcga    2280
atctctctgt tctggtatac catgggtcta gcagaacaaa ggatccttat gagttggcta    2340
aatatgatgt tgttgttacc acattttcta ttgtaagtat ggaagtgcca aagcagcctc    2400
ttgttgatga tgaggacgaa gagaaggatg tgtgtacagga tgggggaact gcagctactg    2460
gcttttgctc aaacaagaaa aggaaatatc ctccggattc taaaaagagg ggctcaaaga    2520
agaagaaaca agttgagttt ctgtctggcc ctcttgcgaa agtttcatgg tttagagttg    2580
ttctagatga ggcacagagc attaagaatt acaaaaccca agttgcaaga gcatgctggg    2640
ggcttcgtgc taaacggagg tggtgttttgt ctggcactcc aatccagaat tcaatcgatg    2700
acctctacag ctactttcga ttcctcaaat atgatcctta ttcttcctac gtattgttct    2760
gtagcacgat taagaaccct ataactagga acccggtgaa aggatatcag aagctgcagg    2820
ctatccttaa aacagtgatg cttcgccgaa ctaaaggttc atttcttgat gggaaaccca    2880 taatttctttt acctccgaag tccattgagc tgagaaaagt ggatttcact gtggaggaac    2940
gtgatttcta ctccaaacta gaggctgaat ctcgtactca attcagggaa tatgcagaag    3000
ccggaacagt gaagcaaaat tatgtaaata tcttgttgat gctcttgcgc cttcgccaag    3060
cttgtgatca ccctcttctg gtgaatggtg aatacagttt tacatgggaa tcttctgttg    3120
gattagcaaa gaaacagatt cagtcagaag cttcattggc aatttgtggt atctgcaatg    3180
atgcacctga agatgctgtt gtttcagtct gtggtcatgt tttctgtaaa cagtgcattt    3240
atgaacgcct tactggtgat aataatcact gtccccttgc aaactgcaat gtcagactca    3300
ccatctcatc attatcttcc aaaacgagat cggacgatgc tatgcctgac atgcaggatc    3360
gtgccgcttc gaatagcctt agcccctgtt ctgatgaaga tcttccatat ggttcatcta    3420
aaatcaaggc tgctctagag atcttacaat cactgcccaa accacaggat ttgacagata    3480
caaatcagat ctctcaaaac agtgaatact ccagtcttcc tgtaactcca gttaagaatg    3540
agggtattag cgttgttgtt ccggttaagg tagctggaga aaaggccatt gtttttttccc    3600 aatggaccaa gatgctagac ctacttgaag cttctcttgt aagttcacat attcagtata    3660
gaaggcttga tggaacaatg tcagttgctg ctcgagataa agcagtgcag gatttcaaca    3720
ctctccctga ggtaactgta atgataatgt ctctcaaggc tgctagtctt ggactgaata    3780
tggtagcagc ttgtcatgtt ctgatgctgg atttatggtg gaacccaaca accgaggatc    3840
aagcaattga tagagcacat cgtataggac agacacgacc agtaacagtc gttcggttca    3900
cagtaaaaga tacagtcgaa gatcggatat tagcccttca gcaaaagaaa agaatgatgg    3960
tagcctctgc atttggagaa gatgaaaagg gaagccgaca gtctcacctc accgtagagg    4020
acttgagcta tctgtttatg gctgattcat gagaacgagc ttcaagctcc ttttttgacca    4080 atgcgggcgg gtacatatga tagggtttttt gtgcagttttt aggaggaaga aactcttcgt    4140
ttaactgact acaggtttgt gcaaaagaaa gattagaaaa gactattggg gtttgggata    4200
taaaaataga aagctgatcc gatttgatta ttggttccat ttagacttta ggtattgaca    4260
attaatggaa gatgacaata tacaggagca tttgctattg aatttatcat tgtacgatca    4320
```

```
caatgtgatt ggtccggcga gttataatag ctt                                    4353
```

<210> SEQ ID NO 40
<211> LENGTH: 1281
<212> TYPE: PRT
<213> ORGANISM: Arabidopsis lyrata

<400> SEQUENCE: 40

| | | | | | | | | | | | | | | |
|---|---|---|---|---|---|---|---|---|---|---|---|---|---|---|
| Met | Gly | Glu | Glu | Gly | Ser | Val | Phe | Gly | Met | Gly | Asp | Glu | Phe | His | Val |
| 1 | | | | 5 | | | | | 10 | | | | | 15 | |
| Asp | Asp | Cys | Asp | Gly | Gly | Phe | Glu | Phe | Glu | Asp | Asp | Glu | Thr | Ile | |
| | 20 | | | | 25 | | | | | 30 | | | | | |
| Asp | Ile | Glu | Thr | Leu | Tyr | Arg | Ile | Leu | Asp | Glu | Lys | Pro | Asp | Ser | Ala |
| 35 | | | | | 40 | | | | | 45 | | | | | |
| Glu | Gly | Ser | Gln | Glu | Asn | Leu | Ser | Pro | Val | Gly | Ser | Ser | Ala | Asp | Glu |
| 50 | | | | | 55 | | | | | 60 | | | | | |
| Leu | Lys | Asp | Ser | His | Leu | Gln | Asn | Gly | Ser | Phe | Asp | Glu | His | Val | Lys |
| 65 | | | | | 70 | | | | | 75 | | | | | 80 |
| Met | Glu | Ala | Gly | Leu | Ser | Pro | Ser | Pro | Ala | His | Thr | Cys | Ser | Ala | Ser |
| | 85 | | | | | 90 | | | | | 95 | | | | |
| Leu | Lys | Asp | Trp | Phe | Ser | Leu | Ser | Gln | Gly | Glu | Gln | Pro | Val | Glu | Thr |
| 100 | | | | | 105 | | | | | 110 | | | | | |
| Cys | Gly | Val | Ser | Gln | Ser | Glu | Met | Thr | Ser | Cys | Ser | Ile | Ser | Ser | Ser |
| 115 | | | | | 120 | | | | | 125 | | | | | |
| Phe | Ser | Asp | His | Asp | Gly | Asn | Met | Met | Ala | Phe | Asn | Pro | Asp | Thr | Val |
| 130 | | | | | 135 | | | | | 140 | | | | | |
| Ser | Lys | Gln | Asp | Asp | Lys | Ile | Ile | Asp | Ser | Lys | Phe | Thr | Ser | His | Ser |
| 145 | | | | | 150 | | | | | 155 | | | | | 160 |
| Pro | Thr | Met | Ala | Thr | Pro | Tyr | Phe | Asp | Asp | Val | Pro | Gly | Tyr | Gly | Val |
| | 165 | | | | | 170 | | | | | 175 | | | | |
| Gly | Leu | Gly | Ala | Asn | His | Asn | Ser | Ser | Val | Met | Ser | Gly | Phe | Leu | Asn |
| | 180 | | | | | 185 | | | | | 190 | | | | |
| Asn | Ser | Asn | Ser | Leu | Ser | Asp | Ser | Ala | Asp | Asn | Tyr | Val | Ser | Ser | Ala |
| 195 | | | | | 200 | | | | | 205 | | | | | |
| Lys | Asp | Cys | Tyr | Asn | Thr | Ser | Gly | Thr | Ser | Leu | Ser | Asp | His | Thr | Pro |
| 210 | | | | | 215 | | | | | 220 | | | | | |
| Asn | Phe | Val | His | Asn | Phe | Ala | Phe | Gln | Phe | Phe | Pro | Asn | Lys | Glu | Glu |
| 225 | | | | | 230 | | | | | 235 | | | | | 240 |
| Ala | Val | Ile | Asp | Val | Glu | Ser | Gly | Val | Ser | Glu | Ser | Gln | Ser | Asp | Gly |
| | 245 | | | | | 250 | | | | | 255 | | | | |
| Ala | Ser | Arg | Met | Ile | Phe | Asp | Arg | His | Gly | Arg | Val | Asp | His | Gly | Ser |
| | 260 | | | | | 265 | | | | | 270 | | | | |
| Leu | Glu | Ser | Lys | Pro | Pro | Ile | Asp | Phe | Ser | Ala | Arg | Gly | Ile | Ser | |
| 275 | | | | | 280 | | | | | 285 | | | | | |
| Phe | Lys | Phe | Glu | Ser | Asn | Pro | Ser | Val | Ser | Pro | Ala | Cys | Val | Lys | Pro |
| 290 | | | | | 295 | | | | | 300 | | | | | |
| Tyr | Asn | Ser | Phe | Asp | Ser | His | Leu | Ala | Asp | Asn | Asp | Leu | Asp | Arg | Pro |
| 305 | | | | | 310 | | | | | 315 | | | | | 320 |
| Asp | Asn | Tyr | Ser | Ser | Ser | Phe | Gln | Asp | Asn | Lys | Ala | Val | His | Val | Thr |
| | 325 | | | | | 330 | | | | | 335 | | | | |
| Val | Lys | Pro | Glu | Val | Glu | Ser | Glu | Lys | Val | Val | Tyr | Ser | Ser | Val | Pro |
| | 340 | | | | | 345 | | | | | 350 | | | | |
| Gly | Glu | Tyr | Ser | Val | Arg | Asp | Asp | Ala | Tyr | Val | Ser | Gly | Glu | Thr | Asn |
| | 355 | | | | | 360 | | | | | 365 | | | | |

```
Pro Trp Trp Ser Gly Ala Ser Ser Ser Ala Ser Tyr Gln Thr Asp
370                 375                 380

Ile Glu Lys Gly Tyr Ser Tyr Met Ala Pro Gln Thr Ala Leu Pro Ser
385                 390                 395                 400

Gln Asp Ser Gly Asp Arg Ser Ala Asn His Phe Tyr Asp Ser Asp Thr
405                 410                 415

Cys Leu Gln Tyr Val Ala Glu Asp Pro Ser Pro Val Thr Gln Ser Ser
420                 425                 430

Glu Tyr Leu Asp Phe Gln Ile Gln Gly Gly His Glu Tyr Val Gln Pro
435                 440                 445

Arg Gly Ile Asp Ser Asn Phe Ser Asn Ala Ser Phe Glu Ser Val Gln
450                 455                 460

Ser His Ser Ser Glu Cys Ile Ser Asp Ser Asp Asp Ser Asp Ile
465                 470                 475                 480

Cys Ile Ile Glu Pro Asn Gly Gln Ser Ala Ile Pro His Arg Pro Leu
485                 490                 495

Ala Met Lys Lys Pro Leu Val Ser Ser Glu Tyr Ser Thr Val Gly His
500                 505                 510

Asn Tyr Asn Gln Ser Gly Gly Leu Lys Leu Gln Ser Asn Lys Glu Asn
515                 520                 525

Met Ile Phe Gln Ala Ala Leu Gln Asp Leu Ser Gln Pro Asn Ser Glu
530                 535                 540

Ala Ser Pro Pro Asp Gly Val Leu Thr Val Pro Leu Leu Arg His Gln
545                 550                 555                 560

Arg Ile Ala Leu Ser Trp Met Ala Gln Lys Glu Thr Ser Gly Phe Pro
565                 570                 575

Cys Ser Gly Gly Ile Leu Ala Asp Asp Gln Gly Leu Gly Lys Thr Val
580                 585                 590

Ser Thr Ile Ala Leu Ile Leu Lys Glu Arg Ser Lys Pro Ala Gln Thr
595                 600                 605

Cys Glu Glu Ser Met Lys Lys Glu Ile Phe Asp Leu Glu Ser Glu Ser
610                 615                 620

Gly Glu Cys Ala Pro Leu Lys Thr Ser Gly Lys Ser Glu His Phe Glu
625                 630                 635                 640

His Ser Gln Leu Leu Ser Asn Glu Asn Lys Val Gly Arg Asp Ser Val
645                 650                 655

Gly Lys Val Arg Gly Arg Pro Ala Ala Gly Thr Leu Val Val Cys Pro
660                 665                 670

Thr Ser Val Met Arg Gln Trp Ala Asp Glu Leu His Lys Lys Val Thr
675                 680                 685

Ser Glu Ala Asn Leu Ser Val Leu Val Tyr His Gly Ser Ser Arg Thr
690                 695                 700

Lys Asp Pro Tyr Glu Leu Ala Lys Tyr Asp Val Val Thr Thr Phe
705                 710                 715                 720

Ser Ile Val Ser Met Glu Val Pro Lys Gln Pro Leu Val Asp Asp Glu
725                 730                 735

Asp Glu Glu Lys Asp Gly Val Gln Asp Gly Gly Thr Ala Ala Thr Gly
740                 745                 750

Phe Cys Ser Asn Lys Lys Arg Lys Tyr Pro Pro Asp Ser Lys Lys Arg
755                 760                 765

Gly Ser Lys Lys Lys Gln Val Glu Phe Leu Ser Gly Pro Leu Ala
770                 775                 780

Lys Val Ser Trp Phe Arg Val Val Leu Asp Glu Ala Gln Ser Ile Lys
```

```
                785                 790                 795                 800
Asn Tyr Lys Thr Gln Val Ala Arg Ala Cys Trp Gly Leu Arg Ala Lys
805                 810                 815

Arg Arg Trp Cys Leu Ser Gly Thr Pro Ile Gln Asn Ser Ile Asp Asp
820                 825                 830

Leu Tyr Ser Tyr Phe Arg Phe Leu Lys Tyr Asp Pro Tyr Ser Ser Tyr
835                 840                 845

Val Leu Phe Cys Ser Thr Ile Lys Asn Pro Ile Thr Arg Asn Pro Val
850                 855                 860

Lys Gly Tyr Gln Lys Leu Gln Ala Ile Leu Lys Thr Val Met Leu Arg
865                 870                 875                 880

Arg Thr Lys Gly Ser Phe Leu Asp Gly Lys Pro Ile Ile Ser Leu Pro
885                 890                 895

Pro Lys Ser Ile Glu Leu Arg Lys Val Asp Phe Thr Val Glu Glu Arg
900                 905                 910

Asp Phe Tyr Ser Lys Leu Glu Ala Glu Ser Arg Thr Gln Phe Arg Glu
915                 920                 925

Tyr Ala Glu Ala Gly Thr Val Lys Gln Asn Tyr Val Asn Ile Leu Leu
930                 935                 940

Met Leu Leu Arg Leu Arg Gln Ala Cys Asp His Pro Leu Leu Val Asn
945                 950                 955                 960

Gly Glu Tyr Ser Phe Thr Trp Glu Ser Ser Val Gly Leu Ala Lys Lys
965                 970                 975

Gln Ile Gln Ser Glu Ala Ser Leu Ala Ile Cys Gly Ile Cys Asn Asp
980                 985                 990

Ala Pro Glu Asp Ala Val Val Ser  Val Cys Gly His Val  Phe Cys Lys
995                 1000                 1005

Gln Cys  Ile Tyr Glu Arg Leu  Thr Gly Asp Asn Asn  His Cys Pro
1010                 1015                 1020

Leu Ala  Asn Cys Asn Val Arg  Leu Thr Ile Ser Ser  Leu Ser Ser
1025                 1030                 1035

Lys Thr  Arg Ser Asp Asp Ala  Met Pro Asp Met Gln  Asp Arg Ala
1040                 1045                 1050

Ala Ser  Asn Ser Leu Ser Pro  Cys Ser Asp Glu Asp  Leu Pro Tyr
1055                 1060                 1065

Gly Ser  Ser Lys Ile Lys Ala  Ala Leu Glu Ile Leu  Gln Ser Leu
1070                 1075                 1080

Pro Lys  Pro Gln Asp Leu Thr  Asp Thr Asn Gln Ile  Ser Gln Asn
1085                 1090                 1095

Ser Glu  Tyr Ser Ser Leu Pro  Val Thr Pro Val Lys  Asn Glu Gly
1100                 1105                 1110

Ile Ser  Val Val Val Pro Val  Lys Val Ala Gly Glu  Lys Ala Ile
1115                 1120                 1125

Val Phe  Ser Gln Trp Thr Lys  Met Leu Asp Leu Leu  Glu Ala Ser
1130                 1135                 1140

Leu Val  Ser Ser His Ile Gln  Tyr Arg Arg Leu Asp  Gly Thr Met
1145                 1150                 1155

Ser Val  Ala Ala Arg Asp Lys  Ala Val Gln Asp Phe  Asn Thr Leu
1160                 1165                 1170

Pro Glu  Val Thr Val Met Ile  Met Ser Leu Lys Ala  Ala Ser Leu
1175                 1180                 1185

Gly Leu  Asn Met Val Ala Ala  Cys His Val Leu Met  Leu Asp Leu
1190                 1195                 1200
```

```
Trp Trp  Asn Pro Thr  Thr Glu  Asp Gln Ala  Ile Asp  Arg Ala His
1205              1210              1215

Arg Ile  Gly Gln Thr  Arg Pro  Val Thr Val  Val Arg  Phe Thr Val
1220              1225              1230

Lys Asp  Thr Val Glu  Asp Arg  Ile Leu Ala  Leu Gln  Gln Lys Lys
1235              1240              1245

Arg Met  Met Val Ala  Ser Ala  Phe Gly Glu  Asp Glu  Lys Gly Ser
1250              1255              1260

Arg Gln  Ser His Leu  Thr Val  Glu Asp Leu  Ser Tyr  Leu Phe Met
1265              1270              1275

Ala Asp  Ser
1280

<210> SEQ ID NO 41
<211> LENGTH: 3926
<212> TYPE: DNA
<213> ORGANISM: Arabidopsis lyrata

<400> SEQUENCE: 41
atgagtgaga aggattcagt atttcagtcg caagcggatg attactctgg tggctttgga      60
tttggagccg aagacgagga ttttatgatt gacattgacg cgatttatag gattcttgat     120
gagaagcctg attctatgga ggttagtgaa gaaaatatga ctcaagttgg ttcatatgct     180
gtagagtctg acgagcttac gaacacactg acgcaaagtg gatctcaggc cactggttgg     240
tttccttacc cggatttgta tggtcctgaa gcctcacaaa gtgaaacagc agtgcaaagt     300
tcatttgctg acccagagaa tggaggattg ggaccaagtg cgacttgttt ctctgactat     360
ggtggcaatg tggtctccta tcctgtgaat tgtgaagatg caatgtatc caacctgtat      420 gacatgagaa ttgattccaa atttacacct tgcagttcca ctatgatgac tccctatttc     480
aataccatgc ctggaaatga ctcaggaatt ggagctacgc aaaattcctc cctggtgtct     540
catttccatt ataattacag ttctattatt gattgtgcct cttctgaacc atatggccac     600
catacaatgg atgcacccct tatcagaagt tccccccaat tggttccagg ttacgcattt     660
cagttctttc caataagga gaacttata atgatttga agagtgcgtt tatccactgt      720
cagtcagatg gtgcaagccg atggttttt gacaaacatg taggatttga taatggaact      780
tcggagagga attctgggcc tgatgtgagc agtgaaaaga aactcagcat caaatatgaa     840
atcattcctt cagtttcccc tgcctgtgtc aatccataca atagttttga tgggcatcaa     900
gttgataagg agcttgagca gccttccaat tgttcaagca gttttcagga agatgaagca     960
gtccctgtga aggttaaacc agagcttgac ctggagaaca cggttttcag tacagttcct    1020
gggaactata gtatatgtag tgatgttcat acagttggag aacgacact gcaatggtct    1080 ggtgtctcta ttgcgcaat ctcctatcag gcagatgtcg ggaagaata cccatctatc     1140 ccacctcaga ctgctttccc tggtcaagat attgacggca ggagcttcta taattgtttt    1200
gtttcagatg actgtttgca aaacgtaaca gatcctgacc cagcaacatc acgcactgag    1260
tctttggatt atctggtagg agacgaggac catgaatata ttgggaggac aggctttaat    1320 cttttctagtc tcagctctgg aacagttgaa agtctttcat caaaacgtat accgaagga    1380 gatgatgatt ctgaaatcca taaaatagaa tcctatggtg aatttgttaa tccacaccaa    1440
tatctagctg tgcagagacc agtgtttct tcagaacatt ctacaggtag tcaaactctt    1500
aataattgtg gaggcttgaa gtttgagtca acaagggaa acatgaattt tcatgcagac    1560
```

```
ttgcaggttc tttctcagcc tcgttctgaa gcaagtcctc ctgaaggtgt cttggcagtc    1620
tcgcttctta gacatcagcg gattgcattg gcgtggatgt ccgaaaagga gacaagcggg    1680
aaccccctgtt ttgggggat tcttgctgat gatcagggac ttggaaaaac agtttccaca    1740
atagcgctta tactgacaga acggtctaca ccttatctac catgtgaaga agattcaaag    1800
aatggaggaa gcaatcaatt tgatcactct caagtggttt tcaatgaaaa caaagtcggc    1860
gaagatagtt tatgcaagat gaggggaagg ccagctgccg gaactcttat tgtctgtccc    1920
actagtctga tgagacaatg ggctgatgaa ttatgcaaga aggttactct tgaagcaaat    1980
ctatctgttc tggtgtacca cggttgcaac agaacaaagg atcctcacga gctagctaaa    2040
tatgatgttg tcattaccac atattccctt gtgagcaaga ggaaacatat ggattgtgaa    2100
cctgttgagt ttctgtctgg ccctctcgcg caagtttcat ggtatagagt tgttcttgat    2160
gaagctcaga gcattaagaa ttacaaaacc caagcttcaa cggcatgttc aggccttcat    2220
gctaagcgta ggtggtgttt gtctggcact cctatccaga attcaattga tgacctctac    2280
agctacttca gattccttaa gtatgattct tattcttgct accaaacatt ttgtgaaacg    2340
attaagaacc caatcagtag ctacccggtg aaaggatatc aaacgttgca ggctatcctg    2400
aaaaaaataa tgcttagacg aactaaagat acacttcttg atggaaaacc ggtaatctct    2460
ttacctccga agtccattga gctgaggaga gtggacttta ccaaggaaga acgtgatttc    2520
tactcaaaac tagagtgcga ctctcgtgac caattcaagg aatatgcaga agctggaacg    2580
gtgaagcaaa attatgtaaa tattttgttg atgttgctgc gtcttcgtca agcgtgtggt    2640
caccctcttc tggtatccag tttggcatgg tcatcctcag ctgaaatggc taaaaagctt    2700
ccatatgaga agctaacctt tcttctgcat agcttagaag cttcactggc attttgtggt    2760
atctgcaatg gtgcacctaa agatgctgtt gtttcagtct gtggtcacgt tttctgtaaa    2820
cagtgcattt atgaatgcct tactcacgac aataatcaat gcccactgtc actctgcaaa    2880
gtcggagttg aaatttcatc attattttcc agagaaacac tggaaaatgc tatgcttggc    2940
ttgcataaac ttgatgctcc atgtgatcgt accacttcag atcctgttgg gagtggtgag    3000
ccttgtattg aaaatttacc atgtggttca tccaaaatca aggctgctct agatatcttg    3060
caatcactga gtagaccaca gagtccgacg actgtaatga atgatgtgga tcagagctcc    3120
gaaaatggag agaagaatca gcagcttgag aagtcattta gtttacctgc aactccagcg    3180
aagagtagcg tggatggtct ggttaaggta gttggagaaa aggccattgt gtttacccaa    3240
tggacaaaga tgctggacct gcttgaagct ggtcttaaga gttcgggtat tcagtataga    3300
aggtttgatg ggaaaatgac ggtaccagct agagatgcag cagtaagaga ttttaatact    3360
ctccctgagg tttctgtaat gataatgtct ctcaaagctg ctagtcttgg gctaaatatg    3420
gttgctgctt gtcatgttat aatgttggac ttatggtgga acccgactac agaagaccag    3480
gcaattgaca gagctcaccg tattggacag acacgaccag taaaagtggt gcggttcaca    3540
gtaaaagata cagttgaaga tcgcatattg gccctccagc aaaggaagag aatgatggtg    3600
gcttctgcat tcggagaaca tgaaaagggt agtcgagaat cgcatctctc tgtggaggat    3660
ttgaactatc tgttcatggc atgagaggtc gatccaatcg aaagcttttc tgacaaactc    3720
aggtacatat ataggatttc cgggtttgtg cagttcaaca gcagaagaaa tctttggaac    3780
taattacagt tatgtgcaaa gaaggaagta gaaaaagatt agctttgccc tgtgtatata    3840
gaatgaaatt gaacattatc aagaaaaatc tgcaagaaca atgtgtacat caatttctag    3900
tcacttaatc caaatactgt tccatg                                         3926
```

<210> SEQ ID NO 42
<211> LENGTH: 1227
<212> TYPE: PRT
<213> ORGANISM: Arabidopsis lyrata

<400> SEQUENCE: 42

```
Met Ser Glu Lys Asp Ser Val Phe Gln Ser Gln Ala Asp Asp Tyr Ser
1               5                   10                  15

Gly Gly Phe Gly Phe Gly Ala Glu Asp Glu Asp Phe Met Ile Asp Ile
            20                  25                  30

Asp Ala Ile Tyr Arg Ile Leu Asp Glu Lys Pro Asp Ser Met Glu Val
        35                  40                  45

Ser Glu Glu Asn Met Thr Gln Val Gly Ser Tyr Ala Val Glu Ser Asp
    50                  55                  60

Glu Leu Thr Asn Thr Leu Thr Gln Ser Gly Ser Gln Ala Thr Gly Trp
65                  70                  75                  80

Phe Pro Tyr Pro Asp Leu Tyr Gly Pro Glu Ala Ser Gln Ser Glu Thr
                85                  90                  95

Ala Val Gln Ser Ser Phe Ala Asp Pro Glu Asn Gly Gly Leu Gly Pro
            100                 105                 110

Ser Ala Thr Cys Phe Ser Asp Tyr Gly Gly Asn Val Val Ser Tyr Pro
        115                 120                 125

Val Asn Cys Glu Asp Gly Asn Val Ser Asn Leu Tyr Asp Met Arg Ile
    130                 135                 140

Asp Ser Lys Phe Thr Pro Cys Ser Ser Thr Met Met Thr Pro Tyr Phe
145                 150                 155                 160

Asn Thr Met Pro Gly Asn Asp Ser Gly Ile Gly Ala Thr Gln Asn Ser
                165                 170                 175

Ser Leu Val Ser His Phe His Tyr Asn Tyr Ser Ser Ile Ile Asp Cys
            180                 185                 190

Ala Ser Ser Glu Pro Tyr Gly His His Thr Met Asp Ala Pro Leu Ser
        195                 200                 205

Glu Val Ser Pro Asn Leu Val Pro Gly Tyr Ala Phe Gln Phe Phe Pro
    210                 215                 220

Asn Lys Glu Glu Leu Ile Asn Asp Leu Lys Ser Ala Phe Ile His Cys
225                 230                 235                 240

Gln Ser Asp Gly Ala Ser Arg Met Val Phe Asp Lys His Val Gly Phe
                245                 250                 255

Asp Asn Gly Thr Ser Glu Arg Asn Ser Gly Pro Asp Val Ser Ser Glu
            260                 265                 270

Arg Glu Leu Ser Ile Lys Tyr Glu Ile Ile Pro Ser Val Ser Pro Ala
        275                 280                 285

Cys Val Asn Pro Tyr Asn Ser Phe Asp Gly His Gln Val Asp Lys Glu
    290                 295                 300

Leu Glu Gln Pro Ser Asn Cys Ser Ser Ser Phe Gln Glu Asn Glu Ala
305                 310                 315                 320

Val Pro Val Lys Val Lys Pro Glu Leu Asp Leu Glu Asn Thr Val Phe
                325                 330                 335

Ser Thr Val Pro Gly Asn Tyr Ser Ile Cys Ser Asp Val His Thr Val
            340                 345                 350

Gly Gly Thr Thr Leu Gln Trp Ser Gly Val Ser Asn Cys Ala Ile Ser
        355                 360                 365

Tyr Gln Ala Asp Val Gly Lys Glu Tyr Pro Ser Ile Pro Pro Gln Thr
```

```
                370             375                 380
Ala Phe Pro Gly Gln Asp Ile Asp Gly Arg Ser Phe Tyr Asn Cys Phe
385                 390                 395                 400

Val Ser Asp Asp Cys Leu Gln Asn Val Thr Asp Pro Asp Pro Ala Thr
405                 410                 415

Ser Arg Thr Glu Ser Leu Asp Tyr Leu Val Gly Asp Glu Asp His Glu
420                 425                 430

Tyr Ile Gly Arg Thr Gly Phe Asn Leu Ser Ser Leu Ser Ser Gly Thr
435                 440                 445

Val Glu Ser Leu Ser Ser Lys Arg Ile Pro Glu Gly Asp Asp Asp Ser
450                 455                 460

Glu Ile His Lys Ile Glu Ser Tyr Gly Glu Phe Val Asn Pro His Gln
465                 470                 475                 480

Tyr Leu Ala Val Gln Arg Pro Val Phe Ser Ser Glu His Ser Thr Gly
485                 490                 495

Ser Gln Thr Leu Asn Asn Cys Gly Gly Leu Lys Phe Glu Ser Asn Lys
500                 505                 510

Gly Asn Met Asn Phe His Ala Asp Leu Gln Val Leu Ser Gln Pro Arg
515                 520                 525

Ser Glu Ala Ser Pro Pro Glu Gly Val Leu Ala Val Ser Leu Leu Arg
530                 535                 540

His Gln Arg Ile Ala Leu Ala Trp Met Ser Glu Lys Glu Thr Ser Gly
545                 550                 555                 560

Asn Pro Cys Phe Gly Gly Ile Leu Ala Asp Asp Gln Gly Leu Gly Lys
565                 570                 575

Thr Val Ser Thr Ile Ala Leu Ile Leu Thr Glu Arg Ser Thr Pro Tyr
580                 585                 590

Leu Pro Cys Glu Glu Asp Ser Lys Asn Gly Gly Ser Asn Gln Phe Asp
595                 600                 605

His Ser Gln Val Val Phe Asn Glu Asn Lys Val Gly Glu Asp Ser Leu
610                 615                 620

Cys Lys Met Arg Gly Arg Pro Ala Ala Gly Thr Leu Ile Val Cys Pro
625                 630                 635                 640

Thr Ser Leu Met Arg Gln Trp Ala Asp Glu Leu Cys Lys Lys Val Thr
645                 650                 655

Leu Glu Ala Asn Leu Ser Val Leu Val Tyr His Gly Cys Asn Arg Thr
660                 665                 670

Lys Asp Pro His Glu Leu Ala Lys Tyr Asp Val Val Ile Thr Thr Tyr
675                 680                 685

Ser Leu Val Ser Lys Arg Lys His Met Asp Cys Glu Pro Val Glu Phe
690                 695                 700

Leu Ser Gly Pro Leu Ala Gln Val Ser Trp Tyr Arg Val Val Leu Asp
705                 710                 715                 720

Glu Ala Gln Ser Ile Lys Asn Tyr Lys Thr Gln Ala Ser Thr Ala Cys
725                 730                 735

Ser Gly Leu His Ala Lys Arg Arg Trp Cys Leu Ser Gly Thr Pro Ile
740                 745                 750

Gln Asn Ser Ile Asp Asp Leu Tyr Ser Tyr Phe Arg Phe Leu Lys Tyr
755                 760                 765

Asp Ser Tyr Ser Cys Tyr Gln Thr Phe Cys Glu Thr Ile Lys Asn Pro
770                 775                 780

Ile Ser Ser Tyr Pro Val Lys Gly Tyr Gln Thr Leu Gln Ala Ile Leu
785                 790                 795                 800
```

```
Lys Lys Ile Met Leu Arg Arg Thr Lys Asp Thr Leu Leu Asp Gly Lys
805                 810                 815

Pro Val Ile Ser Leu Pro Pro Lys Ser Ile Glu Leu Arg Arg Val Asp
820                 825                 830

Phe Thr Lys Glu Glu Arg Asp Phe Tyr Ser Lys Leu Glu Cys Asp Ser
835                 840                 845

Arg Asp Gln Phe Lys Glu Tyr Ala Glu Ala Gly Thr Val Lys Gln Asn
850                 855                 860

Tyr Val Asn Ile Leu Leu Met Leu Leu Arg Leu Arg Gln Ala Cys Gly
865                 870                 875                 880

His Pro Leu Leu Val Ser Ser Leu Ala Trp Ser Ser Ser Ala Glu Met
885                 890                 895

Ala Lys Lys Leu Pro Tyr Glu Lys Leu Thr Phe Leu Leu His Ser Leu
900                 905                 910

Glu Ala Ser Leu Ala Phe Cys Gly Ile Cys Asn Gly Ala Pro Lys Asp
915                 920                 925

Ala Val Ser Val Cys Gly His Val Phe Cys Lys Gln Cys Ile Tyr
930                 935                 940

Glu Cys Leu Thr His Asp Asn Asn Gln Cys Pro Leu Ser Leu Cys Lys
945                 950                 955                 960

Val Gly Val Glu Ile Ser Ser Leu Phe Ser Arg Glu Thr Leu Glu Asn
965                 970                 975

Ala Met Leu Gly Leu His Lys Leu Asp Ala Pro Cys Asp Arg Thr Thr
980                 985                 990

Ser Asp Pro Val Gly Ser Gly Glu  Pro Cys Ile Glu Asn  Leu Pro Cys
995                 1000                 1005

Gly Ser  Ser Lys Ile Lys Ala  Ala Leu Asp Ile Leu  Gln Ser Leu
1010                1015                 1020

Ser Arg  Pro Gln Ser Pro Thr  Thr Val Met Asn Asp  Val Asp Gln
1025                1030                 1035

Ser Ser  Glu Asn Gly Glu Lys  Asn Gln Gln Leu Glu  Lys Ser Phe
1040                1045                 1050

Ser Leu  Pro Ala Thr Pro Ala  Lys Ser Ser Val Asp  Gly Leu Val
1055                1060                 1065

Lys Val  Val Gly Glu Lys Ala  Ile Val Phe Thr Gln  Trp Thr Lys
1070                1075                 1080

Met Leu  Asp Leu Leu Glu Ala  Gly Leu Lys Ser Ser  Gly Ile Gln
1085                1090                 1095

Tyr Arg  Arg Phe Asp Gly Lys  Met Thr Val Pro Ala  Arg Asp Ala
1100                1105                 1110

Ala Val  Arg Asp Phe Asn Thr  Leu Pro Glu Val Ser  Val Met Ile
1115                1120                 1125

Met Ser  Leu Lys Ala Ala Ser  Leu Gly Leu Asn Met  Val Ala Ala
1130                1135                 1140

Cys His  Val Ile Met Leu Asp  Leu Trp Trp Asn Pro  Thr Thr Glu
1145                1150                 1155

Asp Gln  Ala Ile Asp Arg Ala  His Arg Ile Gly Gln  Thr Arg Pro
1160                1165                 1170

Val Lys  Val Val Arg Phe Thr  Val Lys Asp Thr Val  Glu Asp Arg
1175                1180                 1185

Ile Leu  Ala Leu Gln Gln Arg  Lys Arg Met Met Val  Ala Ser Ala
1190                1195                 1200
```

Phe Gly Glu His Glu Lys Gly Ser Arg Glu Ser His Leu Ser Val
1205              1210                1215

Glu Asp Leu Asn Tyr Leu Phe Met Ala
1220            1225

<210> SEQ ID NO 43
<211> LENGTH: 4123
<212> TYPE: DNA
<213> ORGANISM: Zea mays

<400> SEQUENCE: 43

| | | | | | |
|---|---|---|---|---|---|
| ggacaagttt | gtacaaaaaa | gcaggctaaa | aaccatggcg | gaggaaccgg | tggtcggtta | 60 |
| tgatggcttc | gaggccgccg | gtgatgctgg | cgccggtggc | gcggaggaca | acctgtcgat | 120 |
| gtccctcggc | gacttcatgg | cgttcctcga | aactgagccc | acgtcacccg | aggaaggctg | 180 |
| gaaggaggag | cagcagatgc | agcctgcggt | caatcaaggt | tgtttagaga | tgcctgccaa | 240 |
| cactgattgt | tctgaagatt | tattccaaag | ccatgaagca | gaaatgcttg | agaacgcaga | 300 |
| attttggtca | aagtcaaact | actccctgt | ggagcatctg | gagtgccata | tggaagttaa | 360 |
| catggagctg | aacgaaggag | aacaaatgat | tgatcacaca | gaagctagcc | gatatgaatt | 420 |
| gtttagcaac | gatctgcaga | gccaatcaag | aacttccaac | ttggacaatg | aacattttcc | 480 |
| aagggatgca | tcaaaccacg | ctaatgttga | agcaactgga | cctccatatg | atctctcaaa | 540 |
| tggtggtata | tccacagagc | actcagattg | gagtgaaatt | aaatggggga | gtacagatga | 600 |
| gatgcttggt | aatactggtc | aggatgatga | ccatttcact | ccgatgggca | tgttttgtct | 660 |
| taccaataac | acagatattc | ttgatctttc | ttgcattgag | tccaacatgg | gtgagagaac | 720 |
| ggaaagcatt | cgcaatggca | acagtagttg | ccttactatg | caggaagaac | atttacaggc | 780 |
| agaatgtgga | ggatatcctc | atccagatta | tatatctgtt | gatatgattg | atgaaagatc | 840 |
| actgcatgat | ttgccacatg | ggttatcaca | aaacaatgag | cagtatgaga | tggagcagct | 900 |
| cccacagaat | atatgtgaaa | gtggttctat | gcagatggcc | tctccggacc | aatattgttc | 960 |
| ctctccggac | caatattgtg | atgatacatc | tttatcagat | ttttacatgg | atgtatcctc | 1020 |
| cccagagtca | atatcctgtg | agcagaacca | gcctgaagat | atttttttca | agagcgagtc | 1080 |
| tagcactgac | tcttctccag | taccctctag | cagaaattcc | accacagagg | atgctgataa | 1140 |
| atacttaggt | caaccatcaa | aacagttgct | ggactccaaa | atcgttcctt | tcagcaacca | 1200 |
| acacacgttt | aagaacatgg | aatatcaaaa | acctctggta | ttggataaac | aatatgcata | 1260 |
| tagaagcaac | aactcttcta | ttcacaattc | aacaaaaggt | tgcttcagta | gagatggga | 1320 |
| catggtttct | gatttatgtg | tgctagaggg | taataggaat | cctgctcctg | ctcacctatg | 1380 |
| gccttatcag | gggaagttcc | atcataattt | tcagcaacct | gtgtatggta | attccatcat | 1440 |
| tcctgcattt | ggtggtacga | gatacaaacc | acacgatgaa | agaaccactc | tgcgccttgc | 1500 |
| attgcagttt | tggtattaca | ttcttttcttc | gttggggatg | gctaatcttt | ctcctgactc | 1560 |
| taatgagtcc | acttttgctg | actggtgggc | gaaatccttc | aattattggc | ataaaggcat | 1620 |
| tttttttttgg | atgaagttga | gttctggggg | cttgccggtg | ctaggcatct | tgaggctttg | 1680 |
| gttcctggtg | ctggaatttt | taggtcaagg | gttcttttgg | gtgattagtg | aagagcagac | 1740 |
| agaaatgtac | ccatgcaact | tctcaccaag | ggaaggattg | catgaacaac | agaaattacc | 1800 |
| atcactacca | gaatcgaaga | gattaacgac | tgaccaaaaa | accctgcaag | cacaactaag | 1860 |
| tgtttcttac | agggcacctg | cccaaacatc | cacatttgac | atatttggtg | attggcagga | 1920 |
| tatttcacag | ccaaattctg | aggctaatcc | acctgatggg | gttttagcgg | ttcctttatt | 1980 |

```
gaggcatcag aaaattgcct tgtcatggat ggtgaaaaag gagactagta tctcgctttg    2040
ctatggtgga attcttgcag atgatcaggg ccttggtaaa actgtatcag ccatatcact    2100
gattcttact gagcgcccac cagttccaca gtcatctact aagaacgagc catgtgaagc    2160
tgtaactcta gatgaagacg atgactgtat tggacctcat tcggaaaagc tgatgcggac    2220
atgtagctct caagtgacaa gtaacacagt gaagcaagaa aatcctattg tagcggttaa    2280
ggcaaggcca gctgctggta ctttggttgt ttgcccaaca agtgttttgc gacagtgggc    2340
aggagaactg aagaacaaag ttacaagtaa agctaattta tcttttctga tatatcatgg    2400
tagcaatcgc accaaggatc ctaacgaact taccaaatat gatgttgtgc ttactacata    2460
ttctatagta agcatggaag taccaaaaca atcaaatcct gatagtgatg gagaagagaa    2520
agggaagcct gacccgtatg gtgcacctgt gtcctcttca gggagcaaaa agagaaaggc    2580
atcctcttct aagaaaacaa aaaataaaag tgttgcagag agttgcttgc ctgaaaaacc    2640
tcttgcgaaa gttgcttggt ttagggttat tcttgatgaa gcacaaagca ttaagaacta    2700
ccgaactcag ttttgcactc tgataaagat tccaatcagt aggaacccaa ataacggtta    2760
caagaagctt caagctgttt taaagccggt aatgctacgc cggactaaag caaccatgct    2820
tgatggggaa ccgatcatat ccttaccacc caagactgtt tcacttaaga cggtggactt    2880
cactagcgag gagcgtggtt tttataacac tttagaagtt gaatcacgag aacagttcaa    2940
ggaatatgca gctgctggta ctgtaaagca aaattatgtc aacattctat tgatgctttt    3000
gcggctaaga caggcatgcg atcaccctca cctagttaga ggctatgact cctgttctag    3060
ttggatgtct tcgttggaga tggtgaagaa acttcccatg gaacggcagc acaaattact    3120
tatttgcttg caatcttgtt ctgcgttttg tgctctatgc aatggtttcg gtaaggggcc    3180
agtgctgact gatctagtgg tcagaggcgc gggcgtgggg aagttggcgg atgcgccaga    3240
agatcctgtt gtcactctat gtggtcatgt tttttgcaac cagtgcatac tggagcaact    3300
cactggtgac gacagtgtat gcccagtgtc taattgcaga gtccgactaa acacatcctc    3360
actcttctcc agaggcactc ttgaatgctc tctgagtaaa ttagcctctg atttcaagtc    3420
tgatgataca tgtatggaaa tgatacatgc tgaaaagcgc cctgggatgg attcatccta    3480
cgcatcttca aaattgagag ctgcattaga tattcttctc tcattgccta aaatagatcc    3540
cactattgat agcaaatgtt caatcgggat tgaatctgag aagtttgatg gaaagggtat    3600
ttcagaacaa actgacacca agttgacaga gaaggccatt gttttctctc aatggactag    3660
aatgctagac ttgcttgaag tccatttgaa agcttctcat gtgacatatc gaaggcttga    3720
tggaacaatg tctgttgctg cacgggataa agctgtgaac gacttcaata tggttccaga    3780
ggttactgtt atgatcatgt cactcaaagc tgcaagtctt ggcttgaata tggttgctgc    3840
ctgccacgta cttatgctag atctttggtg gaacccaacc accgaggacc aagctgtgga    3900
tagggcacac cgtattggtc aaaaacggcc tgtcacggta tcaagattaa ctataaaaga    3960
caccgtggaa gatcgtattc ttgctctcca ggagaaaaag cgggagatgg ttgcttctgc    4020
gtttggagaa gacaaatctg gttcccgaca gactcgattg accgttgaag acctgaatta    4080
tctgtttatg gtgtagaccc agctttcttg tacaaagtgg tcc                    4123
```

<210> SEQ ID NO 44
<211> LENGTH: 1353
<212> TYPE: PRT
<213> ORGANISM: Zea mays

```
<400> SEQUENCE: 44

Met Ala Glu Glu Pro Val Val Gly Tyr Asp Gly Phe Glu Ala Ala Gly
1               5                   10                  15

Asp Ala Gly Ala Gly Gly Ala Glu Asp Asn Leu Ser Met Ser Leu Gly
            20                  25                  30

Asp Phe Met Ala Phe Leu Glu Thr Glu Pro Thr Ser Pro Glu Glu Gly
        35                  40                  45

Trp Lys Glu Glu Gln Gln Met Gln Pro Ala Val Asn Gln Gly Cys Leu
    50                  55                  60

Glu Met Pro Ala Asn Thr Asp Cys Ser Glu Asp Leu Phe Gln Ser His
65                  70                  75                  80

Glu Ala Glu Met Leu Glu Asn Ala Glu Phe Trp Ser Lys Ser Asn Tyr
                85                  90                  95

Ser Pro Val Glu His Leu Glu Cys His Met Glu Val Asn Met Glu Leu
            100                 105                 110

Asn Glu Gly Glu Gln Met Ile Asp His Thr Glu Ala Ser Arg Tyr Glu
        115                 120                 125

Leu Phe Ser Asn Asp Leu Gln Ser Gln Ser Arg Thr Ser Asn Leu Asp
    130                 135                 140

Asn Glu His Phe Pro Arg Asp Ala Ser Asn His Ala Asn Val Glu Ala
145                 150                 155                 160

Thr Gly Pro Pro Tyr Asp Leu Ser Asn Gly Gly Ile Ser Thr Glu His
                165                 170                 175

Ser Asp Trp Ser Glu Ile Lys Trp Gly Ser Thr Asp Glu Met Leu Gly
            180                 185                 190

Asn Thr Gly Gln Asp Asp His Phe Thr Pro Met Gly Met Phe Cys
        195                 200                 205

Leu Thr Asn Asn Thr Asp Ile Leu Asp Leu Ser Cys Ile Glu Ser Asn
    210                 215                 220

Met Gly Glu Arg Thr Glu Ser Ile Arg Asn Gly Asn Ser Ser Cys Leu
225                 230                 235                 240

Thr Met Gln Glu Glu His Leu Gln Ala Glu Cys Gly Gly Tyr Pro His
                245                 250                 255

Pro Asp Tyr Ile Ser Val Asp Met Ile Asp Glu Arg Ser Leu His Asp
            260                 265                 270

Leu Pro His Gly Leu Ser Gln Asn Asn Glu Gln Tyr Glu Met Glu Gln
        275                 280                 285

Leu Pro Gln Asn Ile Cys Glu Ser Gly Ser Met Gln Met Ala Ser Pro
    290                 295                 300

Asp Gln Tyr Cys Ser Ser Pro Asp Gln Tyr Cys Asp Asp Thr Ser Leu
305                 310                 315                 320

Ser Asp Phe Tyr Met Asp Val Ser Ser Pro Glu Ser Ile Ser Cys Glu
                325                 330                 335

Gln Asn Gln Pro Glu Asp Ile Phe Phe Lys Ser Glu Ser Ser Thr Asp
            340                 345                 350

Ser Ser Pro Val Pro Ser Ser Arg Asn Ser Thr Thr Glu Asp Ala Asp
        355                 360                 365

Lys Tyr Leu Gly Gln Pro Ser Lys Gln Leu Leu Asp Ser Lys Ile Val
    370                 375                 380

Pro Phe Ser Asn Gln His Thr Phe Lys Asn Met Glu Tyr Gln Lys Pro
385                 390                 395                 400

Leu Val Leu Asp Lys Gln Tyr Ala Tyr Arg Ser Asn Asn Ser Ser Ile
                405                 410                 415
```

His Asn Ser Thr Lys Gly Cys Phe Ser Arg Asp Gly Asp Met Val Ser
420                 425                 430

Asp Leu Cys Val Leu Glu Gly Asn Arg Asn Pro Ala Pro Ala His Leu
435                 440                 445

Trp Pro Tyr Gln Gly Lys Phe His His Asn Phe Gln Gln Pro Val Tyr
450                 455                 460

Gly Asn Ser Ile Ile Pro Ala Phe Gly Gly Thr Arg Tyr Lys Pro His
465                 470                 475                 480

Asp Glu Arg Thr Thr Leu Arg Leu Ala Leu Gln Phe Trp Tyr Tyr Ile
485                 490                 495

Leu Ser Ser Leu Gly Met Ala Asn Leu Ser Pro Asp Ser Asn Glu Ser
500                 505                 510

Thr Phe Ala Asp Trp Trp Ala Lys Ser Phe Asn Tyr Trp His Lys Gly
515                 520                 525

Ile Phe Phe Trp Met Lys Leu Ser Ser Gly Gly Leu Pro Val Leu Gly
530                 535                 540

Ile Leu Arg Leu Trp Phe Leu Val Leu Glu Phe Leu Gly Gln Gly Phe
545                 550                 555                 560

Phe Trp Val Ile Ser Glu Glu Gln Thr Glu Met Tyr Pro Cys Asn Phe
565                 570                 575

Ser Pro Arg Glu Gly Leu His Glu Gln Gln Lys Leu Pro Ser Leu Pro
580                 585                 590

Glu Ser Lys Arg Leu Thr Thr Asp Gln Lys Thr Leu Gln Ala Gln Leu
595                 600                 605

Ser Val Ser Tyr Arg Ala Pro Ala Gln Thr Ser Thr Phe Asp Ile Phe
610                 615                 620

Gly Asp Trp Gln Asp Ile Ser Gln Pro Asn Ser Glu Ala Asn Pro Pro
625                 630                 635                 640

Asp Gly Val Leu Ala Val Pro Leu Leu Arg His Gln Lys Ile Ala Leu
645                 650                 655

Ser Trp Met Val Lys Lys Glu Thr Ser Ile Ser Leu Cys Tyr Gly Gly
660                 665                 670

Ile Leu Ala Asp Asp Gln Gly Leu Gly Lys Thr Val Ser Ala Ile Ser
675                 680                 685

Leu Ile Leu Thr Glu Arg Pro Pro Val Pro Gln Ser Ser Thr Lys Asn
690                 695                 700

Glu Pro Cys Glu Ala Val Thr Leu Asp Glu Asp Asp Cys Ile Gly
705                 710                 715                 720

Pro His Ser Glu Lys Leu Met Arg Thr Cys Ser Ser Gln Val Thr Ser
725                 730                 735

Asn Thr Val Lys Gln Glu Asn Pro Ile Val Ala Val Lys Ala Arg Pro
740                 745                 750

Ala Ala Gly Thr Leu Val Val Cys Pro Thr Ser Val Leu Arg Gln Trp
755                 760                 765

Ala Gly Glu Leu Lys Asn Lys Val Thr Ser Lys Ala Asn Leu Ser Phe
770                 775                 780

Leu Ile Tyr His Gly Ser Asn Arg Thr Lys Asp Pro Asn Glu Leu Thr
785                 790                 795                 800

Lys Tyr Asp Val Val Leu Thr Thr Tyr Ser Ile Val Ser Met Glu Val
805                 810                 815

Pro Lys Gln Ser Asn Pro Asp Ser Asp Gly Glu Glu Lys Gly Lys Pro
820                 825                 830

```
Asp Pro Tyr Gly Ala Pro Val Ser Ser Ser Gly Lys Lys Arg Lys
835                 840                 845

Ala Ser Ser Ser Lys Lys Thr Lys Asn Lys Ser Val Ala Glu Ser Cys
850                 855                 860

Leu Pro Glu Lys Pro Leu Ala Lys Val Ala Trp Phe Arg Val Ile Leu
865                 870                 875                 880

Asp Glu Ala Gln Ser Ile Lys Asn Tyr Arg Thr Gln Phe Cys Thr Leu
885                 890                 895

Ile Lys Ile Pro Ile Ser Arg Asn Pro Asn Asn Gly Tyr Lys Lys Leu
900                 905                 910

Gln Ala Val Leu Lys Pro Val Met Leu Arg Arg Thr Lys Ala Thr Met
915                 920                 925

Leu Asp Gly Glu Pro Ile Ile Ser Leu Pro Pro Lys Thr Val Ser Leu
930                 935                 940

Lys Thr Val Asp Phe Thr Ser Glu Glu Arg Gly Phe Tyr Asn Thr Leu
945                 950                 955                 960

Glu Val Glu Ser Arg Glu Gln Phe Lys Glu Tyr Ala Ala Ala Gly Thr
965                 970                 975

Val Lys Gln Asn Tyr Val Asn Ile Leu Leu Met Leu Leu Arg Leu Arg
980                 985                 990

Gln Ala Cys Asp His Pro His Leu Val Arg Gly Tyr Asp Ser Cys Ser
995                 1000                1005

Ser Trp Met Ser Ser Leu Glu Met Val Lys Lys Leu Pro Met Glu
1010                1015                1020

Arg Gln His Lys Leu Leu Ile Cys Leu Gln Ser Cys Ser Ala Phe
1025                1030                1035

Cys Ala Leu Cys Asn Gly Phe Gly Lys Gly Pro Val Leu Thr Asp
1040                1045                1050

Leu Val Val Arg Gly Ala Gly Val Gly Lys Leu Ala Asp Ala Pro
1055                1060                1065

Glu Asp Pro Val Val Thr Leu Cys Gly His Val Phe Cys Asn Gln
1070                1075                1080

Cys Ile Leu Glu Gln Leu Thr Gly Asp Asp Ser Val Cys Pro Val
1085                1090                1095

Ser Asn Cys Arg Val Arg Leu Asn Thr Ser Ser Leu Phe Ser Arg
1100                1105                1110

Gly Thr Leu Glu Cys Ser Leu Ser Lys Leu Ala Ser Asp Phe Lys
1115                1120                1125

Ser Asp Asp Thr Cys Met Glu Met Ile His Ala Glu Lys Arg Pro
1130                1135                1140

Gly Met Asp Ser Ser Tyr Ala Ser Ser Lys Leu Arg Ala Ala Leu
1145                1150                1155

Asp Ile Leu Leu Ser Leu Pro Lys Ile Asp Pro Thr Ile Asp Ser
1160                1165                1170

Lys Cys Ser Ile Gly Ile Glu Ser Glu Lys Phe Asp Gly Lys Gly
1175                1180                1185

Ile Ser Glu Gln Thr Asp Thr Lys Leu Thr Glu Lys Ala Ile Val
1190                1195                1200

Phe Ser Gln Trp Thr Arg Met Leu Asp Leu Leu Glu Val His Leu
1205                1210                1215

Lys Ala Ser His Val Thr Tyr Arg Arg Leu Asp Gly Thr Met Ser
1220                1225                1230

Val Ala Ala Arg Asp Lys Ala Val Asn Asp Phe Asn Met Val Pro
```

| | | | | | | | | |
|---|---|---|---|---|---|---|---|---|
| | | 1235 | | | 1240 | | | 1245 |

Glu Val Thr Val Met Ile Met Ser Leu Lys Ala Ala Ser Leu Gly
1250                     1255                 1260

Leu Asn Met Val Ala Ala Cys His Val Leu Met Leu Asp Leu Trp
1265                 1270                     1275

Trp Asn Pro Thr Thr Glu Asp Gln Ala Val Asp Arg Ala His Arg
1280                 1285                     1290

Ile Gly Gln Lys Arg Pro Val Thr Val Ser Arg Leu Thr Ile Lys
1295                 1300                     1305

Asp Thr Val Glu Asp Arg Ile Leu Ala Leu Gln Glu Lys Lys Arg
1310                     1315                 1320

Glu Met Val Ala Ser Ala Phe Gly Glu Asp Lys Ser Gly Ser Arg
1325                 1330                     1335

Gln Thr Arg Leu Thr Val Glu Asp Leu Asn Tyr Leu Phe Met Val
1340                     1345                 1350

<210> SEQ ID NO 45
<211> LENGTH: 3781
<212> TYPE: DNA
<213> ORGANISM: Zea mays

<400> SEQUENCE: 45

```
ggacaagttt gtacaaaaaa gcaggctaaa aaccatggcg gaggaaccgg tggtcggtta     60
tgatggcttc gaggccgccg gtgatgctgg cgccggtggc gcggaggaca acctgtcgat    120
gtccctcggc gacttcatgg cgttcctcga aactgagccc acgtcacccg aggaaggctg    180
gaaggaggag cagcagatgc agcctgcggt caatcaaggt tgtttagaga tgcctgccaa    240
cactgattgt tctgaagatt tattccaaag ccatgaagca gaaatgcttg agaacgcaga    300
attttggtca aagtcaaact actcccctgt ggagcatctg gagtgccata tggaagttaa    360
catggagctg aacgaaggag aacaaatgat tgatcacaca gaagctagcc gatatgaatt    420
gtttagcaac gatctgcaga gccaatcaag aacttccaac ttggacaatg aacatttttcc   480
aagggatgca tcaaaccacg ctaatgttga agcaactgga cctccatatg atctctcaaa    540
tggtggtata tccacagagc actcagattg gagtgaaatt aaatggggga gtacagatga    600
gatgcttggt aatactggtc aggatgatga ccatttcact ccgatgggca tgttttgtct    660
taccaataac acagatattc ttgatctttc ttgcattgag tccaacatgg gtgagagaac    720
ggaaagcatt cgcaatggca acagtagttg ccttactatg caggaagaac atttacaggc    780
agaatgtgga ggatatcctc atccagatta tatatctgtt gatatgattg atgaaagatc    840
actgcatgat ttgccacatg ggttatcaca aaacaatgag cagtatgaga tggagcagct    900
cccacagaat atatgtgaaa gtggttctat gcagatggcc tctccggacc aatattgttc    960
ctctccggac caatattgtg atgatacatc tttatcagat ttttacatgg atgtatcctc   1020
cccagagtca atatcctgtg agcagaacca gcctgaagat atttttttca agagcgagtc   1080
tagcactgac tcttctccag taccctctag cagaaattcc accacagagg atgctgataa   1140
atacttaggt caaccatcaa aacagttgct ggactccaaa atcgttcctt tcagcaacca   1200
acacacgttt aagaacatgg aatatcaaaa acctctggta ttggataaac aatatgcata   1260
tagaagcaac aactcttcta ttcacaattc aacaaaaggt tgcttcagta gagatgggga   1320
catggttttct gatttatgtg tgctagaggg taataggaat cctgctcctg ctcacctatg   1380
gcccttatcag gggaagttcc atcataattt tcagcaacct gtgtatggta attccatcat   1440
```

```
tcctgcattt ggtggtacga gatacaaacc acacgatgaa agaaccactc tgcgccttgc    1500
attgcaggat atttcacagc caaattctga ggctaatcca cctgatgggg ttttagcggt    1560
tcctttattg aggcatcaga aaattgcctt gtcatggatg gtgaaaaagg agactagtat    1620
ctcgctttgc tatggtggaa ttcttgcaga tgatcagggc cttggtaaaa ctgtatcagc    1680
catatcactg attcttactg agcgcccacc agttccacag tcatctacta agaacgagcc    1740
atgtgaagct gtaactctag atgaagacga tgactgtatt ggacctcatt cggaaaagct    1800
gatgcggaca tgtagctctc aagtgacaag taacacagtg aagcaagaaa tcctattgt     1860
agcggttaag gcaaggccag ctgctggtac tttggttgtt tgcccaacaa gtgttttgcg    1920
acagtgggca ggagaactga agaacaaagt tacaagtaaa gctaatttat cttttctgat    1980
atatcatggt agcaatcgca ccaaggatcc taacgaactt accaaatatg atgttgtgct    2040
tactacatat tctatagtaa gcatggaagt accaaaacaa tcaaatcctg atagtgatgg    2100
agaagagaaa gggaagcctg acccgtatgg tgcacctgtg tcctcttcag ggagcaaaaa    2160
gagaaaggca tcctcttcta agaaaacaaa aaataaaagt gttgcagaga gttgcttgcc    2220
tgaaaaacct cttgcgaaag ttgcttggtt tagggttatt cttgatgaag cacaaagcat    2280
taagaactac cgaactcagg ttgccagggc ttgctggggt tgcgagcca aaagaagatg     2340
gtgtttgtct gggacaccta tacagaatgc tgttgaggat ctctatagct acttcagatt    2400
tctcagatac aatccctacg ctgtatataa gcagttttgc actctgataa agattccaat    2460
cagtaggaac ccaaataacg gttacaagaa gcttcaagct gttttaaagc cggtaatgct    2520
acgccggact aaagcaacca tgcttgatgg ggaaccgatc atatccttac acccaagac     2580
tgtttcactt aagacggtgg acttcactag cgaggagcgt ggttttttata cactttaga    2640
agttgaatca cgagaacagt tcaaggaata tgcagctgct ggtactgtaa agcaaaatta    2700
tgtcaacatt ctattgatgc ttttgcggct aagacaggca tgcgatcacc ctcacctagt    2760
tagaggctat gactcctgtt ctagttggat gtcttcgttg gagatggtga agaaacttcc    2820
catggaacgg cagcacaaat tacttatttg cttgcaatct tgttctgcgt tttgtgctct    2880
atgcaatgat gcgccagaag atcctgttgt cactctatgt ggtcatgttt tttgcaacca    2940
gtgcatactg gagcaactca ctggtgacga cagtgtatgc ccagtgtcta attgcagagt    3000
ccgactaaac acatcctcac tcttctccag aggcactctt gaatgctctc tgagtaaatt    3060
agcctctgat ttcaagtctg atgatacatg tatggaaatg atacatgctg aaaagcgccc    3120
tgggatggat tcatcctacg catcttcaaa attgagagct gcattagata ttcttctctc    3180
attgcctaaa atagatccca ctattgatag caaatgttca atcgggattg aatctgagaa    3240
gtttgatgga agggtatttt cagaacaaac tgacaccaag ttgacagaga aggccattgt    3300
tttctctcaa tggactagaa tgctagactt gcttgaagtc catttgaaag cttctcatgt    3360
gacatatcga aggcttgatg gaacaatgtc tgttgctgca cgggataaag ctgtgaacga    3420
cttcaatatg gttccagagg ttactgttat gatcatgtca ctcaaagctg caagtcttgg    3480
cttgaatatg gttgctgcct gccacgtact tatgctagat cttggtggaa acccaaccac    3540
cgaggaccaa gctgtggata gggcacaccg tattggtcaa aaacggcctg tcacggtatc    3600
aagattaact ataaaagaca ccgtggaaga tcgtattctt gctctccagg agaaaaagcg    3660
ggagatggtt gcttctgcgt ttggagaaga caaatctggt tcccgacaga ctcgattgac    3720
cgttgaagac ctgaattatc tgtttatggt gtagacccag ctttcttgta caaagtggtc    3780
c                                                                   3781
```

<210> SEQ ID NO 46
<211> LENGTH: 1239
<212> TYPE: PRT
<213> ORGANISM: Zea mays

<400> SEQUENCE: 46

```
Met Ala Glu Glu Pro Val Val Gly Tyr Asp Gly Phe Glu Ala Ala Gly
1               5                   10                  15

Asp Ala Gly Ala Gly Ala Glu Asp Asn Leu Ser Met Ser Leu Gly
            20                  25                  30

Asp Phe Met Ala Phe Leu Glu Thr Glu Pro Thr Ser Pro Glu Glu Gly
35                  40                  45

Trp Lys Glu Glu Gln Gln Met Gln Pro Ala Val Asn Gln Gly Cys Leu
50                  55                  60

Glu Met Pro Ala Asn Thr Asp Cys Ser Glu Asp Leu Phe Gln Ser His
65                  70                  75                  80

Glu Ala Glu Met Leu Glu Asn Ala Glu Phe Trp Ser Lys Ser Asn Tyr
                85                  90                  95

Ser Pro Val Glu His Leu Glu Cys His Met Glu Val Asn Met Glu Leu
            100                 105                 110

Asn Glu Gly Glu Gln Met Ile Asp His Thr Glu Ala Ser Arg Tyr Glu
115                 120                 125

Leu Phe Ser Asn Asp Leu Gln Ser Gln Ser Arg Thr Ser Asn Leu Asp
130                 135                 140

Asn Glu His Phe Pro Arg Asp Ala Ser Asn His Ala Asn Val Glu Ala
145                 150                 155                 160

Thr Gly Pro Pro Tyr Asp Leu Ser Asn Gly Gly Ile Ser Thr Glu His
                165                 170                 175

Ser Asp Trp Ser Glu Ile Lys Trp Gly Ser Thr Asp Glu Met Leu Gly
            180                 185                 190

Asn Thr Gly Gln Asp Asp His Phe Thr Pro Met Gly Met Phe Cys
195                 200                 205

Leu Thr Asn Asn Thr Asp Ile Leu Asp Leu Ser Cys Ile Glu Ser Asn
210                 215                 220

Met Gly Glu Arg Thr Glu Ser Ile Arg Asn Gly Asn Ser Ser Cys Leu
225                 230                 235                 240

Thr Met Gln Glu Glu His Leu Gln Ala Glu Cys Gly Gly Tyr Pro His
                245                 250                 255

Pro Asp Tyr Ile Ser Val Asp Met Ile Asp Glu Arg Ser Leu His Asp
            260                 265                 270

Leu Pro His Gly Leu Ser Gln Asn Asn Glu Gln Tyr Glu Met Glu Gln
275                 280                 285

Leu Pro Gln Asn Ile Cys Glu Ser Gly Ser Met Gln Met Ala Ser Pro
290                 295                 300

Asp Gln Tyr Cys Ser Ser Pro Asp Gln Tyr Cys Asp Asp Thr Ser Leu
305                 310                 315                 320

Ser Asp Phe Tyr Met Asp Val Ser Ser Pro Glu Ser Ile Ser Cys Glu
                325                 330                 335

Gln Asn Gln Pro Glu Asp Ile Phe Phe Lys Ser Glu Ser Ser Thr Asp
            340                 345                 350

Ser Ser Pro Val Pro Ser Ser Arg Asn Ser Thr Thr Glu Asp Ala Asp
355                 360                 365

Lys Tyr Leu Gly Gln Pro Ser Lys Gln Leu Leu Asp Ser Lys Ile Val
```

```
                370             375             380
Pro Phe Ser Asn Gln His Thr Phe Lys Asn Met Glu Tyr Gln Lys Pro
385             390             395             400

Leu Val Leu Asp Lys Gln Tyr Ala Tyr Arg Ser Asn Asn Ser Ser Ile
405             410             415

His Asn Ser Thr Lys Gly Cys Phe Ser Arg Asp Gly Asp Met Val Ser
420             425             430

Asp Leu Cys Val Leu Glu Gly Asn Arg Asn Pro Ala Pro Ala His Leu
435             440             445

Trp Pro Tyr Gln Gly Lys Phe His His Asn Phe Gln Gln Pro Val Tyr
450             455             460

Gly Asn Ser Ile Ile Pro Ala Phe Gly Gly Thr Arg Tyr Lys Pro His
465             470             475             480

Asp Glu Arg Thr Thr Leu Arg Leu Ala Leu Gln Asp Ile Ser Gln Pro
485             490             495

Asn Ser Glu Ala Asn Pro Pro Asp Gly Val Leu Ala Val Pro Leu Leu
500             505             510

Arg His Gln Lys Ile Ala Leu Ser Trp Met Val Lys Lys Glu Thr Ser
515             520             525

Ile Ser Leu Cys Tyr Gly Gly Ile Leu Ala Asp Asp Gln Gly Leu Gly
530             535             540

Lys Thr Val Ser Ala Ile Ser Leu Ile Leu Thr Glu Arg Pro Pro Val
545             550             555             560

Pro Gln Ser Ser Thr Lys Asn Glu Pro Cys Glu Ala Val Thr Leu Asp
565             570             575

Glu Asp Asp Cys Ile Gly Pro His Ser Glu Lys Leu Met Arg Thr
580             585             590

Cys Ser Ser Gln Val Thr Ser Asn Thr Val Lys Gln Glu Asn Pro Ile
595             600             605

Val Ala Val Lys Ala Arg Pro Ala Ala Gly Thr Leu Val Val Cys Pro
610             615             620

Thr Ser Val Leu Arg Gln Trp Ala Gly Glu Leu Lys Asn Lys Val Thr
625             630             635             640

Ser Lys Ala Asn Leu Ser Phe Leu Ile Tyr His Gly Ser Asn Arg Thr
645             650             655

Lys Asp Pro Asn Glu Leu Thr Lys Tyr Asp Val Val Leu Thr Thr Tyr
660             665             670

Ser Ile Val Ser Met Glu Val Pro Lys Gln Ser Asn Pro Asp Ser Asp
675             680             685

Gly Glu Glu Lys Gly Lys Pro Asp Pro Tyr Gly Ala Pro Val Ser Ser
690             695             700

Ser Gly Ser Lys Lys Arg Lys Ala Ser Ser Lys Lys Thr Lys Asn
705             710             715             720

Lys Ser Val Ala Glu Ser Cys Leu Pro Glu Lys Pro Leu Ala Lys Val
725             730             735

Ala Trp Phe Arg Val Ile Leu Asp Glu Ala Gln Ser Ile Lys Asn Tyr
740             745             750

Arg Thr Gln Val Ala Arg Ala Cys Trp Gly Leu Arg Ala Lys Arg Arg
755             760             765

Trp Cys Leu Ser Gly Thr Pro Ile Gln Asn Ala Val Glu Asp Leu Tyr
770             775             780

Ser Tyr Phe Arg Phe Leu Arg Tyr Asn Pro Tyr Ala Val Tyr Lys Gln
785             790             795             800
```

-continued

```
Phe Cys Thr Leu Ile Lys Ile Pro Ile Ser Arg Asn Pro Asn Asn Gly
805                 810                  815

Tyr Lys Lys Leu Gln Ala Val Leu Lys Pro Val Met Leu Arg Arg Thr
820                 825                  830

Lys Ala Thr Met Leu Asp Gly Glu Pro Ile Ile Ser Leu Pro Pro Lys
835                 840                  845

Thr Val Ser Leu Lys Thr Val Asp Phe Thr Ser Glu Glu Arg Gly Phe
850                 855                  860

Tyr Asn Thr Leu Glu Val Glu Ser Arg Glu Gln Phe Lys Glu Tyr Ala
865                 870                  875                  880

Ala Ala Gly Thr Val Lys Gln Asn Tyr Val Asn Ile Leu Leu Met Leu
885                 890                  895

Leu Arg Leu Arg Gln Ala Cys Asp His Pro His Leu Val Arg Gly Tyr
900                 905                  910

Asp Ser Cys Ser Ser Trp Met Ser Ser Leu Glu Met Val Lys Lys Leu
915                 920                  925

Pro Met Glu Arg Gln His Lys Leu Leu Ile Cys Leu Gln Ser Cys Ser
930                 935                  940

Ala Phe Cys Ala Leu Cys Asn Asp Ala Pro Glu Asp Pro Val Val Thr
945                 950                  955                  960

Leu Cys Gly His Val Phe Cys Asn Gln Cys Ile Leu Glu Gln Leu Thr
965                 970                  975

Gly Asp Asp Ser Val Cys Pro Val Ser Asn Cys Arg Val Arg Leu Asn
980                 985                  990

Thr Ser Ser Leu Phe Ser Arg Gly  Thr Leu Glu Cys Ser  Leu Ser Lys
995                 1000                 1005

Leu Ala Ser Asp Phe Lys Ser  Asp Asp Thr Cys Met  Glu Met Ile
1010                1015                 1020

His Ala Glu Lys Arg Pro Gly  Met Asp Ser Ser Tyr  Ala Ser Ser
1025                1030                 1035

Lys Leu Arg Ala Ala Leu Asp  Ile Leu Leu Ser Leu  Pro Lys Ile
1040                1045                 1050

Asp Pro Thr Ile Asp Ser Lys  Cys Ser Ile Gly Ile  Glu Ser Glu
1055                1060                 1065

Lys Phe Asp Gly Lys Gly Ile  Ser Glu Gln Thr Asp  Thr Lys Leu
1070                1075                 1080

Thr Glu Lys Ala Ile Val Phe  Ser Gln Trp Thr Arg  Met Leu Asp
1085                1090                 1095

Leu Leu Glu Val His Leu Lys  Ala Ser His Val Thr  Tyr Arg Arg
1100                1105                 1110

Leu Asp Gly Thr Met Ser Val  Ala Ala Arg Asp Lys  Ala Val Asn
1115                1120                 1125

Asp Phe Asn Met Val Pro Glu  Val Thr Val Met Ile  Met Ser Leu
1130                1135                 1140

Lys Ala Ala Ser Leu Gly Leu  Asn Met Val Ala Ala  Cys His Val
1145                1150                 1155

Leu Met Leu Asp Leu Trp Trp  Asn Pro Thr Thr Glu  Asp Gln Ala
1160                1165                 1170

Val Asp Arg Ala His Arg Ile  Gly Gln Lys Arg Pro  Val Thr Val
1175                1180                 1185

Ser Arg Leu Thr Ile Lys Asp  Thr Val Glu Asp Arg  Ile Leu Ala
1190                1195                 1200
```

| Leu | Gln | Glu | Lys | Lys | Arg | Glu | Met | Val | Ala | Ser | Ala | Phe | Gly | Glu |
|-----|-----|-----|-----|-----|-----|-----|-----|-----|-----|-----|-----|-----|-----|-----|
| 1205 |     |     |     | 1210 |     |     |     |     | 1215 |     |     |     |     |     |

| Asp | Lys | Ser | Gly | Ser | Arg | Gln | Thr | Arg | Leu | Thr | Val | Glu | Asp | Leu |
|-----|-----|-----|-----|-----|-----|-----|-----|-----|-----|-----|-----|-----|-----|-----|
| 1220 |     |     |     |     | 1225 |     |     |     |     | 1230 |     |     |     |     |

| Asn | Tyr | Leu | Phe | Met | Val |
|-----|-----|-----|-----|-----|-----|
| 1235 |     |     |     |     |     |

<210> SEQ ID NO 47
<211> LENGTH: 3642
<212> TYPE: DNA
<213> ORGANISM: Oryza sativa

<400> SEQUENCE: 47

```
atggaggaag cggcggcggc ggcggcggat ttcgatggcg gcttcggcgg cgccggggag     60
gacaacctgt ccatgcccct cggcgacttc atggccttcc tcgataacga ggactggaag    120
gagcagcagc acgagggcaa tcaaggttta gagatgccag tggacagcac aagttctgaa    180
aatgcatttc aaaaccatga agatccttca catagtcaga tggatgtaat ggtggaactt    240
aacaatggtg agaatctttt tgatcactca gaggatacct cttatagatt gcttagcaat    300
gattttttgg aaaattcaag gaatggtaat cctgagatgc atttaccaat ggatgcatta    360
aaccatgcta aactgttgaa tgaagaaatt gtccctccat atgaagatta tacaaatggt    420
ttatactatg attcgggatg tgatatgttc gcagagcaat ctggtttaag tgaagttaaa    480
tgtgagggca caggtcccat gcttggtaat tctgagcagg agggtaacca tttcacgtca    540
gtgcctatgt ttgaccatag tgctgttata cctgatattc cttacaccga gttgaacatc    600
ggtgatgtgc ctggaagcat gcagaatgga atggcagtt gcctaactgt acaaggagaa    660
tatctgcagg gggagtatca ggagtatcct cagccagatt atggatcgtt tgatatggct    720
aatgaaatag tgctgcatga tttgccacaa acaatcagt catatgagct ggaacaatta    780
ccacagaata tatgtgaaag cagttcaatg caagtgggct ctccagatca atattgtgat    840
gatacatctc tgtcggatta ttacatggat gatgtatctt cgatagagtc gatgtccagc    900
gagcagaacc gatcagaaga tatctgtttc cggagtgagt ctagcactga ctcttctccg    960
gtgccctcaa gcagaaactc caccactgag gatgctgata aatactttgg agatgcacca   1020
aaacatttgc agaattccat gtttcctgtc agtacccaac accaacactc attcatgaac   1080
tcaagtgatc caatgcatcc aacttttcat aaaaagtatg acattcctag aaatggcagc   1140
tcttctattc tgggtaactc atcaaggaat tgcttcagtt tagatagcaa tcgtgattct   1200
gatttatgta ttcttgaggg tagtagaagt cttgctagtg acatgtgtt gccacccaa   1260
ggattgcagc ataactttca acaatctgtg tgtgccaatc ctaatcttcc tcggtttgga   1320
gggagataca ggccgcatga ggaaagaatg actttgcggc ttgcattaca ggatatttct   1380
cagccaaagt ctgaggctaa tccacctgat ggagttttag cagttccttt attgaggcac   1440
cagaaaattg ccttgtcatg gatggtacaa aaggagagaa atggttcgag ttgctctggc   1500
ggaattcttg cagatgatca gggcctgggt aaaacagtgt cgactatatc actgattttg   1560
acagaaaggt caccagttcc atcttcagct gttaagcaag aaccatgcga agctgtaacc   1620
cttgacgatg acgatgagga tgacgatgct gagcctcatt tgaagaaacc ggcactagca   1680
catctagcag atacatgtaa acctgaagcg acaagtagta ccattaagac agaaaatcct   1740
attgcaaatg ttaaggctag accagctgct gggactttgg ttgtttgccc cacgagtgtt   1800
ctacgtcagt gggcagatga actgaggaat aaagtcacca gtaaagctaa cttgaccttt   1860
```

|  |  |
|---|---|
| ttagtatatc atggtagcaa ccgcacaaag gatcctaatg atcttactaa atacgatgtc | 1920 |
| gtgttaacca catattctat agtaagcatg aagtaccaa acaatcaag tcctgatagt | 1980 |
| gatgatgaag agaaagggaa gcctgacagg tatggtgctc ctgttggctc ctcaggcagc | 2040 |
| aaaaaacgga agacttcctc ttctaagaag aacaaaagtg gaagcacacc agagagtaaa | 2100 |
| ttgcctgaga aacctctcgc aaaagttgca tggtttagag ttatccttga tgaagcacaa | 2160 |
| agtattaaaa attatcgaac ccaggttgct agggcatgct ggggtctgcg agccaaaaga | 2220 |
| agatggtgct tgtcagggac acctatacag aatgctgttg aggatctcta tagctatttc | 2280 |
| agatttctca gatatgatcc atatgctgaa tacaaaaaat tttgcttcat gataaaaaca | 2340 |
| ccaatcagca ggaacccaat tactgggtac aagaagcttc aggttgttct gaagacagta | 2400 |
| atgctgagga ggacaaaagc aacgatgctt gatggaaaac caataatctc attaccccca | 2460 |
| aagaccgtct ctcttaagac agtggacttc actagtgaag agcgtgcttt ctataacact | 2520 |
| ctcgaagcag aatcacgaga gcagttcaag gagtatgcag ctgctggtac tgtcaagcaa | 2580 |
| aactacgtca atatcctgct gatgcttta cggctcagac aggcatgtga tcaccctcac | 2640 |
| ttagttcgag gtcatgagtc tacttctagt tggatgtctt cattggagat ggcaagaaag | 2700 |
| ctgcctgtag aaaggcagca atcgttgctg gtttgcttgc aatcgtgttc tgcgatatgt | 2760 |
| gctctctgca atgatgcgcc agaagatgcc gttgttacta tatgtggtca tgttttctgc | 2820 |
| aaccagtgca tactggagca acttaccggt gatgacagtg tatgtccagt gtccaattgc | 2880 |
| cgagtccgac taaattcaac ttccttattc tcccgaggca cccttgaatg tgctctgagt | 2940 |
| agatcaacct gtgagtttct gtctgatgat tcctgtgaag acatggtgca agggaagcaa | 3000 |
| cctagatttg attcgtctta tgcatcttcc aaagtgagag ctgccctgga tattcttctc | 3060 |
| tcgttgccta aactggattt aacccatatg agtgatgaca aaaataaaat tgtgcatcct | 3120 |
| gacaaaatta acgggaatag tactccctct gaatatgctg gcaccaaaat aactgagaag | 3180 |
| gccatcgttt ctctcaatg gactagaatg ctggatttgg tagaggttca tttgaaatct | 3240 |
| tctcatctat cttatcggag gcttgatgga acaatgtccg tcgcagctcg ggatagagct | 3300 |
| gtaaaagact tcaacacaaa tccagaggtt tctgttatga ttatgtctct caaagctgca | 3360 |
| agtcttggtc tgaatatggt ggcggcctgt catgtacttt tgcttgatct ttggtggaat | 3420 |
| cctactacag aagaccaagc tgttgacaga gcgcatcgta ttggccaaac tcgacctgtc | 3480 |
| acagtgtcac ggttaaccat aaaagatacc gttgaagatc gtattttggc tctccaggag | 3540 |
| aaaaaacggg agatggtggc ttctgcattt ggggaagaca aatctggtgc ccatcaaact | 3600 |
| agattgacgg tggaagactt gaactatttg tttatggttt ag | 3642 |

<210> SEQ ID NO 48
<211> LENGTH: 1213
<212> TYPE: PRT
<213> ORGANISM: Oryza sativa

<400> SEQUENCE: 48

Met Glu Glu Ala Ala Ala Ala Ala Asp Phe Asp Gly Gly Phe Gly
1               5                   10                  15

Gly Ala Gly Glu Asp Asn Leu Ser Met Pro Leu Gly Asp Phe Met Ala
        20                  25                  30

Phe Leu Asp Asn Glu Asp Trp Lys Glu Gln Gln His Glu Gly Asn Gln
    35                  40                  45

Gly Leu Glu Met Pro Val Asp Ser Thr Ser Ser Glu Asn Ala Phe Gln
50                  55                  60

```
Asn His Glu Asp Pro Ser His Ser Gln Met Asp Val Met Val Glu Leu
 65                  70                  75                  80

Asn Asn Gly Gly Glu Ser Phe Asp His Ser Glu Asp Thr Ser Tyr Arg
 85                  90                  95

Leu Leu Ser Asn Asp Phe Leu Glu Asn Ser Arg Asn Gly Asn Pro Glu
100                 105                 110

Met His Leu Pro Met Asp Ala Leu Asn His Ala Lys Thr Val Asp Glu
115                 120                 125

Glu Ile Val Pro Pro Tyr Glu Asp Tyr Thr Asn Gly Leu Tyr Tyr Asp
130                 135                 140

Ser Gly Cys Asp Met Phe Ala Glu Gln Ser Gly Leu Ser Glu Val Lys
145                 150                 155                 160

Cys Glu Gly Thr Gly Pro Met Leu Gly Asn Ser Glu Gln Glu Gly Asn
165                 170                 175

His Phe Thr Ser Val Pro Met Phe Asp His Ser Ala Val Ile Pro Asp
180                 185                 190

Ile Pro Tyr Thr Glu Leu Asn Ile Gly Asp Val Pro Gly Ser Met Gln
195                 200                 205

Asn Gly Asn Gly Ser Cys Leu Thr Val Gln Gly Glu Tyr Leu Gln Gly
210                 215                 220

Glu Tyr Gln Glu Tyr Pro Gln Pro Asp Tyr Gly Ser Phe Asp Met Ala
225                 230                 235                 240

Asn Glu Ile Val Leu His Asp Leu Pro Gln Asn Asn Gln Ser Tyr Glu
245                 250                 255

Leu Glu Gln Leu Pro Gln Asn Ile Cys Glu Ser Ser Ser Met Gln Val
260                 265                 270

Gly Ser Pro Asp Gln Tyr Cys Asp Asp Thr Ser Leu Ser Asp Tyr Tyr
275                 280                 285

Met Asp Asp Val Ser Ser Ile Glu Ser Met Ser Ser Glu Gln Asn Arg
290                 295                 300

Ser Glu Asp Ile Cys Phe Arg Ser Glu Ser Ser Thr Asp Ser Ser Pro
305                 310                 315                 320

Val Pro Ser Ser Arg Asn Ser Thr Thr Glu Asp Ala Asp Lys Tyr Phe
325                 330                 335

Gly Asp Ala Pro Lys His Leu Gln Asn Ser Met Phe Pro Val Ser Thr
340                 345                 350

Gln His Gln His Ser Phe Met Asn Ser Ser Asp Pro Met His Pro Thr
355                 360                 365

Phe His Lys Lys Tyr Asp Ile Pro Arg Asn Gly Ser Ser Ser Ile Leu
370                 375                 380

Gly Asn Ser Ser Arg Asn Cys Phe Ser Leu Asp Ser Asn Arg Asp Ser
385                 390                 395                 400

Asp Leu Cys Ile Leu Glu Gly Ser Arg Ser Leu Ala Ser Gly His Val
405                 410                 415

Leu Pro Pro Gln Gly Leu Gln His Asn Phe Gln Ser Val Cys Ala
420                 425                 430

Asn Pro Asn Leu Pro Arg Phe Gly Gly Arg Tyr Arg Pro His Glu Glu
435                 440                 445

Arg Met Thr Leu Arg Leu Ala Leu Gln Asp Ile Ser Gln Pro Lys Ser
450                 455                 460

Glu Ala Asn Pro Pro Asp Gly Val Leu Ala Val Pro Leu Leu Arg His
465                 470                 475                 480
```

```
Gln Lys Ile Ala Leu Ser Trp Met Val Gln Lys Glu Arg Asn Gly Ser
485                 490                 495
Ser Cys Ser Gly Gly Ile Leu Ala Asp Asp Gln Gly Leu Gly Lys Thr
500                 505                 510
Val Ser Thr Ile Ser Leu Ile Leu Thr Glu Arg Ser Pro Val Pro Ser
515                 520                 525
Ser Ala Val Lys Gln Glu Pro Cys Glu Ala Val Thr Leu Asp Asp Asp
530                 535                 540
Asp Glu Asp Asp Asp Ala Glu Pro His Leu Lys Pro Ala Leu Ala
545                 550                 555                 560
His Leu Ala Asp Thr Cys Lys Pro Glu Ala Thr Ser Ser Thr Ile Lys
565                 570                 575
Thr Glu Asn Pro Ile Ala Asn Val Lys Ala Arg Pro Ala Ala Gly Thr
580                 585                 590
Leu Val Val Cys Pro Thr Ser Val Leu Arg Gln Trp Ala Asp Glu Leu
595                 600                 605
Arg Asn Lys Val Thr Ser Lys Ala Asn Leu Thr Phe Leu Val Tyr His
610                 615                 620
Gly Ser Asn Arg Thr Lys Asp Pro Asn Asp Leu Thr Lys Tyr Asp Val
625                 630                 635                 640
Val Leu Thr Thr Tyr Ser Ile Val Ser Met Glu Val Pro Lys Gln Ser
645                 650                 655
Ser Pro Asp Ser Asp Asp Glu Glu Lys Gly Lys Pro Asp Arg Tyr Gly
660                 665                 670
Ala Pro Val Gly Ser Ser Gly Ser Lys Lys Arg Lys Thr Ser Ser Ser
675                 680                 685
Lys Lys Asn Lys Ser Gly Ser Thr Pro Glu Ser Lys Leu Pro Glu Lys
690                 695                 700
Pro Leu Ala Lys Val Ala Trp Phe Arg Val Ile Leu Asp Glu Ala Gln
705                 710                 715                 720
Ser Ile Lys Asn Tyr Arg Thr Gln Val Ala Arg Ala Cys Trp Gly Leu
725                 730                 735
Arg Ala Lys Arg Arg Trp Cys Leu Ser Gly Thr Pro Ile Gln Asn Ala
740                 745                 750
Val Glu Asp Leu Tyr Ser Tyr Phe Arg Phe Leu Arg Tyr Asp Pro Tyr
755                 760                 765
Ala Glu Tyr Lys Lys Phe Cys Phe Met Ile Lys Thr Pro Ile Ser Arg
770                 775                 780
Asn Pro Ile Thr Gly Tyr Lys Lys Leu Gln Val Val Leu Lys Thr Val
785                 790                 795                 800
Met Leu Arg Arg Thr Lys Ala Thr Met Leu Asp Gly Lys Pro Ile Ile
805                 810                 815
Ser Leu Pro Pro Lys Thr Val Ser Leu Lys Thr Val Asp Phe Thr Ser
820                 825                 830
Glu Glu Arg Ala Phe Tyr Asn Thr Leu Glu Ala Glu Ser Arg Glu Gln
835                 840                 845
Phe Lys Glu Tyr Ala Ala Ala Gly Thr Val Lys Gln Asn Tyr Val Asn
850                 855                 860
Ile Leu Leu Met Leu Leu Arg Leu Arg Gln Ala Cys Asp His Pro His
865                 870                 875                 880
Leu Val Arg Gly His Glu Ser Thr Ser Ser Trp Met Ser Ser Leu Glu
885                 890                 895
Met Ala Lys Lys Leu Pro Val Glu Arg Gln Gln Ser Leu Leu Val Cys
```

```
                        900                 905                 910
Leu Gln Ser Cys Ser Ala Ile Cys Ala Leu Cys Asn Asp Ala Pro Glu
        915                 920                 925

Asp Ala Val Val Thr Ile Cys Gly His Val Phe Cys Asn Gln Cys Ile
        930                 935                 940

Leu Glu Gln Leu Thr Gly Asp Asp Ser Val Cys Pro Val Ser Asn Cys
        945                 950                 955                 960

Arg Val Arg Leu Asn Ser Thr Ser Leu Phe Ser Arg Gly Thr Leu Glu
        965                 970                 975

Cys Ala Leu Ser Arg Ser Thr Cys Glu Phe Leu Ser Asp Asp Ser Cys
        980                 985                 990

Glu Asp Met Val Gln Gly Lys Gln Pro Arg Phe Asp Ser Ser Tyr Ala
        995                1000                1005

Ser Ser Lys Val Arg Ala Ala Leu Asp Ile Leu Leu Ser Leu Pro
       1010                1015                1020

Lys Leu Asp Leu Thr His Met Ser Asp Asp Lys Asn Lys Ile Val
       1025                1030                1035

His Pro Asp Lys Ile Asn Gly Asn Ser Thr Pro Ser Glu Tyr Ala
       1040                1045                1050

Gly Thr Lys Ile Thr Glu Lys Ala Ile Val Phe Ser Gln Trp Thr
       1055                1060                1065

Arg Met Leu Asp Leu Val Glu Val His Leu Lys Ser Ser His Leu
       1070                1075                1080

Ser Tyr Arg Arg Leu Asp Gly Thr Met Ser Val Ala Ala Arg Asp
       1085                1090                1095

Arg Ala Val Lys Asp Phe Asn Thr Asn Pro Glu Val Ser Val Met
       1100                1105                1110

Ile Met Ser Leu Lys Ala Ala Ser Leu Gly Leu Asn Met Val Ala
       1115                1120                1125

Ala Cys His Val Leu Leu Leu Asp Leu Trp Trp Asn Pro Thr Thr
       1130                1135                1140

Glu Asp Gln Ala Val Asp Arg Ala His Arg Ile Gly Gln Thr Arg
       1145                1150                1155

Pro Val Thr Val Ser Arg Leu Thr Ile Lys Asp Thr Val Glu Asp
       1160                1165                1170

Arg Ile Leu Ala Leu Gln Lys Lys Arg Glu Met Val Ala Ser
       1175                1180                1185

Ala Phe Gly Glu Asp Lys Ser Gly Ala His Gln Thr Arg Leu Thr
       1190                1195                1200

Val Glu Asp Leu Asn Tyr Leu Phe Met Val
       1205                1210

<210> SEQ ID NO 49
<211> LENGTH: 1255
<212> TYPE: PRT
<213> ORGANISM: Sorghum bicolor

<400> SEQUENCE: 49

Met Ala Glu Glu Pro Ala Val Gly Tyr Asp Gly Phe Glu Ala Ala Gly
1               5                  10                  15

Asp Ala Gly Ala Gly Gly Ala Glu Asp Asn Leu Ser Met Pro Leu Gly
         20                  25                  30

Asp Phe Met Ala Phe Leu Glu Thr Glu Pro Ala Pro Pro Glu Glu Gly
    35                  40                  45
```

-continued

```
Gly Glu Glu Glu Glu Glu Gln Glu Gln Leu Gln Pro Gly Val Asn Gln
 50                  55                  60

Gly Cys Phe Glu Met Pro Ala Asn Thr Asp Gly Ser Glu Asp Leu Leu
 65                  70                  75                  80

Gln Ser His Glu Glu Met Phe Glu Asn Ala Asp Leu Trp Ser Asn Tyr
 85                  90                  95

Ser His Val Asp Thr Ser Glu Cys His Met Glu Leu Ser Gly Gly Glu
100                 105                 110

Gln Met Ile Asp His Thr Glu Ala Ser Pro Tyr Glu Phe Phe Ser Asn
115                 120                 125

Asp Leu Gln Asn Gln Ser Arg Thr Ser Asn Leu Asp Asn Glu His Phe
130                 135                 140

Pro Arg Asp Ala Ser Asn His Ala Asn Val Glu Glu Val Ala Gly Pro
145                 150                 155                 160

Pro Tyr Glu Asp Leu Ser Asn Gly Leu Tyr Leu Arg Gln Gln Thr Leu
165                 170                 175

Tyr Ser Gly Gln Thr Gln Phe Gln Val Glu Asn Asn Thr Glu Gly Met
180                 185                 190

Glu Thr Gln Met Asn Thr Tyr Phe Ser Gly Gly Ile Ser Thr Glu His
195                 200                 205

Ser Asp Leu Met Leu Gly Ser Thr Gly Gln Asp Gly Asp His Phe Thr
210                 215                 220

Ser Met Gly Met Phe Ser Leu Thr His Lys Thr Asp Val Pro Asp Ile
225                 230                 235                 240

Ser Cys Thr Glu Phe Asn Met Gly Glu Gly Thr Glu Ser Ile Arg Asn
245                 250                 255

Gly Asn Ser Ser Cys Leu Thr Met Gln Glu Ala Glu Cys Gly Gly Tyr
260                 265                 270

Pro His Pro Asp Cys Ile Ser Val Asp Met Val Asp Glu Arg Ser Leu
275                 280                 285

His Asp Leu Pro His Gly Phe Ser Gln Asn Asn Glu Gln Tyr Glu Met
290                 295                 300

Glu Gln Phe Pro Gln Ser Ile Cys Glu Ser Gly Ser Met Gln Met Gly
305                 310                 315                 320

Ser Pro Asp Gln Tyr Cys Asp Thr Ser Leu Ser Asp Phe Tyr Met
325                 330                 335

Asp Val Ser Ser Pro Glu Ser Ile Ser Cys Glu Gln Asn Gln Ser Glu
340                 345                 350

Asp Ile Cys Phe Lys Ser Glu Ser Ser Thr Asp Ser Ser Pro Ile Pro
355                 360                 365

Ser Ser Arg Asn Ser Thr Thr Glu Asp Ala Asp Lys Tyr Leu Gly Gln
370                 375                 380

Thr Ser Lys Gln Leu Leu Asp Ser Lys Ile Val Pro Phe Ser Asn Gln
385                 390                 395                 400

His Thr Phe Lys Asn Met Gly Tyr Gln Lys Pro Leu Ala Leu His Lys
405                 410                 415

Gln Tyr Ala Tyr Arg Ser Asp Asn Ser Ser Ile His Asn Ser Ser Arg
420                 425                 430

Gly Cys Phe Asn Arg Asp Gly Asp Gly Ala Ser Asp Leu Cys Val Leu
435                 440                 445

Glu Gly Asn Arg Asn Pro Ala Pro Asp His Arg Leu Pro Tyr Gln Gly
450                 455                 460

Lys Phe His His Asn Phe Gln Gln His Met Tyr Ser Asn Ser Met Ile
```

-continued

```
            465                 470                 475                 480
Pro Ala Phe Gly Gly Met Arg Tyr Lys Pro His Asp Glu Arg Ile Thr
485                 490                 495
Leu Arg Leu Ala Leu Gln Asp Ile Ser Gln Pro Lys Ser Glu Ala Asn
500                 505                 510
Pro Pro Asp Gly Val Leu Ala Val Pro Leu Leu Arg His Gln Lys Ile
515                 520                 525
Ala Leu Ser Trp Met Val Gln Lys Glu Thr Ser Ser His Cys Ser
530                 535                 540
Gly Gly Ile Leu Ala Asp Asp Gln Gly Leu Gly Lys Thr Val Ser Ala
545                 550                 555                 560
Ile Ser Leu Ile Leu Thr Glu Arg Ser Pro Val Pro Gln Ser Ser Thr
565                 570                 575
Ile Lys Asn Glu Pro Cys Glu Ala Val Thr Leu Asp Asp Asp Glu
580                 585                 590
Asp Asp Ser Val Glu Pro His Pro Lys Lys Leu Met Gln Thr Cys Ser
595                 600                 605
Ser Lys Val Thr Thr Asn Thr Val Lys Gln Glu Asn Pro Phe Val Ala
610                 615                 620
Ile Lys Thr Arg Pro Ala Ala Gly Thr Leu Val Cys Pro Thr Ser
625                 630                 635                 640
Val Leu Arg Gln Trp Ala Gly Glu Leu Lys Asn Lys Val Thr Ser Lys
645                 650                 655
Ala Asn Leu Ser Phe Leu Ile Tyr His Gly Ser Asn Arg Thr Lys Asp
660                 665                 670
Pro Asn Glu Leu Thr Lys Tyr Asp Val Val Leu Thr Thr Tyr Ser Ile
675                 680                 685
Val Ser Met Glu Val Pro Lys Gln Ser Asn Pro Asp Ser Asp Asp Glu
690                 695                 700
Glu Lys Gly Lys Pro Asp Arg Tyr Gly Ala Pro Val Ser Ser Ser Gly
705                 710                 715                 720
Ser Lys Lys Arg Lys Ala Pro Ser Lys Lys Thr Lys Cys Lys Ser Ala
725                 730                 735
Ala Glu Ser Cys Leu Pro Glu Lys Pro Leu Ala Lys Val Ala Trp Phe
740                 745                 750
Arg Val Ile Leu Asp Glu Ala Gln Ser Ile Lys Asn Tyr Arg Thr Gln
755                 760                 765
Val Ala Arg Ala Cys Trp Gly Leu Arg Ala Lys Arg Arg Trp Cys Leu
770                 775                 780
Ser Gly Thr Pro Ile Gln Asn Ala Val Glu Asp Leu Tyr Ser Tyr Phe
785                 790                 795                 800
Arg Phe Leu Arg Tyr Asp Pro Tyr Ala Val Tyr Lys Gln Phe Cys Thr
805                 810                 815
Met Ile Lys Ile Pro Ile Ser Arg Asn Pro Thr Asn Gly Tyr Lys Lys
820                 825                 830
Leu Gln Val Val Leu Lys Thr Val Met Leu Arg Arg Thr Lys Ala Thr
835                 840                 845
Met Leu Asp Gly Lys Pro Ile Ile Ser Leu Pro Pro Lys Thr Val Ser
850                 855                 860
Leu Lys Thr Val Asp Phe Thr Gly Glu Glu Arg Ala Phe Tyr Asn Thr
865                 870                 875                 880
Leu Glu Val Glu Ser Arg Glu Gln Phe Lys Glu Tyr Ala Ala Ala Gly
885                 890                 895
```

```
Thr Val Lys Gln Asn Tyr Val Asn Ile Leu Leu Met Leu Leu Arg Leu
900                 905                 910

Arg Gln Ala Cys Asp His Pro His Leu Val Arg Gly Tyr Asn Ser Ser
915                 920                 925

Ser Ser Trp Met Ser Ser Leu Glu Met Ala Lys Lys Leu Pro Met Glu
930                 935                 940

Arg Gln His Glu Leu Leu Asn Cys Leu Gln Ser Cys Ser Ala Leu Cys
945                 950                 955                 960

Ala Leu Cys Asn Asp Ala Pro Glu Asp Pro Val Val Thr Ile Cys Gly
965                 970                 975

His Val Phe Cys Asn Gln Cys Ile Leu Glu Gln Leu Thr Gly Asp Asp
980                 985                 990

Ser Val Cys Pro Val Ser Asn Cys  Arg Val Arg Leu Asn  Thr Thr Ser
995                 1000                1005

Leu Phe  Ser Arg Gly Thr Leu  Glu Cys Ser Leu Ser  Arg Leu Thr
1010                 1015                1020

Cys Asp  Phe Lys Ser Asp Asp  Asp Thr Cys Met Glu  Met Ile His
1025                 1030                1035

Ala Glu  Lys Arg Pro Gly Ile  Asp Ser Ser Tyr Ala  Ser Ser Lys
1040                 1045                1050

Val Arg  Ala Ala Leu Asp Ile  Leu Leu Ser Leu Pro  Arg Ile Asp
1055                 1060                1065

Pro Thr  Gln Met Thr Asp Ser  Lys Cys Ser Ile Gly  Leu Glu Ser
1070                 1075                1080

Glu Lys  Phe Asp Gly Arg Gly  Thr Ser Glu Gln Ile  Asp Thr Lys
1085                 1090                1095

Leu Thr  Glu Lys Ala Ile Val  Phe Ser Gln Trp Thr  Arg Met Leu
1100                 1105                1110

Asp Leu  Leu Glu Val His Leu  Lys Ala Ser His Val  Thr Tyr Arg
1115                 1120                1125

Arg Leu  Asp Gly Thr Met Ser  Val Ala Ala Arg Asp  Lys Ala Val
1130                 1135                1140

Lys Asp  Phe Asn Thr Val Pro  Glu Val Thr Val Met  Ile Met Ser
1145                 1150                1155

Leu Lys  Ala Ala Ser Leu Gly  Leu Asn Met Val Ala  Ala Cys His
1160                 1165                1170

Val Leu  Met Leu Asp Leu Trp  Trp Asn Pro Thr Thr  Glu Asp Gln
1175                 1180                1185

Ala Val  Asp Arg Ala His Arg  Ile Gly Gln Thr Arg  Pro Val Thr
1190                 1195                1200

Val Ser  Arg Leu Thr Ile Lys  Asp Thr Val Glu Asp  Arg Ile Leu
1205                 1210                1215

Ala Leu  Gln Glu Lys Lys Arg  Glu Met Val Ala Ser  Ala Phe Gly
1220                 1225                1230

Glu Asp  Lys Ser Gly Ser Arg  Gln Thr Arg Leu Thr  Val Glu Asp
1235                 1240                1245

Leu Asn  Tyr Leu Phe Met Val
1250                 1255
```

PLANTS HAVING ALTERED AGRONOMIC CHARACTERISTICS UNDER NITROGEN LIMITING CONDITIONS AND RELATED CONSTRUCTS AND METHODS INVOLVING GENES ENCODING SNF2 DOMAIN-CONTAINING POLYPEPTIDES

CROSS REFERENCE TO RELATED APPLICATIONS

This application claims the benefit of U.S. Provisional Application No. 61/163,887, filed Mar. 27, 2009, the entire content of which is herein incorporated by reference.

FIELD OF THE INVENTION

The field of invention relates to plant breeding and genetics and, in particular, relates to recombinant DNA constructs useful in plants for conferring nitrogen use efficiency and/or tolerance to nitrogen limiting conditions.

BACKGROUND OF THE INVENTION

Abiotic stressors significantly limit crop production worldwide. Cumulatively, these factors are estimated to be responsible for an average 70% reduction in agricultural production. Plants are sessile and have to adjust to the prevailing environmental conditions of their surroundings. This has led to their development of a great plasticity in gene regulation, morphogenesis, and metabolism. Adaptation and defense strategies involve the activation of genes encoding proteins important in the acclimation or defense towards the different stressors.

The absorption of nitrogen by plants plays an important role in their growth (Gallais et al., *J. Exp. Bot.* 55(396):295-306 (2004)). Plants synthesize amino acids from inorganic nitrogen in the environment. Consequently, nitrogen fertilization has been a powerful tool for increasing the yield of cultivated plants, such as maize and soybean. Today farmers desire to reduce the use of nitrogen fertilizer, in order to avoid pollution by nitrates and to maintain a sufficient profit margin. If the nitrogen assimilation capacity of a plant can be increased, then increases in plant growth and yield increase are also expected. In summary, plant varieties that have a better nitrogen use efficiency (NUE) are desirable.

Activation tagging can be utilized to identify genes with the ability to affect a trait. This approach has been used in the model plant species *Arabidopsis thaliana* (Weigel et al., *Plant Physiol.* 122:1003-1013 (2000)). Insertions of transcriptional enhancer elements can dominantly activate and/or elevate the expression of nearby endogenous genes. This method can be used to identify genes of interest for a particular trait (e.g. nitrogen use efficiency in a plant), genes that when placed in an organism as a transgene can alter that trait.

SUMMARY OF THE INVENTION

The present invention includes:

In one embodiment, a plant comprising in its genome a recombinant DNA construct comprising a polynucleotide operably linked to at least one regulatory element, wherein said polynucleotide encodes a polypeptide having an amino acid sequence of at least 50% sequence identity, based on the Clustal V method of alignment, when compared to SEQ ID NO:19, 21, 23, 25, 27, 29, 30, 31, 32, 36, 38, 40, 42, 44, 46, 48, or 49, and wherein said plant exhibits increased nitrogen stress tolerance when compared to a control plant not comprising said recombinant DNA construct.

In another embodiment, a plant comprising in its genome a recombinant DNA construct comprising a polynucleotide operably linked to at least one regulatory element, wherein said polynucleotide encodes a polypeptide having an amino acid sequence of at least 50% sequence identity, based on the Clustal V method of alignment, when compared to SEQ ID NO:19, 21, 23, 25, 27, 29, 30, 31, 32, 36, 38, 40, 42, 44, 46, 48, or 49, and wherein said plant exhibits an alteration of at least one agronomic characteristic when compared to a control plant not comprising said recombinant DNA construct. Optionally, the plant exhibits said alteration of said at least one agronomic characteristic when compared, under nitrogen limiting conditions, to said control plant not comprising said recombinant DNA construct. The at least one agronomic trait may be yield, biomass, or both, and the alteration may be an increase.

In another embodiment, the present invention includes any of the plants of the present invention wherein the plant is selected from the group consisting of: maize, soybean, sunflower, sorghum, canola, wheat, alfalfa, cotton, rice, barley, millet, sugar cane and switchgrass.

In another embodiment, the present invention includes seed of any of the plants of the present invention, wherein said seed comprises in its genome a recombinant DNA construct comprising a polynucleotide operably linked to at least one regulatory element, wherein said polynucleotide encodes a polypeptide having an amino acid sequence of at least 50% sequence identity, based on the Clustal V method of alignment, when compared to SEQ ID NO:19, 21, 23, 25, 27, 29, 30, 31, 32, 36, 38, 40, 42, 44, 46, 48, or 49, and wherein a plant produced from said seed exhibits either an increased nitrogen stress tolerance, or an alteration of at least one agronomic characteristic, or both, when compared to a control plant not comprising said recombinant DNA construct. The at least one agronomic trait may be yield, biomass, or both and the alteration may be an increase.

In another embodiment, a method of increasing nitrogen stress tolerance in a plant, comprising (a) introducing into a regenerable plant cell a recombinant DNA construct comprising a polynucleotide operably linked to at least one regulatory sequence, wherein the polynucleotide encodes a polypeptide having an amino acid sequence of at least 50% sequence identity, based on the Clustal V method of alignment, when compared to SEQ ID NO:19, 21, 23, 25, 27, 29, 30, 31, 32, 36, 38, 40, 42, 44, 46, 48, or 49; (b) regenerating a transgenic plant from the regenerable plant cell after step (a), wherein the transgenic plant comprises in its genome the recombinant DNA construct; and (c) obtaining a progeny plant derived from the transgenic plant of step (b), wherein said progeny plant comprises in its genome the recombinant DNA construct and exhibits increased nitrogen stress tolerance when compared to a control plant not comprising the recombinant DNA construct.

In another embodiment, a method of evaluating nitrogen stress tolerance in a plant, comprising (a) obtaining a transgenic plant, wherein the transgenic plant comprises in its genome a recombinant DNA construct comprising a polynucleotide operably linked to at least one regulatory sequence, wherein the polynucleotide encodes a polypeptide having an amino acid sequence of at least 50% sequence identity, based on the Clustal V method of alignment, when compared to SEQ ID NO:19, 21, 23, 25, 27, 29, 30, 31, 32, 36, 38, 40, 42, 44, 46, 48, or 49; (b) obtaining a progeny plant derived from the transgenic plant, wherein the progeny plant comprises in its genome the recombinant DNA construct; and (c) evaluating the progeny plant for nitrogen stress tolerance compared to a control plant not comprising the recombinant DNA construct.

In another embodiment, a method of determining an alteration of an agronomic characteristic in a plant, comprising (a) obtaining a transgenic plant, wherein the transgenic plant comprises in its genome a recombinant DNA construct comprising a polynucleotide operably linked to at least one regulatory sequence, wherein the polynucleotide encodes a polypeptide having an amino acid sequence of at least 50% sequence identity, based on the Clustal V method of alignment, when compared to SEQ ID NO:19, 21, 23, 25, 27, 29, 30, 31, 32, 36, 38, 40, 42, 44, 46, 48, or 49, wherein the transgenic plant comprises in its genome the recombinant DNA construct; (b) obtaining a progeny plant derived from the transgenic plant, wherein the progeny plant comprises in its genome the recombinant DNA construct; and (c) determining whether the progeny plant exhibits an alteration of at least one agronomic characteristic when compared to a control plant not comprising the recombinant DNA construct. Optionally, said determining step (c) comprises determining whether the transgenic plant exhibits an alteration of at least one agronomic characteristic when compared, under nitrogen limiting conditions, to a control plant not comprising the recombinant DNA construct. The at least one agronomic trait may be yield, biomass, or both and the alteration may be an increase.

In another embodiment, the present invention includes any of the methods of the present invention wherein the plant is selected from the group consisting of: maize, soybean, sunflower, sorghum, canola, wheat, alfalfa, cotton, rice, barley, millet, sugar cane and switchgrass.

In another embodiment, the present invention includes an isolated polynucleotide comprising: (a) a nucleotide sequence encoding a SNF2-domain containing polypeptide, wherein the polypeptide has an amino acid sequence of at least 50%, 55%, 60%, 65%, 70%, 75%, 80%, 85%, 90%, or 95% sequence identity, based on the Clustal V method of alignment, when compared to SEQ ID NO:19, 21, 23, 36, 38, or 46, or (b) a full complement of the nucleotide sequence, wherein the full complement and the nucleotide sequence consist of the same number of nucleotides and are 100% complementary. The polypeptide may comprise the amino acid sequence of SEQ ID NO:19, 21, 23, 36, 38, or 46. The nucleotide sequence may comprise the nucleotide sequence of SEQ ID NO:18, 20, 22, 35, 37, or 45.

In another embodiment, the present invention concerns a recombinant DNA construct comprising any of the isolated polynucleotides of the present invention operably linked to at least one regulatory sequence, and a cell, a plant, and a seed comprising the recombinant DNA construct. The cell may be eukaryotic, e.g., a yeast, insect or plant cell, or prokaryotic, e.g., a bacterial cell.

BRIEF DESCRIPTION OF THE DRAWINGS AND SEQUENCE LISTINGS

The invention can be more fully understood from the following detailed description and the accompanying drawings and Sequence Listing which form a part of this application.

FIG. 12 shows a typical grid pattern for five lines (labeled 1 through 5—eleven individuals for each line), plus wild-type control C1 (nine individuals), used in screens.

FIG. 14 shows the growth medium used for semi-hydroponics maize growth in Example 18.

FIG. 15 shows a chart setting forth data relating to the effect of different nitrate concentrations on the growth and development of Gaspe Flint derived maize lines in Example 18.

Figure 16A:
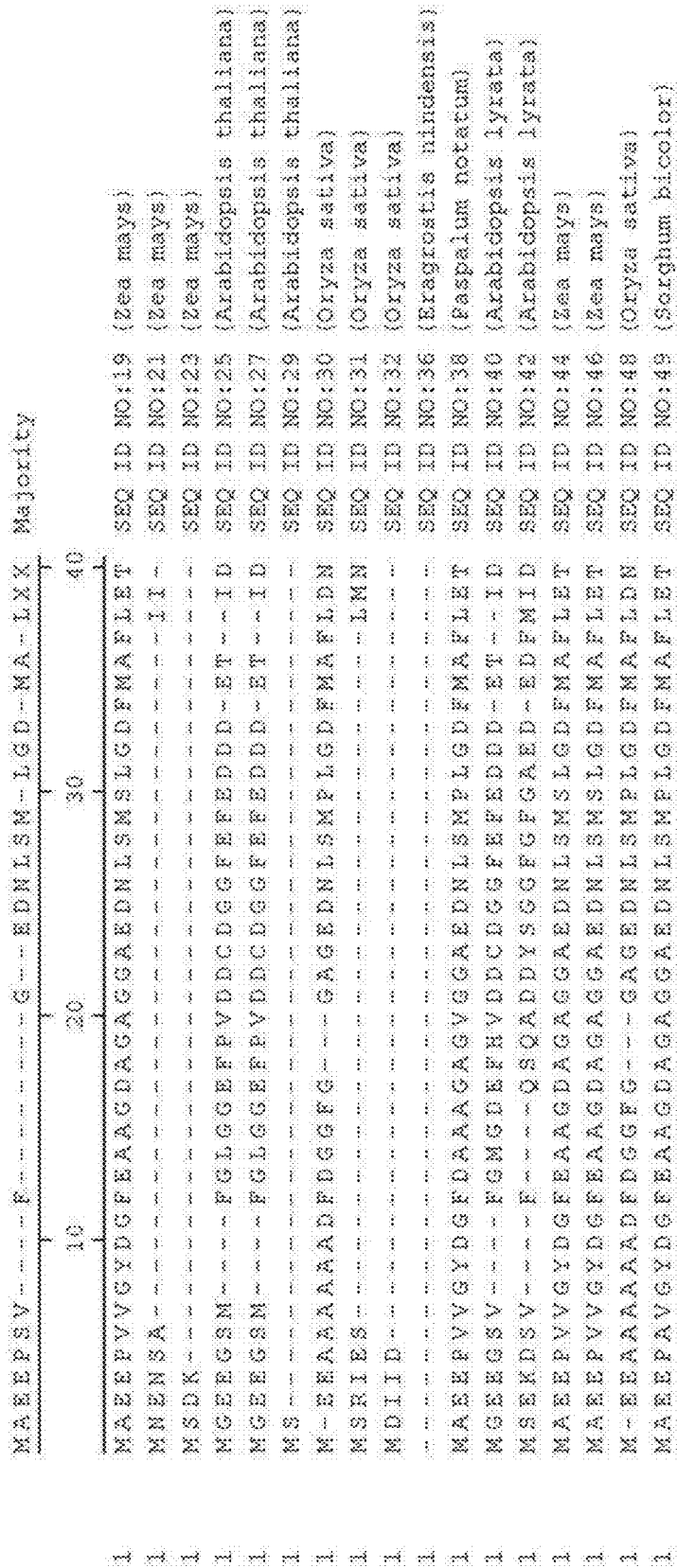
Figure 16B:
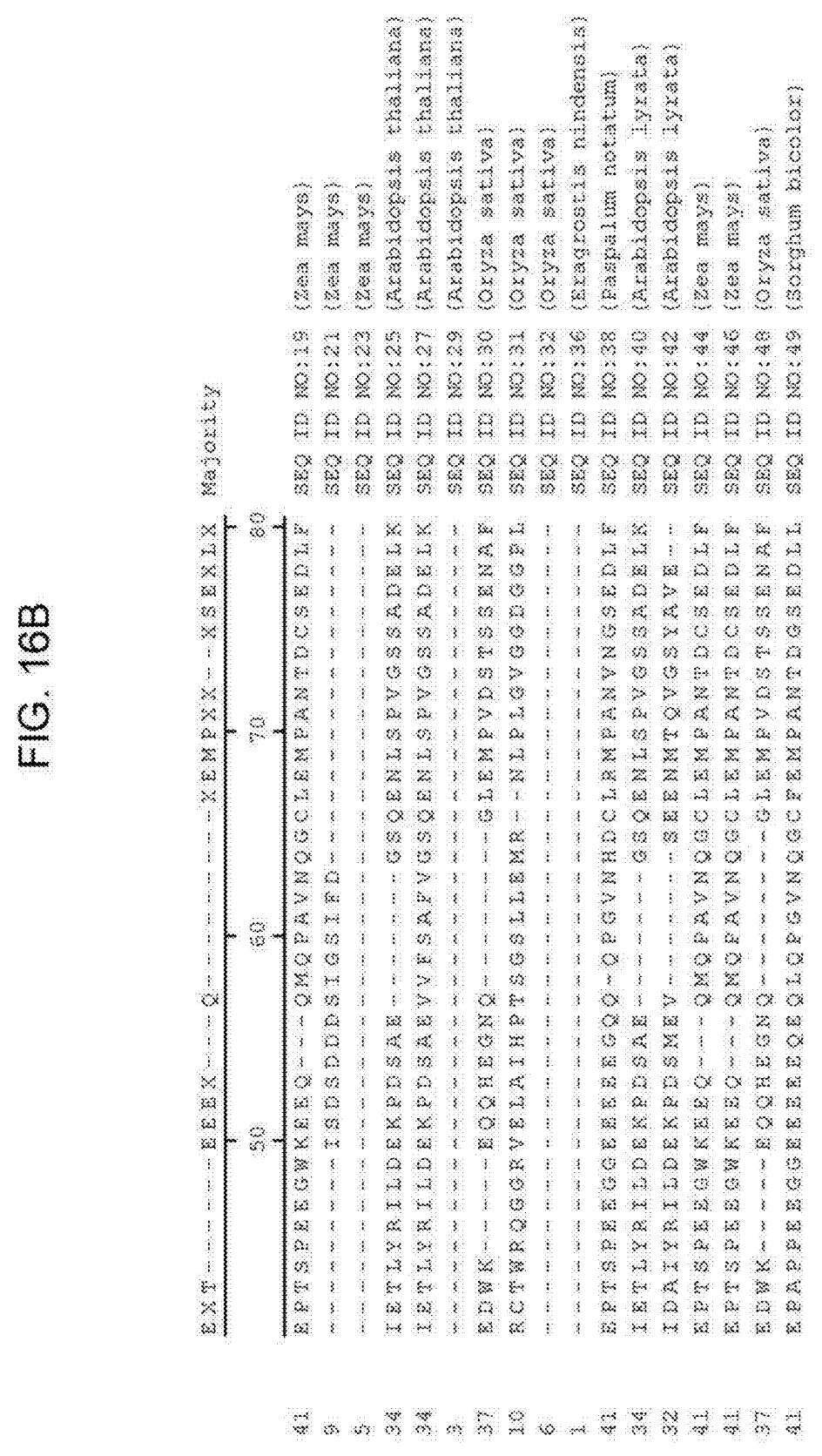
Figure 16C:
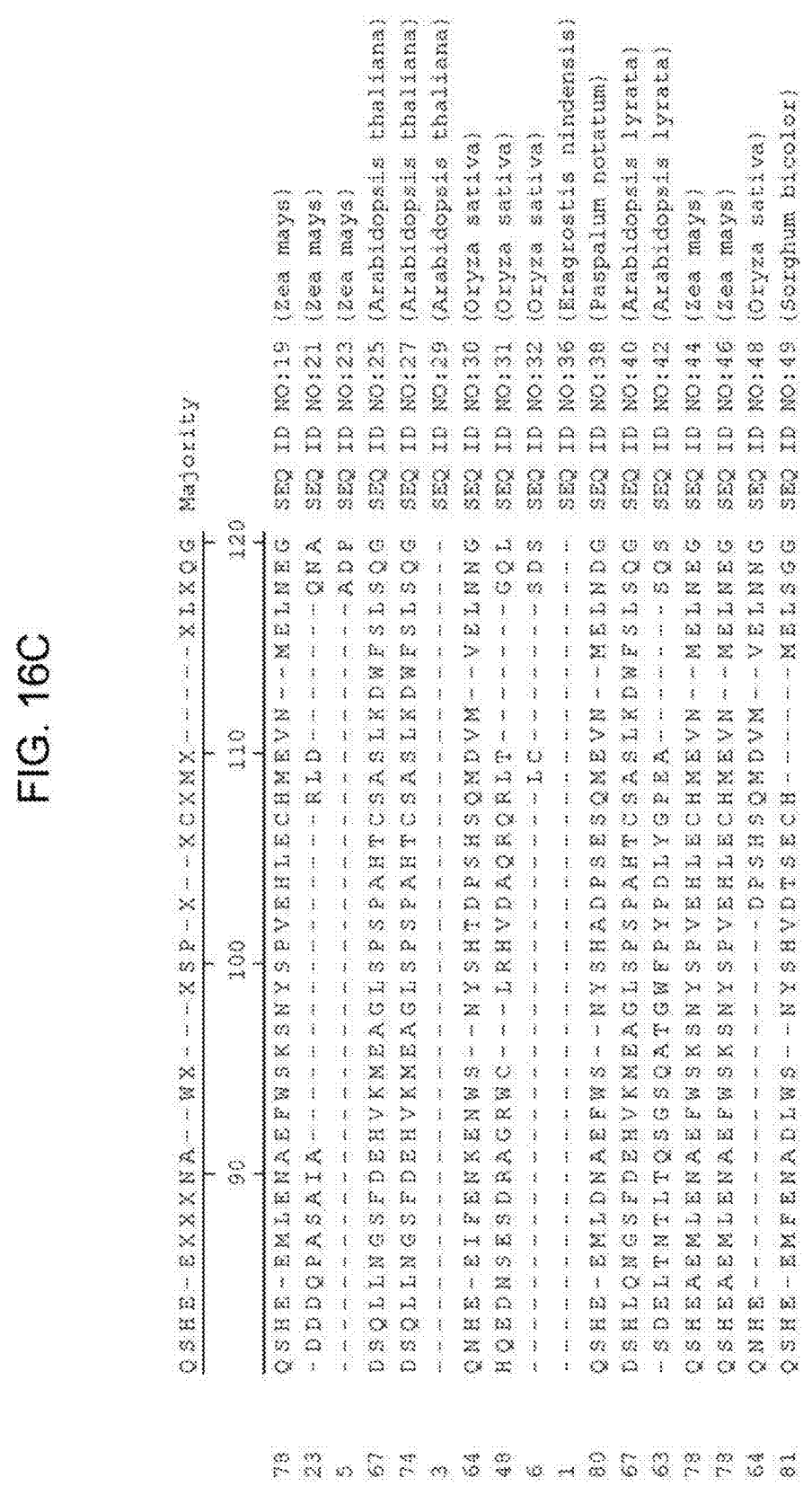
Figure 16F:
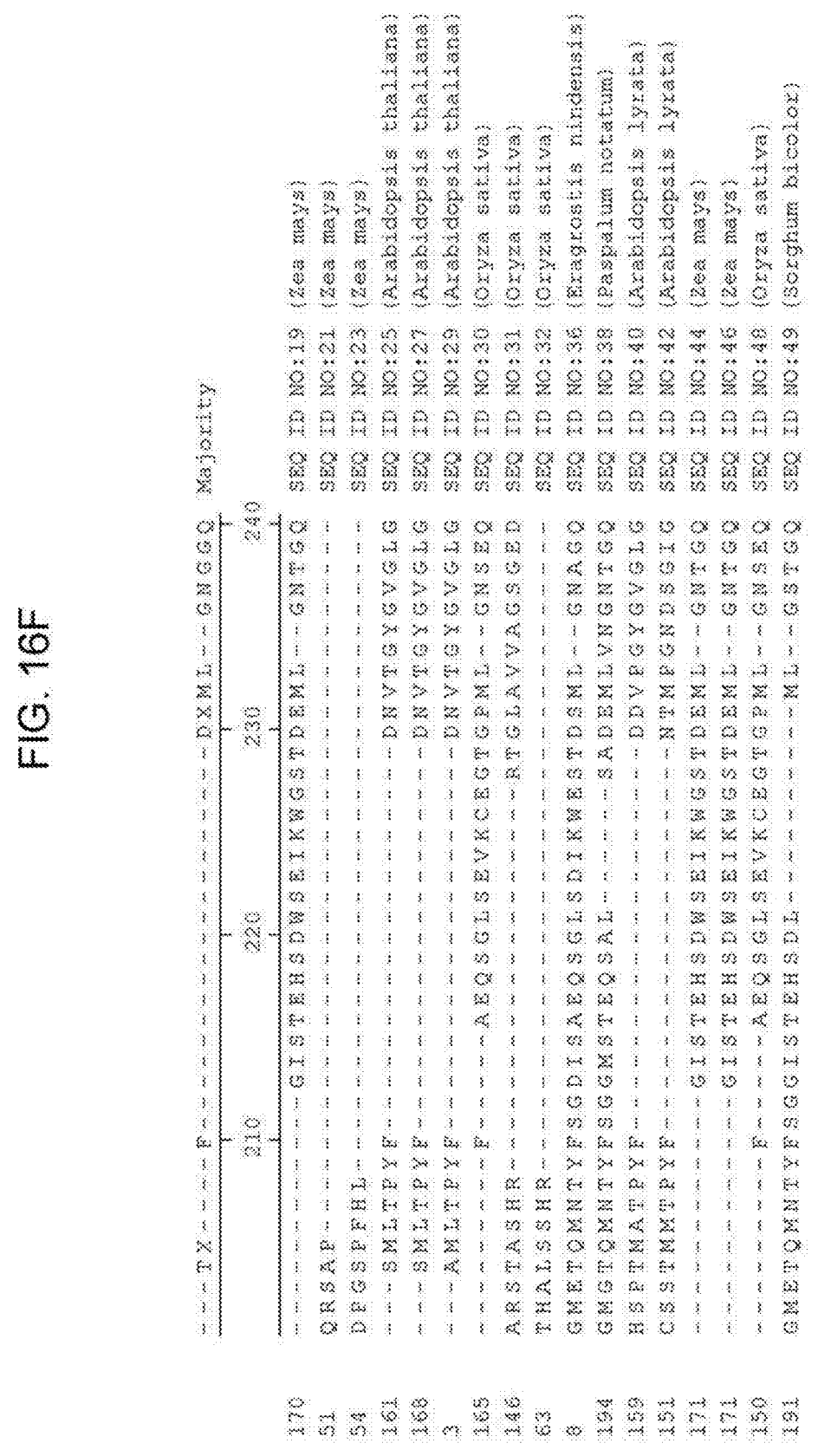
Figure 16G:
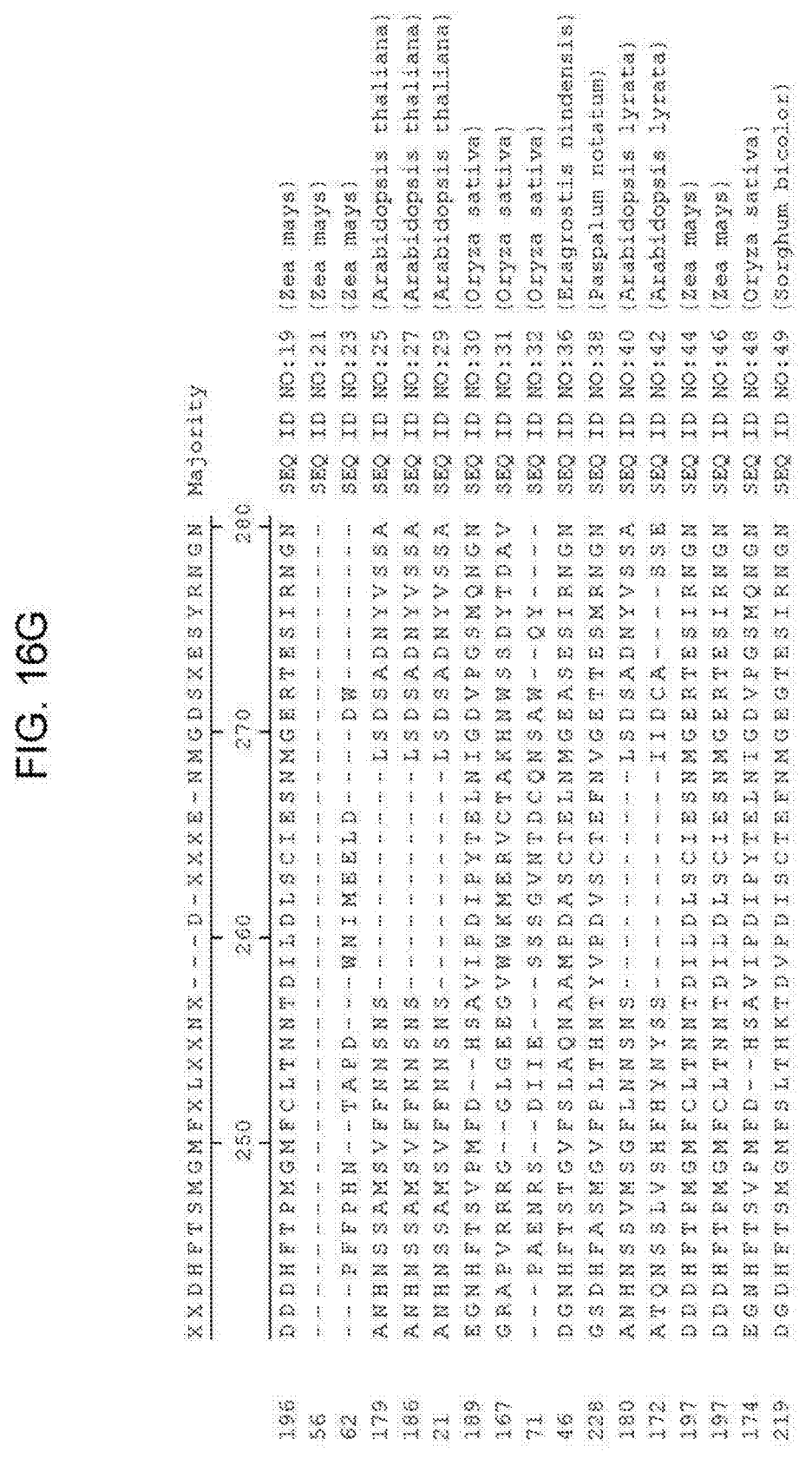
Figure 16I:
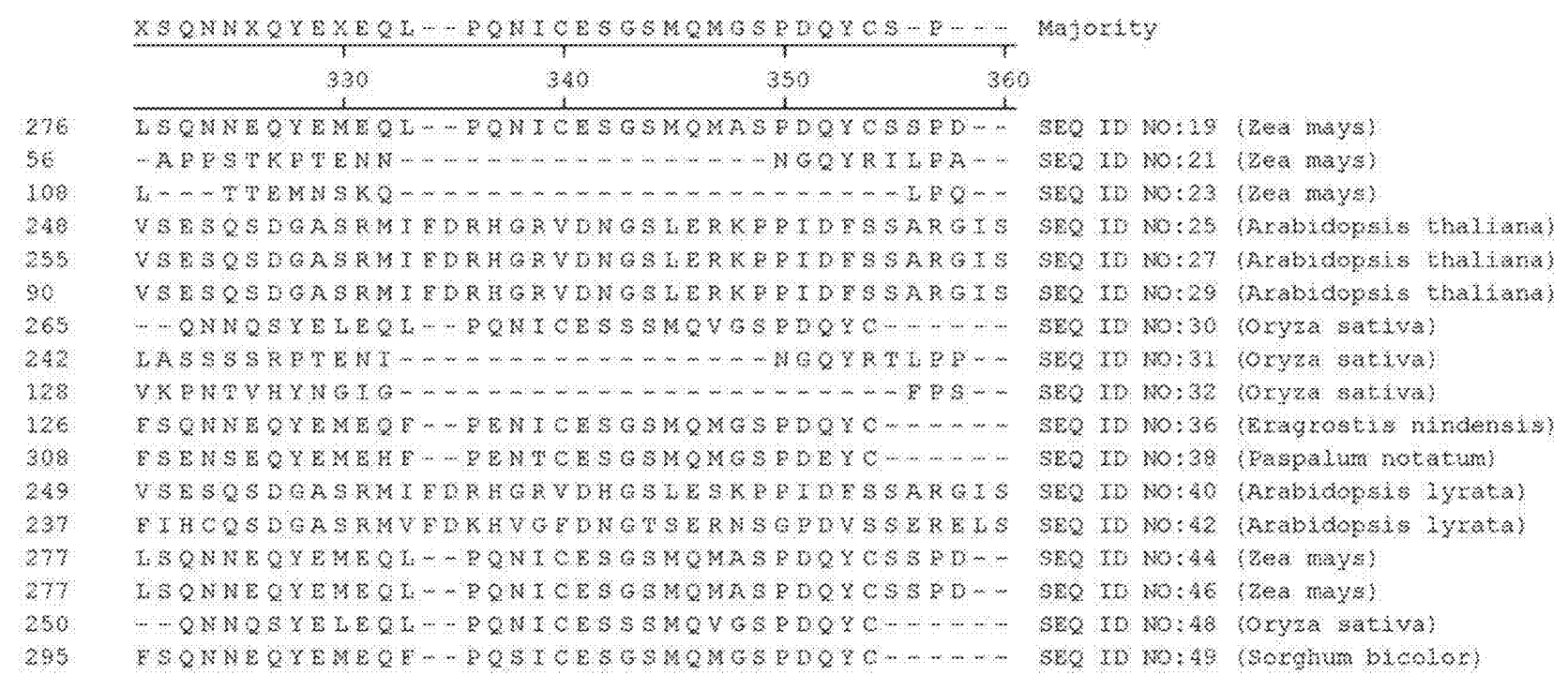
Figure 16L:
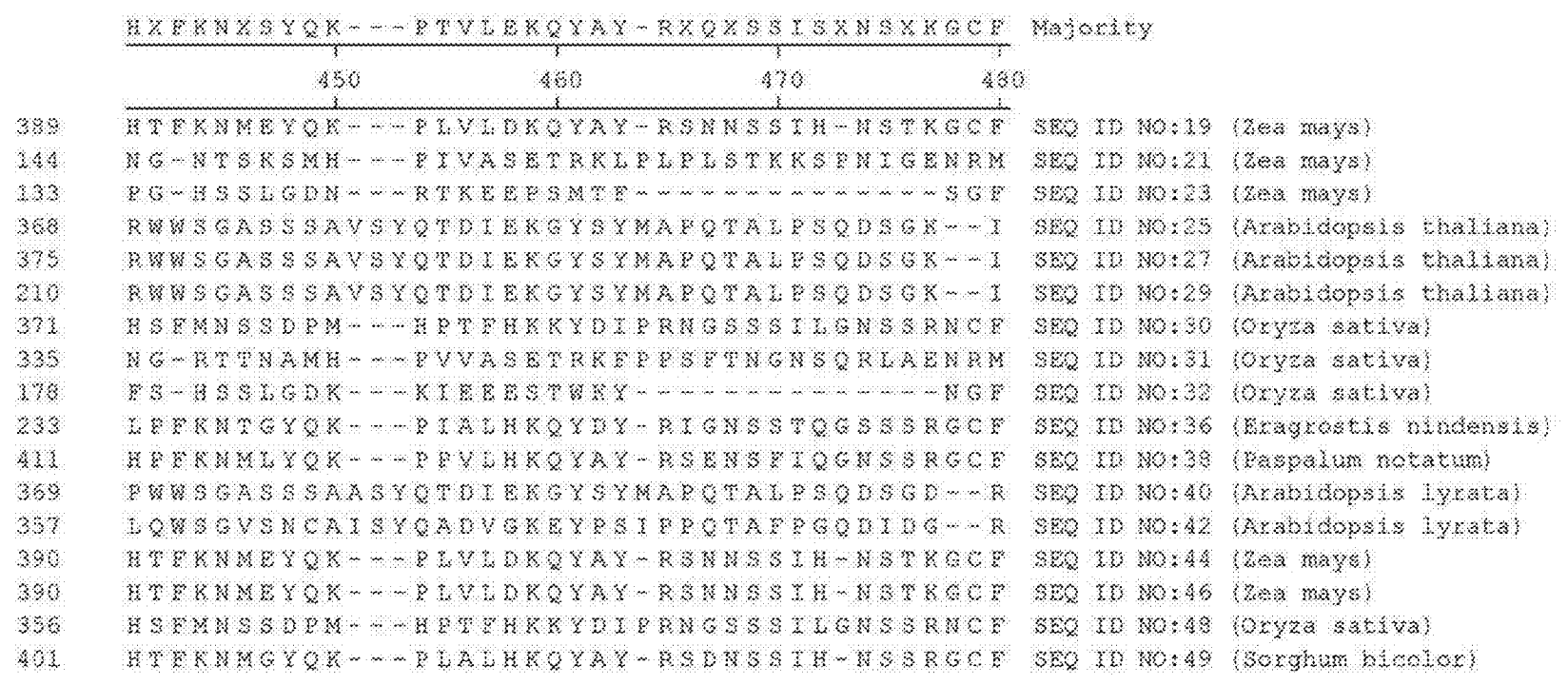
Figure 16P:
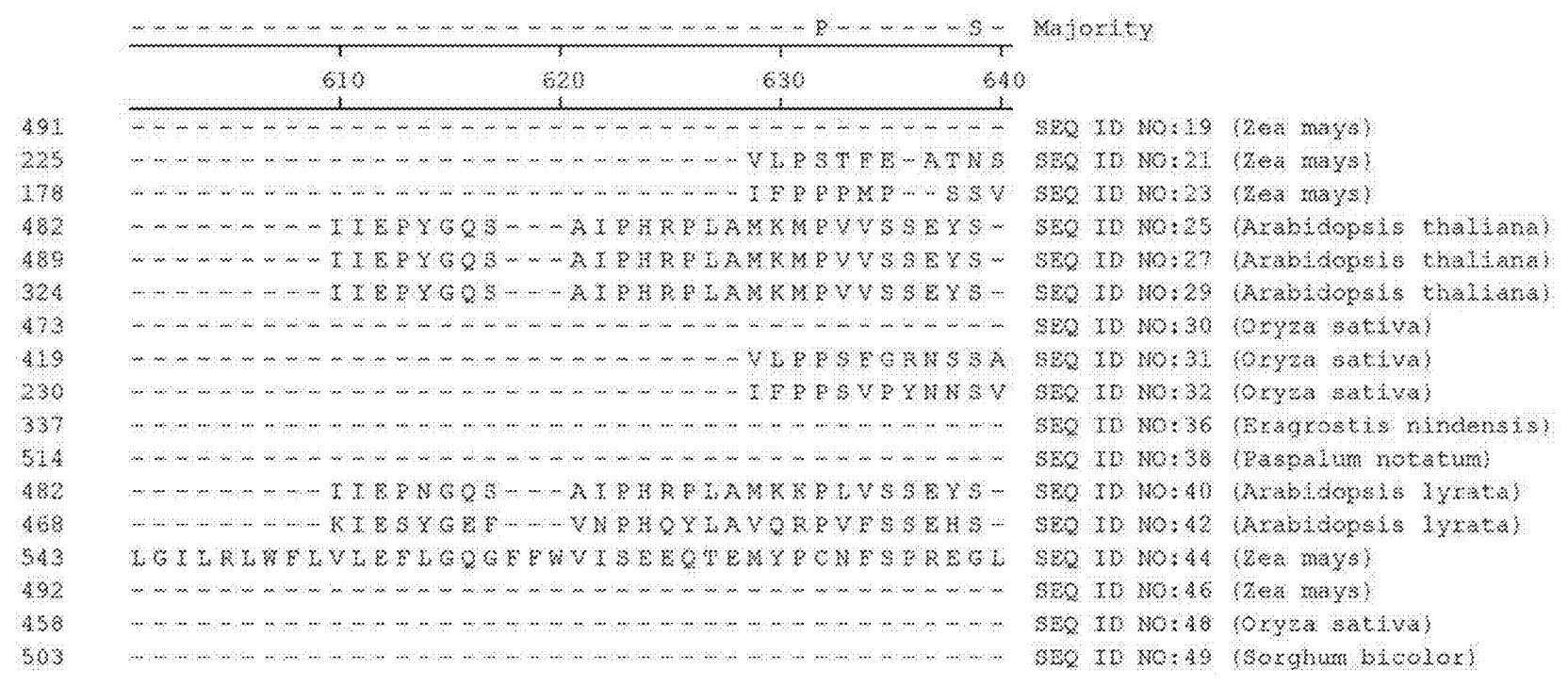
Figure 16S:
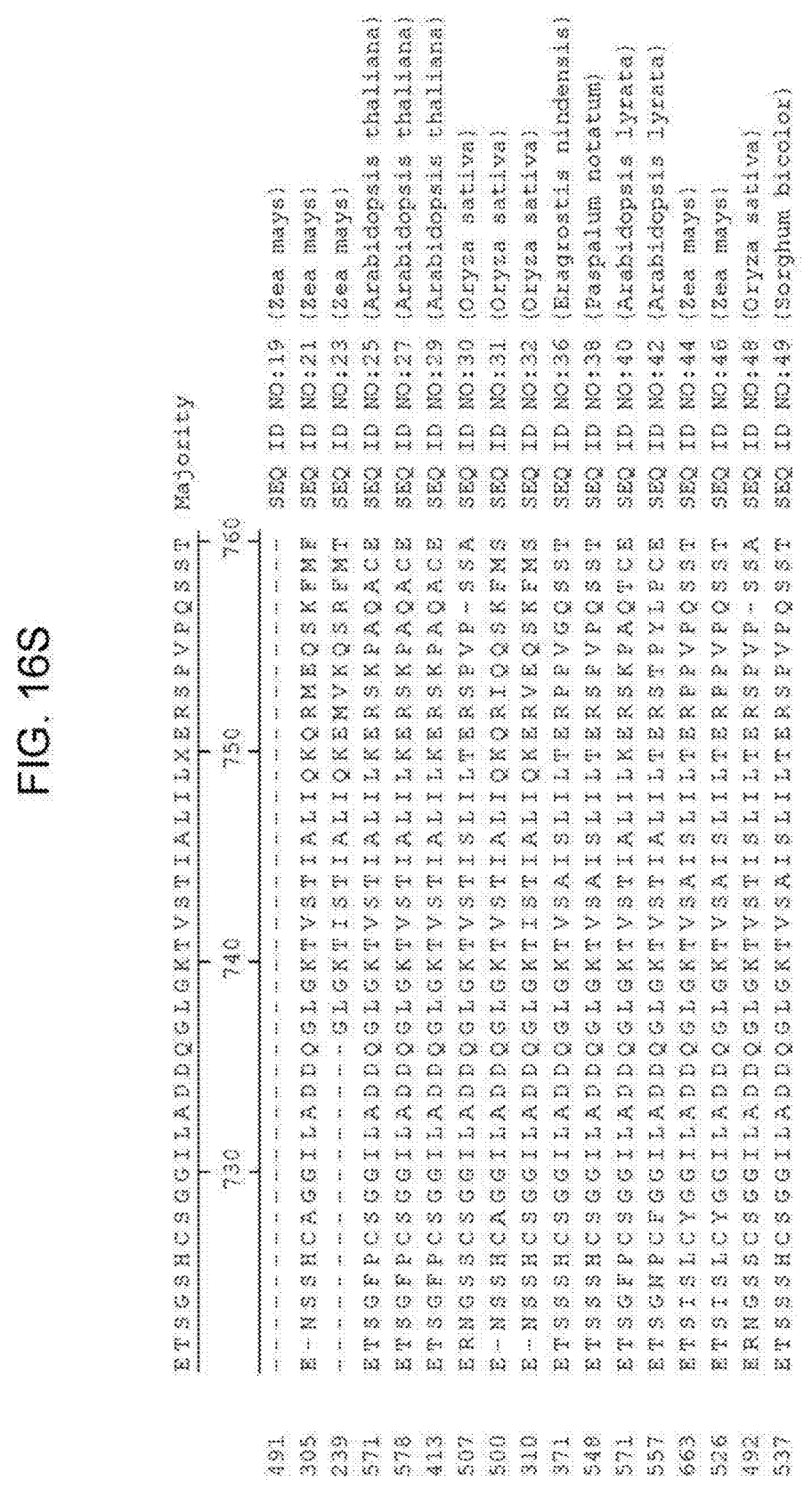
Figure 16T:
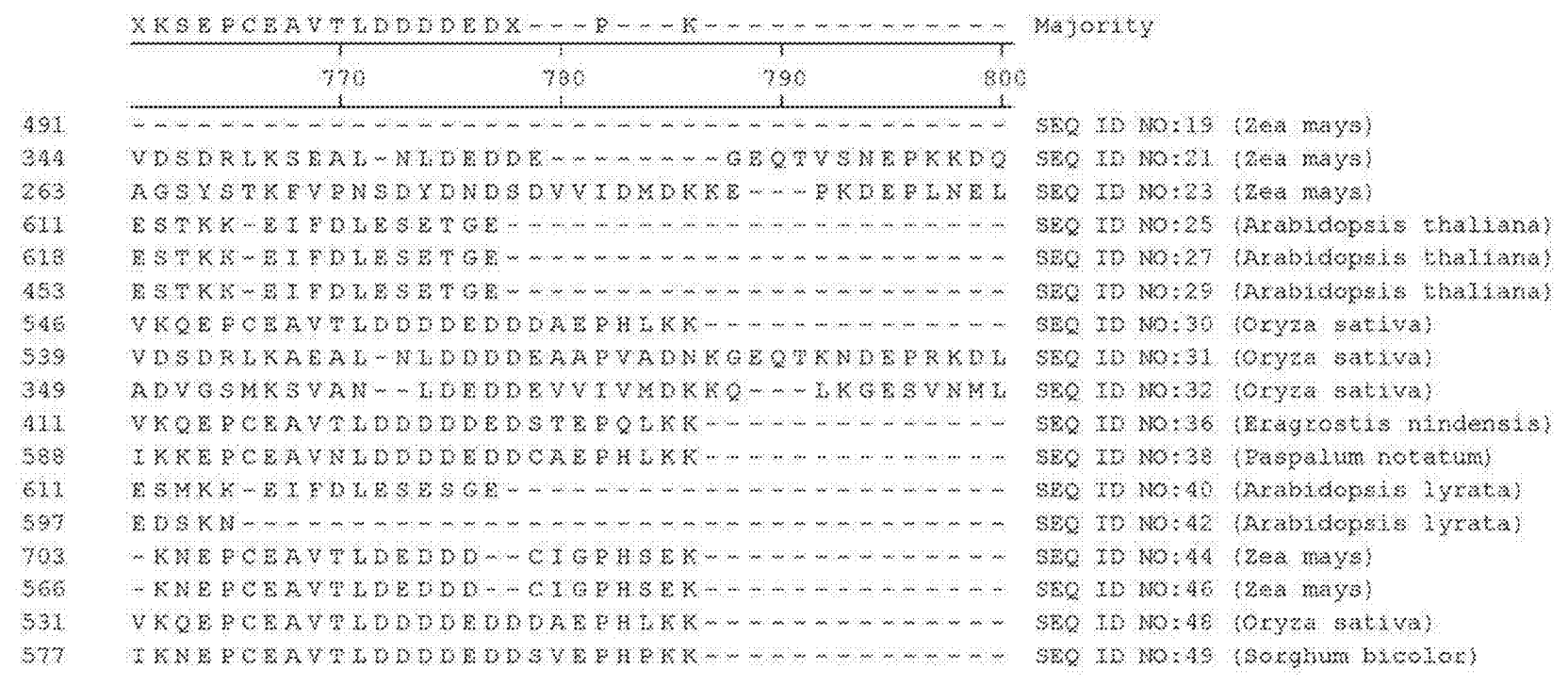
Figure 16V:
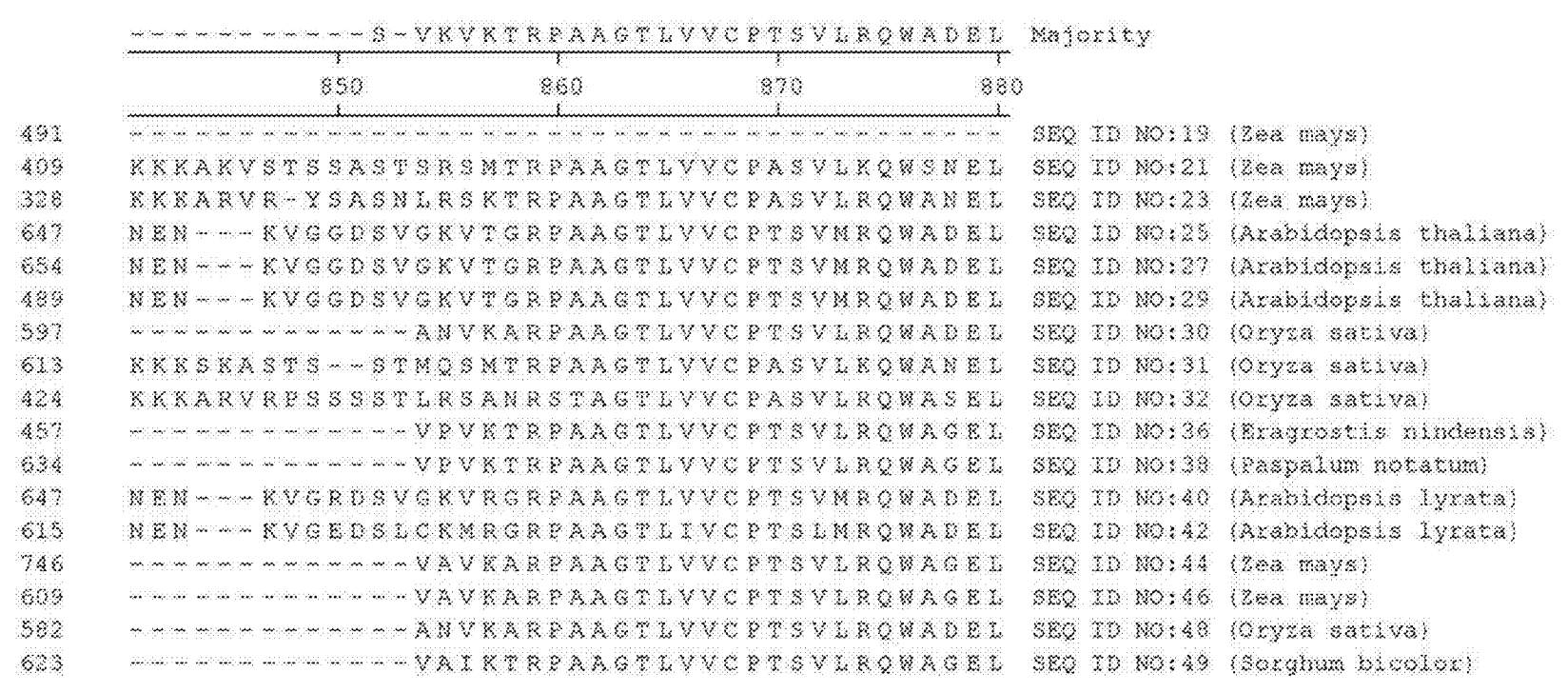
Figure 16X:
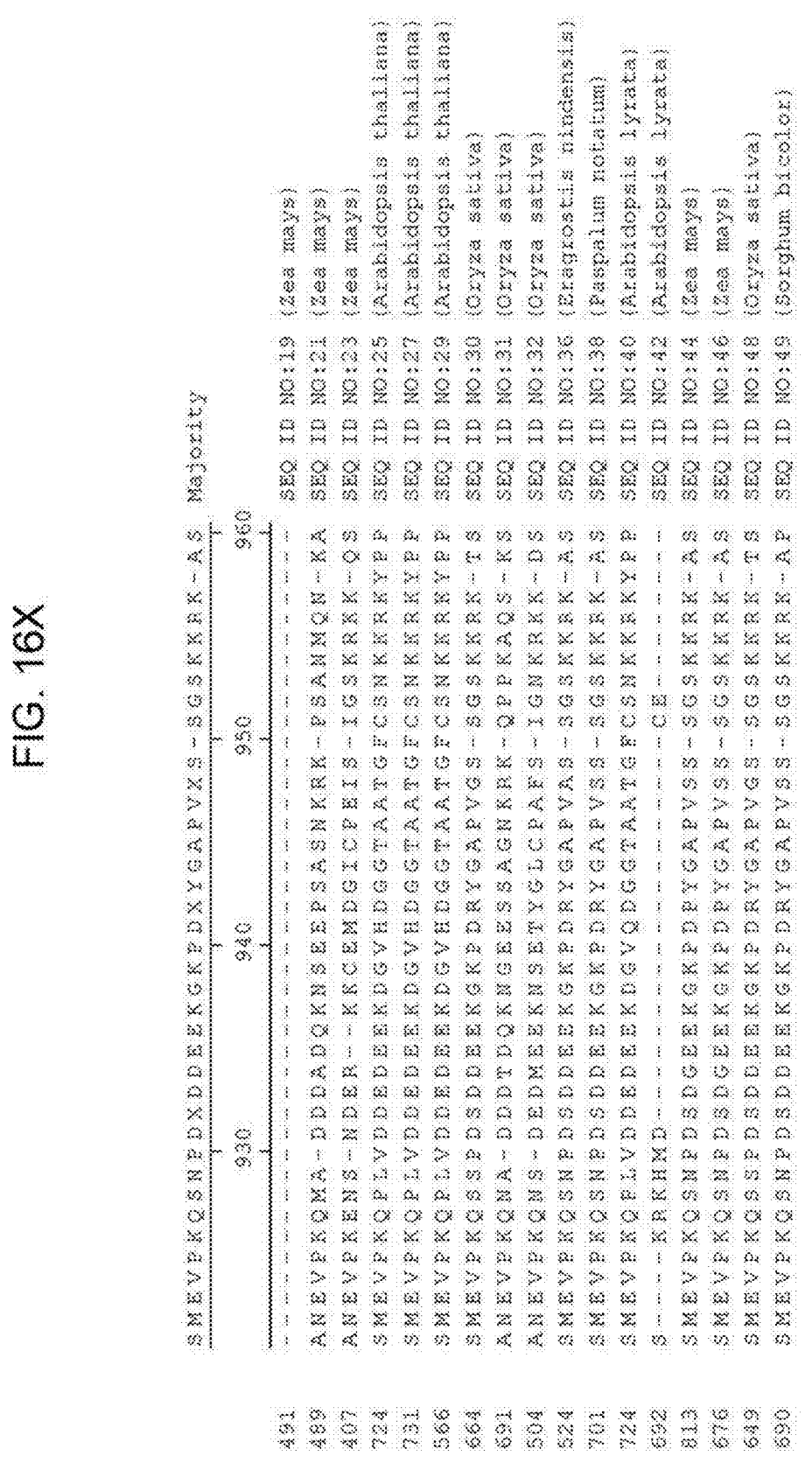
Figure 16Y:
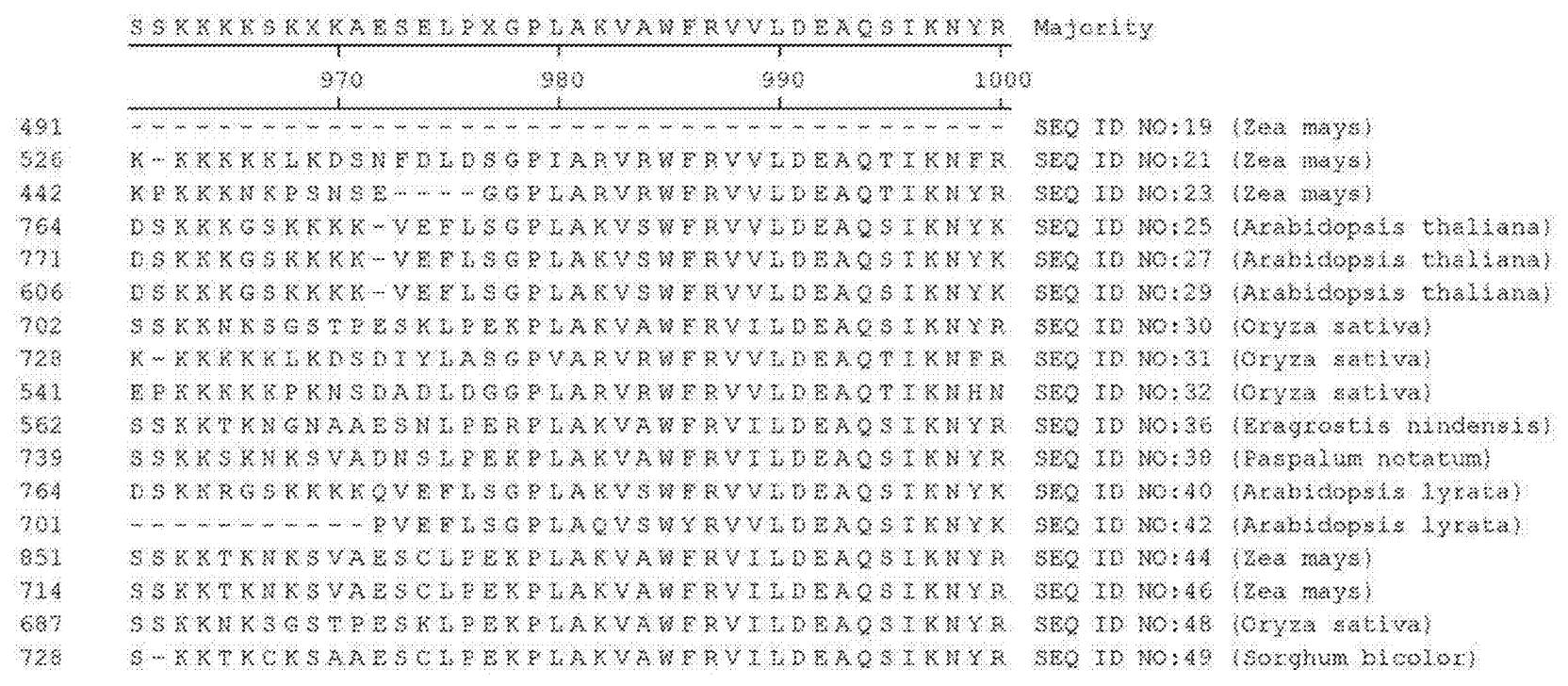
Figure 16A:
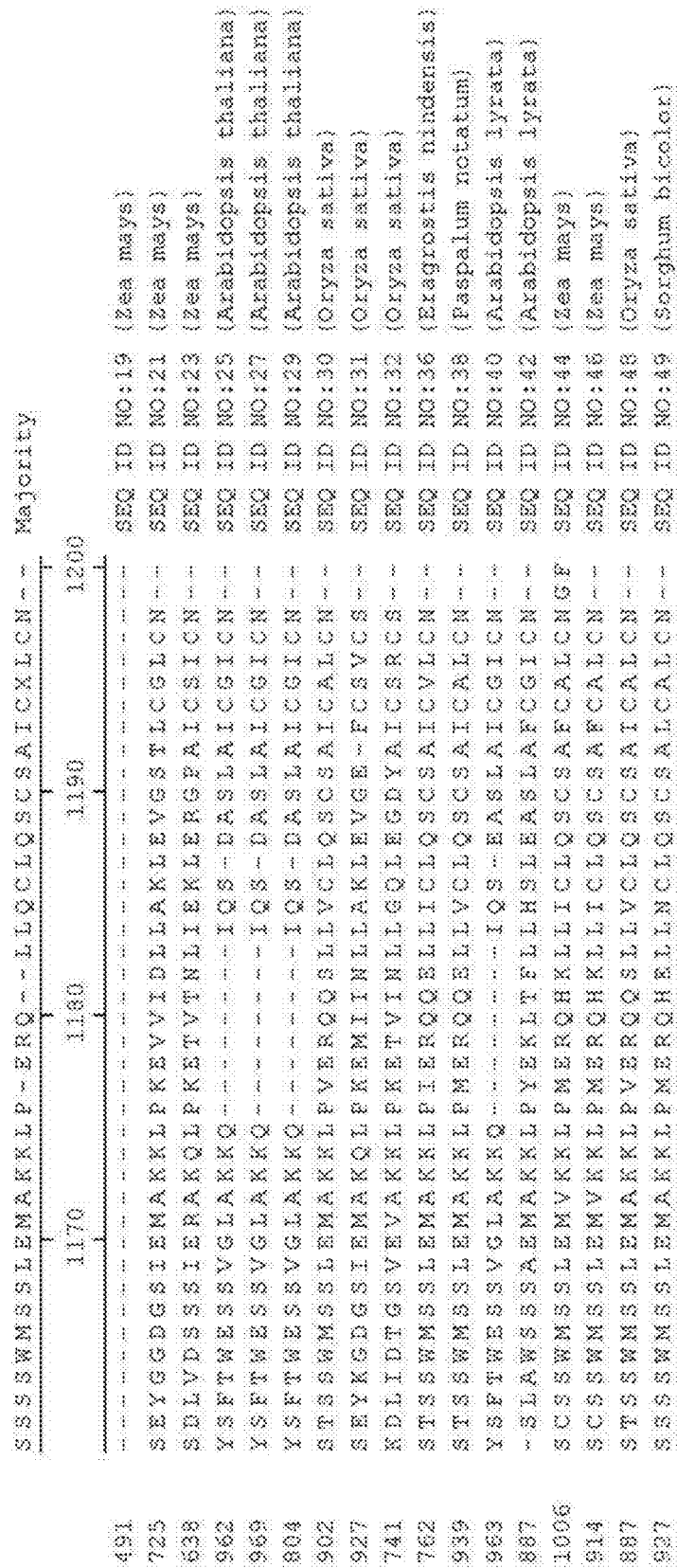

FIGS. 16A-AM show the multiple alignment of the full length amino acid sequences of the *Arabidopsis thaliana* SNF2 domain-containing polypeptides (SEQ ID NOs:25, 27, and 29) and their homologs (SEQ ID NOs: 19, 21, 23, 30, 31, 32, 36, 38, 40, 42, 44, 46, 48, and 49).

Figure 17:
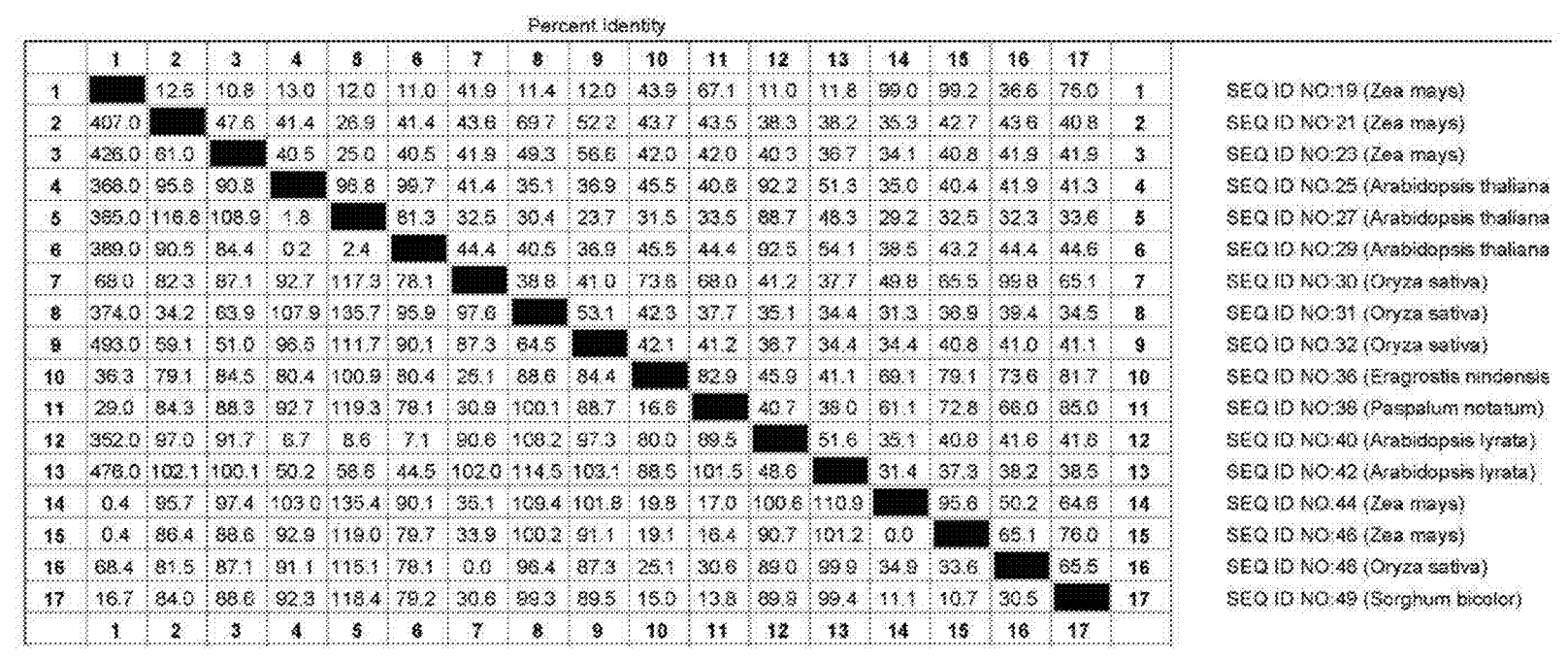

FIG. 17 shows a chart of the percent sequence identity and the divergence values for each pair of amino acids sequences displayed in FIGS. 16A-AM.

The sequence descriptions and Sequence Listing attached hereto comply with the rules governing nucleotide and/or amino acid sequence disclosures in patent applications as set forth in 37 C.F.R. §1.821-1.825. The Sequence Listing contains the one letter code for nucleotide sequence characters and the three letter codes for amino acids as defined in conformity with the IUPAC-IUBMB standards described in *Nucleic Acids Res.* 13:3021-3030 (1985) and in the *Biochemical J.* 219 (2):345-373 (1984) which are herein incorporated by reference. The symbols and format used for nucleotide and amino acid sequence data comply with the rules set forth in 37 C.F.R. §1.822.

Table 1 lists certain polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing.

TABLE 1

SNF2 domain-containing polypeptides

| | | | SEQ ID NO: | |
|---|---|---|---|---|
| | Clone Designation (if applicable) | Species | Nucleotide | Amino Acid |
| SNF2 domain-containing protein | cfp1n.pk008.f7:fis | Zea mays | 18 | 19 |
| SNF2 domain-containing protein | cfp4n.pk061.o18:fis | Zea mays | 20 | 21 |
| SNF2 domain-containing protein | contig of: p0016.ctsca12r | Zea mays | 22 | 23 |
| SNF2 domain-containing protein | N/A | Eragrostis nindensis | 35 | 36 |
| SNF2 domain-containing protein | N/A | Paspalum notatum | 37 | 38 |

Figure 1:
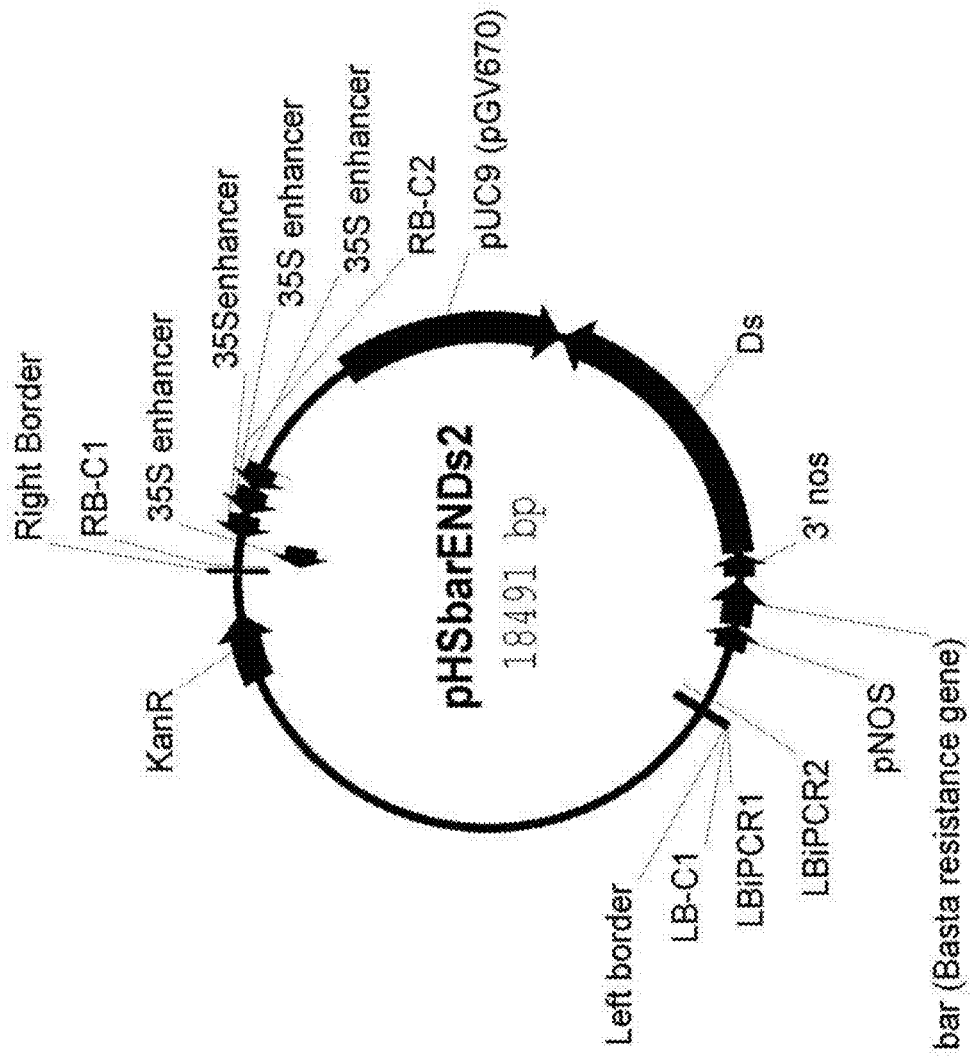
FIG. 1 shows a schematic of the pHSbarENDs2 activation tagging construct used to make the *Arabidopsis* populations (SEQ ID NO:1).

SEQ ID NO:1 is the nucleotide sequence of the pHSbarENDs2 activation tagging vector (FIG. 1).

Figure 2:
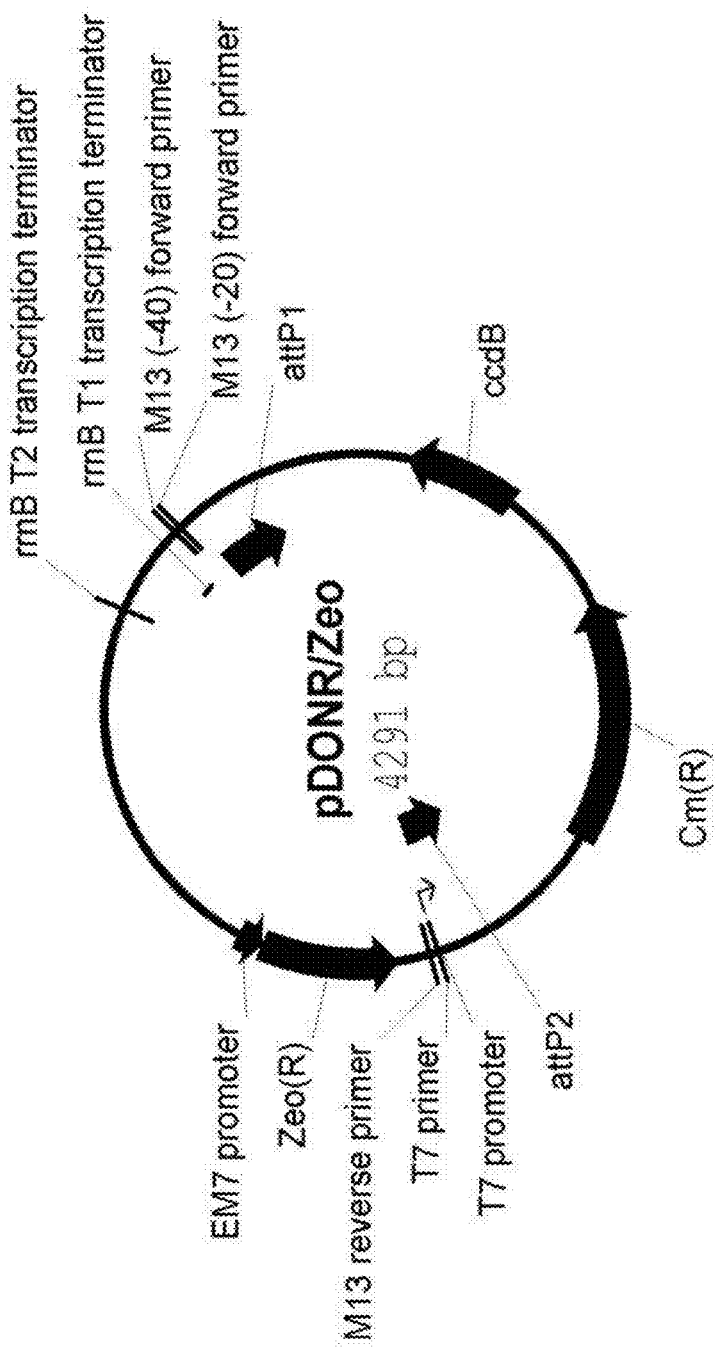
FIG. 2 shows a schematic of the vector pDONR™ Zeo (SEQ ID NO:2), GATEWAY® donor vector. The attP1 site is at nucleotides 570-801; the attP2 site is at nucleotides 2754-2985 (complementary strand).

SEQ ID NO:2 is the nucleotide sequence of the pDONR™ Zeo construct (FIG. 2).

Figure 3:
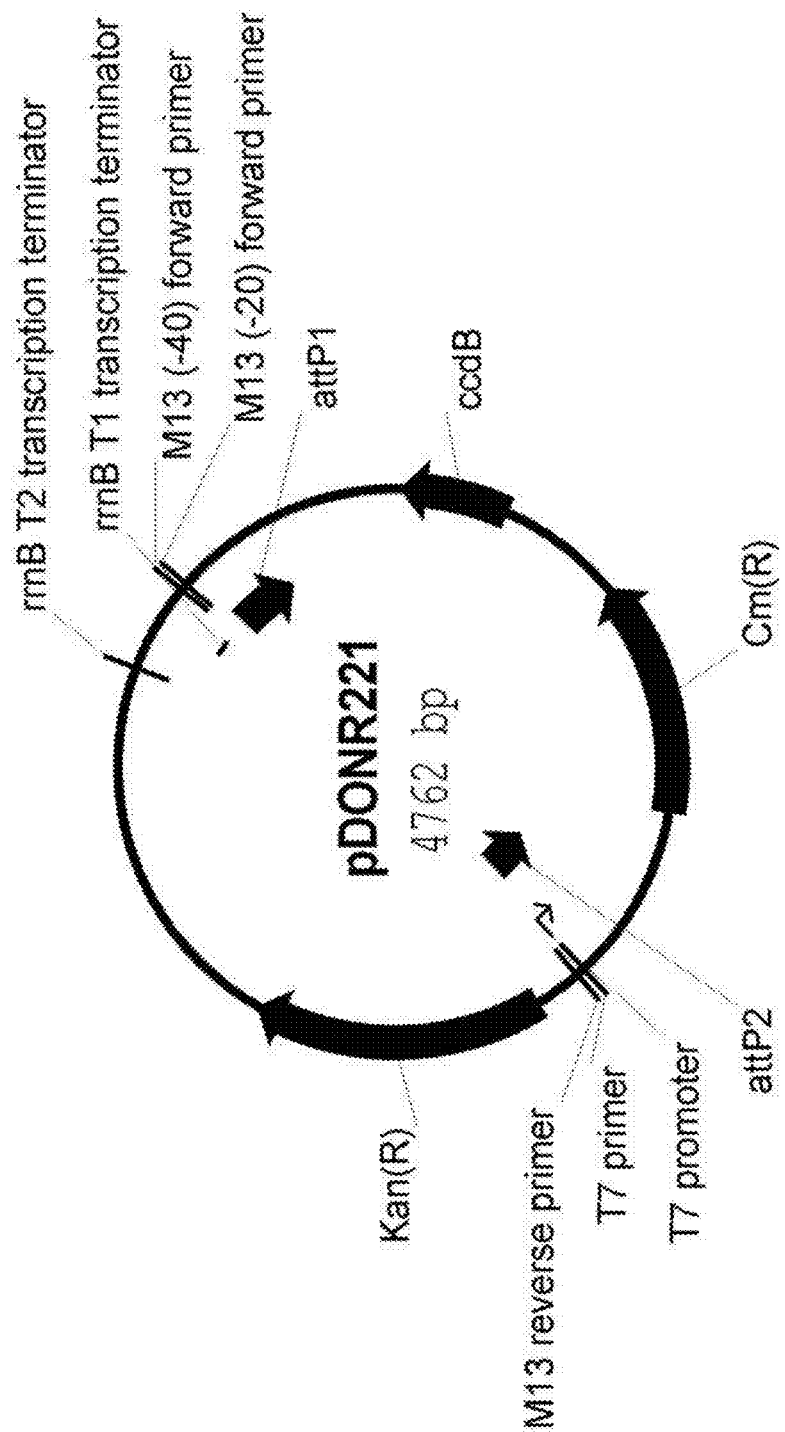
FIG. 3 shows a schematic of the vector pDONR™221 (SEQ ID NO:3), GATEWAY® donor vector. The attP1 site is at nucleotides 570-801; the attP2 site is at nucleotides 2754-2985 (complementary strand).

SEQ ID NO:3 is the nucleotide sequence of the pDONR™ 221 construct (FIG. 3).

Figure 4:
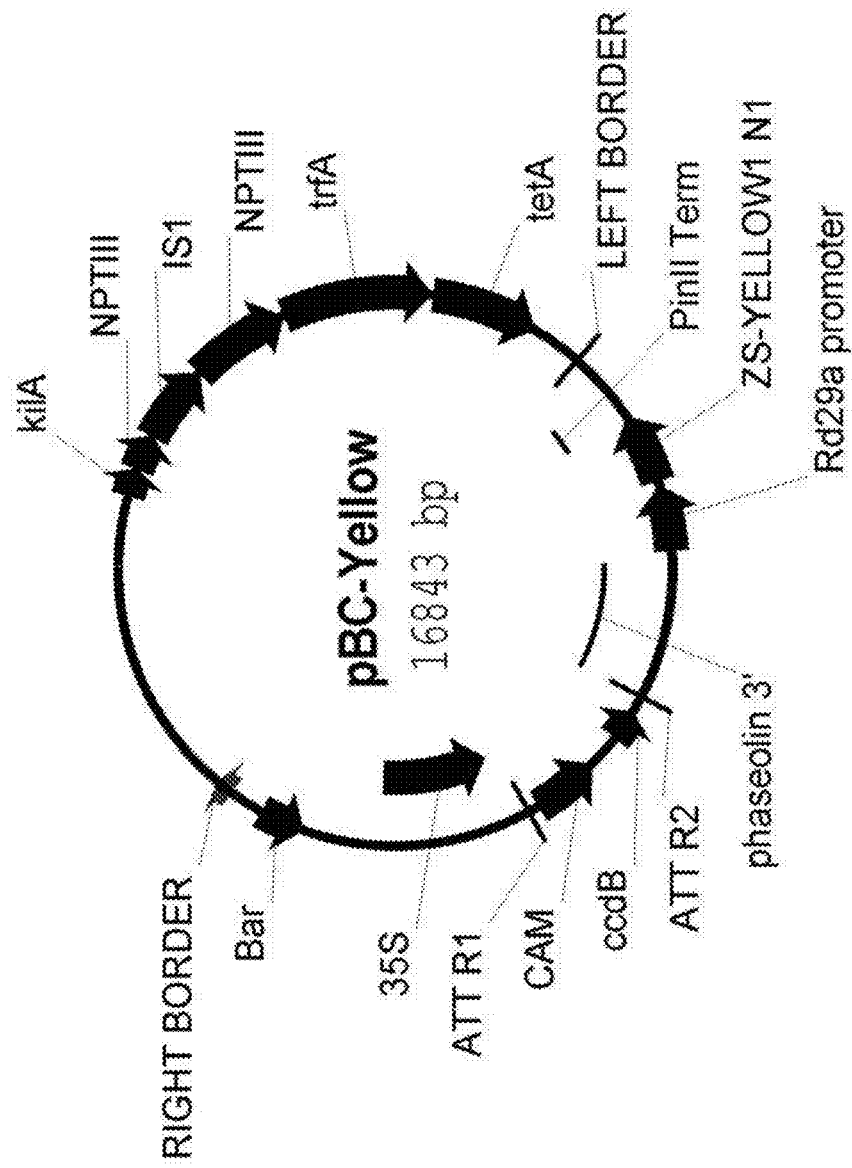
FIG. 4 shows a schematic of the vector pBC-yellow (SEQ ID NO:4), a destination vector for use in construction of expression vectors for *Arabidopsis*. The attR1 site is at nucleotides 11276-11399 (complementary strand); the attR2 site is at nucleotides 9695-9819 (complementary strand).

SEQ ID NO:4 is the nucleotide sequence of the pBC-yellow vector (FIG. 4).

Figure 5:
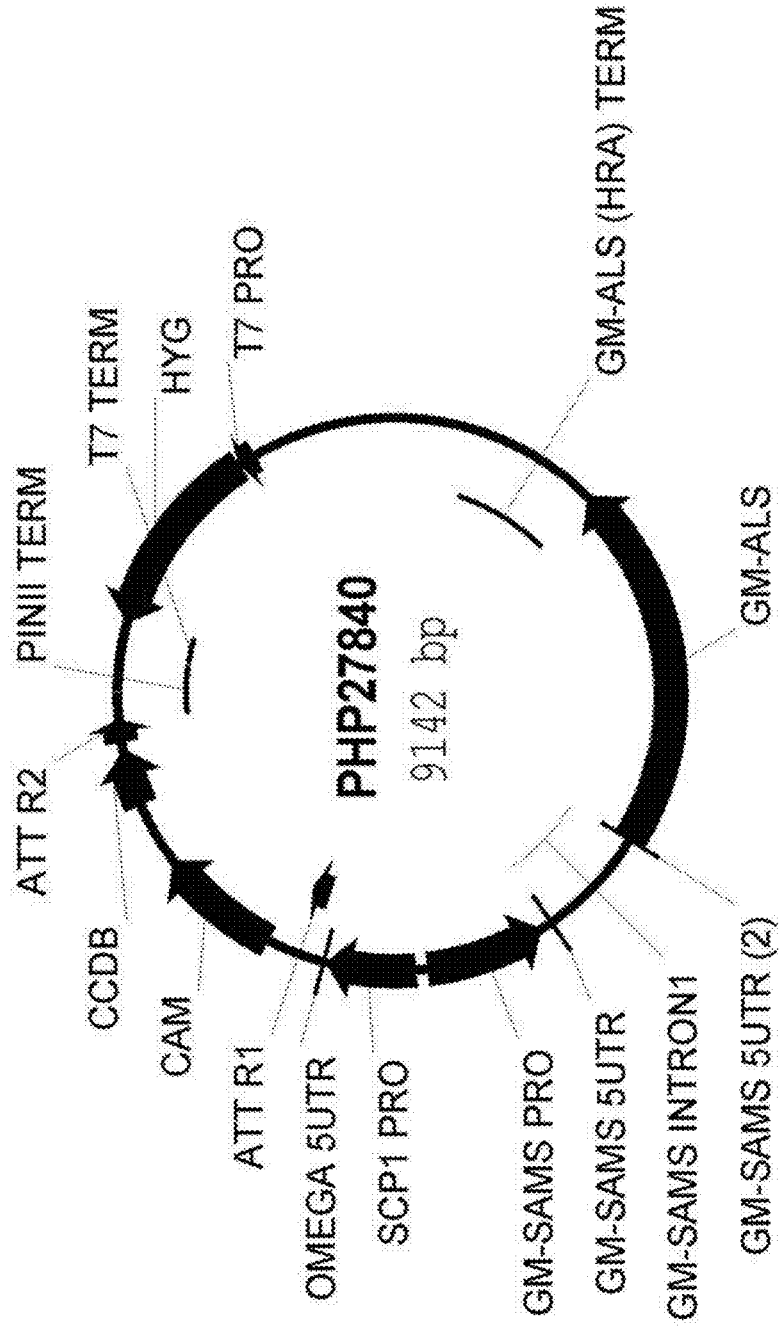
FIG. 5 shows a schematic of the vector PHP27840 (SEQ ID NO:5), a destination vector for use in construction of expression vectors for soybean. The attR1 site is at nucleotides 7310-7434; the attR2 site is at nucleotides 8890-9014.

SEQ ID NO:5 is the nucleotide sequence of the PHP27840 vector (FIG. 5).

Figure 6:
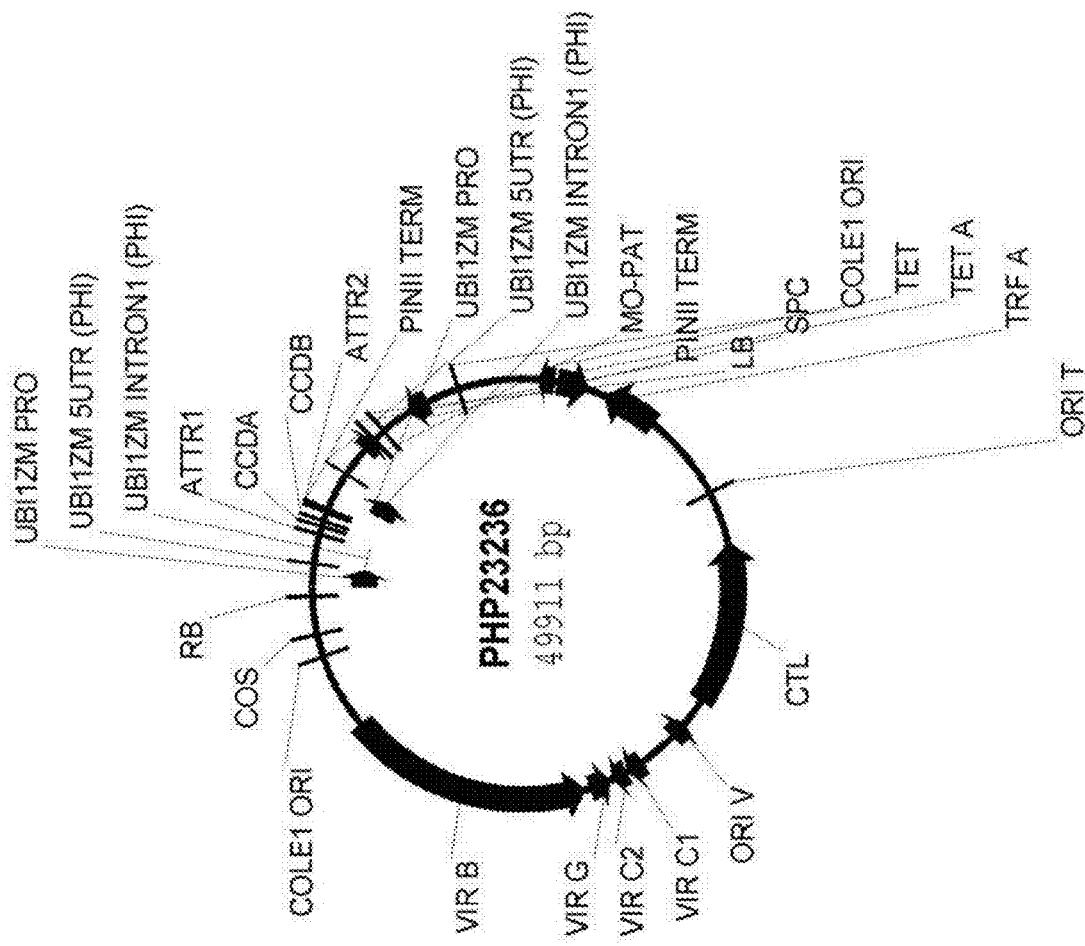
FIG. 6 shows a schematic of the vector PHP23236 (SEQ ID NO:6), a destination vector for use in construction of expression vectors for Gaspe Flint derived maize lines. The attR1 site is at nucleotides 2006-2130; the attR2 site is at nucleotides 2899-3023.

SEQ ID NO:6 is the nucleotide sequence of the destination vector PHP23236 (FIG. 6).

Figure 7:
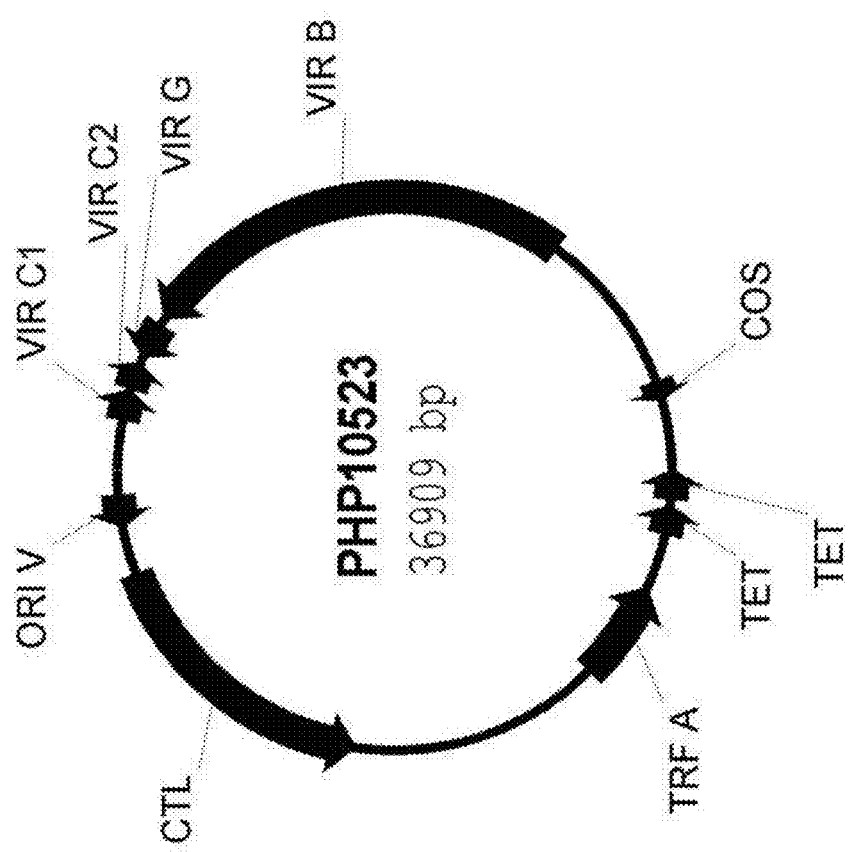
FIG. 7 shows a schematic of the vector PHP10523 (SEQ ID NO:7), a plasmid DNA present in *Agrobacterium* strain LBA4404 (Komari et al., *Plant J.* 10:165-174 (1996); NCBI General Identifier No. 59797027).

SEQ ID NO:7 is the nucleotide sequence of the PHP10523 vector (FIG. 7).

Figure 8:
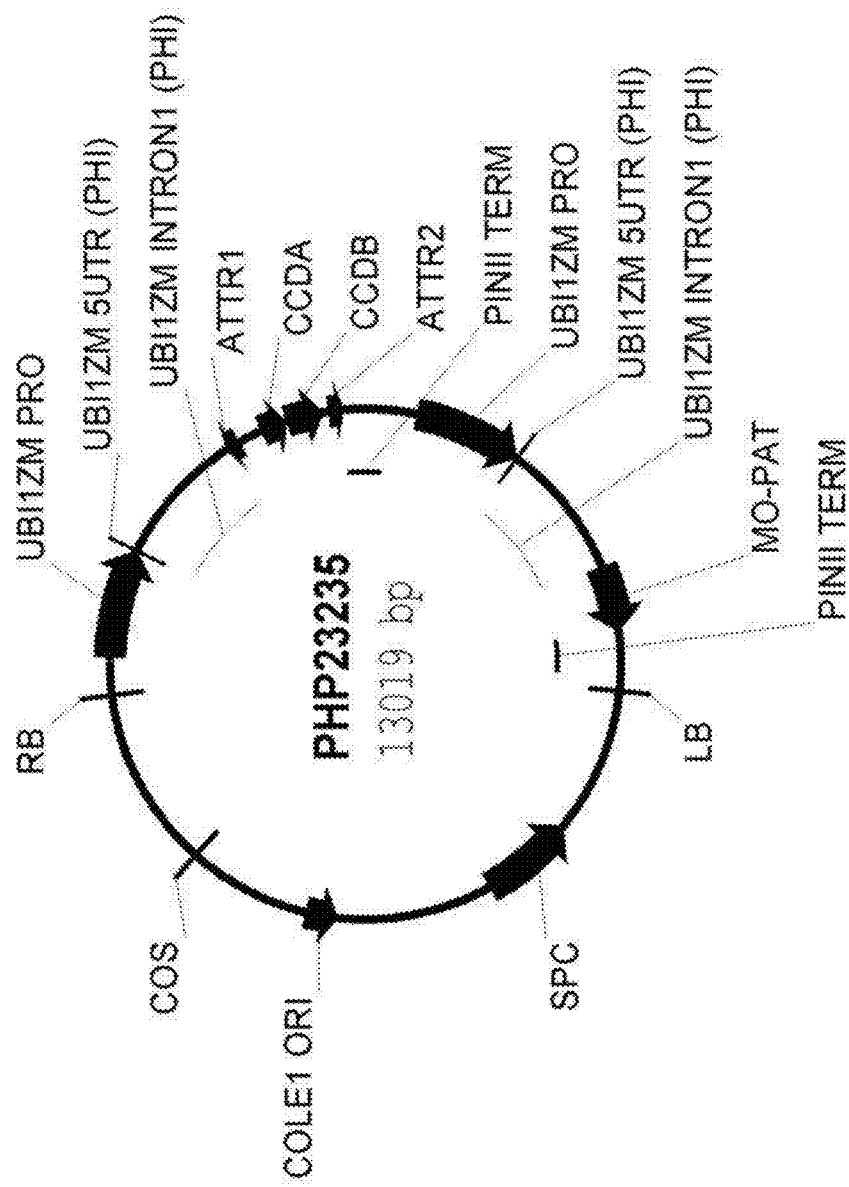
FIG. 8 shows a schematic of the vector PHP23235 (SEQ ID NO:8), a vector used to construct the destination vector PHP23236.

SEQ ID NO:8 is the nucleotide sequence of the PHP23235 vector (FIG. 8).

Figure 9:
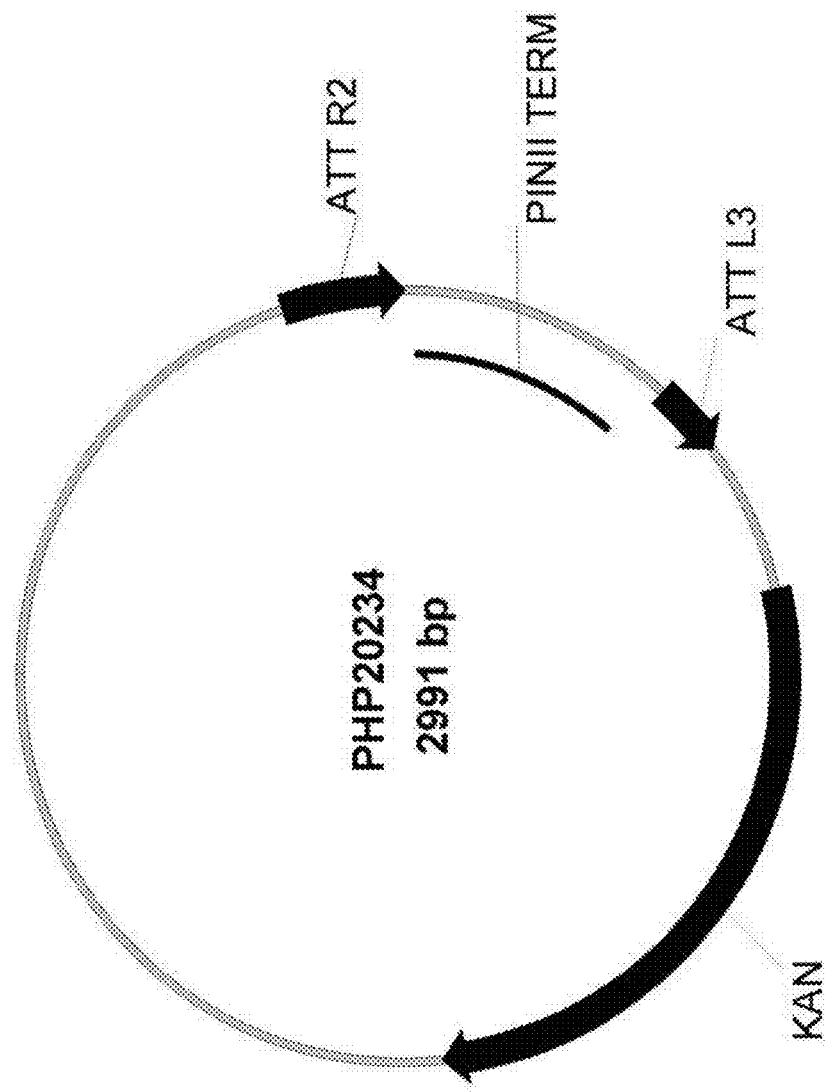
FIG. 9 shows a schematic of the vector PHP20234 (SEQ ID NO:9).

SEQ ID NO:9 is the nucleotide sequence of the PHP20234 vector (FIG. 9).

Figure 10:
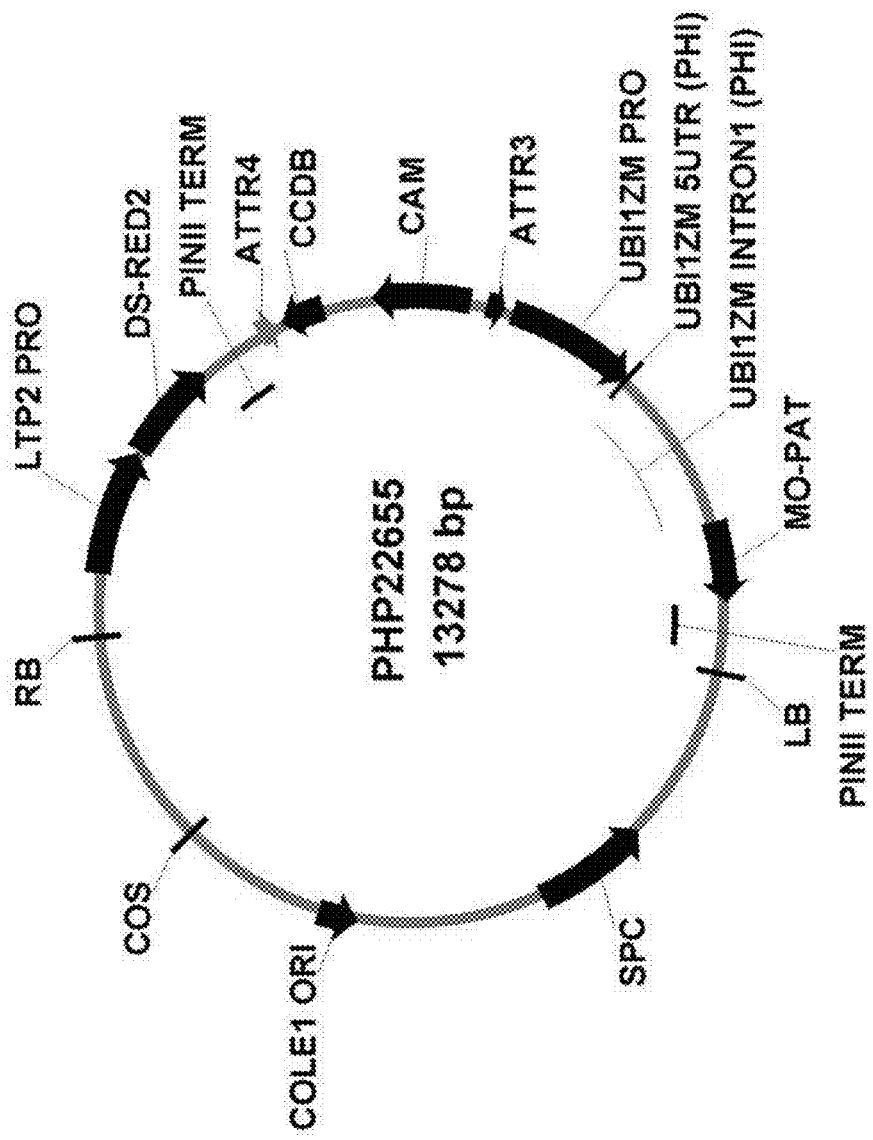
FIG. 10 shows a schematic of the destination vector PHP22655 (SEQ ID NO:10).

SEQ ID NO:10 is the nucleotide sequence of the destination vector PHP22655 (FIG. 10).

SEQ ID NO:11 is the nucleotide sequence of the polylinker used to substitute the PacI restriction site at position 5775 of pHSbarENDs2.

SEQ ID NO:12 is the nucleotide sequence of the attB1 sequence.

SEQ ID NO:13 is the nucleotide sequence of the attB2 sequence.

SEQ ID NO:14 is the nucleotide sequence of the entry clone PHP23112.

Figure 11:
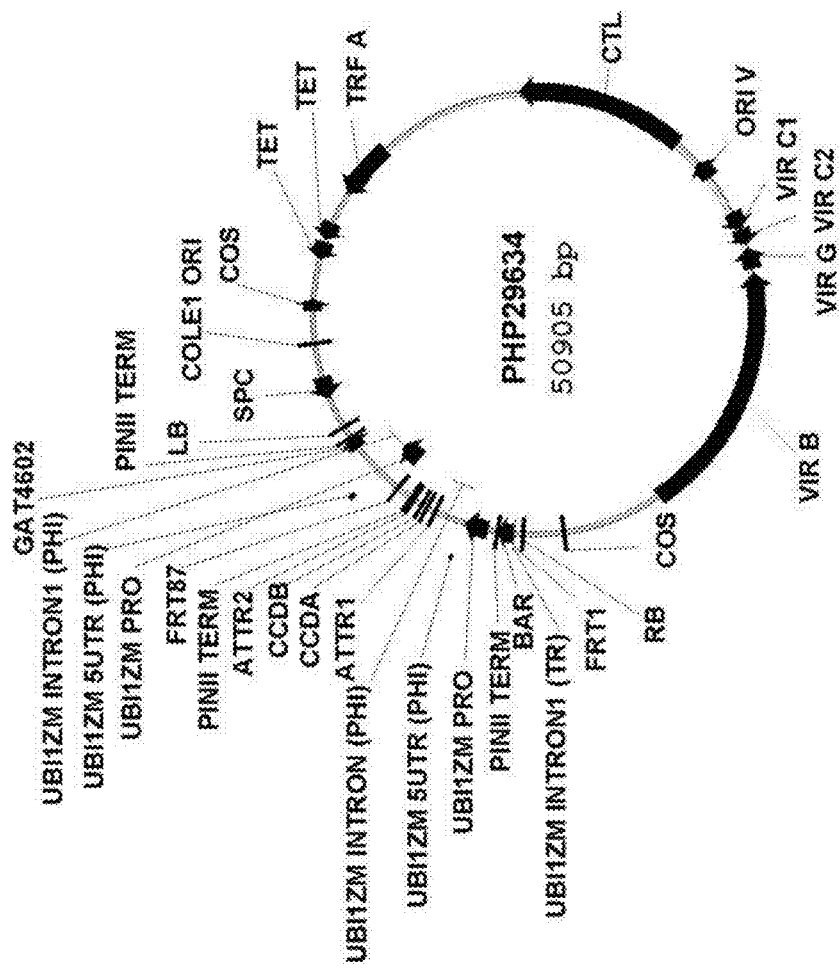
FIG. 11 shows a schematic of the destination vector PHP29634 (SEQ ID NO:15), used in construction of expression vectors for Gaspe Flint derived maize lines.

SEQ ID NO:15 is the nucleotide sequence of the PHP29634 vector (FIG. 11).

SEQ ID NO:16 is the forward primer VC062.

SEQ ID NO:17 is the reverse primer VC063.

SEQ ID NOs:18-23 (see Table 1).

SEQ ID NO:24 is the nucleotide sequence of the gene that encodes the *Arabidopsis thaliana* SNF domain-containing protein, variant 1 (SNF2.1) (At1g61140.1; NCBI General Identifier No. 186492169).

SEQ ID NO:25 is the amino acid sequence of the *Arabidopsis thaliana* SNF domain-containing protein, variant 1 (referred to herein as SNF2.1) (At1g61140.1; NCBI General Identifier No. 186492170).

SEQ ID NO:26 is the nucleotide sequence of the gene that encodes the *Arabidopsis thaliana* SNF domain-containing protein, variant 2 (SNF2.2) (At1g61140.2; NCBI General Identifier No. 186492171).

SEQ ID NO:27 is the amino acid sequence of the *Arabidopsis thaliana* SNF domain-containing protein, variant 2 (referred to herein as SNF2.2) (At1g61140.2; NCBI General Identifier No. 186492172).

SEQ ID NO:28 is the nucleotide sequence of the gene that encodes the *Arabidopsis thaliana* SNF domain-containing protein, variant 3 (SNF2.3) (At1g61140.3; NCBI General Identifier No. 186492174).

SEQ ID NO:29 is the amino acid sequence of the *Arabidopsis thaliana* SNF domain-containing protein, variant 3 (referred to herein as SNF2.3) (At1g61140.3; NCBI General Identifier No. 186492175).

SEQ ID NO:30 is the amino acid sequence of the *Oryza sativa* putative ATPase protein (NCBI General Identifier No. 53792213).

SEQ ID NO:31 is the amino acid sequence of the *Oryza sativa* hypothetical protein Osl__28047 (NCBI General Identifier No. 218200575).

SEQ ID NO:32 is the amino acid sequence of the *Oryza sativa* protein (General Identifier No. 90399293).

SEQ ID NO:33 is the nucleotide sequence of the At1g61140.1-5' attB forward primer.

SEQ ID NO:34 is the nucleotide sequence of the At1g61140.1-3' attB reverse primer.

SEQ ID NOs:35-38 (see Table 1).

SEQ ID NO:39 is the nucleotide sequence of the At1g61140.1 gene (transcript identifier 47522 on the phytozome website) from *Arabidopsis lyrata*.

SEQ ID NO:40 is the amino acid sequence of the protein encoded by SEQ ID NO:39.

SEQ ID NO:41 is the nucleotide sequence of the At1g11100.1 gene (transcript identifier 471244 on the phytozome website) from *Arabidopsis lyrata*.

SEQ ID NO:42 is the amino acid sequence of the protein encoded by SEQ ID NO:41.

SEQ ID NO:43 is the FGENESH prediction of a SNF2 domain-containing *Zea mays* gene on public BAC c0566n04.

SEQ ID NO:44 is the amino acid sequence of the protein encoded by SEQ ID NO:43.

SEQ ID NO:45 is a manually edited version of SEQ ID NO:43 in which SEQ ID NO:43 was aligned with sequences from other species and manually edited to remove putative introns.

SEQ ID NO:46 is the amino acid sequence of the protein encoded by SEQ ID NO:45.

SEQ ID NO:47 is the nucleotide sequence of the *Oryza sativa* locus Os01g57110.2, a SNF2 family N-terminal domain containing protein.

SEQ ID NO:48 is the amino acid sequence of the protein encoded by SEQ ID NO:49.

SEQ ID NO:49 is the amino acid sequence of the *Sorghum bicolor* hypothetical protein (locus Sb03g036380; NCBI GI No. 242058897).

DETAILED DESCRIPTION

The disclosure of each reference set forth herein is hereby incorporated by reference in its entirety.

As used herein and in the appended claims, the singular forms "a", "an", and "the" include plural reference unless the context clearly dictates otherwise. Thus, for example, reference to "a plant" includes a plurality of such plants, reference to "a cell" includes one or more cells and equivalents thereof known to those skilled in the art, and so forth.

As used herein:

The terms "monocot" and "monocotyledonous plant" are used interchangeably herein. A monocot of the current invention includes the Gramineae.

The terms "dicot" and "dicotyledonous plant" are used interchangeably herein. A dicot of the current invention includes the following families: Brassicaceae, Leguminosae, and Solanaceae.

The terms "full complement" and "full-length complement" are used interchangeably herein, and refer to a complement of a given nucleotide sequence, wherein the complement and the nucleotide sequence consist of the same number of nucleotides and are 100% complementary.

A "trait" refers to a physiological, morphological, biochemical, or physical characteristic of a plant or particular plant material or cell. In some instances, this characteristic is visible to the human eye, such as seed or plant size, or can be measured by biochemical techniques, such as detecting the protein, starch, or oil content of seed or leaves, or by observation of a metabolic or physiological process, e.g. by measuring tolerance to water deprivation or particular salt or sugar concentrations, or by the observation of the expression level of a gene or genes, or by agricultural observations such as osmotic stress tolerance or yield.

"Nitrogen limiting conditions" refers to conditions where the amount of total available nitrogen (e.g., from nitrates, ammonia, or other known sources of nitrogen) is not sufficient to sustain optimal plant growth and development. One skilled in the art would recognize conditions where total available nitrogen is sufficient to sustain optimal plant growth and development. One skilled in the art would recognize what constitutes sufficient amounts of total available nitrogen, and what constitutes soils, media and fertilizer inputs for providing nitrogen to plants. Nitrogen limiting conditions will vary depending upon a number of factors, including but not limited to, the particular plant and environmental conditions.

"Agronomic characteristic" is a measurable parameter including but not limited to, greenness, yield, growth rate, biomass, fresh weight at maturation, dry weight at maturation, fruit yield, seed yield, total plant nitrogen content, fruit nitrogen content, seed nitrogen content, nitrogen content in vegetative tissue, whole plant amino acid content, vegetative tissue free amino acid content, fruit free amino acid content, seed free amino acid content, total plant protein content, fruit protein content, seed protein content, protein content in a vegetative tissue, drought tolerance, nitrogen uptake, resistance to root lodging, harvest index, stalk lodging, plant height, ear height, ear length, salt tolerance, early seedling vigor, and seedling emergence under low temperature stress.

Increased biomass can be measured, for example, as an increase in plant height, plant total leaf area, plant fresh weight, plant dry weight or plant seed yield, as compared with control plants.

The ability to increase the biomass or size of a plant would have several important commercial applications. Crop species may be generated that produce larger cultivars, generating higher yield in, for example, plants in which the vegetative portion of the plant is useful as food, biofuel or both.

Increased leaf size may be of particular interest. Increasing leaf biomass can be used to increase production of plant-derived pharmaceutical or industrial products. An increase in total plant photosynthesis is typically achieved by increasing leaf area of the plant. Additional photosynthetic capacity may be used to increase the yield derived from particular plant tissue, including the leaves, roots, fruits or seed, or permit the growth of a plant under decreased light intensity or under high light intensity.

Modification of the biomass of another tissue, such as root tissue, may be useful to improve a plant's ability to grow under harsh environmental conditions, including drought or nutrient deprivation, because larger roots may better reach water or nutrients or take up water or nutrients.

For some ornamental plants, the ability to provide larger varieties would be highly desirable. For many plants, including fruit-bearing trees, trees that are used for lumber production, or trees and shrubs that serve as view or wind screens, increased stature provides improved benefits in the forms of greater yield or improved screening.

"Harvest index" refers to the grain weight divided by the total plant weight.

"SNF2 domains" are found in ATP-dependent chromatin remodeling proteins involved in transcriptional control, DNA repair, and recombination. They contain seven conserved sequence motifs found in the superfamily II of DNA/RNA helicases.

Genes encoding SNF2 domain-containing proteins include without limitation the three variants of the *Arabidopsis thaliana* gene locus At1g61140 (SEQ ID NOs: 24, 26, and 28), referred to herein as snf2.1, snf2.2, and snf2.3, respectively, and the nucleotide homologs from other plant species, including, but not limited to, *Zea mays, Arabidopsis lyrata, Eragrostis nindensis* (Resurrection grass), *Paspalum notatum* (Bahiagrass), and *Oryza sativa* (SEQ ID NOs:18, 20, 22, 35, 37, 39, 41, 43, 45, and 47).

SNF2 domain-containing proteins include without limitation the proteins encoded by SEQ ID NOs: 24, 26, and 28 (and referred to herein as SNF2.1, SNF2.2, and SNF2.3, respectively), and the protein homologs from other plant species, including, but not limited to, *Zea mays, Arabidopsis lyrata, Eragrostis nindensis* (Resurrection grass), *Paspalum notatum* (Bahiagrass), *Oryza sativa*, and *Sorghum bicolor* (SEQ ID NOs: 19, 21, 23, 30, 31, 32, 36, 38, 40, 42, 44, 46, 48, and 49).

"Splice variants" used herein refers to alternative forms of RNA transcribed from a gene. Splice variation naturally occurs as a result of alternative sites being spliced within a single transcribed RNA molecule or between separately transcribed RNA molecules, and may result in several different forms of mRNA transcribed from the same gene. Thus, splice variants may encode polypeptides having different amino acid sequences, which may or may not have similar functions in the organism.

"Nitrogen stress tolerance" is a trait of a plant and refers to the ability of the plant to survive under nitrogen limiting conditions.

"Increased nitrogen stress tolerance" of a plant is measured relative to a reference or control plant, and means that the nitrogen stress tolerance of the plant is increased by any amount or measure when compared to the nitrogen stress tolerance of the reference or control plant.

A "nitrogen stress tolerant plant" is a plant that exhibits nitrogen stress tolerance. A nitrogen stress tolerant plant may be a plant that exhibits an increase in at least one agronomic characteristic relative to a control plant under nitrogen limiting conditions.

"Environmental conditions" refer to conditions under which the plant is grown, such as the availability of water, availability of nutrients (for example nitrogen), or the presence of insects or disease.

"Transgenic" refers to any cell, cell line, callus, tissue, plant part or plant, the genome of which has been altered by the presence of a heterologous nucleic acid, such as a recombinant DNA construct, including those initial transgenic events as well as those created by sexual crosses or asexual propagation from the initial transgenic event. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

"Genome" as it applies to plant cells encompasses not only chromosomal DNA found within the nucleus, but organelle DNA found within subcellular components (e.g., mitochondrial, plastid) of the cell.

"Plant" includes reference to whole plants, plant organs, plant tissues, seeds and plant cells and progeny of same. Plant cells include, without limitation, cells from seeds, suspension cultures, embryos, meristematic regions, callus tissue, leaves, roots, shoots, gametophytes, sporophytes, pollen, and microspores.

"Progeny" comprises any subsequent generation of a plant.

"Transgenic plant" includes reference to a plant which comprises within its genome a heterologous polynucleotide. For example, the heterologous polynucleotide is stably integrated within the genome such that the polynucleotide is passed on to successive generations. The heterologous polynucleotide may be integrated into the genome alone or as part of a recombinant DNA construct.

"Heterologous" with respect to sequence means a sequence that originates from a foreign species, or, if from the same species, is substantially modified from its native form in composition and/or genomic locus by deliberate human intervention.

"Polynucleotide", "nucleic acid sequence", "nucleotide sequence", or "nucleic acid fragment" are used interchangeably to refer to a polymer of RNA or DNA that is single- or double-stranded, optionally containing synthetic, non-natural or altered nucleotide bases. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

"Polypeptide", "peptide", "amino acid sequence" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The terms "polypeptide", "peptide", "amino acid sequence", and "protein" are also inclusive of modifications including, but not limited to, glycosylation, lipid attachment, sulfation, gamma-carboxylation of glutamic acid residues, hydroxylation and ADP-ribosylation.

"Messenger RNA (mRNA)" refers to the RNA that is without introns and that can be translated into protein by the cell.

"cDNA" refers to a DNA that is complementary to and synthesized from an mRNA template using the enzyme reverse transcriptase. The cDNA can be single-stranded or converted into the double-stranded form using the Klenow fragment of DNA polymerase I.

An "Expressed Sequence Tag" ("EST") is a DNA sequence derived from a cDNA library and therefore is a sequence which has been transcribed. An EST is typically obtained by a single sequencing pass of a cDNA insert. The sequence of an entire cDNA insert is termed the "Full-Insert Sequence" ("FIS"). A "Contig" sequence is a sequence assembled from two or more sequences that can be selected from, but not limited to, the group consisting of an EST, FIS and PCR sequence. A sequence encoding an entire or functional protein is termed a "Complete Gene Sequence" ("CGS") and can be derived from an FIS or a contig.

"Mature" protein refers to a post-translationally processed polypeptide; i.e., one from which any pre- or pro-peptides present in the primary translation product have been removed.

"Precursor" protein refers to the primary product of translation of mRNA; i.e., with pre- and pro-peptides still present. Pre- and pro-peptides may be and are not limited to intracellular localization signals.

"Isolated" refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

"Recombinant" refers to an artificial combination of two otherwise separated segments of sequence, e.g., by chemical synthesis or by the manipulation of isolated segments of nucleic acids by genetic engineering techniques. "Recombinant" also includes reference to a cell or vector, that has been modified by the introduction of a heterologous nucleic acid or a cell derived from a cell so modified, but does not encompass the alteration of the cell or vector by naturally occurring events (e.g., spontaneous mutation, natural transformation/transduction/transposition) such as those occurring without deliberate human intervention.

"Recombinant DNA construct" refers to a combination of nucleic acid fragments that are not normally found together in nature. Accordingly, a recombinant DNA construct may comprise regulatory sequences and coding sequences that are derived from different sources, or regulatory sequences and coding sequences derived from the same source, but arranged in a manner different than that normally found in nature.

The terms "entry clone" and "entry vector" are used interchangeably herein.

"Regulatory sequences" and "regulatory elements" are used interchangeably and refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences.

"Promoter" refers to a nucleic acid fragment capable of controlling transcription of another nucleic acid fragment.

"Promoter functional in a plant" is a promoter capable of controlling transcription in plant cells whether or not its origin is from a plant cell.

"Tissue-specific promoter" and "tissue-preferred promoter" are used interchangeably to refer to a promoter that is expressed predominantly but not necessarily exclusively in one tissue or organ, but that may also be expressed in one specific cell.

"Developmentally regulated promoter" refers to a promoter whose activity is determined by developmental events.

"Operably linked" refers to the association of nucleic acid fragments in a single fragment so that the function of one is regulated by the other. For example, a promoter is operably linked with a nucleic acid fragment when it is capable of regulating the transcription of that nucleic acid fragment.

"Expression" refers to the production of a functional product. For example, expression of a nucleic acid fragment may refer to transcription of the nucleic acid fragment (e.g., transcription resulting in mRNA or functional RNA) and/or translation of mRNA into a precursor or mature protein.

"Phenotype" means the detectable characteristics of a cell or organism.

"Introduced" in the context of inserting a nucleic acid fragment (e.g., a recombinant DNA construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

A "transformed cell" is any cell into which a nucleic acid fragment (e.g., a recombinant DNA construct) has been introduced.

"Transformation" as used herein refers to both stable transformation and transient transformation.

"Stable transformation" refers to the introduction of a nucleic acid fragment into a genome of a host organism resulting in genetically stable inheritance. Once stably transformed, the nucleic acid fragment is stably integrated in the genome of the host organism and any subsequent generation.

"Transient transformation" refers to the introduction of a nucleic acid fragment into the nucleus, or DNA-containing organelle, of a host organism resulting in gene expression without genetically stable inheritance.

"Allele" is one of several alternative forms of a gene occupying a given locus on a chromosome. When the alleles present at a given locus on a pair of homologous chromosomes in a diploid plant are the same that plant is homozygous at that locus. If the alleles present at a given locus on a pair of homologous chromosomes in a diploid plant differ that plant is heterozygous at that locus. If a transgene is present on one of a pair of homologous chromosomes in a diploid plant that plant is hemizygous at that locus.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21-53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627-1632). A "mitochondrial signal peptide" is an amino acid sequence which directs a precursor protein into the mitochondria (Zhang and Glaser (2002) *Trends Plant Sci* 7:14-21).

Sequence alignments and percent identity calculations may be determined using a variety of comparison methods designed to detect homologous sequences including, but not limited to, the MEGALIGN® program of the LASERGENE® bioinformatics computing suite (DNASTAR® Inc., Madison, Wis.). Unless stated otherwise, multiple alignment of the sequences provided herein were performed using the Clustal V method of alignment (Higgins and Sharp, *CABIOS.* 5:151-153 (1989)) with the default parameters (GAP PENALTY=10, GAP LENGTH PENALTY=10). Default parameters for pairwise alignments and calculation of percent identity of protein sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences, using the Clustal V program, it is possible to obtain "percent identity" and "divergence" values by viewing the "sequence distances" table on the same program; unless stated otherwise, percent identities and divergences provided and claimed herein were calculated in this manner.

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press: Cold Spring Harbor, 1989 (hereinafter "Sambrook").

Turning now to the embodiments:

Embodiments include isolated polynucleotides and polypeptides, recombinant DNA constructs, compositions (such as plants or seeds) comprising these recombinant DNA constructs, and methods utilizing these recombinant DNA constructs.

Isolated Polynucleotides and Polypeptides

The present invention includes the following isolated polynucleotides and polypeptides:

An isolated polynucleotide comprising: (i) a nucleic acid sequence encoding a polypeptide having an amino acid sequence of at least 50%, 51%, 52%, 53%, 54%, 55%, 56%, 57%, 58%, 59%, 60%, 81%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:19, 21, 23, 36, 38, or 46; or (ii) a full complement of the nucleic acid sequence of (i), wherein the full complement and the nucleic acid sequence of (i) consist of the same number of nucleotides and are 100% complementary. Any of the foregoing isolated polynucleotides may be utilized in any recombinant DNA constructs (including suppression DNA constructs) of the present invention. The polypeptide is a SNF2 domain-containing protein.

An isolated polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:19, 21, 23, 36, 38, 46. The polypeptide is a SNF2 domain-containing protein.

An isolated polynucleotide comprising (i) a nucleic acid sequence of at least 50%, 51%, 52%, 53%, 54%, 55%, 56%, 57%, 58%, 59%, 60% 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:18, 20, 22, 35, 37, or 45; or (ii) a full complement of the nucleic acid sequence of (i). Any of the foregoing isolated polynucleotides may be utilized in any recombinant DNA constructs (including suppression DNA constructs) of the present invention. The isolated polynucleotide encodes a SNF2 domain-containing protein.

Recombinant DNA Constructs and Suppression DNA Constructs

In one aspect, the present invention includes recombinant DNA constructs (including suppression DNA constructs).

In one embodiment, a recombinant DNA construct comprises a polynucleotide operably linked to at least one regulatory sequence (e.g., a promoter functional in a plant), wherein the polynucleotide comprises (i) a nucleic acid sequence encoding an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:19, 21, 23, 25, 27, 29, 30, 31, 32, 36, 38, 40, 42, 44, 46, 48, or 49; or (ii) a full complement of the nucleic acid sequence of (i).

In another embodiment, a recombinant DNA construct comprises a polynucleotide operably linked to at least one regulatory sequence (e.g., a promoter functional in a plant), wherein said polynucleotide comprises (i) a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:18, 20, 22, 24, 26, 28, 35, 37, 39, 41, 43, 45, or 47; or (ii) a full complement of the nucleic acid sequence of (i).

In another embodiment, a recombinant DNA construct comprises a polynucleotide operably linked to at least one regulatory sequence (e.g., a promoter functional in a plant), wherein said polynucleotide encodes a SNF2 domain-containing protein.

In another aspect, the present invention includes suppression DNA constructs.

A suppression DNA construct can comprise at least one regulatory sequence (for example, a promoter functional in a plant) operably linked to (a) all or part of: (i) a nucleic acid sequence encoding a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:19, 21, 23, 25, 27, 29, 30, 31, 32, 36, 38, 40, 42, 44, 46, 48, or 49; or (ii) a full complement of the nucleic acid sequence of (a)(i); or (b) a region derived from all or part of a sense strand or antisense strand of a target gene of interest, said region having a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to said all or part of a sense strand or antisense strand from which said region is derived, and wherein said target gene of interest encodes a SNF2 domain-containing protein; or (c) all or part of: (i) a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:18, 20, 22, 24, 26, 28, 35, 37, 39, 41, 43, 45, or 47; or (ii) a full complement of the nucleic acid sequence of (c)(i). The suppression DNA construct may comprise a cosuppression construct, antisense construct, viral-suppression construct, hairpin suppression construct, stem-loop suppression construct, double-stranded RNA-producing construct, RNAi construct, or small RNA construct (e.g., an siRNA construct or an miRNA construct).

It is understood, as those skilled in the art will appreciate, that the invention encompasses more than the specific exemplary sequences. Alterations in a nucleic acid fragment which result in the production of a chemically equivalent amino acid at a given site, but do not affect the functional properties of the encoded polypeptide, are well known in the art. For example, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

"Suppression DNA construct" is a recombinant DNA construct which when transformed or stably integrated into the genome of the plant, results in "silencing" of a target gene in the plant. The target gene may be endogenous or transgenic to the plant. "Silencing," as used herein with respect to the target gene, refers generally to the suppression of levels of mRNA or protein/enzyme expressed by the target gene, and/or the level of the enzyme activity or protein functionality. The terms "suppression", "suppressing" and "silencing", used interchangeably herein, includes lowering, reducing, declining, decreasing, inhibiting, eliminating or preventing. "Silencing" or "gene silencing" does not specify mechanism and is inclusive, and not limited to, anti-sense, cosuppression, viral-suppression, hairpin suppression, stem-loop suppression, RNAi-based approaches, and small RNA-based approaches.

A suppression DNA construct may comprise a region derived from a target gene of interest and may comprise all or part of the nucleic acid sequence of the sense strand (or antisense strand) of the target gene of interest. Depending upon the approach to be utilized, the region may be 100% identical or less than 100% identical (e.g., at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical) to all or part of the sense strand (or antisense strand) of the gene of interest.

Suppression DNA constructs are well-known in the art, are readily constructed once the target gene of interest is selected, and include, without limitation, cosuppression constructs, antisense constructs, viral-suppression constructs, hairpin suppression constructs, stem-loop suppression constructs, double-stranded RNA-producing constructs, and more generally, RNAi (RNA interference) constructs and small RNA constructs such as siRNA (short interfering RNA) constructs and miRNA (microRNA) constructs.

"Antisense inhibition" refers to the production of antisense RNA transcripts capable of suppressing the expression of the target gene or gene product. "Antisense RNA" refers to an RNA transcript that is complementary to all or part of a target primary transcript or mRNA and that blocks the expression of a target isolated nucleic acid fragment (U.S. Pat. No. 5,107, 065). The complementarity of an antisense RNA may be with any part of the specific gene transcript, i.e., at the 5' non-coding sequence, 3' non-coding sequence, introns, or the coding sequence.

"Cosuppression" refers to the production of sense RNA transcripts capable of suppressing the expression of the target gene or gene product. "Sense" RNA refers to RNA transcript that includes the mRNA and can be translated into protein within a cell or in vitro. Cosuppression constructs in plants have been previously designed by focusing on overexpression of a nucleic acid sequence having homology to a native mRNA, in the sense orientation, which results in the reduction of all RNA having homology to the overexpressed sequence (see Vaucheret et al., *Plant J.* 16:651-659 (1998); and Gura, *Nature* 404:804-808 (2000)).

Another variation describes the use of plant viral sequences to direct the suppression of proximal mRNA encoding sequences (PCT Publication No. WO 98/36083 published on Aug. 20, 1998).

RNA interference refers to the process of sequence-specific post-transcriptional gene silencing in animals mediated by short interfering RNAs (siRNAs) (Fire et al., *Nature* 391: 806 (1998)). The corresponding process in plants is commonly referred to as post-transcriptional gene silencing (PTGS) or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla (Fire et al., *Trends Genet.* 15:358 (1999)).

Small RNAs play an important role in controlling gene expression. Regulation of many developmental processes, including flowering, is controlled by small RNAs. It is now possible to engineer changes in gene expression of plant genes by using transgenic constructs which produce small RNAs in the plant.

Small RNAs appear to function by base-pairing to complementary RNA or DNA target sequences. When bound to RNA, small RNAs trigger either RNA cleavage or translational inhibition of the target sequence. When bound to DNA target sequences, it is thought that small RNAs can mediate DNA methylation of the target sequence. The consequence of these events, regardless of the specific mechanism, is that gene expression is inhibited.

MicroRNAs (miRNAs) are noncoding RNAs of about 19 to about 24 nucleotides (nt) in length that have been identified in both animals and plants (Lagos-Quintana et al., *Science* 294:853-858 (2001), Lagos-Quintana et al., *Curr. Biol.* 12:735-739 (2002); Lau et al., *Science* 294:858-862 (2001); Lee and Ambros, *Science* 294:862-864 (2001); Llave et al., *Plant Cell* 14:1605-1619 (2002); Mourelatos et al., *Genes. Dev.* 16:720-728 (2002); Park et al., *Curr. Biol.* 12:1484-1495 (2002); Reinhart et al., *Genes. Dev.* 16:1616-1626 (2002)). They are processed from longer precursor transcripts that range in size from approximately 70 to 200 nt, and these precursor transcripts have the ability to form stable hairpin structures.

MicroRNAs (miRNAs) appear to regulate target genes by binding to complementary sequences located in the transcripts produced by these genes. It seems likely that miRNAs can enter at least two pathways of target gene regulation: (1) translational inhibition; and (2) RNA cleavage. MicroRNAs entering the RNA cleavage pathway are analogous to the 21-25 nt short interfering RNAs (siRNAs) generated during RNA interference (RNAi) in animals and posttranscriptional gene silencing (PTGS) in plants, and likely are incorporated into an RNA-induced silencing complex (RISC) that is similar or identical to that seen for RNAi.

Regulatory Sequences:

A recombinant DNA construct (including a suppression DNA construct) of the present invention may comprise at least one regulatory sequence.

A regulatory sequence may be a promoter.

A number of promoters can be used in recombinant DNA constructs (and suppression DNA constructs) of the present invention. The promoters can be selected based on the desired outcome, and may include constitutive, tissue-specific, inducible, or other promoters for expression in the host organism.

Promoters that cause a gene to be expressed in most cell types at most times are commonly referred to as "constitutive promoters".

High level, constitutive expression of the candidate gene under control of the 35S or UBI promoter may (or may not) have pleiotropic effects, although candidate gene efficacy may be estimated when driven by a constitutive promoter. Use of tissue-specific and/or stress-specific promoters may eliminate undesirable effects, but retain the ability to enhance nitrogen tolerance. This type of effect has been observed in *Arabidopsis* for drought and cold tolerance (Kasuga et al., *Nature Biotechnol.* 17:287-91 (1999)).

Suitable constitutive promoters for use in a plant host cell include, for example, the core promoter of the Rsyn7 promoter and other constitutive promoters disclosed in WO 99/43838 and U.S. Pat. No. 6,072,050; the core CaMV 35S promoter (Odell et al., *Nature* 313:810-812 (1985)); rice actin (McElroy et al., *Plant Cell* 2:163-171 (1990)); ubiquitin (Christensen et al., *Plant Mol. Biol.* 12:619-632 (1989) and Christensen et al., *Plant Mol. Biol.* 18:675-689 (1992)); pEMU (Last et al., *Theor. Appl. Genet.* 81:581-588 (1991)); MAS (Velten et al., *EMBO J.* 3:2723-2730 (1984)); ALS promoter (U.S. Pat. No. 5,659,026), and the like. Other constitutive promoters include, for example, those discussed in U.S. Pat. Nos. 5,608,149; 5,608,144; 5,604,121; 5,569,597; 5,466,785; 5,399,680; 5,268,463; 5,608,142; and 6,177,611.

In choosing a promoter to use in the methods of the invention, it may be desirable to use a tissue-specific or developmentally regulated promoter.

A tissue-specific or developmentally regulated promoter is a DNA sequence which regulates the expression of a DNA sequence selectively in the cells/tissues of a plant critical to tassel development, seed set, or both, and limits the expression of such a DNA sequence to the period of tassel development or seed maturation in the plant. Any identifiable promoter may be used in the methods of the present invention which causes the desired temporal and spatial expression.

Promoters which are seed or embryo-specific and may be useful in the invention include soybean Kunitz trypsin inhibitor (Kti3, Jofuku and Goldberg, *Plant Cell* 1:1079-1093 (1989)), patatin (potato tubers) (Rocha-Sosa, M., et al., *EMBO J.* 8:23-29 (1989)), convicilin, vicilin, and legumin (pea cotyledons) (Rerie, W. G., et al., *Mol. Gen. Genet.* 259: 149-157 (1991); Newbigin, E. J., et al., *Planta* 180:461-470 (1990); Higgins, T. J. V., et al., *Plant. Mol. Biol.* 11:683-695 (1988)), zein (maize endosperm) (Schemthaner, J. P., et al., *EMBO J.* 7:1249-1255 (1988)), phaseolin (bean cotyledon) (Segupta-Gopalan, C., et al., *Proc. Natl. Acad. Sci. U.S.A.* 82:3320-3324 (1995)), phytohemagglutinin (bean cotyledon) (Voelker, T. et al., *EMBO J.* 6:3571-3577 (1987)), B-conglycinin and glycinin (soybean cotyledon) (Chen, Z-L, et al., *EMBO J.* 7:297-302 (1988)), glutelin (rice endosperm), hordein (barley endosperm) (Marris, C., et al., *Plant Mol. Biol.* 10:359-366 (1988)), glutenin and gliadin (wheat endosperm) (Colot, V., et al., *EMBO J.* 6:3559-3564 (1987)), and sporamin (sweet potato tuberous root) (Hattori, T., et al., *Plant Mol. Biol.* 14:595-604 (1990)). Promoters of seed-specific genes operably linked to heterologous coding regions in chimeric gene constructions maintain their temporal and spatial expression pattern in transgenic plants. Such examples include *Arabidopsis thaliana* 2S seed storage protein gene promoter to express enkephalin peptides in *Arabidopsis* and *Brassica napes* seeds (Vanderkerckhove et al., *Bio/Technology* 7:L929-932 (1989)), bean lectin and bean beta-phaseolin promoters to express luciferase (Riggs et al., *Plant Sci.* 63:47-57 (1989)), and wheat glutenin promoters to express chloramphenicol acetyl transferase (Colot et al., *EMBO J.* 6:3559-3564 (1987)).

Inducible promoters selectively express an operably linked DNA sequence in response to the presence of an endogenous or exogenous stimulus, for example by chemical compounds (chemical inducers) or in response to environmental, hormonal, chemical, and/or developmental signals. Inducible or regulated promoters include, for example, promoters regulated by light, heat, stress, flooding or drought, phytohormones, wounding, or chemicals such as ethanol, jasmonate, salicylic acid, or safeners.

Promoters for use in the current invention include the following: 1) the stress-inducible RD29A promoter (Kasuga et al., *Nature Biotechnol.* 17:287-91 (1999)); 2) the barley promoter, B22E; expression of B22E is specific to the pedicel in developing maize kernels ("Primary Structure of a Novel Barley Gene Differentially Expressed in Immature Aleurone Layers", Klemsdal et al., *Mol. Gen. Genet.* 228(1/2):9-16 (1991)); and 3) maize promoter, Zag2 ("Identification and molecular characterization of ZAG1, the maize homolog of the *Arabidopsis* floral homeotic gene AGAMOUS", Schmidt et al., *Plant Cell* 5(7):729-737 (1993); "Structural characterization, chromosomal localization and phylogenetic evaluation of two pairs of AGAMOUS-like MADS-box genes from maize", Theissen et al., *Gene* 156(2):155-166 (1995); NCBI GenBank Accession No. X80206)). Zag2 transcripts can be detected five days prior to pollination to seven to eight days after pollination ("DAP"), and directs expression in the carpel of developing female inflorescences and CimI which is specific to the nucleus of developing maize kernels. CimI transcript is detected four to five days before pollination to six to eight DAP. Other useful promoters include any promoter which can be derived from a gene whose expression is maternally associated with developing female florets.

Additional promoters for regulating the expression of the nucleotide sequences of the present invention in plants are stalk-specific promoters. Such stalk-specific promoters include the alfalfa S2A promoter (GenBank Accession No. EF030816; Abrahams et al., *Plant Mol. Biol.* 27:513-528 (1995)) and S2B promoter (GenBank Accession No. EF030817) and the like, herein incorporated by reference.

Promoters may be derived in their entirety from a native gene, or be composed of different elements derived from different promoters found in nature, or even comprise synthetic DNA segments.

Promoters for use in the current invention may include: RIP2, mLIP15, ZmCOR1, Rab17, CaMV 35S, RD29A, B22E, Zag2, SAM synthetase, ubiquitin, CaMV 19S, nos, Adh, sucrose synthase, R-allele, the vascular tissue other promoters S2A (Genbank accession number EF030816) and S2B (GenBank Accession No. EF030817), and the constitutive promoter GOS2 from *Zea mays*. Other promoters include root promoters, such as the maize NAS2 promoter, the maize Cyclo promoter (US Publication No. 2006/0156439, published Jul. 13, 2006), the maize ROOTMET2 promoter ONO 2005/063998, published Jul. 14, 2005), the CR1BIO promoter (WO 2006/055487, published May 26, 2006), the CRWAQ81 ONO 20051035770, published Apr. 21, 2005) and the maize ZRP2.47 promoter (NCBI Accession No. U38790; NCBI GI No. 1063664).

Recombinant DNA constructs (and suppression DNA constructs) of the present invention may also include other regulatory sequences including, but not limited to, translation leader sequences, introns, and polyadenylation recognition sequences. In another embodiment of the present invention, a recombinant DNA construct of the present invention further comprises an enhancer or silencer.

An intron sequence can be added to the 5' untranslated region, the protein-coding region or the 3' untranslated region to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg, *Mol. Cell Biol.* 8:4395-4405 (1988); Callis et al., *Genes Dev.* 1:1183-1200 (1987)).

Any plant can be selected for the identification of regulatory sequences and genes to be used in recombinant DNA constructs of the present invention. Examples of suitable plant targets for the isolation of genes and regulatory sequences would include but are not limited to alfalfa, apple, apricot, *Arabidopsis*, artichoke, arugula, asparagus, avocado, banana, barley, beans, beet, blackberry, blueberry, broccoli, brussels sprouts, cabbage, canola, cantaloupe, carrot, cassava, castorbean, cauliflower, celery, cherry, chicory, cilantro, citrus, clementines, clover, coconut, coffee, corn, cotton, cranberry, cucumber, Douglas fir, eggplant, endive, escarole, eucalyptus, fennel, figs, garlic, gourd, grape, grapefruit, honey dew, jicama, kiwifruit, lettuce, leeks, lemon, lime, Loblolly pine, linseed, maize, mango, melon, mushroom, nectarine, nut, oat, oil palm, oil seed rape, okra, olive, onion, orange, an ornamental plant, palm, papaya, parsley, parsnip, pea, peach, peanut, pear, pepper, persimmon, pine, pineapple, plantain, plum, pomegranate, poplar, potato, pumpkin, quince, radiata pine, radicchio, radish, rapeseed, raspberry, rice, rye, sorghum, Southern pine, soybean, spinach, squash, strawberry, sugarbeet, sugarcane, sunflower, sweet potato, sweetgum, tangerine, tea, tobacco, tomato, triticale, turf, turnip, a vine, watermelon, wheat, yams, and zucchini.

Compositions

A composition of the present invention is a plant comprising in its genome any of the recombinant DNA constructs (including any of the suppression DNA constructs) of the present invention (such as any of the other constructs discussed above). Compositions also include any progeny of the plant, and any seed obtained from the plant or its progeny, wherein the progeny or seed comprises within its genome the recombinant DNA construct (or suppression DNA construct).

Progeny includes subsequent generations obtained by self-pollination or out-crossing of a plant. Progeny also includes hybrids and inbreds.

In hybrid seed propagated crops, mature transgenic plants can be self-pollinated to produce a homozygous inbred plant. The inbred plant produces seed containing the newly introduced recombinant DNA construct (or suppression DNA construct). These seeds can be grown to produce plants that would exhibit an altered agronomic characteristic (e.g., an increased agronomic characteristic, e.g. under nitrogen limiting conditions), or used in a breeding program to produce hybrid seed, which can be grown to produce plants that would exhibit such an altered agronomic characteristic. The seeds may be maize seeds.

The plant may be a monocotyledonous or dicotyledonous plant, for example, a maize or soybean plant, such as a maize hybrid plant or a maize inbred plant. The plant may also be sunflower, sorghum, canola, wheat, alfalfa, cotton, rice, barley, millet, sugar cane, or switchgrass.

The recombinant DNA construct may be stably integrated into the genome of the plant.

Particular embodiments include but are not limited to the following:

1. A plant (for example, a maize or soybean plant) comprising in its genome a recombinant DNA construct comprising a polynucleotide operably linked to at least one regulatory sequence, wherein said polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:19, 21, 23, 25, 27, 29, 30, 31, 32, 36, 38, 40, 42, 44, 46, 48, or 49, and wherein said plant exhibits increased nitrogen stress tolerance when compared to a control plant not comprising said recombinant DNA construct. The plant may further exhibit an alteration of at least one agronomic characteristic when compared to the control plant.

2. A plant (for example, a maize or soybean plant) comprising in its genome a recombinant DNA construct comprising a polynucleotide operably linked to at least one regulatory sequence, wherein said polynucleotide encodes a SNF2 domain-containing polypeptide, and wherein said plant exhibits increased nitrogen stress tolerance when compared to a control plant not comprising said recombinant DNA construct. The plant may further exhibit an alteration of at least one agronomic characteristic when compared to the control plant.

3. A plant (for example, a maize or soybean plant) comprising in its genome a recombinant DNA construct comprising a polynucleotide operably linked to at least one regulatory sequence, wherein said polynucleotide encodes a SNF2 domain-containing polypeptide, and wherein said plant exhibits an alteration of at least one agronomic characteristic under nitrogen limiting conditions when compared to a control plant not comprising said recombinant DNA construct.

4. A plant (for example, a maize or soybean plant) comprising in its genome a recombinant DNA construct comprising a polynucleotide operably linked to at least one regulatory element, wherein said polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:19, 21, 23, 25, 27, 29, 30, 31, 32, 36, 38, 40, 42, 44, 46, 48, or 49, and wherein said plant exhibits an alteration of at least one agronomic characteristic under nitrogen limiting conditions when compared to a control plant not comprising said recombinant DNA construct.

5. A plant (for example, a maize or soybean plant) comprising in its genome a suppression DNA construct comprising at least one regulatory element operably linked to a region derived from all or part of a sense strand or antisense strand of a target gene of interest, said region having a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to said all or part of a sense strand or antisense strand from which said region is derived, and wherein said target gene of interest encodes a SN F2 domain-containing polypeptide, and wherein said plant exhibits an alteration of at least one agronomic characteristic under nitrogen limiting conditions when compared to a control plant not comprising said suppression DNA construct.

6. A plant (for example, a maize or soybean plant) comprising in its genome a suppression DNA construct comprising at least one regulatory element operably linked to all or part of: (a) a nucleic acid sequence encoding a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:19, 21, 23, 25, 27, 29, 30, 31, 32, 36, 38, 40, 42, 44, 46, 48, or 49; or (b) a full complement of the nucleic acid sequence of (a), and wherein said plant exhibits an alteration of at least one agronomic characteristic under nitrogen limiting conditions when compared to a control plant not comprising said suppression DNA construct.

7. Any progeny of the above plants in embodiments 1-6, any seeds of the above plants in embodiments 1-6, any seeds of progeny of the above plants in embodiments 1-6, and cells from any of the above plants in embodiments 1-6 and progeny thereof.

In any of the foregoing embodiments 1-7 or any other embodiments of the present invention, the SNF2 domain-containing polypeptide may be from *Arabidopsis thaliana*, *Zea mays*, *Glycine max*, *Glycine tabacina*, *Glycine soja* or *Glycine tomentella*.

In any of the foregoing embodiments 1-7 or any other embodiments of the present invention, the recombinant DNA construct (or suppression DNA construct) may comprise at least a promoter functional in a plant as a regulatory sequence.

In any of the foregoing embodiments 1-7 or any other embodiments of the present invention, the alteration of at least one agronomic characteristic is either an increase or decrease.

In any of the foregoing embodiments 1-7 or any other embodiments of the present invention, the at least one agronomic characteristic may be selected from the group consisting of greenness, yield, growth rate, biomass, fresh weight at maturation, dry weight at maturation, fruit yield, seed yield, total plant nitrogen content, fruit nitrogen content, seed nitrogen content, nitrogen content in a vegetative tissue, whole plant amino acid content, vegetative tissue free amino acid content, fruit free amino acid content, seed free amino acid content, total plant protein content, fruit protein content, seed protein content, protein content in a vegetative tissue, drought tolerance, nitrogen uptake, resistance to root lodging, harvest index, stalk lodging, plant height, ear height, ear length, salt tolerance, early seedling vigor and seedling emergence under low temperature stress. For example, the alteration of at least one agronomic characteristic may be an increase in yield, greenness or biomass.

In any of the foregoing embodiments 1-7 or any other embodiments of the present invention, the plant may exhibit an alteration of at least one agronomic characteristic when compared, under nitrogen stress conditions, to a control plant not comprising said recombinant DNA construct (or suppression DNA construct).

One of ordinary skill in the art is familiar with protocols for simulating nitrogen conditions, whether limiting or non-limiting, and for evaluating plants that have been subjected to simulated or naturally-occurring nitrogen conditions, whether limiting or non-limiting. For example, one can simulate nitrogen conditions by giving plants less nitrogen than normally required or no nitrogen over a period of time, and one can evaluate such plants by looking for differences in agronomic characteristics, e.g., changes in physiological and/or physical condition, including (but not limited to) vigor, growth, size, or root length, or in particular, leaf color or leaf area size. Other techniques for evaluating such plants include measuring chlorophyll fluorescence, photosynthetic rates, root growth or gas exchange rates.

The Examples below describe some representative protocols and techniques for simulating nitrogen limiting conditions and/or evaluating plants under such conditions.

One can also evaluate nitrogen stress tolerance by the ability of a plant to maintain sufficient yield (for example, at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% yield) in field testing under simulated or naturally-occurring low or high nitrogen conditions (e.g., by measuring for substantially equivalent yield under low or high nitrogen conditions compared to normal nitrogen conditions, or by measuring for less yield loss under low or high nitrogen conditions compared to a control or reference plant).

One of ordinary skill in the art would readily recognize a suitable control or reference plant to be utilized when assessing or measuring an agronomic characteristic or phenotype of a transgenic plant in any embodiment of the present invention in which a control plant is utilized (e.g., compositions or methods as described herein). For example, by way of non-limiting illustrations:

1. Progeny of a transformed plant which is hemizygous with respect to a recombinant DNA construct (or suppression DNA construct), such that the progeny are segregating into plants either comprising or not comprising the recombinant DNA construct (or suppression DNA construct): the progeny comprising the recombinant DNA construct (or suppression DNA construct) would be typically measured relative to the progeny not comprising the recombinant DNA construct (or suppression DNA construct) (i.e., the progeny not comprising the recombinant DNA construct (or the suppression DNA construct) is the control or reference plant).

2. Introgression of a recombinant DNA construct (or suppression DNA construct) into an inbred line, such as in maize, or into a variety, such as in soybean: the introgressed line would typically be measured relative to the parent inbred or variety line (i.e., the parent inbred or variety line is the control or reference plant).

3. Two hybrid lines, where the first hybrid line is produced from two parent inbred lines, and the second hybrid line is produced from the same two parent inbred lines except that one of the parent inbred lines contains a recombinant DNA construct (or suppression DNA construct): the second hybrid line would typically be measured relative to the first hybrid line (i.e., the first hybrid line is the control or reference plant).

4. A plant comprising a recombinant DNA construct (or suppression DNA construct): the plant may be assessed or measured relative to a control plant not comprising the recombinant DNA construct (or suppression DNA construct) but otherwise having a comparable genetic background to the plant (e.g., sharing at least 90%, 91%, 92%, 93%, 94%, 95%, 96%, 97%, 98%, 99%, or 100% sequence identity of nuclear genetic material compared to the plant comprising the recombinant DNA construct (or suppression DNA construct)). There are many laboratory-based techniques available for the analysis, comparison and characterization of plant genetic backgrounds; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLP®s), and Simple Sequence Repeats (SSRs) which are also referred to as Microsatellites.

Furthermore, one of ordinary skill in the art would readily recognize that a suitable control or reference plant to be utilized when assessing or measuring an agronomic characteristic or phenotype of a transgenic plant would not include a plant that had been previously selected, via mutagenesis or transformation, for the desired agronomic characteristic or phenotype.

Methods

Methods include but are not limited to methods for increasing nitrogen stress tolerance in a plant, methods for evaluating nitrogen stress tolerance in a plant, methods for altering an agronomic characteristic in a plant, methods for determining an alteration of an agronomic characteristic in a plant, and methods for producing seed. The plant may be a monocotyledonous or dicotyledonous plant, for example, a maize or soybean plant. The plant may also be sunflower, sorghum, canola, wheat, alfalfa, cotton, rice, barley, millet, or sugar cane. The seed may be a maize or soybean seed, for example, a maize hybrid seed or maize inbred seed.

Methods include but are not limited to the following:

A method for transforming a cell comprising transforming a cell with any of the isolated polynucleotides of the present invention. The cell transformed by this method is also included. In particular embodiments, the cell is eukaryotic cell, e.g., a yeast, insect or plant cell, or prokaryotic, e.g., a bacterial cell.

A method for producing a transgenic plant comprising transforming a plant cell with any of the isolated polynucleotides or recombinant DNA constructs (including suppression DNA constructs) of the present invention and regenerating a transgenic plant from the transformed plant cell. The invention is also directed to the transgenic plant produced by this method, and transgenic seed obtained from this transgenic plant. The transgenic plant obtained by this method may be used in other methods of the present invention.

A method for isolating a polypeptide of the invention from a cell or culture medium of the cell, wherein the cell comprises a recombinant DNA construct comprising a polynucleotide of the invention operably linked to at least one regulatory sequence, and wherein the transformed host cell is grown under conditions that are suitable for expression of the recombinant DNA construct.

A method of altering the level of expression of a polypeptide of the invention in a host cell comprising: (a) transforming a host cell with a recombinant DNA construct of the present invention; and (b) growing the transformed host cell under conditions that are suitable for expression of the recombinant DNA construct wherein expression of the recombinant DNA construct results in production of altered levels of the polypeptide of the invention in the transformed host cell.

A method of increasing nitrogen stress tolerance in a plant, comprising: (a) introducing into a regenerable plant cell a recombinant DNA construct comprising a polynucleotide operably linked to at least one regulatory sequence (for example, a promoter functional in a plant), wherein the polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:19, 21, 23, 25, 27, 29, 30, 31, 32, 36, 38, 40, 42, 44, 46, 48, or 49; and (b) regenerating a transgenic plant from the regenerable plant cell after step (a), wherein the transgenic plant comprises in its genome the recombinant DNA construct and exhibits increased nitrogen stress tolerance when compared to a control plant not comprising the recombinant DNA construct. The method may further comprise (c) obtaining a progeny plant derived from the transgenic plant, wherein said progeny plant comprises in its genome the suppression DNA construct and exhibits increased nitrogen tolerance when compared to a control plant not comprising the recombinant DNA construct.

A method of increasing nitrogen stress tolerance in a plant, comprising: (a) introducing into a regenerable plant cell a suppression DNA construct comprising at least one regulatory sequence (for example, a promoter functional in a plant) operably linked to all or part of (i) a nucleic acid sequence encoding a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:19, 21, 23, 25, 27, 29, 30, 31, 32, 36, 38, 40, 42, 44, 46, 48, or 49, or (ii) a full complement of the nucleic acid sequence of (a)(i); and (b) regenerating a transgenic plant from the regenerable plant cell after step (a), wherein the transgenic plant comprises in its genome the suppression DNA construct and exhibits increased nitrogen stress tolerance when compared to a control plant not comprising the suppression DNA construct. The method may further comprise (c) obtaining a progeny plant derived from the transgenic plant, wherein said progeny plant comprises in its genome the suppression DNA construct and exhibits increased nitrogen tolerance when compared to a control plant not comprising the suppression DNA construct.

A method of increasing nitrogen stress tolerance in a plant, comprising: (a) introducing into a regenerable plant cell a suppression DNA construct comprising at least one regulatory sequence (for example, a promoter functional in a plant) operably linked to a region derived from all or part of a sense strand or antisense strand of a target gene of interest, said region having a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to said all or part of a sense strand or antisense strand from which said region is derived, and wherein said target gene of interest encodes a SNF2 domain-containing polypeptide; and (b) regenerating a transgenic plant from the regenerable plant cell after step (a), wherein the transgenic plant comprises in its genome the suppression DNA construct and exhibits increased nitrogen stress tolerance when compared to a control plant not comprising the suppression DNA construct. The method may further comprise (c) obtaining a progeny plant derived from the transgenic plant, wherein said progeny plant comprises in its genome the suppression DNA construct and exhibits increased nitrogen tolerance when compared to a control plant not comprising the suppression DNA construct.

A method of evaluating nitrogen stress tolerance in a plant, comprising (a) obtaining a transgenic plant, wherein the transgenic plant comprises in its genome a recombinant DNA construct comprising a polynucleotide operably linked to at least one regulatory sequence (for example, a promoter functional in a plant), wherein the polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:19, 21, 23, 25, 27, 29, 30, 31, 32, 36, 38, 40, 42, 44, 46, 48, or 49; (b) obtaining a progeny plant derived from the transgenic plant, wherein the progeny plant comprises in its genome the recombinant DNA construct; and (c) evaluating the progeny plant for nitrogen stress tolerance compared to a control plant not comprising the recombinant DNA construct.

A method of evaluating nitrogen stress tolerance in a plant, comprising (a) obtaining a transgenic plant, wherein the transgenic plant comprises in its genome a suppression DNA construct comprising at least one regulatory sequence (for example, a promoter functional in a plant) operably linked to all or part of (i) a nucleic acid sequence encoding a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:19, 21, 23, 25, 27, 29, 30, 31, 32, 36, 38, 40, 42, 44, 46, 48, or 49; or (ii) a full complement of the nucleic acid sequence of (a)(i); (b) obtaining a progeny plant derived from the transgenic plant, wherein the progeny plant comprises in its genome the suppression DNA construct; and (c) evaluating the progeny plant for nitrogen stress tolerance compared to a control plant not comprising the suppression DNA construct.

A method of evaluating nitrogen stress tolerance in a plant, comprising (a) obtaining a transgenic plant, wherein the transgenic plant comprises in its genome a suppression DNA construct comprising at least one regulatory sequence (for example, a promoter functional in a plant) operably linked to a region derived from all or part of a sense strand or antisense strand of a target gene of interest, said region having a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to said all or part of a sense strand or antisense strand from which said region is derived, and wherein said target gene of interest encodes a SNF2 domain-containing polypeptide; (b) obtaining a progeny plant derived from the transgenic plant, wherein the progeny plant comprises in its genome the suppression DNA construct; and (c) evaluating the progeny plant for nitrogen stress tolerance compared to a control plant not comprising the suppression DNA construct.

A method of determining an alteration of an agronomic characteristic in a plant, comprising (a) obtaining a transgenic plant, wherein the transgenic plant comprises in its genome a recombinant DNA construct comprising a polynucleotide operably linked to at least on regulatory sequence (for example, a promoter functional in a plant), wherein said polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:19, 21, 23, 25, 27, 29, 30, 31, 32, 36, 38, 40, 42, 44, 46, 48, or 49; (b) obtaining a progeny plant derived from the transgenic plant, wherein the progeny plant comprises in its genome the recombinant DNA construct; and (c) determining whether the progeny plant exhibits an alteration of at least one agronomic characteristic when compared, optionally under nitrogen limiting conditions, to a control plant not comprising the recombinant DNA construct.

A method of determining an alteration of an agronomic characteristic in a plant, comprising (a) obtaining a transgenic plant, wherein the transgenic plant comprises in its genome a suppression DNA construct comprising at least one regulatory sequence (for example, a promoter functional in a plant) operably linked to all or part of (i) a nucleic acid sequence encoding a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:19, 21, 23, 25, 27, 29, 30, 31, 32, 36, 38, 40, 42, 44, 46, 48, or 49; or (ii) a full complement of the nucleic acid sequence of (i); (b) obtaining a progeny plant derived from the transgenic plant, wherein the progeny plant comprises in its genome the suppression DNA construct; and (c) determining whether the progeny plant exhibits an alteration of at least one agronomic characteristic when compared, optionally under nitrogen limiting conditions, to a control plant not comprising the suppression DNA construct.

A method of determining an alteration of an agronomic characteristic in a plant, comprising (a) obtaining a transgenic plant, wherein the transgenic plant comprises in its genome a suppression DNA construct comprising at least one regulatory sequence (for example, a promoter functional in a plant) operably linked to a region derived from all or part of a sense strand or antisense strand of a target gene of interest, said region having a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to said all or part of a sense strand or antisense strand from which said region is derived, and wherein said target gene of interest encodes a SNF2 domain-containing polypeptide; (b) obtaining a progeny plant derived from the transgenic plant, wherein the progeny plant comprises in its genome the suppression DNA construct; and (c) determining whether the progeny plant exhibits an alteration of at least one agronomic characteristic when compared, optionally under nitrogen limiting conditions, to a control plant not comprising the suppression DNA construct.

A method of producing seed (for example, seed that can be sold as a nitrogen stress tolerant product offering) comprising any of the preceding methods, and further comprising obtaining seeds from said progeny plant, wherein said seeds comprise in their genome said recombinant DNA construct (or suppression DNA construct).

In any of the preceding methods or any other embodiments of methods of the present invention, in said introducing step said regenerable plant cell may comprises a callus cell, an embryogenic callus cell, a gametic cell, a meristematic cell, or a cell of an immature embryo. The regenerable plant cells may derive from an inbred maize plant.

In any of the preceding methods or any other embodiments of methods of the present invention, said regenerating step may comprise: (i) culturing said transformed plant cells in a media comprising an embryogenic promoting hormone until callus organization is observed; (ii) transferring said transformed plant cells of step (i) to a first media which includes a tissue organization promoting hormone; and (iii) subculturing said transformed plant cells after step (ii) onto a second media, to allow for shoot elongation, root development or both.

In any of the preceding methods or any other embodiments of methods of the present invention, the at least one agronomic characteristic may be selected from the group consisting of greenness, yield, growth rate, biomass, fresh weight at maturation, dry weight at maturation, fruit yield, seed yield, total plant nitrogen content, fruit nitrogen content, seed nitrogen content, nitrogen content in a vegetative tissue, whole plant amino acid content, vegetative tissue free amino acid content, fruit free amino acid content, seed free amino acid content, total plant protein content, fruit protein content, seed protein content, protein content in a vegetative tissue, drought tolerance, nitrogen uptake, resistance to root lodging, harvest index, stalk lodging, plant height, ear height, ear length, salt tolerance, early seedling vigor and seedling emergence under low temperature stress. The alteration of at least one agronomic characteristic may be an increase in yield, greenness or biomass.

In any of the preceding methods or any embodiments of methods of the present invention, the plant may exhibit the alteration of at least one agronomic characteristic when compared, under nitrogen stress conditions, to a control plant not comprising said recombinant DNA construct (or suppression DNA construct).

In any of the preceding methods or any other embodiments of methods of the present invention, alternatives exist for introducing into a regenerable plant cell a recombinant DNA construct comprising a polynucleotide operably linked to at least one regulatory sequence. For example, one may introduce into a regenerable plant cell a regulatory sequence (such as one or more enhancers, for example, as part of a transposable element), and then screen for an event in which the regulatory sequence is operably linked to an endogenous gene encoding a polypeptide of the instant invention.

The introduction of recombinant DNA constructs of the present invention into plants may be carried out by any suitable technique, including but not limited to direct DNA uptake, chemical treatment, electroporation, microinjection, cell fusion, infection, vector mediated DNA transfer, bombardment, or *Agrobacterium* mediated transformation. Techniques for plant transformation and regeneration have been described in International Patent Publication WO 2009/006276, the contents of which are herein incorporated by reference.

The development or regeneration of plants containing the foreign, exogenous isolated nucleic acid fragment that encodes a protein of interest is well known in the art. The regenerated plants may be self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide is cultivated using methods well known to one skilled in the art.

EXAMPLES

The present invention is further illustrated in the following Examples, in which parts and percentages are by weight and degrees are Celsius, unless otherwise stated. It should be understood that these Examples, while indicating embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Furthermore, various modifications of the invention in addition to those shown and described herein will be apparent to those skilled in the art from the foregoing description. Such modifications are also intended to fall within the scope of the appended claims.

Example 1

Creation of an *Arabidopsis* Population with Activation-Tagged Genes

An 18.49-kb T-DNA based binary construct was created, pHSbarENDs2 (SEQ ID NO:1; FIG. 1), that contains four multimerized enhancer elements derived from the Cauliflower Mosaic Virus 35S promoter (corresponding to sequences −341 to −64, as defined by Odell et al., *Nature* 313:810-812 (1985)). The construct also contains vector sequences (pUC9) and a poly-linker (SEQ ID NO:11) to allow plasmid rescue, transposon sequences (Ds) to remobilize the T-DNA, and the bar gene to allow for glufosinate selection of transgenic plants. In principle, only the 10.8-kb segment from the right border (RB) to left border (LB) inclusive will be transferred into the host plant genome. Since the enhancer elements are located near the RB, they can induce cis-activation of genomic loci following T-DNA integration.

*Arabidopsis* activation-tagged populations were created by whole plant *Agrobacterium* transformation. The pHSbarENDs2 construct was transformed into *Agrobacterium tumefaciens* strain C58, grown in lysogeny broth medium at 25° C. to OD600 ~1.0. Cells were then pelleted by centrifugation and resuspended in an equal volume of 5% sucrose/0.05% Silwet L-77 (OSI Specialties, Inc). At early bolting, soil grown *Arabidopsis thaliana* ecotype Col-0 were top watered with the *Agrobacterium* suspension. A week later, the same plants were top watered again with the same *Agrobacterium* strain in sucrose/Silwet. The plants were then allowed to set seed as normal. The resulting T1 seed were sown on soil, and transgenic seedlings were selected by spraying with glufosinate (FINALE®; AgrEvo; Bayer Environmental Science). A total of 100,000 glufosinate resistant T1 seedlings were selected. T2 seed from each line was kept separate.

Example 2

Screens to Identify Lines with Tolerance to Low Nitrogen

From each of 100,000 separate T1 activation-tagged lines, eleven T2 plants are sown on square plates (15 mm×15 mm) containing 0.5× N-Free Hoagland's, 0.4 mM potassium nitrate, 0.1% sucrose, 1 mM MES and 0.25% Phytagel™ (Low N medium). Five lines are plated per plate, and the inclusion of 9 wild-type individuals on each plate makes for a total of 64 individuals in an 8×8 grid pattern (see FIG. 12). Plates are kept for three days in the dark at 4° C. to stratify seeds, and then placed horizontally for nine days at 22° C. light and 20° C. dark. Photoperiod is sixteen hours light and eight hours dark, with an average light intensity of ~200 mmol/m$^2$/s. Plates are rotated and shuffled daily within each shelf. At day twelve (nine days of growth), seedling status is evaluated by imaging the entire plate.

Figure 13:
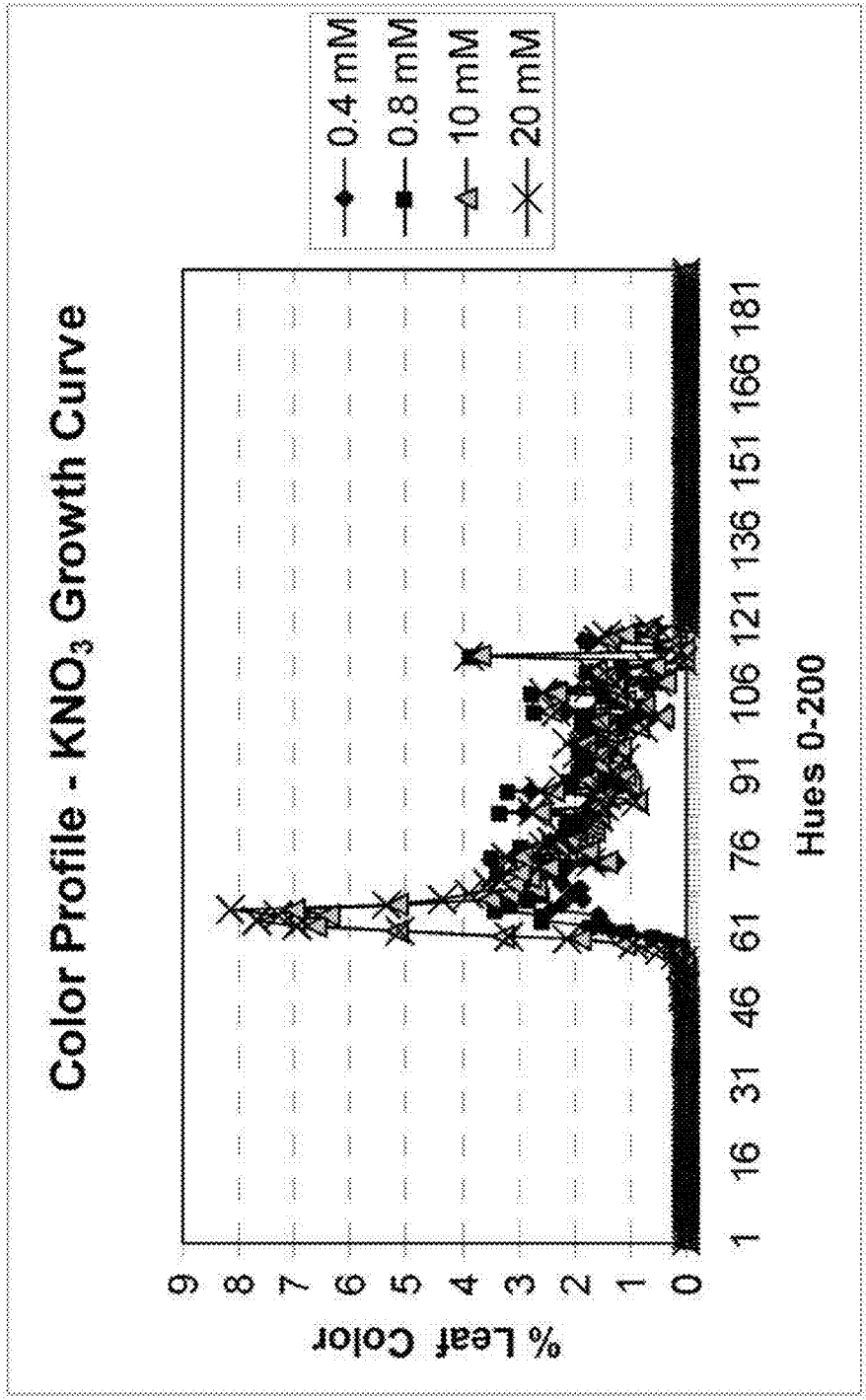
FIG. 13 shows a graph showing the effect of several different potassium nitrate concentrations on plant color as determined by image analysis. The response of the green color bin (hues 50 to 66) to nitrate dosage demonstrates that this bin can be used as an indicator of nitrogen assimilation.

After masking the plate image to remove background color, two different measurements are collected for each individual: total rosette area, and the percentage of color that falls into a green color bin. Using hue, saturation and intensity data (HSI), the green color bin consists of hues 50 to 66. Total rosette area is used as a measure of plant biomass, whereas the green color bin was shown by dose-response studies to be an indicator of nitrogen assimilation (see FIG. 13).

Lines with a significant increase in total rosette area and/or green color bin, when compared to the wild-type controls, are designated as Phase 1 hits. Phase 1 hits are re-screened in duplicate under the same assay conditions (Phase 2 screen). A Phase 3 screen is also employed to further validate mutants that passed through Phases 1 and 2. In Phase 3, each line is plated separately on Low N medium, such that 32 T2 individuals are grown next to 32 wild-type individuals on one plate, providing greater statistical rigor to the analysis. If a line shows a significant difference from the controls in Phase 3, the line is then considered a validated nitrogen-deficiency tolerant line.

Example 3

Identification of Activation-Tagged Genes

Genes flanking the T-DNA insert in nitrogen tolerant lines are identified using one, or both, of the following two standard procedures: (1) thermal asymmetric interlaced (TAIL) PCR (Liu et al., *Plant J.* 8:457-63 (1995)); and (2) SAIFF PCR (Siebert et al., *Nucleic Acids Res.* 23:1087-1088 (1995)). In lines with complex multimerized T-DNA inserts, TAIL PCR and SAIFF PCR may both prove insufficient to identify candidate genes. In these cases, other procedures, including inverse PCR, plasmid rescue and/or genomic library construction, can be employed.

A successful result is one where a single TAIL or SAIFF PCR fragment contains a T-DNA border sequence and *Arabidopsis* genomic sequence. Once a tag of genomic sequence flanking a T-DNA insert is obtained, candidate genes are identified by alignment to publicly available *Arabidopsis* genome sequence. Specifically, the annotated gene nearest the 35S enhancer elements/T-DNA RB are candidates for genes that are activated.

To verify that an identified gene is truly near a T-DNA and to rule out the possibility that the TAIL/SAIFF fragment is a chimeric cloning artifact, a diagnostic PCR on genomic DNA is done with one oligo in the T-DNA and one oligo specific for the candidate gene. Genomic DNA samples that give a PCR product are interpreted as representing a T-DNA insertion. This analysis also verifies a situation in which more than one insertion event occurs in the same line, e.g., if multiple differing genomic fragments are identified in TAIL and/or SAIFF PCR analyses.

Example 4

Identification of Activation-Tagged Gene that Encodes a SNF2 Domain-Containing Polypeptide An activation tagged-line (line 112579) showing nitrogen-deficiency tolerance was further analyzed. DNA from the line was extracted, and genes flanking the T-DNA insert in the mutant line were identified using ligation-mediated PCR (Siebert et al., *Nucleic Acids Res.* 23:1087-1088 (1995)). A single amplified fragment was identified that contained a T-DNA border sequence and *Arabidopsis* genomic sequence. Once a tag of genomic sequence flanking a T-DNA insert was obtained, a candidate gene was identified by alignment to the completed *Arabidopsis* genome. Specifically, the annotated gene nearest the 35S enhancer elements/T-DNA RB was the candidate for the gene activated in the line. In the case of line 112579 the gene nearest the 35S enhancers was At1g61140, encoding the *Arabidopsis thaliana* SNF2 domain-containing polypeptide.

Example 5

Validation of Candidate *Arabidopsis* Gene (At1g61140) Via Transformation into *Arabidopsis*

Candidate genes can be transformed into *Arabidopsis* and overexpressed under the 35S promoter. If the same or similar phenotype is observed in the transgenic line as in the parent activation-tagged line, then the candidate gene is considered to be a validated "lead gene" in *Arabidopsis*.

The candidate *Arabidopsis* gene (At1g61140), encoding a SNF2 domain-containing polypeptide, was tested for its ability to confer nitrogen-deficiency tolerance in the following manner. Primers were designed to amplify variant At1g61140.1.

The At1g61140.1 cDNA (SEQ ID NO:24) was amplified by RT-PCR with the following primers:

1. At1g61140-5' attB Forward Primer (SEQ ID NO:33)

The forward primer contains the attB1 sequence (ACAAGTTTGTACAAAAAAGCAGGCT; SEQ ID NO:12) and a consensus Kozak sequence (CAACA) upstream of the first 21 nucleotides of the protein-coding region, beginning with the ATG start codon, of said cDNA.

2. At1g61140-3' attB Reverse Primer (SEQ ID NO:34)

The reverse primer contains the attB2 sequence (ACCACTTTGTACAAGAAAGCTGGGT; SEQ ID NO:13) adjacent to the reverse complement of the last 21 nucleotides of the protein-coding region, beginning with the reverse complement of the stop codon, of said cDNA.

Using the INVITROGEN™ GATEWAY® CLONASE™ technology, a BP Recombination Reaction was performed for the RT-PCR product with pDONR™ Zeo (SEQ ID NO:2; FIG. 2). This process removes the bacteria lethal ccdB gene, as well as the chloramphenicol resistance gene (CAM), from pDONR™ Zeo and directionally clones the PCR product with flanking attB1 and attB2 sites, creating an entry clone. A positively identified entry clone was used for a subsequent LR Recombination Reaction with a destination vector, as follows.

A 16.8-kb T-DNA based binary vector (destination vector), called pBC-yellow (SEQ ID NO:4; FIG. 4), was constructed with a 1.3-kb 35S promoter immediately upstream of the INVITROGEN™ GATEWAY C1 conversion insert, which contains the bacterial lethal ccdB gene as well as the chloramphenicol resistance gene (CAM) flanked by attR1 and attR2 sequences. The vector also contains the RD29a promoter driving expression of the gene for ZS-Yellow (INVITROGEN™), which confers yellow fluorescence to transformed seed. Using the INVITROGEN™ GATEWAY® technology, an LR Recombination Reaction was performed with the entry clone containing the nucleotide coding sequence of At1g61140.1 (SEQ ID NO:24) and the pBC-yellow vector; however, either of the other variants could also be used (SEQ ID NOs:26 and 28). This amplification allowed for rapid and directional cloning of At1g61140.1 (SNF2.1; SEQ ID NO:24) behind the 35S promoter in pBC-yellow.

Applicants then introduced the 35S promoter:At1g61140 expression constructs into wild-type *Arabidopsis* ecotype Col-0, using the same *Agrobacterium*-mediated transformation procedure described in Example 1. Transgenic T1 seeds were selected by yellow fluorescence, and 32 of these T1 seeds were plated next to 32 wild-type *Arabidopsis* ecotype Col-0 seeds on low nitrogen medium. All subsequent growth and imaging conditions were performed as described in Example 1. It was found that the original phenotype from activation tagging, tolerance to nitrogen limiting conditions, could be recapitulated in wild-type *Arabidopsis* plants that were transformed with a construct where an At1g61140 gene was directly expressed by the 35S promoter.

Example 6A

Preparation of cDNA Libraries and Isolation and Sequencing of cDNA Clones cDNA libraries may be prepared by any one of many methods available. For example, the cDNAs may be introduced into plasmid vectors by first preparing the cDNA libraries in UNI-ZAP™ XR vectors according to the manufacturer's protocol (Stratagene Cloning Systems, La Jolla, Calif.). The UNI-ZAP™ XR libraries are converted into plasmid libraries according to the protocol provided by Stratagene. Upon conversion, cDNA inserts will be contained in the plasmid vector pBLUESCRIPT®. In addition, the cDNAs may be introduced directly into precut BLUESCRIPT® II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBLUESCRIPT® plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., *Science* 252:1651-1656 (1991)). The resulting ESTs are analyzed using a Perkin Elmer Model 377 fluorescent sequencer.

Full-insert sequence (FIS) data is generated utilizing a modified transposition protocol. Clones identified for FIS are recovered from archived glycerol stocks as single colonies, and plasmid DNAs are isolated via alkaline lysis. Isolated DNA templates are reacted with vector primed M13 forward and reverse oligonucleotides in a PCR-based sequencing reaction and loaded onto automated sequencers. Confirmation of clone identification is performed by sequence alignment to the original EST sequence from which the FIS request is made.

Confirmed templates are transposed via the Primer Island transposition kit (PE Applied Biosystems, Foster City, Calif.) which is based upon the *Saccharomyces cerevisiae* Ty1 transposable element (Devine and Boeke, *Nucleic Acids Res.* 22:3765-3772 (1994)). The in vitro transposition system places unique binding sites randomly throughout a population of large DNA molecules. The transposed DNA is then used to transform DH10B electro-competent cells (GIBCO BRL/Life Technologies, Rockville, Md.) via electroporation. The transposable element contains an additional selectable marker (named DHFR; Fling and Richards, *Nucleic Acids Res.* 11:5147-5158 (1983)), allowing for dual selection on agar plates of only those subclones containing the integrated transposon. Multiple subclones are randomly selected from each transposition reaction, plasmid DNAs are prepared via alkaline lysis, and templates are sequenced (ABI PRISM dye-terminator ReadyReaction mix) outward from the transposition event site, utilizing unique primers specific to the binding sites within the transposon.

Sequence data is collected (ABI PRISM® Collections) and assembled using Phred and Phrap (Ewing et al., *Genome Res.* 8:175-185 (1998); Ewing et al., *Genome Res.* 8:186-194 (1998)). Phred is a public domain software program which re-reads the ABI sequence data, re-calls the bases, assigns quality values, and writes the base calls and quality values into editable output files. The Phrap sequence assembly program uses these quality values to increase the accuracy of the assembled sequence contigs. Assemblies are viewed by the Consed sequence editor (Gordon et al., *Genome Res.* 8:195-202 (1998)).

In some of the clones the cDNA fragment corresponds to a portion of the 3'-terminus of the gene and does not cover the entire open reading frame. In order to obtain the upstream information one of two different protocols is used. The first of these methods results in the production of a fragment of DNA containing a portion of the desired gene sequence while the second method results in the production of a fragment containing the entire open reading frame. Both of these methods use two rounds of PCR amplification to obtain fragments from one or more libraries. The libraries sometimes are chosen based on previous knowledge that the specific gene should be found in a certain tissue and sometimes are randomly-chosen. Reactions to obtain the same gene may be performed on several libraries in parallel or on a pool of libraries. Library pools are normally prepared using from 3 to 5 different libraries and normalized to a uniform dilution. In the first round of amplification both methods use a vector-specific (forward) primer corresponding to a portion of the vector located at the 5'-terminus of the clone coupled with a gene-specific (reverse) primer. The first method uses a sequence that is complementary to a portion of the already known gene sequence while the second method uses a gene-specific primer complementary to a portion of the 3'-untranslated region (also referred to as UTR). In the second round of amplification a nested set of primers is used for both methods. The resulting DNA fragment is ligated into a pBLUESCRIPT® vector using a commercial kit and following the manufacturer's protocol. This kit is selected from many available from several vendors including INVITROGEN™ (Carlsbad, Calif.), Promega Biotech (Madison, Wis.), and GIBCO-BRL (Gaithersburg, Md.). The plasmid DNA is isolated by alkaline lysis method and submitted for sequencing and assembly using Phred/Phrap, as above.

Example 6B

Preparation of cDNA Libraries and Obtainment of Sequences mRNAs can be isolated using the Qiagen RNA isolation kit for total RNA isolation, followed by mRNA isolation via attachment to oligo(dT) Dynabeads from Invitrogen (Life Technologies, Carlsbad, Calif.), and sequencing libraries can be prepared using the standard mRNA-Seq kit and protocol from Illumina, Inc. (San Diego, Calif.). In this method, mRNAs are fragmented using a $ZnCl_2$ solution, reverse transcribed into cDNA using random primers, end repaired to create blunt end fragments, 3' A-tailed, and ligated with Illumina paired-end library adaptors. Ligated cDNA fragments can then be PCR amplified using Illumina paired-end library primers, and purified PCR products can be checked for quality and quantity on the Agilent Bioanalyzer DNA 1000 chip prior to sequencing on the Genome Analyzer II equipped with a paired end module.

Reads from the sequencing runs can be soft-trimmed prior to assembly such that the first base pair of each read with an observed FASTQ quality score lower than 15 and all subsequent bases are clipped using a Python script. The Velvet assembler (Zerbino et al. *Genome Research* 18:821-9 (2008)) can be run under varying kmer and coverage cutoff parameters to produce several putative assemblies along a range of stringency. The contiguous sequences (contigs) within those assemblies can be combined into clusters using Vmatch software (available on the Vmatch website) such that contigs which are identified as substrings of longer contigs are grouped and eliminated, leaving a non-redundant set of longest "sentinel" contigs. These non-redundant sets can be used in alignments to homologous sequences from known model plant species.

If a contig does not represent a complete gene the non-redundant sets can be re-queried via Blast or a Perl Script with the sequences discovered in the first search. If sequences that extend the ends of the contigs are discovered, they can be assembled with the original sequences with a desktop assembler such as DNAStar's SeqMan, or GeneCode's Sequencher. These steps can be repeated until no further extending sequences are found. For transcripts that still are not complete, gene fragments that theoretically belong together (based on homology to other grasses) can be artificially joined with linking sequence from another grass.

Example 7

Identification of cDNA Sequences cDNA sequences encoding SNF2 domain-containing polypeptides are identified by conducting BLAST (Basic Local Alignment Search Tool; Altschul et al., *J. Mol. Biol.* 215:403-410 (1993); see also the explanation of the BLAST algorithm on the world wide web site for the National Center for Biotechnology Information at the National Library of Medicine of the National Institutes of Health) searches for similarity to amino acid sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The DNA sequences can be translated in all reading frames and compared for similarity to all publicly available protein sequences contained in the "nr" database using the BLASTX algorithm (Gish and States, *Nat. Genet.* 3:266-272 (1993)) provided by the NCBI. The polypeptides encoded by the cDNA sequences can be analyzed for similarity to all publicly available amino acid sequences contained in the "nr" database using the BLASTP algorithm provided by the National Center for Biotechnology Information (NCBI). For convenience, the P-value (probability) or the E-value (expectation) of observing a match of a cDNA-encoded sequence to a sequence contained in the searched databases merely by chance as calculated by BLAST are reported herein as "p Log" values, which represent the negative of the logarithm of the reported P-value or E-value. Accordingly, the greater the p Log value, the greater the likelihood that the cDNA-encoded sequence and the BLAST "hit" represent homologous proteins.

EST sequences can be compared to the Gen Bank database as described above. ESTs that contain sequences more 5- or 3-prime can be found by using the BLASTN algorithm (Altschul et al., *Nucleic Acids Res.* 25:3389-3402 (1997)) against the Dupont proprietary database comparing nucleotide sequences that share common or overlapping regions of sequence homology. Where common or overlapping sequences exist between two or more nucleic acid fragments, the sequences can be assembled into a single contiguous nucleotide sequence, thus extending the original fragment in either the 5 or 3 prime direction. Once the most 5-prime EST is identified, its complete sequence can be determined by Full Insert Sequencing.

Homologous genes belonging to different species can be found by comparing the amino acid sequence of a known gene (from either a proprietary source or a public database) against an EST database using the tBLASTn algorithm. The tBLASTn algorithm searches an amino acid query against a nucleotide database that is translated in all 6 reading frames. This search allows for differences in nucleotide codon usage between different species, and for codon degeneracy.

Example 8A

Characterization of cDNA Sequences Encoding SNF2 Domain-Containing Polypeptides cDNA libraries representing mRNAs from various tissues of *Zea mays* (maize), *Eragrostis nindensis* (Resurrection grass), and *Paspalum notatum* (Bahiagrass) were prepared. The characteristics of the libraries are described below.

TABLE 2 cDNA Libraries from Maize

| Library | Description (tissue) | Clone | Nucleotide | Amino acid |
|---------|---------------------|-------|------------|------------|
| cfp1n | Maize Tassel V7 to V12 pooled, Full-length enriched normalized | cfp1n.pk008.f7:fis | SEQ ID NO: 18 | SEQ ID NO: 19 |
| cfp4n | Maize Pollinated ear, pooled 48_72 hrs postpollination, Full-length enriched normalized | cfp4n.pk061.o18:fis | SEQ ID NO: 20 | SEQ ID NO: 21 |
| p0016 | Tassel shoots, pooled, 0.1-1.4 cm | p0016.ctsca12r | SEQ ID NO: 22 | SEQ ID NO: 23 |
| N/A | Vegetative stage roots from Resurrection grass (*Eragrostis nindensis*) | N/A | SEQ ID NO: 35 | SEQ ID NO: 36 |
| N/A | Vegetative stage roots from Bahiagrass (*Paspalum nottum*) | N/A | SEQ ID NO: 37 | SEQ ID NO: 38 |

As shown in Table 3, FIGS. 16A-AM, and FIG. 17, cDNAs identified in Table 2 encode polypeptides similar to the SNF2 domain-containing polypeptides from *Arabidopsis thaliana* (At1g61140.1 (GI No. 186492170; SEQ ID NO:25); At1g61140.2 (GI No. 186492172; SEQ ID NO:27); and At1g61140.3 (GI No. 186492175; SEQ ID NO:29)) and to the SNF2 domain-containing polypeptides from *Oryza sativa* (GI No. 53792213 corresponding to SEQ ID NO:30, GI No. 218200575 corresponding to SEQ ID NO:31, and GI No. 90399293 corresponding to SEQ ID NO:32) and from *Sorghum bicolor* (GI No. 242058897 corresponding to SEQ ID NO:49).

Shown in Table 3 (non-patent literature) and Table 4 (patent literature) are the BLASTP results for individual ESTs ("EST"), the sequences of the entire cDNA inserts comprising the indicated cDNA clones ("FIS"), the sequences of contigs assembled from two or more EST, FIS or PCR sequences ("Contig"), or sequences encoding an entire or functional protein derived from an FIS or a contig ("CGS"). Also shown in Tables 3 and 4 are the percent sequence identity values for each pair of amino acid sequences using the Clustal V method of alignment with default parameters (described below).

TABLE 3

BLASTP Results for Polypeptides
Homologous to SNF2 Domain-Containing Polypeptides

| Sequence (SEQ ID NO:#) | Status | NCBI GI No. | % identity | BLAST pLog Score |
|------------------------|--------|-------------|------------|------------------|
| cfp1n.pk008.f7:fis (SEQ ID NO: 19) | CGS | 53792213 (SEQ ID NO: 30) | 100.0 | 98 |
| cfp4n.pk061.o18:fis (SEQ ID NO: 21) | CGS | 218200575 (SEQ ID NO: 31) | 100.0 | >250 |
| contig of: p0016.ctsca12r (SEQ ID NO: 23) | CGS | 90399293 (SEQ ID NO: 32) | 100.0 | >250 |
| SEQ ID NO: 36 | CGS | 242058897 (SEQ ID NO: 49) | 81.7 | >250 |
| SEQ ID NO: 38 | CGS | 242058897 (SEQ ID NO: 49) | 85.0 | >250 |

TABLE 4

BLASTP Results for Polypeptides
Homologous to SNF2 Domain-Containing Polypeptides

| Sequence (SEQ ID NO:#) | Status | Reference | % Identity | BLAST pLog score |
|---|---|---|---|---|
| cfp1n.pk008.f7:fis (SEQ ID NO: 19) | CGS | SEQ ID NO: 17848 In US20080229439 SEQ ID NO: 25068 In US20080229439 SEQ ID NO: 17848 In US20070192889 SEQ ID NO:25068 In US20070192889 SEQ ID NO:110654 In US20040123343 | 51.83 | 109 |
| cfp4n.pk061.o18:fis (SEQ ID NO: 21) | CGS | SEQ ID NO: 48529 In US20060123505 | 72.51 | >250 |
| contig of: p0016.ctsca12r (SEQ ID NO: 23) | CGS | SEQ ID NO:55175 In US20060123505 | 60.02 | >250 |
| SEQ ID NO: 36 | CGS | SEQ ID NO: 16967 In US20090094717 | 79.4 | >250 |
| SEQ ID NO:38 | CGS | SEQ ID NO: 16967 In US20090094717 | 83.9 | >250 |

Example 8B

Identification of Other SNF2 Domain-Containing Polypeptides

Sequences homologous to the lead genes that encode SNF2 domain-containing proteins can be identified using sequence comparison algorithms such as BLAST (Basic Local Alignment Search Tool; Altschul et al., *J. Mol. Biol.* 215:403-410 (1993); see also the explanation of the BLAST algorithm on the world wide web site for the National Center for Biotechnology Information at the National Library of Medicine of the National Institutes of Health). For instance, the amino acid sequence of the protein encoded by At1g61140 was used as a query against the public database using BlastP, and the polypeptide sequences represented in SEQ ID NOs:40, 42, and 48 were subsequently identified as homologs (corresponding nucleotides sequences are SEQ ID NO:39, 41, and 47, respectively). Also, a TblastN search against public BAC sequences identified the maize homolog represented by SEQ ID NO:44 (corresponding nucleotide sequence is SEQ ID NO:43).

Example 8C

Sequence Alignment and Percent Identity Calculations for SNF2 Domain-Containing Polypeptides FIGS. 16A-AM present an alignment of the amino acid sequences set forth in SEQ ID NOs:19, 21, 23, 25, 27, 29, 30, 31, 32, 36, 38, 40, 42, 44, 46, 48, and 49. FIG. 17 is a chart of the percent sequence identity and the divergence values for each pair of amino acid sequences presented in FIGS. 16A-AM.

Sequence alignments and percent identity calculations were performed using the MEGALIGN® program of the LASERGENE® bioinformatics computing suite (DNASTAR® Inc., Madison, Wis.). Multiple alignment of the sequences was performed using the Clustal method of alignment (Higgins and Sharp (1989) *CABIOS.* 5:151-153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

Example 9

Preparation of a Plant Expression Vector Containing a Homolog to the *Arabidopsis* Lead Gene Sequences homologous to the lead genes that encode SNF2 domain-containing proteins can be identified using sequence comparison algorithms such as BLAST (Basic Local Alignment Search Tool; Altschul et al., *J. Mol. Biol.* 215:403-410 (1993); see also the explanation of the BLAST algorithm on the world wide web site for the National Center for Biotechnology Information at the National Library of Medicine of the National Institutes of Health). The nucleotide sequences of similar genes that encode SNF2 domain-containing proteins, such as the ones described in Examples 8A-C, can be PCR-amplified by any of the following methods.

Method 1 (RNA-based): If the 5' and 3' sequence information for the protein-coding region is available, gene-specific primers can be designed as outlined in Example 5. RT-PCR can be used with plant RNA to obtain a nucleic acid fragment containing the protein-coding region flanked by attB1 (SEQ ID NO:12) and attB2 (SEQ ID NO:13) sequences. The primer may contain a consensus Kozak sequence (CAACA) upstream of the start codon.

Method 2 (DNA-based): Alternatively, if a cDNA clone is available, the entire cDNA insert (containing 5' and 3' non-coding regions) can be PCR amplified. Forward and reverse primers can be designed that contain either the attB1 sequence and vector-specific sequence that precedes the cDNA insert or the attB2 sequence and vector-specific sequence that follows the cDNA insert, respectively. For a cDNA insert cloned into the vector pBLUESCRIPT SK+, the forward primer VC062 (SEQ ID NO:16) and the reverse primer VC063 (SEQ ID NO:17) can be used.

Method 3 (genomic DNA): Genomic sequences can be obtained using long range genomic PCR capture. Primers can be designed based on the sequence of the genomic locus and the resulting PCR product can be sequenced. The sequence can be analyzed using the FGENESH (Salamov, A. and Solovyev, V. (2000) *Genome Res.*, 10:516-522) program, and optionally, can be aligned with homologous sequences from other species to assist in identification of putative introns and exons.

Methods 1, 2, and 3 can be modified according to procedures known by one skilled in the art. For example, the primers of Method 1 may contain restriction sites instead of attB1 and attB2 sites, for subsequent cloning of the PCR product into a vector containing attB1 and attB2 sites. Additionally, Method 2 can involve amplification from a cDNA clone, a lambda clone, a BAC clone or genomic DNA.

A PCR product obtained by either method above can be combined with the GATEWAY® donor vector, such as pDONR™ Zeo (SEQ ID NO:2; FIG. 2) or pDONR™221 (SEQ ID NO:3; FIG. 3), using a BP Recombination Reaction. This process removes the bacteria lethal ccdB gene, as well as the chloramphenicol resistance gene (CAM) from pDONR™ Zeo or pDONR™221 and directionally clones the PCR product with flanking attB1 and attB2 sites to create an entry clone. Using the INVITROGEN™ GATEWAY® CLONASE™ technology, the sequence encoding the homologous SNF2 domain-containing polypeptide from the entry clone can then be transferred to a suitable destination vector, such as pBC-Yellow (SEQ ID NO:4; FIG. 4), PHP27840 (SEQ ID NO:5; FIG. 5), or PHP23236 (SEQ ID NO:6; FIG. 6), to obtain a plant expression vector for use with *Arabidopsis*, soybean, and corn, respectively.

The attP1 and attP2 sites of donor vectors pDONR™/Zeo or pDONR™221 are shown in FIGS. 2 and 3, respectively. The attR1 and attR2 sites of destination vectors pBC-Yellow, PHP27840, and PHP23236 are shown in FIGS. 4, 5 and 6, respectively.

Alternatively a MultiSite GATEWAY® LR recombination reaction between multiple entry clones and a suitable destination vector can be performed to create an expression vector.

Example 10

Preparation of Soybean Expression Vectors and Transformation of Soybean with Validated *Arabidopsis* Lead Genes Soybean plants can be transformed to overexpress each validated *Arabidopsis* gene or the corresponding homologs from various species in order to examine the resulting phenotype.

The same GATEWAY® entry clone described in Example 5 can be used to directionally clone each gene into the PHP27840 vector (SEQ ID NO:5; FIG. 5) such that expression of the gene is under control of the SCP1 promoter.

Soybean embryos may then be transformed with the expression vector comprising sequences encoding the instant polypeptides. Techniques for soybean transformation and regeneration have been described in International Patent Publication WO 2009/006276, the contents of which are herein incorporated by reference.

T1 plants can be grown under nitrogen limiting conditions, for example, 1 mM nitrate, and analyzed for phenotypic changes. The following parameters can be quantified using image analysis: plant area, volume, growth rate and color analysis can be collected and quantified. Overexpression constructs that result in an alteration, compared to suitable control plants, in greenness (green color bin), yield, growth rate, biomass, fresh or dry weight at maturation, fruit or seed yield, total plant nitrogen content, fruit or seed nitrogen content, nitrogen content in vegetative tissue, free amino acid content in the whole plant, free amino acid content in vegetative tissue, free amino acid content in the fruit or seed, protein content in the fruit or seed, or protein content in a vegetative tissue can be considered evidence that the *Arabidopsis* lead gene functions in soybean to enhance tolerance to nitrogen deprivation (increased nitrogen tolerance).

Soybean plants transformed with validated genes can be assayed to study agronomic characteristics relative to control or reference plants. For example, yield enhancement and/or stability under low and high nitrogen conditions (e.g., nitrogen limiting conditions and nitrogen-sufficient conditions) can be assayed.

Example 11

Transformation of Maize with Validated *Arabidopsis* Lead Genes Using Particle Bombardment Maize plants can be transformed to overexpress a validated *Arabidopsis* lead gene or the corresponding homologs from various species in order to examine the resulting phenotype.

The same GATEWAY® entry clones described in Example 5 can be used to directionally clone each respective gene into a maize transformation vector. Expression of the gene in the maize transformation vector can be under control of a constitutive promoter such as the maize ubiquitin promoter (Christensen et al., *Plant Mol. Biol.* 12:619-632 (1989) and Christensen et al., *Plant Mol. Biol.* 18:675-689 (1992))

The recombinant DNA construct described above can then be introduced into maize cells by particle bombardment. Techniques for corn transformation by particle bombardment have been described in International Patent Publication WO 2009/006276, the contents of which are herein incorporated by reference.

T1 plants can be grown under nitrogen limiting conditions, for example, 1 mM nitrate, and analyzed for phenotypic changes. The following parameters can be quantified using image analysis: plant area, volume, growth rate and color analysis can be collected and quantified. Overexpression constructs that result in an alteration, compared to suitable control plants, in greenness (green color bin), yield, growth rate, biomass, fresh or dry weight at maturation, fruit or seed yield, total plant nitrogen content, fruit or seed nitrogen content, nitrogen content in vegetative tissue, free amino acid content in the whole plant, free amino acid content in vegetative tissue, free amino acid content in the fruit or seed, protein content in the fruit or seed, or protein content in a vegetative tissue can be considered evidence that the *Arabidopsis* lead gene functions in maize to enhance tolerance to nitrogen deprivation (increased nitrogen tolerance).

Example 12

Electroporation of *Agrobacterium tumefaciens* LBA4404

Electroporation competent cells (40 µL), such as *Agrobacterium tumefaciens* LBA4404 (containing PHP10523), are thawed on ice (20-30 min). PHP10523 contains VIR genes for T-DNA transfer, an *Agrobacterium* low copy number plasmid origin of replication, a tetracycline resistance gene, and a Cos site for in vivo DNA bimolecular recombination. Meanwhile the electroporation cuvette is chilled on ice. The electroporator settings are adjusted to 2.1 kV. A DNA aliquot (0.5 µL parental DNA at a concentration of 0.2 µg-1.0 µg in low salt buffer or twice distilled $H_2O$) is mixed with the thawed *Agrobacterium tumefaciens* LBA4404 cells while still on ice. The mixture is transferred to the bottom of electroporation cuvette and kept at rest on ice for 1-2 min. The cells are electroporated (Eppendorf electroporator 2510) by pushing the "pulse" button twice (ideally achieving a 4.0 millisecond pulse). Subsequently, 0.5 mL of room temperature 2×YT medium (or SOC medium) are added to the cuvette and transferred to a 15 mL snap-cap tube (e.g., FALCON™ tube). The cells are incubated at 28-30° C., 200-250 rpm for 3 h.

Aliquots of 250 µL are spread onto plates containing YM medium and 50 µg/mL spectinomycin and incubated three days at 28-30° C. To increase the number of transformants one of two optional steps can be performed:

Option 1: Overlay plates with 30 µL of 15 mg/mL rifampicin. LBA4404 has a chromosomal resistance gene for rifampicin. This additional selection eliminates some contaminating colonies observed when using poorer preparations of LBA4404 competent cells.

Option 2: Perform two replicates of the electroporation to compensate for poorer electrocompetent cells.

Identification of Transformants:

Four independent colonies are picked and streaked on plates containing AB minimal medium and 50 µg/mL spectinomycin for isolation of single colonies. The plates are incubated at 28° C. for two to three days. A single colony for each putative cointegrate is picked and inoculated with 4 mL of 10 g/L bactopeptone, 10 g/L yeast extract, 5 g/L sodium chloride, and 50 mg/L spectinomycin. The mixture is incubated for 24 h at 28° C. with shaking. Plasmid DNA from 4 mL of culture is isolated using QIAGEN Miniprep and an optional Buffer PB wash. The DNA is eluted in 30 Aliquots of 2 µL are used to electroporate 20 µL of DH10b+20 µL of twice distilled H₂O as per above. Optionally a 15 µL aliquot can be used to transform 75-100 µL of INVITROGEN™ Library Efficiency DH5α. The cells are spread on plates containing LB medium and 50 µg/mL spectinomycin and incubated at 37° C. overnight.

Three to four independent colonies are picked for each putative cointegrate and inoculated 4 mL of 2× YT medium (10 g/L bactopeptone, 10 g/L yeast extract, 5 g/L sodium chloride) with 50 µg/mL spectinomycin. The cells are incubated at 37° C. overnight with shaking. Next, the plasmid DNA is isolated from 4 mL of culture using QIAprep® Miniprep with optional Buffer PB wash (elute in 50 µL). 8 µL are used for digestion with SalI (using parental DNA and PHP10523 as controls). Three more digestions using restriction enzymes BamHI, EcoRI, and HindIII are performed for 4 plasmids that represent 2 putative cointegrates with correct SalI digestion pattern (using parental DNA and PHP10523 as controls). Electronic gels are recommended for comparison.

Example 13

Transformation of Maize Using *Agrobacterium*

Maize plants can be transformed to overexpress a validated *Arabidopsis* lead gene or the corresponding homologs from various species in order to examine the resulting phenotype.

*Agrobacterium*-mediated transformation of maize is performed essentially as described by Zhao et al., in *Meth. Mol. Biol.* 318:315-323 (2006) (see also Zhao et al., Mot Breed. 8:323-333 (2001) and U.S. Pat. No. 5,981,840 issued Nov. 9, 1999, incorporated herein by reference). The transformation process involves bacterium inoculation, co-cultivation, resting, selection, and plant regeneration.

1. Immature Embryo Preparation:
Immature maize embryos are dissected from caryopses and placed in a 2 mL microtube containing 2 mL PHI-A medium.
2. *Agrobacterium* Infection and Co-Cultivation of Immature Embryos:
2.1 Infection Step:
PHI-A medium of (1) is removed with 1 mL micropipettor, and 1 mL of *Agrobacterium* suspension is added. The tube is gently inverted to mix. The mixture is incubated for 5 min at room temperature.
2.2 Co-Culture Step:
The *Agrobacterium* suspension is removed from the infection step with a 1 mL micropipettor. Using a sterile spatula the embryos are scraped from the tube and transferred to a plate of PHI-B medium in a 100×15 mm Petri dish. The embryos are oriented with the embryonic axis down on the surface of the medium. Plates with the embryos are cultured at 20° C., in darkness, for three days. L-Cysteine can be used in the co-cultivation phase. With the standard binary vector, the co-cultivation medium supplied with 100-400 mg/L L-cysteine is critical for recovering stable transgenic events.
3. Selection of Putative Transgenic Events:
To each plate of PHI-D medium in a 100×15 mm Petri dish, 10 embryos are transferred, maintaining orientation, and the dishes are sealed with parafilm. The plates are incubated in darkness at 28° C. Actively growing putative events, evinced as pale yellow embryonic tissue, are expected to be visible in six to eight weeks. Embryos that produce no events may be brown and necrotic, and little friable tissue growth is evident. Putative transgenic embryonic tissue is subcultured to fresh PHI-D plates at two-three week intervals, depending on growth rate. The events are recorded.
4. Regeneration of T0 Plants:
Embryonic tissue propagated on PHI-D medium is subcultured to PHI-E medium (somatic embryo maturation medium), in 100×25 mm Petri dishes and incubated at 28° C., in darkness, until somatic embryos mature, for about ten to eighteen days. Individual, matured somatic embryos with well-defined scutellum and coleoptile are transferred to PHI-F embryo germination medium and incubated at 28° C. in the light (about 80 µE from cool white or equivalent fluorescent lamps). In seven to ten days, regenerated plants, about 10 cm tall, are potted in horticultural mix and hardened-off using standard horticultural methods.

Media for Plant Transformation:
1. PHI-A: 4 g/L CHU basal salts, 1.0 mL/L 1000× Eriksson's vitamin mix, 0.5 mg/L thiamin HCl, 1.5 mg/L 2,4-D, 0.69 g/L L-proline, 68.5 g/L sucrose, 36 g/L glucose, pH 5.2. Add 100 µM acetosyringone (filter-sterilized).
2. PHI-B: PHI-A without glucose, increase 2,4-D to 2 mg/L, reduce sucrose to 30 g/L and supplemented with 0.85 mg/L silver nitrate (filter-sterilized), 3.0 g/L GEL-RITE®, 100 µM acetosyringone (filter-sterilized), pH 5.8.
3. PHI-C: PHI-B without GELRITE® and acetosyringonee, reduce 2,4-D to 1.5 mg/L and supplemented with 8.0 g/L agar, 0.5 g/L 2-[N-morpholino]ethane-sulfonic acid (MES) buffer, 100 mg/L carbenicillin (filter-sterilized).
4. PHI-D: PHI-C supplemented with 3 mg/L bialaphos (filter-sterilized).
5. PHI-E: 4.3 g/L of Murashige and Skoog (MS) salts, (GIBCO, BRL 11117-074), 0.5 mg/L nicotinic acid, 0.1 mg/L thiamine HCl, 0.5 mg/L pyridoxine HCl, 2.0 mg/L glycine, 0.1 g/L myo-inositol, 0.5 mg/L zeatin (Sigma, Cat. No. Z-0164), 1 mg/L indole acetic acid (IAA), 26.4 µg/L abscisic acid (ABA), 60 g/L sucrose, 3 mg/L bialaphos (filter-sterilized), 100 mg/L carbenicillin (filter-sterilized), 8 g/L agar, pH 5.6.
6. PHI-F: PHI-E without zeatin, IAA, ABA; reduce sucrose to 40 g/L; replacing agar with 1.5 g/L GELRITE®; pH 5.6.

Plants can be regenerated from the transgenic callus by first transferring clusters of tissue to N6 medium supplemented with 0.2 mg per liter of 2,4-D. After two weeks the tissue can be transferred to regeneration medium (Fromm et al., *Bio/Technology* 8:833-839 (1990)).

Transgenic T0 plants can be regenerated and their phenotype determined. T1 seed can be collected.

Furthermore, a recombinant DNA construct containing a validated *Arabidopsis* gene can be introduced into a maize inbred line either by direct transformation or introgression from a separately transformed line.

Transgenic plants, either inbred or hybrid, can undergo more vigorous field-based experiments to study yield enhancement and/or stability under nitrogen limiting and nitrogen non-limiting conditions.

Subsequent yield analysis can be done to determine whether plants that contain the validated *Arabidopsis* lead gene have an improvement in yield performance (under nitrogen limiting or non-limiting conditions), when compared to the control (or reference) plants that do not contain the validated *Arabidopsis* lead gene. Plants containing the validated *Arabidopsis* lead gene would have less yield loss relative to the control plants, for example, at least 25% less yield loss, under nitrogen limiting conditions, or would have increased yield relative to the control plants under nitrogen non-limiting conditions.

Example 14A

Preparation of Expression Vector for Transformation of Maize Lines with Validated Candidate *Arabidopsis* Gene (At1g61140) Using *Agrobacterium*

Using the INVITROGEN™ GATEWAY® technology, an LR Recombination Reaction was performed with the GATEWAY® entry clone containing the sequence that encodes the *Arabidopsis* SN F2 domain-containing protein (described in Example 5 and referred to in this and subsequent examples as AT-SNF2.1), entry clone PHP23112 (SEQ ID NO:14), entry clone PHP20234 (SEQ ID NO:9; FIG. 9) and destination vector PHP22655 (SEQ ID NO:10) to generate the precursor plasmid PHP29872. PHP29872 contains the following expression cassettes:
  1. Ubiquitin promoter::moPAT::PinII terminator cassette expressing the PAT herbicide resistance gene used for selection during the transformation process.
  2. LTP2 promoter::DS-RED2::PinII terminator cassette expressing the DS-RED color marker gene used for seed sorting.
  3. Ubiquitin promoter::AT-SNF2.1::PinII terminator cassette overexpressing the *Arabidopsis* SN F2.1 domain-containing protein (At1g61140.1).

Example 14B

Transformation of Maize Lines with Validated Candidate *Arabidopsis* Gene (At1g61140) Using *Agrobacterium*

The SNF2.1 expression cassette present in vector PHP29872 (described in Example 14A) or vectors containing either of the other two At1g61140 variants can be introduced into a maize inbred line, or a transformable maize line derived from an elite maize inbred line, using *Agrobacterium*-mediated transformation as described in Examples 12 and 13.

Expression vector PHP29872 can be electroporated into the LBA4404 *Agrobacterium* strain containing vector PHP10523 (SEQ ID NO:7, FIG. 7) to create the co-integrate vector PHP29875, which contains the SNF2.1 expression cassette. The co-integrate vector is formed by recombination of the two plasmids, PHP29872 and PHP10523, through the COS recombination sites contained on each vector and contains the same three expression cassettes as above (Example 14A) in addition to other genes (TET, TET, TRFA, ORI terminator, CTL, ORI V, VIR C1, VIR C2, VIR G, VIR B) needed for the *Agrobacterium* strain and the *Agrobacterium*-mediated transformation. The electroporation protocol in, but not limited to, Example 12 may be used.

Example 15

Preparation of the Destination Vector PHP23236 for Transformation into Gaspe Flint Derived Maize Lines Destination vector PHP23236 (FIG. 6; SEQ ID NO:6) was obtained by transformation of *Agrobacterium* strain LBA4404 containing PHP10523 (FIG. 7; SEQ ID NO:7) with vector PHP23235 (FIG. 8; SEQ ID NO:8) and isolation of the resulting co-integration product.

Destination vector PHP23236 can be used in a recombination reaction with an entry clone, as described in Example 16, to create a maize expression vector for transformation of Gaspe Flint derived maize lines.

Example 16

Preparation of Expression Constructs for Transformation into Gaspe Flint Derived Maize Lines Using the INVITROGEN™ GATEWAY® LR Recombination technology, the same entry clone described in Example 5 can be directionally cloned into the destination vector PHP29634 (SEQ ID NO:15; FIG. 11) to create an expression vector. Destination vector PHP29634 is similar to destination vector PHP23236, however, destination vector PHP29634 has site-specific recombination sites FRT1 and FRT87 and also encodes the GAT4602 selectable marker protein for selection of transformants using glyphosate. The expression vector would contain the cDNA of interest, encoding either At-SNF2.1, At-SNF2.2, or AtSNF2.3, under control of the UBI promoter and is a T-DNA binary vector for *Agrobacterium*-mediated transformation into corn as described, but not limited to, the examples described herein.

Example 17A

Transformation of Gaspe Flint Derived Maize Lines with Validated Candidate *Arabidopsis* Gene (At1g61140)

Maize plants can be transformed to overexpress the *Arabidopsis* At1g61140 gene (and the corresponding homologs from other species) in order to examine the resulting phenotype. Expression constructs such as the one described in Example 16 may be used.

Recipient Plants

Recipient plant cells can be from a uniform maize line having a short life cycle ("fast cycling"), a reduced size, and high transformation potential. Typical of these plant cells for maize are plant cells from any of the publicly available Gaspe Flint (GF) line varieties. One possible candidate plant line variety is the F1 hybrid of GF×QTM (Quick Turnaround Maize, a publicly available form of Gaspe Flint selected for growth under greenhouse conditions) disclosed in Tomes et al. (U.S. application Ser. No. 10/367,416 filed Feb. 13, 2003; U.S. Patent Publication No. 200310221212 A1 published Nov. 27, 2003). Transgenic plants obtained from this line are of such a reduced size that they can be grown in four inch pots (¼ the space needed for a normal sized maize plant) and mature in less than 2.5 months. (Traditionally 3.5 months is required to obtain transgenic T0 seed once the transgenic plants are acclimated to the greenhouse.) Another suitable line includes but is not limited to a double haploid line of GS3 (a highly transformable line)×Gaspe Flint. Yet another suitable line is a transformable elite maize inbred line carrying a transgene which causes early flowering, reduced stature, or both.

Transformation Protocol

Any suitable method may be used to introduce the transgenes into the maize cells, including but not limited to inoculation type procedures using *Agrobacterium* based vectors (see, for example, Examples 12 and 13). Transformation may be performed on immature embryos of the recipient (target) plant.

Precision Growth and Plant Tracking

The event population of transgenic (T0) plants resulting from the transformed maize embryos is grown in a controlled greenhouse environment using a modified randomized block design to reduce or eliminate environmental error. A randomized block design is a plant layout in which the experimental plants are divided into groups (e.g., thirty plants per group), referred to as blocks, and each plant is randomly assigned a location within the block.

For a group of thirty plants, twenty-four transformed, experimental plants and six control plants (plants with a set phenotype) (collectively, a "replicate group") are placed in pots which are arranged in an array (a.k.a. a replicate group or block) on a table located inside a greenhouse. Each plant, control or experimental, is randomly assigned to a location within the block which is mapped to a unique, physical greenhouse location as well as to the replicate group. Multiple replicate groups of thirty plants each may be grown in the same greenhouse in a single experiment. The layout (arrangement) of the replicate groups should be determined to minimize space requirements as well as environmental effects within the greenhouse. Such a layout may be referred to as a compressed greenhouse layout.

An alternative to the addition of a specific control group is to identify those transgenic plants that do not express the gene of interest. A variety of techniques such as RT-PCR can be applied to quantitatively assess the expression level of the introduced gene. T0 plants that do not express the transgene can be compared to those which do.

Each plant in the event population is identified and tracked throughout the evaluation process, and the data gathered from that plant is automatically associated with that plant so that the gathered data can be associated with the transgene carried by the plant. For example, each plant container can have a machine readable label (such as a Universal Product Code (UPC) bar code) which includes information about the plant identity, which in turn is correlated to a greenhouse location so that data obtained from the plant can be automatically associated with that plant.

Alternatively any efficient, machine readable, plant identification system can be used, such as two-dimensional matrix codes or even radio frequency identification tags (RFID) in which the data is received and interpreted by a radio frequency receiver/processor. See U.S. application Ser. No. 10/324,288 filed Dec. 19, 2002 (U.S. Patent Publication No. 2004/0122592 A1 published Jun. 24, 2004), incorporated herein by reference.

Phenotypic Analysis Using Three-Dimensional Imaging

Each greenhouse plant in the T0 event population, including any control plants, is analyzed for agronomic characteristics of interest, and the agronomic data for each plant is recorded or stored in a manner so that it is associated with the identifying data (see above) for that plant. Confirmation of a phenotype (gene effect) can be accomplished in the T1 generation with a similar experimental design to that described above.

The T0 plants are analyzed at the phenotypic level using quantitative, non-destructive imaging technology throughout the plant's entire greenhouse life cycle to assess the traits of interest. Optionally, a digital imaging analyzer is used for automatic multi-dimensional analyzing of total plants. The imaging may be done inside the greenhouse. Two camera systems, located at the top and side, and an apparatus to rotate the plant, are used to view and image plants from all sides. Images are acquired from the top, front and side of each plant. All three images together provide sufficient information to evaluate, for example, the biomass, size, and morphology of each plant.

Due to the change in size of the plants from the time the first leaf appears from the soil to the time the plants are at the end of their development, the early stages of plant development are optionally documented with a higher magnification from the top. This imaging may be accomplished by using a motorized zoom lens system that is fully controlled by the imaging software.

In a single imaging analysis operation, the following events occur: (1) the plant is conveyed inside the analyzer area, rotated 360 degrees so its machine readable label can be read, and left at rest until its leaves stop moving; (2) the side image is taken and entered into a database; (3) the plant is rotated 90 degrees and again left at rest until its leaves stop moving, and (4) the plant is transported out of the analyzer.

Plants are allowed at least six hours of darkness per twenty four hour period in order to have a normal day/night cycle.

Imaging Instrumentation

Any suitable imaging instrumentation may be used, including but not limited to light spectrum digital imaging instrumentation commercially available from LemnaTec GmbH of Wurselen, Germany. The images are taken and analyzed with a LemnaTec Scanalyzer HTS LT-0001-2 having a ½" IT Progressive Scan IEE CCD imaging device. The imaging cameras may be equipped with a motor zoom, motor aperture, and motor focus. All camera settings may be made using LemnaTec software. Optionally, the instrumental variance of the imaging analyzer is less than about 5% for major components and less than about 10% for minor components.

Software

The imaging analysis system comprises a LemnaTec HTS Bonit software program for color and architecture analysis and a server database for storing data from about 500,000 analyses, including the analysis dates. The original images and the analyzed images are stored together to allow the user to do as much reanalyzing as desired. The database can be connected to the imaging hardware for automatic data collection and storage. A variety of commercially available software systems (e.g., Matlab, others) can be used for quantitative interpretation of the imaging data, and any of these software systems can be applied to the image data set.

Conveyor System

A conveyor system with a plant rotating device may be used to transport the plants to the imaging area and rotate them during imaging. For example, up to four plants, each with a maximum height of 1.5 m, are loaded onto cars that travel over the circulating conveyor system and through the imaging measurement area. In this case the total footprint of the unit (imaging analyzer and conveyor loop) is about 5 m×5 m.

The conveyor system can be enlarged to accommodate more plants at a time. The plants are transported along the conveyor loop to the imaging area and are analyzed for up to 50 seconds per plant. Three views of the plant are taken. The conveyor system, as well as the imaging equipment, should be capable of being used in greenhouse environmental conditions.

Illumination

Any suitable mode of illumination may be used for the image acquisition. For example, a top light above a black background can be used. Alternatively, a combination of top- and backlight using a white background can be used. The illuminated area should be housed to ensure constant illumination conditions. The housing should be longer than the measurement area so that constant light conditions prevail without requiring the opening and closing or doors. Alternatively, the illumination can be varied to cause excitation of either transgene (e.g., green fluorescent protein (GFP), red fluorescent protein (RFP)) or endogenous (e.g. Chlorophyll) fluorophores).

Biomass Estimation Based on Three-Dimensional Imaging

For best estimation of biomass the plant images should be taken from at least three axes, optionally the top and two side (sides 1 and 2) views. These images are then analyzed to separate the plant from the background, pot and pollen control bag (if applicable). The volume of the plant can be estimated by the calculation:

$$\text{Volume(voxels)} = \sqrt{\text{TopArea(pixels)}} \times \sqrt{\text{Side1Area(pixels)}} \times \sqrt{\text{Side2Area(pixels)}}$$

In the equation above the units of volume and area are "arbitrary units". Arbitrary units are entirely sufficient to detect gene effects on plant size and growth in this system because what is desired is to detect differences (both positive-larger and negative-smaller) from the experimental mean, or control mean. The arbitrary units of size (e.g. area) may be trivially converted to physical measurements by the addition of a physical reference to the imaging process. For instance, a physical reference of known area can be included in both top and side imaging processes. Based on the area of these physical references a conversion factor can be determined to allow conversion from pixels to a unit of area such as square centimeters ($cm^2$). The physical reference may or may not be an independent sample. For instance, the pot, with a known diameter and height, could serve as an adequate physical reference.

Color Classification

The imaging technology may also be used to determine plant color and to assign plant colors to various color classes. The assignment of image colors to color classes is an inherent feature of the LemnaTec software. With other image analysis software systems color classification may be determined by a variety of computational approaches.

For the determination of plant size and growth parameters, a useful classification scheme is to define a simple color scheme including two or three shades of green (for example, hues 50-66, see FIG. 13) and, in addition, a color class for chlorosis, necrosis and bleaching, should these conditions occur. A background color class which includes non plant colors in the image (for example pot and soil colors) is also used and these pixels are specifically excluded from the determination of size. The plants are analyzed under controlled constant illumination so that any change within one plant over time, or between plants or different batches of plants (e.g. seasonal differences) can be quantified.

In addition to its usefulness in determining plant size growth, color classification can be used to assess other yield component traits. For these other yield component traits additional color classification schemes may be used. For instance, the trait known as "staygreen", which has been associated with improvements in yield, may be assessed by a color classification that separates shades of green from shades of yellow and brown (which are indicative of senescing tissues). By applying this color classification to images taken toward the end of the T0 or T1 plants' life cycle, plants that have increased amounts of green colors relative to yellow and brown colors (expressed, for instance, as Green/Yellow Ratio) may be identified. Plants with a significant difference in this Green/Yellow ratio can be identified as carrying transgenes which impact this important agronomic trait.

The skilled plant biologist will recognize that other plant colors arise which can indicate plant health or stress response (for instance anthocyanins), and that other color classification schemes can provide further measures of gene action in traits related to these responses.

Plant Architecture Analysis

Transgenes which modify plant architecture parameters may also be identified using the present invention, including such parameters as maximum height and width, internodal distances, angle between leaves and stem, number of leaves starting at nodes, and leaf length. The LemnaTec system software may be used to determine plant architecture as follows. The plant is reduced to its main geometric architecture in a first imaging step and then, based on this image, parameterized identification of the different architecture parameters can be performed. Transgenes that modify any of these architecture parameters either singly or in combination can be identified by applying the statistical approaches previously described.

Pollen Shed Date

Pollen shed date is an important parameter to be analyzed in a transformed plant, and may be determined by the first appearance on the plant of an active male flower. To find the male flower object, the upper end of the stem is classified by color to detect yellow or violet anthers. This color classification analysis is then used to define an active flower, which in turn can be used to calculate pollen shed date.

Alternatively, pollen shed date and other easily visually detected plant attributes (e.g., pollination date, first silk date) can be recorded by the personnel responsible for performing plant care. To maximize data integrity and process efficiency, this data is tracked by utilizing the same barcodes utilized by the LemnaTec light spectrum digital analyzing device. A computer with a barcode reader, a palm device, or a notebook PC may be used for ease of data capture recording time of observation, plant identifier, and the operator who captured the data.

Orientation of the Plants

Mature maize plants grown at densities approximating commercial planting often have a planar architecture. That is, the plant has a clearly discernable broad side, and a narrow side. The image of the plant from the broadside is determined. To each plant a well defined basic orientation is assigned to obtain the maximum difference between the broadside and edgewise images. The top image is used to determine the main axis of the plant, and an additional rotating device is used to turn the plant to the appropriate orientation prior to starting the main image acquisition.

Example 17B

Transformation of Gaspe Flint Derived Maize Lines with a Maize Homolog

Using the INVITROGEN™ GATEWAY® LR Recombination technology, entry clones may be created for any of the maize homologs (SEQ ID NO:18/19, 20/21, 22/23, 43/44, or 45/46) (see Example 5 for entry clone preparation) and can be directionally cloned into the GATEWAY® destination vector 29634 (SEQ ID NO:15; FIG. 11) to create corresponding expression vectors. Each expression vector would contain the cDNA of interest under control of the UBI promoter and would be a T-DNA binary for *Agrobacterium*-mediated transformation into maize as described, but not limited to, the examples described herein.

Example 18

Screening of Maize Lines Under Nitrogen Limiting Conditions

Gaspe Flint Derived Maize Lines

Transgenic plants can contain two or three doses of Gaspe Flint-3 with one dose of GS3 (GS3/(Gaspe-3)2× or GS3/(Gaspe-3)3×) and segregate 1:1 for a dominant transgene. Transgenic plants can be planted in 100% Turface, a commercial potting medium, and can be watered four times each day with 1 mM $KNO_3$ growth medium and with 2 mM $KNO_3$, or higher, growth medium (see FIG. 14). Control plants grown in 1 mM $KNO_3$ medium would be less green, produce less biomass and have a smaller ear at anthesis (see FIG. 15 for an illustration of sample data). Gaspe-derived lines would be grown to the flowering stage.

Statistics would be used to decide if differences seen between treatments are really different. FIG. 15 illustrates one method which places letters after the values. Those values in the same column that have the same letter (not group of letters) following them are not significantly different. Using this method, if there are no letters following the values in a column, then there are no significant differences between any of the values in that column or, in other words, all the values in that column are equal.

Expression of a transgene would result in plants with improved plant growth in 1 mM $KNO_3$ when compared to a transgenic null. Thus biomass and greenness (as described in Examples 2 and 17A) would be monitored during growth and compared to a transgenic null. Improvements in growth, greenness and ear size at anthesis would be indications of increased nitrogen tolerance.

Seedling Assay

Transgenic maize plants can also be evaluated using a seedling assay that assesses plant performance under nitrogen limiting conditions. In an 18 day seedling assay, for example, transgenic plants are planted in Turface, a commercial potting medium, and then watered four times each day with a solution containing the following nutrients: 1 mM $CaCl_2$, 2 mM $MgSO_4$, 0.5 mM $KH_2PO_4$, 83 ppm Sprint330, 3 mM KCl, 1 mM $KNO_3$, 1 μM $ZnSO_4$, 1 μM $MnCl_2$, 3 μM $H_3BO_4$, 0.1 μM $CuSO_4$, and 0.1 μM $NaMoO_4$. Plants are harvested 18 days after planting, and a number of traits are assessed, including but not limited to: SPAD (greenness), stem diameter, root dry weight, shoot dry weight, total dry weight, mg Nitrogen per grams of dry weight (mg N/g dwt), and plant N concentration. Means are compared to null mean parameters using a Student's t test with a minimum (P<t) of 0.1.

Example 19

Nitrogen Utilization Efficiency Seedling Assay

Seed of transgenic events were separated into Transgenic (Treatment 1; contain construct PHP29875) and Null (Treatment 2) seed using a seed color marker.

Treatments (Transgenic or Bulked Null) were each randomly assigned to blocks of 54 pots (experimental units) arranged in 6 rows by 9 columns. Each treatment (Transgenic or Bulked Nulls) was replicated 9 times.

All seeds were planted in 4 inch, square pots containing Turface on 8 inch, staggered centers and watered four times each day with a solution containing the following nutrients:

| | | | |
|---|---|---|---|
| 1 mM $CaCl_2$ | 2 mM $MgSO_4$ | 0.5 mM $KH_2PO_4$ | 83 ppm Sprint330 |
| 3 mM KCl | 1 mM $KNO_3$ | 1 μM $ZnSO_4$ | 1 μM $MnCl_2$ |
| 3 μM $H_3BO_4$ | 1 μM $MnCl_2$ | 0.1 μM $CuSO_4$ | 0.1 μM $NaMoO_4$ |

After emergence the plants were thinned to one seed per pot. At harvest, plants were removed from the pots, and the Turface was washed from the roots. The roots were separated from the shoot, placed in a paper bag, and dried at 70° C. for 70 hr. The dried plant parts (roots and shoots) were weighed and placed in a 50 ml conical tube with approximately 20 5/32 inch steel balls and then ground by shaking in a paint shaker.

The Nitrogen/Protein Analyzer from Thermo Electron Corporation (model Flash EA 1112 N) uses approximately 30 mg of the ground tissue. A sample is dropped from the Autosampler into the crucible inside the oxidation reactor chamber. At 900° C. and pure oxygen, the sample is oxidized by a strong exothermic reaction creating a gas mixture of $N_2$, $CO_2$, $H_2O$, and $SO_2$. After the combustion is complete, the carrier gas helium is turned on and the gas mixture flows into the reduction reaction chamber. At 680° C., the gas mixture flows across the reduction copper where nitrogen oxides possibly formed are converted into elemental nitrogen and the oxygen excess is retained. From the reduction reactor, the gas mixture flows across a series of two absorption filters. The first filter contains soda lime and retains carbon and sulfur dioxides. The second filter contains molecular sieves and granular silica gel to hold back water. Nitrogen is then eluted in the chromatographic column and conveyed to the thermal conductivity detector that generates an electrical signal, which, properly processed by the Eager 300 software, provides the nitrogen-protein percentage.

Using these data, the following parameters were measured and means of Transgenic parameters were compared to means of Null parameters using a Student's t test:

| | |
|---|---|
| Total Plant Biomass | (total dwt (g)) |
| Root Biomass | (root dwt (g)) |
| Shoot Biomass | (shoot dwt (g)) |
| Root/Shoot Ratio | (root:shoot dwt ratio) |
| Plant N concentration | (mg N/g dwt) |
| Total Plant N | (total N (mg)) |

Variance was calculated within each block using an Analysis of Variance (ANOVA) calculation and a completely random design (CRD) model. An overall treatment effect for each block was calculated using an F statistic by dividing overall block treatment mean square by the overall block error mean square. The probability of a greater Student's t test was calculated for each transgenic mean compared to the appropriate null. Variables that show a significant difference (*) have a minimum (P<t) of 0.1.

Table 5 shows the raw data and the two tailed Student's t probability for plants containing construct PHP29875. The mathematical sign of the p value reflects the relative performance of the event vs. the corresponding null, i.e. '+'=increased performance, '−'=decreased performance. Comparisons were made between the transgenic events and construct nulls. A construct null is a negative entry that is made up of a sampling of kernels from the negative segregants and is therefore a representative sample of all negatives.

TABLE 5

Greenhouse Seedling Assay Data for PHP29875

| | | root dwt (g) | | | shoot dwt (g) | | |
|---|---|---|---|---|---|---|---|
| Planting date | Event Name | Mean | Null | t Test | Mean | Null | t Test |
| Aug. 11, 2008 | E7733.53.2.2 | 0.769 | 0.758 | 0.851 | 1.350 | 1.342 | 0.948 |
| Aug. 11, 2008 | E7733.53.2.4 | 0.811 | 0.758 | 0.383 | 1.426 | 1.342 | 0.496 |
| Aug. 11, 2008 | E7733.53.2.7.a | 0.830 | 0.758 | 0.227 | 1.520 | 1.342 | 0.141 |
| Aug. 11, 2008 | E7733.53.2.7.b | 0.833 | 0.758 | 0.206 | 1.529 | 1.342 | 0.123 |
| Aug. 11, 2008 | E7733.53.3.13 | 0.803 | 0.758 | 0.444 | 1.421 | 1.342 | 0.510 |
| Sep. 2, 2009 | E7733.53.2.19 | 0.778 | 0.776 | 0.963 | 1.360 | 1.330 | 0.756 |
| Sep. 2, 2009 | E7733.53.2.2 | 0.800 | 0.776 | 0.607 | 1.366 | 1.330 | 0.713 |
| Sep. 2, 2009 | E7733.53.2.20 | 0.781 | 0.776 | 0.907 | 1.350 | 1.330 | 0.836 |
| Sep. 2, 2009 | E7733.53.2.25 | 0.728 | 0.776 | −0.316 | 1.286 | 1.330 | −0.646 |
| Sep. 2, 2009 | E7733.53.2.4 | 0.706 | 0.776 | −0.144 | 1.204 | 1.330 | −0.197 |

| | | total dwt (g) | | | root:shoot dwt ratio | | |
|---|---|---|---|---|---|---|---|
| Planting date | Event Name | Mean | Null | t Test | Mean | Null | t Test |
| Aug. 11, 2008 | E7733.53.2.2 | 2.119 | 2.100 | 0.913 | 0.575 | 0.569 | 0.798 |
| Aug. 11, 2008 | E7733.53.2.4 | 2.238 | 2.100 | 0.444 | 0.571 | 0.569 | 0.919 |
| Aug. 11, 2008 | E7733.53.2.7.a | 2.350 | 2.100 | 0.155 | 0.552 | 0.569 | 0.445 |
| Aug. 11, 2008 | E7733.53.2.7.b | 2.362 | 2.100 | 0.136 | 0.546 | 0.569 | 0.314 |
| Aug. 11, 2008 | E7733.53.3.13 | 2.224 | 2.100 | 0.475 | 0.567 | 0.569 | 0.918 |
| Sep. 2, 2009 | E7733.53.2.19 | 2.138 | 2.106 | 0.816 | 0.577 | 0.583 | −0.829 |
| Sep. 2, 2009 | E7733.53.2.2 | 2.166 | 2.106 | 0.665 | 0.593 | 0.583 | 0.707 |
| Sep. 2, 2009 | E7733.53.2.20 | 2.131 | 2.106 | 0.854 | 0.581 | 0.583 | −0.963 |
| Sep. 2, 2009 | E7733.53.2.25 | 2.013 | 2.106 | −0.507 | 0.568 | 0.583 | −0.587 |
| Sep. 2, 2009 | E7733.53.2.4 | 1.910 | 2.106 | −0.163 | 0.596 | 0.583 | 0.638 |

| | | mg N/g dwt | | | total N (mg) | | |
|---|---|---|---|---|---|---|---|
| Planting date | Event Name | Mean | Null | t Test | Mean | Null | t Test |
| Aug. 11, 2008 | E7733.53.2.2 | 29.700 | 26.800 | 0.265 | 39.638 | 35.542 | 0.284 |
| Aug. 11, 2008 | E7733.53.2.4 | 24.813 | 26.800 | 0.457 | 34.457 | 35.542 | 0.782 |
| Aug. 11, 2008 | E7733.53.2.7.a | 24.878 | 26.800 | 0.458 | 37.938 | 35.542 | 0.529 |
| Aug. 11, 2008 | E7733.53.2.7.b | 25.844 | 26.800 | 0.712 | 39.253 | 35.542 | 0.331 |
| Aug. 11, 2008 | E7733.53.3.13 | 25.278 | 26.800 | 0.557 | 34.949 | 35.542 | 0.876 |
| Sep. 2, 2009 | E7733.53.2.19 | 21.722 | 21.756 | −0.971 | 29.197 | 28.759 | 0.791 |
| Sep. 2, 2009 | E7733.53.2.2 | 22.289 | 21.756 | 0.564 | 30.363 | 28.759 | 0.334 |
| Sep. 2, 2009 | E7733.53.2.20 | 22.922 | 21.756 | 0.210 | 30.644 | 28.759 | 0.257 |
| Sep. 2, 2009 | E7733.53.2.25 | 23.000 | 21.756 | 0.181 | 29.289 | 28.759 | 0.748 |
| Sep. 2, 2009 | E7733.53.2.4 | 21.989 | 21.756 | 0.800 | 26.311 | 28.759 | −0.143 |

Example 20A

Yield Analysis of Maize Lines with the *Arabidopsis* Lead Genes or Maize Homologs Transgenic plants, either inbreds or topcross hybrids, can undergo more vigorous field-based experiments to study yield enhancement and/or stability under nitrogen limiting and non-limiting conditions. A standardized yield trial will typically include 4 to 6 replications and at least 4 locations.

Yield analysis can be done to determine whether plants that contain the validated *Arabidopsis* gene that encodes a SNF2 domain-containing protein or a related maize gene have an improvement in yield performance (under nitrogen limiting or non-limiting conditions), when compared to the control (or reference) plants, that are either construct null or wild-type. Specifically, nitrogen limiting conditions can be imposed during the flowering and/or grain fill period for plants that contain either the validated *Arabidopsis* lead gene or a maize homolog of Int6 and the control plants. Reduction in yield can be measured for both. Plants containing the validated *Arabidopsis* lead gene or a maize homolog thereof would have less yield loss relative to the control plants, under nitrogen limiting conditions, or would have increased yield relative to the control plants under nitrogen non-limiting conditions.

Example 20B

Yield Analysis of Maize Lines Transformed with PHP29875

Corn hybrid testcrosses, containing the *Arabidopsis thaliana* lead gene (encoding a SNF2 domain-containing polypeptide) expression cassette present in vector PH P29875, and their controls were grown in low nitrogen (LN) and normal nitrogen (NN) environments in 2008 and in 2009 at multiple locations. A low nitrogen (LN) environment consists of a less than normal amount of nitrogen fertilizer applied in early spring or summer, whereas a normal nitrogen (NN) environment consists of adding adequate nitrogen for normal yields, based on soil test standards established for specific growing areas by Federal and State Extension services. A yield reduction was observed in LN conditions as compared to that obtained in NN conditions. For the analysis, a construct null is a negative entry made up of negative segregants from all events within a construct, and a bulk null is a negative entry made up of all negative segregants from all constructs within an experiment.

Nine transgenic events were field tested in 2008 at two locations, York, Nebr. (YK) and Woodland, Calif. (WO), and yield was assessed. The corn hybrid testcrosses were compared to the construct nulls (CN). The results of the 2008 field test are presented in Table 6.

TABLE 6

2008 Field Tests of Maize Transformed with PHP29875

| Event | YK LN | WO LN | YK NN | WO NN |
|---|---|---|---|---|
| CN | 104 | 173 | 198 | 211 |
| E7733.53.2.19 | 107 | 170 | 199 | 208 |
| E7733.53.2.2 | 105 | 175 | N/A | 215 |
| E7733.53.2.20 | 104 | 167 | 194 | 215 |
| E7733.53.2.25 | 105 | 170 | 195 | 209 |
| E7733.53.2.4 | 106 | 174 | 197 | 214 |
| E7733.53.2.7 | 105 | 172 | 196 | 212 |
| E7733.53.2.9 | 105 | 173 | 193 | 211 |
| E7733.53.3.4 | 105 | 173 | 195 | 207 |
| E7733.53.3.13 | 105 | 169 | 197 | 211 |

Unit of measure is bushels/acre.
Shading represents sig. higher (P < 0.1) result compared to the construct null (CN).
Bold represents sig. lower (P < 0.1) result compared to the construct null (CN).

Eight of the nine previously tested transgenic events were field tested in 2009 at the following locations: York, Nebr. (YK); Marion, Iowa (MR); Woodland, Calif. (WO); Dallas Center, Iowa (DS); and Princeton, Ind. (PR). However, in 2009, the corn hybrid testcrosses were compared to the bulk null (BN). The results of the 2009 field test are presented in Table 7. In York, under low nitrogen conditions, three events showed a significant increase in yield over the bulk null, and under normal nitrogen conditions, one event showed a significant increase in yield over the bulk null. In Woodland, under low nitrogen conditions, one event had significantly higher yields as compared to the bulk null. In Marion, under low nitrogen conditions, the yield for three events was significantly higher than the bulk null.

TABLE 7

2009 Field Tests of MaizeTransformed with PHP29875

| Event | YK LN | MR LN | WO LN | DS NN | MR NN | YK NN | PR NN |
|---|---|---|---|---|---|---|---|
| Bulk Null | 158 | 123 | 195 | 165 | 166 | 216 | 176 |
| E7733.53.2.19 | 163 | 127 | 198 | 164 | 170 | 217 | 177 |
| E7733.53.2.2 | 160 | 125 | 201 | 165 | 169 | 220 | 179 |
| E7733.53.2.20 | 159 | 125 | 194 | 162 | 167 | 219 | 178 |
| E7733.53.2.25 | 163 | 125 | 193 | 165 | 155 | 221 | 182 |
| E7733.53.2.4 | 159 | 125 | 197 | 164 | 164 | 212 | 176 |
| E7733.53.2.7 | 159 | 124 | 199 | 166 | 158 | 216 | 181 |
| E7733.53.2.9 | 163 | 126 | 200 | N/A | 167 | N/A | N/A |
| E7733.53.3.4 | 158 | 126 | 196 | N/A | 171 | 225 | N/A |
| E7733.53.3.13 | N/A | N/A | N/A | N/A | N/A | N/A | N/A |

Unit of measure is bushels/acre.
Shading represents sig. higher (P < 0.1) result compared to the bulk null (BN).
Bold represents sig. lower (P < 0.1) result compared to the bulk null (BN).

Example 21

Transformation and Evaluation of Soybean with Soybean Homologs of Validated Lead Genes Based on homology searches, one or several candidate soybean homologs of validated *Arabidopsis* leads can be identified and also be assessed for their ability to enhance tolerance to nitrogen limiting conditions in soybean. Vector construction, plant transformation and phenotypic analysis will be similar to that in previously described Examples.

Example 22

Transformation and Evaluation of Maize with Maize Homologs of Validated Lead Genes Based on homology searches, one or several candidate maize homologs of validated *Arabidopsis* lead genes can be identified (e.g., SEQ ID NOs:18/19, 20/21, 22/23, 43/44, or 45/46) and also be assessed for their ability to enhance tolerance to nitrogen limiting conditions in maize. Vector construction, plant transformation and phenotypic analysis can be similar to that in previously described Examples.

Example 23

Transformation of *Arabidopsis* with Maize and Soybean Homologs of Validated Lead Genes Soybean and maize homologs to validated *Arabidopsis* lead genes can be transformed into *Arabidopsis* under control of the 35S promoter and assayed for leaf area and green color bin accumulation when grown on low nitrogen medium. Vector construction and plant transformation can be as described in the examples herein. Assay conditions, data capture and data analysis can be similar to that in previously described Examples.

What is claimed is:

1. A method of evaluating nitrogen stress tolerance in a plant, comprising:
   (a) obtaining a transgenic plant, wherein the transgenic plant comprises in its genome a recombinant DNA construct comprising a polynucleotide operably linked to at least one regulatory sequence, wherein the polynucleotide encodes a SNF2 domain-containing protein and has an amino acid sequence of at least 95% sequence identity, based on the Clustal V method of alignment, when compared to SEQ ID NO: 25;
   (b) obtaining a progeny plant derived from the transgenic plant, wherein the progeny plant comprises in its genome the recombinant DNA construct; and
   (c) evaluating the progeny plant for nitrogen stress tolerance compared to a control plant not comprising the recombinant DNA construct.

2. A method of determining an increase in yield, biomass, or both in a plant, comprising:
   (a) obtaining a transgenic plant, wherein the transgenic plant comprises in its genome a recombinant DNA construct comprising a polynucleotide operably linked to at least one regulatory sequence, wherein the polynucleotide encodes a SNF2 domain-containing protein and has an amino acid sequence of at least 95% sequence identity, based on the Clustal V method of alignment, when compared to SEQ ID NO:25;
   (b) obtaining a progeny plant derived from the transgenic plant, wherein the progeny plant comprises in its genome the recombinant DNA construct; and
   (c) determining whether the progeny plant exhibits an increase in yield, biomass, or both when compared, under nitrogen limiting conditions, to a control plant not comprising the recombinant DNA construct.

3. The method of claim 1 or 2, wherein said plant is selected from the group consisting of: maize, soybean, sunflower, sorghum, canola, wheat, alfalfa, cotton, rice, barley, millet, sugar cane, and switchgrass.

* * * * *